US011111482B2

(12) United States Patent
Fosmer et al.

(10) Patent No.: US 11,111,482 B2
(45) Date of Patent: Sep. 7, 2021

(54) GENETICALLY MODIFIED LACTATE-CONSUMING YEASTS AND FERMENTATION PROCESSES USING SUCH GENETICALLY MODIFIED YEASTS

(71) Applicant: CARGILL, INCORPORATED, Wayzata, MN (US)

(72) Inventors: Arlene M. Fosmer, Eden Prairie, MN (US); Christopher K. Miller, Andover, MN (US); Gregory Michael Poynter, St. Paul, MN (US); Brian Jeffrey Rush, Minneapolis, MN (US); Jon Veldhouse, Plymouth, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 16/333,070

(22) PCT Filed: Sep. 15, 2017

(86) PCT No.: PCT/US2017/051720
§ 371 (c)(1),
(2) Date: Mar. 13, 2019

(87) PCT Pub. No.: WO2018/053230
PCT Pub. Date: Mar. 22, 2018

(65) Prior Publication Data

US 2019/0264182 A1 Aug. 29, 2019

Related U.S. Application Data

(60) Provisional application No. 62/395,792, filed on Sep. 16, 2016.

(51) Int. Cl.

| | |
|---|---|
| ***C12N 9/02*** | (2006.01) |
| ***C12N 9/18*** | (2006.01) |
| ***C12N 15/74*** | (2006.01) |
| ***C12P 7/06*** | (2006.01) |
| ***C12N 9/04*** | (2006.01) |
| ***C07K 14/395*** | (2006.01) |
| ***C12N 9/34*** | (2006.01) |

(52) U.S. Cl.
CPC .......... *C12N 9/0006* (2013.01); *C07K 14/395* (2013.01); *C12N 9/2428* (2013.01); *C12P 7/06* (2013.01); *C12Y 101/02003* (2013.01); *C12Y 101/02004* (2013.01); *C12Y 302/01003* (2013.01)

(58) Field of Classification Search
CPC .... C12N 9/0006; C12N 9/0028; C12N 15/70; C12N 9/1029; C12Y 402/01; C12Y 201/01; C12Y 114/11022; C12P 7/24; C12P 19/14; C12P 7/00
USPC ....... 435/254.2, 254.21, 190, 139, 161, 157, 435/26
See application file for complete search history.

(56) References Cited

U.S. PATENT DOCUMENTS

| | | | |
|---|---|---|---|
| 5,151,354 | A | 9/1992 | Strasser et al. |
| 10,344,288 | B2 | 7/2019 | Miller et al. |
| 10,364,421 | B2 | 7/2019 | Miller et al. |
| 2016/0024484 | A1 | 1/2016 | Lim et al. |
| 2020/0270644 | A1 | 8/2020 | Miller et al. |

FOREIGN PATENT DOCUMENTS

| | | |
|---|---|---|
| WO | 2018027131 | 2/2018 |

OTHER PUBLICATIONS

Kisselev L., Structure, 2002, vol. 10: 8-9.*
Witkowski et al., Biochemistry 38:11643-11650, 1999.*
Whisstock et al., Quarterly Reviews of Biophysics 2003, vol. 36 (3): 307-340.*
Devos et al., Proteins: Structure, Function and Genetics, 2000, vol. 41: 98-107.*
International Search Report dated Dec. 4, 2017 for PCT/US2017/051720 filed Sep. 15, 2017 (4 pages).
Andrade, Raquel P., et al., "Expression of the Lactate Permease Gene JEN1 from the Yeast *Saccharomyces cerevisiae*", Fungal Genetics and Biology 32, 105-111 (2011), doi: 10.1006/fgbi.2001.1254.
McDermott, Joseph R., et al., "Jen1p: A High Affinity Selenite Transporter in Yeast", Mol Biol Cell. Nov. 15, 2010; 21(22): 3934-3941, doi: 10.1091/mbc.E10-06-0513.
Wakamatsu, Makoto , et al., "Improvement of Ethanol Production from D-Lactic Acid by Constitutive Expression of Lactate Transporter Jen1p in *Saccharomyces cerevisiae*", Biosci. Biotechnol. Biochem. (May 7, 2013) vol. 77, No. 5, pp. 1114-1116.
Xia, Zong-Xiang , et al., "Molecular Structure of Flavocytochrome b2 at 2.4 A Resolution", J. Mol. Biol. (1990) 212, 837-863.
Andrade, Raquel P., et al., "Expression of the Lactate Permease Gene JEN1 from the Yeast *Saccharomyces cerevisiae*," Fungal Genetics and Biology, 32, 105-111, 2001, doi:10.1006/fgbi.2001.1254.
Antonio Pacheco et al: "Lactic acid production in *Saccharomyces cerevisiae* is modulated by expression of the monocarboxylate transporters Jen1 and Ady2", Fems Yeast Research, vol. 12, No. 3, Feb. 12, 2012, pp. 37-381, XP055176423, ISSN: 1567-1356, DOI: 10.1111/j.1567-1364.2012.00790.x.

* cited by examiner

*Primary Examiner* — Robert B Mondesi
*Assistant Examiner* — Mohammad Y Meah

(57) ABSTRACT

The present invention relates to genetically modified yeasts that can use lactate as a carbon source to produce a fermentation product. In one aspect, the yeasts can consume gluconse and lactate simultaneously to produce ethanol. In one aspect, the genetically modified yeast is transformed to include a monocarboxylic/monocarboxylate transporter. In one aspect, the yeast can include one or more heterologous genes encoding lactate dehydrogenase (cytochrome) (EC 1.1.2.3 and/or 1.1.2.4).

9 Claims, 9 Drawing Sheets

Specification includes a Sequence Listing.

C

A

B

C

A

B

A

B

SEQUENCE LISTING

```
<160> NUMBER OF SEQ ID NOS: 89

<210> SEQ ID NO 1
<211> LENGTH: 3182
<212> TYPE: DNA
<213> ORGANISM: Saccharomyces cerevisiae

<400> SEQUENCE: 1

cctactgcgc caattgatga caatacagac gatgataaca aaccgaagtt atctgatgta      60

gaaaaggatt aaagatgcta agagatagtg atgatatttc ataaataatg taattctata     120

tatgttaatt acctttttg cgaggcatat ttatggtgaa ggataagttt tgaccatcaa     180

agaaggttaa tgtggctgtg gtttcagggt ccataaagct tttcaattca tcttttttt     240

ttttgttctt ttttttgatt ccggtttctt tgaaattttt ttgattcggt aatctccgag     300

cagaaggaag aacgaaggaa ggagcacaga cttagattgg tatatatacg catatgtggt     360

gttgaagaaa catgaaattg cccagtattc ttaacccaac tgcacagaac aaaaacctgc     420
```

-continued

```
aggaaacgaa gataaagcgg ccgcataact tcgtataatg tatgctatac gaagttatct    480
gccagtatac agctagcctt gaaagtgatg gaaaacattg tcatcggcac ataaataaaa    540
aaattatgaa tcacgtgatc aacagcaaat tatgtactcg tatatatgca agcgcattcc    600
ttatattgac actctttcat tgggcatgag gctgtgtaaa cataagctgt aacggtctca    660
cggaacactg tgtagttgca ttactgtcag gcagttatgt tgcttaatat aaaggcaaag    720
gcatggcaga atcactttaa aacgtggccc cacccgctgc accctgtgca ttttgtacgt    780
tactgcgaaa tgactcaacg atgaaatgaa aaaattttgc ttgaaatttt gaaaaaaaga    840
tgtgcgggac gcattgttag ctcattgaat acatcgtgat cgaatccaat caatgtttaa    900
tttcatatta atacagaaac tttttctcat actttcttct tcttttcatt ggtatattat    960
ctatatatcg tgttaattcc tctttcgtca tttttagcat cgttataaga gtaattaaga   1020
ataactagaa gagtctctct ttatattcgt ttattttata tatttaaccg ctaaatttag   1080
taaacaaaag aatctatcag aaatgagtga atctccaatg ttcgctgcca acggcatgcc   1140
aaaggtaaat caaggtgctg aagaagatgt cagaatttta ggttacgacc cattagcttc   1200
tccagctctc cttcaagtgc aaatcccagc cacaccaact tctttggaaa ctgccaagag   1260
aggtagaaga gaagctatag atattattac cggtaaagac gacagagttc ttgtcattgt   1320
cggtccttgt tccatccatg atctagaagc cgctcaagaa tacgctttga gattaaagaa   1380
attgtcagat gaattaaaag gtgatttatc catcattatg agagcatact tggagaagcc   1440
aagaacaacc gtcggctgga aaggtctaat taatgaccct gatgttaaca acactttcaa   1500
catcaacaag ggtttgcaat ccgctagaca attgtttgtc aacttgacaa atatcggttt   1560
gccaattggt tctgaaatgc ttgataccat ttctcctaaa tacttggctg atttggtctc   1620
cttcggtgcc attggtgcca gaaccaccga atctcaactg cacagagaat tggcctccgg   1680
tttgtctttc ccagttggtt tcaagaacgg taccgatggt accttaaatg ttgctgtgga   1740
tgcttgtcaa gccgctgctc attctcacca tttcatgggt gttactaagc atggtgttgc   1800
tgctatcacc actactaagg gtaacgaaca ctgcttcgtt attctaagag gtggtaaaaa   1860
gggtaccaac tacgacgcta agtccgttgc agaagctaag gctcaattgc ctgccggttc   1920
caacggtcta atgattgact actctcacgg taactccaat aaggatttca gaaaccaacc   1980
aaaggtcaat gacgttgttt gtgagcaaat cgctaacggt gaaaacgcca ttaccggtgt   2040
catgattgaa tcaaacatca acgaaggtaa ccaaggcatc ccagccgaag gtaaagccgg   2100
cttgaaatat ggtgtttcca tcactgatgc ttgtataggt tgggaaacta ctgaagacgt   2160
cttgaggaaa ttggctgctg ctgtcagaca aagaagagaa gttaacaaga aatagatgtt   2220
tttttaatga tatatgtaac gtacattctt tcctctacca ctgccaattc ggtattattt   2280
aattgtgttt agcgctattt actaattaac tagaaactca atttttaaag gcaaagctcg   2340
ctgacctttc actgatttcg tggatgttat actatcagtt actcttctgc aaaaaaaaat   2400
tgagtcatat cgtagctttg ggattatttt tctctctctc cacggctaat taggtgatca   2460
tgaaaaaatg aaaaattcat gagaaaagag tcagacatcg aaacatacat aagttgatat   2520
tcctttgata tcgacgacta ctcaatcagg ttttaaaaga aaagaggcag ctattgaagt   2580
agcagtatcc agtttaggtt ttttaattat ttacaagtaa agaaaaagag aatgccggtc   2640
gttcacgata acttcgtata atgtatgcta tacgaagtta tgcggccgcg agaagatgcg   2700
gccagcaaaa ctaaaaaact gtattataag taaatgcatg tatactaaac tcacaaatta   2760
gagcttcaat ttaattatat cagttattac ccgggaatct cggtcgtaat gatttctata   2820
```

atgacgaaaa aaaaaaaatt ggaaagaaaa agcttcatgg cctttataaa aaggaactat 2880
ccaatacctc gccagaacca agtaacagta ttttacgggg cacaaatcaa gaacaataag 2940
acaggactgt aaagatggac gcattgaact ccaaagaaca acaagagttc caaaaagtag 3000
tggaacaaaa gcaaatgaag gatttcatgc gtttgtactc taatctggta gaaagatgtt 3060
tcacagactg tgtcaatgac ttcacaacat caaagctaac caataaggaa caaacatgca 3120
tcatgaagtg ctcagaaaag ttcttgaagc atagcgaacg tgtagggcag cgtttccaag 3180
ag 3182

<210> SEQ ID NO 2
<211> LENGTH: 3275
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus nidulans.

<400> SEQUENCE: 2
cctactgcgc caattgatga caatacagac gatgataaca aaccgaagtt atctgatgta 60
gaaaaggatt aaagatgcta agagatagtg atgatatttc ataaataatg taattctata 120
tatgttaatt accttttttg cgaggcatat ttatggtgaa gaataagttt tgaccatcaa 180
agaaggttaa tgtggctgtg gtttcagggt ccataaagct tttcaattca tcattttttt 240
tttattcttt tttttgattc cggtttcctt gaaatttttt tgattcggta atctccgaac 300
agaaggaaga acgaaggaag gagcacagac ttagattggt atatatacgc atatgtagtg 360
ttgaagaaac atgaaattgc ccagtattct taacccaact gcacagaaca aaaatctgca 420
ggaaacgaag ataaagcggc cgcataactt cgtatagcat acattatacg aagttatcgc 480
ctgttaagat ataactgaaa aaagagggga atttttagat actgaaatga tattttagaa 540
taaccagact atatataagg ataaattaca aaaaattaac taatagataa gatttaaata 600
taaaagatat gcaactagaa aagtcttatc aatctcctta tggagtgacg acgttaccca 660
acaatttacc gacttcttcg gcgatagcca aagttctctc ttcggacaat cttctaccaa 720
taacttgaac agcaacagga gcaccgtgat aagcctctgg gtcgtattct tcttgaacca 780
aagcatccaa ttcggaaaca gctttaaaag attcgttctt cttatcaata ttcttatcag 840
cgaaagtgac tgggacgaca acagaggtga aatccaataa gttaataacg gaggcgtaac 900
cgtagtatct gaattgatcg tgtctgacag cggcggtagg agtaattgga gcgataatag 960
cgtccaattc cttaccagct tttcttcag cttcacgcca cttttccaag tattccattt 1020
gatagttcca cttttgtaaa tgagtgtccc acaattcgtt catgttaaca gccttaatat 1080
ttgggttcaa caagtcctta atgttaggga tggctggctc accagaggca gaaatgtctc 1140
tcatgacgtc ggcagaacca tcagcagcat agatgtggga aatcaagtca tgaccgaaat 1200
catgcttgta tggagtccat ggagtaacgg tgtgaccagc cttggccaaa gcggcaacgg 1260
tagtttcgac accacgtaaa attggtgggt gtggcaagac gttaccgtcg aaattgtaat 1320
aaccaatgtt caaaccacca ttcttaatct tagaggcaat gatgtcagat tcagattgtc 1380
tccatggcat tgggatgacc ttagagtcgt acttccaagg ttcttgaccc aagacagatt 1440
tggtgaacaa tctcaagtct tcgacggagt gagtgatagg accaacgacg gagtgaacgg 1500
tttcttgacc ttccatagag ttagccattt tagcatatgg caatctaccg tgagatggtc 1560
tcaaaccgta taaaaagttg aaagcagctg ggactctaat ggaaccacca atgtcagtac 1620

```
cgacaccaat aacaccacct ctaataccaa caatagcacc ttcaccacca gaagaaccac   1680

cacaggacca atttttgttt cttggattga cagttctacc aatgatgttg ttgacggttt   1740

cacagaccat caaggtttgt gggacagagg tcttaacgta gaaaacagca ccagcttttc   1800

tcaacatggt ggttaagacg gaatcacctt catcgtattt gtttaaccag gaaatgtaac   1860

ccatggaggt ttcgtaaccc ttaacacgca attggtcctt taaagagatt ggtaaaccgt   1920

gtaatggacc aactggtctc ttatgcttag cgtagtattc atctaattct ctagcttgag   1980

ctaaagcagc atctgggaag aattcgtgag cacagttggt taattgttga gcaatagcag   2040

ctctcttaca aaaagccaaa gtgacttcaa cagaagtcaa ctcaccagcg gccaacttgg   2100

agaccaaatc agcagcagag gcttcggtaa tcttcaattc agcctcagac aaaataccgg   2160

acttctttgg gaaatcaata acggaatctt cggcaggcaa agtttgaacc ttccattcgt   2220

caggaatggt tttagccaaa cgggcacgtt tgtcggcggc caattcttcc caggattgtg   2280

gcattttgta attaaaactt agattagatt gctatgcttt ctttctaatg agcaagaagt   2340

aaaaaaagtt gtaatagaac aagaaaaacg aaactgaaac ttgagaaatt gaagaccatt   2400

tattaactta aatatcaatg ggaggtcatc gaaagagaaa aaaatcaaaa aaaaaatttt   2460

tcaagaaaaa gaaacgtgat aaaaattttt attgcctttt tcgacgaaga aaaagaaacg   2520

aggcggtctc tttttctttt tccaaacctt tagtacgggt aattaacgcc accctagagg   2580

aagaaagagg ggaaatttag tatgctgtgc ttgggtgttt tgaagtggta cggcgatgcg   2640

cggagtccga gaaaatctgg aagagtaaaa aaggagtaga aacattttga agctatggtg   2700

tgtgggggat cacttgtggg ggattgggtg tgatgtaagg ataacttcgt atagcataca   2760

ttatacgaag ttatgcggcc gcgagaagat gcggccagca aaactaaaaa actgtattat   2820

aagtaaatgc atgtatacta aactcacaaa ttagagcttc aatttaatta tatcagttat   2880

tacccgggaa tctcggtcgt aatgattttt ataatgacga aaaaaaaaaa attggaaaga   2940

aaaagcttca tggcctttat aaaaaggaac catccaatac ctcgccagaa ccaagtaaca   3000

gtattttacg gggcacaaat caagaacaat aagacaggac tgtaaagatg gacgcattga   3060

actccaaaga acaacaagag ttccaaaaag tagtggaaca aaagcaaatg aaggatttca   3120

tgcgtttgta ctctaatctg gtagaaagat gttttacaga ctgtgtcaat gacttcacaa   3180

catcaaagct aaccaataag gaacaaacat gcatcatgaa gtgctcagaa aagttcttga   3240

agcatagcga acgtgtaggg cagcgtttcc aagag                              3275
```

<210> SEQ ID NO 3
<211> LENGTH: 1132
<212> TYPE: DNA
<213> ORGANISM: Artificial Sequence
<220> FEATURE:
<223> OTHER INFORMATION: Sequence put together from multiple organisms:
Saccharomyces cerevisiae and P1 bacteriophage

<400> SEQUENCE: 3

```
ctctttttta cagatcatca aggaagtaat tatctacttt ttacaagaat tcatgtctaa     60

tttacttact gttcaccaaa acttgcctgc attaccagtt gacgcaacct ccgatgaagt    120

cagaaagaac cttatggata tgtttagaga tagacaagct ttctccgaac atacttggaa    180

aatgttatta tccgtttgta gatcctgggc cgcttggtgt aaacttaaca atagaaaatg    240

gtttcctgct gaaccagaag acgtcagaga ttacttactt tacttacaag ctagaggttt    300

ggctgttaaa actatccaac aacacttagg tcaattgaat atgttacaca gaagatccgg    360
```

```
tttaccaaga ccatccgatt ccaacgcagt ttcccttgtt atgagaagaa ttagaaaaga    420

aaatgttgac gctggtgaaa gagctaaaca agcattagca tttgaaagaa ccgatttcga    480

tcaagttaga tccttaatgg aaaattccga tagatgtcaa gatattagaa acttagcttt    540

cttaggtatt gcttacaaca cattattaag aatcgctgaa attgctagaa ttagagttaa    600

agatatttca agaaccgatg gcggtagaat gttaatccac attggcagaa caaaaacctt    660

agtctccaca gcaggcgtcg aaaaagcatt atcattaggt gttactaaat tagttgaacg    720

ttggatttcc gtttccggtg ttgcagatga cccaaacaac tacttattct gtcgtgttag    780

aaaaaatggt gttgccgctc cttccgctac ctcacaatta tccacaagag cattagaagg    840

catttttgaa gctacccaca gacttattta tggtgcaaaa gacgattccg gtcaaagata    900

tttagcttgg tctggtcatt ccgctagagt tggtgccgca agagacatgg caagagctgg    960

tgtttctatt cctgaaatta tgcaagccgg tggttggact aatgttaaca ttgttatgaa   1020

ctatatcaga aacttagatt ccgaaacagg tgctatggtt agattacttg aagacggtga   1080

ttaagctagc taagatccgc tctaaccgaa aaggaaggag ttagacaacc tg           1132
```

<210> SEQ ID NO 4
<211> LENGTH: 6376
<212> TYPE: DNA
<213> ORGANISM: Artificial Sequence
<220> FEATURE:
<223> OTHER INFORMATION: Sequence put together from multiple separate Saccharomyces cerevisiae sequences

<400> SEQUENCE: 4

```
ctagctaaga tccgctctaa ccgaaaagga aggagttaga caacctgaag tctaggtccc     60

tatttatttt tttatagtta tgttagtatt aagaacgtta tttatatttc aaatttttct    120

ttttttctg tacagacgcg tgtacgcatg taacattata ctgaaaacct tgcttgagaa    180

ggttttggga cgctcgaaga tccagctgca ttaatgaatc ggccaacgcg cggggagagg    240

cggtttgcgt attgggcgct cttccgcttc ctcgctcact gactcgctgc gctcggtcgt    300

tcggctgcgg cgagcggtat cagctcactc aaaggcggta atacggttat ccacagaatc    360

aggggataac gcaggaaaga acatgtgagc aaaaggccag caaaaggcca ggaaccgtaa    420

aaaggccgcg ttgctggcgt ttttccatag gctccgcccc cctgacgagc atcacaaaaa    480

tcgacgctca agtcagaggt ggcgaaaccc gacaggacta taaagatacc aggcgtttcc    540

ccctggaagc tccctcgtgc gctctcctgt tccgaccctg ccgcttaccg gatacctgtc    600

cgcctttctc ccttcgggaa gcgtggcgct ttctcatagc tcacgctgta ggtatctcag    660

ttcggtgtag gtcgttcgct ccaagctggg ctgtgtgcac gaaccccccg ttcagcccga    720

ccgctgcgcc ttatccggta actatcgtct tgagtccaac ccggtaagac acgacttatc    780

gccactggca gcagccactg gtaacaggat tagcagagcg aggtatgtag gcggtgctac    840

agagttcttg aagtggtggc ctaactacgg ctacactaga aggacagtat ttggtatctg    900

cgctctgctg aagccagtta ccttcggaaa aagagttggt agctcttgat ccggcaaaca    960

aaccaccgct ggtagcggtg gtttttttgt ttgcaagcag cagattacgc gcagaaaaaa   1020

aggatctcaa gaagatcctt tgatcttttc tacggggtct gacgctcagt ggaacgaaaa   1080

ctcacgttaa gggattttgg tcatgagatt atcaaaaagg atcttcacct agatcctttt   1140

aaattaaaaa tgaagtttta aatcaatcta aagtatatat gagtaaactt ggtctgacag   1200

ttaccaatgc ttaatcagtg aggcacctat ctcagcgatc tgtctatttc gttcatccat   1260
```

agttgcctga ctccccgtcg tgtagataac tacgatacgg gagggcttac catctggccc 1320
cagtgctgca atgataccgc gagacccacg ctcaccggct ccagatttat cagcaataaa 1380
ccagccagcc ggaagggccg agcgcagaag tggtcctgca actttatccg cctccatcca 1440
gtctattaat tgttgccggg aagctagagt aagtagttcg ccagttaata gtttgcgcaa 1500
cgttgttgcc attgctacag gcatcgtggt gtcacgctcg tcgtttggta tggcttcatt 1560
cagctccggt tcccaacgat caaggcgagt tacatgatcc cccatgttgt gcaaaaaagc 1620
ggttagctcc ttcggtcctc cgatcgttgt cagaagtaag ttggccgcag tgttatcact 1680
catggttatg gcagcactgc ataattctct tactgtcatg ccatccgtaa gatgcttttc 1740
tgtgactggt gagtactcaa ccaagtcatt ctgagaatag tgtatgcggc gaccgagttg 1800
ctcttgcccg gcgtcaatac gggataatac cgcgccacat agcagaactt taaaagtgct 1860
catcattgga aaacgttctt cggggcgaaa actctcaagg atcttaccgc tgttgagatc 1920
cagttcgatg taacccactc gtgcacccaa ctgatcttca gcatctttta ctttcaccag 1980
cgtttctggg tgagcaaaaa caggaaggca aaatgccgca aaaaagggaa taagggcgac 2040
acggaaatgt tgaatactca tactcttcct ttttcaatat tattgaagca tttatcaggg 2100
ttattgtctc atgagcggat acatatttga atgtatttag aaaaataaac aaataggggt 2160
tccgcgcaca tttccccgaa aagtgccacc tgaacgaagc atctgtgctt cattttgtag 2220
aacaaaaatg caacgcgaga gcgctaattt ttcaaacaaa gaatctgagc tgcattttta 2280
cagaacagaa atgcaacgcg aaagcgctat tttaccaacg aagaatctgt gcttcatttt 2340
tgtaaaacaa aaatgcaacg cgagagcgct aatttttcaa acaaagaatc tgagctgcat 2400
ttttacagaa cagaaatgca acgcgagagc gctattttac caacaaagaa tctatacttc 2460
ttttttgttc tacaaaaatg catcccgaga gcgctatttt tctaacaaag catcttagat 2520
tacttttttt ctcctttgtg cgctctataa tgcagtctct tgataacttt ttgcactgta 2580
ggtccgttaa ggttagaaga aggctacttt ggtgtctatt ttctcttcca taaaaaaagc 2640
ctgactccac ttcccgcgtt tactgattac tagcgaagct gcgggtgcat tttttcaaga 2700
taaaggcatc cccgattata ttctataccg atgtggattg cgcatacttt gtgaacagaa 2760
agtgatagcg ttgatgattc ttcattggtc agaaaattat gaacggtttc ttctattttg 2820
tctctatata ctacgtatag gaaatgttta cattttcgta ttgttttcga ttcactctat 2880
gaatagttct tactacaatt tttttgtcta aagagtaata ctagagataa acataaaaaa 2940
tgtagaggtc gagtttagat gcaagttcaa ggagcgaaag gtggatgggt aggttatata 3000
gggatatagc acagagatat atagcaaaga gatacttttg agcaatgttt gtggaagcgg 3060
tattcgcaat attttagtag ctcgttacag tccggtgcgt ttttggtttt ttgaaagtgc 3120
gtcttcagag cgcttttggt tttcaaaagc gctctgaagt tcctatactt tctagagaat 3180
aggaacttcg gaataggaac ttcaaagcgt ttccgaaaac gagcgcttcc gaaaatgcaa 3240
cgcgagctgc gcacatacag ctcactgttc acgtcgcacc tatatctgcg tgttgcctgt 3300
atatatatat acatgagaag aacggcatag tgcgtgttta tgcttaaatg cgtacttata 3360
tgcgtctatt tatgtaggat gaaaggtagt ctagtacctc ctgtgatatt atcccattcc 3420
atgcggggta tcgtatgctt ccttcagcac taccctttag ctgttctata tgctgccact 3480
cctcaattgg attagtctca tccttcaatg ctatcatttc ctttgatatt ggatcatact 3540
aagaaaccat tattatcatg acattaacct ataaaaatag gcgtatcacg aggccctttc 3600

-continued

```
gtctcgcgcg tttcggtgat gacggtgaaa acctctgaca catgcagctc ccggagacgg   3660
tcacagcttg tctgtaagcg gatgccggga gcagacaagc ccgtcagggc gcgtcagcgg   3720
gtgttggcgg gtgtcggggc tggcttaact atgcggcatc agagcagatt gtactgagag   3780
tgcaccatac cacagctttt caattcaatt catcattttt tttttattct tttttttgat   3840
ttcggtttct ttgaaatttt tttgattcgg taatctccga acagaaggaa gaacgaagga   3900
aggagcacag acttagattg gtatatatac gcatatgtag tgttgaagaa acatgaaatt   3960
gcccagtatt cttaacccaa ctgcacagaa caaaaacctg caggaaacga agataaatca   4020
tgtcgaaagc tacatataag gaacgtgctg ctactcatcc tagtcctgtt gctgccaagc   4080
tatttaatat catgcacgaa aagcaaacaa acttgtgtgc ttcattggat gttcgtacca   4140
ccaaggaatt actggagtta gttgaagcat taggtcccaa aatttgttta ctaaaaacac   4200
atgtggatat cttgactgat ttttccatgg agggcacagt taagccgcta aaggcattat   4260
ccgccaagta caatttttta ctcttcgaag acagaaaatt tgctgacatt ggtaatacag   4320
tcaaattgca gtactctgcg ggtgtataca gaatagcaga atgggcagac attacgaatg   4380
cacacggtgt ggtgggccca ggtattgtta gcggtttgaa gcaggcggca gaagaagtaa   4440
caaaggaacc tagaggcctt ttgatgttag cagaattgtc atgcaagggc tccctatcta   4500
ctggagaata tactaagggt actgttgaca ttgcgaagag cgacaaagat tttgttatcg   4560
gctttattgc tcaaagagac atgggtggaa gagatgaagg ttacgattgg ttgattatga   4620
cacccggtgt gggtttagat gacaagggag acgcattggg tcaacagtat agaaccgtgg   4680
atgatgtggt ctctacagga tctgacatta ttattgttgg aagaggacta tttgcaaagg   4740
gaagggatgc taaggtagag ggtgaacgtt acagaaaagc aggctgggaa gcatatttga   4800
gaagatgcgg ccagcaaaac taaaaaactg tattataagt aaatgcatgt atactaaact   4860
cacaaattag agcttcaatt taattatatc agttattacc ctatgcggtg tgaaataccg   4920
cacagatgcg taaggagaaa ataccgcatc aggaaattgt aaacgttaat attttgttaa   4980
aattcgcgtt aaatttttgt taaatcagct cattttttaa ccaataggcc gaaatcggca   5040
aaatccctta taaatcaaaa gaatagaccg agatagggtt gagtgttgtt ccagtttgga   5100
acaagagtcc actattaaag aacgtggact ccaacgtcaa agggcgaaaa accgtctatc   5160
agggcgatgg cccactacgt gaaccatcac cctaatcaag ttttttgggg tcgaggtgcc   5220
gtaaagcact aaatcggaac cctaaaggga gcccccgatt tagagcttga cggggaaagc   5280
cggcgaacgt ggcgagaaag gaagggaaga aagcgaaagg agcgggcgct agggcgctgg   5340
caagtgtagc ggtcacgctg cgcgtaacca ccacacccgc cgcgcttaat gcgccgctac   5400
agggcgcgtc cattcgccat tcaggctgcg caactgttgg gaagggcgat cggtgcgggc   5460
ctcttcgcta ttacgccagc tgaattggag cgacctcatg ctatacctga gaaagcaacc   5520
tgacctacag gaaagagtta ctcaagaata agaattttcg ttttaaaacc taagagtcac   5580
tttaaaattt gtatacactt atttttttta taacttattt aataataaaa atcataaatc   5640
ataagaaatt cgcttattta gaagtgtcaa caacgtatct accaacgatt tgaccctttt   5700
ccatcttttc gtaaatttct ggcaaggtag acaagccgac aaccttgatt ggagacttga   5760
ccaaacctct ggcgaagaat tgttaattaa gccagaaaaa ggaagtgttt ccctccttct   5820
tgaattgatg ttaccctcat aaagcacgtg gcctcttatc gagaaagaaa ttaccgtcgc   5880
tcgtgatttg tttgcaaaaa gaacaaaact gaaaaaaccc agacacgctc gacttcctgt   5940
cttcctattg attgcagctt ccaatttcgt cacacaacaa ggtcctagcg acggctcaca   6000
```

```
ggttttgtaa caagcaatcg aaggttctgg aatggcggga aagggtttag taccacatgc   6060

tatgatgccc actgtgatct ccagagcaaa gttcgttcga tcgtactgtt actctctctc   6120

tttcaaacag aattgtccga atcgtgtgac aacaacagcc tgttctcaca cactcttttc   6180

ttctaaccaa gggggtggtt tagtttagta gaacctcgtg aaacttacat ttacatatat   6240

ataaacttgc ataaattggt caatgcaaga aatacatatt tggtcttttc taattcgtag   6300

tttttcaagt tcttagatgc tttctttttc tctttttttac agatcatcaa ggaagtaatt   6360

atctactttt tacaag                                                  6376
```

<210> SEQ ID NO 5
<211> LENGTH: 4632
<212> TYPE: DNA
<213> ORGANISM: Artificial Sequence
<220> FEATURE:
<223> OTHER INFORMATION: Sequence put together from multiple organisms: Saccharomyces cerevisiae and Saccharomycopsis fibuligera

<400> SEQUENCE: 5

```
cagagcctct tatattcact ctgttcctcc atcgcctatt gagaaacgtt ggaataaaac     60

tctaaaaata tcatctagtt ggttagtttt tattttacca gtacattgtc acttgcggag    120

ggaggatgac ataaagattg agacgcagtc atttaatgaa gtttaaacgc aggtatttga    180

taaagtaata cgatattgaa tcatgacgta taaagtgaaa tgaacaaatg attacgtaaa    240

aaatgtcgat ttctcttgga gagactccca tagcctctaa gaggccttct actacgttcc    300

atatatctaa gaatggggcc atatccagtg gaatcccagc aattatttaa ggatcaccta    360

tttctcagcc gatattttag caaaatcact accaatatca gggggcaata gttgatcgcc    420

tactttaaca aaaaatgttg ctcacgtatt aacacaggca acaaaaagga tattacgcaa    480

gaacgtagta tccacatgcc atcctccttg ttgcatcttt ttttttccga aatgattccc    540

tttcctgcac aacacgagat ctttcacgca tacatcggaa ggatcacccc ccactcaagt    600

cgttgcattg ctaacatgtg gcattctgcc catttttttc acgaaaattc tctctctata    660

atgaagaccc ttgtgccctg gactctgtaa tacttgaaac tacttcctca ataatcgctt    720

ggagacctac ccccacgctt ttcaaacaag gcgctagcaa aaagcctgcc gatatctcct    780

tgccccctcc ttctgttcga gagaactacg acccgaccaa taataatgtc atacaagaac    840

cgccaagaac caactgctga accttagatc tccaatactt cagttggagt atgtgaatat    900

ataagtacct ggtcgactaa tcttcttgca tcttttcgta ttcttacatc ctatgtcgct    960

aatacagttc ccgcatagag aagaaagcaa acaaaagtag tcactcgaga tctcccgagt   1020

ttatcattat caatactgcc atttcaaaga atacgtaaat aattaatagt agtgattttc   1080

ctaactttat ttagtcaaaa aattggcctt ttaattctgc tgtaacccgt acatgcccaa   1140

aatagggggc gggttacaca gaatatataa catcataggt gtctgggtga acagtttatt   1200

cctggcatcc actaaatata atggagcccg ctttttttaa gctggcatcc agaaaaaaaa   1260

agaatcccag caccaaaata ttgttttctt caccaaccat cagttcatag gtccattctc   1320

ttagcgcaac tacacagaac aggggcacaa acaggcaaaa aacgggcaca acctcaatgg   1380

agtgatgcaa cctgcttgga gtaaatgatg acacaaggca attgacctac gcatgtatct   1440

atctcatttt cttacacctt ctattacctt ctgctctctc tgatttggaa aaagctgaaa   1500

aaaaaggttg aaaccagttc cctgaaatta ttcccctatt tgactaataa gtatataaag   1560

acggtaggta ttgattgtaa ttctgtaaat ctatttctta aacttcttaa attctacttt   1620
```

-continued

```
tatagttagt cttttttta gtttaaaaca ccaagaactt agtttcgaat aaacacacat   1680
aaacaaacaa atctagaatg attagattaa ccgtattcct cactgcagtt tttgcagcag   1740
tcgcttcctg tgttccagtt gaattggata agagaaatac aggccatttc caagcatatt   1800
ctggttacac cgtagctaga tcaaacttta ctcaatggat tcacgagcaa ccagccgtat   1860
catggtacta tttgcttcag aatatagact atccagaagg acaattcaag tctgccaagc   1920
caggggtcgt tgtggcttcc ccttctacat ccgaacctga ttacttctac caatggacta   1980
gagatactgc tatcaccttc ttgtcactta tcgcggaagt tgaggatcat tctttttcaa   2040
atactacact agccaaggtg gttgaatact acatctctaa tacttacaca ttacaaagag   2100
tttccaaccc atctggtaac ttcgacagtc caaatcacga cggtttggga gaaccaaagt   2160
ttaatgttga tgatacagct tatactgcat cttggggtag accacaaaat gatggcccag   2220
cgttgagagc atacgcaatt tcaagatacc ttaacgcagt agcaaaacac aacaacggta   2280
agttactgct cgctggacaa aacggtattc cttactcttc agcttctgat atctactgga   2340
agattatcaa gccagatctt caacatgtgt caacccattg gtctacatct ggttttgatt   2400
tgtgggaaga gaatcaggga acacatttct ttactgcgtt ggtccagcta aaagcactta   2460
gttacggcat tcctttaagt aagacctaca acgatcctgg tttcactagt tggctagaaa   2520
agcaaaagga tgctttaaac tcttatatca acagctctgg tttcgtaaac tctggcaaaa   2580
agcatatagt ggagagccct caactatctt caagaggagg gttggatagc gccacataca   2640
ttgcagcctt aatcacacat gatattggcg acgacgacac ttacacacct ttcaacgttg   2700
acaactccta tgtcttgaac tcactgtatt accttctagt cgataacaaa aaccgttaca   2760
aaatcaatgg taactacaag gccggtgctg ctgttggtag atacccagag gatgtttaca   2820
acggtgttgg gacatcagaa ggcaatccat ggcaattagc tacagcctac gccggccaaa   2880
cattttacac actggcttac aactcattga aaaacaaaaa aaacttagtg attgaaaagt   2940
tgaactacga cctctacaat tctttcatag cagatttatc caagatcgat agttcttacg   3000
catcaaaaga ctccttgact ttgacctacg gttctgacaa ctacaaaaac gtcataaagt   3060
cactattaca gtttggagat tcattcctga aggtcttgct cgatcacatt gatgataatg   3120
gacaattaac agaagagatc aatagataca cagggttcca ggctggtgct gttagtttga   3180
catggtcctc tggttcatta ctttcagcaa accgtgcgag aaataagttg attgaactat   3240
tgtagttaat taaacaggcc ccttttcctt tgtcgatatc atgtaattag ttatgtcacg   3300
cttacattca cgccctcctc ccacatccgc tctaaccgaa aaggaaggag ttagacaacc   3360
tgaagtctag gtccctattt attttttat agttatgtta gtattaagaa cgttatttat   3420
atttcaaatt tttcttttt ttctgtacaa acgcgtgtac gcatgtaacg ggcagacggc   3480
cggccataac ttcgtataat gtatgctata cgaagttatg gcaacggttc atcatctcat   3540
ggatctgcac atgaacaaac accagagtca aacgacgttg aaattgaggc tactgcgcca   3600
attgatgaca atacagacga tgataacaaa ccgaagttat ctgatgtaga aaaggattag   3660
agatgctaag agatagtgat gatatttcat aaataatgta attctatata tgttaattac   3720
ctttttgcg aggcatattt atggtgaagg ataagttttg accatcaaag aaggttaatg   3780
tggctgtggt ttcagggtcc ataaagcttt tcaattcatc ttttttttt ttgttctttt   3840
ttttgattcc ggtttctttg aaattttttt gattcggtaa tctccgagca gaaggaagaa   3900
cgaaggaagg agcacagact tagattggta tatatacgca tatgtggtgt tgaagaaaca   3960
```

```
tgaaattgcc cagtattctt aacccaactg cacagaacaa aaacctgcag gaaacgaaga   4020
taaatcatgt cgaaagctac atataaggaa cgtgctgcta ctcatcctag tcctgttgct   4080
gccaagctat ttaatatcat gcacgaaaag caaacaaact tgtgtgcttc attggatgtt   4140
cgtaccacca aggaattact ggagttagtt gaagcattag gtcccaaaat ttgtttacta   4200
aaaacacatg tggatatctt gactgatttt tccatggagg gcacagttaa gccgctaaag   4260
gcattatccg ccaagtacaa tttttactc ttcgaagaca gaaaatttgc tgacattggt   4320
aatacagtca aattgcagta ctctgcgggt gtatacagaa tagcagaatg ggcagacatt   4380
acgaatgcac acggtgtggt gggcccaggt attgttagcg gtttgaagca ggcggcggaa   4440
gaagtaacaa aggaacctag aggccttttg atgttagcag aattgtcatg caagggctcc   4500
ctagctactg gagaatatac taagggtact gttgacattg cgaagagcga caaagatttt   4560
gttatcggct ttattgctca aagagacatg ggtggaagag atgaaggtta cgattggttg   4620
attatgacac gc                                                       4632
```

<210> SEQ ID NO 6
<211> LENGTH: 4363
<212> TYPE: DNA
<213> ORGANISM: Artificial Sequence
<220> FEATURE:
<223> OTHER INFORMATION: Sequence put together from multiple organisms: Saccharomyces cerevisiae and Saccharomycopsis fibuligera

<400> SEQUENCE: 6

```
ggccgctcca tggagggcac agttaagccg ctaaaggcat tatccgccaa gtacaatttt     60
ttactcttcg aagacagaaa atttgctgac attggtaata cagtcaaatt gcagtactct    120
gcgggtgtat acagaatagc agaatgggca gacattacga atgcacacgg tgtggtgggc    180
ccaggtattg ttagcggttt gaagcaggcg gcggaagaag taacaaagga acctagaggc    240
cttttgatgt tagcagaatt gtcatgcaag ggctccctag ctactggaga atatactaag    300
ggtactgttg acattgcgaa gagcgacaaa gattttgtta tcggctttat tgctcaaaga    360
gacatgggtg gaagagatga aggttacgat tggttgatta tgacacccgg tgtgggttta    420
gatgacaagg gagacgcatt gggtcaacag tatagaaccg tggatgatgt ggtctctaca    480
ggatctgaca ttattattgt tggaagagga ctatttgcaa agggaaggga tgctaaggta    540
gagggtgaac gttacagaaa agcaggctgg gaagcatatt tgagaagatg cggccagcaa    600
aactaaaaaa ctgtattata agtaaatgca tgtatactaa actcacaaat tagagcttca    660
atttaattat atcagttatt acccgggaat ctcggtcgta atgattttta taatgacgaa    720
aaaaaaaaaa ttggaaagaa aaagcttcat ggcctttata aaaaggaacc atccaatacc    780
tcgccagaac caagtaacag tattttacgg ggcacaaatc aagaacaata agacaggact    840
gtaaagatgg acgcattgaa ctccaaagaa caacaagagt tccaaaaagt agtggaacaa    900
aagcaaatga aggatttcat gcgtttgata acttcgtata atgtatgcta tacgaagtta    960
tctcgagggc cagaaaaagg aagtgtttcc ctccttcttg aattgatgtt accctcataa   1020
agcacgtggc ctcttatcga gaaagaaatt accgtcgctc gtgatttgtt tgcaaaaaga   1080
acaaaactga aaaaacccag acacgctcga cttcctgtct tcctgttgat tgcagcttcc   1140
aatttcgtca cacaacaagg tcctagcgac ggctcacagg ttttgtaaca agcaatcgaa   1200
ggttctggaa tggcgggaaa gggtttagta ccacatgcta tgatgcccac tgtgatctcc   1260
agagcaaagt tcgttcgatc gtactgttac tctctctctt tcaaacagaa ttgtccgaat   1320
```

cgtgtgacaa caacagcctg ttctcacaca ctcttttctt ctaaccaagg gggtggttta 1380
gtttagtaga acctcgtgaa acttacattt acatatatat aaacttgcat aaattggtca 1440
atgcaagaaa tacatatttg gtcttttcta attcgtagtt tttcaagttc ttagatgctt 1500
tctttttctc ttttttacag atcatcaagg aagtaattat ctacttttta caagtctaga 1560
atgatcagac ttacagtttt cctaacagcc gttttcgccg ccgttgcatc atgtgtccca 1620
gtagaattgg ataagagaaa caccggccat ttccaagcat attcaggata caccgttgca 1680
cgttctaatt tcacacaatg gattcatgag cagcctgctg tgtcctggta ctacttatta 1740
caaaacattg attatcctga gggacaattc aagtcagcga aaccaggcgt tgtggttgct 1800
tctccatcca cttcagaacc agactacttc taccagtgga cccgtgacac agcaataact 1860
ttcttatctt tgatagcaga agtagaagat cactcatttt caaatacaac tctagctaag 1920
gttgtcgaat actacatctc taacacatac accctacaaa gagtttctaa cccatctggt 1980
aatttcgata gcccaaatca cgatggtctg ggtgaaccaa agttcaacgt tgacgacact 2040
gcttacactg catcatgggg cagacctcaa aacgacggtc cagccttaag agcttacgcg 2100
atctcaagat atttgaacgc agttgccaag cataacaacg gtaagctatt gctcgcgggt 2160
caaaatggta ttccttactc atctgcatca gatatctact ggaagattat caagccagat 2220
ttacaacatg taagtactca ctggagtaca tctggttttg acttatggga agagaatcaa 2280
ggtacacatt tctttactgc acttgtccag ttaaaagctc tttcatacgg tatacctttg 2340
tctaagacat ataacgatcc aggatttact tcttggttgg aaaagcagaa ggatgccttg 2400
aactcttaca tcaattccag cggcttcgtc aactccggga aaaagcacat tgtcgaatct 2460
cctcaattat ctagtagagg gggtcttgat agcgctactt acatcgctgc tctaattaca 2520
catgatattg gtgatgatga tacatacact ccttttaacg tagataattc ttatgtgctg 2580
aactctttat actatctgct tgtagacaac aaaaacagat acaagatcaa cgggaactac 2640
aaagcaggag ctgcagttgg tagataccca gaagatgtgt acaatggagt gggaacctca 2700
gagggaaacc catggcaatt ggcgacagca tacgccggcc aaacctttta cacactggct 2760
tacaattctc tcaaaaacaa aaaaaatttg gttattgaga agttgaatta cgatctatac 2820
aactccttta tagctgactt aagtaagatt gactcctctt acgcttctaa ggattcattg 2880
acattgacct acggctcaga taactacaaa aatgtcatta agtcactttt acaattcggg 2940
gattctttct tgaaagtctt gttggaccat attgatgata atggtcagct aacagaggaa 3000
atcaacagat atacaggttt tcaagctggc gcagtttccc tcacttggag tagtggttca 3060
ctcttatctg caaacagagc cagaaacaag ttgatcgaat tgctttagtt aattaagaag 3120
ttttgttaga aaataaatca ttttttaatt gagcattctt attcctattt tatttaaata 3180
gttttatgta ttgttagcta catacaacag tttaaatcaa attttctttt tcccaagtcc 3240
aaaatggagg tttattttga tgacccgcat gcgattatgt tttgaaagta taagactaca 3300
tacatgtaca tatatttaaa catgtaaacc cgtccattat attgccgggc agacggccgg 3360
ccttatagcc tagctttaag gctactttaa aaacttttta tttattcata cacatatatt 3420
atcgaacatt cgtataactt aatatcattc aaaaaaaaaa aaaaaaaaaa aagaaaacat 3480
atacacatat atatttatgt ttatagagag agagagagaa aatttgaatt tttgaatcat 3540
ttgcaaagtt atatgtttta tacattattt attcattttt tttggtgtcg aggacattgt 3600
gctgttcaga gaaccactta aaatacgcat cgttctgtaa atatccactt tcattaaaaa 3660
ccttattcac ttctaacttt gccttcaact ccttcttgga gtttctcccc tttttttttct 3720

```
gaacaagctc aaccagatat aatggttcgt tcttttcgaa ctttgtcttt acatatattt   3780

cctcctttgt acctcttctc tttcccacat aaacagtccc cttttcaata aaacgagaga   3840

aataccagaa aagtagcgag agaacaaaat atgcgcctac caaaagcttt tgatacgtaa   3900

caatctgatc tctctcaaat tttttatcca agaagaaact caaaccagct acaacagcta   3960

tggaataacc tatgtacaat ttagcatcga gtaaagcgta tgatctctcg taatttaatc   4020

tcgcgaaaac agaaggtagg gcttcatcta aagcttggtt caactccggg attgaatata   4080

cattaatagg tttagcagaa ctcatcttga acaggcgtct cttttcctta caataacttg   4140

tgcttttcct tctataattc cgtttcaacg tgtacaattg tcattttttg tctggtatga   4200

ttttgcagaa ctgaaaaaat ctcttaaatg ttccgcctca tcaagaaggc atattccttt   4260

acaaaagtac attgatctta caagaagcta gctaatggta ctatttaaaa aacaactaca   4320

ctccatcaat acataaaatt gttatgatag acttgaggga cgg                     4363
```

```
<210> SEQ ID NO 7
<211> LENGTH: 5015
<212> TYPE: DNA
<213> ORGANISM: Artificial Sequence
<220> FEATURE:
<223> OTHER INFORMATION: Sequence put together from multiple organisms:
      Saccharomyces cerevisiae,  Saccharomycopsis fibuligera, and
      Aspergillus nidulans

<400> SEQUENCE: 7
```

```
cagagcctct tatattcact ctgttcctcc atcgcctatt gagaaacgtt ggaataaaac     60

tctaaaaata tcatctagtt ggttagtttt tattttacca gtacattgtc acttgcggag    120

ggaggatgac ataaagattg agacgcagtc atttaatgaa gtttaaacgc aggtatttga    180

taaagtaata cgatattgaa tcatgacgta taaagtgaaa tgaacaaatg attacgtaaa    240

aaatgtcgat tttctcttga gagactccca tagcctctaa gaggccttct actacgttcc    300

atatatctaa gaatggggcc atatccagtg gaatcccagc aattatttaa ggatcaccta    360

tttctcagcc gatattttag caaaatcact accaatatca gggggcaata gttgatcgcc    420

tactttaaca aaaaatgttg ctcacgtatt aacacaggca acaaaaagga tattacgcaa    480

gaacgtagta tccacatgcc atcctccttg ttgcatcttt ttttttccga aatgattccc    540

tttcctgcac aacacgagat ctttcacgca tacatcggaa ggatcacccc ccactcaagt    600

cgttgcattg ctaacatgtg gcattctgcc catttttttc acgaaaattc tctctctata    660

atgaagaccc ttgtgccctg gactctgtaa tacttgaaac tacttcctca ataatcgctt    720

ggagacctac ccccacgctt ttcaaacaag gcgctagcaa aaagcctgcc gatatctcct    780

tgccccctcc ttctgttcga gagaactacg acccgaccaa taataatgtc atacaagaac    840

cgccaagaac caactgctga accttagatc tccaatactt cagttggagt atgtgaatat    900

ataagtacct ggtcgactaa tcttcttgca tcttttcgta ttcttacatc ctatgtcgct    960

aatacagttc ccgcatagag aagaaagcaa acaaaagtag tcactcgaga tctcccgagt   1020

ttatcattat caatactgcc atttcaaaga atacgtaaat aattaatagt agtgattttc   1080

ctaactttat ttagtcaaaa aattggcctt ttaattctgc tgtaacccgt acatgcccaa   1140

aatagggggc gggttacaca gaatatataa catcataggt gtctgggtga acagtttatt   1200

cctggcatcc actaaatata atggagcccg ctttttttaa gctggcatcc agaaaaaaaa   1260

agaatcccag caccaaaata ttgttttctt caccaaccat cagttcatag gtccattctc   1320
```

```
ttagcgcaac tacacagaac aggggcacaa acaggcaaaa aacgggcaca acctcaatgg   1380
agtgatgcaa cctgcttgga gtaaatgatg acacaaggca attgacctac gcatgtatct   1440
atctcatttt cttacacctt ctattacctt ctgctctctc tgatttggaa aaagctgaaa   1500
aaaaaggttg aaaccagttc cctgaaatta ttcccctatt tgactaataa gtatataaag   1560
acggtaggta ttgattgtaa ttctgtaaat ctatttctta aacttcttaa attctacttt   1620
tatagttagt cttttttta gtttaaaaca ccaagaactt agtttcgaat aaacacacat   1680
aaacaaacaa atctagaatg atcagactta ctgttttcct cacagccgtt tttgcagcag   1740
tagcttcttg tgttccagtt gaattggata agagaaatac aggtcatttc caagcttact   1800
ctggttacac tgtggctaga tctaacttca cacaatggat tcatgaacag cctgccgtga   1860
gttggtacta tttgctacaa aacattgatt accctgaggg tcaattcaaa tcagctaagc   1920
caggtgttgt tgtcgcgagc ccatcaactt ctgaaccaga ttacttctac caatggacta   1980
gagataccgc aataaccttc ttatctctaa tcgcagaggt agaagatcac tctttttcaa   2040
atactaccct ggcaaaagtg gtcgagtact acatctcaaa cacatacacc ttgcagagag   2100
tctcaaaccc atcaggaaac ttcgattctc ctaatcatga cggcttagga gaaccaaagt   2160
ttaatgttga cgataccgct tatactgcat cttggggtag accacagaat gatggccctg   2220
ccttacgtgc atacgccatt tccagatatc tcaacgctgt agcgaagcac aacaacggta   2280
agctgctttt agctggtcaa aatgggatac catactcttc cgcttcagac atttactgga   2340
agattatcaa accagacttg cagcatgtca gtacacattg gtcaacttct ggttttgatt   2400
tgtgggaaga gaaccaaggc actcacttct ttacagcctt ggttcaacta aaggcattgt   2460
cttacggaat ccctttgtcc aagacataca atgatcctgg attcactagt tggctagaaa   2520
agcaaaagga tgcactgaac tcatacatta acagttcagg ctttgtgaac tccggtaaaa   2580
agcatattgt tgaaagccca caactatcta gcagaggtgg tttagattct gcaacctaca   2640
tagcagcctt gatcacacac gacattgggg atgacgatac atacacacca ttcaacgtcg   2700
acaattcata cgttttgaat agcttatact acctactggt agataacaaa aacagatata   2760
agatcaatgg caactacaag gccggtgctg ccgtaggaag ataccctgaa gatgtctaca   2820
acggagttgg tacatcagaa ggtaacccat ggcaattagc aacagcatat gcgggccaga   2880
cattttacac tttggcttac aattcattga aaaacaaaaa aaatttagtg atagaaaagc   2940
ttaactatga cctttacaac tctttcattg ccgatttatc caagattgat tcctcctacg   3000
catcaaagga ctccttgaca cttacatacg gttctgacaa ctacaaaaat gttatcaagt   3060
ctctcttgca atttggtgat tctttcttga aggttttact cgatcatatc gatgataatg   3120
gtcaactaac tgaggaaatc aacagataca ctgggttcca agctggagct gtctctttaa   3180
catggagttc agggagtttg ttatctgcta acagagcgcg taacaaactt attgagcttc   3240
tgtagttaat taaacaggcc ccttttcctt tgtcgatatc atgtaattag ttatgtcacg   3300
cttacattca cgccctcctc ccacatccgc tctaaccgaa aaggaaggag ttagacaacc   3360
tgaagtctag gtccctattt atttttttat agttatgtta gtattaagaa cgttatttat   3420
atttcaaatt tttcttttt ttctgtacaa acgcgtgtac gcatgtaacg ggcagacggc   3480
cggccataac ttcgtataat gtatgctata cgaagttatc cttacatcac acccaatccc   3540
ccacaagtga tcccccacac accatagctt caaaatgttt ctactccttt tttactcttc   3600
cagattttct cggactccgc gcatcgccgt accacttcaa aacacccaag cacagcatac   3660
taaatttccc ctctttcttc ctctagggtg gcgttaatta cccgtactaa aggtttggaa   3720
```

```
aagaaaaaag agaccgcctc gtttcttttt cttcgtcgaa aaaggcaata aaaattttta   3780

tcacgtttct ttttcttgaa aaattttttt tttgattttt ttctctttcg atgacctccc   3840

attgatattt aagttaataa atggtcttca atttctcaag tttcagtttc gtttttcttg   3900

ttctattaca actttttttta cttcttgctc attagaaaga aagcatagca atctaatcta   3960

agttttaatt acaaaatgcc acaatcctgg gaagaattgg ccgccgacaa acgtgcccgt   4020

ttggctaaaa ccattcctga cgaatggaag gttcaaactt tgcctgccga agattccgtt   4080

attgatttcc caaagaagtc cggtattttg tctgaggctg aattgaagat taccgaagcc   4140

tctgctgctg atttggtctc caagttggcc gctggtgagt tgacttctgt tgaagtcact   4200

ttggcttttt gtaagagagc tgctattgct caacaattaa ccaactgtgc tcacgaattc   4260

ttcccagatg ctgctttagc tcaagctaga gaattagatg aatactacgc taagcataag   4320

agaccagttg gtccattaca cggtttacca atctctttaa aggaccaatt gcgtgttaag   4380

ggttacgaaa cctccatggg ttacatttcc tggttaaaca aatacgatga aggtgattcc   4440

gtcttaacca ccatgttgag aaaagctggt gctgttttct acgttaagac ctctgtccca   4500

caaaccttga tggtctgtga aaccgtcaac aacatcattg gtagaactgt caatccaaga   4560

aacaaaaatt ggtcctgtgg tggttcttct ggtggtgaag gtgctattgt tggtattaga   4620

ggtggtgtta ttggtgtcgg tactgacatt ggtggttcca ttagagtccc agctgctttc   4680

aactttttat acggtttgag accatctcac ggtagattgc catatgctaa aatggctaac   4740

tctatggaag gtcaagaaac cgttcactcc gtcgttggtc ctatcactca ctccgtcgaa   4800

gacttgagat tgttcaccaa atctgtcttg ggtcaagaac cttggaagta cgactctaag   4860

gtcatcccca tgccatggag acaatctgaa tctgacatca ttgcctctaa gattaagaat   4920

ggtggtttga acattggtta ttacaatttc gacggtaacg tcttgccaca cccaccaatt   4980

ttacgtggtg tcgaaactac cgttgccgct ttggc                            5015
```

```
<210> SEQ ID NO 8
<211> LENGTH: 4771
<212> TYPE: DNA
<213> ORGANISM: Artificial Sequence
<220> FEATURE:
<223> OTHER INFORMATION: Sequence put together from multiple organisms:
      Saccharomyces cerevisiae,  Saccharomycopsis fibuligera, and
      Aspergillus nidulans

<400> SEQUENCE: 8
```

```
ggccgcgaag gtgctattgt tggtattaga ggtggtgtta ttggtgtcgg tactgacatt     60

ggtggttcca ttagagtccc agctgctttc aactttttat acggtttgag accatctcac    120

ggtagattgc catatgctaa aatggctaac tctatggaag gtcaagaaac cgttcactcc    180

gtcgttggtc ctatcactca ctccgtcgaa gacttgagat tgttcaccaa atctgtcttg    240

ggtcaagaac cttggaagta cgactctaag gtcatcccaa tgccatggag acaatctgaa    300

tctgacatca ttgcctctaa gattaagaat ggtggtttga acattggtta ttacaatttc    360

gacggtaacg tcttgccaca cccaccaatt ttacgtggtg tcgaaactac cgttgccgct    420

ttggccaagg ctggtcacac cgttactcca tggactccat acaagcatga tttcggtcat    480

gacttgattt cccacatcta tgctgctgat ggttctgccg acgtcatgag agacatttct    540

gcctctggtg agccagccat ccctaacatt aaggacttgt tgaacccaaa tattaaggct    600

gttaacatga acgaattgtg ggacactcat ttacaaaagt ggaactatca aatggaatac    660
```

-continued

```
ttggaaaagt ggcgtgaagc tgaagaaaaa gctggtaagg aattggacgc tattatcgct    720
ccaattactc ctaccgccgc tgtcagacac gatcaattca gatactacgg ttacgcctcc    780
gttattaact tattggattt cacctctgtt gtcgtcccag tcactttcgc tgataagaat    840
attgataaga agaacgaatc ttttaaagct gtttccgaat tggatgcttt ggttcaagaa    900
gaatacgacc cagaggctta tcacggtgct cctgttgctg ttcaagttat tggtagaaga    960
ttgtccgaag agagaacttt ggctatcgcc gaagaagtcg gtaaattgtt gggtaacgtc   1020
gtcactccat aagcgaattt cttatgattt atgattttta ttattaaata agttataaaa   1080
aaaataagtg tatacaaatt ttaaagtgac tcttaggttt taaaacgaaa attcttattc   1140
ttgagtaact ctttcctgta ggtcaggttg ctttctcagg tatagcatga ggtcgctctt   1200
attgaccaca cctctaccgg catgccgagc aaatgcctgc aaatcgctcc ccatttcacc   1260
caattgtaga tatgctaact ccagcaatga gttgatgaat ctcggtgtgt attttatgtc   1320
ctcagaggac aacacataac ttcgtataat gtatgctata cgaagttatc tcgagggcca   1380
gaaaaaggaa gtgtttccct ccttcttgaa ttgatgttac cctcataaag cacgtggcct   1440
cttatcgaga aagaaattac cgtcgctcgt gatttgtttg caaaaagaac aaaactgaaa   1500
aaacccagac acgctcgact tcctgtcttc ctgttgattg cagcttccaa tttcgtcaca   1560
caacaaggtc ctagcgacgg ctcacaggtt ttgtaacaag caatcgaagg ttctggaatg   1620
gcgggaaagg gtttagtacc acatgctatg atgcccactg tgatctccag agcaaagttc   1680
gttcgatcgt actgttactc tctctctttc aaacagaatt gtccgaatcg tgtgacaaca   1740
acagcctgtt ctcacacact cttttcttct aaccaagggg gtggtttagt ttagtagaac   1800
ctcgtgaaac ttacatttac atatatataa acttgcataa attggtcaat gcaagaaata   1860
catatttggt cttttctaat tcgtagtttt tcaagttctt agatgctttc tttttctctt   1920
ttttacagat catcaaggaa gtaattatct actttttaca agtctagaat gattagatta   1980
acagtatttc ttacagccgt tttcgcagcc gtcgcatcct gtgttccagt agaattagat   2040
aagcgtaata caggacattt tcaagcttac tctggctata cagttgcgag atctaacttt   2100
acacaatgga ttcacgaaca gccagcagtt tcttggtact atttgctcca aaacatcgac   2160
taccctgaag gccaattcaa gtctgcaaag ccaggagtgg tcgtcgcttc tcctagtact   2220
tcagaaccag attacttcta ccagtggaca agagacactg ctattacctt cctgagctta   2280
atcgctgaag ttgaagatca ctctttttct aatacaacac tggccaaagt agttgagtac   2340
tacatctcta acacttacac tctacaaaga gtgtcaaacc cttctgggaa cttcgacagc   2400
ccaaaccatg atggtttggg ggagccaaaa ttcaacgttg atgatacagc ctacaccgca   2460
tcttggggta gaccacaaaa cgacggacca gctttaagag catacgcaat atctcgttac   2520
cttaatgctg ttgcaaagca caataatgga aagttgttgt tggctggtca aaacggtatt   2580
ccttactctt cagcatctga tatctactgg aagattatca agccagatct tcaacacgta   2640
tccacacatt ggtcaacctc cggcttcgat ttatgggagg aaaatcaggg tacacatttc   2700
ttcaccgctc tagtgcaatt gaaggctttg agttacggca ttccattgtc taagacttac   2760
aacgatcctg gtttcacctc atggcttgaa aagcagaagg atgccctgaa tagctacatc   2820
aactcatctg gttttgttaa ctcagggaaa aagcatatag ttgaatcccc acaactatca   2880
tcaagaggag gtttagactc cgccacatac attgctgcct tgattacaca tgatattggg   2940
gatgatgaca catatactcc atttaacgtc gataacagtt atgtccttaa ttccttatac   3000
tatttgttgg tcgataacaa aaatagatac aaaatcaacg gcaactacaa ggctggcgca   3060
```

gcggtgggta gataccctga ggatgtttac aatggtgtag gtacatctga aggcaatcca 3120
tggcaattag cgactgctta cgctggacaa actttctaca cacttgcgta caactcattg 3180
aaaaacaaaa aaaacctagt cattgaaaag ttgaattacg atctgtacaa ctctttcatc 3240
gcagacctat caaagattga ctcatcttat gcaagtaaag attcactaac tttaacctac 3300
ggtagtgata actacaaaaa cgttatcaag tctttactcc agtttggtga ttcattcttg 3360
aaggtgttgt tagatcatat agacgacaat ggtcaactca cagaggagat aaacagatac 3420
actggttttc aagcaggagc tgtttcactt acttggtcaa gtggttcttt gctttccgcc 3480
aacagagcca gaaacaagct catcgaatta ctatagttaa ttaagaagtt ttgttagaaa 3540
ataaatcatt ttttaattga gcattcttat tcctatttta tttaaatagt tttatgtatt 3600
gttagctaca tacaacagtt taaatcaaat ttttcttttttc ccaagtccaa aatggaggtt 3660
tattttgatg acccgcatgc gattatgttt tgaaagtata agactacata catgtacata 3720
tatttaaaca tgtaaacccg tccattatat tgccgggcag acggccggcc ttatagccta 3780
gctttaaggc tactttaaaa actttttatt tattcataca catatattat cgaacattcg 3840
tataacttaa tatcattcaa aaaaaaaaaa aaaaaaaaaa gaaaacatat acacatatat 3900
atttatgttt atagagagag agagagaaaa tttgaatttt tgaatcattt gcaaagttat 3960
atgttttata cattatttat tcattttttt tggtgtcgag gacattgtgc tgttcagaga 4020
accacttaaa atacgcatcg ttctgtaaat atccactttc attaaaaacc ttattcactt 4080
ctaactttgc cttcaactcc ttcttggagt tttctccctt ttttttctga acaagctcaa 4140
ccagatataa tggttcgttc ttttcgaact ttgtctttac atatatttcc tcctttgtac 4200
ctcttctctt tcccacataa acagtcccct tttcaataaa acgagagaaa taccagaaaa 4260
gtagcgagag aacaaaatat gcgcctacca aaagcttttg atacgtaaca atctgatctc 4320
tctcaaattt tttatccaag aagaaactca aaccagctac aacagctatg gaataaccta 4380
tgtacaattt agcatcgagt aaagcgtatg atctctcgta atttaatctc gcgaaaacag 4440
aaggtagggc ttcatctaaa gcttggttca actccgggat tgaatataca ttaataggtt 4500
tagcagaact catcttgaac aggcgtctct tttccttaca ataacttgtg cttttccttc 4560
tataattccg tttcaacgtg tacaattgtc attttttgtc tggtatgatt ttgcagaact 4620
gaaaaaatct cttaaatgtt ccgcctcatc aagaaggcat attcctttac aaaagtacat 4680
tgatcttaca agaagctagc taatggtact atttaaaaaa caactacact ccatcaatac 4740
ataaaattgt tatgatagac ttgagggacg g 4771

<210> SEQ ID NO 9
<211> LENGTH: 8719
<212> TYPE: DNA
<213> ORGANISM: Artificial Sequence
<220> FEATURE:
<223> OTHER INFORMATION: Sequence put together from multiple organisms: Saccharomyces cerevisiae and P1 bacteriophage

<400> SEQUENCE: 9
atcacatagg aagcaacagg cgcgttggac ttttaatttt cgaggaccgc gaatccttac 60
atcacaccca atcccccaca agtgatcccc cacacaccat agcttcaaaa tgtttctact 120 cctttttttac tcttccagat tttctcggac tccgcgcatc gccgtaccac ttcaaaacac 180
ccaagcacag catactaaat ttcccctctt tcttcctcta gggtgtcgtt aattacccgt 240
actaaaggtt tggaaaagaa aaaagagacc gcctcgtttc tttttcttcg tcgaaaaagg 300
caataaaaat ttttatcacg tttctttttc ttgaaaattt ttttttttga tttttttctc 360
tttcgatgac ctcccattga tatttaagtt aataaacggt cttcaatttc tcaagtttca 420
gtttcatttt tcttgttcta ttacaacttt ttttacttct tgctcattag aaagaaagca 480
tagcaatcta atctaagttt taattacaaa tctagaatga gtgaatctcc aatgttcgct 540
gccaacggca tgccaaaggt aaatcaaggt gctgaagaag atgtcagaat tttaggttac 600
gacccattag cttctccagc tctccttcaa gtgcaaatcc cagccacacc aacttctttg 660
gaaactgcca agagaggtag aagagaagct atagatatta ttaccggtaa agacgacaga 720
gttcttgtca ttgtcggtcc ttgttccatc catgatcttg aagccgctca agaatacgct 780
ttgagattaa agaaattgtc agatgaatta aaaggtgatt tatccatcat tatgagagca 840
tacttggaga agccaagaac aaccgtcggc tggaaaggtc taattaatga ccctgatgtt 900
aacaacactt tcaacatcaa caagggtttg caatccgcta gacaattgtt tgtcaacttg 960
acaaatatcg gtttgccaat tggttctgaa atgcttgata ccatttctcc taaatacttg 1020
gctgatttgg tctccttcgg tgccattggt gccagaacca ccgaatctca actgcacaga 1080
gaattggcct ccggtttgtc tttcccagtt ggtttcaaga acggtaccga tggtacctta 1140
aatgttgctg tggatgcttg tcaagccgct gctcattctc accatttcat gggtgttact 1200
aagcatggtg ttgctgctat caccactact aagggtaacg aacactgctt cgttattcta 1260
agaggtggta aaaagggtac caactacgac gctaagtccg ttgcagaagc taaggctcaa 1320
ttgcctgccg gttccaacgg tctaatgatt gactactctc acggtaactc caataaggat 1380
ttcagaaacc aaccaaaggt caatgacgtt gtttgtgagc aaatcgctaa cggtgaaaac 1440
gccattaccg gtgtcatgat tgaatcaaac atcaacgaag gtaaccaagg catcccagcc 1500
gaaggtaaag ccggcttgaa atatggtgtt tccatcactg atgcttgtat aggttgggaa 1560
actactgaag acgtcttgag gaaattggct gctgctgtca gacaaagaag agaagttaac 1620
aagaaataga tgttttttta atgatatatg taacgtacat tctttcctct accactgcca 1680
attcggtatt atttaattgt gtttagcgct atttactaat taactagaaa ctcaattttt 1740
aaaggcaaag ctcgctgacc tttcactgat ttcgtggatg ttatactatc agttactctt 1800
ctgcaaaaaa aaattgagtc atatcgtagc tttgggatta tttttctctc tctccacggc 1860
taattaggtg atcatgaaaa aatgaaaaat tcatgagaaa agagtcagac atcgaaacat 1920
acataagttg atattccttt gatatcgacg actactcaat caggttttaa aagaaaagag 1980
gcagctattg aagtagcagt atccagttta ggttttttaa ttatttacaa gtaaagaaaa 2040
agagaatgcc ggtcgttcac ggcggccgcg ccagaaaaag gaagtgtttc cctccttctt 2100
gaattgatgt taccctcata aagcacgtgg cctcttatcg agaaagaaat taccgtcgct 2160
cgtgatttgt ttgcaaaaag aacaaaactg aaaaaaccca gacacgctcg acttcctgtc 2220
ttcctattga ttgcagcttc caatttcgtc acacaacaag gtcctagcga cggctcacag 2280
gttttgtaac aagcaatcga aggttctgga atggcgggaa agggtttagt accacatgct 2340
atgatgccca ctgtgatctc cagagcaaag ttcgttcgat cgtactgtta ctctctctct 2400
ttcaaacaga attgtccgaa tcgtgtgaca acaacagcct gttctcacac actcttttct 2460
tctaaccaag gggtggttt agtttagtag aacctcgtga aacttacatt tacatatata 2520
taaacttgca taaattggtc aatgcaagaa atacatattt ggtcttttct aattcgtagt 2580
ttttcaagtt cttagatgct ttcttttct ctttttaca gatcatcaac tcttttttac 2640

-continued

```
agatcatcaa ggaagtaatt atctactttt tacaagaatt catgtctaat ttacttactg   2700
ttcaccaaaa cttgcctgca ttaccagttg acgcaacctc cgatgaagtc agaaagaacc   2760
ttatggatat gtttagagat agacaagctt tctccgaaca tacttggaaa atgttattat   2820
ccgtttgtag atcctgggcc gcttggtgta aacttaacaa tagaaaatgg tttcctgctg   2880
aaccagaaga cgtcagagat tacttacttt acttacaagc tagaggtttg gctgttaaaa   2940
ctatccaaca acacttaggt caattgaata tgttacacag aagatccggt ttaccaagac   3000
catccgattc caacgcagtt tcccttgtta tgagaagaat tagaaaagaa aatgttgacg   3060
ctggtgaaag agctaaacaa gcattagcat ttgaaagaac cgatttcgat caagttagat   3120
ccttaatgga aaattccgat agatgtcaag atattagaaa cttagctttc ttaggtattg   3180
cttacaacac attattaaga atcgctgaaa ttgctagaat tagagttaaa gatatttcaa   3240
gaaccgatgg cggtagaatg ttaatccaca ttggcagaac aaaaaccta gtctccacag    3300
caggcgtcga aaaagcatta tcattaggtg ttactaaatt agttgaacgt tggatttccg   3360
tttccggtgt tgcagatgac ccaaacaact acttattctg tcgtgttaga aaaaatggtg   3420
ttgccgctcc ttccgctacc tcacaattat ccacaagagc attagaaggc atttttgaag   3480
ctacccacag acttatttat ggtgcaaaag acgattccgg tcaaagatat ttagcttggt   3540
ctggtcattc cgctagagtt ggtgccgcaa gagacatggc aagagctggt gtttctattc   3600
ctgaaattat gcaagccggt ggttggacta atgttaacat tgttatgaac tatatcagaa   3660
acttagattc cgaaacaggt gctatggtta gattacttga agacggtgat taagctagct   3720
aagatccgct ctaaccgaaa aggaaggagt tagacaacct gaagtctagg tccctattta   3780
ttttttata gttatgttag tattaagaac gttatttata tttcaaattt ttctttttt     3840
tctgtacaga cgcgtgtacg catgtaacat tatactgaaa accttgcttg agaaggtttt   3900
gggacgctcg aaggagctcc aattcgccct atagtgagtc gtattacaat tcactggccg   3960
tcgttttaca acgtcgtgac tgggaaaacc ctggcgttac ccaacttaat cgccttgcag   4020
cacatccccc cttcgccagc tggcgtaata gcgaagaggc ccgcaccgat cgcccttccc   4080
aacagttgcg cagcctgaat ggcgaatggc gcgacgcgcc ctgtagcggc gcattaagcg   4140
cggcgggtgt ggtggttacg cgcagcgtga ccgctacact tgccagcgcc ctagcgcccg   4200
ctcctttcgc tttcttccct tcctttctcg ccacgttcgc cggctttccc cgtcaagctc   4260
taaatcgggg gctcccttta gggttccgat ttagtgcttt acggcacctc gaccccaaaa   4320
aacttgatta gggtgatggt tcacgtagtg ggccatcgcc ctgatagacg gtttttcgcc   4380
ctttgacgtt ggagtccacg ttctttaata gtggactctt gttccaaact ggaacaacac   4440
tcaaccctat ctcggtctat tcttttgatt tataagggat tttgccgatt tcggcctatt   4500
ggttaaaaaa tgagctgatt taacaaaaat ttaacgcgaa ttttaacaaa atattaacgt   4560
ttacaatttc ctgatgcggt attttctcct tacgcatctg tgcggtattt cacaccgcag   4620
ggtaataact gatataatta aattgaagct ctaatttgtg agtttagtat acatgcattt   4680
acttataata cagtttttta gttttgctgg ccgcatcttc tcaaatatgc ttcccagcct   4740
gcttttctgt aacgttcacc ctctacctta gcatcccttc cctttgcaaa tagtcctctt   4800
ccaacaataa taatgtcaga tcctgtagag accacatcat ccacggttct atactgttga   4860
cccaatgcgt ctcccttgtc atctaaaccc acaccgggtg tcataatcaa ccaatcgtaa   4920
ccttcatctc ttccacccat gtctctttga gcaataaagc cgataacaaa atctttgtcg   4980
ctcttcgcaa tgtcaacagt acccttagta tattctccag tagataggga gcccttgcat   5040
```

```
gacaattctg ctaacatcaa aaggcctcta ggttcctttg ttacttcttc tgccgcctgc   5100
ttcaaaccgc taacaatacc tgggcccacc acaccgtgtg cattcgtaat gtctgcccat   5160
tctgctattc tgtatacacc cgcagagtac tgcaatttga ctgtattacc aatgtcagca   5220
aattttctgt cttcgaagag taaaaaattg tacttggcgg ataatgcctt tagcggctta   5280
actgtgccct ccatggaaaa atcagtcaag atatccacat gtgtttttag taaacaaatt   5340
ttgggaccta atgcttcaac taactccagt aattccttgg tggtacgaac atccaatgaa   5400
gcacacaagt ttgtttgctt ttcgtgcatg atattaaata gcttggcagc aacaggacta   5460
ggatgagtag cagcacgttc cttatatgta gctttcgaca tgatttatct tcgtttcctg   5520
caggtttttg ttctgtgcag ttgggttaag aatactgggc aatttcatgt ttcttcaaca   5580
ctacatatgc gtatatatac caatctaagt ctgtgctcct tccttcgttc ttccttctgt   5640
tcggagatta ccgaatcaaa aaaatttcaa agaaaccgaa atcaaaaaaa agaataaaaa   5700
aaaaatgatg aattgaattg aaaagcgtgg tgcactctca gtacaatctg ctctgatgcc   5760
gcatagttaa gccagccccg acacccgcca acacccgctg acgcgccctg acgggcttgt   5820
ctgctcccgg catccgctta cagacaagct gtgaccgtct ccgggagctg catgtgtcag   5880
aggttttcac cgtcatcacc gaaacgcgcg agacgaaagg gcctcgtgat acgcctattt   5940
ttataggtta atgtcatgat aataatggtt tcttaggacg gatcgcttgc ctgtaactta   6000
cacgcgcctc gtatctttta atgatggaat aatttgggaa tttactctgt gtttatttat   6060
ttttatgttt tgtatttgga ttttagaaag taaataaaga aggtagaaga gttacggaat   6120
gaagaaaaaa aaataaacaa aggtttaaaa aatttcaaca aaaagcgtac tttacatata   6180
tatttattag acaagaaaag cagattaaat agatatacat tcgattaacg ataagtaaaa   6240
tgtaaaatca caggattttc gtgtgtggtc ttctacacag acaagatgaa acaattcggc   6300
attaatacct gagagcagga agagcaagat aaaaggtagt atttgttggc gatcccccta   6360
gagtctttta catcttcgga aaacaaaaac tatttttttct ttaatttctt tttttacttt   6420
ctatttttaa tttatatatt tatattaaaa aatttaaatt ataattattt ttatagcacg   6480
tgatgaaaag gacccaggtg gcacttttcg gggaaatgtg cgcggaaccc ctatttgttt   6540
atttttctaa atacattcaa atatgtatcc gctcatgaga caataaccct gataaatgct   6600
tcaataatat tgaaaaagga agagtatgag tattcaacat ttccgtgtcg cccttattcc   6660
cttttttgcg gcattttgcc ttcctgtttt tgctcaccca gaaacgctgg tgaaagtaaa   6720
agatgctgaa gatcagttgg gtgcacgagt gggttacatc gaactggatc tcaacagcgg   6780
taagatcctt gagagttttc gccccgaaga acgttttcca atgatgagca cttttaaagt   6840
tctgctatgt ggcgcggtat tatcccgtat tgacgccggg caagagcaac tcggtcgccg   6900
catacactat tctcagaatg acttggttga gtactcacca gtcacagaaa agcatcttac   6960
ggatggcatg acagtaagag aattatgcag tgctgccata accatgagtg ataacactgc   7020
ggccaactta cttctgacaa cgatcggagg accgaaggag ctaaccgctt ttttcacaa    7080
catgggggat catgtaactc gccttgatcg ttgggaaccg gagctgaatg aagccatacc   7140
aaacgacgag cgtgacacca cgatgcctgt agcaatggca acaacgttgc gcaaactatt   7200
aactggcgaa ctacttactc tagcttcccg gcaacaatta atagactgga tggaggcgga   7260
taaagttgca ggaccacttc tgcgctcggc ccttccggct ggctggttta ttgctgataa   7320
atctggagcc ggtgagcgtg ggtctcgcgg tatcattgca gcactggggc cagatggtaa   7380
```

```
gccctcccgt atcgtagtta tctacacgac gggcagtcag gcaactatgg atgaacgaaa   7440

tagacagatc gctgagatag gtgcctcact gattaagcat tggtaactgt cagaccaagt   7500

ttactcatat atactttaga ttgatttaaa acttcatttt taatttaaaa ggatctaggt   7560

gaagatcctt tttgataatc tcatgaccaa aatcccttaa cgtgagtttt cgttccactg   7620

agcgtcagac cccgtagaaa agatcaaagg atcttcttga gatccttttt ttctgcgcgt   7680

aatctgctgc ttgcaaacaa aaaaaccacc gctaccagcg gtggtttgtt tgccggatca   7740

agagctacca actctttttc cgaaggtaac tggcttcagc agagcgcaga taccaaatac   7800

tgtccttcta gtgtagccgt agttaggcca ccacttcaag aactctgtag caccgcctac   7860

atacctcgct ctgctaatcc tgttaccagt ggctgctgcc agtggcgata agtcgtgtct   7920

taccgggttg gactcaagac gatagttacc ggataaggcg cagcggtcgg gctgaacggg   7980

gggttcgtgc acacagccca gcttggagcg aacgacctac accgaactga gatacctaca   8040

gcgtgagcat tgagaaagcg ccacgcttcc cgaagggaga aaggcggaca ggtatccggt   8100

aagcggcagg gtcggaacag gagagcgcac gagggagctt ccagggggga acgcctggta   8160

tctttatagt cctgtcgggt ttcgccacct ctgacttgag cgtcgatttt tgtgatgctc   8220

gtcagggggg ccgagcctat ggaaaaacgc cagcaacgcg gcctttttac ggttcctggc   8280

cttttgctgg ccttttgctc acatgttctt tcctgcgtta tcccctgatt ctgtggataa   8340

ccgtattacc gcctttgagt gagctgatac cgctcgccgc agccgaacga ccgagcgcag   8400

cgagtcagtg agcgaggaag cggaagagcg cccaatacgc aaaccgcctc tccccgcgcg   8460

ttggccgatt cattaatgca gctggcacga caggtttccc gactggaaag cgggcagtga   8520

gcgcaacgca attaatgtga gttacctcac tcattaggca ccccaggctt tacactttat   8580

gcttccggct cctatgttgt gtggaattgt gagcggataa caatttcaca caggaaacag   8640

ctatgaccat gattacgcca agctcggaat taaccctcac taaagggaac aaaagctggg   8700

taccgggccc cccctcgag                                                8719
```

```
<210> SEQ ID NO 10
<211> LENGTH: 8086
<212> TYPE: DNA
<213> ORGANISM: Artificial Sequence
<220> FEATURE:
<223> OTHER INFORMATION: Sequence put together from multiple organisms:
      Saccharomyces cerevisiae and Saccharomyces mikatae

<400> SEQUENCE: 10

ccgggaaacc atccacttca cgagactgat ctcctctgcc ggaacaccgg gcatctccaa     60

cttataagtt ggagaaataa gagaatttca gattgagaga atgaaaaaaa aaaaaaaaga    120

cagaggagag cataaaaatg ggttcactt tttggtaaag ctatagcatg cctatcacat    180

ataaatagag tgccagtagc gacttttttc acactcgaaa tactcttact actgctctct    240

tgttgttttt atcacttctt gtttcttctt ggtaaataga atatcaagct acaaaaagca    300

tacctcgagg ccagaaaaag gaagtgtttc cctccttctt gaattgatgt taccctcata    360

aagcacgtgg cctcttatcg agaaagaaat taccgtcgct cgtgatttgt ttgcaaaaag    420

aacaaaactg aaaaaaccca gacacgctcg acttcctgtc ttcctgttga ttgcagcttc    480

caatttcgtc acacaacaag gtcctagcga cggctcacag gttttgtaac aagcaatcga    540

aggttctgga atggcgggaa agggtttagt accacatgct atgatgccca ctgtgatctc    600

cagagcaaag ttcgttcgat cgtactgtta ctctctctct ttcaaacaga attgtccgaa    660
```

-continued

```
tcgtgtgaca acaacagcct gttctcacac actcttttct tctaaccaag gggtggttt     720
agtttagtag aacctcgtga aacttacatt tacatatata taaacttgca taaattggtc    780
aatgcaagaa atacatattt ggtcttttct aattcgtagt ttttcaagtt cttagatgct    840
ttctttttct ctttttaca gatcatcaag gaagtaatta tctacttttt acaagtctag     900
aatgactatc tcttctgctc acccagaaac tgaaccaaag tggtggaaag aggcaacttt    960
ttaccaaatc tacccagctt cattcaagga ctccaatgat gatggttggg gtgatatgaa   1020
aggtattgct tccaaattag aatacattaa ggaattaggt gccgatgcta tttggatttc   1080
tccattctat gattctccac aagacgatat gggttatgac atcgctaact atgaaaaggt   1140
ttggccaacc tatggcacta atgaggactg ttttgcatta attgagaaaa cccacaagtt   1200
gggcatgaag ttcattactg atcttgtcat taatcattgt tcatccgaac atgaatggtt   1260
caaggaatcc agatcctcca aaactaatcc aaaaagagat tggtttttct ggagaccacc   1320
taagggttat gatgctgaag gtaagccaat tccaccaaac aattggaagt cttactttgg   1380
tggttccgca tggaccttcg acgaaaagac ccaagagttt tacttgagat tattctgctc   1440
cacccaacca gatttgaact gggaaaatga agattgtaga aaagcaatct acgaatctgc   1500
agttggctat tggttagatc acggtgttga tggtttcaga attgatgttg gttcacttta   1560
ctcaaaggtt gttggtttgc cagatgcacc agttgttgat aaaaactcta catggcaatc   1620
ttctgaccca tacactctta atggtcctag aatccatgaa tttcatcaag agatgaacca   1680
gttcattaga aatagagtta aggatggtag agaaattatg accgttggtg aaatgcaaca   1740
tgcatctgat gaaactaaga gattatacac atcagcctcc cgtcacgaat tgtctgaatt   1800
attcaacttt tcacacacag acgttggcac atccccatta ttccgttata acttggttcc   1860
attcgaattg aaggactgga aaatcgcatt ggcagaattg tttagatata tcaatggtac   1920
tgattgttgg tctaccatct acttggaaaa ccacgaccaa ccaagatcca tcactagatt   1980
cggtgatgac tctcctaaaa accgtgtcat ttctggtaag ttactttctg tcttattatc   2040
cgccttaacc ggtactttgt acgtctatca aggccaggaa ttgggtcaaa ttaactttaa   2100
gaattggcca gtcgaaaagt atgaagatgt cgaaatcaga aacaactaca atgcaattaa   2160
ggaggaacat ggtgaaaatt cagaggaaat gaaaaagttt ttggaagcta ttgctcttat   2220
ttccagagat cacgctagaa ccccaatgca atggtcaaga gaggaaccta acgctggttt   2280
ctctggtcct tccgccaagc cttggtttta cttaaacgac tccttcagag aaggtattaa   2340
cgttgaagat gaaattaagg acccaaattc cgtccttaac ttctggaagg aagcattgaa   2400
gtttagaaag gcccataagg atattaccgt ttatggttat gactttgagt ttatcgattt   2460
ggataacaaa aagttattct cattcactaa aaagtataac aacaagacct tattcgctgc   2520
tttaaacttc tcttctgatg ctactgattt caaaattcct aatgacgatt cctctttcaa   2580
gttggagttt ggtaactacc caaagaagga agttgacgca tcttctcgta cattgaagcc   2640
ttgggaaggt agaatctaca tctccgagta acctgcaggt ttgccagctt actatccttc   2700
ttgaaaatat gcactctata tcttttagtt cttaattgca acacatagat ttgctgtata   2760
acgaatttta tgctattttt taaatttgga gttcagtgat aaaagtgtca cagcgaattt   2820
cctcacatgt agggaccgaa ttgtttacaa gttctctgta ccaccatgga gacatcaaaa   2880
attgaaaatc tatggaaaga tatggacggt agcaacaaga atatagcacg agccggcgac   2940
tagtaacggc cgccagtgtg ctggaattcg gccggccata acttcgtata atgtatgcta   3000
tacgaagtta tggcaacggt tcatcatctc atggatctgc acatgaacaa acaccagagt   3060
```

```
caaacgacgt tgaaattgag gctactgcgc caattgatga caatacagac gatgataaca   3120

aaccgaagtt atctgatgta gaaaaggatt agagatgcta agagatagtg atgatatttc   3180

ataaataatg taattctata tatgttaatt acctttttg cgaggcatat ttatggtgaa   3240

ggataagttt tgaccatcaa agaaggttaa tgtggctgtg gtttcagggt ccataaagct   3300

tttcaattca tcttttttt tttgttcttt tttttgattc cggtttcttt gaaatttttt   3360

tgattcggta atctccgagc agaaggaaga acgaaggaag gagcacagac ttagattggt   3420

atatatacgc atatgtggtg ttgaagaaac atgaaattgc ccagtattct taacccaact   3480

gcacagaaca aaaacctgca ggaaacgaag ataaatcatg tcgaaagcta catataagga   3540

acgtgctgct actcatccta gtcctgttgc tgccaagcta tttaatatca tgcacgaaaa   3600

gcaaacaaac ttgtgtgctt cattggatgt tcgtaccacc aaggaattac tggagttagt   3660

tgaagcatta ggtcccaaaa tttgtttact aaaaacacat gtggatatct tgactgattt   3720

ttccatggag ggcacagtta agccgctaaa ggcattatcc gccaagtaca atttttact   3780

cttcgaagac agaaaatttg ctgacattgg taatacagtc aaattgcagt actctgcggg   3840

tgtatacaga atagcagaat gggcagacat tacgaatgcg cacggtgtgg tgggcccagg   3900

tattgttagc ggtttgaagc aggcggcgga agaagtaaca aaggaaccta gaggcctttt   3960

gatgttagca gaattgtcat gcaagggctc cctagctact ggagaatata ctaagggtac   4020

tgttgacatt gcgaagagcg acaaagattt tgttatcggc tttattgctc aaagagacat   4080

gggtggaaga gatgaaggtt acgattggtt gattatgaca cccggtgtgg gtttagatga   4140

caagggagac gcattgggtc aacagtatag agccgtggat gatgtggtct ctacaggatc   4200

tgacattatt attgttggaa gaggactatt tgcaaaggga agggatgcta aggtagaggg   4260

tgaacgttac agaaaagcag gctgggaagc atatttgaga agatgcggcc agcaaaacta   4320

aaaaactgta ttataagtaa atgcatgtat actaaactca caaattagag cttcaattta   4380

attatatcag ttattacccg ggaatctcgg tcgtaatgat tttataatg acgaaaaaaa   4440

aaaattggaa agaaaaagct tcatggcctt tataaaaagg aaccatccaa tacctcgcca   4500

gaaccaagta acagtatttt acggggcaca aatcaagaac aataagacag gactgtaaag   4560

atggacgcat tgaactccaa agaacaacaa gagttccaaa aagtagtgga acaaaagcaa   4620

atgaaggatt tcatgcgttt gataacttcg tataatgtat gctatacgaa gttatgcggc   4680

cgcctcgaga tctcccctaa accgtggaat atttcggata tccttttgtt gtttccgggt   4740

gtacaatatg gacttcctct tttctggcaa ccaaacccat acatcgggat tcctataata   4800

ccttcgttgg tctccctaac atgtaggtgg cggaggggag atatacaata gaacagatac   4860

cagacaagac ataatgggct aaacaagact acaccaatta cactgcctca ttgatggtgg   4920

tacataacga actaatactg tagccctaga cttgatagcc atcatcatat cgaagtttca   4980

ctacccttt tccatttgcc atctattgaa gtaataatag gcgcatgcaa cttcttttct   5040

tttttttct tttctctctc ccccgttgtt gtctcaccat atccgcaatg acaaaaaaat   5100

gatggaagac actaaaggaa aaaattaacg acaaagacag caccaacaga tgtcgttgtt   5160

ccagagctga tggggggtat ctcgaagcac acgaaacttt ttccttcctt cattcacgca   5220

cactactctc taatgagcaa cggtatacgg ccttccttcc agttacttga atttgaaata   5280

aaaaaagttt gctgtcttgc tatcaagtat aaatagacct gcaattatta atcttttgtt   5340

tcctcgtcat tgttctcgtt ccctttcttc cttgtttctt tttctgcaca atatttcaag   5400
```

```
ctataccaag catacaatca actatctcat atacaatgaa gaacttcata tcactggtga   5460
acaagaaaaa gggtaccctg gatgatagga atagtagcgt tccggaatct tccagtggta   5520
taatacacca acgtggagct ttaaacactg aggattttga agaaggaaag aaagatggtg   5580
cattcgaatt gggtcacctc gaattcacca ccaattcagc ccaattgggt gattcagacg   5640
atgataatga taatgcaatt aagatagcga atgctgccac tgatgaagcc aatgaggcta   5700
atagtgaaga aaaaagcatg accttaaggc aagctttgag aaaatatcca aaggcagccc   5760
tatggtccat cttggtgtct actaccttag tcatggaagg ttatgatact gcgcttttga   5820
gtgcacttta tgcattaccg gttttccaga ggaaattcgg tactatgaat gcggaaggct   5880
cctacgaaat tacctcgcag tggcaaattg gtttgaacat gtgtgtcctt tgtggtgaaa   5940
tgattggttt acagatgacc acttacatgg tcgagttcat gggtaatcgt tacacaatga   6000
ttacggcgct cggcttgttg actgcttata tttttatcct ttactactgc aaaagtttgg   6060
ccatgatcgc tgtagggcaa attctgtctg ctatgccatg ggttgcttc cagagtctgg   6120
ctgttaccta tgcttcggag gtttgccccc tagcgctgag atattacatg accagttact   6180
ccaatatttg ttggttgttt ggtcaaattt tcgcttctgg tatcatgaaa aactcccagg   6240
agaatttggg agactccgat ttaggctaca agttgccatt tgccttacaa tggatctggc   6300
ctgcaccttt gattattggt atcttctttg ctcctgagtc gccttggtgg ctggtgagaa   6360
agaataagat tgcggaggcc aaaaagtcct tgaatagaat cctgagcggc actgctgccg   6420
agagggagat tcaagtggat atcactttaa agcaaattga gatgaccatt gagaaggaga   6480
gacttctggc atctaaatca gggtcgttct tcaactgttt caaaggcgtt gatggaagaa   6540
gaacaaggct tgcgtgtttg acttgggttg ctcaaaacag tagtggtgcc gttttactag   6600
gttactcgac gtatttcttt gaaagggcag ggatggccac tgacaaggcg tttactttct   6660
cgcttatcca gtactgtcta ggtttagcag gcactctttg ttcctgggtg atatctggcc   6720
gtgttggtag atggagtatc ctggcttatg gtcttgcatt tcaaatggtg tgtctattca   6780
tcattggtgg aatggggttt gcatccggaa gcaatgccag taatggtgct ggtggtctac   6840
tgctggcttt atcgttcttt tacaacgctg gtatcggagc tgtcgtttac tgtattgtgg   6900
ctgaaattcc gtctgcagaa ttaaggacca aaactattgt aatggctcgt atttgctata   6960
atttgatggc cgtcatcaat gccattttaa cgccatatat gctgaacgtg agtgactgga   7020
actggggtgc taaaaccggc ctatactggg gtggtttcac tgcagtcact ttggcttggg   7080
ttatcattga tttgcctgag acaactggta gaacatttag cgaaattaat gagcttttca   7140
atcaaggtgt ccctgctaga aaatttgcat ctactgtagt tgatcctttc gggaagggac   7200
agcgtcaaaa tgattcgcaa gtggataacg tcattgacca gtcctcaagc gcaatgcagc   7260
aagagctaaa tgaagctaac gaattctaat taattaaaca ggcccctttt cctttgtcga   7320
tatcatgtaa ttagttatgt cacgcttaca ttcacgccct cctcccacat ccgctctaac   7380
cgaaaaggaa ggagttagac aacctgaagt ctaggtccct atttattttt ttatagttat   7440
gttagtatta agaacgttat ttatatttca aatttttctt ttttttctgt acaaacgcgt   7500
gtacgcatgt aacgggcaga cgaattcgat atcaagctta tcgataccgt cgacgcggat   7560
ctcttatgtc tttacgattt atagttttca ttatcaagta tgcctatatt agtatatagc   7620
atctttagat gacagtgttc gaagtttcac gaataaaaga taatattcta ctttttgctc   7680
ccaccgcgtt tgctagcacg agtgaacacc atccctcgcc tgtgagttgt acccattcct   7740
ctaaactgta gacatggtag cttcagcagt gttcgttatg tacggcatcc tccaacaaac   7800
```

```
agtcggttat agtttgtcct gctcctctga atcgtctccc tcgatatttc tcattttcct   7860

tcgcatgcca gcattgaaat gatcgaagtt caatgatgaa acggtaattc ttctgtcatt   7920

tactcatctc atctcatcaa gttatataat tctatacgga tgtaattttt cacttttcgt   7980

cttgacgtcc accctataat ttcaattatt gaaccctcac aaatgatgca ctgcaatgta   8040

cacaccctca tatagtttct cagggcttga tcagggttcc gtagag                  8086


<210> SEQ ID NO 11
<211> LENGTH: 8685
<212> TYPE: DNA
<213> ORGANISM: Artificial Sequence
<220> FEATURE:
<223> OTHER INFORMATION: Sequence put together from multiple organisms:
      Saccharomyces cerevisiae,  Saccharomyces mikatae, and Aspergillus
      nidulans

<400> SEQUENCE: 11

ccgggaaacc atccacttca cgagactgat ctcctctgcc ggaacaccgg gcatctccaa     60

cttataagtt ggagaaataa gagaatttca gattgagaga atgaaaaaaa aaaaaaaaga    120

cagaggagag cataaaaatg gggttcactt tttggtaaag ctatagcatg cctatcacat    180

ataaatagag tgccagtagc gactttttc acactcgaaa tactcttact actgctctct     240

tgttgttttt atcacttctt gtttcttctt ggtaaataga atatcaagct acaaaaagca    300

tacctcgagg ccagaaaaag gaagtgtttc cctccttctt gaattgatgt taccctcata    360

aagcacgtgg cctcttatcg agaaagaaat taccgtcgct cgtgatttgt ttgcaaaaag    420

aacaaaactg aaaaaaccca gacacgctcg acttcctgtc ttcctgttga ttgcagcttc    480

caatttcgtc acacaacaag gtcctagcga cggctcacag gttttgtaac aagcaatcga    540

aggttctgga atggcgggaa agggtttagt accacatgct atgatgccca ctgtgatctc    600

cagagcaaag ttcgttcgat cgtactgtta ctctctctct ttcaaacaga attgtccgaa    660

tcgtgtgaca acaacagcct gttctcacac actcttttct tctaaccaag gggtggttt     720

agtttagtag aacctcgtga aacttacatt tacatatata taaacttgca taaattggtc    780

aatgcaagaa atacatattt ggtcttttct aattcgtagt ttttcaagtt cttagatgct    840

ttctttttct ctttttaca gatcatcaag gaagtaatta tctactttt acaagtctag      900

aatgactatc tcttctgctc acccagaaac tgaaccaaag tggtggaaag aggcaacttt    960

ttaccaaatc tacccagctt cattcaagga ctccaatgat gatggttggg gtgatatgaa   1020

aggtattgct tccaaattag aatacattaa ggaattaggt gccgatgcta tttggatttc   1080

tccattctat gattctccac aagacgatat gggttatgac atcgctaact atgaaaaggt   1140

ttggccaacc tatggcacta atgaggactg ttttgcatta attgagaaaa cccacaagtt   1200

gggcatgaag ttcattactg atcttgtcat taatcattgt tcatccgaac atgaatggtt   1260

caaggaatcc agatcctcca aaactaatcc aaaaagagat tggtttttct ggagaccacc   1320

taagggttat gatgctgaag gtaagccaat tccaccaaac aattggaagt cttactttgg   1380

tggttccgca tggaccttcg acgaaaagac ccaagagttt tacttgagat tattctgctc   1440

cacccaacca gatttgaact gggaaaatga agattgtaga aaagcaatct acgaatctgc   1500

agttggctat tggttagatc acggtgttga tggtttcaga attgatgttg gttcacttta   1560

ctcaaaggtt gttggtttgc cagatgcacc agttgttgat aaaaactcta catggcaatc   1620

ttctgaccca tacactctta atggtcctag aatccatgaa tttcatcaag agatgaacca   1680
```

-continued gttcattaga aatagagtta aggatggtag agaaattatg accgttggtg aaatgcaaca 1740
tgcatctgat gaaactaaga gattatacac atcagcctcc cgtcacgaat tgtctgaatt 1800
attcaacttt tcacacacag acgttggcac atccccatta ttccgttata acttggttcc 1860
attcgaattg aaggactgga aaatcgcatt ggcagaattg tttagatata tcaatggtac 1920
tgattgttgg tctaccatct acttggaaaa ccacgaccaa ccaagatcca tcactagatt 1980
cggtgatgac tctcctaaaa accgtgtcat ttctggtaag ttactttctg tcttattatc 2040
cgccttaacc ggtactttgt acgtctatca aggccaggaa ttgggtcaaa ttaactttaa 2100
gaattggcca gtcgaaaagt atgaagatgt cgaaatcaga aacaactaca atgcaattaa 2160
ggaggaacat ggtgaaaatt cagaggaaat gaaaaagttt ttggaagcta ttgctcttat 2220
ttccagagat cacgctagaa ccccaatgca atggtcaaga gaggaaccta acgctggttt 2280
ctctggtcct tccgccaagc cttggtttta cttaaacgac tccttcagag aaggtattaa 2340
cgttgaagat gaaattaagg acccaaattc cgtccttaac ttctggaagg aagcattgaa 2400
gtttagaaag gcccataagg atattaccgt ttatggttat gactttgagt ttatcgattt 2460
ggataacaaa aagttattct cattcactaa aaagtataac aacaagacct tattcgctgc 2520
tttaaacttc tcttctgatg ctactgattt caaaattcct aatgacgatt cctctttcaa 2580
gttggagttt ggtaactacc caaagaagga agttgacgca tcttctcgta cattgaagcc 2640
ttgggaaggt agaatctaca tctccgagta acctgcaggt ttgccagctt actatccttc 2700
ttgaaaatat gcactctata tcttttagtt cttaattgca acacatagat ttgctgtata 2760
acgaatttta tgctattttt taaatttgga gttcagtgat aaaagtgtca cagcgaattt 2820
cctcacatgt agggaccgaa ttgtttacaa gttctctgta ccaccatgga gacatcaaaa 2880
attgaaaatc tatggaaaga tatggacggt agcaacaaga atatagcacg agccggcgac 2940
tagtaacggc cgccagtgtg ctggaattcg gccggccagg ccgcataact tcgtatagca 3000
tacattatac gaagttatcg cctgttaaga tataactgaa aaaagagggg aatttttaga 3060
tactgaaatg atattttaga ataaccagac tatatataag gataaattac aaaaaattaa 3120
ctaatagata agatttaaat ataaaagata tgcaactaga aaagtcttat caatctcctt 3180
atggagtgac gacgttaccc aacaatttac cgacttcttc ggcgatagcc aaagttctct 3240
cttcggacaa tcttctacca ataacttgaa cagcaacagg agcaccgtga taagcctctg 3300
ggtcgtattc ttcttgaacc aaagcatcca attcggaaac agctttaaaa gattcgttct 3360
tcttatcaat attcttatca gcgaaagtga ctgggacgac aacagaggtg aaatccaata 3420
agttaataac ggaggcgtaa ccgtagtatc tgaattgatc gtgtctgaca gcggcggtag 3480
gagtaattgg agcgataata gcgtccaatt ccttaccagc tttttcttca gcttcacgcc 3540
acttttccaa gtattccatt tgatagttcc acttttgtaa atgagtgtcc cacaattcgt 3600
tcatgttaac agccttaata tttgggttca acaagtcctt aatgttaggg atggctggct 3660
caccagaggc agaaatgtct ctcatgacgt cggcagaacc atcagcagca tagatgtggg 3720
aaatcaagtc atgaccgaaa tcatgcttgt atggagtcca tggagtaacg gtgtgaccag 3780
ccttggccaa agcggcaacg gtagtttcga caccacgtaa aattggtggg tgtggcaaga 3840
cgttaccgtc gaaattgtaa taaccaatgt tcaaaccacc attcttaatc ttagaggcaa 3900
tgatgtcaga ttcagattgt ctccatggca ttgggatgac cttagagtcg tacttccaag 3960
gttcttgacc caagacagat ttggtgaaca atctcaagtc ttcgacggag tgagtgatag 4020
gaccaacgac ggagtgaacg gtttcttgac cttccataga gttagccatt ttagcatatg 4080

-continued

```
gcaatctacc gtgagatggt ctcaaaccgt ataaaaagtt gaaagcagct gggactctaa   4140
tggaaccacc aatgtcagta ccgacaccaa taacaccacc tctaatacca acaatagcac   4200
cttcaccacc agaagaacca ccacaggacc aatttttgtt tcttggattg acagttctac   4260
caatgatgtt gttgacggtt tcacagacca tcaaggtttg tgggacagag gtcttaacgt   4320
agaaaacagc accagctttt ctcaacatgg tggttaagac ggaatcacct tcatcgtatt   4380
tgtttaacca ggaaatgtaa cccatggagg tttcgtaacc cttaacacgc aattggtcct   4440
ttaaagagat tggtaaaccg tgtaatggac caactggtct cttatgctta gcgtagtatt   4500
catctaattc tctagcttga gctaaagcag catctgggaa gaattcgtga gcacagttgg   4560
ttaattgttg agcaatagca gctctcttac aaaaagccaa agtgacttca acagaagtca   4620
actcaccagc ggccaacttg gagaccaaat cagcagcaga ggcttcggta atcttcaatt   4680
cagcctcaga caaaataccg gacttctttg ggaaatcaat aacggaatct tcggcaggca   4740
aagtttgaac cttccattcg tcaggaatgg ttttagccaa acgggcacgt ttgtcggcgg   4800
ccaattcttc ccaggattgt ggcattttgt aattaaaact tagattagat tgctatgctt   4860
tctttctaat gagcaagaag taaaaaaagt tgtaatagaa caagaaaaac gaaactgaaa   4920
cttgagaaat tgaagaccat ttattaactt aaatatcaat gggaggtcat cgaaagagaa   4980
aaaaatcaaa aaaaaaattt ttcaagaaaa agaaacgtga taaaaatttt tattgccttt   5040
ttcgacgaag aaaaagaaac gaggcggtct ctttttttctt ttccaaacct ttagtacggg   5100
taattaacgc caccctagag gaagaaagag gggaaattta gtatgctgtg cttgggtgtt   5160
ttgaagtggt acggcgatgc gcggagtccg agaaaatctg gaagagtaaa aaaggagtag   5220
aaacattttg aagctatggt gtgtggggga tcacttgtgg gggattgggt gtgatgtaag   5280
gataacttcg tatagcatac attatacgaa gttatgcggc cgcgtctgcc cgttacatgc   5340
gtacacgcgt ttgtacagaa aaaaaagaaa aatttgaaat ataaataacg ttcttaatac   5400
taacataact ataaaaaaat aaatagggac ctagacttca ggttgtctaa ctccttcctt   5460
ttcggttaga gcggatgtgg gaggagggcg tgaatgtaag cgtgacataa ctaattacat   5520
gatatcgaca aaggaaaagg ggcctgttta attaattaga attcgttagc ttcatttagc   5580
tcttgctgca ttgcgcttga ggactggtca atgacgttat ccacttgcga atcattttga   5640
cgctgtccct tcccgaaagg atcaactaca gtagatgcaa attttctagc agggacacct   5700
tgattgaaaa gctcattaat ttcgctaaat gttctaccag ttgtctcagg caaatcaatg   5760
ataacccaag ccaaagtgac tgcagtgaaa ccaccccagt ataggccggt tttagcaccc   5820
cagttccagt cactcacgtt cagcatatat ggcgttaaaa tggcattgat gacggccatc   5880
aaattatagc aaatacgagc cattacaata gttttggtcc ttaattctgc agacggaatt   5940
tcagccacaa tacagtaaac gacagctccg ataccagcgt tgtaaaagaa cgataaagcc   6000
agcagtagac caccagcacc attactggca ttgcttccgg atgcaaaccc cattccacca   6060
atgatgaata gacacaccat ttgaaatgca agaccataag ccaggatact ccatctacca   6120
acacggccag atatcaccca ggaacaaaga gtgcctgcta aacctagaca gtactggata   6180
agcgagaaag taaacgcctt gtcagtggcc atccctgccc tttcaaagaa atacgtcgag   6240
taacctagta aaacggcacc actactgttt tgagcaaccc aagtcaaaca cgcaagcctt   6300
gttcttcttc catcaacgcc tttgaaacag ttgaagaacg accctgattt agatgccaga   6360
agtctctcct tctcaatggt catctcaatt tgctttaaag tgatatccac ttgaatctcc   6420
```

-continued

```
ctctcggcag cagtgccgct caggattcta ttcaaggact ttttggcctc cgcaatctta   6480
ttctttctca ccagccacca aggcgactca ggagcaaaga agataccaat aatcaaaggt   6540
gcaggccaga tccattgtaa ggcaaatggc aacttgtagc ctaaatcgga gtctcccaaa   6600
ttctcctggg agtttttcat gataccagaa gcgaaaattt gaccaaacaa ccaacaaata   6660
ttggagtaac tggtcatgta atatctcagc gctagggggc aaacctccga agcataggta   6720
acagccagac tctggaagca accccatggc atagcagaca gaatttgccc tacagcgatc   6780
atggccaaac ttttgcagta gtaaaggata aaaatataag cagtcaacaa gccgagcgcc   6840
gtaatcattg tgtaacgatt acccatgaac tcgaccatgt aagtggtcat ctgtaaacca   6900
atcatttcac cacaaaggac acacatgttc aaaccaattt gccactgcga ggtaatttcg   6960
taggagcctt ccgcattcat agtaccgaat ttcctctgga aaaccggtaa tgcataaagt   7020
gcactcaaaa gcgcagtatc ataaccttcc atgactaagg tagtagacac caagatggac   7080
catagggctg cctttggata ttttctcaaa gcttgcctta aggtcatgct tttttcttca   7140
ctattagcct cattggcttc atcagtggca gcattcgcta tcttaattgc attatcatta   7200
tcatcgtctg aatcacccaa ttgggctgaa ttggtggtga attcgaggtg acccaattcg   7260
aatgcaccat ctttctttcc ttcttcaaaa tcctcagtgt ttaaagctcc acgttggtgt   7320
attataccac tggaagattc cggaacgcta ctattcctat catccagggt accctttttc   7380
ttgttcacca gtgatatgaa gttcttcatt gtatatgaga tagttgattg tatgcttggt   7440
atagcttgaa atattgtgca gaaaaagaaa caaggaagaa agggaacgag aacaatgacg   7500
aggaaacaaa agattaataa ttgcaggtct atttatactt gatagcaaga cagcaaactt   7560
tttttatttc aaattcaagt aactggaagg aaggccgtat accgttgctc attagagagt   7620
agtgtgcgtg aatgaaggaa ggaaaaagtt tcgtgtgctt cgagataccc cccatcagct   7680
ctggaacaac gacatctgtt ggtgctgtct ttgtcgttaa ttttttcctt tagtgtcttc   7740
catcattttt ttgtcattgc ggatatggtg agacaacaac gggggagaga gaaaagaaaa   7800
aaaaagaaaa gaagttgcat gcgcctatta ttacttcaat agatggcaaa tggaaaaagg   7860
gtagtgaaac ttcgatatga tgatggctat caagtctagg gctacagtat tagttcgtta   7920
tgtaccacca tcaatgaggc agtgtaattg gtgtagtctt gtttagccca ttatgtcttg   7980
tctggtatct gttctattgt atatctcccc tccgccacct acatgttagg gagaccaacg   8040
aaggtattat aggaatcccg atgtatgggt ttggttgcca gaaaagagga agtccatatt   8100
gtacacccgg aaacaacaaa aggatatccg aaatattcca cggtttaggt cgacgcggat   8160
ctcttatgtc tttacgattt atagttttca ttatcaagta tgcctatatt agtgtatagc   8220
atctttagat gacagtgttc gaagtttcac gaataaaaga taatattcta ctttttgctc   8280
ccaccgcgtt tgctagcacg agtgaacacc atccctcgcc tgtgagttgt acccattcct   8340
ctaaactgta gacatggtag cttcagcagt gttcgttatg tacggcatcc tccaacaaac   8400
agtcggttat agtttgtcct gctcctctga atcgtctccc tcgatatttc tcattttcct   8460
tcgcatgcca gcattgaaat gatcgaagtt caatgatgaa acggtaattc ttctgtcatt   8520
tactcatctc atctcatcaa gttatataat tctatacgga tgtaattttt cacttttcgt   8580
cttgacgtca ccctataatt tcaattgttg aaccctcaca aatgatgcac tgcaatgtac   8640
acaccctcat atagtttctc agggcttgat cagggttccg tagag                   8685
```

<210> SEQ ID NO 12
<211> LENGTH: 1632

<212> TYPE: DNA
<213> ORGANISM: Saccharomyces cerevisiae

<400> SEQUENCE: 12
ggcaacggtt catcatctca tggatctgca catgaacaaa caccagagtc aaacgacgtt 60
gaaattgagg ctactgcgcc aattgatgac aatacagacg atgataacaa accgaagtta 120
tctgatgtag aaaaggatta gagatgctaa gagatagtga tgatatttca taaataatgt 180
aattctatat atgttaatta cctttttgc gaggcatatt tatggtgaag gataagtttt 240
gaccatcaaa gaaggttaat gtggctgtgg tttcagggtc cataaagctt ttcaattcat 300
cttttttttt tttgttcttt tttttgattc cggtttcttt gaaatttttt tgattcggta 360
atctccgagc agaaggaaga acgaaggaag gagcacagac ttagattggt atatatacgc 420
atatgtggtg ttgaagaaac atgaaattgc ccagtattct taacccaact gcacagaaca 480
aaaacctgca ggaaacgaag ataaatcatg tcgaaagcta catataagga acgtgctgct 540
actcatccta gtcctgttgc tgccaagcta tttaatatca tgcacgaaaa gcaaacaaac 600
ttgtgtgctt cattggatgt tcgtaccacc aaggaattac tggagttagt tgaagcatta 660
ggtcccaaaa tttgtttact aaaaacacat gtggatatct tgactgattt ttccatggag 720
ggcacagtta agccgctaaa ggcattatcc gccaagtaca attttttact cttcgaagac 780
agaaaatttg ctgacattgg taatacagtc aaattgcagt actctgcggg tgtatacaga 840
atagcagaat gggcagacat tacgaatgca cacggtgtgg tgggcccagg tattgttagc 900
ggtttgaagc aggcggcgga agaagtaaca aaggaaccta gaggcctttt gatgttagca 960
gaattgtcat gcaagggctc cctagctact ggagaatata ctaagggtac tgttgacatt 1020
gcgaagagcg acaaagattt tgttatcggc tttattgctc aaagagacat gggtggaaga 1080
gatgaaggtt acgattggtt gattatgaca cccggtgtgg gtttagatga caagggagac 1140
gcattgggtc aacagtatag aaccgtggat gatgtggtct ctacaggatc tgacattatt 1200
attgttggaa gaggactatt tgcaaaggga agggatgcta aggtagaggg tgaacgttac 1260
agaaaagcag gctgggaagc atatttgaga agatgcggcc agcaaaacta aaaaactgta 1320
ttataagtaa atgcatgtat actaaactca caaattagag cttcaattta attatatcag 1380
ttattacccg ggaatctcgg tcgtaatgat tttataatg acgaaaaaaa aaaaaattgga 1440 aagaaaaagc ttcatggcct ttataaaaag gaaccatcca atacctcgcc agaaccaagt 1500
aacagtattt tacggggcac aaatcaagaa caataagaca ggactgtaaa gatggacgca 1560
ttgaactcca aagaacaaca agagttccaa aaagtagtgg aacaaaagca aatgaaggat 1620
ttcatgcgtt tg 1632

<210> SEQ ID NO 13
<211> LENGTH: 4701
<212> TYPE: DNA
<213> ORGANISM: Saccharomyces cerevisiae

<400> SEQUENCE: 13
tcctattcgg agatacaggc aacaagtgat agagggccca ttatgaatac gcacctctat 60
gtatttccga gatacgatta ctccagttcc tcttacaaga aatgcataaa aatagttaca 120
attaattaga acaagaactt atttagaaca cgttcacact gagtaagaac tcttgtccct 180
tattagcctt gatagtgctg aaaaaaagaa aaaaaacaaa aaaaagaaat aaaataacgg 240
caaacagcaa aggccacaga accgtattca tgttacttct gcaatatcaa tcacttactg 300

```
gcaagtgcgt ataaattaaa cctatttctt tatcatcata tttacttata tctttaacag    360
attccaaacc ctaaagtgtc cgaattttca atagggcgaa cttgaagaat aaccaaggtc    420
aataatatat cttttagtat aaccctgaaa tttgccctat agaaatctag ggtttctgtg    480
tggtttccgg gtgagtcata cggctttttt gaatttcttt ttttgcagtt gtctctatca    540
atgaaaattt cgaggaagac gataaggtta agataagtag ataagagaat gatacgagat    600
aaagcacaaa ttagcagaaa gaagagtggt tgcgaacaga gtaaaccgaa tcagggaatc    660
ccttttgca aaaacatcaa ttatcctttt cttttttta cgtatatatc tggaacagaa    720
atatataagt tactattata cttatagttg gatccagttt ttaatctgtc gtcaatcgaa    780
agtttatttc agagttcttc agacttctta actcctgtaa aaacaaaaaa aaaaaaaggc    840
atagcactcg agatctcccg agtttatcat tatcaatact gccatttcaa agaatacgta    900
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat ttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgctaaaat acaaaccttt   1560
actaaaaatc tcgaagaact gtgaggctgc tatcctcaga gcgtctaaga ctagattgaa   1620
cacaatccgc gcgtacggtt ctaccgttcc aaaatccaag tcgttcgaac aagactcaag   1680
aaaacgcaca cagtcatgga ctgccttgag agtcggtgca attctagccg ctactagttc   1740
cgtggcgtat ctaaactggc ataatggcca aatagacaac gagccgaaac tggatatgaa   1800
taaacaaaag atttcgcccg ctgaagttgc caagcataac aagcccgatg attgttgggt   1860
tgtgatcaat ggttacgtat acgacttaac gcgattccta ccaaatcatc caggtgggca   1920
ggatgttatc aagtttaacg ccgggaaaga tgtcactgct atttttgaac cactacatgc   1980
tcctaatgtc atcgataagt atatagctcc cgagaaaaaa ttgggtcccc ttcaaggatc   2040
catgcctcct gaacttgtct gtcctcctta tgctcctggt gaaactaagg aagatatcgc   2100
tagaaaagaa caactaaaat cgctgctacc tcctctagat aatattatta acctttacga   2160
ctttgaatac ttggcctctc aaactttgac taaacaagcg tgggcctact attcctccgg   2220
tgctaacgac gaagttactc acagagaaaa ccataatgct tatcatagga tttttttcaa   2280
accaaagatc cttgtagatg tacgcaaagt agacatttca actgacatgt tgggttctca   2340
tgtggatgtt cccttctacg tgtctgctac agctttgtgt aaactgggaa acccccttaga   2400
aggtgaaaaa gatgtcgcca gaggttgtgg ccaaggtgtg acaaaagtcc cacaaatgat   2460
atctactttg gcttcatgtt cccctgagga aattattgaa gcagcaccct ctgataaaca   2520
aattcaatgg taccaactat atgttaactc tgatagaaag atcactgatg atttggttaa   2580
aaatgtagaa aagctgggtg taaaggcatt atttgtcact gtggatgctc caagtttagg   2640
tcaaagagaa aaagatatga agctgaaatt ttccaataca aaggctggtc caaaagcgat   2700
```

gaagaaaact aatgtagaag aatctcaagg tgcttcgaga gcgttatcaa agtttattga 2760
cccctctttg acttggaaag atatagaaga gttgaagaaa aagacaaaac tacctattgt 2820
tatcaaaggt gttcaacgta ccgaagatgt tatcaaagca gcagaaatcg gtgtaagtgg 2880
ggtggttcta tccaatcatg gtggtagaca attagatttt tcaagggctc ccattgaagt 2940
cctggctgaa accatgccaa tcctggaaca acgtaacttg aaggataagt tggaagtttt 3000
cgtggacggt ggtgttcgtc gtggtacaga tgtcttgaaa gcgttatgtc taggtgctaa 3060
aggtgttggt ttgggtagac cattcttgta tgcgaactca tgctatggtc gtaatggtgt 3120
tgaaaaagcc attgaaattt taagagatga aattgaaatg tctatgagac tattaggtgt 3180
tactagcatt gcggaattga agcctgatct tttagatcta tcaacactaa aggcaagaac 3240
agttggagta ccaaacgacg tgctgtataa tgaagtttat gagggaccta ctttaacaga 3300
atttgaggat gcatgattaa ttaaacaggc cccttttcct ttgtcgatat catgtaatta 3360
gttatgtcac gcttacattc acgccctcct cccacatccg ctctaaccga aaaggaagga 3420
gttagacaac ctgaagtcta ggtccctatt tattttttta tagttatgtt agtattaaga 3480
acgttattta tatttcaaat ttttcttttt tttctgtaca aacgcgtgta cgcatgtaac 3540
gggcagacgg ccggccataa cttcgtataa tgtatgctat acgaagttat ggcaacggtt 3600
catcatctca tggatctgca catgaacaaa caccagagtc aaacgacgtt gaaattgagg 3660
ctactgcgcc aattgatgac aatacagacg atgataacaa accgaagtta tctgatgtag 3720
aaaaggatta gagatgctaa gagatagtga tgatatttca taaataatgt aattctatat 3780
atgttaatta cctttttttgc gaggcatatt tatggtgaag gataagtttt gaccatcaaa 3840
gaaggttaat gtggctgtgg tttcagggtc cataaagctt ttcaattcat cttttttttt 3900
tttgttcttt tttttgattc cggtttcttt gaaatttttt tgattcggta atctccgagc 3960
agaaggaaga acgaaggaag gagcacagac ttagattggt atatatacgc atatgtggtg 4020
ttgaagaaac atgaaattgc ccagtattct taacccaact gcacagaaca aaaacctgca 4080
ggaaacgaag ataaatcatg tcgaaagcta catataagga acgtgctgct actcatccta 4140
gtcctgttgc tgccaagcta tttaatatca tgcacgaaaa gcaaacaaac ttgtgtgctt 4200
cattggatgt tcgtaccacc aaggaattac tggagttagt tgaagcatta ggtcccaaaa 4260
tttgtttact aaaaacacat gtggatatct tgactgattt ttccatggag ggcacagtta 4320
agccgctaaa ggcattatcc gccaagtaca atttttttact cttcgaagac agaaaatttg 4380
ctgacattgg taatacagtc aaattgcagt actctgcggg tgtatacaga atagcagaat 4440
gggcagacat tacgaatgca cacggtgtgg tgggcccagg tattgttagc ggtttgaagc 4500
aggcggcgga agaagtaaca aaggaaccta gaggcctttt gatgttagca gaattgtcat 4560
gcaagggctc cctagctact ggagaatata ctaagggtac tgttgacatt gcgaagagcg 4620
acaaagattt tgttatcggc tttattgctc aaagagacat gggtggaaga gatgaaggtt 4680
acgattggtt gattatgaca c 4701

<210> SEQ ID NO 14
<211> LENGTH: 3126
<212> TYPE: DNA
<213> ORGANISM: Saccharomyces cerevisiae

<400> SEQUENCE: 14
tccatggagg gcacagttaa gccgctaaag gcattatccg ccaagtacaa tttttttactc 60

-continued

```
ttcgaagaca gaaaatttgc tgacattggt aatacagtca aattgcagta ctctgcgggt    120
gtatacagaa tagcagaatg ggcagacatt acgaatgcac acggtgtggt gggcccaggt    180
attgttagcg gtttgaagca ggcggcggaa gaagtaacaa aggaacctag aggccttttg    240
atgttagcag aattgtcatg caagggctcc ctagctactg gagaatatac taagggtact    300
gttgacattg cgaagagcga caaagatttt gttatcggct ttattgctca aagagacatg    360
ggtggaagag atgaaggtta cgattggttg attatgacac ccggtgtggg tttagatgac    420
aagggagacg cattgggtca acagtataga accgtggatg atgtggtctc tacaggatct    480
gacattatta ttgttggaag aggactattt gcaaagggaa gggatgctaa ggtagagggt    540
gaacgttaca gaaaagcagg ctgggaagca tatttgagaa gatgcggcca gcaaaactaa    600
aaaactgtat tataagtaaa tgcatgtata ctaaactcac aaattagagc ttcaatttaa    660
ttatatcagt tattacccgg gaatctcggt cgtaatgatt tttataatga cgaaaaaaaa    720
aaaattggaa agaaaaagct tcatggcctt tataaaaagg aaccatccaa tacctcgcca    780
gaaccaagta acagtatttt acggggcaca aatcaagaac aataagacag gactgtaaag    840
atggacgcat tgaactccaa agaacaacaa gagttccaaa aagtagtgga acaaaagcaa    900
atgaaggatt tcatgcgttt gataacttcg tataatgtat gctatacgaa gttatctcga    960
gatctcccct aaaccgtgga atatttcgga tatccttttg ttgtttccgg gtgtacaata   1020
tggacttcct cttttctggc aaccaaaccc atacatcggg attcctataa taccttcgtt   1080
ggtctcccta acatgtaggt ggcggagggg agatatacaa tagaacagat accagacaag   1140
acataatggg ctaaacaaga ctacaccatt tacactgcct cattgatggt ggtacataac   1200
gaactaatac tgtagcccta gacttgatag ccatcatcat atcgaagttt cactaccctt   1260
tttccatttg ccatctattg aagtaataat aggcgcatgc aacttctttt tttttttttt   1320
ttttctctct cccccgttgt tgtctcacca tatccgcaat gacaaaaaaa tgatggaaga   1380
cactaaagga aaaaattaac gacaaagaca gcaccaacag atgtcgttgt tccagagctg   1440
atgaggggta tctcgaagca cacgaaactt tttccttcct tcattcacgc acactactct   1500
ctaatgagca acggtatacg gccttccttc cagttacttg aatttgaaat aaaaaaaagt   1560
ttgctgtctt gctatcaagt ataaatagac ctgcaattat taatcttttg tttcctcgtc   1620
attgttctcg ttccctttct tccttgtttc tttttctgca caatatttca agctatacca   1680
agcatacaat caactatctc atatacatct agtaatttac cagcttacta tccttcttga   1740
aaatatgcac tctatatctt ttagttctta attgcaacac atagatttgc tgtataacga   1800
attttatgct attttttttaa tttggagttc ggtgatgaaa gtgtcacagc gaatttcctc   1860
acatgtaggg accgaattgt ttacaagttc tctgtaccac catggagaca tcaaagattg   1920
aaaatctatg gaaagatatg gacggtagca acaagaatat agcacgagcc gcggagttca   1980
tttcgttact tttgatatcg ctcacaacta ttgcgaagcg cttcagtgaa aaaatcataa   2040
ggaaaagttg taaatattat tggtagtatt cgtttggtaa agtagagggg gtaatttttc   2100
ccctttattt tgttcataca ttcttaaatt gctttgcctc tccttttgga aagctatact   2160
tcggagcact gttgagcgaa ggctcaggcc ggcatatgac gttttattac ctttgatcac   2220
atttccacgc catttcgcat tctcaccctc ataagtcata caccgaaaag aaagtttaag   2280
ggatcaatga gcttactata atctcagtat atttattttt atcgatgatt caccacaaca   2340
atcttgctcc cgaaaagaaa gcagacggag tagaagcatt tgaaactcct tcagaccttc   2400
aagtatatat atatatatat atatatgtat atgtgtacat tttcacgcta atactaatgt   2460
```

-continued

```
ataattagaa gataattttt actcattttt cgttatcttc acgtcacccg aacctagaac   2520

caaatgtcat tttcacgata tgtaaatagt gaaataggca aaaacgccaa aaagtagtaa   2580

gcgcaacata cactaaacca ttaaagaata tctcgaccag aatctaacag atatacatgt   2640

tccgataatg tctgagttag gtgagtattc taaattagaa aacaaagagc ttagaacgga   2700

gtttgaattg acaaattttc cttttccagg cacaactgat aacgactccg atgacggaag   2760

ccaagggcag aactctttga atatcattac tcctgacatg gatgatactc tggttaatga   2820

tgtacttcga gaaaacgata aaaagtctag tatgagaatg gcttttatga atctagcaaa   2880

ctctattctt ggtgccggaa taattactca gccgttcgcg atcaaaaatg ctggtatatt   2940

aggcgggcta ttatcatacg tagccctcgg atttatagtt gattggacgt taagacttat   3000

tgtcattaac ttgactcttg ctggcaagag aacataccag ggtacggtcg aacatgtaat   3060

gggtaaaaaa gggaaattgc tgattctatt tacaaacggg ttatttgcat ttggtggatg   3120

tattgg                                                              3126
```

<210> SEQ ID NO 15
<211> LENGTH: 591
<212> TYPE: PRT
<213> ORGANISM: Saccharomyces cerevisiae

<400> SEQUENCE: 15

```
Met Leu Lys Tyr Lys Pro Leu Leu Lys Ile Ser Lys Asn Cys Glu Ala
1               5                   10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80

Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
```

-continued

```
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590
```

<210> SEQ ID NO 16
<211> LENGTH: 4662
<212> TYPE: DNA
<213> ORGANISM: Artificial Sequence
<220> FEATURE:
<223> OTHER INFORMATION: Sequence put together from multiple organisms: Saccharomyces cerevisiae and Issatchenkia orientalis.

<400> SEQUENCE: 16

```
tcctattcgg agatacaggc aacaagtgat agagggccca ttatgaatac gcacctctat      60

gtatttccga gatacgatta ctccagttcc tcttacaaga aatgcataaa aatagttaca     120
```

```
attaattaga acaagaactt atttagaaca cgttcacact gagtaagaac tcttgtccct    180
tattagcctt gatagtgctg aaaaaaagaa aaaaaacaaa aaaaagaaat aaaataacgg    240
caaacagcaa aggccacaga accgtattca tgttacttct gcaatatcaa tcacttactg    300
gcaagtgcgt ataaattaaa cctatttctt tatcatcata tttacttata tctttaacag    360
attccaaacc ctaaagtgtc cgaattttca atagggcgaa cttgaagaat aaccaaggtc    420
aataatatat cttttagtat aaccctgaaa tttgccctat agaaatctag ggtttctgtg    480
tggtttccgg gtgagtcata cggctttttt gaatttcttt ttttgcagtt gtctctatca    540
atgaaaattt cgaggaagac gataaggtta agataagtag ataagagaat gatacgagat    600
aaagcacaaa ttagcagaaa gaagagtggt tgcgaacaga gtaaaccgaa tcagggaatc    660
ccttttttgca aaaacatcaa ttatcctttt cttttttta cgtatatatc tggaacagaa    720
atatataagt tactattata cttatagttg gatccagttt ttaatctgtc gtcaatcgaa    780
agtttatttc agagttcttc agacttctta actcctgtaa aaacaaaaaa aaaaaaaggc    840
atagcactcg agatctcccg agtttatcat tatcaatact gccatttcaa agaatacgta    900
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgttactca gatcactaaa   1560
ctcttctgct cgttgtgtca aacaaacaac cagaacaaag gttaggtatc tcagccacgt   1620
cagtggtgca agcatggcga aacctacatt gaagaacaac tcgagagaat ccaacaaatc   1680
cagaaactat ctaattgctg ctgtgacagc attggctgta tcaacctcaa ttggagttgc   1740
cgtacatgtg aaggacccct tgtataacga tgctaccggc agtgattctc cgagaagtat   1800
atctgttgac gagtttgtca agcataattc acaaaacgac tgttggattg caatcaatgg   1860
caaggtttat gatttcactg attttattcc aaaccatcca ggtggggtac ctccattagt   1920
taatcatgct ggttatgatg gtactaaact ttatgagaaa ttgcatccaa aaggtacaat   1980
tgagaaattc ttgccaaagg ataagtttct gggtgtgtta gatggtgaag cgccaaaatt   2040
ggaagcagac tatttggtgg acgatgatga acaagagaga ctggattatt tgaacaactt   2100
acctcctttg tcatctattc agaatgttta tgatttcgaa tacttggcca agaagatttt   2160
acctaaagat gcctgggcat attattcttg tggtgccgat gatgaaatca caatgagaga   2220
aaaccattat gcttatcaaa gagtttattt cagaccaaga atttgtgttg atgtcaagga   2280
agttgatact tcttatgaaa tgttaggcac taaaacctct gttccttttt atgtatctgc   2340
caccgctttg gctaaattag gccatcctga tggtgaatgc tcaattgcta gaggcgctgg   2400
taaggaaggt gtcgttcaaa tgatttcgac cctttcctca atgtcattag atgaaattgc   2460
```

-continued

```
cgctgctaga atcccaggtg caacccaatg gttccaatta tacattaatg aggatagaaa   2520
tgtcgctaaa ggtctggtca aacatgcaga agacttgggt atgaaggcta tctttataac   2580
tgttgatgct ccttctctag gtaacagaga aaaggataaa agattaaagt ttgttaatga   2640
caccgatgtc gatttgggtg attccgcaga tcgaaacagt ggtgcttcaa aggcactatc   2700
ttcgttcatt gatgcttctg tctcttggaa tgacgtcaaa gcggtcaagt cgtggactaa   2760
attgcctgtc ttagttaaag gtgttcaaac agttgaagac gttattgaag cttacgatgc   2820
tggttgtcaa ggtgttgttt tgtcaaacca cggtggtagg caactagata ctgctcctcc   2880
tccaatcgaa ttattagctg aaactgttcc aactttgaag agattgggta aattaagacc   2940
agattttgaa attttaattg acggtggtgt caaaagaggt accgatattt tgaaagcagt   3000
cgcaatcggt ggccaagatg tcagagtttc agttggtatg ggtagacctt tcttatatgc   3060
caactcttgc tatggtgaag caggtgttag aaaattaatt caaaatctaa aggatgaatt   3120
agaaatggat atgagattgt tgggtgtcac taaaatggac cagctatctt cgaaacatgt   3180
cgatactaaa cgtttgattg gtagagatgc gatcaactat ttgtatgata atgtatacag   3240
cccaatcgaa accgttaaat tcaacaatga agattgatta attaaacagg ccccttttcc   3300
tttgtcgata tcatgtaatt agttatgtca cgcttacatt cacgccctcc tcccacatcc   3360
gctctaaccg aaaaggaagg agttagacaa cctgaagtct aggtccctat ttattttttt   3420
atagttatgt tagtattaag aacgttattt atatttcaaa tttttctttt ttttctgtac   3480
aaacgcgtgt acgcatgtaa cgggcagacg gccggccata acttcgtata atgtatgcta   3540
tacgaagtta tggcaacggt tcatcatctc atggatctgc acatgaacaa acaccagagt   3600
caaacgacgt tgaaattgag gctactgcgc caattgatga caatacagac gatgataaca   3660
aaccgaagtt atctgatgta gaaaaggatt agagatgcta agagatagtg atgatatttc   3720
ataaataatg taattctata tatgttaatt accttttttg cgaggcatat ttatggtgaa   3780
ggataagttt tgaccatcaa agaaggttaa tgtggctgtg gtttcagggt ccataaagct   3840
tttcaattca tctttttttt ttttgttctt ttttttgatt ccggtttctt tgaaattttt   3900
ttgattcggt aatctccgag cagaaggaag aacgaaggaa ggagcacaga cttagattgg   3960
tatatatacg catatgtggt gttgaagaaa catgaaattg cccagtattc ttaacccaac   4020
tgcacagaac aaaaacctgc aggaaacgaa gataaatcat gtcgaaagct acatataagg   4080
aacgtgctgc tactcatcct agtcctgttg ctgccaagct atttaatatc atgcacgaaa   4140
agcaaacaaa cttgtgtgct tcattggatg ttcgtaccac caaggaatta ctggagttag   4200
ttgaagcatt aggtcccaaa atttgtttac taaaaacaca tgtggatatc ttgactgatt   4260
tttccatgga gggcacagtt aagccgctaa aggcattatc cgccaagtac aatttttttac   4320
tcttcgaaga cagaaaattt gctgacattg gtaatacagt caaattgcag tactctgcgg   4380
gtgtatacag aatagcagaa tgggcagaca ttacgaatgc acacggtgtg gtgggcccag   4440
gtattgttag cggtttgaag caggcggcgg aagaagtaac aaaggaacct agaggccttt   4500
tgatgttagc agaattgtca tgcaagggct ccctagctac tggagaatat actaagggta   4560
ctgttgacat tgcgaagagc gacaaagatt ttgttatcgg ctttattgct caaagagaca   4620
tgggtggaag agatgaaggt tacgattggt tgattatgac ac                      4662
```

<210> SEQ ID NO 17
<211> LENGTH: 578
<212> TYPE: PRT
<213> ORGANISM: Issatchenkia orientalis

<400> SEQUENCE: 17

Met Leu Leu Arg Ser Leu Asn Ser Ser Ala Arg Cys Val Lys Gln Thr
1 5 10 15

Thr Arg Thr Lys Val Arg Tyr Leu Ser His Val Ser Gly Ala Ser Met
20 25 30

Ala Lys Pro Thr Leu Lys Asn Asn Ser Arg Glu Ser Asn Lys Ser Arg
35 40 45

Asn Tyr Leu Ile Ala Ala Val Thr Ala Leu Ala Val Ser Thr Ser Ile
50 55 60

Gly Val Ala Val His Val Lys Asp Pro Leu Tyr Asn Asp Ala Thr Gly
65 70 75 80

Ser Asp Ser Pro Arg Ser Ile Ser Val Asp Glu Phe Val Lys His Asn
85 90 95

Ser Gln Asn Asp Cys Trp Ile Ala Ile Asn Gly Lys Val Tyr Asp Phe
100 105 110

Thr Asp Phe Ile Pro Asn His Pro Gly Gly Val Pro Pro Leu Val Asn
115 120 125

His Ala Gly Tyr Asp Gly Thr Lys Leu Tyr Glu Lys Leu His Pro Lys
130 135 140

Gly Thr Ile Glu Lys Phe Leu Pro Lys Asp Lys Phe Leu Gly Val Leu
145 150 155 160

Asp Gly Glu Ala Pro Lys Leu Glu Ala Asp Tyr Leu Val Asp Asp Asp
165 170 175

Glu Gln Glu Arg Leu Asp Tyr Leu Asn Asn Leu Pro Pro Leu Ser Ser
180 185 190

Ile Gln Asn Val Tyr Asp Phe Glu Tyr Leu Ala Lys Lys Ile Leu Pro
195 200 205

Lys Asp Ala Trp Ala Tyr Tyr Ser Cys Gly Ala Asp Asp Glu Ile Thr
210 215 220

Met Arg Glu Asn His Tyr Ala Tyr Gln Arg Val Tyr Phe Arg Pro Arg
225 230 235 240

Ile Cys Val Asp Val Lys Glu Val Asp Thr Ser Tyr Glu Met Leu Gly
245 250 255

Thr Lys Thr Ser Val Pro Phe Tyr Val Ser Ala Thr Ala Leu Ala Lys
260 265 270

Leu Gly His Pro Asp Gly Glu Cys Ser Ile Ala Arg Gly Ala Gly Lys
275 280 285

Glu Gly Val Val Gln Met Ile Ser Thr Leu Ser Ser Met Ser Leu Asp
290 295 300

Glu Ile Ala Ala Ala Arg Ile Pro Gly Ala Thr Gln Trp Phe Gln Leu
305 310 315 320

Tyr Ile Asn Glu Asp Arg Asn Val Ala Lys Gly Leu Val Lys His Ala
325 330 335

Glu Asp Leu Gly Met Lys Ala Ile Phe Ile Thr Val Asp Ala Pro Ser
340 345 350

Leu Gly Asn Arg Glu Lys Asp Lys Arg Leu Lys Phe Val Asn Asp Thr
355 360 365

Asp Val Asp Leu Gly Asp Ser Ala Asp Arg Asn Ser Gly Ala Ser Lys
370 375 380

Ala Leu Ser Ser Phe Ile Asp Ala Ser Val Ser Trp Asn Asp Val Lys
385 390 395 400

Ala Val Lys Ser Trp Thr Lys Leu Pro Val Leu Val Lys Gly Val Gln

```
                405                 410                 415

Thr Val Glu Asp Val Ile Glu Ala Tyr Asp Ala Gly Cys Gln Gly Val
            420                 425                 430

Val Leu Ser Asn His Gly Gly Arg Gln Leu Asp Thr Ala Pro Pro Pro
        435                 440                 445

Ile Glu Leu Leu Ala Glu Thr Val Pro Thr Leu Lys Arg Leu Gly Lys
    450                 455                 460

Leu Arg Pro Asp Phe Glu Ile Leu Ile Asp Gly Gly Val Lys Arg Gly
465                 470                 475                 480

Thr Asp Ile Leu Lys Ala Val Ala Ile Gly Gly Gln Asp Val Arg Val
                485                 490                 495

Ser Val Gly Met Gly Arg Pro Phe Leu Tyr Ala Asn Ser Cys Tyr Gly
            500                 505                 510

Glu Ala Gly Val Arg Lys Leu Ile Gln Asn Leu Lys Asp Glu Leu Glu
        515                 520                 525

Met Asp Met Arg Leu Leu Gly Val Thr Lys Met Asp Gln Leu Ser Ser
    530                 535                 540

Lys His Val Asp Thr Lys Arg Leu Ile Gly Arg Asp Ala Ile Asn Tyr
545                 550                 555                 560

Leu Tyr Asp Asn Val Tyr Ser Pro Ile Glu Thr Val Lys Phe Asn Asn
                565                 570                 575

Glu Asp
```

<210> SEQ ID NO 18
<211> LENGTH: 4419
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus niger.

<400> SEQUENCE: 18

```
tcctattcgg agatacaggc aacaagtgat agagggccca ttatgaatac gcacctctat     60

gtatttccga gatacgatta ctccagttcc tcttacaaga aatgcataaa aatagttaca    120

attaattaga acaagaactt atttagaaca cgttcacact gagtaagaac tcttgtccct    180

tattagcctt gatagtgctg aaaaaaagaa aaaaaacaaa aaaaagaaat aaaataacgg    240

caaacagcaa aggccacaga accgtattca tgttacttct gcaatatcaa tcacttactg    300

gcaagtgcgt ataaattaaa cctatttctt tatcatcata tttacttata tctttaacag    360

attccaaacc ctaaagtgtc cgaattttca atagggcgaa cttgaagaat aaccaaggtc    420

aataatatat cttttagtat aaccctgaaa tttgccctat agaaatctag ggtttctgtg    480

tggtttccgg gtgagtcata cggctttttt gaatttcttt ttttgcagtt gtctctatca    540

atgaaaattt cgaggaagac gataaggtta agataagtag ataagagaat gatacgagat    600

aaagcacaaa ttagcagaaa gaagagtggt tgcgaacaga gtaaaccgaa tcagggaatc    660

cctttttgca aaaacatcaa ttatcctttt cttttttta cgtatatatc tggaacagaa    720

atatataagt tactattata cttatagttg gatccagttt ttaatctgtc gtcaatcgaa    780

agtttatttc agagttcttc agacttctta actcctgtaa aaacaaaaaa aaaaaaaggc    840

atagcactcg agatctcccg agtttatcat tatcaatact gccatttcaa agaatacgta    900

aataattaat agtagtgatt ttcctaactt tatttagtca aaaaattggc cttttaattc    960

tgctgtaacc cgtacatgcc caaaataggg ggcgggttac acagaatata taacatcata   1020
```

```
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgtctaaag gaaaactaac   1560
tggcgcagct gtcgcggaac acaactctaa ggattcatgt tgggttattg ttcatggtaa   1620
ggcatacgat gtgacagaat tcttgccaga acacccagga ggccaaaaga ttatactgaa   1680
atacgctggg aaagatgcaa cagaagagtt cgatcctatt cacccaccag atacattgga   1740
taagtacttg gactcatcaa agcatttagg tgaggtggat atgactactg tcgaacaaga   1800
ggaaaagacc gcagatccag aagaggaggc aagacaggaa cgtattaagt gcatgccaag   1860
tcttgcagcg tgttacaatt tgatggattt tgaaacagta gcacgttcag ttatgaaaaa   1920
gaccgcgtgg gcttattaca gttctggtgc tgacgatgaa atcacaatga gagagaacca   1980
ctctgctttt cataagatct ggttcagacc tagagttttg gtcgacgtag aacatgtgga   2040
tttctctacc actatgttag gtacaaaggt ttcagtccca ttctatgtaa ctgcaacagc   2100
cttaggaaag ttgggtaacc cagaaggtga ggttgttctg accagagcag cacacacaca   2160
tgatgttatt caaatgatac caacattagc ctcatgcagc ttcgatgaaa tcgttgatgc   2220
cagacagggg gatcaagtcc agtggcttca actctacgtt aacaaggata gaaatatcac   2280
taagagaatc gttcaacatg ctgaggcaag aggatgcaaa ggtttattca tcacagttga   2340
tgcccctcaa ttaggtagaa gagaaaaaga catgagatca aagttttccg acgtaggttc   2400
taacgtacaa gcttctggtg gcagctccgt tgatagatct caaggtgcag ccagagccat   2460
ctctagtttc atcgatccag ccctgtcatg gaaagatatt ccttggtttc aatccatcac   2520
taagatgcct atactattga aaggtgtgca atgtgttgag gacgtgctta gagcggtaga   2580
aatgggtgtc caaggtgttg tgctatccaa ccatgggggt agacagttag aattcgcacg   2640
ttctgctatt gaagtgcttg cagaagtcat gcctatattg agagaaagag gctgggagaa   2700
taagatagag atttacattg acggcgggat tcgtagagcc acagatatgc tcaaagcact   2760
ctgtctagga gctaaaggtg ttggaatcgg cagaccattt ttgtacgcta tgtcagctta   2820
cggccaacca ggtgtcgaaa gagctatgca gttattgaag gacgaaatgg aaatgaatat   2880
gagacttatt ggggctacca agattgagga attgaaccca tctctaatcg acgttagagg   2940
attagtcggt ggtcattctg ctccagttcc aagtgataca cttactactg gagcttacga   3000
ccctttgcaa gcccctagat tctccgaaaa gtagttaatt aaacaggccc cttttccttt   3060
gtcgatatca tgtaattagt tatgtcacgc ttacattcac gccctcctcc cacatccgct   3120
ctaaccgaaa aggaaggagt tagacaacct gaagtctagg tccctattta tttttttata   3180
gttatgttag tattaagaac gttatttata tttcaaattt ttcttttttt tctgtacaaa   3240
cgcgtgtacg catgtaacgg gcagacggcc ggccataact tcgtataatg tatgctatac   3300
gaagttatgg caacggttca tcatctcatg gatctgcaca tgaacaaaca ccagagtcaa   3360
acgacgttga aattgaggct actgcgccaa ttgatgacaa tacagacgat gataacaaac   3420
```

```
cgaagttatc tgatgtagaa aaggattaga gatgctaaga gatagtgatg atatttcata   3480

aataatgtaa ttctatatat gttaattacc tttttgcga ggcatattta tggtgaagga   3540

taagttttga ccatcaaaga aggttaatgt ggctgtggtt tcagggtcca taaagctttt   3600

caattcatct ttttttttt tgttcttttt tttgattccg gtttctttga aattttttg   3660

attcggtaat ctccgagcag aaggaagaac gaaggaagga gcacagactt agattggtat   3720

atatacgcat atgtggtgtt gaagaaacat gaaattgccc agtattctta acccaactgc   3780

acagaacaaa aacctgcagg aaacgaagat aaatcatgtc gaaagctaca tataaggaac   3840

gtgctgctac tcatcctagt cctgttgctg ccaagctatt taatatcatg cacgaaaagc   3900

aaacaaactt gtgtgcttca ttggatgttc gtaccaccaa ggaattactg gagttagttg   3960

aagcattagg tcccaaaatt tgtttactaa aaacacatgt ggatatcttg actgattttt   4020

ccatggaggg cacagttaag ccgctaaagg cattatccgc caagtacaat tttttactct   4080

tcgaagacag aaaatttgct gacattggta atacagtcaa attgcagtac tctgcgggtg   4140

tatacagaat agcagaatgg gcagacatta cgaatgcaca cggtgtggtg ggcccaggta   4200

ttgttagcgg tttgaagcag gcggcggaag aagtaacaaa ggaacctaga ggcctttga   4260

tgttagcaga attgtcatgc aagggctccc tagctactgg agaatatact aagggtactg   4320

ttgacattgc gaagagcgac aaagattttg ttatcggctt tattgctcaa agagacatgg   4380

gtggaagaga tgaaggttac gattggttga ttatgacac                        4419
```

```
<210> SEQ ID NO 19
<211> LENGTH: 497
<212> TYPE: PRT
<213> ORGANISM: Aspergillus niger

<400> SEQUENCE: 19

Met Ser Lys Gly Lys Leu Thr Gly Ala Ala Val Ala Glu His Asn Ser
1               5                   10                  15

Lys Asp Ser Cys Trp Val Ile Val His Gly Lys Ala Tyr Asp Val Thr
            20                  25                  30

Glu Phe Leu Pro Glu His Pro Gly Gly Gln Lys Ile Ile Leu Lys Tyr
        35                  40                  45

Ala Gly Lys Asp Ala Thr Glu Glu Phe Asp Pro Ile His Pro Pro Asp
    50                  55                  60

Thr Leu Asp Lys Tyr Leu Asp Ser Ser Lys His Leu Gly Glu Val Asp
65                  70                  75                  80

Met Thr Thr Val Glu Gln Glu Glu Lys Thr Ala Asp Pro Glu Glu Glu
                85                  90                  95

Ala Arg Gln Glu Arg Ile Lys Cys Met Pro Ser Leu Ala Ala Cys Tyr
            100                 105                 110

Asn Leu Met Asp Phe Glu Thr Val Ala Arg Ser Val Met Lys Lys Thr
        115                 120                 125

Ala Trp Ala Tyr Tyr Ser Ser Gly Ala Asp Asp Glu Ile Thr Met Arg
    130                 135                 140

Glu Asn His Ser Ala Phe His Lys Ile Trp Phe Arg Pro Arg Val Leu
145                 150                 155                 160

Val Asp Val Glu His Val Asp Phe Ser Thr Thr Met Leu Gly Thr Lys
                165                 170                 175

Val Ser Val Pro Phe Tyr Val Thr Ala Thr Ala Leu Gly Lys Leu Gly
            180                 185                 190
```

-continued

```
Asn Pro Glu Gly Glu Val Val Leu Thr Arg Ala Ala His Thr His Asp
        195                 200                 205

Val Ile Gln Met Ile Pro Thr Leu Ala Ser Cys Ser Phe Asp Glu Ile
    210                 215                 220

Val Asp Ala Arg Gln Gly Asp Gln Val Gln Trp Leu Gln Leu Tyr Val
225                 230                 235                 240

Asn Lys Asp Arg Asn Ile Thr Lys Arg Ile Val Gln His Ala Glu Ala
                245                 250                 255

Arg Gly Cys Lys Gly Leu Phe Ile Thr Val Asp Ala Pro Gln Leu Gly
            260                 265                 270

Arg Arg Glu Lys Asp Met Arg Ser Lys Phe Ser Asp Val Gly Ser Asn
        275                 280                 285

Val Gln Ala Ser Gly Gly Ser Ser Val Asp Arg Ser Gln Gly Ala Ala
    290                 295                 300

Arg Ala Ile Ser Ser Phe Ile Asp Pro Ala Leu Ser Trp Lys Asp Ile
305                 310                 315                 320

Pro Trp Phe Gln Ser Ile Thr Lys Met Pro Ile Leu Leu Lys Gly Val
                325                 330                 335

Gln Cys Val Glu Asp Val Leu Arg Ala Val Glu Met Gly Val Gln Gly
            340                 345                 350

Val Val Leu Ser Asn His Gly Gly Arg Gln Leu Glu Phe Ala Arg Ser
        355                 360                 365

Ala Ile Glu Val Leu Ala Glu Val Met Pro Ile Leu Arg Glu Arg Gly
    370                 375                 380

Trp Glu Asn Lys Ile Glu Ile Tyr Ile Asp Gly Gly Ile Arg Arg Ala
385                 390                 395                 400

Thr Asp Met Leu Lys Ala Leu Cys Leu Gly Ala Lys Gly Val Gly Ile
                405                 410                 415

Gly Arg Pro Phe Leu Tyr Ala Met Ser Ala Tyr Gly Gln Pro Gly Val
            420                 425                 430

Glu Arg Ala Met Gln Leu Leu Lys Asp Glu Met Glu Met Asn Met Arg
        435                 440                 445

Leu Ile Gly Ala Thr Lys Ile Glu Glu Leu Asn Pro Ser Leu Ile Asp
    450                 455                 460

Val Arg Gly Leu Val Gly Gly His Ser Ala Pro Val Pro Ser Asp Thr
465                 470                 475                 480

Leu Thr Thr Gly Ala Tyr Asp Pro Leu Gln Ala Pro Arg Phe Ser Glu
                485                 490                 495

Lys
```

<210> SEQ ID NO 20
<211> LENGTH: 4398
<212> TYPE: DNA
<213> ORGANISM: Artificial Sequence
<220> FEATURE:
<223> OTHER INFORMATION: Sequence put together from multiple organisms: Saccharomyces cerevisiae and Yarrowia lipolytica.

<400> SEQUENCE: 20

```
tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180

tattagcctt gatagtgctg aaaaaaagaa aaaaaacaaa aaaaagaaat aaaataacgg     240

caaacagcaa aggccacaga accgtattca tgttacttct gcaatatcaa tcacttactg     300
```

```
gcaagtgcgt ataaattaaa cctatttctt tatcatcata tttacttata tctttaacag    360
attccaaacc ctaaagtgtc cgaattttca atagggcgaa cttgaagaat aaccaaggtc    420
aataatatat cttttagtat aaccctgaaa tttgccctat agaaatctag ggtttctgtg    480
tggtttccgg gtgagtcata cggctttttt gaatttcttt ttttgcagtt gtctctatca    540
atgaaaattt cgaggaagac gataaggtta agataagtag ataagagaat gatacgagat    600
aaagcacaaa ttagcagaaa gaagagtggt tgcgaacaga gtaaaccgaa tcagggaatc    660
ccttttttgca aaaacatcaa ttatcctttt cttttttttta cgtatatatc tggaacagaa   720
atatataagt tactattata cttatagttg gatccagttt ttaatctgtc gtcaatcgaa    780
agtttatttc agagttcttc agacttctta actcctgtaa aaacaaaaaa aaaaaaaggc    840
atagcactcg agatctcccg agtttatcat tatcaatact gccatttcaa agaatacgta    900
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atggtttcag ttgaagaggt   1560
tgctaaacat aacagtaagg attcatgttg ggttatactt catggtaagg catacgactt   1620
gacagaattc ttaccagaac atcctggtgg gcaagcgatt attctcaagt acgctggtaa   1680
ggatgcaaca aaggctttcg atccaataca tcctagagat gttgtcgata agttcttgga   1740
caaagacaaa caccttggtg aggtaactgg tgaaattgca gctgaggaag aggaagaggt   1800
cacaccagag gagaaggcca gactggaaag atatgaaaac agaccacctt tgtcccaaat   1860
ctttaactct tttgattttg aatacgtggc aagacacacc atgtccccaa acgcctgggc   1920
ctattactct tctgggagcg atgacgagat cactgtcaga gaaaatcata gagctttcca   1980
caaaatctgg tttcgtccaa gagttctagt ggatgtcaaa aatgttgata tctcaacaac   2040
aatgcttggg actaaatcat cagttccatt ctacattaca gcgacagcat tgggtaaatt   2100
gggacaccca gaaggtgaag tggttcttac tagaggagct gataagatgg acgtgatcca   2160
aatgatacct accttagcat catgttcttt cgatgaaatt gtcgatgctg ccaccgataa   2220
gcagactcaa tggatgcaac tgtatgtaaa catggataga gaagttacta aaaagattgt   2280
gcaacatgca gaaaagagag gcgttaaggg cctgtttatc acagttgacg caccacaatt   2340
aggcagaaga gaaaaggaca tgagaacaaa gttcggtgat ccaggcgctc aagtacagca   2400
atccgatgat tctgtggaca gatctcaggg agctgctaga gctatctcaa gcttcattga   2460
tccttcctta tcatggaagg acattccttg gttccagagt atcacaaaga tgcctatcat   2520
cttaaaaggt gtgcaatgtg ccgaagatgc gctaaaggct gtagagtaca aagtagacgg   2580
tattttgtta tctaaccatg gtggacgtca gctagagttt gccagaccat ctattgaggt   2640
```

-continued

```
cctcgttgaa gtaatggcag ctttaagagc caagggttgg caagattaca tagaagttta   2700
catagacgga ggcatcagac gtgcaactga tgtcattaag gctctatgcc taggtgcaaa   2760
aggagtcggg attggcagac catttctcta cgcgatgtct acctacggag aagatggtgt   2820
ttgccacttg attcaattgt tgaaagatga aatggaaatg aatatgagac ttatcggtgc   2880
cacaaagata gaggatttga atccaagtat ggttgatttg aagtctattt tcactcattc   2940
tgcagacaca gcaagagata tcttaggcga aaacgtttac caacatatgg aaatgccatt   3000
attcaagggt tagttaatta aacaggcccc ttttcctttg tcgatatcat gtaattagtt   3060
atgtcacgct tacattcacg ccctcctccc acatccgctc taaccgaaaa ggaaggagtt   3120
agacaacctg aagtctaggt ccctatttat ttttttatag ttatgttagt attaagaacg   3180
ttatttatat ttcaaatttt tctttttttt ctgtacaaac gcgtgtacgc atgtaacggg   3240
cagacggccg gccataactt cgtataatgt atgctatacg aagttatggc aacggttcat   3300
catctcatgg atctgcacat gaacaaacac cagagtcaaa cgacgttgaa attgaggcta   3360
ctgcgccaat tgatgacaat acagacgatg ataacaaacc gaagttatct gatgtagaaa   3420
aggattagag atgctaagag atagtgatga tatttcataa ataatgtaat tctatatatg   3480
ttaattacct tttttgcgag gcatatttat ggtgaaggat aagttttgac catcaaagaa   3540
ggttaatgtg gctgtggttt cagggtccat aaagcttttc aattcatctt tttttttttt   3600
gttctttttt ttgattccgg tttctttgaa attttttttga ttcggtaatc tccgagcaga   3660
aggaagaacg aaggaaggag cacagactta gattggtata tatacgcata tgtggtgttg   3720
aagaaacatg aaattgccca gtattcttaa cccaactgca cagaacaaaa acctgcagga   3780
aacgaagata aatcatgtcg aaagctacat ataaggaacg tgctgctact catcctagtc   3840
ctgttgctgc caagctattt aatatcatgc acgaaaagca aacaaacttg tgtgcttcat   3900
tggatgttcg taccaccaag gaattactgg agttagttga agcattaggt cccaaaattt   3960
gtttactaaa aacacatgtg gatatcttga ctgatttttc catggagggc acagttaagc   4020
cgctaaaggc attatccgcc aagtacaatt ttttactcttt cgaagacaga aaatttgctg   4080
acattggtaa tacagtcaaa ttgcagtact ctgcgggtgt atacagaata gcagaatggg   4140
cagacattac gaatgcacac ggtgtggtgg gcccaggtat tgttagcggt ttgaagcagg   4200
cggcggaaga agtaacaaag gaacctagag gccttttgat gttagcagaa ttgtcatgca   4260
agggctccct agctactgga gaatatacta agggtactgt tgacattgcg aagagcgaca   4320
aagattttgt tatcggcttt attgctcaaa gagacatggg tggaagagat gaaggttacg   4380
attggttgat tatgacac                                                 4398
```

<210> SEQ ID NO 21
<211> LENGTH: 490
<212> TYPE: PRT
<213> ORGANISM: Yarrowia lipolytica

<400> SEQUENCE: 21

```
Met Val Ser Val Glu Glu Val Ala Lys His Asn Ser Lys Asp Ser Cys
1               5                   10                  15

Trp Val Ile Leu His Gly Lys Ala Tyr Asp Leu Thr Glu Phe Leu Pro
            20                  25                  30

Glu His Pro Gly Gly Gln Ala Ile Ile Leu Lys Tyr Ala Gly Lys Asp
        35                  40                  45

Ala Thr Lys Ala Phe Asp Pro Ile His Pro Arg Asp Val Val Asp Lys
    50                  55                  60
```

```
Phe Leu Asp Lys Asp Lys His Leu Gly Glu Val Thr Gly Glu Ile Ala
65                  70                  75                  80

Ala Glu Glu Glu Glu Glu Val Thr Pro Glu Glu Lys Ala Arg Leu Glu
                85                  90                  95

Arg Tyr Glu Asn Arg Pro Pro Leu Ser Gln Ile Phe Asn Ser Phe Asp
            100                 105                 110

Phe Glu Tyr Val Ala Arg His Thr Met Ser Pro Asn Ala Trp Ala Tyr
        115                 120                 125

Tyr Ser Ser Gly Ser Asp Asp Glu Ile Thr Val Arg Glu Asn His Arg
    130                 135                 140

Ala Phe His Lys Ile Trp Phe Arg Pro Arg Val Leu Val Asp Val Lys
145                 150                 155                 160

Asn Val Asp Ile Ser Thr Thr Met Leu Gly Thr Lys Ser Ser Val Pro
                165                 170                 175

Phe Tyr Ile Thr Ala Thr Ala Leu Gly Lys Leu Gly His Pro Glu Gly
            180                 185                 190

Glu Val Val Leu Thr Arg Gly Ala Asp Lys Met Asp Val Ile Gln Met
        195                 200                 205

Ile Pro Thr Leu Ala Ser Cys Ser Phe Asp Glu Ile Val Asp Ala Ala
    210                 215                 220

Thr Asp Lys Gln Thr Gln Trp Met Gln Leu Tyr Val Asn Met Asp Arg
225                 230                 235                 240

Glu Val Thr Lys Lys Ile Val Gln His Ala Glu Lys Arg Gly Val Lys
                245                 250                 255

Gly Leu Phe Ile Thr Val Asp Ala Pro Gln Leu Gly Arg Arg Glu Lys
            260                 265                 270

Asp Met Arg Thr Lys Phe Gly Asp Pro Gly Ala Gln Val Gln Gln Ser
        275                 280                 285

Asp Asp Ser Val Asp Arg Ser Gln Gly Ala Ala Arg Ala Ile Ser Ser
    290                 295                 300

Phe Ile Asp Pro Ser Leu Ser Trp Lys Asp Ile Pro Trp Phe Gln Ser
305                 310                 315                 320

Ile Thr Lys Met Pro Ile Ile Leu Lys Gly Val Gln Cys Ala Glu Asp
                325                 330                 335

Ala Leu Lys Ala Val Glu Tyr Lys Val Asp Gly Ile Leu Leu Ser Asn
            340                 345                 350

His Gly Gly Arg Gln Leu Glu Phe Ala Arg Pro Ser Ile Glu Val Leu
        355                 360                 365

Val Glu Val Met Ala Ala Leu Arg Ala Lys Gly Trp Gln Asp Tyr Ile
    370                 375                 380

Glu Val Tyr Ile Asp Gly Gly Ile Arg Arg Ala Thr Asp Val Ile Lys
385                 390                 395                 400

Ala Leu Cys Leu Gly Ala Lys Gly Val Gly Ile Gly Arg Pro Phe Leu
                405                 410                 415

Tyr Ala Met Ser Thr Tyr Gly Glu Asp Gly Val Cys His Leu Ile Gln
            420                 425                 430

Leu Leu Lys Asp Glu Met Glu Met Asn Met Arg Leu Ile Gly Ala Thr
        435                 440                 445

Lys Ile Glu Asp Leu Asn Pro Ser Met Val Asp Leu Lys Ser Ile Phe
    450                 455                 460

Thr His Ser Ala Asp Thr Ala Arg Asp Ile Leu Gly Glu Asn Val Tyr
465                 470                 475                 480
```

Gln His Met Glu Met Pro Leu Phe Lys Gly
485 490

<210> SEQ ID NO 22
<211> LENGTH: 2919
<212> TYPE: DNA
<213> ORGANISM: Saccharomyces cerevisiae

<400> SEQUENCE: 22
tcctattcgg agatacaggc aacaagtgat agagggccca ttatgaatac gcacctctat 60
gtatttccga gatacgatta ctccagttcc tcttacaaga aatgcataaa aatagttaca 120
attaattaga acaagaactt atttagaaca cgttcacact gagtaagaac tcttgtccct 180
tattagcctt gatagtgctg aaaaaaagaa aaaaaacaaa aaaaagaaat aaaataacgg 240
caaacagcaa aggccacaga accgtattca tgttacttct gcaatatcaa tcacttactg 300
gcaagtgcgt ataaattaaa cctatttctt tatcatcata tttacttata tctttaacag 360
attccaaacc ctaaagtgtc cgaattttca atagggcgaa cttgaagaat aaccaaggtc 420
aataatatat cttttagtat aaccctgaaa tttgccctat agaaatctag ggtttctgtg 480
tggtttccgg gtgagtcata cggctttttt gaatttcttt ttttgcagtt gtctctatca 540
atgaaaattt cgaggaagac gataaggtta agataagtag ataagagaat gatacgagat 600
aaagcacaaa ttagcagaaa gaagagtggt tgcgaacaga gtaaaccgaa tcagggaatc 660
cctttttgca aaaacatcaa ttatcctttt cttttttta cgtatatatc tggaacagaa 720
atatataagt tactattata cttatagttg gatccagttt ttaatctgtc gtcaatcgaa 780
agtttatttc agagttcttc agacttctta actcctgtaa aaacaaaaaa aaaaaaaggc 840
atagcactcg agatctcccg agtttatcat tatcaatact gccatttcaa agaatacgta 900
aataattaat agtagtgatt ttcctaactt tatttagtca aaaaattggc cttttaattc 960
tgctgtaacc cgtacatgcc caaaataggg ggcgggttac acagaatata taacatcata 1020
ggtgtctggg tgaacagttt attcctggca tccactaaat ataatggagc ccgctttttt 1080
taagctggca tccagaaaaa aaaagaatcc cagcaccaaa atattgtttt cttcaccaac 1140
catcagttca taggtccatt ctcttagcgc aactacacag aacaggggca caaacaggca 1200
aaaaacgggc acaacctcaa tggagtgatg caacctgctt ggagtaaatg atgacacaag 1260
gcaattgacc tacgcatgta tctatctcat tttcttacac cttctattac cttctgctct 1320
ctctgatttg gaaaaagctg aaaaaaaagg ttgaaaccag ttccctgaaa ttattcccct 1380
atttgactaa taagtatata aagacggtag gtattgattg taattctgta aatctatttc 1440
ttaaacttct taaattctac ttttatagtt agtctttttt ttagtttaaa acaccaagaa 1500
cttagtttcg aataaacaca cataaacaaa caaatctagt aaacaggccc cttttccttt 1560
gtcgatatca tgtaattagt tatgtcacgc ttacattcac gccctcctcc cacatccgct 1620
ctaaccgaaa aggaaggagt tagacaacct gaagtctagg tccctattta ttttttttata 1680 gttatgttag tattaagaac gttatttata tttcaaattt ttcttttttt tctgtacaaa 1740
cgcgtgtacg catgtaacgg gcagacggcc ggccataact tcgtataatg tatgctatac 1800
gaagttatgg caacggttca tcatctcatg gatctgcaca tgaacaaaca ccagagtcaa 1860
acgacgttga aattgaggct actgcgccaa ttgatgacaa tacagacgat gataacaaac 1920
cgaagttatc tgatgtagaa aaggattaga gatgctaaga gatagtgatg atatttcata 1980
aataatgtaa ttctatatat gttaattacc ttttttgcga ggcatattta tggtgaagga 2040

-continued

```
taagttttga ccatcaaaga aggttaatgt ggctgtggtt tcagggtcca taaagctttt   2100

caattcatct ttttttttt tgttcttttt tttgattccg gtttctttga aatttttttg   2160

attcggtaat ctccgagcag aaggaagaac gaaggaagga gcacagactt agattggtat   2220

atatacgcat atgtggtgtt gaagaaacat gaaattgccc agtattctta acccaactgc   2280

acagaacaaa aacctgcagg aaacgaagat aaatcatgtc gaaagctaca tataaggaac   2340

gtgctgctac tcatcctagt cctgttgctg ccaagctatt taatatcatg cacgaaaagc   2400

aaacaaactt gtgtgcttca ttggatgttc gtaccaccaa ggaattactg gagttagttg   2460

aagcattagg tcccaaaatt tgtttactaa aaacacatgt ggatatcttg actgattttt   2520

ccatggaggg cacagttaag ccgctaaagg cattatccgc caagtacaat tttttactct   2580

tcgaagacag aaaatttgct gacattggta atacagtcaa attgcagtac tctgcgggtg   2640

tatacagaat agcagaatgg gcagacatta cgaatgcaca cggtgtggtg ggcccaggta   2700

ttgttagcgg tttgaagcag gcggcggaag aagtaacaaa ggaacctaga ggccttttga   2760

tgttagcaga attgtcatgc aagggctccc tagctactgg agaatatact aagggtactg   2820

ttgacattgc gaagagcgac aaagattttg ttatcggctt tattgctcaa agagacatgg   2880

gtggaagaga tgaaggttac gattggttga ttatgacac                          2919
```

```
<210> SEQ ID NO 23
<211> LENGTH: 4700
<212> TYPE: DNA
<213> ORGANISM: Artificial Sequence
<220> FEATURE:
<223> OTHER INFORMATION: Sequence put together from multiple organisms:
      Saccharomyces cerevisiae and Issatchenkia orientalis.

<400> SEQUENCE: 23
```

```
tccatggagg gcacagttaa gccgctaaag gcattatccg ccaagtacaa tttttttactc    60

ttcgaagaca gaaaatttgc tgacattggt aatacagtca aattgcagta ctctgcgggt    120

gtatacagaa tagcagaatg ggcagacatt acgaatgcac acggtgtggt gggcccaggt    180

attgttagcg gtttgaagca ggcggcggaa gaagtaacaa aggaacctag aggccttttg    240

atgttagcag aattgtcatg caagggctcc ctagctactg gagaatatac taagggtact    300

gttgacattg cgaagagcga caaagatttt gttatcggct ttattgctca aagagacatg    360

ggtggaagag atgaaggtta cgattggttg attatgacac ccggtgtggg tttagatgac    420

aagggagacg cattgggtca acagtataga accgtggatg atgtggtctc tacaggatct    480

gacattatta ttgttggaag aggactattt gcaaagggaa gggatgctaa ggtagagggt    540

gaacgttaca gaaaagcagg ctgggaagca tatttgagaa gatgcggcca gcaaaactaa    600

aaaactgtat tataagtaaa tgcatgtata ctaaactcac aaattagagc ttcaatttaa    660

ttatatcagt tattacccgg gaatctcggt cgtaatgatt tttataatga cgaaaaaaaa    720

aaaattggaa agaaaaagct tcatggcctt tataaaaagg aaccatccaa tacctcgcca    780

gaaccaagta acagtatttt acggggcaca aatcaagaac aataagacag gactgtaaag    840

atggacgcat tgaactccaa agaacaacaa gagttccaaa aagtagtgga acaaaagcaa    900

atgaaggatt tcatgcgttt gataacttcg tataatgtat gctatacgaa gttatctcga    960

gatctcccct aaaccgtgga atatttcgga tatccttttg ttgtttccgg gtgtacaata   1020

tggacttcct cttttctggc aaccaaaccc atacatcggg attcctataa taccttcgtt   1080

ggtctcccta acatgtaggt ggcggagggg agatatacaa tagaacagat accagacaag   1140
```

```
acataatggg ctaaacaaga ctacaccatt tacactgcct cattgatggt ggtacataac   1200
gaactaatac tgtagcccta gacttgatag ccatcatcat atcgaagttt cactaccctt   1260
tttccatttg ccatctattg aagtaataat aggcgcatgc aacttctttt tttttttttt   1320
ttttctctct cccccgttgt tgtctcacca tatccgcaat gacaaaaaaa tgatggaaga   1380
cactaaagga aaaaattaac gacaaagaca gcaccaacag atgtcgttgt tccagagctg   1440
atgaggggta tctcgaagca cacgaaactt tttccttcct tcattcacgc acactactct   1500
ctaatgagca acggtatacg gccttccttc cagttacttg aatttgaaat aaaaaaaagt   1560
ttgctgtctt gctatcaagt ataaatagac ctgcaattat taatcttttg tttcctcgtc   1620
attgttctcg ttccctttct tccttgtttc tttttctgca caatatttca agctatacca   1680
agcatacaat caactatctc atatacatct agaatgtctg atttagagtc acaacataca   1740
cgagaagagc tcgataagtc cgaggatgag gaaatccaac tcatcaatga aagccggcca   1800
ccaaagttgg ataaagagac gatcaagcgg tatctgaaaa ccagattcac tgagctattg   1860
ccaacaaagc aacagatgaa acaaaataaa catttgttga atccattgcc aggcttgaga   1920
atgatgggtc gtagacaatg gctgatgttt ctgagtgcct tctgcgcatg gacctgggac   1980
gcgtatgatt tctttacagt gtctctaaac accgtacaat tggccaaaga ttttgataag   2040
aacgtcaagg acattacatg gggattacaa cttgtgttga tgctaagatc agtgggggt   2100
atcacttttg gttatttggg tgataggtat ggtagaaaat ggcctttggt tgcaaacttg   2160
ttaattgttt gtattttaga aatcggaagc gggtttatca aaacctatag gcaatttcta   2220
ggcgtgagag cactatttgg tatttgttta ggggggggttt atggtaatgc cactgccact   2280
gcattggatg attgtcctac agaagccaga gggttcattg gtgggttgtt gcaacagggt   2340
tatgcttttg gttatttgct tgccgttgta tttaaaagag ctattgctga caattcgtca   2400
cataagtgga gagctacctt ttggtttggt gctggtattt cctttctatt tgcacttttc   2460
agagcctctt tacctgaaac aaaggcattt ctaagaaaaa aggagattga gaggtacaac   2520
aaggaacacg ggatttatca gccaacattc caaatgaaaa ttgtggaatc gttgaagaac   2580
tactggttga tgatgatata ccttgttttg tttatgtcgg gattctcatt tatgtcacat   2640
tcatcacaag atttgtatcc taccctattg actgtgagat actccttttc agagaacaag   2700
gccacagtga ccaattgcgt tgccaatatc ggtgcattta ttggcggtgt atttaccggc   2760
catatctcta actttttggg cagacggttg acgatcatgt tgatatgcat ctttggaggt   2820
gcgttgattt accccttggc ttttattgat ggcacaggta tcaatgcagg agttttcttt   2880
ctacaatggt gtgtgcaagg tggactaggg gtcgtgcctt cgcatttatc ggagttagca   2940
ccacctgatt tacgtgcatt tgtcgttgga atcagttatc aattaggtaa ccttgccgct   3000
tcagcctctt cgacaatcga aacgacaatt ggtgaacagt tcccaatgac ttcaccaagt   3060
ggcgaaccca tctacgacta cgcaaaagtc atggccatat ttgtaggttg cgtctttgct   3120
tttgtcctta tagtcacctt atttggccca gagagaagga atgcatcctt tgagaatgct   3180
gtaactacta atgaggagtt cggcaattcc gccggagccg ttgacaagat tgagcacgtg   3240
gaagaatgca ttgttccaaa gcacgctcgt aaccagcaat gttaattaat ttaccagctt   3300
actatccttc ttgaaaatat gcactctata tcttttagtt cttaattgca acacatagat   3360
ttgctgtata acgaatttta tgctattttt ttaatttgga gttcggtgat gaaagtgtca   3420
cagcgaattt cctcacatgt agggaccgaa ttgtttacaa gttctctgta ccaccatgga   3480
gacatcaaag attgaaaatc tatggaaaga tatggacggt agcaacaaga atatagcacg   3540
```

agccgcggag ttcatttcgt tacttttgat atcgctcaca actattgcga agcgcttcag 3600
tgaaaaaatc ataaggaaaa gttgtaaata ttattggtag tattcgtttg gtaaagtaga 3660
gggggtaatt tttccccttt attttgttca tacattctta aattgctttg cctctccttt 3720
tggaaagcta tacttcggag cactgttgag cgaaggctca ggccggcata tgacgtttta 3780
ttacctttga tcacatttcc acgccatttc gcattctcac cctcataagt catacaccga 3840
aaagaaagtt taagggatca atgagcttac tataatctca gtatatttat ttttatcgat 3900
gattcaccac aacaatcttg ctcccgaaaa gaaagcagac ggagtagaag catttgaaac 3960
tccttcagac cttcaagtat atatatatat atatatatat gtatatgtgt acattttcac 4020
gctaatacta atgtataatt agaagataat ttttactcat ttttcgttat cttcacgtca 4080
cccgaaccta gaaccaaatg tcattttcac gatatgtaaa tagtgaaata ggcaaaaacg 4140
ccaaaaagta gtaagcgcaa catacactaa accattaaag aatatctcga ccagaatcta 4200
acagatatac atgttccgat aatgtctgag ttaggtgagt attctaaatt agaaaacaaa 4260
gagcttagaa cggagtttga attgacaaat tttccttttc caggcacaac tgataacgac 4320
tccgatgacg gaagccaagg gcagaactct ttgaatatca ttactcctga catggatgat 4380
actctggtta atgatgtact tcgagaaaac gataaaaagt ctagtatgag aatggctttt 4440
atgaatctag caaactctat tcttggtgcc ggaataatta ctcagccgtt cgcgatcaaa 4500
aatgctggta tattaggcgg gctattatca tacgtagccc tcggatttat agttgattgg 4560
acgttaagac ttattgtcat taacttgact cttgctggca agagaacata ccagggtacg 4620
gtcgaacatg taatgggtaa aaaagggaaa ttgctgattc tatttacaaa cgggttattt 4680
gcatttggtg gatgtattgg 4700

<210> SEQ ID NO 24
<211> LENGTH: 523
<212> TYPE: PRT
<213> ORGANISM: Issatchenkia orientalis

<400> SEQUENCE: 24

Met Ser Asp Leu Glu Ser Gln His Thr Arg Glu Glu Leu Asp Lys Ser
1 5 10 15

Glu Asp Glu Glu Ile Gln Leu Ile Asn Glu Ser Arg Pro Pro Lys Leu
20 25 30

Asp Lys Glu Thr Ile Lys Arg Tyr Leu Lys Thr Arg Phe Thr Glu Leu
35 40 45

Leu Pro Thr Lys Gln Gln Met Lys Gln Asn Lys His Leu Leu Asn Pro
50 55 60

Leu Pro Gly Leu Arg Met Met Gly Arg Arg Gln Trp Leu Met Phe Leu
65 70 75 80

Ser Ala Phe Cys Ala Trp Thr Trp Asp Ala Tyr Asp Phe Phe Thr Val
85 90 95

Ser Leu Asn Thr Val Gln Leu Ala Lys Asp Phe Asp Lys Asn Val Lys
100 105 110

Asp Ile Thr Trp Gly Ile Thr Leu Val Leu Met Leu Arg Ser Val Gly
115 120 125

Gly Ile Thr Phe Gly Tyr Leu Gly Asp Arg Tyr Gly Arg Lys Trp Pro
130 135 140

Leu Val Ala Asn Leu Leu Ile Val Cys Ile Leu Glu Ile Gly Ser Gly
145 150 155 160

-continued

```
Phe Ile Lys Thr Tyr Arg Gln Phe Leu Gly Val Arg Ala Leu Phe Gly
                165                 170                 175

Ile Cys Leu Gly Gly Val Tyr Gly Asn Ala Thr Ala Thr Ala Leu Asp
            180                 185                 190

Asp Cys Pro Thr Glu Ala Arg Gly Phe Ile Gly Gly Leu Leu Gln Gln
        195                 200                 205

Gly Tyr Ala Phe Gly Tyr Leu Leu Ala Val Val Phe Lys Arg Ala Ile
    210                 215                 220

Ala Asp Asn Ser Ser His Lys Trp Arg Ala Thr Phe Trp Phe Gly Ala
225                 230                 235                 240

Gly Ile Ser Phe Leu Phe Ala Leu Phe Arg Ala Ser Leu Pro Glu Thr
                245                 250                 255

Lys Ala Phe Leu Arg Lys Lys Glu Ile Glu Arg Tyr Asn Lys Glu His
            260                 265                 270

Gly Ile Tyr Gln Pro Thr Phe Gln Met Lys Ile Val Glu Ser Leu Lys
        275                 280                 285

Asn Tyr Trp Leu Met Met Ile Tyr Leu Val Leu Phe Met Ser Gly Phe
    290                 295                 300

Ser Phe Met Ser His Ser Ser Gln Asp Leu Tyr Pro Thr Leu Leu Thr
305                 310                 315                 320

Val Arg Tyr Ser Phe Ser Glu Asn Lys Ala Thr Val Thr Asn Cys Val
                325                 330                 335

Ala Asn Ile Gly Ala Phe Ile Gly Gly Val Phe Thr Gly His Ile Ser
            340                 345                 350

Asn Phe Leu Gly Arg Arg Leu Thr Ile Met Leu Ile Cys Ile Phe Gly
        355                 360                 365

Gly Ala Leu Ile Tyr Pro Trp Ala Phe Ile Asp Gly Thr Gly Ile Asn
    370                 375                 380

Ala Gly Val Phe Phe Leu Gln Trp Cys Val Gln Gly Gly Leu Gly Val
385                 390                 395                 400

Val Pro Ser His Leu Ser Glu Leu Ala Pro Pro Asp Leu Arg Ala Phe
                405                 410                 415

Val Val Gly Ile Ser Tyr Gln Leu Gly Asn Leu Ala Ala Ser Ala Ser
            420                 425                 430

Ser Thr Ile Glu Thr Thr Ile Gly Glu Gln Phe Pro Met Thr Ser Pro
        435                 440                 445

Ser Gly Glu Pro Ile Tyr Asp Tyr Ala Lys Val Met Ala Ile Phe Val
    450                 455                 460

Gly Cys Val Phe Ala Phe Val Leu Ile Val Thr Leu Phe Gly Pro Glu
465                 470                 475                 480

Arg Arg Asn Ala Ser Phe Glu Asn Ala Val Thr Thr Asn Glu Glu Phe
                485                 490                 495

Gly Asn Ser Ala Gly Ala Val Asp Lys Ile Glu His Val Glu Glu Cys
            500                 505                 510

Ile Val Pro Lys His Ala Arg Asn Gln Gln Cys
        515                 520
```

<210> SEQ ID NO 25
<211> LENGTH: 4979
<212> TYPE: DNA
<213> ORGANISM: Saccharomyces cerevisiae

<400> SEQUENCE: 25

```
tccatggagg gcacagttaa gccgctaaag gcattatccg ccaagtacaa tttttactc     60
```

```
ttcgaagaca gaaaatttgc tgacattggt aatacagtca aattgcagta ctctgcgggt    120
gtatacagaa tagcagaatg ggcagacatt acgaatgcac acggtgtggt gggcccaggt    180
attgttagcg gtttgaagca ggcggcggaa gaagtaacaa aggaacctag aggccttttg    240
atgttagcag aattgtcatg caagggctcc ctagctactg gagaatatac taagggtact    300
gttgacattg cgaagagcga caaagatttt gttatcggct ttattgctca aagagacatg    360
ggtggaagag atgaaggtta cgattggttg attatgacac ccggtgtggg tttagatgac    420
aagggagacg cattgggtca acagtataga accgtggatg atgtggtctc tacaggatct    480
gacattatta ttgttggaag aggactattt gcaaagggaa gggatgctaa ggtagagggt    540
gaacgttaca gaaaagcagg ctgggaagca tatttgagaa gatgcggcca gcaaaactaa    600
aaaactgtat tataagtaaa tgcatgtata ctaaactcac aaattagagc ttcaatttaa    660
ttatatcagt tattacccgg gaatctcggt cgtaatgatt tttataatga cgaaaaaaaa    720
aaaattggaa agaaaaagct tcatggcctt tataaaaagg aaccatccaa tacctcgcca    780
gaaccaagta acagtatttt acggggcaca aatcaagaac aataagacag gactgtaaag    840
atggacgcat tgaactccaa agaacaacaa gagttccaaa aagtagtgga acaaaagcaa    900
atgaaggatt tcatgcgttt gataacttcg tataatgtat gctatacgaa gttatctcga    960
gatctcccct aaaccgtgga atatttcgga tatccttttg ttgtttccgg gtgtacaata   1020
tggacttcct cttttctggc aaccaaaccc atacatcggg attcctataa taccttcgtt   1080
ggtctcccta acatgtaggt ggcggagggg agatatacaa tagaacagat accagacaag   1140
acataatggg ctaaacaaga ctacaccatt tacactgcct cattgatggt ggtacataac   1200
gaactaatac tgtagcccta gacttgatag ccatcatcat atcgaagttt cactaccctt   1260
tttccatttg ccatctattg aagtaataat aggcgcatgc aacttctttt tttttttttt   1320
ttttctctct cccccgttgt tgtctcacca tatccgcaat gacaaaaaaa tgatggaaga   1380
cactaaagga aaaaattaac gacaaagaca gcaccaacag atgtcgttgt tccagagctg   1440
atgaggggta tctcgaagca cacgaaactt tttccttcct tcattcacgc acactactct   1500
ctaatgagca acggtatacg gccttccttc cagttacttg aatttgaaat aaaaaaaagt   1560
ttgctgtctt gctatcaagt ataaatagac ctgcaattat taatcttttg tttcctcgtc   1620
attgttctcg ttccctttct tccttgtttc tttttctgca caatatttca agctatacca   1680
agcatacaat caactatctc atatacatct agaatgtcgt cgtcaattac agatgagaaa   1740
atatctggtg aacagcaaca acctgctggc agaaaactat actataacac aagtacattt   1800
gcagagcctc ctctagtgga cggagaaggt aaccctataa attatgagcc ggaagtttac   1860
aacccggatc acgaaaagct ataccataac ccatcactgc ctgcacaatc aattcaggat   1920
acaagagatg atgaattgct ggaaagagtt tatagccagg atcaaggtgt agagtatgag   1980
gaagatgaag aggataagcc aaacctaagc gctgcgtcca ttaaaagtta tgctttaacg   2040
agatttacgt ccttactgca catccacgag ttttcttggg agaatgtcaa tcccataccc   2100
gaactgcgca aaatgacatg gcagaattgg aactattttt ttatgggtta ttttgcgtgg   2160
ttgtctgcgg cttgggcctt cttttgcgtt tcagtatcag tcgctccatt ggctgaacta   2220
tatgacagac caaccaagga catcacctgg gggttgggat tggtgttatt tgttcgttca   2280
gcaggtgctg tcatatttgg tttatggaca gataagtctt ccagaaagtg gccgtacatt   2340
acatgtttgt tcttatttgt cattgcacaa ctctgtactc catggtgtga cacatacgag   2400
aaatttctgg gcgtaaggtg gataaccggt attgctatgg gaggaattta cggatgtgct   2460
```

-continued

```
tctgcaacag cgattgaaga tgcacctgtg aaagcacgtt cgttcctatc aggtctattt   2520
ttttctgctt acgctatggg gttcatattt gctatcattt tttacagagc ctttggctac   2580
tttagggatg atggctggaa aatattgttt tggtttagta tttttctacc aattctacta   2640
attttctgga gattgttatg gcctgaaacg aaatacttca ccaaggtttt gaaagcccgt   2700
aaattaatat tgagtgacgc agtgaaagct aatggtggcg agcctctacc aaaagccaac   2760
tttaaacaaa agatggtatc catgaagaga acagttcaaa agtactggtt gttgttcgca   2820
tatttggttg ttttattggt gggtccaaat tacttgactc atgcttctca agacttgttg   2880
ccaaccatgc tgcgtgccca attaggccta tccaaggatg ctgtcactgt cattgtagtg   2940
gttaccaaca tcggtgctat ttgtgggggt atgatatttg gacagttcat ggaagttact   3000
ggaagaagat taggcctatt gattgcatgc acaatgggtg gttgcttcac ctaccctgca   3060
tttatgttga gaagcgaaaa ggctatatta ggtgccggtt tcatgttata tttttgtgtc   3120
tttggtgtct ggggtatcct gcccattcac cttgcagagt tggcccctgc tgatgcaagg   3180
gctttggttg ccggtttatc ttaccagcta ggtaatctag cttctgcagc ggcttccacg   3240
attgagacac agttagctga tagataccca ttagaaagag atgcctctgg tgctgtgatt   3300
aaagaagatt atgccaaagt tatggctatc ttgactggtt ctgttttcat cttcacattt   3360
gcttgtgttt ttgttggcca tgagaaattc catcgtgatt tgtcctctcc tgttatgaag   3420
aaatatataa accaagtgga agaatacgaa gccgatggtc tttcgattag tgacattgtt   3480
gaacaaaaga cggaatgtgc ttcagtgaag atgattgatt cgaacgtctc aaagacatat   3540
gaggagcata ttgagaccgt ttaattaatt taccagctta ctatccttct tgaaaatatg   3600
cactctatat cttttagttc ttaattgcaa cacatagatt tgctgtataa cgaattttat   3660
gctatttttt taatttggag ttcggtgatg aaagtgtcac agcgaatttc ctcacatgta   3720
gggaccgaat tgtttacaag ttctctgtac caccatggag acatcaaaga ttgaaaatct   3780
atggaaagat atggacggta gcaacaagaa tatagcacga gccgcggagt tcatttcgtt   3840
acttttgata tcgctcacaa ctattgcgaa gcgcttcagt gaaaaaatca taaggaaaag   3900
ttgtaaatat tattggtagt attcgtttgg taaagtagag gggtaattt ttcccctttta   3960
ttttgttcat acattcttaa attgctttgc ctctcctttt ggaaagctat acttcggagc   4020
actgttgagc gaaggctcag gccggcatat gacgttttat tacctttgat cacatttcca   4080
cgccatttcg cattctcacc ctcataagtc atacaccgaa aagaaagttt aagggatcaa   4140
tgagcttact ataatctcag tatatttatt tttatcgatg attcaccaca acaatcttgc   4200
tcccgaaaag aaagcagacg gagtagaagc atttgaaact ccttcagacc ttcaagtata   4260
tatatatata tatatatatg tatatgtgta cattttcacg ctaatactaa tgtataatta   4320
gaagataatt tttactcatt tttcgttatc ttcacgtcac ccgaacctag aaccaaatgt   4380
cattttcacg atatgtaaat agtgaaatag gcaaaaacgc caaaaagtag taagcgcaac   4440
atacactaaa ccattaaaga atatctcgac cagaatctaa cagatataca tgttccgata   4500
atgtctgagt taggtgagta ttctaaatta gaaaacaaag agcttagaac ggagtttgaa   4560
ttgacaaatt ttcctttttcc aggcacaact gataacgact ccgatgacgg aagccaaggg   4620
cagaactctt tgaatatcat tactcctgac atggatgata ctctggttaa tgatgtactt   4680
cgagaaaacg ataaaaagtc tagtatgaga atggctttta tgaatctagc aaactctatt   4740
cttggtgccg gaataattac tcagccgttc gcgatcaaaa atgctggtat attaggcggg   4800
```

```
ctattatcat acgtagccct cggatttata gttgattgga cgttaagact tattgtcatt   4860

aacttgactc ttgctggcaa gagaacatac cagggtacgg tcgaacatgt aatgggtaaa   4920

aaagggaaat tgctgattct atttacaaac gggttatttg catttggtgg atgtattgg    4979


<210> SEQ ID NO 26
<211> LENGTH: 616
<212> TYPE: PRT
<213> ORGANISM: Saccharomyces cerevisiae

<400> SEQUENCE: 26

Met Ser Ser Ser Ile Thr Asp Glu Lys Ile Ser Gly Glu Gln Gln Gln
1               5                   10                  15

Pro Ala Gly Arg Lys Leu Tyr Tyr Asn Thr Ser Thr Phe Ala Glu Pro
            20                  25                  30

Pro Leu Val Asp Gly Glu Gly Asn Pro Ile Asn Tyr Glu Pro Glu Val
        35                  40                  45

Tyr Asn Pro Asp His Glu Lys Leu Tyr His Asn Pro Ser Leu Pro Ala
    50                  55                  60

Gln Ser Ile Gln Asp Thr Arg Asp Asp Glu Leu Leu Glu Arg Val Tyr
65                  70                  75                  80

Ser Gln Asp Gln Gly Val Glu Tyr Glu Glu Asp Glu Glu Asp Lys Pro
                85                  90                  95

Asn Leu Ser Ala Ala Ser Ile Lys Ser Tyr Ala Leu Thr Arg Phe Thr
            100                 105                 110

Ser Leu Leu His Ile His Glu Phe Ser Trp Glu Asn Val Asn Pro Ile
        115                 120                 125

Pro Glu Leu Arg Lys Met Thr Trp Gln Asn Trp Asn Tyr Phe Phe Met
    130                 135                 140

Gly Tyr Phe Ala Trp Leu Ser Ala Ala Trp Ala Phe Phe Cys Val Ser
145                 150                 155                 160

Val Ser Val Ala Pro Leu Ala Glu Leu Tyr Asp Arg Pro Thr Lys Asp
                165                 170                 175

Ile Thr Trp Gly Leu Gly Leu Val Leu Phe Val Arg Ser Ala Gly Ala
            180                 185                 190

Val Ile Phe Gly Leu Trp Thr Asp Lys Ser Ser Arg Lys Trp Pro Tyr
        195                 200                 205

Ile Thr Cys Leu Phe Leu Phe Val Ile Ala Gln Leu Cys Thr Pro Trp
    210                 215                 220

Cys Asp Thr Tyr Glu Lys Phe Leu Gly Val Arg Trp Ile Thr Gly Ile
225                 230                 235                 240

Ala Met Gly Gly Ile Tyr Gly Cys Ala Ser Ala Thr Ala Ile Glu Asp
                245                 250                 255

Ala Pro Val Lys Ala Arg Ser Phe Leu Ser Gly Leu Phe Phe Ser Ala
            260                 265                 270

Tyr Ala Met Gly Phe Ile Phe Ala Ile Ile Phe Tyr Arg Ala Phe Gly
        275                 280                 285

Tyr Phe Arg Asp Asp Gly Trp Lys Ile Leu Phe Trp Phe Ser Ile Phe
    290                 295                 300

Leu Pro Ile Leu Leu Ile Phe Trp Arg Leu Leu Trp Pro Glu Thr Lys
305                 310                 315                 320

Tyr Phe Thr Lys Val Leu Lys Ala Arg Lys Leu Ile Leu Ser Asp Ala
                325                 330                 335

Val Lys Ala Asn Gly Gly Glu Pro Leu Pro Lys Ala Asn Phe Lys Gln
            340                 345                 350
```

```
Lys Met Val Ser Met Lys Arg Thr Val Gln Lys Tyr Trp Leu Leu Phe
        355                 360                 365

Ala Tyr Leu Val Val Leu Leu Val Gly Pro Asn Tyr Leu Thr His Ala
    370                 375                 380

Ser Gln Asp Leu Leu Pro Thr Met Leu Arg Ala Gln Leu Gly Leu Ser
385                 390                 395                 400

Lys Asp Ala Val Thr Val Ile Val Val Val Thr Asn Ile Gly Ala Ile
                405                 410                 415

Cys Gly Gly Met Ile Phe Gly Gln Phe Met Glu Val Thr Gly Arg Arg
            420                 425                 430

Leu Gly Leu Leu Ile Ala Cys Thr Met Gly Gly Cys Phe Thr Tyr Pro
        435                 440                 445

Ala Phe Met Leu Arg Ser Glu Lys Ala Ile Leu Gly Ala Gly Phe Met
    450                 455                 460

Leu Tyr Phe Cys Val Phe Gly Val Trp Gly Ile Leu Pro Ile His Leu
465                 470                 475                 480

Ala Glu Leu Ala Pro Ala Asp Ala Arg Ala Leu Val Ala Gly Leu Ser
                485                 490                 495

Tyr Gln Leu Gly Asn Leu Ala Ser Ala Ala Ala Ser Thr Ile Glu Thr
            500                 505                 510

Gln Leu Ala Asp Arg Tyr Pro Leu Glu Arg Asp Ala Ser Gly Ala Val
        515                 520                 525

Ile Lys Glu Asp Tyr Ala Lys Val Met Ala Ile Leu Thr Gly Ser Val
    530                 535                 540

Phe Ile Phe Thr Phe Ala Cys Val Phe Val Gly His Glu Lys Phe His
545                 550                 555                 560

Arg Asp Leu Ser Ser Pro Val Met Lys Lys Tyr Ile Asn Gln Val Glu
                565                 570                 575

Glu Tyr Glu Ala Asp Gly Leu Ser Ile Ser Asp Ile Val Glu Gln Lys
            580                 585                 590

Thr Glu Cys Ala Ser Val Lys Met Ile Asp Ser Asn Val Ser Lys Thr
        595                 600                 605

Tyr Glu Glu His Ile Glu Thr Val
    610                 615


<210> SEQ ID NO 27
<211> LENGTH: 4935
<212> TYPE: DNA
<213> ORGANISM: Artificial Sequence
<220> FEATURE:
<223> OTHER INFORMATION: Sequence put together from multiple organisms:
      Saccharomyces cerevisiae and Kluyveromyces lactis.

<400> SEQUENCE: 27

tccatggagg gcacagttaa gccgctaaag gcattatccg ccaagtacaa tttttactc      60

ttcgaagaca gaaaatttgc tgacattggt aatacagtca aattgcagta ctctgcgggt    120

gtatacagaa tagcagaatg ggcagacatt acgaatgcac acggtgtggt gggcccaggt    180

attgttagcg gtttgaagca ggcggcggaa gaagtaacaa aggaacctag aggccttttg    240

atgttagcag aattgtcatg caagggctcc ctagctactg gagaatatac taagggtact    300

gttgacattg cgaagagcga caaagatttt gttatcggct ttattgctca aagagacatg    360

ggtggaagag atgaaggtta cgattggttg attatgacac ccggtgtggg tttagatgac    420

aagggagacg cattgggtca acagtataga accgtggatg atgtggtctc tacaggatct    480
```

```
gacattatta ttgttggaag aggactattt gcaaagggaa gggatgctaa ggtagagggt    540
gaacgttaca gaaaagcagg ctgggaagca tatttgagaa gatgcggcca gcaaaactaa    600
aaaactgtat tataagtaaa tgcatgtata ctaaactcac aaattagagc ttcaatttaa    660
ttatatcagt tattacccgg gaatctcggt cgtaatgatt tttataatga cgaaaaaaaa    720
aaaattggaa agaaaaagct tcatggcctt tataaaaagg aaccatccaa tacctcgcca    780
gaaccaagta acagtatttt acggggcaca aatcaagaac aataagacag gactgtaaag    840
atggacgcat tgaactccaa agaacaacaa gagttccaaa aagtagtgga acaaaagcaa    900
atgaaggatt tcatgcgttt gataacttcg tataatgtat gctatacgaa gttatctcga    960
gatctcccct aaaccgtgga atatttcgga tatccttttg ttgtttccgg gtgtacaata   1020
tggacttcct cttttctggc aaccaaaccc atacatcggg attcctataa taccttcgtt   1080
ggtctcccta acatgtaggt ggcggagggg agatatacaa tagaacagat accagacaag   1140
acataatggg ctaaacaaga ctacaccatt tacactgcct cattgatggt ggtacataac   1200
gaactaatac tgtagcccta gacttgatag ccatcatcat atcgaagttt cactaccctt   1260
tttccatttg ccatctattg aagtaataat aggcgcatgc aacttctttt tttttttttt   1320
ttttctctct cccccgttgt tgtctcacca tatccgcaat gacaaaaaaa tgatggaaga   1380
cactaaagga aaaaattaac gacaaagaca gcaccaacag atgtcgttgt tccagagctg   1440
atgaggggta tctcgaagca cacgaaactt tttccttcct tcattcacgc acactactct   1500
ctaatgagca acggtatacg gccttccttc cagttacttg aatttgaaat aaaaaaaagt   1560
ttgctgtctt gctatcaagt ataaatagac ctgcaattat taatcttttg tttcctcgtc   1620
attgttctcg ttccctttct tccttgtttc tttttctgca caatatttca agctatacca   1680
agcatacaat caactatctc atatacatct agaatgaata acaacaacat tacaccagag   1740
tcagactcaa tgaagagtaa cgataacgat caaaccaatg attacatgcc agatgtggct   1800
gatttcgatc atacacaaac aaacacaaac gaaattgcta gagcaatttc tcacccaggt   1860
tctgttctgt caagagttgc aagctacgtc agcagaaagg acagatacgt agacgagaat   1920
ggcaatgaag tttggcaaga cgatgaagtg agtatcctaa tggaggaaga tgagactcct   1980
gatttcacat ggaaaaacat tagacattac gctatcacta gattcactac attgacagaa   2040
cttcacagag tgtctatgga aaacatcaac ccaattccag aattgagaaa aatgacatta   2100
cataattgga actacttctt tatggggtat gccgcgtggt tgtgtgctgc ttgggcattt   2160
ttcgccgttt ccgttagtac agcccctctt gcaacccttt atggcaagga aacaaaagac   2220
atttcatggg gtctatcctt agtcttattc gtcagatctg ctggagcgat tatctttggc   2280
atctggaccg acaattactc cagaaagtgg ccatacatta catgcttagg tcttttcttg   2340
atctgtcagc tttgcacacc ttgggcaaag acctacactc aattcttggg agttcgttgg   2400
atttccggta tcgcaatggg tggaatttac gcctgtgctt ctgcaacagc gattgaggat   2460
gcaccagtaa aggctcgttc tttcttatcc ggcttattct tcactgccta cgccatgggt   2520
tttatcttcg caataatctt ttacagagca ttcttaaacg tcaacggtga aaactactgg   2580
aaggttcaat tctggttttc aatatggtta ccagctgtac tgatattgtg gagactcgta   2640
tggccagaaa ctaagtactt caccaaagta ctaaaagcta gacaactaat gcgtgatgat   2700
gcaatagcca aaaacggtgg tcaaccactc ccaaagttgt ctttcaagca aaagttcgcc   2760
aatgtgaaaa agaccgttag taaatactgg cttttgtttg gttacttaat tctcttgttg   2820
gttggtccta actacctaac acacgcctct caagacttgt ttcctacaat gttaagagca   2880
```

```
caattgagat tttctgaaga tgctgtcacc gtggccattg tagttgtttg tctgggtagc   2940
attgctgggg ggatgttttt cggacagttg atggagatca ctggtagaag agttggccta   3000
ctattggccc taatcatggc tggctgcttt acttaccctg ccttcatgct taaaacttca   3060
tctgcagtgc tgggggcagg ctttatgctc tggttctcaa tcttaggtgt gtggggtgtt   3120
ttaccaatcc atttatcaga attgtcccct ccagaagcta gagcattagt ctctggatta   3180
gcatatcagc tgggtaatct agcttcagca gcttctgttg ttatagagaa tgatttggcg   3240
gatttgtatc caatagaatg gaattctgct ggagaagtta caaacaagga ctactctaag   3300
gtaatggcta ttcttacagg ttcttcagtc attttcactt tcgtgttggt tttcgttggt   3360
cacgaaaagt ttcatagaga tttgtcatcc ccacatctta agtcatacat cgagagagtc   3420
gatcaaacag aagaggtcgc agctatgact ggatctactg cgaactctat ctctagtaag   3480
ccttcagatg atcagctcga aaaagtttca gtctagttaa ttaatttacc agcttactat   3540
ccttcttgaa aatatgcact ctatatcttt tagttcttaa ttgcaacaca tagatttgct   3600
gtataacgaa ttttatgcta ttttttaat ttggagttcg gtgatgaaag tgtcacagcg    3660
aatttcctca catgtaggga ccgaattgtt tacaagttct ctgtaccacc atggagacat   3720
caaagattga aaatctatgg aaagatatgg acggtagcaa caagaatata gcacgagccg   3780
cggagttcat ttcgttactt ttgatatcgc tcacaactat tgcgaagcgc ttcagtgaaa   3840
aaatcataag gaaaagttgt aaatattatt ggtagtattc gtttggtaaa gtagaggggg   3900
taatttttcc cctttatttt gttcatacat tcttaaattg ctttgcctct ccttttggaa   3960
agctatactt cggagcactg ttgagcgaag gctcaggccg gcatatgacg ttttattacc   4020
tttgatcaca tttccacgcc atttcgcatt ctcaccctca taagtcatac accgaaaaga   4080
aagtttaagg gatcaatgag cttactataa tctcagtata tttattttta tcgatgattc   4140
accacaacaa tcttgctccc gaaaagaaag cagacggagt agaagcattt gaaactcctt   4200
cagaccttca agtatatata tatatatata tatatgtata tgtgtacatt ttcacgctaa   4260
tactaatgta taattagaag ataattttta ctcatttttc gttatcttca cgtcacccga   4320
acctagaacc aaatgtcatt ttcacgatat gtaaatagtg aaataggcaa aaacgccaaa   4380
aagtagtaag cgcaacatac actaaaccat taaagaatat ctcgaccaga atctaacaga   4440
tatacatgtt ccgataatgt ctgagttagg tgagtattct aaattagaaa acaaagagct   4500
tagaacggag tttgaattga caaattttcc ttttccaggc acaactgata acgactccga   4560
tgacggaagc caagggcaga actctttgaa tatcattact cctgacatgg atgatactct   4620
ggttaatgat gtacttcgag aaaacgataa aaagtctagt atgagaatgg cttttatgaa   4680
tctagcaaac tctattcttg gtgccggaat aattactcag ccgttcgcga tcaaaaatgc   4740
tggtatatta ggcgggctat tatcatacgt agccctcgga tttatagttg attggacgtt   4800
aagacttatt gtcattaact tgactcttgc tggcaagaga acataccagg gtacggtcga   4860
acatgtaatg ggtaaaaaag ggaaattgct gattctattt acaaacgggt tatttgcatt   4920
tggtggatgt attgg                                                     4935
```

<210> SEQ ID NO 28
<211> LENGTH: 600
<212> TYPE: PRT
<213> ORGANISM: Kluyveromyces lactis

<400> SEQUENCE: 28

```
Met Asn Asn Asn Asn Ile Thr Pro Glu Ser Asp Ser Met Lys Ser Asn
1               5                   10                  15

Asp Asn Asp Gln Thr Asn Asp Tyr Met Pro Asp Val Ala Asp Phe Asp
            20                  25                  30

His Thr Gln Thr Asn Thr Asn Glu Ile Ala Arg Ala Ile Ser His Pro
        35                  40                  45

Gly Ser Val Leu Ser Arg Val Ala Ser Tyr Val Ser Arg Lys Asp Arg
    50                  55                  60

Tyr Val Asp Glu Asn Gly Asn Glu Val Trp Gln Asp Asp Glu Val Ser
65                  70                  75                  80

Ile Leu Met Glu Glu Asp Glu Thr Pro Asp Phe Thr Trp Lys Asn Ile
                85                  90                  95

Arg His Tyr Ala Ile Thr Arg Phe Thr Thr Leu Thr Glu Leu His Arg
            100                 105                 110

Val Ser Met Glu Asn Ile Asn Pro Ile Pro Glu Leu Arg Lys Met Thr
        115                 120                 125

Leu His Asn Trp Asn Tyr Phe Phe Met Gly Tyr Ala Ala Trp Leu Cys
    130                 135                 140

Ala Ala Trp Ala Phe Phe Ala Val Ser Val Ser Thr Ala Pro Leu Ala
145                 150                 155                 160

Thr Leu Tyr Gly Lys Glu Thr Lys Asp Ile Ser Trp Gly Leu Ser Leu
                165                 170                 175

Val Leu Phe Val Arg Ser Ala Gly Ala Ile Ile Phe Gly Ile Trp Thr
            180                 185                 190

Asp Asn Tyr Ser Arg Lys Trp Pro Tyr Ile Thr Cys Leu Gly Leu Phe
        195                 200                 205

Leu Ile Cys Gln Leu Cys Thr Pro Trp Ala Lys Thr Tyr Thr Gln Phe
    210                 215                 220

Leu Gly Val Arg Trp Ile Ser Gly Ile Ala Met Gly Gly Ile Tyr Ala
225                 230                 235                 240

Cys Ala Ser Ala Thr Ala Ile Glu Asp Ala Pro Val Lys Ala Arg Ser
                245                 250                 255

Phe Leu Ser Gly Leu Phe Phe Thr Ala Tyr Ala Met Gly Phe Ile Phe
            260                 265                 270

Ala Ile Ile Phe Tyr Arg Ala Phe Leu Asn Val Asn Gly Glu Asn Tyr
        275                 280                 285

Trp Lys Val Gln Phe Trp Phe Ser Ile Trp Leu Pro Ala Val Leu Ile
    290                 295                 300

Leu Trp Arg Leu Val Trp Pro Glu Thr Lys Tyr Phe Thr Lys Val Leu
305                 310                 315                 320

Lys Ala Arg Gln Leu Met Arg Asp Asp Ala Ile Ala Lys Asn Gly Gly
                325                 330                 335

Gln Pro Leu Pro Lys Leu Ser Phe Lys Gln Lys Phe Ala Asn Val Lys
            340                 345                 350

Lys Thr Val Ser Lys Tyr Trp Leu Leu Phe Gly Tyr Leu Ile Leu Leu
        355                 360                 365

Leu Val Gly Pro Asn Tyr Leu Thr His Ala Ser Gln Asp Leu Phe Pro
    370                 375                 380

Thr Met Leu Arg Ala Gln Leu Arg Phe Ser Glu Asp Ala Val Thr Val
385                 390                 395                 400

Ala Ile Val Val Val Cys Leu Gly Ser Ile Ala Gly Gly Met Phe Phe
                405                 410                 415

Gly Gln Leu Met Glu Ile Thr Gly Arg Arg Val Gly Leu Leu Leu Ala
```

```
            420                 425                 430

Leu Ile Met Ala Gly Cys Phe Thr Tyr Pro Ala Phe Met Leu Lys Thr
        435                 440                 445

Ser Ser Ala Val Leu Gly Ala Gly Phe Met Leu Trp Phe Ser Ile Leu
    450                 455                 460

Gly Val Trp Gly Val Leu Pro Ile His Leu Ser Glu Leu Ser Pro Pro
465                 470                 475                 480

Glu Ala Arg Ala Leu Val Ser Gly Leu Ala Tyr Gln Leu Gly Asn Leu
                485                 490                 495

Ala Ser Ala Ala Ser Val Val Ile Glu Asn Asp Leu Ala Asp Leu Tyr
            500                 505                 510

Pro Ile Glu Trp Asn Ser Ala Gly Glu Val Thr Asn Lys Asp Tyr Ser
        515                 520                 525

Lys Val Met Ala Ile Leu Thr Gly Ser Ser Val Ile Phe Thr Phe Val
    530                 535                 540

Leu Val Phe Val Gly His Glu Lys Phe His Arg Asp Leu Ser Ser Pro
545                 550                 555                 560

His Leu Lys Ser Tyr Ile Glu Arg Val Asp Gln Thr Glu Glu Val Ala
                565                 570                 575

Ala Met Thr Gly Ser Thr Ala Asn Ser Ile Ser Ser Lys Pro Ser Asp
            580                 585                 590

Asp Gln Leu Glu Lys Val Ser Val
        595                 600
```

<210> SEQ ID NO 29
<211> LENGTH: 3981
<212> TYPE: DNA
<213> ORGANISM: Saccharomyces cerevisiae

<400> SEQUENCE: 29

```
tccatggagg gcacagttaa gccgctaaag gcattatccg ccaagtacaa tttttttactc     60

ttcgaagaca gaaaatttgc tgacattggt aatacagtca aattgcagta ctctgcgggt    120

gtatacagaa tagcagaatg ggcagacatt acgaatgcac acggtgtggt gggcccaggt    180

attgttagcg gtttgaagca ggcggcggaa gaagtaacaa aggaacctag aggccttttg    240

atgttagcag aattgtcatg caagggctcc ctagctactg gagaatatac taagggtact    300

gttgacattg cgaagagcga caaagatttt gttatcggct ttattgctca aagagacatg    360

ggtggaagag atgaaggtta cgattggttg attatgacac ccggtgtggg tttagatgac    420

aagggagacg cattgggtca acagtataga accgtggatg atgtggtctc tacaggatct    480

gacattatta ttgttggaag aggactattt gcaaagggaa gggatgctaa ggtagagggt    540

gaacgttaca gaaaagcagg ctgggaagca tatttgagaa gatgcggcca gcaaaactaa    600

aaaactgtat tataagtaaa tgcatgtata ctaaactcac aaattagagc ttcaatttaa    660

ttatatcagt tattacccgg gaatctcggt cgtaatgatt tttataatga cgaaaaaaaa    720

aaaattggaa agaaaaagct tcatggcctt tataaaaagg aaccatccaa tacctcgcca    780

gaaccaagta acagtatttt acggggcaca aatcaagaac aataagacag gactgtaaag    840

atggacgcat tgaactccaa agaacaacaa gagttccaaa aagtagtgga acaaaagcaa    900

atgaaggatt tcatgcgttt gataacttcg tataatgtat gctatacgaa gttatctcga    960

gatctcccct aaaccgtgga atatttcgga tatccttttg ttgtttccgg gtgtacaata   1020

tggacttcct cttttctggc aaccaaaccc atacatcggg attcctataa taccttcgtt   1080
```

```
ggtctcccta acatgtaggt ggcggagggg agatatacaa tagaacagat accagacaag   1140
acataatggg ctaaacaaga ctacaccatt tacactgcct cattgatggt ggtacataac   1200
gaactaatac tgtagcccta gacttgatag ccatcatcat atcgaagttt cactaccctt   1260
tttccatttg ccatctattg aagtaataat aggcgcatgc aacttctttt tttttttttt   1320
ttttctctct cccccgttgt tgtctcacca tatccgcaat gacaaaaaaa tgatggaaga   1380
cactaaagga aaaaattaac gacaaagaca gcaccaacag atgtcgttgt tccagagctg   1440
atgaggggta tctcgaagca cacgaaactt tttccttcct tcattcacgc acactactct   1500
ctaatgagca acggtatacg gccttccttc cagttacttg aatttgaaat aaaaaaaagt   1560
ttgctgtctt gctatcaagt ataaatagac ctgcaattat taatcttttg tttcctcgtc   1620
attgttctcg ttccctttct tccttgtttc tttttctgca caatatttca agctatacca   1680
agcatacaat caactatctc atatacatct agaatgtcag acaaagagca aacatctggt   1740
aataccgatt tagaaaacgc tccagcaggg tactacagct cccacgataa tgacgtcaac   1800
ggtgttgcag aagatgaaag accttcacat gattctttgg gtaagattta cactggaggt   1860
gataacaacg agtacatcta tatcgggaga caaaagtttt tgaaatctga cttgtatcaa   1920
gcattcggag ggactttgaa tcctggtctt gctccagcac ctgttcataa gttcgccaac   1980
ccagctccac ttggcttatc agcttttgct ctgacaacat tcgttttaag tatgttcaac   2040
gcaagagcac agggcattac agtgccaaac gttgttgtag gctgcgcaat gttctacggt   2100
ggtttagttc aactaattgc tggtatatgg gagatcgcac tagaaaacac ctttggtggc   2160
actgcgttgt gttcatacgg aggtttctgg ctttcttttg ccgctattta cattccttgg   2220
ttcggaatcc tggaagcata cgaggataac gaatcagatt tgaacaatgc cctaggtttc   2280
tacctcttag ggtgggcaat tttcacattt ggtttaactg tatgtacaat gaagtctacc   2340
gtcatgtttt tcctgctatt cttcttagtg gccttgacat tcttgctctt atctatcgga   2400
cactttgcca atagacttgg cgtgactaga gctggcggtg tgttgggagt tgtcgttgcc   2460
ttcataggtt ggtataatgc gtacgctggt gtagcgacta aacagaactc ctacgtcttg   2520
gctagaccat ttccacttcc aagtacagaa cgtgttatct tcttaattaa tttaccagct   2580
tactatcctt cttgaaaata tgcactctat atcttttagt tcttaattgc aacacataga   2640
tttgctgtat aacgaatttt atgctatttt tttaatttgg agttcggtga tgaaagtgtc   2700
acagcgaatt tcctcacatg tagggaccga attgtttaca agttctctgt accaccatgg   2760
agacatcaaa gattgaaaat ctatggaaag atatggacgg tagcaacaag aatatagcac   2820
gagccgcgga gttcatttcg ttacttttga tatcgctcac aactattgcg aagcgcttca   2880
gtgaaaaaat cataaggaaa agttgtaaat attattggta gtattcgttt ggtaaagtag   2940
agggggtaat tttcccctt tattttgttc atacattctt aaattgcttt gcctctcctt   3000
ttggaaagct atacttcgga gcactgttga gcgaaggctc aggccggcat atgacgtttt   3060
attacctttg atcacatttc cacgccattt cgcattctca ccctcataag tcatacaccg   3120
aaaagaaagt ttaagggatc aatgagctta ctataatctc agtatattta tttttatcga   3180
tgattcacca caacaatctt gctcccgaaa agaaagcaga cggagtagaa gcatttgaaa   3240
ctccttcaga ccttcaagta tatatatata tatatatata tgtatatgtg tacattttca   3300
cgctaatact aatgtataat tagaagataa tttttactca tttttcgtta tcttcacgtc   3360
acccgaacct agaaccaaat gtcattttca cgatatgtaa atagtgaaat aggcaaaaac   3420
gccaaaaagt agtaagcgca acatacacta aaccattaaa gaatatctcg accagaatct   3480
```

```
aacagatata catgttccga taatgtctga gttaggtgag tattctaaat tagaaaacaa   3540

agagcttaga acggagtttg aattgacaaa ttttcctttt ccaggcacaa ctgataacga   3600

ctccgatgac ggaagccaag ggcagaactc tttgaatatc attactcctg acatggatga   3660

tactctggtt aatgatgtac ttcgagaaaa cgataaaaag tctagtatga gaatggcttt   3720

tatgaatcta gcaaactcta ttcttggtgc cggaataatt actcagccgt tcgcgatcaa   3780

aaatgctggt atattaggcg ggctattatc atacgtagcc ctcggattta tagttgattg   3840

gacgttaaga cttattgtca ttaacttgac tcttgctggc aagagaacat accagggtac   3900

ggtcgaacat gtaatgggta aaaaagggaa attgctgatt ctatttacaa acgggttatt   3960

tgcatttggt ggatgtattg g                                              3981
```

<210> SEQ ID NO 30
<211> LENGTH: 293
<212> TYPE: PRT
<213> ORGANISM: Saccharomyces cerevisiae

<400> SEQUENCE: 30

```
Met Ser Asp Lys Glu Gln Thr Ser Gly Asn Thr Asp Leu Glu Asn Ala
1               5                   10                  15

Pro Ala Gly Tyr Tyr Ser Ser His Asp Asn Asp Val Asn Gly Val Ala
            20                  25                  30

Glu Asp Glu Arg Pro Ser His Asp Ser Leu Gly Lys Ile Tyr Thr Gly
        35                  40                  45

Gly Asp Asn Asn Glu Tyr Ile Tyr Ile Gly Arg Gln Lys Phe Leu Lys
    50                  55                  60

Ser Asp Leu Tyr Gln Ala Phe Gly Gly Thr Leu Asn Pro Gly Leu Ala
65                  70                  75                  80

Pro Ala Pro Val His Lys Phe Ala Asn Pro Ala Pro Leu Gly Leu Ser
                85                  90                  95

Ala Phe Ala Leu Thr Thr Phe Val Leu Ser Met Phe Asn Ala Arg Ala
            100                 105                 110

Gln Gly Ile Thr Val Pro Asn Val Val Val Gly Cys Ala Met Phe Tyr
        115                 120                 125

Gly Gly Leu Val Gln Leu Ile Ala Gly Ile Trp Glu Ile Ala Leu Glu
    130                 135                 140

Asn Thr Phe Gly Gly Thr Ala Leu Cys Ser Tyr Gly Gly Phe Trp Leu
145                 150                 155                 160

Ser Phe Ala Ala Ile Tyr Ile Pro Trp Phe Gly Ile Leu Glu Ala Tyr
                165                 170                 175

Glu Asp Asn Glu Ser Asp Leu Asn Asn Ala Leu Gly Phe Tyr Leu Leu
            180                 185                 190

Gly Trp Ala Ile Phe Thr Phe Gly Leu Thr Val Cys Thr Met Lys Ser
        195                 200                 205

Thr Val Met Phe Phe Leu Leu Phe Phe Leu Val Ala Leu Thr Phe Leu
    210                 215                 220

Leu Leu Ser Ile Gly His Phe Ala Asn Arg Leu Gly Val Thr Arg Ala
225                 230                 235                 240

Gly Gly Val Leu Gly Val Val Val Ala Phe Ile Gly Trp Tyr Asn Ala
                245                 250                 255

Tyr Ala Gly Val Ala Thr Lys Gln Asn Ser Tyr Val Leu Ala Arg Pro
            260                 265                 270

Phe Pro Leu Pro Ser Thr Glu Arg Val Ile Phe Leu Ile Asn Leu Pro
```

```
        275                 280                 285

Ala Tyr Tyr Pro Ser
    290


<210> SEQ ID NO 31
<211> LENGTH: 3921
<212> TYPE: DNA
<213> ORGANISM: Artificial Sequence
<220> FEATURE:
<223> OTHER INFORMATION: Sequence put together from multiple organisms:
      Saccharomyces cerevisiae and Aggregatibacter
      actinomycetemcomitans.

<400> SEQUENCE: 31

tcctattcgg agatacaggc aacaagtgat agagggccca ttatgaatac gcacctctat     60

gtatttccga gatacgatta ctccagttcc tcttacaaga aatgcataaa aatagttaca    120

attaattaga acaagaactt atttagaaca cgttcacact gagtaagaac tcttgtccct    180

tattagcctt gatagtgctg aaaaaaagaa aaaaaacaaa aaaaagaaat aaaataacgg    240

caaacagcaa aggccacaga accgtattca tgttacttct gcaatatcaa tcacttactg    300

gcaagtgcgt ataaattaaa cctatttctt tatcatcata tttacttata tctttaacag    360

attccaaacc ctaaagtgtc cgaattttca atagggcgaa cttgaagaat aaccaaggtc    420

aataatatat cttttagtat aaccctgaaa tttgccctat agaaatctag ggtttctgtg    480

tggtttccgg gtgagtcata cggctttttt gaatttcttt ttttgcagtt gtctctatca    540

atgaaaattt cgaggaagac gataaggtta agataagtag ataagagaat gatacgagat    600

aaagcacaaa ttagcagaaa gaagagtggt tgcgaacaga gtaaaccgaa tcagggaatc    660

ccttttttgca aaaacatcaa ttatcctttt ctttttttta cgtatatatc tggaacagaa    720

atatataagt tactattata cttatagttg gatccagttt ttaatctgtc gtcaatcgaa    780

agtttatttc agagttcttc agacttctta actcctgtaa aaacaaaaaa aaaaaaaggc    840

atagcactcg agatctcccg agtttatcat tatcaatact gccatttcaa agaatacgta    900

aataattaat agtagtgatt ttcctaactt tatttagtca aaaaattggc cttttaattc    960

tgctgtaacc cgtacatgcc caaaataggg ggcgggttac acagaatata taacatcata   1020

ggtgtctggg tgaacagttt attcctggca tccactaaat ataatggagc ccgctttttt   1080

taagctggca tccagaaaaa aaaagaatcc cagcaccaaa atattgtttt cttcaccaac   1140

catcagttca taggtccatt ctcttagcgc aactacacag aacaggggca caaacaggca   1200

aaaaacgggc acaacctcaa tggagtgatg caacctgctt ggagtaaatg atgacacaag   1260

gcaattgacc tacgcatgta tctatctcat tttcttacac cttctattac cttctgctct   1320

ctctgatttg gaaaaagctg aaaaaaaagg ttgaaaccag ttccctgaaa ttattcccct   1380

atttgactaa taagtatata aagacggtag gtattgattg taattctgta aatctatttc   1440

ttaaacttct taaattctac ttttatagtt agtctttttt ttagtttaaa acaccaagaa   1500

cttagtttcg aataaacaca cataaacaaa caaatctaga atgaaagtgg cagtgtactc   1560

aacaaaatct tacgacagaa agtacctcga actgatagat gcgaagtacg gattggattt   1620

ggaattctac gacttcatgc tttctgaacg tactgctaag atggccgaac attgcgaagc   1680

cgtttgtatc tttgttaacg atgatggctc cagaaaggta cttgaaaagt tagctgcttt   1740

gggtgttaag ataattgcac ttagatgcgc tggatttaac aatgtggacc ttaaagcagc   1800

acaagagcta gggctaacag ttgtgagagt tccagcatac tcaccagagg cagtcgcaga   1860
```

acatacagtt ggattaatga tgaccctaaa tagacgtatt cacagagctt accagagaac 1920
aagagaagcc aatttctctt tagagggtct aatcgggttc aatatgtacg gtagaactgt 1980
tggtgtcatt ggtactggga agatcggtgt tgctgtgatg agaattttga agggtttcgg 2040
catgcatata ctggcttttg atccattcaa aaacccaact gctgaggaac tcggcgctga 2100
atatgtctct ttagatgaga tttacagaag atctcacgtt attacattgc attgtcctgc 2160
cacccctgaa aactatcatt tgttaaacag agaagccttt gctaaaatga aggatggagt 2220
catgatcatc aatacatcaa gaggtacact catagacacc aaggcggcca ttgacgccct 2280
aaagcaacgt aaaatcggtg cattaggtat ggatgtttac gagaacgaaa gagatttgtt 2340
cttcgaggat aagtcaaacg aagtaatcct ggacgatgta ttcagaagat taagtagctg 2400
ccataacgtc ttattgacag gacaccaagc gtttttgaca gaggaagcat tgacttccat 2460
tgctgatgta actcttagta acatttacgc aatcggtaaa ggcaagccat gtgataacgt 2520
cgttttgtca tcttagttaa ttaaacaggc cccttttcct ttgtcgatat catgtaatta 2580
gttatgtcac gcttacattc acgccctcct cccacatccg ctctaaccga aaaggaagga 2640
gttagacaac ctgaagtcta ggtccctatt tattttttta tagttatgtt agtattaaga 2700
acgttattta tatttcaaat ttttcttttt tttctgtaca aacgcgtgta cgcatgtaac 2760
gggcagacgg ccggccataa cttcgtataa tgtatgctat acgaagttat ggcaacggtt 2820
catcatctca tggatctgca catgaacaaa caccagagtc aaacgacgtt gaaattgagg 2880
ctactgcgcc aattgatgac aatacagacg atgataacaa accgaagtta tctgatgtag 2940
aaaaggatta gagatgctaa gagatagtga tgatatttca taaataatgt aattctatat 3000
atgttaatta cctttttttgc gaggcatatt tatggtgaag gataagtttt gaccatcaaa 3060
gaaggttaat gtggctgtgg tttcagggtc cataaagctt ttcaattcat cttttttttt 3120
tttgttcttt tttttgattc cggtttcttt gaaatttttt tgattcggta atctccgagc 3180
agaaggaaga acgaaggaag gagcacagac ttagattggt atatatacgc atatgtggtg 3240
ttgaagaaac atgaaattgc ccagtattct taacccaact gcacagaaca aaaacctgca 3300
ggaaacgaag ataaatcatg tcgaaagcta catataagga acgtgctgct actcatccta 3360
gtcctgttgc tgccaagcta tttaatatca tgcacgaaaa gcaaacaaac ttgtgtgctt 3420
cattggatgt tcgtaccacc aaggaattac tggagttagt tgaagcatta ggtcccaaaa 3480
tttgtttact aaaaacacat gtggatatct tgactgattt ttccatggag ggcacagtta 3540
agccgctaaa ggcattatcc gccaagtaca atttttact cttcgaagac agaaaatttg 3600
ctgacattgg taatacagtc aaattgcagt actctgcggg tgtatacaga atagcagaat 3660
gggcagacat tacgaatgca cacggtgtgg tgggcccagg tattgttagc ggtttgaagc 3720
aggcggcgga agaagtaaca aaggaaccta gaggcctttt gatgttagca gaattgtcat 3780
gcaagggctc cctagctact ggagaatata ctaagggtac tgttgacatt gcgaagagcg 3840
acaaagattt tgttatcggc tttattgctc aaagagacat gggtggaaga gatgaaggtt 3900
acgattggtt gattatgaca c 3921

<210> SEQ ID NO 32
<211> LENGTH: 331
<212> TYPE: PRT
<213> ORGANISM: Aggregatibacter actinomycetemcomitans

<400> SEQUENCE: 32

Met Lys Val Ala Val Tyr Ser Thr Lys Ser Tyr Asp Arg Lys Tyr Leu

-continued

```
1               5                   10                  15

Glu Leu Ile Asp Ala Lys Tyr Gly Leu Asp Leu Glu Phe Tyr Asp Phe
            20                  25                  30

Met Leu Ser Glu Arg Thr Ala Lys Met Ala Glu His Cys Glu Ala Val
        35                  40                  45

Cys Ile Phe Val Asn Asp Asp Gly Ser Arg Lys Val Leu Glu Lys Leu
    50                  55                  60

Ala Ala Leu Gly Val Lys Ile Ile Ala Leu Arg Cys Ala Gly Phe Asn
65                  70                  75                  80

Asn Val Asp Leu Lys Ala Ala Gln Glu Leu Gly Leu Thr Val Val Arg
                85                  90                  95

Val Pro Ala Tyr Ser Pro Glu Ala Val Ala Glu His Thr Val Gly Leu
            100                 105                 110

Met Met Thr Leu Asn Arg Arg Ile His Arg Ala Tyr Gln Arg Thr Arg
        115                 120                 125

Glu Ala Asn Phe Ser Leu Glu Gly Leu Ile Gly Phe Asn Met Tyr Gly
    130                 135                 140

Arg Thr Val Gly Val Ile Gly Thr Gly Lys Ile Gly Val Ala Val Met
145                 150                 155                 160

Arg Ile Leu Lys Gly Phe Gly Met His Ile Leu Ala Phe Asp Pro Phe
                165                 170                 175

Lys Asn Pro Thr Ala Glu Glu Leu Gly Ala Glu Tyr Val Ser Leu Asp
            180                 185                 190

Glu Ile Tyr Arg Arg Ser His Val Ile Thr Leu His Cys Pro Ala Thr
        195                 200                 205

Pro Glu Asn Tyr His Leu Leu Asn Arg Glu Ala Phe Ala Lys Met Lys
    210                 215                 220

Asp Gly Val Met Ile Ile Asn Thr Ser Arg Gly Thr Leu Ile Asp Thr
225                 230                 235                 240

Lys Ala Ala Ile Asp Ala Leu Lys Gln Arg Lys Ile Gly Ala Leu Gly
                245                 250                 255

Met Asp Val Tyr Glu Asn Glu Arg Asp Leu Phe Phe Glu Asp Lys Ser
            260                 265                 270

Asn Glu Val Ile Leu Asp Asp Val Phe Arg Arg Leu Ser Ser Cys His
        275                 280                 285

Asn Val Leu Leu Thr Gly His Gln Ala Phe Leu Thr Glu Glu Ala Leu
    290                 295                 300

Thr Ser Ile Ala Asp Val Thr Leu Ser Asn Ile Tyr Ala Ile Gly Lys
305                 310                 315                 320

Gly Lys Pro Cys Asp Asn Val Val Leu Ser Ser
                325                 330
```

<210> SEQ ID NO 33
<211> LENGTH: 3924
<212> TYPE: DNA
<213> ORGANISM: Artificial Sequence
<220> FEATURE:
<223> OTHER INFORMATION: Sequence put together from multiple organisms: Saccharomyces cerevisiae and Ornithorhynchus anatinus.

<400> SEQUENCE: 33

```
tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180
```

-continued

```
tattagcctt gatagtgctg aaaaaaagaa aaaaaacaaa aaaaagaaat aaaataacgg    240
caaacagcaa aggccacaga accgtattca tgttacttct gcaatatcaa tcacttactg    300
gcaagtgcgt ataaattaaa cctatttctt tatcatcata tttacttata tctttaacag    360
attccaaacc ctaaagtgtc cgaattttca atagggcgaa cttgaagaat aaccaaggtc    420
aataatatat cttttagtat aaccctgaaa tttgccctat agaaatctag ggtttctgtg    480
tggtttccgg gtgagtcata cggctttttt gaatttcttt ttttgcagtt gtctctatca    540
atgaaaattt cgaggaagac gataaggtta agataagtag ataagagaat gatacgagat    600
aaagcacaaa ttagcagaaa gaagagtggt tgcgaacaga gtaaaccgaa tcagggaatc    660
ccttttttgca aaaacatcaa ttatcctttt ctttttttta cgtatatatc tggaacagaa   720
atatataagt tactattata cttatagttg gatccagttt ttaatctgtc gtcaatcgaa    780
agtttatttc agagttcttc agacttctta actcctgtaa aaacaaaaaa aaaaaaaggc    840
atagcactcg agatctcccg agtttatcat tatcaatact gccatttcaa agaatacgta    900
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atggctggtg ttaaagagca   1560
attgatccaa aacttactaa aggaagagta cgcacctcaa aacaagataa cagttgtggg   1620
ggttggagct gttggtatgg catgtgccat ttctatccta atgaaagatc tggctgatga   1680
gcttgccttg gtcgacgtaa tcgaagataa gctgaaggga gaaatgatgg atttacaaca   1740
cggttctctt ttcttgagaa caccaaagat agtctccggc aaagattaca gcgtgaccgc   1800
aaacagcaag ttagtgatta tcacagcggg agcaagacag caggaaggtg aatcaagatt   1860
gaatcttgtg caacgtaacg ttaacatatt caagtttatc atcccaaatg ttgttaagta   1920
cagtccaaat tgcaagttgt tggttgtttc caatcctgtt gatattctta cttatgttgc   1980
atggaaaatc tcaggttttc ctaaaaacag agtcataggt tcaggttgta acctagattc   2040
tgccagattc agatacttaa tgggtgaaag attaggcatt cattctactt cctgccatgg   2100
gtgggtgatt ggtgaacatg gagactcctc agttccagtg tggtctggtg tcaacgtagc   2160
gggcgttagt ttgaaaaacc ttcaccctga tttggggact gacgcagaca aggaacagtg   2220
gaaagatgtt cataagcaag tagtagattc tgcttacgaa gtcattaagt taaagggcta   2280
cacatcttgg gctattggtt tgagtgtcgc tgatctggca gagtcaatcg tcaaaaactt   2340
aagacgtgta cacccaatct ctacaatgat taaaggctta tacggtatta aggacgaagt   2400
ttttctatca gtaccatgtg ttctcggaca aaatggaatt tcagacgttg tcaagatcac   2460
cctcaagtct gaggaagagg cccatttgaa aaagtcagct gatactttgt ggggtattca   2520
aaaggaacta caattctagt taattaaaca ggccccttttt cctttgtcga tatcatgtaa  2580
```

```
ttagttatgt cacgcttaca ttcacgccct cctcccacat ccgctctaac cgaaaaggaa   2640

ggagttagac aacctgaagt ctaggtccct atttattttt ttatagttat gttagtatta   2700

agaacgttat ttatatttca aatttttctt ttttttctgt acaaacgcgt gtacgcatgt   2760

aacgggcaga cggccggcca taacttcgta taatgtatgc tatacgaagt tatggcaacg   2820

gttcatcatc tcatggatct gcacatgaac aaacaccaga gtcaaacgac gttgaaattg   2880

aggctactgc gccaattgat gacaatacag acgatgataa caaaccgaag ttatctgatg   2940

tagaaaagga ttagagatgc taagagatag tgatgatatt tcataaataa tgtaattcta   3000

tatatgttaa ttaccttttt tgcgaggcat atttatggtg aaggataagt tttgaccatc   3060

aaagaaggtt aatgtggctg tggtttcagg gtccataaag cttttcaatt catctttttt   3120

ttttttgttc tttttttttga ttccggtttc tttgaaattt ttttgattcg gtaatctccg   3180

agcagaagga agaacgaagg aaggagcaca gacttagatt ggtatatata cgcatatgtg   3240

gtgttgaaga aacatgaaat tgcccagtat tcttaaccca actgcacaga acaaaaacct   3300

gcaggaaacg aagataaatc atgtcgaaag ctacatataa ggaacgtgct gctactcatc   3360

ctagtcctgt tgctgccaag ctatttaata tcatgcacga aaagcaaaca aacttgtgtg   3420

cttcattgga tgttcgtacc accaaggaat tactggagtt agttgaagca ttaggtccca   3480

aaatttgttt actaaaaaca catgtggata tcttgactga tttttccatg gagggcacag   3540

ttaagccgct aaaggcatta tccgccaagt acaatttttt actcttcgaa gacagaaaat   3600

ttgctgacat tggtaataca gtcaaattgc agtactctgc gggtgtatac agaatagcag   3660

aatgggcaga cattacgaat gcacacggtg tggtgggccc aggtattgtt agcggtttga   3720

agcaggcggc ggaagaagta acaaaggaac ctagaggcct tttgatgtta gcagaattgt   3780

catgcaaggg ctccctagct actggagaat atactaaggg tactgttgac attgcgaaga   3840

gcgacaaaga ttttgttatc ggctttattg ctcaaagaga catgggtgga agagatgaag   3900

gttacgattg gttgattatg acac                                           3924
```

<210> SEQ ID NO 34
<211> LENGTH: 332
<212> TYPE: PRT
<213> ORGANISM: Ornithorhynchus anatinus

<400> SEQUENCE: 34

```
Met Ala Gly Val Lys Glu Gln Leu Ile Gln Asn Leu Leu Lys Glu Glu
1               5                   10                  15

Tyr Ala Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125
```

```
Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Asp Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
    290                 295                 300

Lys Ile Thr Leu Lys Ser Glu Glu Glu Ala His Leu Lys Lys Ser Ala
305                 310                 315                 320

Asp Thr Leu Trp Gly Ile Gln Lys Glu Leu Gln Phe
                325                 330
```

<210> SEQ ID NO 35
<211> LENGTH: 4641
<212> TYPE: DNA
<213> ORGANISM: Artificial Sequence
<220> FEATURE:
<223> OTHER INFORMATION: Sequence put together from multiple organisms: Saccharomyces cerevisiae and Acetobacter aceti.

<400> SEQUENCE: 35

```
tcctattcgg agatacaggc aacaagtgat agagggccca ttatgaatac gcacctctat     60

gtatttccga gatacgatta ctccagttcc tcttacaaga aatgcataaa aatagttaca    120

attaattaga acaagaactt atttagaaca cgttcacact gagtaagaac tcttgtccct    180

tattagcctt gatagtgctg aaaaaaagaa aaaaaacaaa aaaaagaaat aaaataacgg    240

caaacagcaa aggccacaga accgtattca tgttacttct gcaatatcaa tcacttactg    300

gcaagtgcgt ataaattaaa cctatttctt tatcatcata tttacttata tctttaacag    360

attccaaacc ctaaagtgtc cgaattttca atagggcgaa cttgaagaat aaccaaggtc    420

aataatatat cttttagtat aaccctgaaa tttgccctat agaaatctag ggtttctgtg    480

tggtttccgg gtgagtcata cggctttttt gaatttcttt ttttgcagtt gtctctatca    540

atgaaaattt cgaggaagac gataaggtta agataagtag ataagagaat gatacgagat    600

aaagcacaaa ttagcagaaa gaagagtggt tgcgaacaga gtaaaccgaa tcagggaatc    660

ccttttttgca aaaacatcaa ttatcctttt cttttttttta cgtatatatc tggaacagaa    720

atatataagt tactattata cttatagttg gatccagttt ttaatctgtc gtcaatcgaa    780

agtttatttc agagttcttc agacttctta actcctgtaa aaacaaaaaa aaaaaaaggc    840

atagcactcg agatctcccg agtttatcat tatcaatact gccatttcaa agaatacgta    900
```

```
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgacaaccg ctgcagaaaa   1560
caacaagcaa ttacttgaac aactgaaaaa catagctggt caacatcacg ttctaacagg   1620
tgaagattct acttacagat tcacacacgg ttttagattt ggtgctggaa aagttctagc   1680
agtagtccaa ccagggtctt taatcgagct gtggagagta gcagacgctt gtgtcaatgc   1740
ggacaagatc atcattatgc aggccgccaa tactggtttg actggtggat caacacctga   1800
tggtaataac tacgacagag atattgtttt gatttcaacc ttgagattag acaaatctca   1860
tctcattggc aatggtaagc aagtggtatg ccttcctggt gctacactat atgaactaga   1920
gtccaagttg gccgctatcg gcagagaacc tcattcagta ataggttcat cttgcatcgg   1980
ggcaagtgtc ttgggaggcg tgtctaacaa ctctgggggt gccttggtcc aaagagggcc   2040
agcatacaca gagatggctg tttttggtca ggttggcaag gatggaaagc ttcaattggt   2100
taatcacttg ggtattaagt tgggaaacga tccagaagcc attttgcaga aactagaagc   2160
aggcacattt actgaggctg acatcgattg ggacgcgggt aagggtcatg atggcgatta   2220
cattaaccat gttagagaaa ttgatgcgga tactccagcg agatacaacg ctgatccagc   2280
acgttggtac gaagctgctg gatgtgctgg aaagttggtc gttttcgccg ttagattgga   2340
tactttccca gccaataagg acacatccgt cttttacatt ggaacaaaca atacagatga   2400
actagaaaat ctccgtagac atgtgttaac tgcatttgat gaattaccaa tttgtggtga   2460
atacattcat agagatgcct ttaacattgc agagaaatac ggtaaggata cctttgctgt   2520
tataagatac ttcggtacca agttcttacc aaaaatgttc gcaatgaaat ccagattcga   2580
tatcttcgcc aaaaagttag gcttcttgcc agaccacttg tctgatagaa taatgcaagc   2640
actaagtact cttttaccaa gacagcttcc tcaacgtatg ttagactaca gagacaagta   2700
cgaacatcac ctgatgctaa aggtcagcca taatctcgca ggcccaatga gacaatactt   2760
acaaacatac ttcggttcag ctacaggtga ctatttcgag tgtactccag aggaaggcaa   2820
gcttgcattc cttcatagat tcgctgcagc aggcgctgct gtcagataca gagcagtaca   2880
ccataaggaa gcagaggata tcgttgcttt agatgtggca ttacgtagaa acgatagaga   2940
gtggttcgaa aagctccctc aggacatcga aaacaaactg atagtgaagc tttactacgg   3000
acatttcttg tgccatgtta tgcaccaaga ttacgttgtg aaaaagggtt ataacgcaat   3060
cgccgttgaa cacgagatgt tgccaggttt ggatgccaga ggtgctagat acccagccga   3120
acacaacgtt ggtcatttgt acaaagctcc acaaaaacatg ttagatcatt atcagcaact   3180
ggatccttgc aactgtatga atcctggaat cgggcaaggg accaagagaa aaaactgggt   3240
```

-continued

```
agcggaatca gtttagttaa ttaaacaggc cccttttcct ttgtcgatat catgtaatta   3300

gttatgtcac gcttacattc acgccctcct cccacatccg ctctaaccga aaaggaagga   3360

gttagacaac ctgaagtcta ggtccctatt tattttttta tagttatgtt agtattaaga   3420

acgttattta tatttcaaat ttttcttttt tttctgtaca aacgcgtgta cgcatgtaac   3480

gggcagacgg ccggccataa cttcgtataa tgtatgctat acgaagttat ggcaacggtt   3540

catcatctca tggatctgca catgaacaaa caccagagtc aaacgacgtt gaaattgagg   3600

ctactgcgcc aattgatgac aatacagacg atgataacaa accgaagtta tctgatgtag   3660

aaaaggatta gagatgctaa gagatagtga tgatatttca taaataatgt aattctatat   3720

atgttaatta ccttttttgc gaggcatatt tatggtgaag gataagtttt gaccatcaaa   3780

gaaggttaat gtggctgtgg tttcagggtc cataaagctt ttcaattcat cttttttttt   3840

tttgttcttt tttttgattc cggtttcttt gaaatttttt tgattcggta atctccgagc   3900

agaaggaaga acgaaggaag gagcacagac ttagattggt atatatacgc atatgtggtg   3960

ttgaagaaac atgaaattgc ccagtattct taacccaact gcacagaaca aaaacctgca   4020

ggaaacgaag ataaatcatg tcgaaagcta catataagga acgtgctgct actcatccta   4080

gtcctgttgc tgccaagcta tttaatatca tgcacgaaaa gcaaacaaac ttgtgtgctt   4140

cattggatgt tcgtaccacc aaggaattac tggagttagt tgaagcatta ggtcccaaaa   4200

tttgtttact aaaaacacat gtggatatct tgactgattt ttccatggag ggcacagtta   4260

agccgctaaa ggcattatcc gccaagtaca attttttact cttcgaagac agaaaatttg   4320

ctgacattgg taatacagtc aaattgcagt actctgcggg tgtatacaga atagcagaat   4380

gggcagacat tacgaatgca cacggtgtgg tgggcccagg tattgttagc ggtttgaagc   4440

aggcggcgga agaagtaaca aaggaaccta gaggcctttt gatgttagca gaattgtcat   4500

gcaagggctc cctagctact ggagaatata ctaagggtac tgttgacatt gcgaagagcg   4560

acaaagattt tgttatcggc tttattgctc aaagagacat gggtggaaga gatgaaggtt   4620

acgattggtt gattatgaca c                                              4641
```

<210> SEQ ID NO 36
<211> LENGTH: 571
<212> TYPE: PRT
<213> ORGANISM: Acetobacter aceti

<400> SEQUENCE: 36

```
Met Thr Thr Ala Ala Glu Asn Asn Lys Gln Leu Leu Glu Gln Leu Lys
1               5                   10                  15

Asn Ile Ala Gly Gln His His Val Leu Thr Gly Glu Asp Ser Thr Tyr
            20                  25                  30

Arg Phe Thr His Gly Phe Arg Phe Gly Ala Gly Lys Val Leu Ala Val
        35                  40                  45

Val Gln Pro Gly Ser Leu Ile Glu Leu Trp Arg Val Ala Asp Ala Cys
    50                  55                  60

Val Asn Ala Asp Lys Ile Ile Ile Met Gln Ala Ala Asn Thr Gly Leu
65                  70                  75                  80

Thr Gly Gly Ser Thr Pro Asp Gly Asn Asn Tyr Asp Arg Asp Ile Val
                85                  90                  95

Leu Ile Ser Thr Leu Arg Leu Asp Lys Ser His Leu Ile Gly Asn Gly
            100                 105                 110

Lys Gln Val Val Cys Leu Pro Gly Ala Thr Leu Tyr Glu Leu Glu Ser
        115                 120                 125
```

-continued

```
Lys Leu Ala Ala Ile Gly Arg Glu Pro His Ser Val Ile Gly Ser Ser
    130                 135                 140

Cys Ile Gly Ala Ser Val Leu Gly Gly Val Ser Asn Asn Ser Gly Gly
145                 150                 155                 160

Ala Leu Val Gln Arg Gly Pro Ala Tyr Thr Glu Met Ala Val Phe Gly
                165                 170                 175

Gln Val Gly Lys Asp Gly Lys Leu Gln Leu Val Asn His Leu Gly Ile
            180                 185                 190

Lys Leu Gly Asn Asp Pro Glu Ala Ile Leu Gln Lys Leu Glu Ala Gly
        195                 200                 205

Thr Phe Thr Glu Ala Asp Ile Asp Trp Asp Ala Gly Lys Gly His Asp
    210                 215                 220

Gly Asp Tyr Ile Asn His Val Arg Glu Ile Asp Ala Asp Thr Pro Ala
225                 230                 235                 240

Arg Tyr Asn Ala Asp Pro Ala Arg Trp Tyr Glu Ala Ala Gly Cys Ala
                245                 250                 255

Gly Lys Leu Val Val Phe Ala Val Arg Leu Asp Thr Phe Pro Ala Asn
            260                 265                 270

Lys Asp Thr Ser Val Phe Tyr Ile Gly Thr Asn Asn Thr Asp Glu Leu
        275                 280                 285

Glu Asn Leu Arg Arg His Val Leu Thr Ala Phe Asp Glu Leu Pro Ile
    290                 295                 300

Cys Gly Glu Tyr Ile His Arg Asp Ala Phe Asn Ile Ala Glu Lys Tyr
305                 310                 315                 320

Gly Lys Asp Thr Phe Ala Val Ile Arg Tyr Phe Gly Thr Lys Phe Leu
                325                 330                 335

Pro Lys Met Phe Ala Met Lys Ser Arg Phe Asp Ile Phe Ala Lys Lys
            340                 345                 350

Leu Gly Phe Leu Pro Asp His Leu Ser Asp Arg Ile Met Gln Ala Leu
        355                 360                 365

Ser Thr Leu Leu Pro Arg Gln Leu Pro Gln Arg Met Leu Asp Tyr Arg
    370                 375                 380

Asp Lys Tyr Glu His His Leu Met Leu Lys Val Ser His Asn Leu Ala
385                 390                 395                 400

Gly Pro Met Arg Gln Tyr Leu Gln Thr Tyr Phe Gly Ser Ala Thr Gly
                405                 410                 415

Asp Tyr Phe Glu Cys Thr Pro Glu Glu Gly Lys Leu Ala Phe Leu His
            420                 425                 430

Arg Phe Ala Ala Ala Gly Ala Ala Val Arg Tyr Arg Ala Val His His
        435                 440                 445

Lys Glu Ala Glu Asp Ile Val Ala Leu Asp Val Ala Leu Arg Arg Asn
    450                 455                 460

Asp Arg Glu Trp Phe Glu Lys Leu Pro Gln Asp Ile Glu Asn Lys Leu
465                 470                 475                 480

Ile Val Lys Leu Tyr Tyr Gly His Phe Leu Cys His Val Met His Gln
                485                 490                 495

Asp Tyr Val Val Lys Lys Gly Tyr Asn Ala Ile Ala Val Glu His Glu
            500                 505                 510

Met Leu Pro Gly Leu Asp Ala Arg Gly Ala Arg Tyr Pro Ala Glu His
        515                 520                 525

Asn Val Gly His Leu Tyr Lys Ala Pro Gln Asn Met Leu Asp His Tyr
    530                 535                 540
```

```
Gln Gln Leu Asp Pro Cys Asn Cys Met Asn Pro Gly Ile Gly Gln Gly
545                 550                 555                 560

Thr Lys Arg Lys Asn Trp Val Ala Glu Ser Val
                565                 570


<210> SEQ ID NO 37
<211> LENGTH: 4360
<212> TYPE: DNA
<213> ORGANISM: Artificial Sequence
<220> FEATURE:
<223> OTHER INFORMATION: Sequence put together from multiple organisms:
      Saccharomyces cerevisiae and Gluconobacter oxydans.

<400> SEQUENCE: 37

tcctattcgg agatacaggc aacaagtgat agagggccca ttatgaatac gcacctctat     60

gtatttccga gatacgatta ctccagttcc tcttacaaga aatgcataaa aatagttaca    120

attaattaga acaagaactt atttagaaca cgttcacact gagtaagaac tcttgtccct    180

tattagcctt gatagtgctg aaaaaaagaa aaaaaacaaa aaaaagaaat aaaataacgg    240

caaacagcaa aggccacaga accgtattca tgttacttct gcaatatcaa tcacttactg    300

gcaagtgcgt ataaattaaa cctatttctt tatcatcata tttacttata tctttaacag    360

attccaaacc ctaaagtgtc cgaattttca atagggcgaa cttgaagaat aaccaaggtc    420

aataatatat cttttagtat aaccctgaaa tttgccctat agaaatctag ggtttctgtg    480

tggtttccgg gtgagtcata cggctttttt gaatttcttt ttttgcagtt gtctctatca    540

atgaaaattt cgaggaagac gataaggtta agataagtag ataagagaat gatacgagat    600

aaagcacaaa ttagcagaaa gaagagtggt tgcgaacaga gtaaaccgaa tcagggaatc    660

cctttttgca aaaacatcaa ttatcctttt cttttttttta cgtatatatc tggaacagaa    720

atatataagt tactattata cttatagttg gatccagttt ttaatctgtc gtcaatcgaa    780

agtttatttc agagttcttc agacttctta actcctgtaa aaacaaaaaa aaaaaaaggc    840

atagcactcg agatctcccg agtttatcat tatcaatact gccatttcaa agaatacgta    900

aataattaat agtagtgatt ttcctaactt tatttagtca aaaaattggc cttttaattc    960

tgctgtaacc cgtacatgcc caaaataggg ggcgggttac acagaatata taacatcata   1020

ggtgtctggg tgaacagttt attcctggca tccactaaat ataatggagc ccgctttttt   1080

taagctggca tccagaaaaa aaaagaatcc cagcaccaaa atattgtttt cttcaccaac   1140

catcagttca taggtccatt ctcttagcgc aactacacag aacaggggca caaacaggca   1200

aaaaacgggc acaacctcaa tggagtgatg caacctgctt ggagtaaatg atgacacaag   1260

gcaattgacc tacgcatgta tctatctcat tttcttacac cttctattac cttctgctct   1320

ctctgatttg gaaaaagctg aaaaaaaagg ttgaaaccag ttccctgaaa ttattcccct   1380

atttgactaa taagtatata aagacggtag gtattgattg taattctgta aatctatttc   1440

ttaaacttct taaattctac ttttatagtt agtctttttt ttagtttaaa acaccaagaa   1500

cttagtttcg aataaacaca cataaacaaa caaatctaga atgccagaac cagttatgac   1560

agcctcctct gcatctgctc cagatagact acaagccgta ttgaaagcct tacagccagt   1620

tatgggagaa cgtatatcta ctgctccttc cgttagagag gagcatagtc atggtgaggc   1680

tatgaacgct tccaaccttc ctgaagcagt agtttttgct gaatctactc aagatgttgc   1740

aaccgttctc agacactgcc acgaatggcg tgtcccagtc gttgcattcg gtgcaggaac   1800

ttcagtagag ggtcacgtgg tgccacctga acaagcaata agtcttgatc tgagtagaat   1860
```

-continued

```
gactgggatt gtggacttga acgcagaaga tttggattgt agagtccaag ctggtataac   1920
tagacaaacc cttaacgtcg agattagaga cactggccta ttctttccag tcgatcctgg   1980
tggtgaggca acaatcggtg gaatgtgtgc cacaagagct tcaggtacag cagcagttag   2040
atacggtaca atgaaggaaa atgttttagg actcacagtg gttttagcca ctggtgaaat   2100
cattagaaca ggaggaagag tcagaaagtc tagtacagga tatgatttaa cctctttgtt   2160
cgtcggctct gaaggcacac tgggaattat caccgaggtt caattaagac tacatggccg   2220
tcctgattca gtttcagctg caatttgtca atttgagtca ttgcatgacg ccattcaaac   2280
agctatggaa atcatccaat gcggtattcc aatcacaaga gtagaattga tggacagcgt   2340
tcaaatggca gcctcaatcc agtactctgg cctcaacgaa taccaacctc taacaacttt   2400
attcttcgaa ttcacaggct ctcctgctgc cgtcagagaa caggtggaaa ctacagaggc   2460
tatagcttcc ggtaataacg gtctaggttt cgcgtgggct gaatccccag aagatagaac   2520
tagattgtgg aaggccagac atgatgctta ctgggcggct aaagcgattg ttcctgatgc   2580
aagagttatt tctacagatt gtatcgttcc aatttcaaga ttaggtgaac ttattgaagg   2640
tgtccataga gatattgaag catcaggtct gagagcccca cttttgggcc atgtgggtga   2700
tgggaacttt cacacattga tcataaccga cgacactcca gagggtcatc agcaagcttt   2760
ggatttggat agaaagatcg tggctcgtgc acttagccta aatgggtcat gctctgggga   2820
acacggcgta ggtatgggga agttagagtt cttagagaca gaacacgggc ctggttcatt   2880
gtctgttatg agagcattga aaaacaccat ggacccacat catatcttaa atccaggaaa   2940
gctgttgcca ccaggcgcgg tatacactgg ttagttaatt aaacaggccc cttttccttt   3000
gtcgatatca tgtaattagt tatgtcacgc ttacattcac gccctcctcc cacatccgct   3060
ctaaccgaaa aggaaggagt tagacaacct gaagtctagg tccctattta ttttttttata   3120
gttatgttag tattaagaac gttatttata tttcaaattt ttctttttttt tctgtacaaa   3180
cgcgtgtacg catgtaacgg gcagacggcc ggccataact tcgtataatg tatgctatac   3240
gaagttatgg caacggttca tcatctcatg gatctgcaca tgaacaaaca ccagagtcaa   3300
acgacgttga aattgaggct actgcgccaa ttgatgacaa tacagacgat gataacaaac   3360
cgaagttatc tgatgtagaa aaggattaga gatgctaaga gatagtgatg atatttcata   3420
aataatgtaa ttctatatat gttaattacc ttttttgcga ggcatattta tggtgaagga   3480
taagttttga ccatcaaaga aggttaatgt ggctgtggtt tcagggtcca taaagctttt   3540
caattcatct tttttttttt tgttcttttt tttgattccg gtttctttga aattttttttg   3600
attcggtaat ctccgagcag aaggaagaac gaaggaagga gcacagactt agattggtat   3660
atatacgcat atgtggtgtt gaagaaacat gaaattgccc agtattctta acccaactgc   3720
acagaacaaa aacctgcagg aaacgaagat aaatcatgtc gaaagctaca tataaggaac   3780
gtgctgctac tcatcctagt cctgttgctg ccaagctatt taatatcatg cacgaaaagc   3840
aaacaaactt gtgtgcttca ttggatgttc gtaccaccaa ggaattactg gagttagttg   3900
aagcattagg tcccaaaatt tgtttactaa aaacacatgt ggatatcttg actgattttt   3960
ccatggaggg cacagttaag ccgctaaagg cattatccgc caagtacaat tttttactct   4020
tcgaagacag aaaatttgct gacattggta atacagtcaa attgcagtac tctgcgggtg   4080
tatacagaat agcagaatgg gcagacatta cgaatgcaca cggtgtggtg ggcccaggta   4140
ttgttagcgg tttgaagcag gcggcggaag aagtaacaaa ggaacctaga ggccttttga   4200
tgttagcaga attgtcatgc aagggctccc tagctactgg agaatatact aagggtactg   4260
```

ttgacattgc gaagagcgac aaagattttg ttatcggctt tattgctcaa agagacatgg 4320
gtggaagaga tgaaggttac gattggttga ttatgacacg 4360

<210> SEQ ID NO 38
<211> LENGTH: 477
<212> TYPE: PRT
<213> ORGANISM: Gluconobacter oxydans

<400> SEQUENCE: 38

Met Pro Glu Pro Val Met Thr Ala Ser Ser Ala Ser Ala Pro Asp Arg
1 5 10 15

Leu Gln Ala Val Leu Lys Ala Leu Gln Pro Val Met Gly Glu Arg Ile
20 25 30

Ser Thr Ala Pro Ser Val Arg Glu Glu His Ser His Gly Glu Ala Met
35 40 45

Asn Ala Ser Asn Leu Pro Glu Ala Val Val Phe Ala Glu Ser Thr Gln
50 55 60

Asp Val Ala Thr Val Leu Arg His Cys His Glu Trp Arg Val Pro Val
65 70 75 80

Val Ala Phe Gly Ala Gly Thr Ser Val Glu Gly His Val Val Pro Pro
85 90 95

Glu Gln Ala Ile Ser Leu Asp Leu Ser Arg Met Thr Gly Ile Val Asp
100 105 110

Leu Asn Ala Glu Asp Leu Asp Cys Arg Val Gln Ala Gly Ile Thr Arg
115 120 125

Gln Thr Leu Asn Val Glu Ile Arg Asp Thr Gly Leu Phe Phe Pro Val
130 135 140

Asp Pro Gly Gly Glu Ala Thr Ile Gly Gly Met Cys Ala Thr Arg Ala
145 150 155 160

Ser Gly Thr Ala Ala Val Arg Tyr Gly Thr Met Lys Glu Asn Val Leu
165 170 175

Gly Leu Thr Val Val Leu Ala Thr Gly Glu Ile Ile Arg Thr Gly Gly
180 185 190

Arg Val Arg Lys Ser Ser Thr Gly Tyr Asp Leu Thr Ser Leu Phe Val
195 200 205

Gly Ser Glu Gly Thr Leu Gly Ile Ile Thr Glu Val Gln Leu Arg Leu
210 215 220

His Gly Arg Pro Asp Ser Val Ser Ala Ala Ile Cys Gln Phe Glu Ser
225 230 235 240

Leu His Asp Ala Ile Gln Thr Ala Met Glu Ile Ile Gln Cys Gly Ile
245 250 255

Pro Ile Thr Arg Val Glu Leu Met Asp Ser Val Gln Met Ala Ala Ser
260 265 270

Ile Gln Tyr Ser Gly Leu Asn Glu Tyr Gln Pro Leu Thr Thr Leu Phe
275 280 285

Phe Glu Phe Thr Gly Ser Pro Ala Ala Val Arg Glu Gln Val Glu Thr
290 295 300

Thr Glu Ala Ile Ala Ser Gly Asn Asn Gly Leu Gly Phe Ala Trp Ala
305 310 315 320

Glu Ser Pro Glu Asp Arg Thr Arg Leu Trp Lys Ala Arg His Asp Ala
325 330 335

Tyr Trp Ala Ala Lys Ala Ile Val Pro Asp Ala Arg Val Ile Ser Thr
340 345 350

```
Asp Cys Ile Val Pro Ile Ser Arg Leu Gly Glu Leu Ile Glu Gly Val
        355                 360                 365

His Arg Asp Ile Glu Ala Ser Gly Leu Arg Ala Pro Leu Leu Gly His
    370                 375                 380

Val Gly Asp Gly Asn Phe His Thr Leu Ile Ile Thr Asp Asp Thr Pro
385                 390                 395                 400

Glu Gly His Gln Gln Ala Leu Asp Leu Asp Arg Lys Ile Val Ala Arg
                405                 410                 415

Ala Leu Ser Leu Asn Gly Ser Cys Ser Gly Glu His Gly Val Gly Met
            420                 425                 430

Gly Lys Leu Glu Phe Leu Glu Thr Glu His Gly Pro Gly Ser Leu Ser
        435                 440                 445

Val Met Arg Ala Leu Lys Asn Thr Met Asp Pro His His Ile Leu Asn
    450                 455                 460

Pro Gly Lys Leu Leu Pro Pro Gly Ala Val Tyr Thr Gly
465                 470                 475
```

<210> SEQ ID NO 39
<211> LENGTH: 4689
<212> TYPE: DNA
<213> ORGANISM: Saccharomyces cerevisiae

<400> SEQUENCE: 39

```
tcctattcgg agatacaggc aacaagtgat agagggccca ttatgaatac gcacctctat     60

gtatttccga gatacgatta ctccagttcc tcttacaaga aatgcataaa aatagttaca    120

attaattaga acaagaactt atttagaaca cgttcacact gagtaagaac tcttgtccct    180

tattagcctt gatagtgctg aaaaaaagaa aaaaaacaaa aaaaagaaat aaaataacgg    240

caaacagcaa aggccacaga accgtattca tgttacttct gcaatatcaa tcacttactg    300

gcaagtgcgt ataaattaaa cctatttctt tatcatcata tttacttata tctttaacag    360

attccaaacc ctaaagtgtc cgaattttca atagggcgaa cttgaagaat aaccaaggtc    420

aataatatat cttttagtat aaccctgaaa tttgccctat agaaatctag ggtttctgtg    480

tggtttccgg gtgagtcata cggctttttt gaatttcttt ttttgcagtt gtctctatca    540

atgaaaattt cgaggaagac gataaggtta agataagtag ataagagaat gatacgagat    600

aaagcacaaa ttagcagaaa gaagagtggt tgcgaacaga gtaaaccgaa tcagggaatc    660

cctttttgca aaaacatcaa ttatcctttt cttttttta cgtatatatc tggaacagaa    720

atatataagt tactattata cttatagttg gatccagttt ttaatctgtc gtcaatcgaa    780

agtttatttc agagttcttc agacttctta actcctgtaa aaacaaaaaa aaaaaaaggc    840

atagcactcg agatctcccg agtttatcat tatcaatact gccatttcaa agaatacgta    900

aataattaat agtagtgatt ttcctaactt tatttagtca aaaaattggc cttttaattc    960

tgctgtaacc cgtacatgcc caaaataggg ggcgggttac acagaatata taacatcata   1020

ggtgtctggg tgaacagttt attcctggca tccactaaat ataatggagc ccgctttttt   1080

taagctggca tccagaaaaa aaaagaatcc cagcaccaaa atattgtttt cttcaccaac   1140

catcagttca taggtccatt ctcttagcgc aactacacag aacaggggca caaacaggca   1200

aaaaacgggc acaacctcaa tggagtgatg caacctgctt ggagtaaatg atgacacaag   1260

gcaattgacc tacgcatgta tctatctcat tttcttacac cttctattac cttctgctct   1320

ctctgatttg gaaaaagctg aaaaaaaagg ttgaaaccag ttccctgaaa ttattcccct   1380

atttgactaa taagtatata aagacggtag gtattgattg taattctgta aatctatttc   1440
```

ttaaacttct taaattctac ttttatagtt agtctttttt ttagtttaaa acaccaagaa 1500
cttagtttcg aataaacaca cataaacaaa caaatctaga atgttgtgga agcgtacttg 1560
cacaaggcta ataaagccta ttgcacaacc tagaggaagg ctggtgagaa gatcatgcta 1620
cagatacgcc tcaacaggca caggcagcac cgacagcagc agtcagtggt taaaatactc 1680
tgtcatcgcc tcttcagcta ctctattcgg ttatttgttc gctaagaacc tctattctag 1740
ggagactaag gaggacctga tagagaaact ggaaatggtc aaaaagatcg acccagtaaa 1800
ttctacgtta aagctgtcct cattggactc accagactat ttgcacgacc cggccaagat 1860
cgataaggtt gttgaggacc tgaagcaggt gctgggaaac aagcctgaaa actactctga 1920
tgcgaaatcc gatttggacg cccattcaga tacctacttc aacacgcatc acccctctct 1980
cgagcaaaga cctaggatta tattattccc tcatactacc gaagaagttt ccaaaatttt 2040
gaaaatatgt cacgataaca acatgccagt tgtacccttc tcgggcggaa cgtccttgga 2100
ggggcacttc ctgcctacaa gaattggaga taccataacc gtagacctgt ccaagtttat 2160
gaataacgtc gtaaaatttg acaagctgga cctggacatc accgtgcagg ccggtctacc 2220
ctgggaggat ttgaatgact atttgagcga ccacggtttg atgtttggct gtgaccctgg 2280
tccaggtgca cagattggtg gttgcattgc taattcttgt tcaggaacca acgcctaccg 2340
ttacggtacc atgaaggaga atattataaa catgactata gtgttgccgg acgggaccat 2400
cgtcaagacg aagaaaagac ccagaaagtc gagcgctggc tataacttaa atgggttatt 2460
tgtgggaagt gaaggtacct taggtattgt tactgaagct actgtcaagt gtcatgtcaa 2520
gcccaaagct gaaactgttg cggtggtatc ctttgatact atcaaggatg cggccgcatg 2580
tgcttctaat ctgactcaga gtggtattca tttgaacgcc atggagttac tggatgaaaa 2640
tatgatgaag ttgatcaacg catctgaatc cacggacaga tgtgattggg tagagaaacc 2700
aactatgttt ttcaagattg gtgggagatc tcccaacatt gtcaatgctc ttgtggatga 2760
agttaaggct gtcgcccagt taaatcactg caacagtttt cagtttgcta aagatgatga 2820 cgaaaaaattg gaattatggg aagctagaaa ggtcgcgcta tggtctgtgc tagacgctga 2880
taagagcaaa gacaaatctg ctaaaatttg gacaactgat gtagctgttc ctgtgtcgca 2940
gttcgacaag gttattcacg aaactaaaaa ggacatgcaa gctagtaagc tgatcaacgc 3000
cattgttggt catgcaggtg atggtaactt ccatgcattc atcgtctaca gaacccctga 3060
agaacacgaa acctgtagcc aacttgttga cagaatggtc aagagagcac tggacgcaga 3120
aggcacttgc acgggtgaac acggtgttgg tattggtaaa agagagtact tgctcgaaga 3180
attaggtgaa gcacccgtcg atttgatgag aaagattaag ctagctattg acccaaagag 3240
aatcatgaac ccggacaaaa tctttaaaac tgatccaaac gagcccgcta atgattacag 3300
gtgattaatt aaacaggccc cttttccttt gtcgatatca tgtaattagt tatgtcacgc 3360
ttacattcac gccctcctcc cacatccgct ctaaccgaaa aggaaggagt tagacaacct 3420
gaagtctagg tccctattta tttttttata gttatgttag tattaagaac gttatttata 3480
tttcaaattt ttcttttttt tctgtacaaa cgcgtgtacg catgtaacgg gcagacggcc 3540
ggccataact tcgtataatg tatgctatac gaagttatgg caacggttca tcatctcatg 3600
gatctgcaca tgaacaaaca ccagagtcaa acgacgttga aattgaggct actgcgccaa 3660
ttgatgacaa tacagacgat gataacaaac cgaagttatc tgatgtagaa aaggattaga 3720
gatgctaaga gatagtgatg atatttcata aataatgtaa ttctatatat gttaattacc 3780

```
tttttgcga ggcatattta tggtgaagga taagttttga ccatcaaaga aggttaatgt   3840

ggctgtggtt tcagggtcca taaagctttt caattcatct ttttttttt tgttcttttt   3900

tttgattccg gtttctttga aattttttg attcggtaat ctccgagcag aaggaagaac   3960

gaaggaagga gcacagactt agattggtat atatacgcat atgtggtgtt gaagaaacat   4020

gaaattgccc agtattctta acccaactgc acagaacaaa aacctgcagg aaacgaagat   4080

aaatcatgtc gaaagctaca tataaggaac gtgctgctac tcatcctagt cctgttgctg   4140

ccaagctatt taatatcatg cacgaaaagc aaacaaactt gtgtgcttca ttggatgttc   4200

gtaccaccaa ggaattactg gagttagttg aagcattagg tcccaaaatt tgtttactaa   4260

aaacacatgt ggatatcttg actgattttt ccatggaggg cacagttaag ccgctaaagg   4320

cattatccgc caagtacaat tttttactct tcgaagacag aaaatttgct gacattggta   4380

atacagtcaa attgcagtac tctgcgggtg tatacagaat agcagaatgg gcagacatta   4440

cgaatgcaca cggtgtggtg ggcccaggta ttgttagcgg tttgaagcag gcggcggaag   4500

aagtaacaaa ggaacctaga ggccttttga tgttagcaga attgtcatgc aagggctccc   4560

tagctactgg agaatatact aagggtactg ttgacattgc gaagagcgac aaagattttg   4620

ttatcggctt tattgctcaa agagacatgg gtggaagaga tgaaggttac gattggttga   4680

ttatgacac                                                          4689
```

```
<210> SEQ ID NO 40
<211> LENGTH: 587
<212> TYPE: PRT
<213> ORGANISM: Saccharomyces cerevisiae

<400> SEQUENCE: 40

Met Leu Trp Lys Arg Thr Cys Thr Arg Leu Ile Lys Pro Ile Ala Gln
1               5                   10                  15

Pro Arg Gly Arg Leu Val Arg Arg Ser Cys Tyr Arg Tyr Ala Ser Thr
            20                  25                  30

Gly Thr Gly Ser Thr Asp Ser Ser Ser Gln Trp Leu Lys Tyr Ser Val
        35                  40                  45

Ile Ala Ser Ser Ala Thr Leu Phe Gly Tyr Leu Phe Ala Lys Asn Leu
    50                  55                  60

Tyr Ser Arg Glu Thr Lys Glu Asp Leu Ile Glu Lys Leu Glu Met Val
65                  70                  75                  80

Lys Lys Ile Asp Pro Val Asn Ser Thr Leu Lys Leu Ser Ser Leu Asp
                85                  90                  95

Ser Pro Asp Tyr Leu His Asp Pro Ala Lys Ile Asp Lys Val Val Glu
            100                 105                 110

Asp Leu Lys Gln Val Leu Gly Asn Lys Pro Glu Asn Tyr Ser Asp Ala
        115                 120                 125

Lys Ser Asp Leu Asp Ala His Ser Asp Thr Tyr Phe Asn Thr His His
    130                 135                 140

Pro Ser Leu Glu Gln Arg Pro Arg Ile Ile Leu Phe Pro His Thr Thr
145                 150                 155                 160

Glu Glu Val Ser Lys Ile Leu Lys Ile Cys His Asp Asn Asn Met Pro
                165                 170                 175

Val Val Pro Phe Ser Gly Gly Thr Ser Leu Glu Gly His Phe Leu Pro
            180                 185                 190

Thr Arg Ile Gly Asp Thr Ile Thr Val Asp Leu Ser Lys Phe Met Asn
        195                 200                 205
```

```
Asn Val Val Lys Phe Asp Lys Leu Asp Leu Asp Ile Thr Val Gln Ala
    210                 215                 220

Gly Leu Pro Trp Glu Asp Leu Asn Asp Tyr Leu Ser Asp His Gly Leu
225                 230                 235                 240

Met Phe Gly Cys Asp Pro Gly Pro Gly Ala Gln Ile Gly Gly Cys Ile
                245                 250                 255

Ala Asn Ser Cys Ser Gly Thr Asn Ala Tyr Arg Tyr Gly Thr Met Lys
            260                 265                 270

Glu Asn Ile Ile Asn Met Thr Ile Val Leu Pro Asp Gly Thr Ile Val
        275                 280                 285

Lys Thr Lys Lys Arg Pro Arg Lys Ser Ser Ala Gly Tyr Asn Leu Asn
    290                 295                 300

Gly Leu Phe Val Gly Ser Glu Gly Thr Leu Gly Ile Val Thr Glu Ala
305                 310                 315                 320

Thr Val Lys Cys His Val Lys Pro Lys Ala Glu Thr Val Ala Val Val
                325                 330                 335

Ser Phe Asp Thr Ile Lys Asp Ala Ala Ala Cys Ala Ser Asn Leu Thr
            340                 345                 350

Gln Ser Gly Ile His Leu Asn Ala Met Glu Leu Leu Asp Glu Asn Met
        355                 360                 365

Met Lys Leu Ile Asn Ala Ser Glu Ser Thr Asp Arg Cys Asp Trp Val
    370                 375                 380

Glu Lys Pro Thr Met Phe Phe Lys Ile Gly Gly Arg Ser Pro Asn Ile
385                 390                 395                 400

Val Asn Ala Leu Val Asp Glu Val Lys Ala Val Ala Gln Leu Asn His
                405                 410                 415

Cys Asn Ser Phe Gln Phe Ala Lys Asp Asp Asp Glu Lys Leu Glu Leu
            420                 425                 430

Trp Glu Ala Arg Lys Val Ala Leu Trp Ser Val Leu Asp Ala Asp Lys
        435                 440                 445

Ser Lys Asp Lys Ser Ala Lys Ile Trp Thr Thr Asp Val Ala Val Pro
    450                 455                 460

Val Ser Gln Phe Asp Lys Val Ile His Glu Thr Lys Lys Asp Met Gln
465                 470                 475                 480

Ala Ser Lys Leu Ile Asn Ala Ile Val Gly His Ala Gly Asp Gly Asn
                485                 490                 495

Phe His Ala Phe Ile Val Tyr Arg Thr Pro Glu Glu His Glu Thr Cys
            500                 505                 510

Ser Gln Leu Val Asp Arg Met Val Lys Arg Ala Leu Asp Ala Glu Gly
        515                 520                 525

Thr Cys Thr Gly Glu His Gly Val Gly Ile Gly Lys Arg Glu Tyr Leu
    530                 535                 540

Leu Glu Glu Leu Gly Glu Ala Pro Val Asp Leu Met Arg Lys Ile Lys
545                 550                 555                 560

Leu Ala Ile Asp Pro Lys Arg Ile Met Asn Pro Asp Lys Ile Phe Lys
                565                 570                 575

Thr Asp Pro Asn Glu Pro Ala Asn Asp Tyr Arg
            580                 585
```

<210> SEQ ID NO 41
<211> LENGTH: 4527
<212> TYPE: DNA
<213> ORGANISM: Artificial Sequence
<220> FEATURE:
<223> OTHER INFORMATION: Sequence put together from multiple organisms:

Saccharomyces cerevisiae and Issatchenkia orientalis.

<400> SEQUENCE: 41

```
tcctattcgg agatacaggc aacaagtgat agagggccca ttatgaatac gcacctctat     60
gtatttccga gatacgatta ctccagttcc tcttacaaga aatgcataaa aatagttaca    120
attaattaga acaagaactt atttagaaca cgttcacact gagtaagaac tcttgtccct    180
tattagcctt gatagtgctg aaaaaaagaa aaaaaacaaa aaaaagaaat aaaataacgg    240
caaacagcaa aggccacaga accgtattca tgttacttct gcaatatcaa tcacttactg    300
gcaagtgcgt ataaattaaa cctatttctt tatcatcata tttacttata tctttaacag    360
attccaaacc ctaaagtgtc cgaattttca atagggcgaa cttgaagaat aaccaaggtc    420
aataatatat cttttagtat aaccctgaaa tttgccctat agaaatctag ggtttctgtg    480
tggtttccgg gtgagtcata cggctttttt gaatttcttt ttttgcagtt gtctctatca    540
atgaaaattt cgaggaagac gataaggtta agataagtag ataagagaat gatacgagat    600
aaagcacaaa ttagcagaaa gaagagtggt tgcgaacaga gtaaaccgaa tcagggaatc    660
ccttttgca aaaacatcaa ttatcctttt cttttttta cgtatatatc tggaacagaa    720
atatataagt tactattata cttatagttg gatccagttt ttaatctgtc gtcaatcgaa    780
agtttatttc agagttcttc agacttctta actcctgtaa aaacaaaaaa aaaaaaaggc    840
atagcactcg agatctcccg agtttatcat tatcaatact gccatttcaa agaatacgta    900
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgtcaagat tgtttaaggt   1560
gctcaaagca actcaattca aatatgtgtc ttcatttctt cttggatcga caatctccgg   1620
cggagtggtg tattacaatt ataagaaatc attgaatttc agctttcctc caacatccac   1680
taccccaatt acagctgcac cacctttaca atatggggat gtatccaaag ctatatctga   1740
gatcacatca aaattgggac cttcaaagat aactttctca gagagcgaaa ttttacacca   1800
ctctgacagt tcattctcaa cggatcatgc aaaaccacat gaacgccccc atgctgttgt   1860
ttatcctgaa tccactgaag atgtttctga agtcttgaaa atttgtcata ctttgaaagt   1920
ccctgtcgtg ccattcaccg gtgggacctc gcttgaaggt cactttatat ccacaagaaa   1980
tggtatctct gttgatttgt cgaggatgaa caaagtcctt gcaattcatc cagaagattt   2040
ggatgcagtt gttcagcctg ctgttggctg ggaagagtta agagatacgt tatccgacta   2100
taacttgttg tttggccctg atcctggccc aggtgcttgt attggtggta tggttgcgac   2160
ttcctgttcc ggtacaaatg ctgcaaggta tggtacaatg agagaaaatg ttgtttctgt   2220
taaagttgtg cttccagatg ggactattgt gaaaactaaa agaagaccaa ggaaatcaag   2280
```

```
tgctggttat aatctaacta atttattcat tggtagtgaa ggtaccttgg gtattgtgac   2340
cgaagttact ttgaaactga acgtcaagcc aaaatatgag agtgttgcat tggtctcgtt   2400
tgataagtta aaagatgctg ctggatcagt tactagcttt gtccaagaag gtctacaact   2460
aaacgcgatt gaattacttg atgataagat ggtacatttt gttaatgagt ccggtgaaac   2520
cgatttgaaa tacgatgagc ttccaacttt acttttaaag attggcggct catctcctga   2580
gtcggtgaat ttgctaatca aaactgtcga gaggattgtc aatgctaaca atgctaagac   2640
ttttaagttt gcctccaacg aagaggagaa gtatcaattg tggaatgccc gtaaaactgc   2700
actttggtca actatcgaat atggccgcag aaatatagac aaggatatcc aggtttggac   2760
gactgacgtt gcagttccaa tgtcaaaatt tgtggaagca gtcgaagaaa cccaaaagga   2820
aatcgaagaa tccgatttgc ttgcatctat tgttggccac gcaggtgatg gaaactatca   2880
taccgttatt ttattcaagg aagaacagcg tgccttggct gcaaaattgg tctcaaatat   2940
ggttgatcgt gctctagcct ttgatggtac cgttagtggt gagcatggga ttggtgttgg   3000
caagaaggag tttttgattg atgaagttgg tcaagaatct gtggacttga tgaggaaaat   3060
taaattctct attgaccctc ataaaatttt gaaccctgat aaggtcttct cgatcgatcc   3120
tgtaaacgat agatcgatat aattaattaa acaggcccct tttcctttgt cgatatcatg   3180
taattagtta tgtcacgctt acattcacgc cctcctccca catccgctct aaccgaaaag   3240
gaaggagtta gacaacctga agtctaggtc cctatttatt tttttatagt tatgttagta   3300
ttaagaacgt tatttatatt tcaaattttt cttttttttc tgtacaaacg cgtgtacgca   3360
tgtaacgggc agacggccgg ccataacttc gtataatgta tgctatacga agttatggca   3420
acggttcatc atctcatgga tctgcacatg aacaaacacc agagtcaaac gacgttgaaa   3480
ttgaggctac tgcgccaatt gatgacaata cagacgatga taacaaaccg aagttatctg   3540
atgtagaaaa ggattagaga tgctaagaga tagtgatgat atttcataaa taatgtaatt   3600
ctatatatgt taattacctt ttttgcgagg catatttatg gtgaaggata agttttgacc   3660
atcaaagaag gttaatgtgg ctgtggtttc agggtccata aagcttttca attcatcttt   3720
tttttttttg ttcttttttt tgattccggt ttctttgaaa tttttttgat tcggtaatct   3780
ccgagcagaa ggaagaacga aggaaggagc acagacttag attggtatat atacgcatat   3840
gtggtgttga agaaacatga aattgcccag tattcttaac ccaactgcac agaacaaaaa   3900
cctgcaggaa acgaagataa atcatgtcga aagctacata taaggaacgt gctgctactc   3960
atcctagtcc tgttgctgcc aagctattta atatcatgca cgaaaagcaa acaaacttgt   4020
gtgcttcatt ggatgttcgt accaccaagg aattactgga gttagttgaa gcattaggtc   4080
ccaaaatttg tttactaaaa acacatgtgg atatcttgac tgatttttcc atggagggca   4140
cagttaagcc gctaaaggca ttatccgcca agtacaattt tttactcttc gaagacagaa   4200
aatttgctga cattggtaat acagtcaaat tgcagtactc tgcgggtgta tacagaatag   4260
cagaatgggc agacattacg aatgcacacg gtgtggtggg cccaggtatt gttagcggtt   4320
tgaagcaggc ggcggaagaa gtaacaaagg aacctagagg ccttttgatg ttagcagaat   4380
tgtcatgcaa gggctcccta gctactggag aatatactaa gggtactgtt gacattgcga   4440
agagcgacaa agattttgtt atcggcttta ttgctcaaag agacatgggt ggaagagatg   4500
aaggttacga ttggttgatt atgacac                                       4527
```

<210> SEQ ID NO 42

<211> LENGTH: 533
<212> TYPE: PRT
<213> ORGANISM: Issatchenkia orientalis

<400> SEQUENCE: 42

Met Ser Arg Leu Phe Lys Val Leu Lys Ala Thr Gln Phe Lys Tyr Val
1 5 10 15

Ser Ser Phe Leu Leu Gly Ser Thr Ile Ser Gly Gly Val Val Tyr Tyr
20 25 30

Asn Tyr Lys Lys Ser Leu Asn Phe Ser Phe Pro Pro Thr Ser Thr Thr
35 40 45

Pro Ile Thr Ala Ala Pro Pro Leu Gln Tyr Gly Asp Val Ser Lys Ala
50 55 60

Ile Ser Glu Ile Thr Ser Lys Leu Gly Pro Ser Lys Ile Thr Phe Ser
65 70 75 80

Glu Ser Glu Ile Leu His His Ser Asp Ser Ser Phe Ser Thr Asp His
85 90 95

Ala Lys Pro His Glu Arg Pro His Ala Val Val Tyr Pro Glu Ser Thr
100 105 110

Glu Asp Val Ser Glu Val Leu Lys Ile Cys His Thr Leu Lys Val Pro
115 120 125

Val Val Pro Phe Thr Gly Gly Thr Ser Leu Glu Gly His Phe Ile Ser
130 135 140

Thr Arg Asn Gly Ile Ser Val Asp Leu Ser Arg Met Asn Lys Val Leu
145 150 155 160

Ala Ile His Pro Glu Asp Leu Asp Ala Val Val Gln Pro Ala Val Gly
165 170 175

Trp Glu Glu Leu Arg Asp Thr Leu Ser Asp Tyr Asn Leu Leu Phe Gly
180 185 190

Pro Asp Pro Gly Pro Gly Ala Cys Ile Gly Gly Met Val Ala Thr Ser
195 200 205

Cys Ser Gly Thr Asn Ala Ala Arg Tyr Gly Thr Met Arg Glu Asn Val
210 215 220

Val Ser Val Lys Val Val Leu Pro Asp Gly Thr Ile Val Lys Thr Lys
225 230 235 240

Arg Arg Pro Arg Lys Ser Ser Ala Gly Tyr Asn Leu Thr Asn Leu Phe
245 250 255

Ile Gly Ser Glu Gly Thr Leu Gly Ile Val Thr Glu Val Thr Leu Lys
260 265 270

Leu Asn Val Lys Pro Lys Tyr Glu Ser Val Ala Leu Val Ser Phe Asp
275 280 285

Lys Leu Lys Asp Ala Ala Gly Ser Val Thr Ser Phe Val Gln Glu Gly
290 295 300

Leu Gln Leu Asn Ala Ile Glu Leu Leu Asp Asp Lys Met Val His Phe
305 310 315 320

Val Asn Glu Ser Gly Glu Thr Asp Leu Lys Tyr Asp Glu Leu Pro Thr
325 330 335

Leu Leu Leu Lys Ile Gly Gly Ser Ser Pro Glu Ser Val Asn Leu Leu
340 345 350

Ile Lys Thr Val Glu Arg Ile Val Asn Ala Asn Asn Ala Lys Thr Phe
355 360 365

Lys Phe Ala Ser Asn Glu Glu Glu Lys Tyr Gln Leu Trp Asn Ala Arg
370 375 380

Lys Thr Ala Leu Trp Ser Thr Ile Glu Tyr Gly Arg Arg Asn Ile Asp

```
385                 390                 395                 400

Lys Asp Ile Gln Val Trp Thr Thr Asp Val Ala Val Pro Met Ser Lys
                405                 410                 415

Phe Val Glu Ala Val Glu Glu Thr Gln Lys Glu Ile Glu Glu Ser Asp
            420                 425                 430

Leu Leu Ala Ser Ile Val Gly His Ala Gly Asp Gly Asn Tyr His Thr
        435                 440                 445

Val Ile Leu Phe Lys Glu Glu Gln Arg Ala Leu Ala Ala Lys Leu Val
    450                 455                 460

Ser Asn Met Val Asp Arg Ala Leu Ala Phe Asp Gly Thr Val Ser Gly
465                 470                 475                 480

Glu His Gly Ile Gly Val Gly Lys Lys Glu Phe Leu Ile Asp Glu Val
                485                 490                 495

Gly Gln Glu Ser Val Asp Leu Met Arg Lys Ile Lys Phe Ser Ile Asp
            500                 505                 510

Pro His Lys Ile Leu Asn Pro Asp Lys Val Phe Ser Ile Asp Pro Val
        515                 520                 525

Asn Asp Arg Ser Ile
    530


<210> SEQ ID NO 43
<211> LENGTH: 4506
<212> TYPE: DNA
<213> ORGANISM: Artificial Sequence
<220> FEATURE:
<223> OTHER INFORMATION: Sequence put together from multiple organisms:
      Saccharomyces cerevisiae and Issatchenkia orientalis.

<400> SEQUENCE: 43

tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180

tattagcctt gatagtgctg aaaaaaagaa aaaaaacaaa aaaaagaaat aaaataacgg     240

caaacagcaa aggccacaga accgtattca tgttacttct gcaatatcaa tcacttactg     300

gcaagtgcgt ataaattaaa cctatttctt tatcatcata tttacttata tctttaacag     360

attccaaacc ctaaagtgtc cgaattttca atagggcgaa cttgaagaat aaccaaggtc     420

aataatatat cttttagtat aaccctgaaa tttgccctat agaaatctag ggtttctgtg     480

tggtttccgg gtgagtcata cggctttttt gaatttcttt ttttgcagtt gtctctatca     540

atgaaaattt cgaggaagac gataaggtta agataagtag ataagagaat gatacgagat     600

aaagcacaaa ttagcagaaa gaagagtggt tgcgaacaga gtaaaccgaa tcagggaatc     660

cctttttgca aaaacatcaa ttatcctttt cttttttta cgtatatatc tggaacagaa      720

atatataagt tactattata cttatagttg gatccagttt ttaatctgtc gtcaatcgaa     780

agtttatttc agagttcttc agacttctta actcctgtaa aaacaaaaaa aaaaaaaggc     840

atagcactcg agatctcccg agtttatcat tatcaatact gccatttcaa agaatacgta     900

aataattaat agtagtgatt ttcctaactt tatttagtca aaaaattggc cttttaattc     960

tgctgtaacc cgtacatgcc caaaataggg ggcgggttac acagaatata taacatcata    1020

ggtgtctggg tgaacagttt attcctggca tccactaaat ataatggagc ccgctttttt    1080

taagctggca tccagaaaaa aaaagaatcc cagcaccaaa atattgtttt cttcaccaac    1140

catcagttca taggtccatt ctcttagcgc aactacacag aacaggggca caaacaggca    1200
```

-continued

```
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgtttgcat tagcttctat   1560
ttcacgtctg ggacgtgcaa gcgcaagcgc acgtgcacgt gcatccgcag ctctgtctat   1620
ccgtggattt gcgttgactg ctgaaaaata tccttcagtt aagcgtggag actacgccaa   1680
actaaccgat gaagatctcg gtaaattcca ttcgattttg aacccaaacc agattattac   1740
ggatgctgca gatttggctg catttaatca ggattggatg aagaaatacg ctggtcaatc   1800
gcaacttgta ttgaaaccaa agacaactca acaggtttct caaattttga agtattgtaa   1860
cgagaggaaa cttgccgttg ttccacaagg tggtaatacc ggattggttg gaggttctgt   1920
tccagttttc gacgaaatcg ttatttctat ggccggcatg aaccaaatta gatcctttga   1980
tgaaaattct ggaacattga aagtggacgc tggtgtcata cttgaaaatg cggacaacta   2040
tctggcagag aggggttata tattccccct tgatttggga gctaaaggtt catgttttgt   2100
tggtggtaac gttgcaacca atgctggtgg gttgagatta ttaagattcg gctcattaca   2160
tggctcagtg ttggggttgg aagttgtctt agctgatggt accattgtgg actccatgca   2220
ttctttaaga aaagacaata ccgggtttga tttgaagcag ctattcattg gttccgaagg   2280
taccttggga attattactg gtgtatcgat cttatgtccc gcaagaccaa aggccgtcaa   2340
tatcgcattt cttggcttgg agagctacga gcatgtgatc cagtgcttca aggaagcacg   2400
ttctgatttg ggcgaaatct taagtgcctt tgagtttatg gatcgtgatt cccagttggt   2460
tgcctccaaa ttcttgaaaa cgacccatcc attgtgtcaa gaggacgaag ttgctgaagc   2520
ttctgttccg gaatatccat tctatgtatt gctggagaca tcaggatcaa acaaagacca   2580
tgatgatgag aaactagaaa agtttttaga aaaagttatg gaaaacgaag ttgtagttga   2640
cggtacagtg tcgcaggatg aagctcaact caagactcta tggacttgga gagaaggtat   2700
cgctgaagca tcacagcaat ttggtggtgt ttataagtac gatgtctcat taccattgga   2760
ttccttgtac aaactagtcg aagagaccca ggagagacta aagagtttca gtttggcatc   2820
gaccgaggat gaatcaaaac ctgtatatga ggctattggt tatggtcata tcggtgacgg   2880
caatttacat ttgaacgttg ccgttagaga gtataacaaa gaggttgaaa aggcacttga   2940
accttttgta tatgagttta tcgagaaaca caatggttcc atcagtgccg aacatggtct   3000
tggattccaa aagaagaatt acattggtta ttctaagagt gaggttgaaa tcaaaatgat   3060
gaaggagttg aagaaccact atgatccgaa cggtattttg aacccttata agtatatctg   3120
attaattaaa caggcccctt ttcctttgtc gatatcatgt aattagttat gtcacgctta   3180
cattcacgcc ctcctcccac atccgctcta accgaaaagg aaggagttag acaacctgaa   3240
gtctaggtcc ctatttattt ttttatagtt atgttagtat taagaacgtt atttatattt   3300
caaatttttc ttttttttct gtacaaacgc gtgtacgcat gtaacgggca gacggccggc   3360
cataacttcg tataatgtat gctatacgaa gttatggcaa cggttcatca tctcatggat   3420
ctgcacatga acaaacacca gagtcaaacg acgttgaaat tgaggctact gcgccaattg   3480
atgacaatac agacgatgat aacaaaccga agttatctga tgtagaaaag gattagagat   3540
```

```
gctaagagat agtgatgata tttcataaat aatgtaattc tatatatgtt aattaccttt   3600

tttgcgaggc atatttatgg tgaaggataa gttttgacca tcaaagaagg ttaatgtggc   3660

tgtggtttca gggtccataa agcttttcaa ttcatctttt tttttttgt tctttttttt   3720

gattccggtt tctttgaaat ttttttgatt cggtaatctc cgagcagaag gaagaacgaa   3780

ggaaggagca cagacttaga ttggtatata tacgcatatg tggtgttgaa gaaacatgaa   3840

attgcccagt attcttaacc caactgcaca gaacaaaaac ctgcaggaaa cgaagataaa   3900

tcatgtcgaa agctacatat aaggaacgtg ctgctactca tcctagtcct gttgctgcca   3960

agctatttaa tatcatgcac gaaaagcaaa caaacttgtg tgcttcattg gatgttcgta   4020

ccaccaagga attactggag ttagttgaag cattaggtcc caaaatttgt ttactaaaaa   4080

cacatgtgga tatcttgact gatttttcca tggagggcac agttaagccg ctaaaggcat   4140

tatccgccaa gtacaatttt ttactcttcg aagacagaaa atttgctgac attggtaata   4200

cagtcaaatt gcagtactct gcgggtgtat acagaatagc agaatgggca gacattacga   4260

atgcacacgg tgtggtgggc ccaggtattg ttagcggttt gaagcaggcg gcggaagaag   4320

taacaaagga acctagaggc cttttgatgt tagcagaatt gtcatgcaag ggctccctag   4380

ctactggaga atatactaag ggtactgttg acattgcgaa gagcgacaaa gatttgttta   4440

tcggctttat tgctcaaaga gacatgggtg gaagagatga aggttacgat tggttgatta   4500

tgacac                                                              4506
```

<210> SEQ ID NO 44
<211> LENGTH: 526
<212> TYPE: PRT
<213> ORGANISM: Issatchenkia orientalis

<400> SEQUENCE: 44

```
Met Phe Ala Leu Ala Ser Ile Ser Arg Leu Gly Arg Ala Ser Ala Ser
1               5                   10                  15

Ala Arg Ala Arg Ala Ser Ala Ala Leu Ser Ile Arg Gly Phe Ala Leu
            20                  25                  30

Thr Ala Glu Lys Tyr Pro Ser Val Lys Arg Gly Asp Tyr Ala Lys Leu
        35                  40                  45

Thr Asp Glu Asp Leu Gly Lys Phe His Ser Ile Leu Asn Pro Asn Gln
    50                  55                  60

Ile Ile Thr Asp Ala Ala Asp Leu Ala Ala Phe Asn Gln Asp Trp Met
65                  70                  75                  80

Lys Lys Tyr Ala Gly Gln Ser Gln Leu Val Leu Lys Pro Lys Thr Thr
                85                  90                  95

Gln Gln Val Ser Gln Ile Leu Lys Tyr Cys Asn Glu Arg Lys Leu Ala
            100                 105                 110

Val Val Pro Gln Gly Gly Asn Thr Gly Leu Val Gly Gly Ser Val Pro
        115                 120                 125

Val Phe Asp Glu Ile Val Ile Ser Met Ala Gly Met Asn Gln Ile Arg
    130                 135                 140

Ser Phe Asp Glu Asn Ser Gly Thr Leu Lys Val Asp Ala Gly Val Ile
145                 150                 155                 160

Leu Glu Asn Ala Asp Asn Tyr Leu Ala Glu Arg Gly Tyr Ile Phe Pro
                165                 170                 175

Leu Asp Leu Gly Ala Lys Gly Ser Cys Phe Val Gly Gly Asn Val Ala
            180                 185                 190

Thr Asn Ala Gly Gly Leu Arg Leu Leu Arg Phe Gly Ser Leu His Gly
```

```
        195                 200                 205

Ser Val Leu Gly Leu Glu Val Val Leu Ala Asp Gly Thr Ile Val Asp
    210                 215                 220

Ser Met His Ser Leu Arg Lys Asp Asn Thr Gly Phe Asp Leu Lys Gln
225                 230                 235                 240

Leu Phe Ile Gly Ser Glu Gly Thr Leu Gly Ile Ile Thr Gly Val Ser
                245                 250                 255

Ile Leu Cys Pro Ala Arg Pro Lys Ala Val Asn Ile Ala Phe Leu Gly
            260                 265                 270

Leu Glu Ser Tyr Glu His Val Ile Gln Cys Phe Lys Glu Ala Arg Ser
        275                 280                 285

Asp Leu Gly Glu Ile Leu Ser Ala Phe Glu Phe Met Asp Arg Asp Ser
    290                 295                 300

Gln Leu Val Ala Ser Lys Phe Leu Lys Thr Thr His Pro Leu Cys Gln
305                 310                 315                 320

Glu Asp Glu Val Ala Glu Ala Ser Val Pro Glu Tyr Pro Phe Tyr Val
                325                 330                 335

Leu Leu Glu Thr Ser Gly Ser Asn Lys Asp His Asp Asp Glu Lys Leu
            340                 345                 350

Glu Lys Phe Leu Glu Lys Val Met Glu Asn Glu Val Val Val Asp Gly
        355                 360                 365

Thr Val Ser Gln Asp Glu Ala Gln Leu Lys Thr Leu Trp Thr Trp Arg
    370                 375                 380

Glu Gly Ile Ala Glu Ala Ser Gln Gln Phe Gly Gly Val Tyr Lys Tyr
385                 390                 395                 400

Asp Val Ser Leu Pro Leu Asp Ser Leu Tyr Lys Leu Val Glu Glu Thr
                405                 410                 415

Gln Glu Arg Leu Lys Ser Phe Ser Leu Ala Ser Thr Glu Asp Glu Ser
            420                 425                 430

Lys Pro Val Tyr Glu Ala Ile Gly Tyr Gly His Ile Gly Asp Gly Asn
        435                 440                 445

Leu His Leu Asn Val Ala Val Arg Glu Tyr Asn Lys Glu Val Glu Lys
    450                 455                 460

Ala Leu Glu Pro Phe Val Tyr Glu Phe Ile Glu Lys His Asn Gly Ser
465                 470                 475                 480

Ile Ser Ala Glu His Gly Leu Gly Phe Gln Lys Lys Asn Tyr Ile Gly
                485                 490                 495

Tyr Ser Lys Ser Glu Val Glu Ile Lys Met Met Lys Glu Leu Lys Asn
            500                 505                 510

His Tyr Asp Pro Asn Gly Ile Leu Asn Pro Tyr Lys Tyr Ile
        515                 520                 525
```

<210> SEQ ID NO 45
<211> LENGTH: 4629
<212> TYPE: DNA
<213> ORGANISM: Artificial Sequence
<220> FEATURE:
<223> OTHER INFORMATION: Sequence put together from multiple organisms: Saccharomyces cerevisiae and Issatchenkia orientalis.

<400> SEQUENCE: 45

```
tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180
```

-continued

```
tattagcctt gatagtgctg aaaaaaagaa aaaaaacaaa aaaaagaaat aaaataacgg    240
caaacagcaa aggccacaga accgtattca tgttacttct gcaatatcaa tcacttactg    300
gcaagtgcgt ataaattaaa cctatttctt tatcatcata tttacttata tctttaacag    360
attccaaacc ctaaagtgtc cgaattttca atagggcgaa cttgaagaat aaccaaggtc    420
aataatatat cttttagtat aaccctgaaa tttgccctat agaaatctag ggtttctgtg    480
tggtttccgg gtgagtcata cggctttttt gaatttcttt ttttgcagtt gtctctatca    540
atgaaaattt cgaggaagac gataaggtta agataagtag ataagagaat gatacgagat    600
aaagcacaaa ttagcagaaa gaagagtggt tgcgaacaga gtaaaccgaa tcagggaatc    660
cctttttgca aaaacatcaa ttatcctttt cttttttttta cgtatatatc tggaacagaa    720
atatataagt tactattata cttatagttg gatccagttt ttaatctgtc gtcaatcgaa    780
agtttatttc agagttcttc agacttctta actcctgtaa aaacaaaaaa aaaaaaaggc    840
atagcactcg agatctcccg agtttatcat tatcaatact gccatttcaa agaatacgta    900
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgataatgt tgccgttgtc   1560
acgtgccgcc gtgcacctat cgagaactag acattcctct ctagtctcac taagacatgc   1620
acttgcaatt cctcaaaggg tgcaatactc tcaccaccgt cactactccg ccaataccga   1680
aaagactgca aaaactggtt ctgaaaagga tcccaagtct caagctagaa aggatttagg   1740
aaagtccttc ttgtctacaa cagccatact attcattggt gccttggtgg ggacatcatg   1800
ggcctcattc cagctatgca agaatccgcc tgagttttta ttcccacata catcgacatt   1860
cccgctaaag gatgccatgc cgccactata tggggattcc cagaaggtca ttgacgagtt   1920
gaaaccgctt ctgcgagaag accaaatcac aatttcaaag agtgaactcg atacacattc   1980
cgatgcttat ttctccacag accacccgag cgatgaggaa agaccagatg ctattgtcta   2040
tcctgaatcg accgaacagg tttcccagat cctcaaaata gcccataacc atcacgttcc   2100
aattgtcccc tacactggtg gcacctcatt ggagggacat tatattccaa ctaggaaggg   2160
tatctgtgtt gatttgtcta ggttaaacaa agttttggct ttacataagg aagatttgga   2220
tattgttgtc caaccagcag ttggttggga agatctggat gagtttttaa gacctcaagg   2280
tcttttattt ggacctgatc caggacctgg cgcttgtatt ggtggtatgt gtggtacatc   2340
ttgttctgga actaatgctg cgagatatgg tacaatgaga gaaaatgtgg tctcattaac   2400
tgtggtcttg gccgatggta ctttgggtat tgtcacagaa gcaactttga aactacacgt   2460
tgctccaaaa tttgaaaacg tggcagttgt taatttccct acattgaggg atgccgccaa   2520
tgcagttgcc aaaatcgtcc agtccggttt acaagtcaat gctttggaaa tgttggatac   2580
```

```
cgaaatgatg caattcgtca accaatctgg taatgtcacc aagaaatatg cagagtcgcc   2640
aactttaatg atgaaattgg gaggtaattc caagactgtg gttgatgcgc ttactaagga   2700
tgtgaagagt atctgtaccg agtgtaacat tggtcgcaag gatttcaaat ttgccgaaga   2760
tgaggaggaa aaggaggaat tatggactgc cagaaaagtt gcactttggt caactctaga   2820
tgcaggtaag gaaaaattgg gtcaagatgt tcaactgtgg acaaccgacg tggcagttcc   2880
aatttctaag ctggttgaca gcttggagaa cactagaagg ttactcaatg aagccggatt   2940
catgtcttcc atagtttcgc atgcaggtga tggtaattat cacgccttta ttgtgtacga   3000
caaaaaggat tacgtaaaag ctgcaaatgt cgtcaaagaa atggtccatc atgccctcga   3060
gttggatggg acagcaactg gtgaacacgg tattggaata ggtaagagag aattcttgag   3120
agaagaacta ggggatgccc caattgattt gatgaggaag atcaaatttg cccttgatcc   3180
attgctatta ttaaacccag acaaagtatt caaaattgac cctgaagaca caagattatc   3240
ttgattaatt aaacaggccc cttttccttt gtcgatatca tgtaattagt tatgtcacgc   3300
ttacattcac gccctcctcc cacatccgct ctaaccgaaa aggaaggagt tagacaacct   3360
gaagtctagg tccctattta ttttttttata gttatgttag tattaagaac gttatttata   3420
tttcaaattt ttcttttttt tctgtacaaa cgcgtgtacg catgtaacgg gcagacggcc   3480
ggccataact tcgtataatg tatgctatac gaagttatgg caacggttca tcatctcatg   3540
gatctgcaca tgaacaaaca ccagagtcaa acgacgttga aattgaggct actgcgccaa   3600
ttgatgacaa tacagacgat gataacaaac cgaagttatc tgatgtagaa aaggattaga   3660
gatgctaaga gatagtgatg atatttcata aataatgtaa ttctatatat gttaattacc   3720
tttttttgcga ggcatattta tggtgaagga taagttttga ccatcaaaga aggttaatgt   3780
ggctgtggtt tcagggtcca taaagctttt caattcatct tttttttttt tgttcttttt   3840
tttgattccg gtttctttga aatttttttg attcggtaat ctccgagcag aaggaagaac   3900
gaaggaagga gcacagactt agattggtat atatacgcat atgtggtgtt gaagaaacat   3960
gaaattgccc agtattctta acccaactgc acagaacaaa aacctgcagg aaacgaagat   4020
aaatcatgtc gaaagctaca tataaggaac gtgctgctac tcatcctagt cctgttgctg   4080
ccaagctatt taatatcatg cacgaaaagc aaacaaactt gtgtgcttca ttggatgttc   4140
gtaccaccaa ggaattactg gagttagttg aagcattagg tcccaaaatt tgtttactaa   4200
aaacacatgt ggatatcttg actgattttt ccatggaggg cacagttaag ccgctaaagg   4260
cattatccgc caagtacaat tttttactct tcgaagacag aaaatttgct gacattggta   4320
atacagtcaa attgcagtac tctgcgggtg tatacagaat agcagaatgg gcagacatta   4380
cgaatgcaca cggtgtggtg ggcccaggta ttgttagcgg tttgaagcag gcggcggaag   4440
aagtaacaaa ggaacctaga ggccttttga tgttagcaga attgtcatgc aagggctccc   4500
tagctactgg agaatatact aagggtactg ttgacattgc gaagagcgac aaagattttg   4560
ttatcggctt tattgctcaa agagacatgg gtggaagaga tgaaggttac gattggttga   4620
ttatgacac                                                            4629
```

<210> SEQ ID NO 46
<211> LENGTH: 567
<212> TYPE: PRT
<213> ORGANISM: Issatchenkia orientalis

<400> SEQUENCE: 46

-continued

```
Met Ile Met Leu Pro Leu Ser Arg Ala Ala Val His Leu Ser Arg Thr
1               5                   10                  15

Arg His Ser Ser Leu Val Ser Leu Arg His Ala Leu Ala Ile Pro Gln
            20                  25                  30

Arg Val Gln Tyr Ser His His Arg His Tyr Ser Ala Asn Thr Glu Lys
        35                  40                  45

Thr Ala Lys Thr Gly Ser Glu Lys Asp Pro Lys Ser Gln Ala Arg Lys
    50                  55                  60

Asp Leu Gly Lys Ser Phe Leu Ser Thr Thr Ala Ile Leu Phe Ile Gly
65                  70                  75                  80

Ala Leu Val Gly Thr Ser Trp Ala Ser Phe Gln Leu Cys Lys Asn Pro
                85                  90                  95

Pro Glu Phe Leu Phe Pro His Thr Ser Thr Phe Pro Leu Lys Asp Ala
            100                 105                 110

Met Pro Pro Leu Tyr Gly Asp Ser Gln Lys Val Ile Asp Glu Leu Lys
        115                 120                 125

Pro Leu Leu Arg Glu Asp Gln Ile Thr Ile Ser Lys Ser Glu Leu Asp
    130                 135                 140

Thr His Ser Asp Ala Tyr Phe Ser Thr Asp His Pro Ser Asp Glu Glu
145                 150                 155                 160

Arg Pro Asp Ala Ile Val Tyr Pro Glu Ser Thr Glu Gln Val Ser Gln
                165                 170                 175

Ile Leu Lys Ile Ala His Asn His His Val Pro Ile Val Pro Tyr Thr
            180                 185                 190

Gly Gly Thr Ser Leu Glu Gly His Tyr Ile Pro Thr Arg Lys Gly Ile
        195                 200                 205

Cys Val Asp Leu Ser Arg Leu Asn Lys Val Leu Ala Leu His Lys Glu
    210                 215                 220

Asp Leu Asp Ile Val Val Gln Pro Ala Val Gly Trp Glu Asp Leu Asp
225                 230                 235                 240

Glu Phe Leu Arg Pro Gln Gly Leu Leu Phe Gly Pro Asp Pro Gly Pro
                245                 250                 255

Gly Ala Cys Ile Gly Gly Met Cys Gly Thr Ser Cys Ser Gly Thr Asn
            260                 265                 270

Ala Ala Arg Tyr Gly Thr Met Arg Glu Asn Val Val Ser Leu Thr Val
        275                 280                 285

Val Leu Ala Asp Gly Thr Leu Gly Ile Val Thr Glu Ala Thr Leu Lys
    290                 295                 300

Leu His Val Ala Pro Lys Phe Glu Asn Val Ala Val Val Asn Phe Pro
305                 310                 315                 320

Thr Leu Arg Asp Ala Ala Asn Ala Val Ala Lys Ile Val Gln Ser Gly
                325                 330                 335

Leu Gln Val Asn Ala Leu Glu Met Leu Asp Thr Glu Met Met Gln Phe
            340                 345                 350

Val Asn Gln Ser Gly Asn Val Thr Lys Lys Tyr Ala Glu Ser Pro Thr
        355                 360                 365

Leu Met Met Lys Leu Gly Gly Asn Ser Lys Thr Val Val Asp Ala Leu
    370                 375                 380

Thr Lys Asp Val Lys Ser Ile Cys Thr Glu Cys Asn Ile Gly Arg Lys
385                 390                 395                 400

Asp Phe Lys Phe Ala Glu Asp Glu Glu Glu Lys Glu Glu Leu Trp Thr
                405                 410                 415

Ala Arg Lys Val Ala Leu Trp Ser Thr Leu Asp Ala Gly Lys Glu Lys
```

-continued

```
            420                 425                 430

Leu Gly Gln Asp Val Gln Leu Trp Thr Thr Asp Val Ala Val Pro Ile
        435                 440                 445

Ser Lys Leu Val Asp Ser Leu Glu Asn Thr Arg Arg Leu Leu Asn Glu
    450                 455                 460

Ala Gly Phe Met Ser Ser Ile Val Ser His Ala Gly Asp Gly Asn Tyr
465                 470                 475                 480

His Ala Phe Ile Val Tyr Asp Lys Lys Asp Tyr Val Lys Ala Ala Asn
                485                 490                 495

Val Val Lys Glu Met Val His His Ala Leu Glu Leu Asp Gly Thr Ala
            500                 505                 510

Thr Gly Glu His Gly Ile Gly Ile Gly Lys Arg Glu Phe Leu Arg Glu
        515                 520                 525

Glu Leu Gly Asp Ala Pro Ile Asp Leu Met Arg Lys Ile Lys Phe Ala
    530                 535                 540

Leu Asp Pro Leu Leu Leu Leu Asn Pro Asp Lys Val Phe Lys Ile Asp
545                 550                 555                 560

Pro Glu Asp Thr Arg Leu Ser
                565
```

<210> SEQ ID NO 47
<211> LENGTH: 4199
<212> TYPE: DNA
<213> ORGANISM: Artificial Sequence
<220> FEATURE:
<223> OTHER INFORMATION: Sequence put together from multiple organisms: Saccharomyces cerevisiae and Lactobacillus plantarum.

<400> SEQUENCE: 47

```
tcctattcgg agatacaggc aacaagtgat agagggccca ttatgaatac gcacctctat     60

gtatttccga gatacgatta ctccagttcc tcttacaaga aatgcataaa aatagttaca    120

attaattaga acaagaactt atttagaaca cgttcacact gagtaagaac tcttgtccct    180

tattagcctt gatagtgctg aaaaaaagaa aaaaaacaaa aaaaagaaat aaaataacgg    240

caaacagcaa aggccacaga accgtattca tgttacttct gcaatatcaa tcacttactg    300

gcaagtgcgt ataaattaaa cctatttctt tatcatcata tttacttata tctttaacag    360

attccaaacc ctaaagtgtc cgaattttca atagggcgaa cttgaagaat aaccaaggtc    420

aataatatat cttttagtat aaccctgaaa tttgccctat agaaatctag ggtttctgtg    480

tggtttccgg gtgagtcata cggctttttt gaatttcttt ttttgcagtt gtctctatca    540

atgaaaattt cgaggaagac gataaggtta agataagtag ataagagaat gatacgagat    600

aaagcacaaa ttagcagaaa gaagagtggt tgcgaacaga gtaaaccgaa tcagggaatc    660

cctttttgca aaaacatcaa ttatcctttt cttttttttta cgtatatatc tggaacagaa    720

atatataagt tactattata cttatagttg gatccagttt ttaatctgtc gtcaatcgaa    780

agtttatttc agagttcttc agacttctta actcctgtaa aaacaaaaaa aaaaaaaggc    840

atagcactcg agatctcccg agtttatcat tatcaatact gccatttcaa agaatacgta    900

aataattaat agtagtgatt ttcctaactt tatttagtca aaaaattggc cttttaattc    960

tgctgtaacc cgtacatgcc caaaataggg ggcgggttac acagaatata taacatcata   1020

ggtgtctggg tgaacagttt attcctggca tccactaaat ataatggagc ccgctttttt   1080

taagctggca tccagaaaaa aaaagaatcc cagcaccaaa atattgtttt cttcaccaac   1140

catcagttca taggtccatt ctcttagcgc aactacacag aacaggggca caaacaggca   1200
```

```
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atggtcgcca ttgatttgcc   1560
atacgacaag agaactatta ctgctcaaat tgacgatgag aactacgcgg gcaagttggt   1620
gagccaggct gccacctacc acaacaaact gtcagaacag gaaacagttg agaaaagttt   1680
ggataaccca ataggatctg ataagctaga ggaacttgca cgtggtaaac ataacattgt   1740
gattatctca tctgatcata ccagacctgt tccatcacac atcatcacac ctattttgct   1800
tagaagatta agatctgtcg ctcctgacgc ccgtattaga atcttagttg caactggatt   1860
tcatagacca tctacccatg aggaactcgt taacaagtac ggtgaagata tcgtgaacaa   1920
tgaggaaatt gtcatgcatg tatctacaga tgactcatct atggtaaaga ttggtcaatt   1980
gccatccggc ggtgactgta tcatcaataa ggttgcagca gaagctgact tactaatatc   2040
cgaagggttc attgaatcac acttctttgc tgggttttct ggaggtagaa agtctgttct   2100
gccaggcatc gcaagttata agacaataat ggctaaccat agtggggagt tcattaacag   2160
ccctaaagcc agaactggca acttgatgca caattcaatt cataaagata tggtatacgc   2220
tgctagaaca gcaaaacttg cgttcattat caacgttgta ttagatgagg acaaaaagat   2280
aataggttca ttcgcgggtg atatggaagc agctcacaag gttgggtgcg atttcgtaaa   2340
ggaactgtcc tccgttccag ccatcgattg tgatatagca atttcaacaa acggaggtta   2400
ccctttggat caaaacattt accaggcggt gaagggtatg acagccgcag aagcaactaa   2460
taaggaaggt ggcactatca tcatggtcgc cggtgctaga gatggtcatg gaggcgaagg   2520
tttctatcat aatctagcag atgttgacga cccaaaggaa ttcttagatc aagcaatcaa   2580
tacacctaga ctaaagacaa ttccagatca atggacagct caaatctttg ccagaatact   2640
tgttcaccat catgtgatct ttgtttctga tctcgtcgat ccagatttga tcactaatat   2700
gcacatggaa ttggctaaaa ccttagatga ggcaatggag aaggcttacg ctagagaagg   2760
tcaagcagcc aaagtcacag tcattccaga cggattaggt gttattgtta agtagttaat   2820
taaacaggcc ccttttcctt tgtcgatatc atgtaattag ttatgtcacg cttacattca   2880
cgccctcctc ccacatccgc tctaaccgaa aaggaaggag ttagacaacc tgaagtctag   2940
gtccctattt attttttat agttatgtta gtattaagaa cgttatttat atttcaaatt   3000
tttctttttt ttctgtacaa acgcgtgtac gcatgtaacg ggcagacggc cggccataac   3060
ttcgtataat gtatgctata cgaagttatg gcaacggttc atcatctcat ggatctgcac   3120
atgaacaaac accagagtca aacgacgttg aaattgaggc tactgcgcca attgatgaca   3180
atacagacga tgataacaaa ccgaagttat ctgatgtaga aaaggattag agatgctaag   3240
agatagtgat gatatttcat aaataatgta attctatata tgttaattac ctttttgcg    3300
aggcatattt atggtgaagg ataagttttg accatcaaag aaggttaatg tggctgtggt   3360
ttcagggtcc ataaagcttt tcaattcatc ttttttttt ttgttctttt ttttgattcc   3420
ggtttctttg aaattttttt gattcggtaa tctccgagca gaaggaagaa cgaaggaagg   3480
agcacagact tagattggta tatatacgca tatgtggtgt tgaagaaaca tgaaattgcc   3540
```

-continued

```
cagtattctt aacccaactg cacagaacaa aaacctgcag gaaacgaaga taaatcatgt   3600

cgaaagctac atataaggaa cgtgctgcta ctcatcctag tcctgttgct gccaagctat   3660

ttaatatcat gcacgaaaag caaacaaact tgtgtgcttc attggatgtt cgtaccacca   3720

aggaattact ggagttagtt gaagcattag gtcccaaaat ttgtttacta aaaacacatg   3780

tggatatctt gactgatttt tccatggagg gcacagttaa gccgctaaag gcattatccg   3840

ccaagtacaa tttttactc ttcgaagaca gaaaatttgc tgacattggt aatacagtca   3900

aattgcagta ctctgcgggt gtatacagaa tagcagaatg ggcagacatt acgaatgcac   3960

acggtgtggt gggcccaggt attgttagcg gtttgaagca ggcggcggaa gaagtaacaa   4020

aggaacctag aggccttttg atgttagcag aattgtcatg caagggctcc ctagctactg   4080

gagaatatac taagggtact gttgacattg cgaagagcga caaagatttt gttatcggct   4140

ttattgctca aagagacatg ggtggaagag atgaaggtta cgattggttg attatgaca    4199


<210> SEQ ID NO 48
<211> LENGTH: 424
<212> TYPE: PRT
<213> ORGANISM: Lactobacillus plantarum

<400> SEQUENCE: 48

Met Val Ala Ile Asp Leu Pro Tyr Asp Lys Arg Thr Ile Thr Ala Gln
1               5                   10                  15

Ile Asp Asp Glu Asn Tyr Ala Gly Lys Leu Val Ser Gln Ala Ala Thr
            20                  25                  30

Tyr His Asn Lys Leu Ser Glu Gln Glu Thr Val Glu Lys Ser Leu Asp
        35                  40                  45

Asn Pro Ile Gly Ser Asp Lys Leu Glu Glu Leu Ala Arg Gly Lys His
    50                  55                  60

Asn Ile Val Ile Ile Ser Ser Asp His Thr Arg Pro Val Pro Ser His
65                  70                  75                  80

Ile Ile Thr Pro Ile Leu Leu Arg Arg Leu Arg Ser Val Ala Pro Asp
                85                  90                  95

Ala Arg Ile Arg Ile Leu Val Ala Thr Gly Phe His Arg Pro Ser Thr
            100                 105                 110

His Glu Glu Leu Val Asn Lys Tyr Gly Glu Asp Ile Val Asn Asn Glu
        115                 120                 125

Glu Ile Val Met His Val Ser Thr Asp Asp Ser Ser Met Val Lys Ile
    130                 135                 140

Gly Gln Leu Pro Ser Gly Gly Asp Cys Ile Ile Asn Lys Val Ala Ala
145                 150                 155                 160

Glu Ala Asp Leu Leu Ile Ser Glu Gly Phe Ile Glu Ser His Phe Phe
                165                 170                 175

Ala Gly Phe Ser Gly Gly Arg Lys Ser Val Leu Pro Gly Ile Ala Ser
            180                 185                 190

Tyr Lys Thr Ile Met Ala Asn His Ser Gly Glu Phe Ile Asn Ser Pro
        195                 200                 205

Lys Ala Arg Thr Gly Asn Leu Met His Asn Ser Ile His Lys Asp Met
    210                 215                 220

Val Tyr Ala Ala Arg Thr Ala Lys Leu Ala Phe Ile Ile Asn Val Val
225                 230                 235                 240

Leu Asp Glu Asp Lys Lys Ile Ile Gly Ser Phe Ala Gly Asp Met Glu
                245                 250                 255

Ala Ala His Lys Val Gly Cys Asp Phe Val Lys Glu Leu Ser Ser Val
```

```
            260                 265                 270

Pro Ala Ile Asp Cys Asp Ile Ala Ile Ser Thr Asn Gly Gly Tyr Pro
        275                 280                 285

Leu Asp Gln Asn Ile Tyr Gln Ala Val Lys Gly Met Thr Ala Ala Glu
    290                 295                 300

Ala Thr Asn Lys Glu Gly Gly Thr Ile Ile Met Val Ala Gly Ala Arg
305                 310                 315                 320

Asp Gly His Gly Gly Glu Gly Phe Tyr His Asn Leu Ala Asp Val Asp
                325                 330                 335

Asp Pro Lys Glu Phe Leu Asp Gln Ala Ile Asn Thr Pro Arg Leu Lys
            340                 345                 350

Thr Ile Pro Asp Gln Trp Thr Ala Gln Ile Phe Ala Arg Ile Leu Val
        355                 360                 365

His His His Val Ile Phe Val Ser Asp Leu Val Asp Pro Asp Leu Ile
    370                 375                 380

Thr Asn Met His Met Glu Leu Ala Lys Thr Leu Asp Glu Ala Met Glu
385                 390                 395                 400

Lys Ala Tyr Ala Arg Glu Gly Gln Ala Ala Lys Val Thr Val Ile Pro
                405                 410                 415

Asp Gly Leu Gly Val Ile Val Lys
            420


<210> SEQ ID NO 49
<211> LENGTH: 5084
<212> TYPE: DNA
<213> ORGANISM: Artificial Sequence
<220> FEATURE:
<223> OTHER INFORMATION: Sequence put together from multiple organisms:
      Saccharomyces cerevisiae and Aspergillus nidulans.

<400> SEQUENCE: 49

tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180

tattagcctt gatagtgctg aaaaaaagaa aaaaaacaaa aaaaagaaat aaaataacgg     240

caaacagcaa aggccacaga accgtattca tgttacttct gcaatatcaa tcacttactg     300

gcaagtgcgt ataaattaaa cctatttctt tatcatcata tttacttata tctttaacag     360

attccaaacc ctaaagtgtc cgaattttca atagggcgaa cttgaagaat aaccaaggtc     420

aataatatat cttttagtat aaccctgaaa tttgccctat agaaatctag ggtttctgtg     480

tggtttccgg gtgagtcata cggctttttt gaatttcttt ttttgcagtt gtctctatca     540

atgaaaattt cgaggaagac gataaggtta agataagtag ataagagaat gatacgagat     600

aaagcacaaa ttagcagaaa gaagagtggt tgcgaacaga gtaaaccgaa tcagggaatc     660

ccttttttgca aaaacatcaa ttatcctttt cttttttttta cgtatatatc tggaacagaa     720

atatataagt tactattata cttatagttg gatccagttt ttaatctgtc gtcaatcgaa     780

agtttatttc agagttcttc agacttctta actcctgtaa aaacaaaaaa aaaaaaaggc     840

atagcactcg agatctcccg agtttatcat tatcaatact gccatttcaa agaatacgta     900

aataattaat agtagtgatt ttcctaactt tatttagtca aaaaattggc cttttaattc     960

tgctgtaacc cgtacatgcc caaaataggg ggcgggttac acagaatata taacatcata    1020

ggtgtctggg tgaacagttt attcctggca tccactaaat ataatggagc ccgctttttt    1080
```

```
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgctaaaat acaaaccttt   1560
actaaaaatc tcgaagaact gtgaggctgc tatcctcaga gcgtctaaga ctagattgaa   1620
cacaatccgc gcgtacggtt ctaccgttcc aaaatccaag tcgttcgaac aagactcaag   1680
aaaacgcaca cagtcatgga ctgccttgag agtcggtgca attctagccg ctactagttc   1740
cgtggcgtat ctaaactggc ataatggcca aatagacaac gagccgaaac tggatatgaa   1800
taaacaaaag atttcgcccg ctgaagttgc caagcataac aagcccgatg attgttgggt   1860
tgtgatcaat ggttacgtat acgacttaac gcgattccta ccaaatcatc caggtgggca   1920
ggatgttatc aagtttaacg ccgggaaaga tgtcactgct atttttgaac cactacatgc   1980
tcctaatgtc atcgataagt atatagctcc cgagaaaaaa ttgggtcccc ttcaaggatc   2040
catgcctcct gaacttgtct gtcctcctta tgctcctggt gaaactaagg aagatatcgc   2100
tagaaaagaa caactaaaat cgctgctacc tcctctagat aatattatta acctttacga   2160
ctttgaatac ttggcctctc aaactttgac taaacaagcg tgggcctact attcctccgg   2220
tgctaacgac gaagttactc acagagaaaa ccataatgct tatcatagga ttttttttcaa   2280
accaaagatc cttgtagatg tacgcaaagt agacatttca actgacatgt tgggttctca   2340
tgtggatgtt cccttctacg tgtctgctac agctttgtgt aaactgggaa acccccttaga   2400
aggtgaaaaa gatgtcgcca gaggttgtgg ccaaggtgtg acaaaagtcc cacaaatgat   2460
atctactttg gcttcatgtt cccctgagga aattattgaa gcagcaccct ctgataaaca   2520
aattcaatgg taccaactat atgttaactc tgatagaaag atcactgatg atttggttaa   2580
aaatgtagaa aagctgggtg taaaggcatt atttgtcact gtggatgctc caagtttagg   2640
tcaaagagaa aaagatatga agctgaaatt ttccaataca aaggctggtc caaaagcgat   2700
gaagaaaact aatgtagaag aatctcaagg tgcttcgaga gcgttatcaa agtttattga   2760
cccctctttg acttggaaag atatagaaga gttgaagaaa aagacaaaac tacctattgt   2820
tatcaaaggt gttcaacgta ccgaagatgt tatcaaagca gcagaaatcg gtgtaagtgg   2880
ggtggttcta tccaatcatg gtggtagaca attagatttt tcaagggctc ccattgaagt   2940
cctggctgaa accatgccaa tcctggaaca acgtaacttg aaggataagt tggaagtttt   3000
cgtggacggt ggtgttcgtc gtggtacaga tgtcttgaaa gcgttatgtc taggtgctaa   3060
aggtgttggt ttgggtagac cattcttgta tgcgaactca tgctatggtc gtaatggtgt   3120
tgaaaaagcc attgaaattt taagagatga aattgaaatg tctatgagac tattaggtgt   3180
tactagcatt gcggaattga agcctgatct tttagatcta tcaacactaa aggcaagaac   3240
agttggagta ccaaacgacg tgctgtataa tgaagtttat gagggaccta ctttaacaga   3300
atttgaggat gcatgattaa ttaaacaggc cccttttcct ttgtcgatat catgtaatta   3360
gttatgtcac gcttacattc acgccctcct cccacatccg ctctaaccga aaaggaagga   3420
gttagacaac ctgaagtcta ggtccctatt tatttttta tagttatgtt agtattaaga   3480
```

acgttattta tatttcaaat ttttcttttt tttctgtaca aacgcgtgta cgcatgtaac 3540
gggcagacgg ccggccataa cttcgtataa tgtatgctat acgaagttat ccttacatca 3600
cacccaatcc cccacaagtg atcccccaca caccatagct tcaaaatgtt tctactcctt 3660
ttttactctt ccagattttc tcggactccg cgcatcgccg taccacttca aaacacccaa 3720
gcacagcata ctaaatttcc cctctttctt cctctagggt ggcgttaatt acccgtacta 3780
aaggtttgga aaagaaaaaa gagaccgcct cgtttctttt tcttcgtcga aaaaggcaat 3840
aaaaattttt atcacgtttc tttttcttga aaaatttttt ttttgatttt tttctctttc 3900
gatgacctcc cattgatatt taagttaata aatggtcttc aatttctcaa gtttcagttt 3960
cgtttttctt gttctattac aacttttttt acttcttgct cattagaaag aaagcatagc 4020
aatctaatct aagttttaat tacaaaatgc cacaatcctg ggaagaattg gccgccgaca 4080
aacgtgcccg tttggctaaa accattcctg acgaatggaa ggttcaaact ttgcctgccg 4140
aagattccgt tattgatttc ccaaagaagt ccggtatttt gtctgaggct gaattgaaga 4200
ttaccgaagc ctctgctgct gatttggtct ccaagttggc cgctggtgag ttgacttctg 4260
ttgaagtcac tttggctttt tgtaagagag ctgctattgc tcaacaatta accaactgtg 4320
ctcacgaatt cttcccagat gctgctttag ctcaagctag agaattagat gaatactacg 4380
ctaagcataa gagaccagtt ggtccattac acggtttacc aatctcttta aaggaccaat 4440
tgcgtgttaa gggttacgaa acctccatgg gttacatttc ctggttaaac aaatacgatg 4500
aaggtgattc cgtcttaacc accatgttga gaaaagctgg tgctgttttc tacgttaaga 4560
cctctgtccc acaaaccttg atggtctgtg aaaccgtcaa caacatcatt ggtagaactg 4620
tcaatccaag aaacaaaaat tggtcctgtg gtggttcttc tggtggtgaa ggtgctattg 4680
ttggtattag aggtggtgtt attggtgtcg gtactgacat tggtggttcc attagagtcc 4740
cagctgcttt caacttttta tacggtttga gaccatctca cggtagattg ccatatgcta 4800
aaatggctaa ctctatggaa ggtcaagaaa ccgttcactc cgtcgttggt cctatcactc 4860
actccgtcga agacttgaga ttgttcacca aatctgtctt gggtcaagaa ccttggaagt 4920
acgactctaa ggtcatcccc atgccatgga gacaatctga atctgacatc attgcctcta 4980
agattaagaa tggtggtttg aacattggtt attacaattt cgacggtaac gtcttgccac 5040
acccaccaat tttacgtggt gtcgaaacta ccgttgccgc tttg 5084

<210> SEQ ID NO 50
<211> LENGTH: 5343
<212> TYPE: DNA
<213> ORGANISM: Artificial Sequence
<220> FEATURE:
<223> OTHER INFORMATION: Sequence put together from multiple organisms: Saccharomyces cerevisiae, Kluyveromyces lactis and Aspergillus nidulans.

<400> SEQUENCE: 50
gaaggtgcta ttgttggtat tagaggtggt gttattggtg tcggtactga cattggtggt 60
tccattagag tcccagctgc tttcaacttt ttatacggtt tgagaccatc tcacggtaga 120
ttgccatatg ctaaaatggc taactctatg gaaggtcaag aaaccgttca ctccgtcgtt 180
ggtcctatca ctcactccgt cgaagacttg agattgttca ccaaatctgt cttgggtcaa 240
gaaccttgga agtacgactc taaggtcatc cccatgccat ggagacaatc tgaatctgac 300
atcattgcct ctaagattaa gaatggtggt ttgaacattg gttattacaa tttcgacggt 360

-continued

```
aacgtcttgc cacacccacc aattttacgt ggtgtcgaaa ctaccgttgc cgctttggcc    420
aaggctggtc acaccgttac tccatggact ccatacaagc atgatttcgg tcatgacttg    480
atttcccaca tctatgctgc tgatggttct gccgacgtca tgagagacat ttctgcctct    540
ggtgagccag ccatccctaa cattaaggac ttgttgaacc caaatattaa ggctgttaac    600
atgaacgaat tgtgggacac tcatttacaa aagtggaact atcaaatgga atacttggaa    660
aagtggcgtg aagctgaaga aaaagctggt aaggaattgg acgctattat cgctccaatt    720
actcctaccg ccgctgtcag acacgatcaa ttcagatact acggttacgc ctccgttatt    780
aacttattgg atttcacctc tgttgtcgtc ccagtcactt tcgctgataa gaatattgat    840
aagaagaacg aatcttttaa agctgtttcc gaattggatg ctttggttca agaagaatac    900
gacccagagg cttatcacgg tgctcctgtt gctgttcaag ttattggtag aagattgtcc    960
gaagagagaa ctttggctat cgccgaagaa gtcggtaaat tgttgggtaa cgtcgtcact   1020
ccataagcga atttcttatg atttatgatt tttattatta aataagttat aaaaaaaata   1080
agtgtataca aattttaaag tgactcttag gttttaaaac gaaaattctt attcttgagt   1140
aactctttcc tgtaggtcag gttgctttct caggtatagc atgaggtcgc tcttattgac   1200
cacacctcta ccggcatgcc gagcaaatgc ctgcaaatcg ctccccattt cacccaattg   1260
tagatatgct aactccagca atgagttgat gaatctcggt gtgtatttta tgtcctcaga   1320
ggacaacaca taacttcgta taatgtatgc tatacgaagt tatctcgaga tctcccctaa   1380
accgtggaat atttcggata tccttttgtt gtttccgggt gtacaatatg gacttcctct   1440
tttctggcaa ccaaacccat acatcgggat tcctataata ccttcgttgg tctccctaac   1500
atgtaggtgg cggaggggag atatacaata gaacagatac cagacaagac ataatgggct   1560
aaacaagact acaccattta cactgcctca ttgatggtgg tacataacga actaatactg   1620
tagccctaga cttgatagcc atcatcatat cgaagtttca ctaccctttt tccatttgcc   1680
atctattgaa gtaataatag gcgcatgcaa cttctttttt tttttttttt ttctctctcc   1740
cccgttgttg tctcaccata tccgcaatga caaaaaaatg atggaagaca ctaaaggaaa   1800
aaattaacga caaagacagc accaacagat gtcgttgttc cagagctgat gaggggtatc   1860
tcgaagcaca cgaaactttt tccttccttc attcacgcac actactctct aatgagcaac   1920
ggtatacggc cttccttcca gttacttgaa tttgaaataa aaaaaagttt gctgtcttgc   1980
tatcaagtat aaatagacct gcaattatta atcttttgtt tcctcgtcat tgttctcgtt   2040
ccctttcttc cttgtttctt tttctgcaca atatttcaag ctataccaag catacaatca   2100
actatctcat atacatctag aatgaataac aacaacatta caccagagtc agactcaatg   2160
aagagtaacg ataacgatca aaccaatgat tacatgccag atgtggctga tttcgatcat   2220
acacaaacaa acacaaacga aattgctaga gcaatttctc acccaggttc tgttctgtca   2280
agagttgcaa gctacgtcag cagaaaggac agatacgtag acgagaatgg caatgaagtt   2340
tggcaagacg atgaagtgag tatcctaatg gaggaagatg agactcctga tttcacatgg   2400
aaaaacatta gacattacgc tatcactaga ttcactacat tgacagaact tcacagagtg   2460
tctatggaaa acatcaaccc aattccagaa ttgagaaaaa tgacattaca taattggaac   2520
tacttcttta tggggtatgc cgcgtggttg tgtgctgctt gggcattttt cgccgtttcc   2580
gttagtacag cccctcttgc aaccctttat ggcaaggaaa caaaagacat ttcatggggt   2640
ctatccttag tcttattcgt cagatctgct ggagcgatta tctttggcat ctggaccgac   2700
aattactcca gaaagtggcc atacattaca tgcttaggtc ttttcttgat ctgtcagctt   2760
```

tgcacacctt gggcaaagac ctacactcaa ttcttgggag ttcgttggat ttccggtatc 2820
gcaatgggtg gaatttacgc ctgtgcttct gcaacagcga ttgaggatgc accagtaaag 2880
gctcgttctt tcttatccgg cttattcttc actgcctacg ccatgggttt tatcttcgca 2940
ataatctttt acagagcatt cttaaacgtc aacggtgaaa actactggaa ggttcaattc 3000
tggttttcaa tatggttacc agctgtactg atattgtgga gactcgtatg gccagaaact 3060
aagtacttca ccaaagtact aaaagctaga caactaatgc gtgatgatgc aatagccaaa 3120
aacggtggtc aaccactccc aaagttgtct ttcaagcaaa agttcgccaa tgtgaaaaag 3180
accgttagta aatactggct tttgtttggt tacttaattc tcttgttggt tggtcctaac 3240
tacctaacac acgcctctca agacttgttt cctacaatgt taagagcaca attgagattt 3300
tctgaagatg ctgtcaccgt ggccattgta gttgtttgtc tgggtagcat tgctgggggg 3360
atgtttttcg gacagttgat ggagatcact ggtagaagag ttggcctact attggcccta 3420
atcatggctg gctgctttac ttaccctgcc ttcatgctta aaacttcatc tgcagtgctg 3480
ggggcaggct ttatgctctg gttctcaatc ttaggtgtgt ggggtgtttt accaatccat 3540
ttatcagaat tgtcccctcc agaagctaga gcattagtct ctggattagc atatcagctg 3600
ggtaatctag cttcagcagc ttctgttgtt atagagaatg atttggcgga tttgtatcca 3660
atagaatgga attctgctgg agaagttaca aacaaggact actctaaggt aatggctatt 3720
cttacaggtt cttcagtcat tttcactttc gtgttggttt tcgttggtca cgaaaagttt 3780
catagagatt tgtcatcccc acatcttaag tcatacatcg agagagtcga tcaaacagaa 3840
gaggtcgcag ctatgactgg atctactgcg aactctatct ctagtaagcc ttcagatgat 3900
cagctcgaaa aagtttcagt ctagttaatt aatttaccag cttactatcc ttcttgaaaa 3960
tatgcactct atatctttta gttcttaatt gcaacacata gatttgctgt ataacgaatt 4020
ttatgctatt tttttaattt ggagttcggt gatgaaagtg tcacagcgaa tttcctcaca 4080
tgtagggacc gaattgttta caagttctct gtaccaccat ggagacatca aagattgaaa 4140
atctatggaa agatatggac ggtagcaaca agaatatagc acgagccgcg gagttcattt 4200
cgttactttt gatatcgctc acaactattg cgaagcgctt cagtgaaaaa atcataagga 4260
aaagttgtaa atattattgg tagtattcgt ttggtaaagt agagggggta atttttcccc 4320
tttattttgt tcatacattc ttaaattgct ttgcctctcc ttttggaaag ctatacttcg 4380
gagcactgtt gagcgaaggc tcaggccggc atatgacgtt ttattacctt tgatcacatt 4440
tccacgccat ttcgcattct caccctcata agtcatacac cgaaaagaaa gtttaaggga 4500
tcaatgagct tactataatc tcagtatatt tatttttatc gatgattcac cacaacaatc 4560
ttgctcccga aaagaaagca gacggagtag aagcatttga aactccttca gaccttcaag 4620
tatatatata tatatatata tatgtatatg tgtacatttt cacgctaata ctaatgtata 4680
attagaagat aatttttact cattttttcgt tatcttcacg tcacccgaac ctagaaccaa 4740
atgtcatttt cacgatatgt aaatagtgaa ataggcaaaa acgccaaaaa gtagtaagcg 4800
caacatacac taaaccatta aagaatatct cgaccagaat ctaacagata tacatgttcc 4860
gataatgtct gagttaggtg agtattctaa attagaaaac aaagagctta gaacggagtt 4920
tgaattgaca aattttcctt ttccaggcac aactgataac gactccgatg acggaagcca 4980
agggcagaac tctttgaata tcattactcc tgacatggat gatactctgg ttaatgatgt 5040
acttcgagaa aacgataaaa agtctagtat gagaatggct tttatgaatc tagcaaactc 5100

```
tattcttggt gccggaataa ttactcagcc gttcgcgatc aaaaatgctg gtatattagg   5160

cgggctatta tcatacgtag ccctcggatt tatagttgat tggacgttaa gacttattgt   5220

cattaacttg actcttgctg gcaagagaac ataccagggt acggtcgaac atgtaatggg   5280

taaaaaaggg aaattgctga ttctatttac aaacgggtta tttgcatttg gtggatgtat   5340

tgg                                                                 5343


<210> SEQ ID NO 51
<211> LENGTH: 562
<212> TYPE: PRT
<213> ORGANISM: Saccharomyces cerevisiae

<400> SEQUENCE: 51

Met Asn Val Phe Gly Lys Lys Glu Glu Lys Gln Glu Lys Val Tyr Ser
1               5                   10                  15

Leu Gln Asn Gly Phe Pro Tyr Ser His His Pro Tyr Ala Ser Gln Tyr
            20                  25                  30

Ser Arg Pro Asp Gly Pro Ile Leu Leu Gln Asp Phe His Leu Leu Glu
        35                  40                  45

Asn Ile Ala Ser Phe Asp Arg Glu Arg Val Pro Glu Arg Val Val His
    50                  55                  60

Ala Lys Gly Gly Gly Cys Arg Leu Glu Phe Glu Leu Thr Asp Ser Leu
65                  70                  75                  80

Ser Asp Ile Thr Tyr Ala Ala Pro Tyr Gln Asn Val Gly Tyr Lys Cys
                85                  90                  95

Pro Gly Leu Val Arg Phe Ser Thr Val Gly Gly Glu Ser Gly Thr Pro
            100                 105                 110

Asp Thr Ala Arg Asp Pro Arg Gly Val Ser Phe Lys Phe Tyr Thr Glu
        115                 120                 125

Trp Gly Asn His Asp Trp Val Phe Asn Asn Thr Pro Val Phe Phe Leu
    130                 135                 140

Arg Asp Ala Ile Lys Phe Pro Val Phe Ile His Ser Gln Lys Arg Asp
145                 150                 155                 160

Pro Gln Ser His Leu Asn Gln Phe Gln Asp Thr Thr Ile Tyr Trp Asp
                165                 170                 175

Tyr Leu Thr Leu Asn Pro Glu Ser Ile His Gln Ile Thr Tyr Met Phe
            180                 185                 190

Gly Asp Arg Gly Thr Pro Ala Ser Trp Ala Ser Met Asn Ala Tyr Ser
        195                 200                 205

Gly His Ser Phe Ile Met Val Asn Lys Glu Gly Lys Asp Thr Tyr Val
    210                 215                 220

Gln Phe His Val Leu Ser Asp Thr Gly Phe Glu Thr Leu Thr Gly Asp
225                 230                 235                 240

Lys Ala Ala Glu Leu Ser Gly Ser His Pro Asp Tyr Asn Gln Ala Lys
                245                 250                 255

Leu Phe Thr Gln Leu Gln Asn Gly Glu Lys Pro Lys Phe Asn Cys Tyr
            260                 265                 270

Val Gln Thr Met Thr Pro Glu Gln Ala Thr Lys Phe Arg Tyr Ser Val
        275                 280                 285

Asn Asp Leu Thr Lys Ile Trp Pro His Lys Glu Phe Pro Leu Arg Lys
    290                 295                 300

Phe Gly Thr Ile Thr Leu Thr Glu Asn Val Asp Asn Tyr Phe Gln Glu
305                 310                 315                 320

Ile Glu Gln Val Ala Phe Ser Pro Thr Asn Thr Cys Ile Pro Gly Ile
```

```
                325                 330                 335

Lys Pro Ser Asn Asp Ser Val Leu Gln Ala Arg Leu Phe Ser Tyr Pro
            340                 345                 350

Asp Thr Gln Arg His Arg Leu Gly Ala Asn Tyr Gln Gln Leu Pro Val
        355                 360                 365

Asn Arg Pro Arg Asn Leu Gly Cys Pro Tyr Ser Lys Gly Asp Ser Gln
    370                 375                 380

Tyr Thr Ala Glu Gln Cys Pro Phe Lys Ala Val Asn Phe Gln Arg Asp
385                 390                 395                 400

Gly Pro Met Ser Tyr Tyr Asn Phe Gly Pro Glu Pro Asn Tyr Ile Ser
                405                 410                 415

Ser Leu Pro Asn Gln Thr Leu Lys Phe Lys Asn Glu Asp Asn Asp Glu
            420                 425                 430

Val Ser Asp Lys Phe Lys Gly Ile Val Leu Asp Glu Val Thr Glu Val
        435                 440                 445

Ser Val Arg Lys Gln Glu Gln Asp Gln Ile Arg Asn Glu His Ile Val
    450                 455                 460

Asp Ala Lys Ile Asn Gln Tyr Tyr Tyr Val Tyr Gly Ile Ser Pro Leu
465                 470                 475                 480

Asp Phe Glu Gln Pro Arg Ala Leu Tyr Glu Lys Val Tyr Asn Asp Glu
                485                 490                 495

Gln Lys Lys Leu Phe Val His Asn Val Val Cys His Ala Cys Lys Ile
            500                 505                 510

Lys Asp Pro Lys Val Lys Lys Arg Val Thr Gln Tyr Phe Gly Leu Leu
        515                 520                 525

Asn Glu Asp Leu Gly Lys Val Ile Ala Glu Cys Leu Gly Val Pro Trp
    530                 535                 540

Glu Pro Val Asp Leu Glu Gly Tyr Ala Lys Thr Trp Ser Ile Ala Ser
545                 550                 555                 560

Ala Asn


<210> SEQ ID NO 52
<211> LENGTH: 524
<212> TYPE: PRT
<213> ORGANISM: Yarrowia lipolytica

<400> SEQUENCE: 52

Met Glu Ala Pro Asn Leu Ser Pro Ala Ser Ile Arg Arg Tyr Phe Ala
1               5                   10                  15

Thr Arg Leu Pro Thr Leu Ile Pro Gln Lys Leu Thr Pro Glu Glu Lys
            20                  25                  30

Lys Leu Leu Asn Pro Phe Pro Ala Leu Ala Leu Ile Asn Lys Lys Thr
        35                  40                  45

Trp Leu Phe Ile Ala Cys Ala Phe Cys Gly Trp Thr Trp Asp Ala Phe
    50                  55                  60

Asp Phe Phe Ser Val Gly Leu Val Ala Pro Glu Ile Ala Lys Ser Leu
65                  70                  75                  80

Asn Arg Ser Val Thr Asp Ile Thr Trp Gly Ile Thr Leu Val Leu Met
                85                  90                  95

Leu Arg Ser Ile Gly Ala Val Val Phe Gly Ile Ala Ser Asp Arg Tyr
            100                 105                 110

Gly Arg Lys Trp Pro Phe Ile Val Asn Leu Leu Cys Phe Ile Ala Leu
        115                 120                 125

Glu Leu Gly Ser Gly Phe Val Gln Thr Tyr Lys Gln Phe Leu Gly Val
```

```
    130                 135                 140

Arg Ala Ile Tyr Gly Ile Ala Met Gly Gly Leu Tyr Gly Asn Ala Ala
145                 150                 155                 160

Ala Thr Ala Leu Glu Asp Cys Pro Pro Gln Ala Arg Gly Ile Ile Ser
                165                 170                 175

Gly Phe Leu Gln Ser Gly Tyr Ala Leu Gly Tyr Leu Leu Cys Val Val
            180                 185                 190

Phe Thr Arg Ala Ile Ala Asp Thr Ser Pro Tyr Gly Trp Arg Ala Leu
        195                 200                 205

Phe Trp Phe Gly Ser Gly Pro Pro Val Leu Phe Ile Ile Phe Arg Tyr
    210                 215                 220

Phe Leu Pro Glu Thr Glu Thr Tyr Leu Ala Ser Lys Ala Ser Gln Glu
225                 230                 235                 240

Glu Ala Gly Ile Glu Lys Lys Phe Trp Asn Gly Ile Lys Val Thr Phe
                245                 250                 255

Lys Asn Tyr Trp Leu Met Phe Ile Tyr Leu Val Ile Leu Met Ala Gly
            260                 265                 270

Phe Asn Phe Met Ser His Gly Ser Gln Asp Leu Tyr Pro Thr Met Leu
        275                 280                 285

Lys Asn Gln Arg His Phe Ser Ala Asp Arg Ser Thr Val Thr Asn Cys
    290                 295                 300

Val Ala Asn Phe Gly Ala Ile Ala Gly Gly Met Leu Ile Gly His Phe
305                 310                 315                 320

Ser Thr Ala Leu Gly Arg Arg Leu Ser Ile Met Ile Ser Cys Val Ile
                325                 330                 335

Gly Gly Ala Leu Ile Tyr Pro Trp Ala Phe Val Gly Asn Ser Ala Gly
            340                 345                 350

Thr Asn Ala Gly Val Phe Phe Leu Gln Phe Phe Val Gln Gly Ala Trp
        355                 360                 365

Gly Val Val Pro Ile His Leu Ser Glu Leu Ser Pro Pro Glu Leu Arg
    370                 375                 380

Ser Ser Met Val Gly Ile Ala Tyr Gln Met Gly Asn Leu Ala Ser Ser
385                 390                 395                 400

Ala Ser Ser Thr Ile Glu Ser Lys Ile Gly Glu Arg Phe Pro Leu Lys
                405                 410                 415

Asn Ala Lys Gly Glu Phe Glu Lys Gly Phe Tyr Asp Tyr Gly Lys Val
            420                 425                 430

Met Ala Ile Phe Met Gly Cys Val Phe Gly Phe Val Leu Ile Val Thr
        435                 440                 445

Phe Val Gly Pro Glu Asn Arg Gly Ala Thr Met Leu Thr Glu Asp Ala
    450                 455                 460

Gln Met Met Val Asp Ala Glu His Arg Leu Asp Ala Glu Glu Lys Gly
465                 470                 475                 480

Asp Phe Glu Asn Leu Glu Arg Val Asp Ser Glu Gly Lys Gln Met Asp
                485                 490                 495

Asn Phe Val Glu Glu Val Ala Glu Pro Glu Gly Val Tyr Thr Gly Ser
            500                 505                 510

His Pro Pro Gln Tyr Asp Ser Pro Tyr Glu Ser Lys
        515                 520
```

<210> SEQ ID NO 53
<211> LENGTH: 4656
<212> TYPE: DNA
<213> ORGANISM: Artificial Sequence
<220> FEATURE:
<223> OTHER INFORMATION: Sequence put together from multiple organisms:
Saccharomyces cerevisiae and Saccharomyces kluyveri.

<400> SEQUENCE: 53

```
tcctattcgg agatacaggc aacaagtgat agagggccca ttatgaatac gcacctctat     60

gtatttccga gatacgatta ctccagttcc tcttacaaga aatgcataaa aatagttaca    120

attaattaga acaagaactt atttagaaca cgttcacact gagtaagaac tcttgtccct    180

tattagcctt gatagtgctg aaaaaaagaa aaaaaacaaa aaaaagaaat aaaataacgg    240

caaacagcaa aggccacaga accgtattca tgttacttct gcaatatcaa tcacttactg    300

gcaagtgcgt ataaattaaa cctatttctt tatcatcata tttacttata tctttaacag    360

attccaaacc ctaaagtgtc cgaattttca atagggcgaa cttgaagaat aaccaaggtc    420

aataatatat cttttagtat aaccctgaaa tttgccctat agaaatctag ggtttctgtg    480

tggtttccgg gtgagtcata cggctttttt gaatttcttt ttttgcagtt gtctctatca    540

atgaaaattt cgaggaagac gataaggtta agataagtag ataagagaat gatacgagat    600

aaagcacaaa ttagcagaaa gaagagtggt tgcgaacaga gtaaaccgaa tcagggaatc    660

cctttttgca aaaacatcaa ttatcctttt cttttttttta cgtatatatc tggaacagaa    720

atatataagt tactattata cttatagttg gatccagttt ttaatctgtc gtcaatcgaa    780

agtttatttc agagttcttc agacttctta actcctgtaa aaacaaaaaa aaaaaaaggc    840

atagcactcg agatctcccg agtttatcat tatcaatact gccatttcaa agaatacgta    900

aataattaat agtagtgatt ttcctaactt tatttagtca aaaaattggc cttttaattc    960

tgctgtaacc cgtacatgcc caaaataggg ggcgggttac acagaatata taacatcata   1020

ggtgtctggg tgaacagttt attcctggca tccactaaat ataatggagc ccgctttttt   1080

taagctggca tccagaaaaa aaaagaatcc cagcaccaaa atattgtttt cttcaccaac   1140

catcagttca taggtccatt ctcttagcgc aactacacag aacaggggca caaacaggca   1200

aaaaacgggc acaacctcaa tggagtgatg caacctgctt ggagtaaatg atgacacaag   1260

gcaattgacc tacgcatgta tctatctcat tttcttacac cttctattac cttctgctct   1320

ctctgatttg gaaaaagctg aaaaaaaagg ttgaaaccag ttccctgaaa ttattcccct   1380

atttgactaa taagtatata aagacggtag gtattgattg taattctgta aatctatttc   1440

ttaaacttct taaattctac ttttatagtt agtctttttt ttagtttaaa acaccaagaa   1500

cttagtttcg aataaacaca cataaacaaa caaatctaga ttgcatcctc gcttacttcg   1560

tggattgacc tcgaagaaat ctgtgatcaa cggatctaaa caactccgtc tcgcgtcaac   1620

tttgcgcaaa acttcccatg gttcctattc caaaaacagg ttttctaatg gtttgactgc   1680

tggtgctatt gctactgctg ctattggtgt atctctgtat tcttactcca ttgaaaacgg   1740

tactgttacg gactcttcca aaaaaccaat cgaccctcaa gatgtcgcta aacacaatga   1800

tccaaaggac tgctgggtag tcatcgacgg atacgtttat gatttgaccg agtttattca   1860

ttctcatcca ggtggtccaa ccattatcga aaataacgcc ggtaaagacg ttaccgcaat   1920

ttttggtcca attcatgctc cagacgtgat tgaaaaatat attgctcccg agaagagaat   1980

tggcccgttg gatggcgtca tgccacagga tttggtctgt tctcctctga ctcctggtga   2040

aacaccggac gacattgtcc gcaaagaaga actgcgtagc cgtctcccca gtttggacgc   2100

attggtcaac ctgtatgact ttgaatactt ggcgtcgcaa atattgacca agcaggcatg   2160

gtcttactac tcgtctgctg cagacgatga agtcacccat agggaaaacc atgcagctta   2220
```

```
ccaccgtata tttttcaaac caaaggtctt ggtcgatgtc agagaggttg atacttcaac   2280
gaaaatttta ggccaagatg ttcctgtgcc attttacgtt tctgcaaccg cgctatgtaa   2340
acttgggaat ccaaaggaag gtgaaaagga tgtcgcgcgc ggttgtggcc aagggccgat   2400
caagtgtcct caaatgattt ccacgttggc gtcatgttcc ttacaggaaa tcgtcgaagc   2460
agccccatcg aaagaacaaa tccagtggtt ccaactgtac gtcaatacag acagaaagat   2520
taccgatgac ttgatcaagc aggttgaaaa attggggttg aaggccatct ttgtgactgt   2580
ggatgctcct tctctaggta gacgggaaaa ggacatgaag gttaagttta caaactctaa   2640
cggtgctaag gcaatggaaa agactaaagt caaggaatct aagggtgctt ccgcagcatt   2700
gtctaccttc atcgaccctg ctttgagttg ggacgatatc gttgaaatca agaaaaagac   2760
aaatttgcca attgtcatta agggtgttca acgtgtcgaa gatgtgttga aggctgcaga   2820
agtaggtgct gctggtgtcg ttctttccaa ccacggtggt aggcagctgg acttttcgcg   2880
tgcgccaatt gaagtgttgg ccgaatctgt gccagttttg aaagagcgca atctaagcga   2940
caagctggag atctttatcg acggtggtgt gcgtcgtggt aacgatgtgc tgaaggccct   3000
atgtttgggt gccaagggtg ttggtctcgg tagaccattt ttgtatgcca acagttgtta   3060
cggtaaagac ggtgttcaaa aggctataga aatgttgact gaagagattc aaatgtccat   3120
gagattgttg ggtgtcacaa agattgaaga tttgaagccc gaactactgg atatgagcag   3180
ctttagcggc aggactgtca acgttccaca agacagccta tacaggtctg tctatgaaaa   3240
gagtgaaacc gtacaatttt tggatgaatg attaattaaa caggcccctt ttcctttgtc   3300
gatatcatgt aattagttat gtcacgctta cattcacgcc ctcctcccac atccgctcta   3360
accgaaaagg aaggagttag acaacctgaa gtctaggtcc ctatttattt ttttatagtt   3420
atgttagtat taagaacgtt atttatattt caaatttttc ttttttttct gtacaaacgc   3480
gtgtacgcat gtaacgggca gacggccggc cataacttcg tataatgtat gctatacgaa   3540
gttatggcaa cggttcatca tctcatggat ctgcacatga acaaacacca gagtcaaacg   3600
acgttgaaat tgaggctact gcgccaattg atgacaatac agacgatgat aacaaaccga   3660
agttatctga tgtagaaaag gattagagat gctaagagat agtgatgata tttcataaat   3720
aatgtaattc tatatatgtt aattaccttt tttgcgaggc atatttatgg tgaaggataa   3780
gttttgacca tcaaagaagg ttaatgtggc tgtggtttca gggtccataa agcttttcaa   3840
ttcatctttt tttttttgt tcttttttt gattccggtt tctttgaaat ttttttgatt   3900
cggtaatctc cgagcagaag gaagaacgaa ggaaggagca cagacttaga ttggtatata   3960
tacgcatatg tggtgttgaa gaaacatgaa attgcccagt attcttaacc caactgcaca   4020
gaacaaaaac ctgcaggaaa cgaagataaa tcatgtcgaa agctacatat aaggaacgtg   4080
ctgctactca tcctagtcct gttgctgcca agctatttaa tatcatgcac gaaaagcaaa   4140
caaacttgtg tgcttcattg gatgttcgta ccaccaagga attactggag ttagttgaag   4200
cattaggtcc caaaatttgt ttactaaaaa cacatgtgga tatcttgact gatttttcca   4260
tggagggcac agttaagccg ctaaaggcat tatccgccaa gtacaatttt ttactcttcg   4320
aagacagaaa atttgctgac attggtaata cagtcaaatt gcagtactct gcgggtgtat   4380
acagaatagc agaatgggca gacattacga atgcacacgg tgtggtgggc ccaggtattg   4440
ttagcggttt gaagcaggcg gcggaagaag taacaaagga acctagaggc cttttgatgt   4500
tagcagaatt gtcatgcaag ggctccctag ctactggaga atatactaag ggtactgttg   4560
```

```
acattgcgaa gagcgacaaa gattttgtta tcggctttat tgctcaaaga gacatgggtg   4620

gaagagatga aggttacgat tggttgatta tgacac                             4656


<210> SEQ ID NO 54
<211> LENGTH: 423
<212> TYPE: PRT
<213> ORGANISM: Saccharomyces kluyveri

<400> SEQUENCE: 54

Met Pro Gln Asp Leu Val Cys Ser Pro Leu Thr Pro Gly Glu Thr Pro
1               5                   10                  15

Asp Asp Ile Val Arg Lys Glu Glu Leu Arg Ser Arg Leu Pro Ser Leu
            20                  25                  30

Asp Ala Leu Val Asn Leu Tyr Asp Phe Glu Tyr Leu Ala Ser Gln Ile
        35                  40                  45

Leu Thr Lys Gln Ala Trp Ser Tyr Tyr Ser Ser Ala Ala Asp Asp Glu
    50                  55                  60

Val Thr His Arg Glu Asn His Ala Ala Tyr His Arg Ile Phe Phe Lys
65                  70                  75                  80

Pro Lys Val Leu Val Asp Val Arg Glu Val Asp Thr Ser Thr Lys Ile
                85                  90                  95

Leu Gly Gln Asp Val Pro Val Pro Phe Tyr Val Ser Ala Thr Ala Leu
            100                 105                 110

Cys Lys Leu Gly Asn Pro Lys Glu Gly Glu Lys Asp Val Ala Arg Gly
        115                 120                 125

Cys Gly Gln Gly Pro Ile Lys Cys Pro Gln Met Ile Ser Thr Leu Ala
    130                 135                 140

Ser Cys Ser Leu Gln Glu Ile Val Glu Ala Ala Pro Ser Lys Glu Gln
145                 150                 155                 160

Ile Gln Trp Phe Gln Leu Tyr Val Asn Thr Asp Arg Lys Ile Thr Asp
                165                 170                 175

Asp Leu Ile Lys Gln Val Glu Lys Leu Gly Leu Lys Ala Ile Phe Val
            180                 185                 190

Thr Val Asp Ala Pro Ser Leu Gly Arg Arg Glu Lys Asp Met Lys Val
        195                 200                 205

Lys Phe Thr Asn Ser Asn Gly Ala Lys Ala Met Glu Lys Thr Lys Val
    210                 215                 220

Lys Glu Ser Lys Gly Ala Ser Ala Ala Leu Ser Thr Phe Ile Asp Pro
225                 230                 235                 240

Ala Leu Ser Trp Asp Asp Ile Val Glu Ile Lys Lys Lys Thr Asn Leu
                245                 250                 255

Pro Ile Val Ile Lys Gly Val Gln Arg Val Glu Asp Val Leu Lys Ala
            260                 265                 270

Ala Glu Val Gly Ala Ala Gly Val Val Leu Ser Asn His Gly Gly Arg
        275                 280                 285

Gln Leu Asp Phe Ser Arg Ala Pro Ile Glu Val Leu Ala Glu Ser Val
    290                 295                 300

Pro Val Leu Lys Glu Arg Asn Leu Ser Asp Lys Leu Glu Ile Phe Ile
305                 310                 315                 320

Asp Gly Gly Val Arg Arg Gly Asn Asp Val Leu Lys Ala Leu Cys Leu
                325                 330                 335

Gly Ala Lys Gly Val Gly Leu Gly Arg Pro Phe Leu Tyr Ala Asn Ser
            340                 345                 350

Cys Tyr Gly Lys Asp Gly Val Gln Lys Ala Ile Glu Met Leu Thr Glu
```

```
        355                 360                 365

Glu Ile Gln Met Ser Met Arg Leu Leu Gly Val Thr Lys Ile Glu Asp
    370                 375                 380

Leu Lys Pro Glu Leu Leu Asp Met Ser Ser Phe Ser Gly Arg Thr Val
385                 390                 395                 400

Asn Val Pro Gln Asp Ser Leu Tyr Arg Ser Val Tyr Glu Lys Ser Glu
                405                 410                 415

Thr Val Gln Phe Leu Asp Glu
            420


<210> SEQ ID NO 55
<211> LENGTH: 4704
<212> TYPE: DNA
<213> ORGANISM: Artificial Sequence
<220> FEATURE:
<223> OTHER INFORMATION: Sequence put together from multiple organisms:
      Saccharomyces cerevisiae and Saccharomyces bayanus.

<400> SEQUENCE: 55

tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180

tattagcctt gatagtgctg aaaaaaagaa aaaaaacaaa aaaaagaaat aaaataacgg     240

caaacagcaa aggccacaga accgtattca tgttacttct gcaatatcaa tcacttactg     300

gcaagtgcgt ataaattaaa cctatttctt tatcatcata tttacttata tctttaacag     360

attccaaacc ctaaagtgtc cgaattttca atagggcgaa cttgaagaat aaccaaggtc     420

aataatatat cttttagtat aaccctgaaa tttgccctat agaaatctag ggtttctgtg     480

tggtttccgg gtgagtcata cggctttttt gaatttcttt ttttgcagtt gtctctatca     540

atgaaaattt cgaggaagac gataaggtta agataagtag ataagagaat gatacgagat     600

aaagcacaaa ttagcagaaa gaagagtggt tgcgaacaga gtaaaccgaa tcagggaatc     660

cctttttgca aaaacatcaa ttatcctttt cttttttttta cgtatatatc tggaacagaa     720

atatataagt tactattata cttatagttg gatccagttt ttaatctgtc gtcaatcgaa     780

agtttatttc agagttcttc agacttctta actcctgtaa aaacaaaaaa aaaaaaaggc     840

atagcactcg agatctcccg agtttatcat tatcaatact gccatttcaa agaatacgta     900

aataattaat agtagtgatt ttcctaactt tatttagtca aaaaattggc cttttaattc     960

tgctgtaacc cgtacatgcc caaaataggg ggcgggttac acagaatata taacatcata    1020

ggtgtctggg tgaacagttt attcctggca tccactaaat ataatggagc ccgctttttt    1080

taagctggca tccagaaaaa aaaagaatcc cagcaccaaa atattgtttt cttcaccaac    1140

catcagttca taggtccatt ctcttagcgc aactacacag aacaggggca caaacaggca    1200

aaaaacgggc acaacctcaa tggagtgatg caacctgctt ggagtaaatg atgacacaag    1260

gcaattgacc tacgcatgta tctatctcat tttcttacac cttctattac cttctgctct    1320

ctctgatttg gaaaaagctg aaaaaaaagg ttgaaaccag ttccctgaaa ttattcccct    1380

atttgactaa taagtatata aagacggtag gtattgattg taattctgta aatctatttc    1440

ttaaacttct taaattctac ttttatagtt agtctttttt ttagtttaaa acaccaagaa    1500

cttagtttcg aataaacaca cataaacaaa caaatctaga atgttaaaat acaaatctct    1560

gctgagaatc tcgagagtct ccgaggcagc cgctctcaga acgtccagga ctagattaaa    1620
```

```
cacagtccgc tcttacagtt ctgctgtggg caagtctaag tcgttcgaga aacattccgg   1680
aaaacgcaca cagtcatgga ctgctttgag cgtcggtgcc atcttagccg ctgctggttc   1740
aatggcttat gtaaactggg gtagtggcca gataggtaac gacccaaaac tagacatgaa   1800
taagcagaaa atatcgcctg cagaagtcgc taaacacaac tcggctgacg attgctgggt   1860
cgtgatcaac ggttatgtgt atgatctgac gcggttcgta cctaaccatc caggtggccc   1920
ggatgttatc aaatacaatg ctgggagaga cgtcactgcc atttttgagc cattgcatgc   1980
ccccaacgtc atcgataaat acattgctcc tgagaagaag ctgggaccgc tacaggggtc   2040
catgccacca gaactggttt gcccgccata cgctccaggc gaaaccaaag aagacattgc   2100
taggaaagag caactaaaat cattactccc cccactggat aacattatta atctttatga   2160
tttcgagtac ttggcttctc aaactttgac taggcaagcc tgggcttact actcctctgg   2220
ttccaatgac gaagtctcgc acagggaaaa ccataatgca taccacagga ttttcttcaa   2280
gccaaagatt cttgttgacg tgagcaaagt ggacatctcg acggacatgc tgggttctca   2340
tgtcgacgtc ccattctacg tgtctgcaac agccctgtgt aaactgggga acccactaga   2400
aggtgaaaag gacattgcta gaggctgtgg ccaaggcgca acgaaagtcc cacaaatgat   2460
ctccactttg gcgtcatgct caccagaaga aatcatcagt gcggcgccat ccgatgagca   2520
gattcaatgg tatcaactat acgttaactc tgatagaaag atcactgacg aattggttaa   2580
gagtgttgaa aaattgggcg tgaaggcact gtttgttact gtagatgcac caagtttagg   2640
ccagagagag aaggatatga agttaaaatt ctccaattca aaagctggcc caaaggcaat   2700
gaagaaaaca gatgtagagg aatctaaagg cgcctcaaga gcgttgtcca agtttattga   2760
cccctctttg acttggaagg atattgaaga gttgaaatca aagacaaacc tacccattgt   2820
catcaaaggt gttcaacgca ccgaagatgt cgttaaagca gctgaggttg gtgtaagtgg   2880
cgtggtgcta tccaaccacg gtggtagaca attagacttt tcgagagccc ccatcgaagt   2940
cttggctgaa gccatgccag ttctggaaga acgtaaattg aaggataaac tggaagtata   3000
catagacggt ggcgttcgtc gtggtacaga tatcctaaag gcgctgtgtc tgggcgctaa   3060
aggtgttggt ttgggtagac cattcctgta cgccaactca tgctatggtc gcgacggtgt   3120
tgagaaagcc attgaaattt tgcgagatga agtcgaaatg tccatgagac tcctgggtgt   3180
tgccagtgtt gcggaattga agcctgagct gttagatctg tcaacattga aggcaagaac   3240
agtggcagtg cccaacgatg tcttgtataa tgaggtttac gaaggcccca ctttaacaga   3300
ttttgaggac gcatgattat taattaaaca ggcccctttt cctttgtcga tatcatgtaa   3360
ttagttatgt cacgcttaca ttcacgccct cctcccacat ccgctctaac cgaaaaggaa   3420
ggagttagac aacctgaagt ctaggtccct atttattttt ttatagttat gttagtatta   3480
agaacgttat ttatatttca aatttttctt ttttttctgt acaaacgcgt gtacgcatgt   3540
aacgggcaga cggccggcca taacttcgta taatgtatgc tatacgaagt tatggcaacg   3600
gttcatcatc tcatggatct gcacatgaac aaacaccaga gtcaaacgac gttgaaattg   3660
aggctactgc gccaattgat gacaatacag acgatgataa caaaccgaag ttatctgatg   3720
tagaaaagga ttagagatgc taagagatag tgatgatatt tcataaataa tgtaattcta   3780
tatatgttaa ttaccttttt tgcgaggcat atttatggtg aaggataagt tttgaccatc   3840
aaagaaggtt aatgtggctg tggtttcagg gtccataaag cttttcaatt catctttttt   3900
ttttttgttc ttttttttga ttccggtttc tttgaaattt ttttgattcg gtaatctccg   3960
agcagaagga agaacgaagg aaggagcaca gacttagatt ggtatatata cgcatatgtg   4020
```

```
gtgttgaaga aacatgaaat tgcccagtat tcttaaccca actgcacaga acaaaaacct   4080

gcaggaaacg aagataaatc atgtcgaaag ctacatataa ggaacgtgct gctactcatc   4140

ctagtcctgt tgctgccaag ctatttaata tcatgcacga aaagcaaaca aacttgtgtg   4200

cttcattgga tgttcgtacc accaaggaat tactggagtt agttgaagca ttaggtccca   4260

aaatttgttt actaaaaaca catgtggata tcttgactga tttttccatg gagggcacag   4320

ttaagccgct aaaggcatta tccgccaagt acaatttttt actcttcgaa gacagaaaat   4380

ttgctgacat tggtaataca gtcaaattgc agtactctgc gggtgtatac agaatagcag   4440

aatgggcaga cattacgaat gcacacggtg tggtgggccc aggtattgtt agcggtttga   4500

agcaggcggc ggaagaagta acaaaggaac ctagaggcct tttgatgtta gcagaattgt   4560

catgcaaggg ctccctagct actggagaat atactaaggg tactgttgac attgcgaaga   4620

gcgacaaaga ttttgttatc ggctttattg ctcaaagaga catgggtgga agagatgaag   4680

gttacgattg gttgattatg acac                                         4704
```

<210> SEQ ID NO 56
<211> LENGTH: 591
<212> TYPE: PRT
<213> ORGANISM: Saccharomyces bayanus

<400> SEQUENCE: 56

```
Met Leu Lys Tyr Lys Ser Leu Leu Arg Ile Ser Arg Val Ser Glu Ala
1               5                   10                  15

Ala Ala Leu Arg Thr Ser Arg Thr Arg Leu Asn Thr Val Arg Ser Tyr
            20                  25                  30

Ser Ser Ala Val Gly Lys Ser Lys Ser Phe Glu Lys His Ser Gly Lys
        35                  40                  45

Arg Thr Gln Ser Trp Thr Ala Leu Ser Val Gly Ala Ile Leu Ala Ala
    50                  55                  60

Ala Gly Ser Met Ala Tyr Val Asn Trp Gly Ser Gly Gln Ile Gly Asn
65                  70                  75                  80

Asp Pro Lys Leu Asp Met Asn Lys Gln Lys Ile Ser Pro Ala Glu Val
                85                  90                  95

Ala Lys His Asn Ser Ala Asp Asp Cys Trp Val Val Ile Asn Gly Tyr
            100                 105                 110

Val Tyr Asp Leu Thr Arg Phe Val Pro Asn His Pro Gly Gly Pro Asp
        115                 120                 125

Val Ile Lys Tyr Asn Ala Gly Arg Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Arg Gln Ala Trp Ala Tyr Tyr
    210                 215                 220

Ser Ser Gly Ser Asn Asp Glu Val Ser His Arg Glu Asn His Asn Ala
225                 230                 235                 240

Tyr His Arg Ile Phe Phe Lys Pro Lys Ile Leu Val Asp Val Ser Lys
```

```
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Ile Ala Arg Gly Cys Gly Gln Gly Ala Thr Lys Val Pro
    290                 295                 300

Gln Met Ile Ser Thr Leu Ala Ser Cys Ser Pro Glu Glu Ile Ile Ser
305                 310                 315                 320

Ala Ala Pro Ser Asp Glu Gln Ile Gln Trp Tyr Gln Leu Tyr Val Asn
                325                 330                 335

Ser Asp Arg Lys Ile Thr Asp Glu Leu Val Lys Ser Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Ser Lys Ala Gly Pro
    370                 375                 380

Lys Ala Met Lys Lys Thr Asp Val Glu Glu Ser Lys Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Ser Lys Thr Asn Leu Pro Ile Val Ile Lys Gly Val Gln
            420                 425                 430

Arg Thr Glu Asp Val Val Lys Ala Ala Glu Val Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Ala Met Pro Val Leu Glu Glu Arg Lys Leu
465                 470                 475                 480

Lys Asp Lys Leu Glu Val Tyr Ile Asp Gly Gly Val Arg Arg Gly Thr
                485                 490                 495

Asp Ile Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asp Gly Val Glu
        515                 520                 525

Lys Ala Ile Glu Ile Leu Arg Asp Glu Val Glu Met Ser Met Arg Leu
    530                 535                 540

Leu Gly Val Ala Ser Val Ala Glu Leu Lys Pro Glu Leu Leu Asp Leu
545                 550                 555                 560

Ser Thr Leu Lys Ala Arg Thr Val Ala Val Pro Asn Asp Val Leu Tyr
                565                 570                 575

Asn Glu Val Tyr Glu Gly Pro Thr Leu Thr Asp Phe Glu Asp Ala
            580                 585                 590


<210> SEQ ID NO 57
<211> LENGTH: 4722
<212> TYPE: DNA
<213> ORGANISM: Artificial Sequence
<220> FEATURE:
<223> OTHER INFORMATION: Sequence put together from multiple organisms:
      Saccharomyces cerevisiae and Zygosaccharomyces rouxii.

<400> SEQUENCE: 57

tcctattcgg agatacaggc aacaagtgat agagggccca ttatgaatac gcacctctat      60

gtatttccga gatacgatta ctccagttcc tcttacaaga aatgcataaa aatagttaca     120
```

attaattaga acaagaactt atttagaaca cgttcacact gagtaagaac tcttgtccct 180
tattagcctt gatagtgctg aaaaaaagaa aaaaaacaaa aaaaagaaat aaaataacgg 240
caaacagcaa aggccacaga accgtattca tgttacttct gcaatatcaa tcacttactg 300
gcaagtgcgt ataaattaaa cctatttctt tatcatcata tttacttata tctttaacag 360
attccaaacc ctaaagtgtc cgaattttca atagggcgaa cttgaagaat aaccaaggtc 420
aataatatat cttttagtat aaccctgaaa tttgccctat agaaatctag ggtttctgtg 480
tggtttccgg gtgagtcata cggctttttt gaatttcttt ttttgcagtt gtctctatca 540
atgaaaattt cgaggaagac gataaggtta agataagtag ataagagaat gatacgagat 600
aaagcacaaa ttagcagaaa gaagagtggt tgcgaacaga gtaaaccgaa tcagggaatc 660
ccttttttgca aaaacatcaa ttatcctttt cttttttttta cgtatatatc tggaacagaa 720
atatataagt tactattata cttatagttg gatccagttt ttaatctgtc gtcaatcgaa 780
agtttatttc agagttcttc agacttctta actcctgtaa aaacaaaaaa aaaaaaaggc 840
atagcactcg agatctcccg agtttatcat tatcaatact gccatttcaa agaatacgta 900
aataattaat agtagtgatt ttcctaactt tatttagtca aaaaattggc cttttaattc 960
tgctgtaacc cgtacatgcc caaaataggg ggcgggttac acagaatata taacatcata 1020
ggtgtctggg tgaacagttt attcctggca tccactaaat ataatggagc ccgctttttt 1080
taagctggca tccagaaaaa aaaagaatcc cagcaccaaa atattgtttt cttcaccaac 1140
catcagttca taggtccatt ctcttagcgc aactacacag aacaggggca caaacaggca 1200
aaaaacgggc acaacctcaa tggagtgatg caacctgctt ggagtaaatg atgacacaag 1260
gcaattgacc tacgcatgta tctatctcat tttcttacac cttctattac cttctgctct 1320
ctctgatttg gaaaaagctg aaaaaaaagg ttgaaaccag ttccctgaaa ttattcccct 1380
atttgactaa taagtatata aagacggtag gtattgattg taattctgta aatctatttc 1440
ttaaacttct taaattctac ttttatagtt agtctttttt ttagtttaaa acaccaagaa 1500
cttagtttcg aataaacaca cataaacaaa caaatctaga atgtggttta gatcgaagcc 1560
tatttggaag ttatcagagg ttactgctag atctttacgt ggtatcaata ctaagagatc 1620
ttttacctgg aattctaagg gcagcaatgc attcgtacgc tcctctattt tgaagaagcg 1680
tagtatggct actgcgttat tggttaccgc tgtagccgct gcatcgagtg ttaaattgtc 1740
ctctcgacct ttagataacg gaccgaaagt agatatgtca aaacctgcca ttagtccaga 1800
tgaagtcgct aaacacaatt cgcccgatga ttgttgggtt gttattgatg gatatgtcta 1860
cgatttgacg gaatttgctc ctgtacatcc tggtggacct acagtaatta aatcaaacgc 1920
aggtaaagat gtcagtgcaa tttttgatcc attgcatgct ccagatgtta ttgagaaatt 1980
tattgatcca agtaaaaggt taggtccctt ggagggcgat atgccaaagg aattggtttg 2040
tgcgcctttt acacccggtg aaacccctga tgatgttcaa agaaaattga aattaagagc 2100
taggttacct ccgctggatg caattaccaa tctgtacgat tttgaattct tagcatctca 2160
agttttaacc aagcaggcat gggcttacta ttcaagtggt gctgatgatg aaattaccat 2220
gagagaaaac cactttgcat accatagaat tttctttaag cctaaagttt tggtgaacgt 2280
tgctgaggtg gatacaaaga ctgaaatgct gggtgcacct gttgatgtgc cattctatgt 2340
tactgctaca gcattgtgta aactgggtaa tccagctgag ggtgaaaaag atattgcaag 2400
aggttgtgga tctggtgaga aaaaggtgcc tcaaatggtt tccacattag catcctgttc 2460

```
cttagaagaa gtggttaatg caggcaaaga agatcaaata agatggtttc agttgtacat   2520
gaatgaggat cgtagtgtag tggatcaaat gatctccagt gcagaaaaat tgggttacaa   2580
aggtatattc gtaactgtcg atgcacctgg gcttggtaat agagaaaagg atacaaaggt   2640
taaattttct agtcaggccg gtccgttgag tgtgaaaaag aaggaaaagg aggataaagg   2700
taaagataat ggagaatcta gtggagcctc taaatattta tctaaattta ttgatccttc   2760
attcgactgg gatgacttgg ttgaagtgaa gaaaaagaca aaattaccaa ttgtgattaa   2820
aggtgttcaa agagttgaag atgttgttaa ggctgctgaa gttggcgcta gtggtgttgt   2880
gctttcaaat catggtggta ggcaattaga tttctctagg tcaccaattg aagttttggc   2940
tgaagctcaa ccaattctca aagaacgcaa ttttgaaaac tttgatgttt tcgttgatgg   3000
tggtattcgc agaggtactg atgtggttaa ggctctttgt cttggtgcta aaggtgttgg   3060
tttaggtagg cctttcctat atgccaactc ggtttatggg aaggaaggtg ttcaaaaagc   3120
aattgatatt ctcaattttg aagtggagat gacgatgaga ttgcttggtg ttacttctat   3180
caagcaattg gggccggagt tgatagatac ttcatgtatt aaatccagat ctgttcaagt   3240
accaagggac tacctctacg acaagactta catgagttct gatttggtta gtttcatgcc   3300
accacaagaa gacgaggctg atggcgagaa cgagtgatta attaaacagg cccctttcc    3360
tttgtcgata tcatgtaatt agttatgtca cgcttacatt cacgccctcc tcccacatcc   3420
gctctaaccg aaaaggaagg agttagacaa cctgaagtct aggtccctat ttattttttt   3480
atagttatgt tagtattaag aacgttattt atatttcaaa tttttctttt ttttctgtac   3540
aaacgcgtgt acgcatgtaa cgggcagacg gccggccata acttcgtata atgtatgcta   3600
tacgaagtta tggcaacggt tcatcatctc atggatctgc acatgaacaa acaccagagt   3660
caaacgacgt tgaaattgag gctactgcgc caattgatga caatacagac gatgataaca   3720
aaccgaagtt atctgatgta gaaaaggatt agagatgcta agagatagtg atgatatttc   3780
ataaataatg taattctata tatgttaatt accttttttg cgaggcatat ttatggtgaa   3840
ggataagttt tgaccatcaa agaaggttaa tgtggctgtg gtttcagggt ccataaagct   3900
tttcaattca tcttttttt ttttgttctt tttttgatt ccggtttctt tgaaattttt     3960
ttgattcggt aatctccgag cagaaggaag aacgaaggaa ggagcacaga cttagattgg   4020
tatatatacg catatgtggt gttgaagaaa catgaaattg cccagtattc ttaacccaac   4080
tgcacagaac aaaaacctgc aggaaacgaa gataaatcat gtcgaaagct acatataagg   4140
aacgtgctgc tactcatcct agtcctgttg ctgccaagct atttaatatc atgcacgaaa   4200
agcaaacaaa cttgtgtgct tcattggatg ttcgtaccac caaggaatta ctggagttag   4260
ttgaagcatt aggtcccaaa atttgtttac taaaaacaca tgtggatatc ttgactgatt   4320
tttccatgga gggcacagtt aagccgctaa aggcattatc cgccaagtac aattttttac   4380
tcttcgaaga cagaaaattt gctgacattg gtaatacagt caaattgcag tactctgcgg   4440
gtgtatacag aatagcagaa tgggcagaca ttacgaatgc acacggtgtg gtgggcccag   4500
gtattgttag cggtttgaag caggcggcgg aagaagtaac aaaggaacct agaggccttt   4560
tgatgttagc agaattgtca tgcaagggct ccctagctac tggagaatat actaagggta   4620
ctgttgacat tgcgaagagc gacaaagatt ttgttatcgg ctttattgct caaagagaca   4680
tgggtggaag agatgaaggt tacgattggt tgattatgac ac                      4722
```

<210> SEQ ID NO 58
<211> LENGTH: 598

<212> TYPE: PRT
<213> ORGANISM: Zygosaccharomyces rouxii

<400> SEQUENCE: 58

```
Met Trp Phe Arg Ser Lys Pro Ile Trp Lys Leu Ser Glu Val Thr Ala
1               5                   10                  15

Arg Ser Leu Arg Gly Ile Asn Thr Lys Arg Ser Phe Thr Trp Asn Ser
            20                  25                  30

Lys Gly Ser Asn Ala Phe Val Arg Ser Ser Ile Leu Lys Lys Arg Ser
        35                  40                  45

Met Ala Thr Ala Leu Leu Val Thr Ala Val Ala Ala Ala Ser Ser Val
    50                  55                  60

Lys Leu Ser Ser Arg Pro Leu Asp Asn Gly Pro Lys Val Asp Met Ser
65                  70                  75                  80

Lys Pro Ala Ile Ser Pro Asp Glu Val Ala Lys His Asn Ser Pro Asp
                85                  90                  95

Asp Cys Trp Val Val Ile Asp Gly Tyr Val Tyr Asp Leu Thr Glu Phe
            100                 105                 110

Ala Pro Val His Pro Gly Gly Pro Thr Val Ile Lys Ser Asn Ala Gly
        115                 120                 125

Lys Asp Val Ser Ala Ile Phe Asp Pro Leu His Ala Pro Asp Val Ile
    130                 135                 140

Glu Lys Phe Ile Asp Pro Ser Lys Arg Leu Gly Pro Leu Glu Gly Asp
145                 150                 155                 160

Met Pro Lys Glu Leu Val Cys Ala Pro Phe Thr Pro Gly Glu Thr Pro
                165                 170                 175

Asp Asp Val Gln Arg Lys Leu Lys Leu Arg Ala Arg Leu Pro Pro Leu
            180                 185                 190

Asp Ala Ile Thr Asn Leu Tyr Asp Phe Glu Phe Leu Ala Ser Gln Val
        195                 200                 205

Leu Thr Lys Gln Ala Trp Ala Tyr Tyr Ser Ser Gly Ala Asp Asp Glu
    210                 215                 220

Ile Thr Met Arg Glu Asn His Phe Ala Tyr His Arg Ile Phe Phe Lys
225                 230                 235                 240

Pro Lys Val Leu Val Asn Val Ala Glu Val Asp Thr Lys Thr Glu Met
                245                 250                 255

Leu Gly Ala Pro Val Asp Val Pro Phe Tyr Val Thr Ala Thr Ala Leu
            260                 265                 270

Cys Lys Leu Gly Asn Pro Ala Glu Gly Glu Lys Asp Ile Ala Arg Gly
        275                 280                 285

Cys Gly Ser Gly Glu Lys Lys Val Pro Gln Met Val Ser Thr Leu Ala
    290                 295                 300

Ser Cys Ser Leu Glu Glu Val Val Asn Ala Gly Lys Glu Asp Gln Ile
305                 310                 315                 320

Arg Trp Phe Gln Leu Tyr Met Asn Glu Asp Arg Ser Val Val Asp Gln
                325                 330                 335

Met Ile Ser Ser Ala Glu Lys Leu Gly Tyr Lys Gly Ile Phe Val Thr
            340                 345                 350

Val Asp Ala Pro Gly Leu Gly Asn Arg Glu Lys Asp Thr Lys Val Lys
        355                 360                 365

Phe Ser Ser Gln Ala Gly Pro Leu Ser Val Lys Lys Glu Lys Glu
    370                 375                 380

Asp Lys Gly Lys Asp Asn Gly Glu Ser Ser Gly Ala Ser Lys Tyr Leu
385                 390                 395                 400
```

```
Ser Lys Phe Ile Asp Pro Ser Phe Asp Trp Asp Asp Leu Val Glu Val
                405                 410                 415

Lys Lys Lys Thr Lys Leu Pro Ile Val Ile Lys Gly Val Gln Arg Val
            420                 425                 430

Glu Asp Val Val Lys Ala Ala Glu Val Gly Ala Ser Gly Val Val Leu
        435                 440                 445

Ser Asn His Gly Gly Arg Gln Leu Asp Phe Ser Arg Ser Pro Ile Glu
    450                 455                 460

Val Leu Ala Glu Ala Gln Pro Ile Leu Lys Glu Arg Asn Phe Glu Asn
465                 470                 475                 480

Phe Asp Val Phe Val Asp Gly Gly Ile Arg Arg Gly Thr Asp Val Val
                485                 490                 495

Lys Ala Leu Cys Leu Gly Ala Lys Gly Val Gly Leu Gly Arg Pro Phe
            500                 505                 510

Leu Tyr Ala Asn Ser Val Tyr Gly Lys Glu Gly Val Gln Lys Ala Ile
        515                 520                 525

Asp Ile Leu Asn Phe Glu Val Glu Met Thr Met Arg Leu Leu Gly Val
    530                 535                 540

Thr Ser Ile Lys Gln Leu Gly Pro Glu Leu Ile Asp Thr Ser Cys Ile
545                 550                 555                 560

Lys Ser Arg Ser Val Gln Val Pro Arg Asp Tyr Leu Tyr Asp Lys Thr
                565                 570                 575

Tyr Met Ser Ser Asp Leu Val Ser Phe Met Pro Pro Gln Glu Asp Glu
            580                 585                 590

Ala Asp Gly Glu Asn Glu
        595


<210> SEQ ID NO 59
<211> LENGTH: 4695
<212> TYPE: DNA
<213> ORGANISM: Artificial Sequence
<220> FEATURE:
<223> OTHER INFORMATION: Sequence put together from multiple organisms:
      Saccharomyces cerevisiae and Kluyveromyces lactis.

<400> SEQUENCE: 59

tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180

tattagcctt gatagtgctg aaaaaaagaa aaaaaacaaa aaaaagaaat aaaataacgg     240

caaacagcaa aggccacaga accgtattca tgttacttct gcaatatcaa tcacttactg     300

gcaagtgcgt ataaattaaa cctatttctt tatcatcata tttacttata tctttaacag     360

attccaaacc ctaaagtgtc cgaattttca atagggcgaa cttgaagaat aaccaaggtc     420

aataatatat cttttagtat aaccctgaaa tttgccctat agaaatctag ggtttctgtg     480

tggtttccgg gtgagtcata cggctttttt gaatttcttt ttttgcagtt gtctctatca     540

atgaaaattt cgaggaagac gataaggtta agataagtag ataagagaat gatacgagat     600

aaagcacaaa ttagcagaaa gaagagtggt tgcgaacaga gtaaaccgaa tcagggaatc     660

cctttttgca aaaacatcaa ttatcctttt cttttttta cgtatatatc tggaacagaa     720

atatataagt tactattata cttatagttg gatccagttt ttaatctgtc gtcaatcgaa     780

agtttatttc agagttcttc agacttctta actcctgtaa aaacaaaaaa aaaaaaaggc     840
```

```
atagcactcg agatctcccg agtttatcat tatcaatact gccatttcaa agaatacgta    900
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgagatcag ccgtaagagt   1560
ttttggtaag aaccgtgtta gtgggttgag atttgctagc accagtagta aatctccaat   1620
tcataagtct agtgctactc tgcgttttgg gagatcagct aagtctggct atagtgcgtt   1680
ttcgttcggt aagaaagtca tcactggtgg tgcctttctt gttgccggtt cggttggtat   1740
tgcattgatt tctcaattca atgatagcgt tgaaaatggt gccaaggtcg atatgacgaa   1800
accaaaggtt tctccaacag aagtcgcaaa gcactcttct cccaaagact gttgggtggt   1860
cattgagggt tacgtataca atttgactga tttcatcagc gcccatcctg gtggtccagc   1920
tatcattgag aacaacgcag gaaaagatgt gaccaagatc tttgctccaa ttcatgctcc   1980
agatgtcatc gaaaaataca ttgctccaga gaacagaatt ggtccactag atggtacaat   2040
gcctgatgac ttggtctgtg ctgcattgac cccaggtgaa actcccgaag atgtggcaag   2100
aaaggaacaa ttgcgtcaat ctttacccga tattgattcc ttggttaaca tctatgattt   2160
cgaattcttg gcatcccaaa tcttgactaa gcaagcttgg tcttactact cttctgccgc   2220
tgatgatgaa gttacacata gagaaaacca cgctgcatac catcgtatat tcttcaagcc   2280
aagaatcttg gttaacgtta aggaagttga cacttccact acaatgttag gtgaaaaagt   2340
cggtgttcca ttttatgtgt ctgccaccgc attgtgtaaa ctaggtaacc ccaaggaagg   2400
tgaaaaggac atcgcaagag gttgcggtga aagtgacgtg aaacctgttc aaatgatttc   2460
cactttggct tcttgttctt tacaagaaat cgtggaagca gccccatcta aggaacaaat   2520
ccaatggttc caattgtatg tgaacagtga ccgtaagatc actgaagatc taatcaagaa   2580
cgttgaaaaa ttaggattaa aggccatttt cgttacagta gatgctcctt ccttaggtaa   2640
cagagaaaaa gatgctaaag tcaaatttac aaactcaaac ggtgccaagg ctatggaaaa   2700
aagtaaggtt aaggaatcta agggtgcttc tagagctctc tcgtcattca ttgatcctgc   2760
attaaactgg gatgatatca tcgaatttaa gaaaaagacc aaattgccaa tcgtcatcaa   2820
gggtgttcaa tgtgttgaag atgtcttgaa agctgctgaa atcggtgttg caggtgtcgt   2880
tctatctaac cacggtggta gacaattgga tttctctagg gctcctatcg aagtgttggc   2940
tgagactatg ccagtgctaa gagaaaagaa attggatgat aaaatcgaaa ttttcattga   3000
tggtggtgtt agaagaggta ccgatatcct aaaggcattg tgtcttggtg ccaagggtgt   3060
cggtctaggt agaccattct tatactctaa cagttgctac ggtaaagaag gtgtcaagaa   3120
agccattgag ctattaaagg acgaattgga aatgtcgatg agattactcg gtgtcacaag   3180
tatagaccaa ttatccgaaa aatacctaga tctatctaca atccatggta gaactgtcaa   3240
```

```
tgttcctcgc gataacctat accgtgaggt atatgtccca catgaaccaa ctcaattctt   3300

agaggaatga ttaattaaac aggccccttt tcctttgtcg atatcatgta attagttatg   3360

tcacgcttac attcacgccc tcctcccaca tccgctctaa ccgaaaagga aggagttaga   3420

caacctgaag tctaggtccc tatttatttt tttatagtta tgttagtatt aagaacgtta   3480

tttatatttc aaatttttct tttttttctg tacaaacgcg tgtacgcatg taacgggcag   3540

acggccggcc ataacttcgt ataatgtatg ctatacgaag ttatggcaac ggttcatcat   3600

ctcatggatc tgcacatgaa caaacaccag agtcaaacga cgttgaaatt gaggctactg   3660

cgccaattga tgacaataca gacgatgata acaaaccgaa gttatctgat gtagaaaagg   3720

attagagatg ctaagagata gtgatgatat ttcataaata atgtaattct atatatgtta   3780

attacctttt ttgcgaggca tatttatggt gaaggataag ttttgaccat caaagaaggt   3840

taatgtggct gtggtttcag ggtccataaa gcttttcaat tcatcttttt tttttttgtt   3900

cttttttttg attccggttt ctttgaaatt tttttgattc ggtaatctcc gagcagaagg   3960

aagaacgaag gaaggagcac agacttagat tggtatatat acgcatatgt ggtgttgaag   4020

aaacatgaaa ttgcccagta ttcttaaccc aactgcacag aacaaaaacc tgcaggaaac   4080

gaagataaat catgtcgaaa gctacatata aggaacgtgc tgctactcat cctagtcctg   4140

ttgctgccaa gctatttaat atcatgcacg aaaagcaaac aaacttgtgt gcttcattgg   4200

atgttcgtac caccaaggaa ttactggagt tagttgaagc attaggtccc aaaatttgtt   4260

tactaaaaac acatgtggat atcttgactg atttttccat ggagggcaca gttaagccgc   4320

taaaggcatt atccgccaag tacaattttt tactcttcga agacagaaaa tttgctgaca   4380

ttggtaatac agtcaaattg cagtactctg cgggtgtata cagaatagca gaatgggcag   4440

acattacgaa tgcacacggt gtggtgggcc caggtattgt tagcggtttg aagcaggcgg   4500

cggaagaagt aacaaaggaa cctagaggcc ttttgatgtt agcagaattg tcatgcaagg   4560

gctccctagc tactggagaa tatactaagg gtactgttga cattgcgaag agcgacaaag   4620

attttgttat cggctttatt gctcaaagag acatgggtgg aagagatgaa ggttacgatt   4680

ggttgattat gacac                                                    4695
```

<210> SEQ ID NO 60
<211> LENGTH: 589
<212> TYPE: PRT
<213> ORGANISM: Kluyveromyces lactis

<400> SEQUENCE: 60

```
Met Arg Ser Ala Val Arg Val Phe Gly Lys Asn Arg Val Ser Gly Leu
1               5                   10                  15

Arg Phe Ala Ser Thr Ser Ser Lys Ser Pro Ile His Lys Ser Ser Ala
            20                  25                  30

Thr Leu Arg Phe Gly Arg Ser Ala Lys Ser Gly Tyr Ser Ala Phe Ser
        35                  40                  45

Phe Gly Lys Lys Val Ile Thr Gly Gly Ala Phe Leu Val Ala Gly Ser
    50                  55                  60

Val Gly Ile Ala Leu Ile Ser Gln Phe Asn Asp Ser Val Glu Asn Gly
65                  70                  75                  80

Ala Lys Val Asp Met Thr Lys Pro Lys Val Ser Pro Thr Glu Val Ala
                85                  90                  95

Lys His Ser Ser Pro Lys Asp Cys Trp Val Val Ile Glu Gly Tyr Val
            100                 105                 110
```

```
Tyr Asn Leu Thr Asp Phe Ile Ser Ala His Pro Gly Gly Pro Ala Ile
        115                 120                 125

Ile Glu Asn Asn Ala Gly Lys Asp Val Thr Lys Ile Phe Ala Pro Ile
    130                 135                 140

His Ala Pro Asp Val Ile Glu Lys Tyr Ile Ala Pro Glu Asn Arg Ile
145                 150                 155                 160

Gly Pro Leu Asp Gly Thr Met Pro Asp Asp Leu Val Cys Ala Ala Leu
                165                 170                 175

Thr Pro Gly Glu Thr Pro Glu Asp Val Ala Arg Lys Glu Gln Leu Arg
            180                 185                 190

Gln Ser Leu Pro Asp Ile Asp Ser Leu Val Asn Ile Tyr Asp Phe Glu
        195                 200                 205

Phe Leu Ala Ser Gln Ile Leu Thr Lys Gln Ala Trp Ser Tyr Tyr Ser
    210                 215                 220

Ser Ala Ala Asp Asp Glu Val Thr His Arg Glu Asn His Ala Ala Tyr
225                 230                 235                 240

His Arg Ile Phe Phe Lys Pro Arg Ile Leu Val Asn Val Lys Glu Val
                245                 250                 255

Asp Thr Ser Thr Thr Met Leu Gly Glu Lys Val Gly Val Pro Phe Tyr
            260                 265                 270

Val Ser Ala Thr Ala Leu Cys Lys Leu Gly Asn Pro Lys Glu Gly Glu
        275                 280                 285

Lys Asp Ile Ala Arg Gly Cys Gly Glu Ser Asp Val Lys Pro Val Gln
    290                 295                 300

Met Ile Ser Thr Leu Ala Ser Cys Ser Leu Gln Glu Ile Val Glu Ala
305                 310                 315                 320

Ala Pro Ser Lys Glu Gln Ile Gln Trp Phe Gln Leu Tyr Val Asn Ser
                325                 330                 335

Asp Arg Lys Ile Thr Glu Asp Leu Ile Lys Asn Val Glu Lys Leu Gly
            340                 345                 350

Leu Lys Ala Ile Phe Val Thr Val Asp Ala Pro Ser Leu Gly Asn Arg
        355                 360                 365

Glu Lys Asp Ala Lys Val Lys Phe Thr Asn Ser Asn Gly Ala Lys Ala
    370                 375                 380

Met Glu Lys Ser Lys Val Lys Glu Ser Lys Gly Ala Ser Arg Ala Leu
385                 390                 395                 400

Ser Ser Phe Ile Asp Pro Ala Leu Asn Trp Asp Asp Ile Ile Glu Phe
                405                 410                 415

Lys Lys Lys Thr Lys Leu Pro Ile Val Ile Lys Gly Val Gln Cys Val
            420                 425                 430

Glu Asp Val Leu Lys Ala Ala Glu Ile Gly Val Ala Gly Val Val Leu
        435                 440                 445

Ser Asn His Gly Gly Arg Gln Leu Asp Phe Ser Arg Ala Pro Ile Glu
    450                 455                 460

Val Leu Ala Glu Thr Met Pro Val Leu Arg Glu Lys Lys Leu Asp Asp
465                 470                 475                 480

Lys Ile Glu Ile Phe Ile Asp Gly Gly Val Arg Arg Gly Thr Asp Ile
                485                 490                 495

Leu Lys Ala Leu Cys Leu Gly Ala Lys Gly Val Gly Leu Gly Arg Pro
            500                 505                 510

Phe Leu Tyr Ser Asn Ser Cys Tyr Gly Lys Glu Gly Val Lys Lys Ala
        515                 520                 525
```

```
Ile Glu Leu Leu Lys Asp Glu Leu Glu Met Ser Met Arg Leu Leu Gly
    530                 535                 540

Val Thr Ser Ile Asp Gln Leu Ser Glu Lys Tyr Leu Asp Leu Ser Thr
545                 550                 555                 560

Ile His Gly Arg Thr Val Asn Val Pro Arg Asp Asn Leu Tyr Arg Glu
                565                 570                 575

Val Tyr Val Pro His Glu Pro Thr Gln Phe Leu Glu Glu
            580                 585


<210> SEQ ID NO 61
<211> LENGTH: 4704
<212> TYPE: DNA
<213> ORGANISM: Artificial Sequence
<220> FEATURE:
<223> OTHER INFORMATION: Sequence put together from multiple organisms:
      Saccharomyces cerevisiae and Kluyveromyces dobzhanskii.

<400> SEQUENCE: 61

tcctattcgg agatacaggc aacaagtgat agagggccca ttatgaatac gcacctctat     60

gtatttccga gatacgatta ctccagttcc tcttacaaga aatgcataaa aatagttaca    120

attaattaga acaagaactt atttagaaca cgttcacact gagtaagaac tcttgtccct    180

tattagcctt gatagtgctg aaaaaaagaa aaaaaacaaa aaaaagaaat aaaataacgg    240

caaacagcaa aggccacaga accgtattca tgttacttct gcaatatcaa tcacttactg    300

gcaagtgcgt ataaattaaa cctatttctt tatcatcata tttacttata tctttaacag    360

attccaaacc ctaaagtgtc cgaattttca atagggcgaa cttgaagaat aaccaaggtc    420

aataatatat cttttagtat aaccctgaaa tttgccctat agaaatctag ggtttctgtg    480

tggtttccgg gtgagtcata cggctttttt gaatttcttt ttttgcagtt gtctctatca    540

atgaaaattt cgaggaagac gataaggtta agataagtag ataagagaat gatacgagat    600

aaagcacaaa ttagcagaaa gaagagtggt tgcgaacaga gtaaaccgaa tcagggaatc    660

ccttttgca aaaacatcaa ttatcctttt ctttttttta cgtatatatc tggaacagaa     720

atatataagt tactattata cttatagttg gatccagttt ttaatctgtc gtcaatcgaa    780

agtttatttc agagttcttc agacttctta actcctgtaa aaacaaaaaa aaaaaaaggc    840

atagcactcg agatctcccg agtttatcat tatcaatact gccatttcaa agaatacgta    900

aataattaat agtagtgatt ttcctaactt tatttagtca aaaaattggc cttttaattc    960

tgctgtaacc cgtacatgcc caaaataggg ggcgggttac acagaatata taacatcata   1020

ggtgtctggg tgaacagttt attcctggca tccactaaat ataatggagc ccgctttttt   1080

taagctggca tccagaaaaa aaaagaatcc cagcaccaaa atattgtttt cttcaccaac   1140

catcagttca taggtccatt ctcttagcgc aactacacag aacaggggca caaacaggca   1200

aaaaacgggc acaacctcaa tggagtgatg caacctgctt ggagtaaatg atgacacaag   1260

gcaattgacc tacgcatgta tctatctcat tttcttacac cttctattac cttctgctct   1320

ctctgatttg gaaaaagctg aaaaaaaagg ttgaaaccag ttccctgaaa ttattcccct   1380

atttgactaa taagtatata aagacggtag gtattgattg taattctgta aatctatttc   1440

ttaaacttct taaattctac ttttatagtt agtctttttt ttagtttaaa acaccaagaa   1500

cttagtttcg aataaacaca cataaacaaa caaatctaga atgcgttctg cagttagagt   1560

ttttcgtaaa aacagatttc caacaggttt gagattgtca tcaacagcat cttccgctag   1620

acaaggtatc gctctttccg tagggaaata caacaagtac aacaaaaatg gtaccaacgg   1680
```

-continued

```
gtcttggaaa tcttccagaa aatcaaccac ctacggaggt gccttccttg tggcgagtgc   1740
agtcgcaatt gctttcagct ctcaaattac ccaatcctta gaaaatggtg ttaaggtgga   1800
tatggggaag ccatctgttt ctccagcgga agtagttaag cactcatcac cagatgattg   1860
ttgggttgtc atagatggtt acgtatacaa tctaactgaa ttcatcggcg cccatcctgg   1920
tggtccagcg ataatcaaaa acaacgcagg caaggacgtt actaagatat ttgcaccaat   1980
ccatgctcca gacgttattg aaaagtacat cgctcctaaa aacagactgg gtccattgga   2040
aggtacaatg cctgaggacc gtatttgcgc tgcactcaca ccaggtgaaa ctgccgagga   2100
tgtcgcgaga aaggaacaac tgagacagtt gttgcctgac gtcaacaact taactaacct   2160
ttatgatttc gaattcttag catcacagat tttgactaag caagcttggt cttactactc   2220
tagcgccgca gatgacgaag tgacacaaag agagaatcac gcagcatatc atagaatttt   2280
ctttaagcct agaatcttag ttaatgtcaa ggaggtagac acttccacaa caatgctggg   2340
agagaaggtt ggagtcccat tctacgtatc agctaccgcc ttgtgcaagt tgggtaaccc   2400
acaagagggt gaaaaagaca tagcaagagg atgtggtgaa tccgatgcta aacctgtgca   2460
aatgatttct acattggctt catgttcact acaggaaatc gttgaagctg ccccttcaaa   2520
ggaacaaata caatggtttc aactatatgt taacagcgat cgtaagatta ctgatgatct   2580
tgttaaaaac gctgaaaagc tcggtttaaa ggccattttt gtgactgttg atgccccttc   2640
tttaggaaat agagagaagg acgctaaggt taagttcaca aattctaacg gtgcaaaagc   2700
tatggaaaag tcaaatgtag atgaaagtaa gggcgcttcc agagcattat cttcattcat   2760
tgacccagcc ctaaattggg atgatatcgt ggaactcaag acaaaaacaa agttaccaat   2820
cgtcatcaaa ggagtgcaat gtgttgaaga tgtccttaaa gcagctgagg ttggagcggc   2880
cggtgtagtt ttgtctaacc atggtggcag acaattggat ttcagtagag caccaatcga   2940
agtgttagct gaaactatgc ctgcattgag agagaaaaag ctagatgata agttagaagt   3000
tttcattgat ggcggggtca gaagaggcac agatatccta aaggctttat gtctaggagc   3060
aaaaggcgtt ggactgggta gaccatttct ttactctaac agttgctacg gtaaagaggg   3120
ggtcaaaaag gccattgaat tgttgaagga tgagttggaa atgtctatga gattgcttgg   3180
cgtgacaagt attgaccagt tatcagaaaa gtacctcgat ctttcaacta tccacggtag   3240
aacagtttct gtcccaagag ataacattta cagagatgta tacgttgcac aagagccatc   3300
tcagttcaga gaggactagt taattaaaca ggcccctttt cctttgtcga tatcatgtaa   3360
ttagttatgt cacgcttaca ttcacgccct cctcccacat ccgctctaac cgaaaaggaa   3420
ggagttagac aacctgaagt ctaggtccct atttattttt ttatagttat gttagtatta   3480
agaacgttat ttatatttca aatttttctt ttttttctgt acaaacgcgt gtacgcatgt   3540
aacgggcaga cggccggcca taacttcgta taatgtatgc tatacgaagt tatggcaacg   3600
gttcatcatc tcatggatct gcacatgaac aaacaccaga gtcaaacgac gttgaaattg   3660
aggctactgc gccaattgat gacaatacag acgatgataa caaaccgaag ttatctgatg   3720
tagaaaagga ttagagatgc taagagatag tgatgatatt tcataaataa tgtaattcta   3780
tatatgttaa ttaccttttt tgcgaggcat atttatggtg aaggataagt tttgaccatc   3840
aaagaaggtt aatgtggctg tggtttcagg gtccataaag cttttcaatt catctttttt   3900
ttttttgttc ttttttttga ttccggtttc tttgaaattt ttttgattcg gtaatctccg   3960
agcagaagga agaacgaagg aaggagcaca gacttagatt ggtatatata cgcatatgtg   4020
gtgttgaaga aacatgaaat tgcccagtat tcttaaccca actgcacaga acaaaaacct   4080
```

```
gcaggaaacg aagataaatc atgtcgaaag ctacatataa ggaacgtgct gctactcatc   4140

ctagtcctgt tgctgccaag ctatttaata tcatgcacga aaagcaaaca aacttgtgtg   4200

cttcattgga tgttcgtacc accaaggaat tactggagtt agttgaagca ttaggtccca   4260

aaatttgttt actaaaaaca catgtggata tcttgactga tttttccatg gagggcacag   4320

ttaagccgct aaaggcatta tccgccaagt acaatttttt actcttcgaa gacagaaaat   4380

ttgctgacat tggtaataca gtcaaattgc agtactctgc gggtgtatac agaatagcag   4440

aatgggcaga cattacgaat gcacacggtg tggtgggccc aggtattgtt agcggtttga   4500

agcaggcggc ggaagaagta acaaaggaac ctagaggcct tttgatgtta gcagaattgt   4560

catgcaaggg ctccctagct actggagaat atactaaggg tactgttgac attgcgaaga   4620

gcgacaaaga ttttgttatc ggctttattg ctcaaagaga catgggtgga agagatgaag   4680

gttacgattg gttgattatg acac                                           4704
```

<210> SEQ ID NO 62
<211> LENGTH: 592
<212> TYPE: PRT
<213> ORGANISM: Kluyveromyces dobzhanskii

<400> SEQUENCE: 62

```
Met Arg Ser Ala Val Arg Val Phe Arg Lys Asn Arg Phe Pro Thr Gly
1               5                   10                  15

Leu Arg Leu Ser Ser Thr Ala Ser Ser Ala Arg Gln Gly Ile Ala Leu
            20                  25                  30

Ser Val Gly Lys Tyr Asn Lys Tyr Asn Lys Asn Gly Thr Asn Gly Ser
        35                  40                  45

Trp Lys Ser Ser Arg Lys Ser Thr Thr Tyr Gly Gly Ala Phe Leu Val
    50                  55                  60

Ala Ser Ala Val Ala Ile Ala Phe Ser Ser Gln Ile Thr Gln Ser Leu
65                  70                  75                  80

Glu Asn Gly Val Lys Val Asp Met Gly Lys Pro Ser Val Ser Pro Ala
                85                  90                  95

Glu Val Val Lys His Ser Ser Pro Asp Asp Cys Trp Val Val Ile Asp
            100                 105                 110

Gly Tyr Val Tyr Asn Leu Thr Glu Phe Ile Gly Ala His Pro Gly Gly
        115                 120                 125

Pro Ala Ile Ile Lys Asn Asn Ala Gly Lys Asp Val Thr Lys Ile Phe
    130                 135                 140

Ala Pro Ile His Ala Pro Asp Val Ile Glu Lys Tyr Ile Ala Pro Lys
145                 150                 155                 160

Asn Arg Leu Gly Pro Leu Glu Gly Thr Met Pro Glu Asp Arg Ile Cys
                165                 170                 175

Ala Ala Leu Thr Pro Gly Glu Thr Ala Glu Asp Val Ala Arg Lys Glu
            180                 185                 190

Gln Leu Arg Gln Leu Leu Pro Asp Val Asn Asn Leu Thr Asn Leu Tyr
        195                 200                 205

Asp Phe Glu Phe Leu Ala Ser Gln Ile Leu Thr Lys Gln Ala Trp Ser
    210                 215                 220

Tyr Tyr Ser Ser Ala Ala Asp Asp Glu Val Thr Gln Arg Glu Asn His
225                 230                 235                 240

Ala Ala Tyr His Arg Ile Phe Phe Lys Pro Arg Ile Leu Val Asn Val
                245                 250                 255
```

```
Lys Glu Val Asp Thr Ser Thr Thr Met Leu Gly Glu Lys Val Gly Val
            260                 265                 270

Pro Phe Tyr Val Ser Ala Thr Ala Leu Cys Lys Leu Gly Asn Pro Gln
        275                 280                 285

Glu Gly Glu Lys Asp Ile Ala Arg Gly Cys Gly Glu Ser Asp Ala Lys
    290                 295                 300

Pro Val Gln Met Ile Ser Thr Leu Ala Ser Cys Ser Leu Gln Glu Ile
305                 310                 315                 320

Val Glu Ala Ala Pro Ser Lys Glu Gln Ile Gln Trp Phe Gln Leu Tyr
                325                 330                 335

Val Asn Ser Asp Arg Lys Ile Thr Asp Asp Leu Val Lys Asn Ala Glu
            340                 345                 350

Lys Leu Gly Leu Lys Ala Ile Phe Val Thr Val Asp Ala Pro Ser Leu
        355                 360                 365

Gly Asn Arg Glu Lys Asp Ala Lys Val Lys Phe Thr Asn Ser Asn Gly
    370                 375                 380

Ala Lys Ala Met Glu Lys Ser Asn Val Asp Glu Ser Lys Gly Ala Ser
385                 390                 395                 400

Arg Ala Leu Ser Ser Phe Ile Asp Pro Ala Leu Asn Trp Asp Asp Ile
                405                 410                 415

Val Glu Leu Lys Thr Lys Thr Lys Leu Pro Ile Val Ile Lys Gly Val
            420                 425                 430

Gln Cys Val Glu Asp Val Leu Lys Ala Ala Glu Val Gly Ala Ala Gly
        435                 440                 445

Val Val Leu Ser Asn His Gly Gly Arg Gln Leu Asp Phe Ser Arg Ala
    450                 455                 460

Pro Ile Glu Val Leu Ala Glu Thr Met Pro Ala Leu Arg Glu Lys Lys
465                 470                 475                 480

Leu Asp Asp Lys Leu Glu Val Phe Ile Asp Gly Gly Val Arg Arg Gly
                485                 490                 495

Thr Asp Ile Leu Lys Ala Leu Cys Leu Gly Ala Lys Gly Val Gly Leu
            500                 505                 510

Gly Arg Pro Phe Leu Tyr Ser Asn Ser Cys Tyr Gly Lys Glu Gly Val
        515                 520                 525

Lys Lys Ala Ile Glu Leu Leu Lys Asp Glu Leu Glu Met Ser Met Arg
    530                 535                 540

Leu Leu Gly Val Thr Ser Ile Asp Gln Leu Ser Glu Lys Tyr Leu Asp
545                 550                 555                 560

Leu Ser Thr Ile His Gly Arg Thr Val Ser Val Pro Arg Asp Asn Ile
                565                 570                 575

Tyr Arg Asp Val Tyr Val Ala Gln Glu Pro Ser Gln Phe Arg Glu Asp
            580                 585                 590
```

<210> SEQ ID NO 63
<211> LENGTH: 4620
<212> TYPE: DNA
<213> ORGANISM: Artificial Sequence
<220> FEATURE:
<223> OTHER INFORMATION: Sequence put together from multiple organisms: Saccharomyces cerevisiae and Saccharomyces kluyveri.

<400> SEQUENCE: 63

```
tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180
```

tattagcctt gatagtgctg aaaaaaagaa aaaaaacaaa aaaaagaaat aaaataacgg 240
caaacagcaa aggccacaga accgtattca tgttacttct gcaatatcaa tcacttactg 300
gcaagtgcgt ataaattaaa cctatttctt tatcatcata tttacttata tctttaacag 360
attccaaacc ctaaagtgtc cgaattttca atagggcgaa cttgaagaat aaccaaggtc 420
aataatatat cttttagtat aaccctgaaa tttgccctat agaaatctag ggtttctgtg 480
tggtttccgg gtgagtcata cggctttttt gaatttcttt ttttgcagtt gtctctatca 540
atgaaaattt cgaggaagac gataaggtta agataagtag ataagagaat gatacgagat 600
aaagcacaaa ttagcagaaa gaagagtggt tgcgaacaga gtaaaccgaa tcagggaatc 660
cctttttgca aaaacatcaa ttatcctttt cttttttta cgtatatatc tggaacagaa 720
atatataagt tactattata cttatagttg gatccagttt ttaatctgtc gtcaatcgaa 780
agtttatttc agagttcttc agacttctta actcctgtaa aaacaaaaaa aaaaaaaggc 840
atagcactcg agatctcccg agtttatcat tatcaatact gccatttcaa agaatacgta 900
aataattaat agtagtgatt ttcctaactt tatttagtca aaaaattggc cttttaattc 960
tgctgtaacc cgtacatgcc caaaataggg ggcgggttac acagaatata taacatcata 1020
ggtgtctggg tgaacagttt attcctggca tccactaaat ataatggagc ccgctttttt 1080
taagctggca tccagaaaaa aaaagaatcc cagcaccaaa atattgtttt cttcaccaac 1140
catcagttca taggtccatt ctcttagcgc aactacacag aacaggggca caaacaggca 1200
aaaaacgggc acaacctcaa tggagtgatg caacctgctt ggagtaaatg atgacacaag 1260
gcaattgacc tacgcatgta tctatctcat tttcttacac cttctattac cttctgctct 1320
ctctgatttg gaaaaagctg aaaaaaaagg ttgaaaccag ttccctgaaa ttattcccct 1380
atttgactaa taagtatata aagacggtag gtattgattg taattctgta aatctatttc 1440
ttaaacttct taaattctac ttttatagtt agtctttttt ttagtttaaa acaccaagaa 1500
cttagtttcg aataaacaca cataaacaaa caaatctaga atgtttaaaa gagccttttt 1560
gagacctcaa ttgtggtcct cgacgactcg tcgctgcaca atagctagca ttcggtgcta 1620
ctcgaaacaa ccgttaaaac cggcctcagc tagtaagttg actcttggtt tgatcggtgg 1680
tatcggcttg ggatctgctg ctacagcata cggactattg atgggggacg acgatacttc 1740
tgcctcgaca acgagactag atgaattagc gcctccaagc tattgccagg atcctaagaa 1800
gtttgaagac gcaattataa aactaaaaca cattcttgat gacaatccag acaacttttc 1860
tgtttctaaa agtgagcttg atgctcattc cgacacttac ttcaactctc accatgccag 1920
gcccgaccaa agaccacaga ttatcctatt tccacgtact acatcagatg tttccgagat 1980
tttgaaagtt tgccacgaat acgaggtgcc agttatccca ttttccggtg gtacttctct 2040
ggagggccat ttcttaccaa caagaattgg ctgcaccgta gtgttagaca tgtccaaata 2100
tatgaacaaa attttgaagc tcaacaagca ggacttggat gttgaggtcc aagccggtgt 2160
accatgggaa gatctaaacg attatttgaa ttctgaaggt gtcttatttg gttgcgatcc 2220
tggtccaggt gctcaaatcg gtggctgtat tgctaactcc tgttccggta ctaatgctta 2280
ccgttacggt acgatgaagg aaaacatagt gaacatcact gtggtcctag ctgatggtac 2340
tgttgtcaag actaagagac gtcctagaaa atcaagtgct ggttacaact tgaacgggtt 2400
gtttgttggt agcgagggta ctctcggtgt tgtcactcaa gctaccgtaa aatgtcatgt 2460
catgcccaag atcgaaactg tcgctgtcgt ttcctttcca actgtgggtg atgcagcatc 2520

```
ttgctcctct catatcatcc aagaaggtat acagctaaat gctatggaac tattggacga   2580

taatatgatg aaggtgatca accaatccgg tgccacatcc aagacggact gggtcgaatc   2640

tccaacgttg tttttcaaga ttggaggaag atctcaaaat aacgtcaaag aattggttga   2700

tgaagtttcc aagattgctc aaaaatacca ttgcaagaag tttgaattcg cctctagtga   2760

cgatgaaaag ttggaattat gggaagccag aaaggtcgcg ctatggtcta ccatcaatgc   2820

ggggaaagcc aaggacagta actccaacgt ttggaccaca gacgttgcag tcccactgtc   2880

tcagtttgca cctgtcatcg aagccaccaa gcaagagatg aacgccagcg gcttaattac   2940

cactctggtt ggccatgcgg gtgatggtaa tttccacgct ttcattgttt acaacgacga   3000

ccaacgtgac atcgccgaaa aaatcgtcga taacatggtc catagggcca tagaagcaga   3060

aggcacttgt accggtgagc acggcgttgg tatcggaaaa agaaaattct tgcttcatga   3120

gttaggtgct gaaacagttg atctaatgag acagttaaaa ttagccttgg atccaaagag   3180

aatattgaat ccagacaaga tcttcaagat tgatcctaac gagcatgaac actgattaat   3240

taaacaggcc ccttttcctt tgtcgatatc atgtaattag ttatgtcacg cttacattca   3300

cgccctcctc ccacatccgc tctaaccgaa aaggaaggag ttagacaacc tgaagtctag   3360

gtccctattt atttttttat agttatgtta gtattaagaa cgttatttat atttcaaatt   3420

tttctttttt ttctgtacaa acgcgtgtac gcatgtaacg ggcagacggc cggccataac   3480

ttcgtataat gtatgctata cgaagttatg gcaacggttc atcatctcat ggatctgcac   3540

atgaacaaac accagagtca aacgacgttg aaattgaggc tactgcgcca attgatgaca   3600

atacagacga tgataacaaa ccgaagttat ctgatgtaga aaaggattag agatgctaag   3660

agatagtgat gatatttcat aaataatgta attctatata tgttaattac ctttttttgcg  3720

aggcatattt atggtgaagg ataagttttg accatcaaag aaggttaatg tggctgtggt   3780

ttcagggtcc ataaagcttt tcaattcatc tttttttttt ttgttctttt ttttgattcc   3840

ggtttctttg aaattttttt gattcggtaa tctccgagca gaaggaagaa cgaaggaagg   3900

agcacagact tagattggta tatatacgca tatgtggtgt tgaagaaaca tgaaattgcc   3960

cagtattctt aacccaactg cacagaacaa aaacctgcag gaaacgaaga taaatcatgt   4020

cgaaagctac atataaggaa cgtgctgcta ctcatcctag tcctgttgct gccaagctat   4080

ttaatatcat gcacgaaaag caaacaaact tgtgtgcttc attggatgtt cgtaccacca   4140

aggaattact ggagttagtt gaagcattag gtcccaaaat ttgtttacta aaaacacatg   4200

tggatatctt gactgatttt tccatggagg gcacagttaa gccgctaaag gcattatccg   4260

ccaagtacaa ttttttactc ttcgaagaca gaaaatttgc tgacattggt aatacagtca   4320

aattgcagta ctctgcgggt gtatacagaa tagcagaatg ggcagacatt acgaatgcac   4380

acggtgtggt gggcccaggt attgttagcg gtttgaagca ggcggcggaa gaagtaacaa   4440

aggaacctag aggccttttg atgttagcag aattgtcatg caagggctcc ctagctactg   4500

gagaatatac taagggtact gttgacattg cgaagagcga caaagatttt gttatcggct   4560

ttattgctca aagagacatg ggtggaagag atgaaggtta cgattggttg attatgacac   4620
```

<210> SEQ ID NO 64
<211> LENGTH: 564
<212> TYPE: PRT
<213> ORGANISM: Saccharomyces kluyveri

<400> SEQUENCE: 64

Met Phe Lys Arg Ala Phe Leu Arg Pro Gln Leu Trp Ser Ser Thr Thr

-continued

```
1               5                   10                  15

Arg Arg Cys Thr Ile Ala Ser Ile Arg Cys Tyr Ser Lys Gln Pro Leu
            20                  25                  30

Lys Pro Ala Ser Ala Ser Lys Leu Thr Leu Gly Leu Ile Gly Gly Ile
        35                  40                  45

Gly Leu Gly Ser Ala Ala Thr Ala Tyr Gly Leu Leu Met Gly Asp Asp
    50                  55                  60

Asp Thr Ser Ala Ser Thr Thr Arg Leu Asp Glu Leu Ala Pro Pro Ser
65                  70                  75                  80

Tyr Cys Gln Asp Pro Lys Lys Phe Glu Asp Ala Ile Ile Lys Leu Lys
                85                  90                  95

His Ile Leu Asp Asp Asn Pro Asp Asn Phe Ser Val Ser Lys Ser Glu
            100                 105                 110

Leu Asp Ala His Ser Asp Thr Tyr Phe Asn Ser His His Ala Arg Pro
        115                 120                 125

Asp Gln Arg Pro Gln Ile Ile Leu Phe Pro Arg Thr Thr Ser Asp Val
    130                 135                 140

Ser Glu Ile Leu Lys Val Cys His Glu Tyr Glu Val Pro Val Ile Pro
145                 150                 155                 160

Phe Ser Gly Gly Thr Ser Leu Glu Gly His Phe Leu Pro Thr Arg Ile
                165                 170                 175

Gly Cys Thr Val Val Leu Asp Met Ser Lys Tyr Met Asn Lys Ile Leu
            180                 185                 190

Lys Leu Asn Lys Gln Asp Leu Asp Val Glu Val Gln Ala Gly Val Pro
        195                 200                 205

Trp Glu Asp Leu Asn Asp Tyr Leu Asn Ser Glu Gly Val Leu Phe Gly
    210                 215                 220

Cys Asp Pro Gly Pro Gly Ala Gln Ile Gly Gly Cys Ile Ala Asn Ser
225                 230                 235                 240

Cys Ser Gly Thr Asn Ala Tyr Arg Tyr Gly Thr Met Lys Glu Asn Ile
                245                 250                 255

Val Asn Ile Thr Val Val Leu Ala Asp Gly Thr Val Val Lys Thr Lys
            260                 265                 270

Arg Arg Pro Arg Lys Ser Ser Ala Gly Tyr Asn Leu Asn Gly Leu Phe
        275                 280                 285

Val Gly Ser Glu Gly Thr Leu Gly Val Val Thr Gln Ala Thr Val Lys
    290                 295                 300

Cys His Val Met Pro Lys Ile Glu Thr Val Ala Val Val Ser Phe Pro
305                 310                 315                 320

Thr Val Gly Asp Ala Ala Ser Cys Ser Ser His Ile Ile Gln Glu Gly
                325                 330                 335

Ile Gln Leu Asn Ala Met Glu Leu Leu Asp Asp Asn Met Met Lys Val
            340                 345                 350

Ile Asn Gln Ser Gly Ala Thr Ser Lys Thr Asp Trp Val Glu Ser Pro
        355                 360                 365

Thr Leu Phe Phe Lys Ile Gly Gly Arg Ser Gln Asn Asn Val Lys Glu
    370                 375                 380

Leu Val Asp Glu Val Ser Lys Ile Ala Gln Lys Tyr His Cys Lys Lys
385                 390                 395                 400

Phe Glu Phe Ala Ser Ser Asp Asp Glu Lys Leu Glu Leu Trp Glu Ala
                405                 410                 415

Arg Lys Val Ala Leu Trp Ser Thr Ile Asn Ala Gly Lys Ala Lys Asp
            420                 425                 430
```

Ser Asn Ser Asn Val Trp Thr Thr Asp Val Ala Val Pro Leu Ser Gln
435 440 445

Phe Ala Pro Val Ile Glu Ala Thr Lys Gln Glu Met Asn Ala Ser Gly
450 455 460

Leu Ile Thr Thr Leu Val Gly His Ala Gly Asp Gly Asn Phe His Ala
465 470 475 480

Phe Ile Val Tyr Asn Asp Asp Gln Arg Asp Ile Ala Glu Lys Ile Val
485 490 495

Asp Asn Met Val His Arg Ala Ile Glu Ala Glu Gly Thr Cys Thr Gly
500 505 510

Glu His Gly Val Gly Ile Gly Lys Arg Lys Phe Leu Leu His Glu Leu
515 520 525

Gly Ala Glu Thr Val Asp Leu Met Arg Gln Leu Lys Leu Ala Leu Asp
530 535 540

Pro Lys Arg Ile Leu Asn Pro Asp Lys Ile Phe Lys Ile Asp Pro Asn
545 550 555 560

Glu His Glu His

<210> SEQ ID NO 65
<211> LENGTH: 4521
<212> TYPE: DNA
<213> ORGANISM: Artificial Sequence
<220> FEATURE:
<223> OTHER INFORMATION: Sequence put together from multiple organisms: Saccharomyces cerevisiae and Saccharomyces bayanus.

<400> SEQUENCE: 65
tcctattcgg agatacaggc aacaagtgat agagggccca ttatgaatac gcacctctat 60
gtatttccga gatacgatta ctccagttcc tcttacaaga aatgcataaa aatagttaca 120
attaattaga acaagaactt atttagaaca cgttcacact gagtaagaac tcttgtccct 180
tattagcctt gatagtgctg aaaaaaagaa aaaaaacaaa aaaaagaaat aaaataacgg 240
caaacagcaa aggccacaga accgtattca tgttacttct gcaatatcaa tcacttactg 300
gcaagtgcgt ataaattaaa cctatttctt tatcatcata tttacttata tctttaacag 360
attccaaacc ctaaagtgtc cgaattttca atagggcgaa cttgaagaat aaccaaggtc 420
aataatatat cttttagtat aaccctgaaa tttgccctat agaaatctag ggtttctgtg 480
tggtttccgg gtgagtcata cggctttttt gaatttcttt ttttgcagtt gtctctatca 540
atgaaaattt cgaggaagac gataaggtta agataagtag ataagagaat gatacgagat 600
aaagcacaaa ttagcagaaa gaagagtggt tgcgaacaga gtaaaccgaa tcagggaatc 660
cctttttgca aaaacatcaa ttatcctttt cttttttta cgtatatatc tggaacagaa 720
atatataagt tactattata cttatagttg gatccagttt ttaatctgtc gtcaatcgaa 780
agtttatttc agagttcttc agacttctta actcctgtaa aaacaaaaaa aaaaaaaggc 840
atagcactcg agatctcccg agtttatcat tatcaatact gccatttcaa agaatacgta 900
aataattaat agtagtgatt ttcctaactt tatttagtca aaaaattggc cttttaattc 960
tgctgtaacc cgtacatgcc caaaataggg ggcgggttac acagaatata taacatcata 1020
ggtgtctggg tgaacagttt attcctggca tccactaaat ataatggagc ccgctttttt 1080
taagctggca tccagaaaaa aaaagaatcc cagcaccaaa atattgtttt cttcaccaac 1140
catcagttca taggtccatt ctcttagcgc aactacacag aacaggggca caaacaggca 1200
aaaaacgggc acaacctcaa tggagtgatg caacctgctt ggagtaaatg atgacacaag 1260
gcaattgacc tacgcatgta tctatctcat tttcttacac cttctattac cttctgctct 1320
ctctgatttg gaaaaagctg aaaaaaaagg ttgaaaccag ttccctgaaa ttattcccct 1380
atttgactaa taagtatata aagacggtag gtattgattg taattctgta aatctatttc 1440
ttaaacttct taaattctac ttttatagtt agtctttttt ttagtttaaa acaccaagaa 1500
cttagtttcg aataaacaca cataaacaaa caaatctaga atgctgagaa acattttggt 1560
gagaggcgcc ggcaaacatc tgaaatatgg ttgcagatat gtgaaatcgt ctgctctttt 1620
ggggtgtagg acaaaaatca actactattc cactaagata caaacaaaac taaccagcga 1680
aaactaccca gacgtgcaaa gagatgcgag attcaagaaa ctgacttctg atgatttgaa 1740
ctatttcagg tccattttgt cagaacagga ggtattacag gccagcgaat tagaggacct 1800
gtcattttat aatgaagact ggatgagaaa atataaaggc cagtccaagt tagttttgag 1860
gcctaaaacc gtggaaaaga tttcactgat tttgaattat tgtaatgatg aaaaaattgc 1920
tgttgtacca caaggtggta acactggatt ggtaggtggt tcggtaccta ttttcgatga 1980
gttgattcta tcattagcca atttgaacaa aataagagat ttcgaccctg tgtcaggtat 2040
tttaaagtgt gatgccggtg ttatcttgga aaatgctaat aattacgtaa tggagcaaaa 2100
ttatatgttc ccgttggatt taggtgctaa aggttcttgc catgttggtg gggtggttgc 2160
caccaacgca ggtggattga gattattgcg ttatggctca ctacatggca gcgtgttagg 2220
tttggaagta gtcatgccta atggtcaaat cgttaatagt atgcattcga tgagaaagga 2280
caacaccggt tatgacttaa aacaactatt catcggctct gaaggtacta ttggtatcat 2340
tactggtgtt tcggtcttga cggttcctaa gccaaaggct ttcaatgttt cctatttagc 2400
tgttgagagt tttgaagatg ttcaaaaagt attcgtcaga gccagacagg agttgtctga 2460
aattctatca gcttttgagt tcatggattc caaatctcaa atcttggcca aaagtcagtt 2520
gaaagatgcc actttcccct tagaagacga acatccattt tatattctta tcgagacatc 2580
gggatcaaac aaggatcacg atgattctaa acttgaaaca ttcttagaaa gcgtcatgga 2640
agaaggcgta gtaacagatg gtgtggtagc acaagacgaa actgagttgc aaaacttatg 2700
gaagtggaga gaaatgattc cagaggcaag ccaagctaat ggtggtgttt acaaatacga 2760
tgtttctctt ccattaaagg atctatactc cctggttgat gccaccaatg ccaggctatc 2820
tgaagcagga ctggtcggag attcacccaa acccgtcgtg ggtgccattg ggtatggcca 2880
tgtgggggat ggtaatctac atttaaacgt tgctgttaga gaatacaaca aggaaattga 2940
aaaggtttta gaaccatttg tttatgaatt cgtttcctca aagcatggtt ccgtgagtgc 3000
tgagcatggt ttgggtttcc agaagaaaaa ttacattggt tattccaaga gtcctgaaga 3060
agttacaatg ataaaggatc tgaaagcaca ttacgacccc aatgcaatct tgaaccctta 3120
caaatacgtt tgaaaattaa ttaaacaggc cccttttcct ttgtcgatat catgtaatta 3180
gttatgtcac gcttacattc acgccctcct cccacatccg ctctaaccga aaaggaagga 3240
gttagacaac ctgaagtcta ggtccctatt tattttttta tagttatgtt agtattaaga 3300
acgttattta tatttcaaat ttttcttttt tttctgtaca aacgcgtgta cgcatgtaac 3360
gggcagacgg ccggccataa cttcgtataa tgtatgctat acgaagttat ggcaacggtt 3420
catcatctca tggatctgca catgaacaaa caccagagtc aaacgacgtt gaaattgagg 3480
ctactgcgcc aattgatgac aatacagacg atgataacaa accgaagtta tctgatgtag 3540
aaaaggatta gagatgctaa gagatagtga tgatatttca taaataatgt aattctatat 3600

```
atgttaatta cctttttgc gaggcatatt tatggtgaag gataagtttt gaccatcaaa    3660

gaaggttaat gtggctgtgg tttcagggtc cataaagctt ttcaattcat cttttttttt   3720

tttgttcttt tttttgattc cggtttcttt gaaatttttt tgattcggta atctccgagc   3780

agaaggaaga acgaaggaag gagcacagac ttagattggt atatatacgc atatgtggtg   3840

ttgaagaaac atgaaattgc ccagtattct taacccaact gcacagaaca aaaacctgca   3900

ggaaacgaag ataaatcatg tcgaaagcta catataagga acgtgctgct actcatccta   3960

gtcctgttgc tgccaagcta tttaatatca tgcacgaaaa gcaaacaaac ttgtgtgctt   4020

cattggatgt tcgtaccacc aaggaattac tggagttagt tgaagcatta ggtcccaaaa   4080

tttgtttact aaaaacacat gtggatatct tgactgattt ttccatggag ggcacagtta   4140

agccgctaaa ggcattatcc gccaagtaca atttttttact cttcgaagac agaaaatttg  4200

ctgacattgg taatacagtc aaattgcagt actctgcggg tgtatacaga atagcagaat   4260

gggcagacat tacgaatgca cacggtgtgg tgggcccagg tattgttagc ggtttgaagc   4320

aggcggcgga agaagtaaca aaggaaccta gaggcctttt gatgttagca gaattgtcat   4380

gcaagggctc cctagctact ggagaatata ctaagggtac tgttgacatt gcgaagagcg   4440

acaaagattt tgttatcggc tttattgctc aaagagacat gggtggaaga gatgaaggtt   4500

acgattggtt gattatgaca c                                             4521
```

<210> SEQ ID NO 66
<211> LENGTH: 530
<212> TYPE: PRT
<213> ORGANISM: Saccharomyces bayanus

<400> SEQUENCE: 66

```
Met Leu Arg Asn Ile Leu Val Arg Gly Ala Gly Lys His Leu Lys Tyr
1               5                   10                  15

Gly Cys Arg Tyr Val Lys Ser Ser Ala Leu Leu Gly Cys Arg Thr Lys
            20                  25                  30

Ile Asn Tyr Tyr Ser Thr Lys Ile Gln Thr Lys Leu Thr Ser Glu Asn
        35                  40                  45

Tyr Pro Asp Val Gln Arg Asp Ala Arg Phe Lys Lys Leu Thr Ser Asp
    50                  55                  60

Asp Leu Asn Tyr Phe Arg Ser Ile Leu Ser Glu Gln Glu Val Leu Gln
65                  70                  75                  80

Ala Ser Glu Leu Glu Asp Leu Ser Phe Tyr Asn Glu Asp Trp Met Arg
                85                  90                  95

Lys Tyr Lys Gly Gln Ser Lys Leu Val Leu Arg Pro Lys Thr Val Glu
            100                 105                 110

Lys Ile Ser Leu Ile Leu Asn Tyr Cys Asn Asp Glu Lys Ile Ala Val
        115                 120                 125

Val Pro Gln Gly Gly Asn Thr Gly Leu Val Gly Gly Ser Val Pro Ile
    130                 135                 140

Phe Asp Glu Leu Ile Leu Ser Leu Ala Asn Leu Asn Lys Ile Arg Asp
145                 150                 155                 160

Phe Asp Pro Val Ser Gly Ile Leu Lys Cys Asp Ala Gly Val Ile Leu
                165                 170                 175

Glu Asn Ala Asn Asn Tyr Val Met Glu Gln Asn Tyr Met Phe Pro Leu
            180                 185                 190

Asp Leu Gly Ala Lys Gly Ser Cys His Val Gly Gly Val Val Ala Thr
        195                 200                 205
```

-continued

```
Asn Ala Gly Gly Leu Arg Leu Leu Arg Tyr Gly Ser Leu His Gly Ser
    210                 215                 220

Val Leu Gly Leu Glu Val Val Met Pro Asn Gly Gln Ile Val Asn Ser
225                 230                 235                 240

Met His Ser Met Arg Lys Asp Asn Thr Gly Tyr Asp Leu Lys Gln Leu
                245                 250                 255

Phe Ile Gly Ser Glu Gly Thr Ile Gly Ile Ile Thr Gly Val Ser Val
            260                 265                 270

Leu Thr Val Pro Lys Pro Lys Ala Phe Asn Val Ser Tyr Leu Ala Val
        275                 280                 285

Glu Ser Phe Glu Asp Val Gln Lys Val Phe Val Arg Ala Arg Gln Glu
    290                 295                 300

Leu Ser Glu Ile Leu Ser Ala Phe Glu Phe Met Asp Ser Lys Ser Gln
305                 310                 315                 320

Ile Leu Ala Lys Ser Gln Leu Lys Asp Ala Thr Phe Pro Leu Glu Asp
                325                 330                 335

Glu His Pro Phe Tyr Ile Leu Ile Glu Thr Ser Gly Ser Asn Lys Asp
            340                 345                 350

His Asp Asp Ser Lys Leu Glu Thr Phe Leu Glu Ser Val Met Glu Glu
        355                 360                 365

Gly Val Val Thr Asp Gly Val Val Ala Gln Asp Glu Thr Glu Leu Gln
    370                 375                 380

Asn Leu Trp Lys Trp Arg Glu Met Ile Pro Glu Ala Ser Gln Ala Asn
385                 390                 395                 400

Gly Gly Val Tyr Lys Tyr Asp Val Ser Leu Pro Leu Lys Asp Leu Tyr
                405                 410                 415

Ser Leu Val Asp Ala Thr Asn Ala Arg Leu Ser Glu Ala Gly Leu Val
            420                 425                 430

Gly Asp Ser Pro Lys Pro Val Val Gly Ala Ile Gly Tyr Gly His Val
        435                 440                 445

Gly Asp Gly Asn Leu His Leu Asn Val Ala Val Arg Glu Tyr Asn Lys
    450                 455                 460

Glu Ile Glu Lys Val Leu Glu Pro Phe Val Tyr Glu Phe Val Ser Ser
465                 470                 475                 480

Lys His Gly Ser Val Ser Ala Glu His Gly Leu Gly Phe Gln Lys Lys
                485                 490                 495

Asn Tyr Ile Gly Tyr Ser Lys Ser Pro Glu Glu Val Thr Met Ile Lys
            500                 505                 510

Asp Leu Lys Ala His Tyr Asp Pro Asn Ala Ile Leu Asn Pro Tyr Lys
        515                 520                 525

Tyr Val
    530
```

<210> SEQ ID NO 67
<211> LENGTH: 4721
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus fumigatus.

<400> SEQUENCE: 67

```
tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180
```

```
tattagcctt gatagtgctg aaaaaaagaa aaaaaacaaa aaaaagaaat aaaataacgg    240
caaacagcaa aggccacaga accgtattca tgttacttct gcaatatcaa tcacttactg    300
gcaagtgcgt ataaattaaa cctatttctt tatcatcata tttacttata tctttaacag    360
attccaaacc ctaaagtgtc cgaattttca atagggcgaa cttgaagaat aaccaaggtc    420
aataatatat cttttagtat aaccctgaaa tttgccctat agaaatctag ggtttctgtg    480
tggtttccgg gtgagtcata cggctttttt gaatttcttt ttttgcagtt gtctctatca    540
atgaaaattt cgaggaagac gataaggtta agataagtag ataagagaat gatacgagat    600
aaagcacaaa ttagcagaaa gaagagtggt tgcgaacaga gtaaaccgaa tcagggaatc    660
cctttttgca aaaacatcaa ttatcctttt cttttttta cgtatatatc tggaacagaa     720
atatataagt tactattata cttatagttg gatccagttt ttaatctgtc gtcaatcgaa    780
agtttatttc agagttcttc agacttctta actcctgtaa aaacaaaaaa aaaaaaaggc    840
atagcactcg agatctcccg agtttatcat tatcaatact gccatttcaa agaatacgta    900
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atggtcggat caatagtctt   1560
attacaacca tggaagagag cagtttccca cgcagttaga cctagaactt accaatacag   1620
atacttcaga acaactgcta gaatatcagc taacgacaaa ccacaatcat tcaaaaacca   1680
actatacgaa tcaacacaac aacgtttgag aagagaaaga gcagaacagg aaagattctc   1740
tcagtaccaa actcagtctc ctggtgggag atacgcggct ttaaccttcg cacttgtatt   1800
cttttctaca ggtgcttact acctgggaag cctcaagcca gccagtttac caacatcatc   1860
tacaaccacc ctttttgaaa ttgaacctcc actgcacaat atcagtccag caaatttgca   1920
agccgcttgg gcagatttcg ttgaaattct aggtaaagag aatgtctcaa cagaacatgg   1980
tgatcttgat gttcattctg gtagcgattg gagttcatat actctgaaaa aggacgaaag   2040
acctttctta gttctctacc catctactac agaggaagtt agcagaatta tgaaggtgtg   2100
tcaccagaga gtgatccctg tcacaccata ctcaggaggc acatcactcg aagggcactt   2160
tgctccaaca agaggtggtg tctgtattga ttttagacgt atgaacagaa tcttggagtt   2220
gcataaaaag gacttggatg ttgttgttca accagcagtt ggatgggagg accttaatga   2280
ggaactttct aaggacggct tgtttttccc acctgatcca ggacctggtg ctatgatcgg   2340
tggtatggtt ggtacaggat gctctggaac caacgcatat agatacggaa ccatgagaga   2400
atgggttctt tcactgacag ttgttttggc cgatggcact gttatcaaga caagacaaag   2460
accacgtaaa tcatctgctg gttatgactt aactagattg tttattgggt ctgaaggtac   2520
```

```
tttaggtttg gtgactgaag ccaccttgaa gttaacagta aagccaaagt cccagagtgt   2580
tgctgtggct tcttttccat ccattcataa cgccgccgaa tgtgttacta gagtagtcga   2640
ggaaggtata ccagtcgctg gtgtcgagat attggatgac gtgcaaatga agtgcatcaa   2700
cgatagtaga acaacacgta gacaatggaa ggaatcccct acacttttct tcaagttcac   2760
tggcacacca gttggcgtaa aagagcagat tgaattggtt agaaagattg tatcatcttc   2820
agcagggcaa tctttcgagt ttgccagagg tgaagatgag atgaaggaat tgtggtccgc   2880
cagaaaggaa gctttatggt ctgtaatgtc tatgagaaga gggcctgaag atagagtttg   2940
gacaaccgac gtggcggtcc ctatgtctaa gttaccagac atcattgaag caaccaaaca   3000
agatatgaca gagtccggct tactagcagg gatatgtggt catgttggtg atggtaactt   3060
ccacgcaatc attttgttca acgaagatga gaaaaagatt gctgaaggtg ttgtacatag   3120
aatggtgaag agagcggtcg agatggaggg caccgtaact ggagaacatg gcgtgggtct   3180
aatcaaaaga gattacctac aacatgaagt cggtgaaact actgtagata caatgcgtag   3240
aatcaaaatg gcattagatc cactaagatt gctaaattgc gataaggtgg ttagagtcga   3300
gcaaccaact acagttgaat tgaaaaagtg gtgattaatt aaacaggccc cttttccttt   3360
gtcgatatca tgtaattagt tatgtcacgc ttacattcac gccctcctcc cacatccgct   3420
ctaaccgaaa aggaaggagt tagacaacct gaagtctagg tccctattta ttttttttata   3480
gttatgttag tattaagaac gttatttata tttcaaattt ttcttttttt tctgtacaaa   3540
cgcgtgtacg catgtaacgg gcagacggcc ggccataact tcgtataatg tatgctatac   3600
gaagttatgg caacggttca tcatctcatg gatctgcaca tgaacaaaca ccagagtcaa   3660
acgacgttga aattgaggct actgcgccaa ttgatgacaa tacagacgat gataacaaac   3720
cgaagttatc tgatgtagaa aaggattaga gatgctaaga gatagtgatg atatttcata   3780
aataatgtaa ttctatatat gttaattacc ttttttgcga ggcatattta tggtgaagga   3840
taagttttga ccatcaaaga aggttaatgt ggctgtggtt tcagggtcca taaagctttt   3900
caattcatct tttttttttt tgttcttttt tttgattccg gtttctttga aattttttttg   3960
attcggtaat ctccgagcag aaggaagaac gaaggaagga gcacagactt agattggtat   4020
atatacgcat atgtggtgtt gaagaaacat gaaattgccc agtattctta acccaactgc   4080
acagaacaaa aacctgcagg aaacgaagat aaatcatgtc gaaagctaca tataaggaac   4140
gtgctgctac tcatcctagt cctgttgctg ccaagctatt taatatcatg cacgaaaagc   4200
aaacaaactt gtgtgcttca ttggatgttc gtaccaccaa ggaattactg gagttagttg   4260
aagcattagg tcccaaaatt tgtttactaa aaacacatgt ggatatcttg actgattttt   4320
ccatggaggg cacagttaag ccgctaaagg cattatccgc caagtacaat tttttactct   4380
tcgaagacag aaaatttgct gacattggta atacagtcaa attgcagtac tctgcgggtg   4440
tatacagaat agcagaatgg gcagacatta cgaatgcaca cggtgtggtg ggcccaggta   4500
ttgttagcgg tttgaagcag gcggcggaag aagtaacaaa ggaacctaga ggcctttttga   4560
tgttagcaga attgtcatgc aagggctccc tagctactgg agaatatact aagggtactg   4620
ttgacattgc gaagagcgac aaagattttg ttatcggctt tattgctcaa agagacatgg   4680
gtggaagaga tgaaggttac gattggttga ttatgacacg c                      4721
```

<210> SEQ ID NO 68
<211> LENGTH: 597
<212> TYPE: PRT
<213> ORGANISM: Aspergillus fumigatus

<400> SEQUENCE: 68

Met Val Gly Ser Ile Val Leu Leu Gln Pro Trp Lys Arg Ala Val Ser
1 5 10 15

His Ala Val Arg Pro Arg Thr Tyr Gln Tyr Arg Tyr Phe Arg Thr Thr
20 25 30

Ala Arg Ile Ser Ala Asn Asp Lys Pro Gln Ser Phe Lys Asn Gln Leu
35 40 45

Tyr Glu Ser Thr Gln Gln Arg Leu Arg Arg Glu Arg Ala Glu Gln Glu
50 55 60

Arg Phe Ser Gln Tyr Gln Thr Gln Ser Pro Gly Gly Arg Tyr Ala Ala
65 70 75 80

Leu Thr Phe Ala Leu Val Phe Phe Ser Thr Gly Ala Tyr Tyr Leu Gly
85 90 95

Ser Leu Lys Pro Ala Ser Leu Pro Thr Ser Ser Thr Thr Thr Leu Phe
100 105 110

Glu Ile Glu Pro Pro Leu His Asn Ile Ser Pro Ala Asn Leu Gln Ala
115 120 125

Ala Trp Ala Asp Phe Val Glu Ile Leu Gly Lys Glu Asn Val Ser Thr
130 135 140

Glu His Gly Asp Leu Asp Val His Ser Gly Ser Asp Trp Ser Ser Tyr
145 150 155 160

Thr Leu Lys Lys Asp Glu Arg Pro Phe Leu Val Leu Tyr Pro Ser Thr
165 170 175

Thr Glu Glu Val Ser Arg Ile Met Lys Val Cys His Gln Arg Val Ile
180 185 190

Pro Val Thr Pro Tyr Ser Gly Gly Thr Ser Leu Glu Gly His Phe Ala
195 200 205

Pro Thr Arg Gly Gly Val Cys Ile Asp Phe Arg Arg Met Asn Arg Ile
210 215 220

Leu Glu Leu His Lys Lys Asp Leu Asp Val Val Val Gln Pro Ala Val
225 230 235 240

Gly Trp Glu Asp Leu Asn Glu Glu Leu Ser Lys Asp Gly Leu Phe Phe
245 250 255

Pro Pro Asp Pro Gly Pro Gly Ala Met Ile Gly Gly Met Val Gly Thr
260 265 270

Gly Cys Ser Gly Thr Asn Ala Tyr Arg Tyr Gly Thr Met Arg Glu Trp
275 280 285

Val Leu Ser Leu Thr Val Val Leu Ala Asp Gly Thr Val Ile Lys Thr
290 295 300

Arg Gln Arg Pro Arg Lys Ser Ser Ala Gly Tyr Asp Leu Thr Arg Leu
305 310 315 320

Phe Ile Gly Ser Glu Gly Thr Leu Gly Leu Val Thr Glu Ala Thr Leu
325 330 335

Lys Leu Thr Val Lys Pro Lys Ser Gln Ser Val Ala Val Ala Ser Phe
340 345 350

Pro Ser Ile His Asn Ala Ala Glu Cys Val Thr Arg Val Val Glu Glu
355 360 365

Gly Ile Pro Val Ala Gly Val Glu Ile Leu Asp Asp Val Gln Met Lys
370 375 380

Cys Ile Asn Asp Ser Arg Thr Thr Arg Arg Gln Trp Lys Glu Ser Pro
385 390 395 400

Thr Leu Phe Phe Lys Phe Thr Gly Thr Pro Val Gly Val Lys Glu Gln

```
                405                 410                 415

Ile Glu Leu Val Arg Lys Ile Val Ser Ser Ser Ala Gly Gln Ser Phe
            420                 425                 430

Glu Phe Ala Arg Gly Glu Asp Glu Met Lys Glu Leu Trp Ser Ala Arg
        435                 440                 445

Lys Glu Ala Leu Trp Ser Val Met Ser Met Arg Arg Gly Pro Glu Asp
    450                 455                 460

Arg Val Trp Thr Thr Asp Val Ala Val Pro Met Ser Lys Leu Pro Asp
465                 470                 475                 480

Ile Ile Glu Ala Thr Lys Gln Asp Met Thr Glu Ser Gly Leu Leu Ala
                485                 490                 495

Gly Ile Cys Gly His Val Gly Asp Gly Asn Phe His Ala Ile Ile Leu
            500                 505                 510

Phe Asn Glu Asp Glu Lys Lys Ile Ala Glu Gly Val Val His Arg Met
        515                 520                 525

Val Lys Arg Ala Val Glu Met Glu Gly Thr Val Thr Gly Glu His Gly
    530                 535                 540

Val Gly Leu Ile Lys Arg Asp Tyr Leu Gln His Glu Val Gly Glu Thr
545                 550                 555                 560

Thr Val Asp Thr Met Arg Arg Ile Lys Met Ala Leu Asp Pro Leu Arg
                565                 570                 575

Leu Leu Asn Cys Asp Lys Val Val Arg Val Glu Gln Pro Thr Thr Val
            580                 585                 590

Glu Leu Lys Lys Trp
        595


<210> SEQ ID NO 69
<211> LENGTH: 4652
<212> TYPE: DNA
<213> ORGANISM: Artificial Sequence
<220> FEATURE:
<223> OTHER INFORMATION: Sequence put together from multiple organisms:
      Saccharomyces cerevisiae and Kluyveromyces lactis.

<400> SEQUENCE: 69

tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180

tattagcctt gatagtgctg aaaaaaagaa aaaaaacaaa aaaaagaaat aaaataacgg     240

caaacagcaa aggccacaga accgtattca tgttacttct gcaatatcaa tcacttactg     300

gcaagtgcgt ataaattaaa cctatttctt tatcatcata tttacttata tctttaacag     360

attccaaacc ctaaagtgtc cgaattttca atagggcgaa cttgaagaat aaccaaggtc     420

aataatatat cttttagtat aaccctgaaa tttgccctat agaaatctag ggtttctgtg     480

tggtttccgg gtgagtcata cggctttttt gaatttcttt ttttgcagtt gtctctatca     540

atgaaaattt cgaggaagac gataaggtta agataagtag ataagagaat gatacgagat     600

aaagcacaaa ttagcagaaa gaagagtggt tgcgaacaga gtaaaccgaa tcagggaatc     660

cctttttgca aaaacatcaa ttatcctttt cttttttta cgtatatatc tggaacagaa     720

atatataagt tactattata cttatagttg gatccagttt ttaatctgtc gtcaatcgaa     780

agtttatttc agagttcttc agacttctta actcctgtaa aaacaaaaaa aaaaaaaggc     840

atagcactcg agatctcccg agtttatcat tatcaatact gccatttcaa agaatacgta     900
```

-continued

```
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgttcaggt ttgttggaag   1560
atccggtttt gctttgcgtg gttcgctgca actacgtaag gacgttctgc gttctaggac   1620
cactgccgtt gcaaaaagac attattcgtc ttctaacggt aataacggcg gtggattttc   1680
gtccgccatt ttaagcgttc ttggtggttc tttaattggt ggtgggtttg ttgcatatgc   1740
tctaggctct cagttcgaga aggaaaagtc cgtgagtgat ttgtccattg ctagattgga   1800
agaccttgat tctcccgagt actgtgataa ggaaactttt gctaaagctc ttgttgaatt   1860
gaaagatgtc ttagaaaacg atcctgaaaa cttcactgtg gctaaggacg atttggatgc   1920
tcattcggat acctatttca actctcatca tgctgaagct aatcaaagac cagaaattgt   1980
tttgtatcca cgcaacacag aagatgtttc caaattattg aaaatctgtc acaaatactc   2040
tatcccagtg atcccatttt caggtggtac ctctttggaa gggcatttcc taccaactag   2100
accagggtct tgtgtcgtct tggatatttc aaaatatttg aataagatta ttcaattgaa   2160
taaagaggat ttggatgttg tggtacaagg tggtgttcca tgggaagaat tgaacgaata   2220
tttgaacgat catggtttgt tgttcggttg tgaccctggt ccaggtgctc aaatcgccgg   2280
ttgcattgct aattcttgtt ctggtaccaa cgcttatcgt tatggtacca tgaaggaaaa   2340
cgttgttaat attactatgt gtatggctga tggtactatt gttaagacca agagaagacc   2400
tagaaaatcg tctgctggtt acaatttgaa cgggttaatt attggtagtg aaggtacttt   2460
gggtatcgtt actgaagcta ctattaaatg tcatgttaga tctacttttg aaactgtcgc   2520
tgtcgttccg ttcccaactg tcagtgatgc tgcatcttgt tcctctcatt tgattcaagc   2580
cggtattcaa ttgaatgcta tggaattgtt ggatgataac atgatgaaaa tcatcaacca   2640
aagtggtgct acttcaaagg ataactgggt cgaatctcca actttgttct tcaagattgg   2700
tggtagatct gaacagatta ttcaagaagt cattaaagaa gtggaaaaaa ttgcttctca   2760
acacaacaat accaaatttg aatttgctac tgatgaagat tccaagctag aactatggga   2820
agctagaaaa gttgctcttt ggtcaaccat tgataccggc agaaagacca acccagatgc   2880
caacatttgg acaaccgatg ttgctgttcc aatctcgaaa ttcgcagatg ttattaatgc   2940
taccaaggaa gaaatgaacg catctggttt attaacctct ttggttggtc atgctggtga   3000
tggtaacttc catgcattca tcatctacaa cactgaacaa agaaaaacag ctgaaactat   3060
tgttgaaaat atggtcaaga gagccattga tgctgaaggt acttgtaccg gtgaacacgg   3120
tgtcggtatc ggtaagagag actacttgtt ggaagaagtt ggtgaagaca ctgttgcagt   3180
tatgagaaag ttgaagctcg ctttggatcc taagagaatc ttgaatccag ataagatctt   3240
caagattgat ccaaacgatc atcaacatta attaaacagg ccccttttcc tttgtcgata   3300
```

```
tcatgtaatt agttatgtca cgcttacatt cacgccctcc tcccacatcc gctctaaccg   3360
aaaaggaagg agttagacaa cctgaagtct aggtccctat ttattttttt atagttatgt   3420
tagtattaag aacgttattt atatttcaaa tttttctttt ttttctgtac aaacgcgtgt   3480
acgcatgtaa cgggcagacg gccggccata acttcgtata atgtatgcta tacgaagtta   3540
tggcaacggt tcatcatctc atggatctgc acatgaacaa acaccagagt caaacgacgt   3600
tgaaattgag gctactgcgc caattgatga caatacagac gatgataaca aaccgaagtt   3660
atctgatgta gaaaaggatt agagatgcta agagatagtg atgatatttc ataaataatg   3720
taattctata tatgttaatt accttttttg cgaggcatat ttatggtgaa ggataagttt   3780
tgaccatcaa agaaggttaa tgtggctgtg gtttcagggt ccataaagct tttcaattca   3840
tctttttttt ttttgttctt ttttttgatt ccggtttctt tgaaattttt ttgattcggt   3900
aatctccgag cagaaggaag aacgaaggaa ggagcacaga cttagattgg tatatatacg   3960
catatgtggt gttgaagaaa catgaaattg cccagtattc ttaacccaac tgcacagaac   4020
aaaaacctgc aggaaacgaa gataaatcat gtcgaaagct acatataagg aacgtgctgc   4080
tactcatcct agtcctgttg ctgccaagct atttaatatc atgcacgaaa agcaaacaaa   4140
cttgtgtgct tcattggatg ttcgtaccac caaggaatta ctggagttag ttgaagcatt   4200
aggtcccaaa atttgtttac taaaaacaca tgtggatatc ttgactgatt tttccatgga   4260
gggcacagtt aagccgctaa aggcattatc cgccaagtac aatttttac tcttcgaaga   4320
cagaaaattt gctgacattg gtaatacagt caaattgcag tactctgcgg gtgtatacag   4380
aatagcagaa tgggcagaca ttacgaatgc acacggtgtg gtgggcccag gtattgttag   4440
cggtttgaag caggcggcgg aagaagtaac aaaggaacct agaggccttt tgatgttagc   4500
agaattgtca tgcaagggct ccctagctac tggagaatat actaagggta ctgttgacat   4560
tgcgaagagc gacaaagatt ttgttatcgg ctttattgct caaagagaca tgggtggaag   4620
agatgaaggt tacgattggt tgattatgac ac                                  4652
```

<210> SEQ ID NO 70
<211> LENGTH: 576
<212> TYPE: PRT
<213> ORGANISM: Kluyveromyces lactis

<400> SEQUENCE: 70

```
Met Phe Arg Phe Val Gly Arg Ser Gly Phe Ala Leu Arg Gly Ser Leu
1               5                   10                  15

Gln Leu Arg Lys Asp Val Leu Arg Ser Arg Thr Thr Ala Val Ala Lys
            20                  25                  30

Arg His Tyr Ser Ser Ser Asn Gly Asn Asn Gly Gly Gly Phe Ser Ser
        35                  40                  45

Ala Ile Leu Ser Val Leu Gly Gly Ser Leu Ile Gly Gly Gly Phe Val
    50                  55                  60

Ala Tyr Ala Leu Gly Ser Gln Phe Glu Lys Glu Lys Ser Val Ser Asp
65                  70                  75                  80

Leu Ser Ile Ala Arg Leu Glu Asp Leu Asp Ser Pro Glu Tyr Cys Asp
                85                  90                  95

Lys Glu Thr Phe Ala Lys Ala Leu Val Glu Leu Lys Asp Val Leu Glu
            100                 105                 110

Asn Asp Pro Glu Asn Phe Thr Val Ala Lys Asp Asp Leu Asp Ala His
        115                 120                 125
```

-continued

```
Ser Asp Thr Tyr Phe Asn Ser His His Ala Glu Ala Asn Gln Arg Pro
    130                 135                 140

Glu Ile Val Leu Tyr Pro Arg Asn Thr Glu Asp Val Ser Lys Leu Leu
145                 150                 155                 160

Lys Ile Cys His Lys Tyr Ser Ile Pro Val Ile Pro Phe Ser Gly Gly
                165                 170                 175

Thr Ser Leu Glu Gly His Phe Leu Pro Thr Arg Pro Gly Ser Cys Val
            180                 185                 190

Val Leu Asp Ile Ser Lys Tyr Leu Asn Lys Ile Ile Gln Leu Asn Lys
        195                 200                 205

Glu Asp Leu Asp Val Val Val Gln Gly Gly Val Pro Trp Glu Glu Leu
    210                 215                 220

Asn Glu Tyr Leu Asn Asp His Gly Leu Leu Phe Gly Cys Asp Pro Gly
225                 230                 235                 240

Pro Gly Ala Gln Ile Ala Gly Cys Ile Ala Asn Ser Cys Ser Gly Thr
                245                 250                 255

Asn Ala Tyr Arg Tyr Gly Thr Met Lys Glu Asn Val Val Asn Ile Thr
            260                 265                 270

Met Cys Met Ala Asp Gly Thr Ile Val Lys Thr Lys Arg Arg Pro Arg
        275                 280                 285

Lys Ser Ser Ala Gly Tyr Asn Leu Asn Gly Leu Ile Ile Gly Ser Glu
    290                 295                 300

Gly Thr Leu Gly Ile Val Thr Glu Ala Thr Ile Lys Cys His Val Arg
305                 310                 315                 320

Ser Thr Phe Glu Thr Val Ala Val Val Pro Phe Pro Thr Val Ser Asp
                325                 330                 335

Ala Ala Ser Cys Ser Ser His Leu Ile Gln Ala Gly Ile Gln Leu Asn
            340                 345                 350

Ala Met Glu Leu Leu Asp Asp Asn Met Met Lys Ile Ile Asn Gln Ser
        355                 360                 365

Gly Ala Thr Ser Lys Asp Asn Trp Val Glu Ser Pro Thr Leu Phe Phe
    370                 375                 380

Lys Ile Gly Gly Arg Ser Glu Gln Ile Ile Gln Glu Val Ile Lys Glu
385                 390                 395                 400

Val Glu Lys Ile Ala Ser Gln His Asn Asn Thr Lys Phe Glu Phe Ala
                405                 410                 415

Thr Asp Glu Asp Ser Lys Leu Glu Leu Trp Glu Ala Arg Lys Val Ala
            420                 425                 430

Leu Trp Ser Thr Ile Asp Thr Gly Arg Lys Thr Asn Pro Asp Ala Asn
        435                 440                 445

Ile Trp Thr Thr Asp Val Ala Val Pro Ile Ser Lys Phe Ala Asp Val
    450                 455                 460

Ile Asn Ala Thr Lys Glu Glu Met Asn Ala Ser Gly Leu Leu Thr Ser
465                 470                 475                 480

Leu Val Gly His Ala Gly Asp Gly Asn Phe His Ala Phe Ile Ile Tyr
                485                 490                 495

Asn Thr Glu Gln Arg Lys Thr Ala Glu Thr Ile Val Glu Asn Met Val
            500                 505                 510

Lys Arg Ala Ile Asp Ala Glu Gly Thr Cys Thr Gly Glu His Gly Val
        515                 520                 525

Gly Ile Gly Lys Arg Asp Tyr Leu Leu Glu Glu Val Gly Glu Asp Thr
    530                 535                 540

Val Ala Val Met Arg Lys Leu Lys Leu Ala Leu Asp Pro Lys Arg Ile
```

545 550 555 560

Leu Asn Pro Asp Lys Ile Phe Lys Ile Asp Pro Asn Asp His Gln His
565 570 575

<210> SEQ ID NO 71
<211> LENGTH: 4676
<212> TYPE: DNA
<213> ORGANISM: Artificial Sequence
<220> FEATURE:
<223> OTHER INFORMATION: Sequence put together from multiple organisms: Saccharomyces cerevisiae and Kluyveromyces dobzhanskii.

<400> SEQUENCE: 71
tcctattcgg agatacaggc aacaagtgat agagggccca ttatgaatac gcacctctat 60
gtatttccga gatacgatta ctccagttcc tcttacaaga aatgcataaa aatagttaca 120
attaattaga acaagaactt atttagaaca cgttcacact gagtaagaac tcttgtccct 180
tattagcctt gatagtgctg aaaaaaagaa aaaaaacaaa aaaaagaaat aaaataacgg 240
caaacagcaa aggccacaga accgtattca tgttacttct gcaatatcaa tcacttactg 300
gcaagtgcgt ataaattaaa cctatttctt tatcatcata tttacttata tctttaacag 360
attccaaacc ctaaagtgtc cgaattttca atagggcgaa cttgaagaat aaccaaggtc 420
aataatatat cttttagtat aaccctgaaa tttgccctat agaaatctag ggtttctgtg 480
tggtttccgg gtgagtcata cggctttttt gaatttcttt ttttgcagtt gtctctatca 540
atgaaaattt cgaggaagac gataaggtta agataagtag ataagagaat gatacgagat 600
aaagcacaaa ttagcagaaa gaagagtggt tgcgaacaga gtaaaccgaa tcagggaatc 660
cctttttgca aaaacatcaa ttatcctttt cttttttta cgtatatatc tggaacagaa 720
atatataagt tactattata cttatagttg gatccagttt ttaatctgtc gtcaatcgaa 780
agtttatttc agagttcttc agacttctta actcctgtaa aaacaaaaaa aaaaaaaggc 840
atagcactcg agatctcccg agtttatcat tatcaatact gccatttcaa agaatacgta 900
aataattaat agtagtgatt ttcctaactt tatttagtca aaaaattggc cttttaattc 960
tgctgtaacc cgtacatgcc caaaataggg ggcgggttac acagaatata taacatcata 1020
ggtgtctggg tgaacagttt attcctggca tccactaaat ataatggagc ccgctttttt 1080
taagctggca tccagaaaaa aaaagaatcc cagcaccaaa atattgtttt cttcaccaac 1140
catcagttca taggtccatt ctcttagcgc aactacacag aacaggggca caaacaggca 1200
aaaaacgggc acaacctcaa tggagtgatg caacctgctt ggagtaaatg atgacacaag 1260
gcaattgacc tacgcatgta tctatctcat tttcttacac cttctattac cttctgctct 1320
ctctgatttg gaaaaagctg aaaaaaaagg ttgaaaccag ttccctgaaa ttattcccct 1380
atttgactaa taagtatata aagacggtag gtattgattg taattctgta aatctatttc 1440
ttaaacttct taaattctac ttttatagtt agtctttttt ttagtttaaa acaccaagaa 1500
cttagtttcg aataaacaca cataaacaaa caaatctaga atgttcaaat ttgttggtag 1560
aagtggcaca gccttgagat cttcattgca agcacgtaga aatggagcgg tttggaagag 1620
aggatacgca tctggttctg gtagcggtag tggttcaggt agtggctcat catcactcgt 1680
tctaggagtg ttagccggat ctatgatagg aggtggtatt gtggcataca cattaggtaa 1740
ccaattcgaa aaggacaaaa aggtttccgg ctcctctgct gctgccgcag cttctgattt 1800
atccatcttg aagttggagg acttagagag cccagtttat tgtgactccg aaactttttc 1860
aacagcagtt gaagagttaa agaccgtgct gaacaatgac cctgaaaact ttaccacagc 1920
taaagcagat cttgacagcc attctgatac ttacttcaac tctcatcacg ctgaaccaga 1980
tcaaagacca gaaatcgttt tgttccctag aaacactgaa gatgtctctc agttgttgaa 2040
gatctgtcat aagtactcta tccctgtcat tccatttttct ggcggtacat cattggaagg 2100
tcatttccta ccaactagac ctggttcctg cgtcgtacta gatattagta aatacttgaa 2160
taagatcata catcttaaca aggaggacct cgacgtcgtt gttcaagggg gggtaccatg 2220
ggaagatttg aacgattacc ttattgacca aggtctgttg ttcggctgcg atccaggccc 2280
aggcgcacag atcgctggtt gcatagctaa ttcatgtagt ggaacaaacg catacagata 2340
cgggactatg aaagagaatg tagttaacat cacaatgtgt atggccgatg gtaccattat 2400
caagaccaaa aagcgtccac gtaaatctgc agccggttac aatcttaatg gtctaattgt 2460
cggctctgaa ggtacattgg gtattgtgac cgaggccaca atcaagtgcc acgtcagatc 2520
tttattcgag acagtagcag ttgttccttt cccaacagtc tctgatgccg ctagttgttc 2580
atcacatctt atacaagcgg gtattcaact aaacgccatg gaactgttag atgataacat 2640
gatgaagatt atcaatcaat ctggggcaac ttccaaaatt gattgggttg agtcaccaac 2700
actattcttt aagatagggg gtagaaccga aaaatctatt caagatgtgg tagatgaagt 2760
tgaaaagatt gcgtcacaac acaacaatta caagttcgaa ttcgcaacag atgccgattc 2820
taagctagaa ttatgggaag ctagaaaagt tgctttgtgg agcactattg atgcagggaa 2880
aaagttagat cctaaagtca acgtgtggac tactgatgtt gcagtaccaa tctcaagatt 2940
tgccgaagtg atcaacgcta caaaacaaga gatgaactct tcaggcttat tgacttcact 3000
tgtcggccat gcgggtgacg gtaactttca cgctttcatc atctataact ccgaacagag 3060
aaagcaggct gagacaatag ttgaaaacat ggttaagaga gcaattgatg ctgaaggaac 3120
atgtactgga gaacatggag tgggtattgg taagagagac tacttagtag aggaattagg 3180
agaggacgca atcgctgtta tgagaaagct taagttggct ctcgatccta agagaatact 3240
gaatccagat aagattttca aaattgatcc aaacgataat cagcactagt taattaaaca 3300
ggccccttttt cctttgtcga tatcatgtaa ttagttatgt cacgcttaca ttcacgccct 3360
cctccccacat ccgctctaac cgaaaaggaa ggagttagac aacctgaagt ctaggtccct 3420
atttattttt ttatagttat gttagtatta agaacgttat ttatatttca aatttttctt 3480
ttttttctgt acaaacgcgt gtacgcatgt aacgggcaga cggccggcca taacttcgta 3540
taatgtatgc tatacgaagt tatggcaacg gttcatcatc tcatggatct gcacatgaac 3600
aaacaccaga gtcaaacgac gttgaaattg aggctactgc gccaattgat gacaatacag 3660
acgatgataa caaaccgaag ttatctgatg tagaaaagga ttagagatgc taagagatag 3720
tgatgatatt tcataaataa tgtaattcta tatatgttaa ttaccttttt tgcgaggcat 3780
atttatggtg aaggataagt tttgaccatc aaagaaggtt aatgtggctg tggtttcagg 3840
gtccataaag cttttcaatt catctttttt tttttttgttc tttttttttga ttccggtttc 3900
tttgaaattt ttttgattcg gtaatctccg agcagaagga agaacgaagg aaggagcaca 3960
gacttagatt ggtatatata cgcatatgtg gtgttgaaga aacatgaaat tgcccagtat 4020
tcttaaccca actgcacaga acaaaaacct gcaggaaacg aagataaatc atgtcgaaag 4080
ctacatataa ggaacgtgct gctactcatc ctagtcctgt tgctgccaag ctatttaata 4140
tcatgcacga aaagcaaaca aacttgtgtg cttcattgga tgttcgtacc accaaggaat 4200
tactggagtt agttgaagca ttaggtccca aaatttgttt actaaaaaca catgtggata 4260

```
tcttgactga tttttccatg gagggcacag ttaagccgct aaaggcatta tccgccaagt   4320

acaatttttt actcttcgaa gacagaaaat ttgctgacat tggtaataca gtcaaattgc   4380

agtactctgc gggtgtatac agaatagcag aatgggcaga cattacgaat gcacacggtg   4440

tggtgggccc aggtattgtt agcggtttga agcaggcggc ggaagaagta acaaaggaac   4500

ctagaggcct tttgatgtta gcagaattgt catgcaaggg ctccctagct actggagaat   4560

atactaaggg tactgttgac attgcgaaga gcgacaaaga ttttgttatc ggctttattg   4620

ctcaaagaga catgggtgga agagatgaag gttacgattg gttgattatg acacgc       4676


<210> SEQ ID NO 72
<211> LENGTH: 582
<212> TYPE: PRT
<213> ORGANISM: Kluyveromyces dobzhanskii

<400> SEQUENCE: 72

Met Phe Lys Phe Val Gly Arg Ser Gly Thr Ala Leu Arg Ser Ser Leu
1               5                   10                  15

Gln Ala Arg Arg Asn Gly Ala Val Trp Lys Arg Gly Tyr Ala Ser Gly
            20                  25                  30

Ser Gly Ser Gly Ser Gly Ser Gly Ser Gly Ser Ser Ser Leu Val Leu
        35                  40                  45

Gly Val Leu Ala Gly Ser Met Ile Gly Gly Gly Ile Val Ala Tyr Thr
    50                  55                  60

Leu Gly Asn Gln Phe Glu Lys Asp Lys Lys Val Ser Gly Ser Ser Ala
65                  70                  75                  80

Ala Ala Ala Ala Ser Asp Leu Ser Ile Leu Lys Leu Glu Asp Leu Glu
                85                  90                  95

Ser Pro Val Tyr Cys Asp Ser Glu Thr Phe Ser Thr Ala Val Glu Glu
            100                 105                 110

Leu Lys Thr Val Leu Asn Asn Asp Pro Glu Asn Phe Thr Thr Ala Lys
        115                 120                 125

Ala Asp Leu Asp Ser His Ser Asp Thr Tyr Phe Asn Ser His His Ala
    130                 135                 140

Glu Pro Asp Gln Arg Pro Glu Ile Val Leu Phe Pro Arg Asn Thr Glu
145                 150                 155                 160

Asp Val Ser Gln Leu Leu Lys Ile Cys His Lys Tyr Ser Ile Pro Val
                165                 170                 175

Ile Pro Phe Ser Gly Gly Thr Ser Leu Glu Gly His Phe Leu Pro Thr
            180                 185                 190

Arg Pro Gly Ser Cys Val Val Leu Asp Ile Ser Lys Tyr Leu Asn Lys
        195                 200                 205

Ile Ile His Leu Asn Lys Glu Asp Leu Asp Val Val Val Gln Gly Gly
    210                 215                 220

Val Pro Trp Glu Asp Leu Asn Asp Tyr Leu Ile Asp Gln Gly Leu Leu
225                 230                 235                 240

Phe Gly Cys Asp Pro Gly Pro Gly Ala Gln Ile Ala Gly Cys Ile Ala
                245                 250                 255

Asn Ser Cys Ser Gly Thr Asn Ala Tyr Arg Tyr Gly Thr Met Lys Glu
            260                 265                 270

Asn Val Val Asn Ile Thr Met Cys Met Ala Asp Gly Thr Ile Ile Lys
        275                 280                 285

Thr Lys Lys Arg Pro Arg Lys Ser Ala Ala Gly Tyr Asn Leu Asn Gly
    290                 295                 300
```

```
Leu Ile Val Gly Ser Glu Gly Thr Leu Gly Ile Val Thr Glu Ala Thr
305                 310                 315                 320

Ile Lys Cys His Val Arg Ser Leu Phe Glu Thr Val Ala Val Val Pro
                325                 330                 335

Phe Pro Thr Val Ser Asp Ala Ala Ser Cys Ser Ser His Leu Ile Gln
            340                 345                 350

Ala Gly Ile Gln Leu Asn Ala Met Glu Leu Leu Asp Asp Asn Met Met
        355                 360                 365

Lys Ile Ile Asn Gln Ser Gly Ala Thr Ser Lys Ile Asp Trp Val Glu
    370                 375                 380

Ser Pro Thr Leu Phe Phe Lys Ile Gly Gly Arg Thr Glu Lys Ser Ile
385                 390                 395                 400

Gln Asp Val Val Asp Glu Val Glu Lys Ile Ala Ser Gln His Asn Asn
                405                 410                 415

Tyr Lys Phe Glu Phe Ala Thr Asp Ala Asp Ser Lys Leu Glu Leu Trp
            420                 425                 430

Glu Ala Arg Lys Val Ala Leu Trp Ser Thr Ile Asp Ala Gly Lys Lys
        435                 440                 445

Leu Asp Pro Lys Val Asn Val Trp Thr Thr Asp Val Ala Val Pro Ile
    450                 455                 460

Ser Arg Phe Ala Glu Val Ile Asn Ala Thr Lys Gln Glu Met Asn Ser
465                 470                 475                 480

Ser Gly Leu Leu Thr Ser Leu Val Gly His Ala Gly Asp Gly Asn Phe
                485                 490                 495

His Ala Phe Ile Ile Tyr Asn Ser Glu Gln Arg Lys Gln Ala Glu Thr
            500                 505                 510

Ile Val Glu Asn Met Val Lys Arg Ala Ile Asp Ala Glu Gly Thr Cys
        515                 520                 525

Thr Gly Glu His Gly Val Gly Ile Gly Lys Arg Asp Tyr Leu Val Glu
    530                 535                 540

Glu Leu Gly Glu Asp Ala Ile Ala Val Met Arg Lys Leu Lys Leu Ala
545                 550                 555                 560

Leu Asp Pro Lys Arg Ile Leu Asn Pro Asp Lys Ile Phe Lys Ile Asp
                565                 570                 575

Pro Asn Asp Asn Gln His
            580
```

<210> SEQ ID NO 73
<211> LENGTH: 4704
<212> TYPE: DNA
<213> ORGANISM: Artificial Sequence
<220> FEATURE:
<223> OTHER INFORMATION: Sequence put together from multiple organisms: Saccharomyces cerevisiae and Kluyveromyces marxianus.

<400> SEQUENCE: 73

```
tcctattcgg agatacaggc aacaagtgat agagggccca ttatgaatac gcacctctat      60

gtatttccga gatacgatta ctccagttcc tcttacaaga aatgcataaa aatagttaca     120

attaattaga acaagaactt atttagaaca cgttcacact gagtaagaac tcttgtccct     180

tattagcctt gatagtgctg aaaaaaagaa aaaaaacaaa aaaaagaaat aaaataacgg     240

caaacagcaa aggccacaga accgtattca tgttacttct gcaatatcaa tcacttactg     300

gcaagtgcgt ataaattaaa cctatttctt tatcatcata tttacttata tctttaacag     360

attccaaacc ctaaagtgtc cgaattttca atagggcgaa cttgaagaat aaccaaggtc     420
```

-continued

```
aataatatat cttttagtat aaccctgaaa tttgccctat agaaatctag ggtttctgtg    480
tggtttccgg gtgagtcata cggctttttt gaatttcttt ttttgcagtt gtctctatca    540
atgaaaattt cgaggaagac gataaggtta agataagtag ataagagaat gatacgagat    600
aaagcacaaa ttagcagaaa gaagagtggt tgcgaacaga gtaaaccgaa tcagggaatc    660
ccttttttgca aaaacatcaa ttatcctttt cttttttttta cgtatatatc tggaacagaa    720
atatataagt tactattata cttatagttg gatccagttt ttaatctgtc gtcaatcgaa    780
agtttatttc agagttcttc agacttctta actcctgtaa aaacaaaaaa aaaaaaaggc    840
atagcactcg agatctcccg agtttatcat tatcaatact gccatttcaa agaatacgta    900
aataattaat agtagtgatt ttcctaactt tatttagtca aaaaattggc cttttaattc    960
tgctgtaacc cgtacatgcc caaaataggg ggcgggttac acagaatata taacatcata   1020
ggtgtctggg tgaacagttt attcctggca tccactaaat ataatggagc ccgctttttt   1080
taagctggca tccagaaaaa aaaagaatcc cagcaccaaa atattgtttt cttcaccaac   1140
catcagttca taggtccatt ctcttagcgc aactacacag aacaggggca caaacaggca   1200
aaaaacgggc acaacctcaa tggagtgatg caacctgctt ggagtaaatg atgacacaag   1260
gcaattgacc tacgcatgta tctatctcat tttcttacac cttctattac cttctgctct   1320
ctctgatttg gaaaaagctg aaaaaaaagg ttgaaaccag ttccctgaaa ttattcccct   1380
atttgactaa taagtatata aagacggtag gtattgattg taattctgta aatctatttc   1440
ttaaacttct taaattctac ttttatagtt agtctttttt ttagtttaaa acaccaagaa   1500
cttagtttcg aataaacaca cataaacaaa caaatctaga atgttaccaa gatttgttgt   1560
gagatcaggc gctgcaggga gaaatttggg tttcagcttc acacgtaaat gtgaccacac   1620
ttttctgagc aagaccgtca gaaacgattt atctcataga ccatacagta caggtactaa   1680
tggaaacgga tctgcaaatg ctggtaaaag tcaatctggt ctattgttcg gtgtattcgg   1740
aggaactttg attgggggag gcttggttgc atacttcttg ggttctaagt tcgatcaaca   1800
acaatcttcc tcacaacaag tttctgacct ctcaatagcg agacttgaag atttagactc   1860
ccctaagtac tgcgacaaaa agacctttgc aactgctgtc gaggaactga agcaagtctt   1920
agataacaac cctgagaact tctctgacgc caagtcagat ttggattccc actcagatac   1980
atactttaac tctcatcacg caactccaga acaaagacca gaaatcgtac tattccctag   2040
aaacacagag gacgtttcta agctactcaa gatttgccac aaatactcaa tcccagtaat   2100
cccattctcc ggtggtacct cacttgaagg tcatttcatg ccaaccagac caggttcatg   2160
tgtagtgttg gacatttcta aatacatgaa tcagattatt caactaaaca aggaagattt   2220
ggatgttgtg gtacaaggtg gcgttccttg ggaggatttg aatgattacc ttaatgatca   2280
tgggttgtta tttggatgtg acccaggtcc aggggctcaa atagccggtt gcatcgctaa   2340
ttcttgttct gggaccaacg catatcgtta cggcactatg aaggaaaacg ttgttaacat   2400
aacaatgtgc ctcgcagatg gtactattat caagactaag cgtagaccta gaaagtcaag   2460
tgccggttac aacttaaacg gtttgataat cgggtccgaa ggtactttag gaattgtgac   2520
agaagcgaca atcaagtgcc atgtcagatc aaatttcgaa actgtcgcag tcgttccatt   2580
cccttcagtt gctgatgctg cttcttgttc ttctcatttg attcaggctg gcattcagtt   2640
gaacgccatg gaattgctcg atgataacat gatgaagatc atcaataagt ccggagcaac   2700
tagtagaaca aattgggtag aatcaccaac ccttttcttc aagataggtg gtagaagcga   2760
aaaagctatt aaggaagttg ttaaagaggt tgagaaaatt gcttcacagc acaataactc   2820
```

```
taactttgaa tttgcatcag atgaagagac aaaactagaa ctttgggagg ccagaaaggt   2880
tgccctgtgg tccacaattg atgcaggcaa aaagctagat cctaacgtga acgtttggac   2940
aacagatgtt gcagtcccaa taagtaaatt cgcacaagtc atcaatgata caaaggagga   3000
aatgaacgcg tctggcctgt taacctcatt ggtcggtcat gctggtgatg gtaactttca   3060
tgcgtttatc atctataacg ctgaacagag aaagactgct gaaacaatcg tagagaacat   3120
ggttaaaaga gcaattgatg ccgaaggcac atgtacagga gaacatggag tgggtattgg   3180
caaaagagaa ttccttgttg aggaattagg tgaggataca attgccgtta tgagaaagct   3240
taagttagcc ttagacccaa agagaatctt gaaccctgat aaagtgttta agattgaccc   3300
aaatgaccat caacactagt taattaaaca ggcccctttt cctttgtcga tatcatgtaa   3360
ttagttatgt cacgcttaca ttcacgccct cctcccacat ccgctctaac cgaaaaggaa   3420
ggagttagac aacctgaagt ctaggtccct atttattttt ttatagttat gttagtatta   3480
agaacgttat ttatatttca aatttttctt ttttttctgt acaaacgcgt gtacgcatgt   3540
aacgggcaga cggccggcca taacttcgta taatgtatgc tatacgaagt tatggcaacg   3600
gttcatcatc tcatggatct gcacatgaac aaacaccaga gtcaaacgac gttgaaattg   3660
aggctactgc gccaattgat gacaatacag acgatgataa caaaccgaag ttatctgatg   3720
tagaaaagga ttagagatgc taagagatag tgatgatatt tcataaataa tgtaattcta   3780
tatatgttaa ttaccttttt tgcgaggcat atttatggtg aaggataagt tttgaccatc   3840
aaagaaggtt aatgtggctg tggtttcagg gtccataaag cttttcaatt catctttttt   3900
ttttttgttc tttttttga ttccggtttc tttgaaattt ttttgattcg gtaatctccg   3960
agcagaagga agaacgaagg aaggagcaca gacttagatt ggtatatata cgcatatgtg   4020
gtgttgaaga aacatgaaat tgcccagtat tcttaaccca actgcacaga acaaaaacct   4080
gcaggaaacg aagataaatc atgtcgaaag ctacatataa ggaacgtgct gctactcatc   4140
ctagtcctgt tgctgccaag ctatttaata tcatgcacga aaagcaaaca aacttgtgtg   4200
cttcattgga tgttcgtacc accaaggaat tactggagtt agttgaagca ttaggtccca   4260
aaatttgttt actaaaaaca catgtggata tcttgactga tttttccatg gagggcacag   4320
ttaagccgct aaaggcatta tccgccaagt acaatttttt actcttcgaa gacagaaaat   4380
ttgctgacat tggtaataca gtcaaattgc agtactctgc gggtgtatac agaatagcag   4440
aatgggcaga cattacgaat gcacacggtg tggtgggccc aggtattgtt agcggtttga   4500
agcaggcggc ggaagaagta acaaaggaac ctagaggcct tttgatgtta gcagaattgt   4560
catgcaaggg ctccctagct actggagaat atactaaggg tactgttgac attgcgaaga   4620
gcgacaaaga ttttgttatc ggctttattg ctcaaagaga catgggtgga agagatgaag   4680
gttacgattg gttgattatg acac                                          4704
```

<210> SEQ ID NO 74
<211> LENGTH: 592
<212> TYPE: PRT
<213> ORGANISM: Kluyveromyces marxianus

<400> SEQUENCE: 74

```
Met Leu Pro Arg Phe Val Val Arg Ser Gly Ala Ala Gly Arg Asn Leu
1               5                   10                  15

Gly Phe Ser Phe Thr Arg Lys Cys Asp His Thr Phe Leu Ser Lys Thr
            20                  25                  30
```

-continued

```
Val Arg Asn Asp Leu Ser His Arg Pro Tyr Ser Thr Gly Thr Asn Gly
        35                  40                  45

Asn Gly Ser Ala Asn Ala Gly Lys Ser Gln Ser Gly Leu Leu Phe Gly
    50                  55                  60

Val Phe Gly Gly Thr Leu Ile Gly Gly Gly Leu Val Ala Tyr Phe Leu
65                  70                  75                  80

Gly Ser Lys Phe Asp Gln Gln Gln Ser Ser Ser Gln Gln Val Ser Asp
                85                  90                  95

Leu Ser Ile Ala Arg Leu Glu Asp Leu Asp Ser Pro Lys Tyr Cys Asp
            100                 105                 110

Lys Lys Thr Phe Ala Thr Ala Val Glu Glu Leu Lys Gln Val Leu Asp
        115                 120                 125

Asn Asn Pro Glu Asn Phe Ser Asp Ala Lys Ser Asp Leu Asp Ser His
    130                 135                 140

Ser Asp Thr Tyr Phe Asn Ser His His Ala Thr Pro Glu Gln Arg Pro
145                 150                 155                 160

Glu Ile Val Leu Phe Pro Arg Asn Thr Glu Asp Val Ser Lys Leu Leu
                165                 170                 175

Lys Ile Cys His Lys Tyr Ser Ile Pro Val Ile Pro Phe Ser Gly Gly
            180                 185                 190

Thr Ser Leu Glu Gly His Phe Met Pro Thr Arg Pro Gly Ser Cys Val
        195                 200                 205

Val Leu Asp Ile Ser Lys Tyr Met Asn Gln Ile Ile Gln Leu Asn Lys
    210                 215                 220

Glu Asp Leu Asp Val Val Val Gln Gly Gly Val Pro Trp Glu Asp Leu
225                 230                 235                 240

Asn Asp Tyr Leu Asn Asp His Gly Leu Leu Phe Gly Cys Asp Pro Gly
                245                 250                 255

Pro Gly Ala Gln Ile Ala Gly Cys Ile Ala Asn Ser Cys Ser Gly Thr
            260                 265                 270

Asn Ala Tyr Arg Tyr Gly Thr Met Lys Glu Asn Val Val Asn Ile Thr
        275                 280                 285

Met Cys Leu Ala Asp Gly Thr Ile Ile Lys Thr Lys Arg Arg Pro Arg
    290                 295                 300

Lys Ser Ser Ala Gly Tyr Asn Leu Asn Gly Leu Ile Ile Gly Ser Glu
305                 310                 315                 320

Gly Thr Leu Gly Ile Val Thr Glu Ala Thr Ile Lys Cys His Val Arg
                325                 330                 335

Ser Asn Phe Glu Thr Val Ala Val Val Pro Phe Pro Ser Val Ala Asp
            340                 345                 350

Ala Ala Ser Cys Ser Ser His Leu Ile Gln Ala Gly Ile Gln Leu Asn
        355                 360                 365

Ala Met Glu Leu Leu Asp Asp Asn Met Met Lys Ile Ile Asn Lys Ser
    370                 375                 380

Gly Ala Thr Ser Arg Thr Asn Trp Val Glu Ser Pro Thr Leu Phe Phe
385                 390                 395                 400

Lys Ile Gly Gly Arg Ser Glu Lys Ala Ile Lys Glu Val Val Lys Glu
                405                 410                 415

Val Glu Lys Ile Ala Ser Gln His Asn Asn Ser Asn Phe Glu Phe Ala
            420                 425                 430

Ser Asp Glu Glu Thr Lys Leu Glu Leu Trp Glu Ala Arg Lys Val Ala
        435                 440                 445

Leu Trp Ser Thr Ile Asp Ala Gly Lys Lys Leu Asp Pro Asn Val Asn
```

```
    450                 455                 460

Val Trp Thr Thr Asp Val Ala Val Pro Ile Ser Lys Phe Ala Gln Val
465                 470                 475                 480

Ile Asn Asp Thr Lys Glu Glu Met Asn Ala Ser Gly Leu Leu Thr Ser
                485                 490                 495

Leu Val Gly His Ala Gly Asp Gly Asn Phe His Ala Phe Ile Ile Tyr
            500                 505                 510

Asn Ala Glu Gln Arg Lys Thr Ala Glu Thr Ile Val Glu Asn Met Val
        515                 520                 525

Lys Arg Ala Ile Asp Ala Glu Gly Thr Cys Thr Gly Glu His Gly Val
    530                 535                 540

Gly Ile Gly Lys Arg Glu Phe Leu Val Glu Glu Leu Gly Glu Asp Thr
545                 550                 555                 560

Ile Ala Val Met Arg Lys Leu Lys Leu Ala Leu Asp Pro Lys Arg Ile
                565                 570                 575

Leu Asn Pro Asp Lys Val Phe Lys Ile Asp Pro Asn Asp His Gln His
            580                 585                 590


<210> SEQ ID NO 75
<211> LENGTH: 4953
<212> TYPE: DNA
<213> ORGANISM: Artificial Sequence
<220> FEATURE:
<223> OTHER INFORMATION: Sequence put together from multiple organisms:
      Saccharomyces cerevisiae and Kluyveromyces dobzhanskii.

<400> SEQUENCE: 75

tccatggagg gcacagttaa gccgctaaag gcattatccg ccaagtacaa tttttactc     60

ttcgaagaca gaaaatttgc tgacattggt aatacagtca aattgcagta ctctgcgggt    120

gtatacagaa tagcagaatg ggcagacatt acgaatgcac acggtgtggt gggcccaggt    180

attgttagcg gtttgaagca ggcggcggaa gaagtaacaa aggaacctag aggccttttg    240

atgttagcag aattgtcatg caagggctcc ctagctactg gagaatatac taagggtact    300

gttgacattg cgaagagcga caaagatttt gttatcggct ttattgctca aagagacatg    360

ggtggaagag atgaaggtta cgattggttg attatgacac ccggtgtggg tttagatgac    420

aagggagacg cattgggtca acagtataga accgtggatg atgtggtctc tacaggatct    480

gacattatta ttgttggaag aggactattt gcaaagggaa gggatgctaa ggtagagggt    540

gaacgttaca gaaaagcagg ctgggaagca tatttgagaa gatgcggcca gcaaaactaa    600

aaaactgtat tataagtaaa tgcatgtata ctaaactcac aaattagagc ttcaatttaa    660

ttatatcagt tattacccgg gaatctcggt cgtaatgatt tttataatga cgaaaaaaaa    720

aaaattggaa agaaaaagct tcatggcctt tataaaaagg aaccatccaa tacctcgcca    780

gaaccaagta acagtatttt acggggcaca aatcaagaac aataagacag gactgtaaag    840

atggacgcat tgaactccaa agaacaacaa gagttccaaa aagtagtgga acaaaagcaa    900

atgaaggatt tcatgcgttt gataacttcg tataatgtat gctatacgaa gttatctcga    960

gatctcccct aaaccgtgga atatttcgga tatccttttg ttgtttccgg gtgtacaata   1020

tggacttcct cttttctggc aaccaaaccc atacatcggg attcctataa taccttcgtt   1080

ggtctcccta acatgtaggt ggcggagggg agatatacaa tagaacagat accagacaag   1140

acataatggg ctaaacaaga ctacaccatt tacactgcct cattgatggt ggtacataac   1200

gaactaatac tgtagcccta gacttgatag ccatcatcat atcgaagttt cactaccctt   1260
```

tttccatttg ccatctattg aagtaataat aggcgcatgc aacttctttt tttttttttt 1320
ttttctctct cccccgttgt tgtctcacca tatccgcaat gacaaaaaaa tgatggaaga 1380
cactaaagga aaaaattaac gacaaagaca gcaccaacag atgtcgttgt tccagagctg 1440
atgaggggta tctcgaagca cacgaaactt tttccttcct tcattcacgc acactactct 1500
ctaatgagca acggtatacg gccttccttc cagttacttg aatttgaaat aaaaaaaagt 1560
ttgctgtctt gctatcaagt ataaatagac ctgcaattat taatcttttg tttcctcgtc 1620
attgttctcg ttccctttct tccttgtttc tttttctgca caatatttca agctatacca 1680
agcatacaat caactatctc atatacatct agaatgcata caatttctcc agaatctgac 1740
tccctgaaat catctaagag taacactaac tcacatgaat acatgagtgc aacaaccgat 1800
tacaataacg gggtgcgtc tgcagcccca ctttctgcta agagaaaaga gacaggaaac 1860
agctacgaac tccaagacca tgctgcgtcc gccagcgcca gtgcatctgc ttcagcctca 1920
gcatcagctt ctgcaagcgc actagctttt gattacgatc cagaagatga cgatgtttca 1980
atcatgatgc aagatgaaga ggttcctgat ttgacctgga agcatgtatc taactatgca 2040
atcactagat ttacttcatt agcccatatt catccagtct caatgcaaaa catcaatcca 2100
ttcccagagt tgagaaagat gacattacac aactggaatt acttctttat gggctacggt 2160
gcgtggcttt gcgctagttg ggctttcttt gctgtatcag tctcaacagc cccattagca 2220
gaactatacg acaaacagac taaagatatt tcttggggtt tgtccttagt cttgttcgtt 2280
agatctgccg gtgctatcat tttcggtatc tggactgaca actattccag aaagtggcca 2340
tacattacat gtcttggatt gtttttgatt tgtcagctgt gcacaccatt tgcgacaaat 2400
tacactcaat tcttaggggt gagatggatc tctggtgtgg ctatgggagg aatttacgca 2460
tgtgcaagtg caacagctat cgaggatgct ccagttaagg caagatcttt cttatccggt 2520
ctattcttta ccgcatacgc aatggggttc attttcgcca ctgttttcta cagagcattc 2580
ttgaacatta atgggaagga ttattggaag atacagtttt ggttctctat atggttgcct 2640
gccgctctta tcttgtggag actagtatgg ccagaaacaa gatactttac aaaggttcta 2700
aaggctagac aactgatgct tgatgatgct attgcggcaa atggcgggca acctctacct 2760
aaaaagacat tccaggaaaa ggttaccaac gtcaaaaaga tcatatcaac ctactggctg 2820
ttattcacct acttgatact cttgcttgtc ggtcctaatt acctgactca cgcctctatg 2880
gacttgttcc caacaatgct tcgtgctcaa ttgaagtttt ccgaagatgc tgtaactgtt 2940
gcaatcgtgg tagtttgcat tggtgcaatt tgtggcggta tgtttttcgg tcaactaatg 3000
gaaataacag gtcgtagact aggattgttg atagccttgg tcatggcagg ctgttttact 3060
tatccagcat tcatgttgaa cactggtcct gccgttctcg gtggtggttt cttcctgtgg 3120
ttctctgtaa ttggcgtctg gggcgttatc cctatccact tgtccgaatt atcacctcca 3180
gaagcaagag ctttagtatc tggattagct taccaacttg gaaatctcgc gtcagctgcc 3240
tctgtcgtta tcgaatctga cttagctgat ctttacccaa tcgcgtggaa cgcagctggt 3300
gaggtgacaa acaaaaacta ctctaaggtt atggctattt tgacaggctc agtggtgatt 3360
ttcacctttg ttttagtctt agttggacat gaaaagttcc acagagattt aagttcccct 3420
cacttgaaag agtacacaga tagagttgat agagccgaag aggctgcagg catgggtagc 3480
tctgccgcat ctgtttcatc aaaaccagaa caaaacttcg ttgagaaggt gtgattaatt 3540
aatttaccag cttactatcc ttcttgaaaa tatgcactct atatctttta gttcttaatt 3600
gcaacacata gatttgctgt ataacgaatt ttatgctatt tttttaattt ggagttcggt 3660

```
gatgaaagtg tcacagcgaa tttcctcaca tgtagggacc gaattgttta caagttctct   3720

gtaccaccat ggagacatca aagattgaaa atctatggaa agatatggac ggtagcaaca   3780

agaatatagc acgagccgcg gagttcattt cgttactttt gatatcgctc acaactattg   3840

cgaagcgctt cagtgaaaaa atcataagga aaagttgtaa atattattgg tagtattcgt   3900

ttggtaaagt agagggggta atttttcccc tttattttgt tcatacattc ttaaattgct   3960

ttgcctctcc ttttggaaag ctatacttcg gagcactgtt gagcgaaggc tcaggccggc   4020

atatgacgtt ttattacctt tgatcacatt tccacgccat ttcgcattct caccctcata   4080

agtcatacac cgaaaagaaa gtttaaggga tcaatgagct tactataatc tcagtatatt   4140

tatttttatc gatgattcac cacaacaatc ttgctcccga aaagaaagca gacggagtag   4200

aagcatttga aactccttca gaccttcaag tatatatata tatatatata tatgtatatg   4260

tgtacatttt cacgctaata ctaatgtata attagaagat aatttttact catttttcgt   4320

tatcttcacg tcacccgaac ctagaaccaa atgtcatttt cacgatatgt aaatagtgaa   4380

ataggcaaaa acgccaaaaa gtagtaagcg caacatacac taaaccatta aagaatatct   4440

cgaccagaat ctaacagata tacatgttcc gataatgtct gagttaggtg agtattctaa   4500

attagaaaac aaagagctta gaacggagtt tgaattgaca aattttcctt ttccaggcac   4560

aactgataac gactccgatg acggaagcca agggcagaac tctttgaata tcattactcc   4620

tgacatggat gatactctgg ttaatgatgt acttcgagaa aacgataaaa agtctagtat   4680

gagaatggct tttatgaatc tagcaaactc tattcttggt gccggaataa ttactcagcc   4740

gttcgcgatc aaaaatgctg gtatattagg cgggctatta tcatacgtag ccctcggatt   4800

tatagttgat tggacgttaa gacttattgt cattaacttg actcttgctg gcaagagaac   4860

ataccagggt acggtcgaac atgtaatggg taaaaaaggg aaattgctga ttctatttac   4920

aaacgggtta tttgcatttg gtggatgtat tgg                                4953


<210> SEQ ID NO 76
<211> LENGTH: 606
<212> TYPE: PRT
<213> ORGANISM: Kluyveromyces dobzhanskii

<400> SEQUENCE: 76

Met His Thr Ile Ser Pro Glu Ser Asp Ser Leu Lys Ser Ser Lys Ser
1               5                   10                  15

Asn Thr Asn Ser His Glu Tyr Met Ser Ala Thr Thr Asp Tyr Asn Asn
            20                  25                  30

Gly Gly Ala Ser Ala Ala Pro Leu Ser Ala Lys Arg Lys Glu Thr Gly
        35                  40                  45

Asn Ser Tyr Glu Leu Gln Asp His Ala Ala Ser Ala Ser Ala Ser Ala
    50                  55                  60

Ser Ala Ser Ala Ser Ala Ser Ala Ser Ala Ser Ala Leu Ala Phe Asp
65                  70                  75                  80

Tyr Asp Pro Glu Asp Asp Asp Val Ser Ile Met Met Gln Asp Glu Glu
                85                  90                  95

Val Pro Asp Leu Thr Trp Lys His Val Ser Asn Tyr Ala Ile Thr Arg
            100                 105                 110

Phe Thr Ser Leu Ala His Ile His Pro Val Ser Met Gln Asn Ile Asn
        115                 120                 125

Pro Phe Pro Glu Leu Arg Lys Met Thr Leu His Asn Trp Asn Tyr Phe
    130                 135                 140
```

```
Phe Met Gly Tyr Gly Ala Trp Leu Cys Ala Ser Trp Ala Phe Phe Ala
145                 150                 155                 160

Val Ser Val Ser Thr Ala Pro Leu Ala Glu Leu Tyr Asp Lys Gln Thr
                165                 170                 175

Lys Asp Ile Ser Trp Gly Leu Ser Leu Val Leu Phe Val Arg Ser Ala
            180                 185                 190

Gly Ala Ile Ile Phe Gly Ile Trp Thr Asp Asn Tyr Ser Arg Lys Trp
        195                 200                 205

Pro Tyr Ile Thr Cys Leu Gly Leu Phe Leu Ile Cys Gln Leu Cys Thr
    210                 215                 220

Pro Phe Ala Thr Asn Tyr Thr Gln Phe Leu Gly Val Arg Trp Ile Ser
225                 230                 235                 240

Gly Val Ala Met Gly Gly Ile Tyr Ala Cys Ala Ser Ala Thr Ala Ile
                245                 250                 255

Glu Asp Ala Pro Val Lys Ala Arg Ser Phe Leu Ser Gly Leu Phe Phe
            260                 265                 270

Thr Ala Tyr Ala Met Gly Phe Ile Phe Ala Thr Val Phe Tyr Arg Ala
        275                 280                 285

Phe Leu Asn Ile Asn Gly Lys Asp Tyr Trp Lys Ile Gln Phe Trp Phe
    290                 295                 300

Ser Ile Trp Leu Pro Ala Ala Leu Ile Leu Trp Arg Leu Val Trp Pro
305                 310                 315                 320

Glu Thr Arg Tyr Phe Thr Lys Val Leu Lys Ala Arg Gln Leu Met Leu
                325                 330                 335

Asp Asp Ala Ile Ala Ala Asn Gly Gly Gln Pro Leu Pro Lys Lys Thr
            340                 345                 350

Phe Gln Glu Lys Val Thr Asn Val Lys Lys Ile Ile Ser Thr Tyr Trp
        355                 360                 365

Leu Leu Phe Thr Tyr Leu Ile Leu Leu Leu Val Gly Pro Asn Tyr Leu
    370                 375                 380

Thr His Ala Ser Met Asp Leu Phe Pro Thr Met Leu Arg Ala Gln Leu
385                 390                 395                 400

Lys Phe Ser Glu Asp Ala Val Thr Val Ala Ile Val Val Val Cys Ile
                405                 410                 415

Gly Ala Ile Cys Gly Gly Met Phe Phe Gly Gln Leu Met Glu Ile Thr
            420                 425                 430

Gly Arg Arg Leu Gly Leu Leu Ile Ala Leu Val Met Ala Gly Cys Phe
        435                 440                 445

Thr Tyr Pro Ala Phe Met Leu Asn Thr Gly Pro Ala Val Leu Gly Gly
    450                 455                 460

Gly Phe Phe Leu Trp Phe Ser Val Ile Gly Val Trp Gly Val Ile Pro
465                 470                 475                 480

Ile His Leu Ser Glu Leu Ser Pro Pro Glu Ala Arg Ala Leu Val Ser
                485                 490                 495

Gly Leu Ala Tyr Gln Leu Gly Asn Leu Ala Ser Ala Ala Ser Val Val
            500                 505                 510

Ile Glu Ser Asp Leu Ala Asp Leu Tyr Pro Ile Ala Trp Asn Ala Ala
        515                 520                 525

Gly Glu Val Thr Asn Lys Asn Tyr Ser Lys Val Met Ala Ile Leu Thr
    530                 535                 540

Gly Ser Val Val Ile Phe Thr Phe Val Leu Val Leu Val Gly His Glu
545                 550                 555                 560
```

-continued

```
Lys Phe His Arg Asp Leu Ser Ser Pro His Leu Lys Glu Tyr Thr Asp
                565                 570                 575

Arg Val Asp Arg Ala Glu Glu Ala Ala Gly Met Gly Ser Ser Ala Ala
            580                 585                 590

Ser Val Ser Ser Lys Pro Glu Gln Asn Phe Val Glu Lys Val
        595                 600                 605


<210> SEQ ID NO 77
<211> LENGTH: 4947
<212> TYPE: DNA
<213> ORGANISM: Artificial Sequence
<220> FEATURE:
<223> OTHER INFORMATION: Sequence put together from multiple organisms:
      Saccharomyces cerevisiae and Kluyveromyces marxianus.

<400> SEQUENCE: 77

tccatggagg gcacagttaa gccgctaaag gcattatccg ccaagtacaa tttttactc     60

ttcgaagaca gaaaatttgc tgacattggt aatacagtca aattgcagta ctctgcgggt    120

gtatacagaa tagcagaatg ggcagacatt acgaatgcac acggtgtggt gggcccaggt    180

attgttagcg gtttgaagca ggcggcggaa gaagtaacaa aggaacctag aggccttttg    240

atgttagcag aattgtcatg caagggctcc ctagctactg gagaatatac taagggtact    300

gttgacattg cgaagagcga caaagatttt gttatcggct ttattgctca aagagacatg    360

ggtggaagag atgaaggtta cgattggttg attatgacac ccggtgtggg tttagatgac    420

aagggagacg cattgggtca acagtataga accgtggatg atgtggtctc tacaggatct    480

gacattatta ttgttggaag aggactattt gcaaagggaa gggatgctaa ggtagagggt    540

gaacgttaca gaaaagcagg ctgggaagca tatttgagaa gatgcggcca gcaaaactaa    600

aaaactgtat tataagtaaa tgcatgtata ctaaactcac aaattagagc ttcaatttaa    660

ttatatcagt tattacccgg gaatctcggt cgtaatgatt tttataatga cgaaaaaaaa    720

aaaattggaa agaaaaagct tcatggcctt tataaaaagg aaccatccaa tacctcgcca    780

gaaccaagta acagtatttt acggggcaca aatcaagaac aataagacag gactgtaaag    840

atggacgcat tgaactccaa agaacaacaa gagttccaaa aagtagtgga acaaaagcaa    900

atgaaggatt tcatgcgttt gataacttcg tataatgtat gctatacgaa gttatctcga    960

gatctcccct aaaccgtgga atatttcgga tatccttttg ttgtttccgg gtgtacaata   1020

tggacttcct cttttctggc aaccaaaccc atacatcggg attcctataa taccttcgtt   1080

ggtctcccta acatgtaggt ggcggagggg agatatacaa tagaacagat accagacaag   1140

acataatggg ctaaacaaga ctacaccatt tacactgcct cattgatggt ggtacataac   1200

gaactaatac tgtagcccta gacttgatag ccatcatcat atcgaagttt cactaccctt   1260

tttccatttg ccatctattg aagtaataat aggcgcatgc aacttctttt tttttttttt   1320

ttttctctct cccccgttgt tgtctcacca tatccgcaat gacaaaaaaa tgatggaaga   1380

cactaaagga aaaaattaac gacaaagaca gcaccaacag atgtcgttgt tccagagctg   1440

atgaggggta tctcgaagca cacgaaactt tttccttcct tcattcacgc acactactct   1500

ctaatgagca acggtatacg gccttccttc cagttacttg aatttgaaat aaaaaaaagt   1560

ttgctgtctt gctatcaagt ataaatagac ctgcaattat taatcttttg tttcctcgtc   1620

attgttctcg ttccctttct tccttgtttc tttttctgca caatatttca agctatacca   1680

agcatacaat caactatctc atatacatct agaatgtccg aaggtaatga agagaaaggc   1740

caaggtcagg ggcagggtca agatcacgga cacttcccag aaggcagaac tttccttcac   1800
```

caagttgaga gtaagagatc tgttcataca catcatagtg tgcctatgaa ctcatcagat 1860
tcacaatcaa atgcgtcaga tcctgaggaa ttggcgccat ttccttctgt tgttgatgaa 1920
tcagaattag acgaatccga actagaggag atacaaaacg aagatgtctc tatcatttac 1980
aaagacgacg aagagaaacc agatttgagc tgggcatcaa tctgcagata cgctggtact 2040
cgtattactt ctttattcca aatccacaag gtgtctatgg ataacattaa tccattccct 2100
gaacttagaa agatgacatt gtccaattgg aactacttct tcatgggcta tttggcttgg 2160
ttgtgtgccg cctgggcctt cttcgctgtt tctgtatcta cagcaccatt agcaaagctc 2220
tatgacaaac caacaaagga catctcttgg ggtttatctc tagttctgtt cgtcagatct 2280
gctggggcta ttatctttgg actctggact gataactact ccagaaagtg gccatacatt 2340
acttgtctgg gcctattctt gatttgtcag ttgtgcacac catgggctaa aacctacaca 2400
caattcttag gcgtaagatg gatatcaggt atcgcaatgg gtggtatata cggttgtgct 2460
tctgccactg ccatagaaga tgcaccagtg aaggccagaa gtatcctctc aggtttgttc 2520
ttttcagcat acgcaatggg attcattttt gccatcatct tctatagagc attccttcat 2580
gttaatggag aaaactactg gaaggtccag ttttggtttt caatattctt gccagccctc 2640
ttgatgctat ggagattggt gtggccagag acaaagtact tcacaaaagt cttaaaggca 2700
agagagctaa tgaagcagga tgctattgca tctaacggtg ggaacccaat tcctaaaaca 2760
accttcaagg aaaagatggc aaacacaaag agaattatct gcaaatactg gcttttgttc 2820
ggatacttgg ttttgctgtt agtaggacca aactacttaa cccatggaag tcaagactta 2880
ttccctacta tgattcgttc tcaattgaat ttcagtgaag atgctgtcac agttgctatt 2940
gtagttgtta acttaggtgg catttgtggt gggcttttct ttggtcaact aatggaagta 3000
acaggtcgta gacttggact gttaattgcg ttgactatgg ctggttgctt tacctaccct 3060
gctttcatgt tgaaaacatc ttccgccgtc ttaggtgcag gctttatgct ctttttctca 3120
gtgtttggtg tgtggggcgt tatccctatc catctaagtg agctgtcacc accagaagcg 3180
agagcattgg tagctggttt agcttaccaa ctaggtaatc ttgcgtccgc cgcatctgtc 3240
gttatagaaa acgatttagc tgacatttac ccacttgcaa gagatgctgc tggtaaagtg 3300
atcaaaaagg actacgccaa ggtcatggca atcttgactg gttctgttgt catctttacc 3360
tttgttatgg ttctgattgg gcatgaaaag tttcacagag atttgtcaag cgcagtgcta 3420
aaggcatata tggaaaaggt tgatagaaac gaggaagatg ctagattggg cgtatcttct 3480
ctttctatta gctcaaagtc caaggaggaa caagttgaaa acgcatagtt aattaattta 3540
ccagcttact atccttcttg aaaatatgca ctctatatct tttagttctt aattgcaaca 3600
catagatttg ctgtataacg aattttatgc tattttttta atttggagtt cggtgatgaa 3660
agtgtcacag cgaatttcct cacatgtagg gaccgaattg tttacaagtt ctctgtacca 3720
ccatggagac atcaaagatt gaaaatctat ggaaagatat ggacggtagc aacaagaata 3780
tagcacgagc cgcggagttc atttcgttac ttttgatatc gctcacaact attgcgaagc 3840
gcttcagtga aaaaatcata aggaaaagtt gtaaatatta ttggtagtat tcgtttggta 3900
aagtagaggg ggtaattttt cccctttatt ttgttcatac attcttaaat tgctttgcct 3960
ctccttttgg aaagctatac ttcggagcac tgttgagcga aggctcaggc cggcatatga 4020
cgttttatta cctttgatca catttccacg ccatttcgca ttctcaccct cataagtcat 4080
acaccgaaaa gaaagtttaa gggatcaatg agcttactat aatctcagta tatttatttt 4140

-continued

```
tatcgatgat tcaccacaac aatcttgctc ccgaaaagaa agcagacgga gtagaagcat   4200

ttgaaactcc ttcagacctt caagtatata tatatatata tatatatgta tatgtgtaca   4260

ttttcacgct aatactaatg tataattaga agataatttt tactcatttt tcgttatctt   4320

cacgtcaccc gaacctagaa ccaaatgtca ttttcacgat atgtaaatag tgaaataggc   4380

aaaaacgcca aaaagtagta agcgcaacat acactaaacc attaaagaat atctcgacca   4440

gaatctaaca gatatacatg ttccgataat gtctgagtta ggtgagtatt ctaaattaga   4500

aaacaaagag cttagaacgg agtttgaatt gacaaatttt ccttttccag gcacaactga   4560

taacgactcc gatgacggaa gccaagggca gaactctttg aatatcatta ctcctgacat   4620

ggatgatact ctggttaatg atgtacttcg agaaaacgat aaaaagtcta gtatgagaat   4680

ggcttttatg aatctagcaa actctattct tggtgccgga ataattactc agccgttcgc   4740

gatcaaaaat gctggtatat taggcgggct attatcatac gtagccctcg gatttatagt   4800

tgattggacg ttaagactta ttgtcattaa cttgactctt gctggcaaga gaacatacca   4860

gggtacggtc gaacatgtaa tggtaaaaa agggaaattg ctgattctat ttacaaacgg   4920

gttatttgca tttggtggat gtattgg                                       4947
```

<210> SEQ ID NO 78
<211> LENGTH: 604
<212> TYPE: PRT
<213> ORGANISM: Kluyveromyces marxianus

<400> SEQUENCE: 78

```
Met Ser Glu Gly Asn Glu Glu Lys Gly Gln Gly Gln Gly Gln Gly Gln
1               5                   10                  15

Asp His Gly His Phe Pro Glu Gly Arg Thr Phe Leu His Gln Val Glu
            20                  25                  30

Ser Lys Arg Ser Val His Thr His His Ser Val Pro Met Asn Ser Ser
        35                  40                  45

Asp Ser Gln Ser Asn Ala Ser Asp Pro Glu Glu Leu Ala Pro Phe Pro
    50                  55                  60

Ser Val Val Asp Glu Ser Glu Leu Asp Glu Ser Glu Leu Glu Glu Ile
65                  70                  75                  80

Gln Asn Glu Asp Val Ser Ile Ile Tyr Lys Asp Asp Glu Glu Lys Pro
                85                  90                  95

Asp Leu Ser Trp Ala Ser Ile Cys Arg Tyr Ala Gly Thr Arg Ile Thr
            100                 105                 110

Ser Leu Phe Gln Ile His Lys Val Ser Met Asp Asn Ile Asn Pro Phe
        115                 120                 125

Pro Glu Leu Arg Lys Met Thr Leu Ser Asn Trp Asn Tyr Phe Phe Met
    130                 135                 140

Gly Tyr Leu Ala Trp Leu Cys Ala Ala Trp Ala Phe Phe Ala Val Ser
145                 150                 155                 160

Val Ser Thr Ala Pro Leu Ala Lys Leu Tyr Asp Lys Pro Thr Lys Asp
                165                 170                 175

Ile Ser Trp Gly Leu Ser Leu Val Leu Phe Val Arg Ser Ala Gly Ala
            180                 185                 190

Ile Ile Phe Gly Leu Trp Thr Asp Asn Tyr Ser Arg Lys Trp Pro Tyr
        195                 200                 205

Ile Thr Cys Leu Gly Leu Phe Leu Ile Cys Gln Leu Cys Thr Pro Trp
    210                 215                 220

Ala Lys Thr Tyr Thr Gln Phe Leu Gly Val Arg Trp Ile Ser Gly Ile
```

```
225                 230                 235                 240

Ala Met Gly Gly Ile Tyr Gly Cys Ala Ser Ala Thr Ala Ile Glu Asp
                245                 250                 255

Ala Pro Val Lys Ala Arg Ser Ile Leu Ser Gly Leu Phe Phe Ser Ala
            260                 265                 270

Tyr Ala Met Gly Phe Ile Phe Ala Ile Ile Phe Tyr Arg Ala Phe Leu
        275                 280                 285

His Val Asn Gly Glu Asn Tyr Trp Lys Val Gln Phe Trp Phe Ser Ile
    290                 295                 300

Phe Leu Pro Ala Leu Leu Met Leu Trp Arg Leu Val Trp Pro Glu Thr
305                 310                 315                 320

Lys Tyr Phe Thr Lys Val Leu Lys Ala Arg Glu Leu Met Lys Gln Asp
                325                 330                 335

Ala Ile Ala Ser Asn Gly Gly Asn Pro Ile Pro Lys Thr Thr Phe Lys
            340                 345                 350

Glu Lys Met Ala Asn Thr Lys Arg Ile Ile Cys Lys Tyr Trp Leu Leu
        355                 360                 365

Phe Gly Tyr Leu Val Leu Leu Leu Val Gly Pro Asn Tyr Leu Thr His
    370                 375                 380

Gly Ser Gln Asp Leu Phe Pro Thr Met Ile Arg Ser Gln Leu Asn Phe
385                 390                 395                 400

Ser Glu Asp Ala Val Thr Val Ala Ile Val Val Val Asn Leu Gly Gly
                405                 410                 415

Ile Cys Gly Gly Leu Phe Phe Gly Gln Leu Met Glu Val Thr Gly Arg
            420                 425                 430

Arg Leu Gly Leu Leu Ile Ala Leu Thr Met Ala Gly Cys Phe Thr Tyr
        435                 440                 445

Pro Ala Phe Met Leu Lys Thr Ser Ser Ala Val Leu Gly Ala Gly Phe
    450                 455                 460

Met Leu Phe Phe Ser Val Phe Gly Val Trp Gly Val Ile Pro Ile His
465                 470                 475                 480

Leu Ser Glu Leu Ser Pro Pro Glu Ala Arg Ala Leu Val Ala Gly Leu
                485                 490                 495

Ala Tyr Gln Leu Gly Asn Leu Ala Ser Ala Ala Ser Val Val Ile Glu
            500                 505                 510

Asn Asp Leu Ala Asp Ile Tyr Pro Leu Ala Arg Asp Ala Ala Gly Lys
        515                 520                 525

Val Ile Lys Lys Asp Tyr Ala Lys Val Met Ala Ile Leu Thr Gly Ser
    530                 535                 540

Val Val Ile Phe Thr Phe Val Met Val Leu Ile Gly His Glu Lys Phe
545                 550                 555                 560

His Arg Asp Leu Ser Ser Ala Val Leu Lys Ala Tyr Met Glu Lys Val
                565                 570                 575

Asp Arg Asn Glu Glu Asp Ala Arg Leu Gly Val Ser Ser Leu Ser Ile
            580                 585                 590

Ser Ser Lys Ser Lys Glu Glu Gln Val Glu Asn Ala
        595                 600
```

<210> SEQ ID NO 79
<211> LENGTH: 4707
<212> TYPE: DNA
<213> ORGANISM: Artificial Sequence
<220> FEATURE:
<223> OTHER INFORMATION: Sequence put together from multiple organisms:
      Saccharomyces cerevisiae and Yarrowia lipolytica.

<400> SEQUENCE: 79
tccatggagg gcacagttaa gccgctaaag gcattatccg ccaagtacaa tttttactc 60 ttcgaagaca gaaaatttgc tgacattggt aatacagtca aattgcagta ctctgcgggt 120
gtatacagaa tagcagaatg ggcagacatt acgaatgcac acggtgtggt gggcccaggt 180
attgttagcg gtttgaagca ggcggcggaa gaagtaacaa aggaacctag aggccttttg 240
atgttagcag aattgtcatg caagggctcc ctagctactg gagaatatac taagggtact 300
gttgacattg cgaagagcga caaagatttt gttatcggct ttattgctca aagagacatg 360
ggtggaagag atgaaggtta cgattggttg attatgacac ccggtgtggg tttagatgac 420
aagggagacg cattgggtca acagtataga accgtggatg atgtggtctc tacaggatct 480
gacattatta ttgttggaag aggactattt gcaaagggaa gggatgctaa ggtagagggt 540
gaacgttaca gaaaagcagg ctgggaagca tatttgagaa gatgcggcca gcaaaactaa 600
aaaactgtat tataagtaaa tgcatgtata ctaaactcac aaattagagc ttcaatttaa 660
ttatatcagt tattacccgg gaatctcggt cgtaatgatt tttataatga cgaaaaaaaa 720
aaaattggaa agaaaaagct tcatggcctt tataaaaagg aaccatccaa tacctcgcca 780
gaaccaagta acagtatttt acggggcaca aatcaagaac aataagacag gactgtaaag 840
atggacgcat tgaactccaa agaacaacaa gagttccaaa aagtagtgga acaaaagcaa 900
atgaaggatt tcatgcgttt gataacttcg tataatgtat gctatacgaa gttatctcga 960
gatctcccct aaaccgtgga atatttcgga tatccttttg ttgtttccgg gtgtacaata 1020
tggacttcct cttttctggc aaccaaaccc atacatcggg attcctataa taccttcgtt 1080
ggtctcccta acatgtaggt ggcggagggg agatatacaa tagaacagat accagacaag 1140
acataatggg ctaaacaaga ctacaccatt tacactgcct cattgatggt ggtacataac 1200
gaactaatac tgtagcccta gacttgatag ccatcatcat atcgaagttt cactaccctt 1260
tttccatttg ccatctattg aagtaataat aggcgcatgc aacttctttt tttttttttt 1320
ttttctctct cccccgttgt tgtctcacca tatccgcaat gacaaaaaaa tgatggaaga 1380
cactaaagga aaaaattaac gacaaagaca gcaccaacag atgtcgttgt tccagagctg 1440
atgaggggta tctcgaagca cacgaaactt tttccttcct tcattcacgc acactactct 1500
ctaatgagca acggtatacg gccttccttc cagttacttg aatttgaaat aaaaaaaagt 1560
ttgctgtctt gctatcaagt ataaatagac ctgcaattat taatcttttg tttcctcgtc 1620
attgttctcg ttccctttct tccttgtttc tttttctgca caatatttca agctatacca 1680
agcatacaat caactatctc atatacatct agaatggaag cgccaaatct ttcaccagct 1740
tcaattagaa gatacttcgc aacaagattg cctaccctta ttccacaaaa actaacacca 1800
gaagagaaaa agcttctcaa cccatttcca gcactagctt tgattaacaa aaagacctgg 1860
ctattcattg cctgtgcatt ctgtggttgg acttgggatg cctttgactt tttcagcgtc 1920
ggtctagttg ctccagaaat agcaaagtct ctaaatcgtt cagttaccga tattacttgg 1980
ggtattaccc tggtcttgat gttgcgttct attggagccg tggtatttgg tatcgcatcc 2040
gatagatatg ggagaaagtg gcctttcatc gttaacttac tatgctttat agctctggag 2100
ttgggttctg gcttcgtgca aacatacaag caattcttgg gcgttagagc aatttacggt 2160
atcgctatgg ggggactcta cggtaatgca gcagccactg cgttagagga ctgccctcca 2220
caagcaagag ggataatcag cggtttcctt caatccggat acgcattagg ttacctgtta 2280

-continued

```
tgtgttgtgt tcacaagagc tattgcggat acatccccat atggatggag agctttgttt   2340
tggttcggtt caggtcctcc agttttgttt atcattttca gatacttttt accagaaact   2400
gaaacttacc ttgcttcaaa ggccagtcag gaagaggccg gaatcgagaa aaagttctgg   2460
aacggcatta aggtaacttt caaaaactat tggttgatgt tcatctactt agttattctg   2520
atggctggtt tcaatttcat gagtcatggt tcccaagatt tgtacccaac aatgctcaaa   2580
aaccagagac atttttcagc cgacagatca acagtcacta attgtgtggc aaatttcgga   2640
gcaattgcag gcggcatgtt aattggtcat tttctaccg ctctcggtag acgtttgtct   2700
ataatgatct cttgtgttat aggtggtgct ttgatctacc cttgggcatt tgtcggtaac   2760
tccgctggga caaacgccgg agtattcttc ttacagttct ttgtccaagg tgcttggggg   2820
gttgttccaa tccacctatc agaattaagt ccacctgaat taagatcttc tatggtcgga   2880
atcgcttacc aaatgggtaa cttggcttct tctgcatcaa gtacaatcga atctaagata   2940
ggcgaaagat ttccattgaa aaatgctaag ggcgaattcg aaaaaggctt ctacgactac   3000
ggtaaggtta tggcaatctt catgggatgc gtattcgggt tcgttttgat tgttacattc   3060
gtaggaccag agaacagagg cgccactatg ttaacagagg atgcccaaat gatggttgat   3120
gctgaacata gacttgatgc ggaggagaag ggtgattttg aaaaccttga aagagttgac   3180
tctgaaggta agcagatgga taactttgtg gaagaggtgg cagaacctga aggtgtctac   3240
acaggctcac accctccaca atatgattca ccttacgaat ctaagtagtt aattaattta   3300
ccagcttact atccttcttg aaaatatgca ctctatatct tttagttctt aattgcaaca   3360
catagatttg ctgtataacg aattttatgc tattttttta atttggagtt cggtgatgaa   3420
agtgtcacag cgaatttcct cacatgtagg gaccgaattg tttacaagtt ctctgtacca   3480
ccatggagac atcaaagatt gaaaatctat ggaaagatat ggacggtagc aacaagaata   3540
tagcacgagc cgcggagttc atttcgttac ttttgatatc gctcacaact attgcgaagc   3600
gcttcagtga aaaaatcata aggaaaagtt gtaaatatta ttggtagtat tcgtttggta   3660
aagtagaggg ggtaattttt cccctttatt ttgttcatac attcttaaat tgctttgcct   3720
ctccttttgg aaagctatac ttcggagcac tgttgagcga aggctcaggc cggcatatga   3780
cgttttatta cctttgatca catttccacg ccatttcgca ttctcaccct cataagtcat   3840
acaccgaaaa gaaagtttaa gggatcaatg agcttactat aatctcagta tatttatttt   3900
tatcgatgat tcaccacaac aatcttgctc ccgaaaagaa agcagacgga gtagaagcat   3960
ttgaaactcc ttcagacctt caagtatata tatatatata tatatatgta tatgtgtaca   4020
ttttcacgct aatactaatg tataattaga agataatttt tactcatttt tcgttatctt   4080
cacgtcaccc gaacctagaa ccaaatgtca ttttcacgat atgtaaatag tgaaataggc   4140
aaaaacgcca aaaagtagta agcgcaacat acactaaacc attaaagaat atctcgacca   4200
gaatctaaca gatatacatg ttccgataat gtctgagtta ggtgagtatt ctaaattaga   4260
aaacaaagag cttagaacgg agtttgaatt gacaaatttt ccttttccag gcacaactga   4320
taacgactcc gatgacggaa gccaagggca gaactctttg aatatcatta ctcctgacat   4380
ggatgatact ctggttaatg atgtacttcg agaaaacgat aaaaagtcta gtatgagaat   4440
ggcttttatg aatctagcaa actctattct tggtgccgga ataattactc agccgttcgc   4500
gatcaaaaat gctggtatat taggcgggct attatcatac gtagccctcg gatttatagt   4560
tgattggacg ttaagactta ttgtcattaa cttgactctt gctggcaaga gaacatacca   4620
gggtacggtc gaacatgtaa tgggtaaaaa agggaaattg ctgattctat ttacaaacgg   4680
```

gttatttgca tttggtggat gtattgg 4707

<210> SEQ ID NO 80
<211> LENGTH: 7332
<212> TYPE: DNA
<213> ORGANISM: Saccharomyces cerevisiae

<400> SEQUENCE: 80
tcctattcgg agatacaggc aacaagtgat agagggccca ttatgaatac gcacctctat 60
gtatttccga gatacgatta ctccagttcc tcttacaaga aatgcataaa aatagttaca 120
attaattaga acaagaactt atttagaaca cgttcacact gagtaagaac tcttgtccct 180
tattagcctt gatagtgctg aaaaaaagaa aaaaaacaaa aaaaagaaat aaaataacgg 240
caaacagcaa aggccacaga accgtattca tgttacttct gcaatatcaa tcacttactg 300
gcaagtgcgt ataaattaaa cctatttctt tatcatcata tttacttata tctttaacag 360
attccaaacc ctaaagtgtc cgaattttca atagggcgaa cttgaagaat aaccaaggtc 420
aataatatat cttttagtat aaccctgaaa tttgccctat agaaatctag ggtttctgtg 480
tggtttccgg gtgagtcata cggctttttt gaatttcttt ttttgcagtt gtctctatca 540
atgaaaattt cgaggaagac gataaggtta agataagtag ataagagaat gatacgagat 600
aaagcacaaa ttagcagaaa gaagagtggt tgcgaacaga gtaaaccgaa tcagggaatc 660
cctttttgca aaaacatcaa ttatcctttt cttttttta cgtatatatc tggaacagaa 720
atatataagt tactattata cttatagttg gatccagttt ttaatctgtc gtcaatcgaa 780
agtttatttc agagttcttc agacttctta actcctgtaa aaacaaaaaa aaaaaaaggc 840
atagcactcg agtttaaacg gccagaaaaa ggaagtgttt ccctccttct tgaattgatg 900
ttaccctcat aaagcacgtg gcctcttatc gagaaagaaa ttaccgtcgc tcgtgatttg 960
tttgcaaaaa gaacaaaact gaaaaaaccc agacacgctc gacttcctgt cttcctgttg 1020
attgcagctt ccaatttcgt cacacaacaa ggtcctagcg acggctcaca ggttttgtaa 1080
caagcaatcg aaggttctgg aatggcggga aagggtttag taccacatgc tatgatgccc 1140
actgtgatct ccagagcaaa gttcgttcga tcgtactgtt actctctctc tttcaaacag 1200
aattgtccga atcgtgtgac aacaacagcc tgttctcaca cactcttttc ttctaaccaa 1260
gggggtggtt tagtttagta gaacctcgtg aaacttacat ttacatatat ataaacttgc 1320
ataaattggt caatgcaaga aatacatatt tggtcttttc taattcgtag tttttcaagt 1380
tcttagatgc tttctttttc tctttttac agatcatcaa ggaagtaatt atttttacaa 1440
gtctaggcta gcatgttgtg gaagcgtact tgcacaaggc taataaagcc tattgcacaa 1500
cctagaggaa ggctggtgag aagatcatgc tacagatacg cctcaacagg cacaggcagc 1560
accgacagca gcagtcagtg gttaaaatac tctgtcatcg cctcttcagc tactctattc 1620
ggttatttgt tcgctaagaa cctctattct agggagacta aggaggacct gatagagaaa 1680
ctggaaatgg tcaaaaagat cgacccagta aattctacgt taaagctgtc ctcattggac 1740
tcaccagact atttgcacga cccggccaag atcgataagg ttgttgagga cctgaagcag 1800
gtgctgggaa acaagcctga aaactactct gatgcgaaat ccgatttgga cgcccattca 1860
gatacctact tcaacacgca tcacccctct ctcgagcaaa gacctaggat tatattattc 1920
cctcatacta ccgaagaagt ttccaaaatt ttgaaaatat gtcacgataa caacatgcca 1980
gttgtaccct tctcgggcgg aacgtccttg gaggggcact tcctgcctac aagaattgga 2040
gataccataa ccgtagacct gtccaagttt atgaataacg tcgtaaaatt tgacaagctg 2100
gacctggaca tcaccgtgca ggccggtcta ccctgggagg atttgaatga ctatttgagc 2160
gaccacggtt tgatgtttgg ctgtgaccct ggtccaggtg cacagattgg tggttgcatt 2220
gctaattctt gttcaggaac caacgcctac cgttacggta ccatgaagga gaatattata 2280
aacatgacta tagtgttgcc ggacgggacc atcgtcaaga cgaagaaaag acccagaaag 2340
tcgagcgctg gctataactt aaatgggtta tttgtgggaa gtgaaggtac cttaggtatt 2400
gttactgaag ctactgtcaa gtgtcatgtc aagcccaaag ctgaaactgt tgcggtggta 2460
tcctttgata ctatcaagga tgcggccgca tgtgcttcta atctgactca gagtggtatt 2520
catttgaacg ccatggagtt actggatgaa aatatgatga agttgatcaa cgcatctgaa 2580
tccacggaca gatgtgattg ggtagagaaa ccaactatgt ttttcaagat tggtgggaga 2640
tctcccaaca ttgtcaatgc tcttgtggat gaagttaagg ctgtcgccca gttaaatcac 2700
tgcaacagtt ttcagtttgc taaagatgat gacgaaaaat tggaattatg ggaagctaga 2760
aaggtcgcgc tatggtctgt gctagacgct gataagagca aagacaaatc tgctaaaatt 2820
tggacaactg atgtagctgt tcctgtgtcg cagttcgaca aggttattca cgaaactaaa 2880
aaggacatgc aagctagtaa gctgatcaac gccattgttg gtcatgcagg tgatggtaac 2940
ttccatgcat tcatcgtcta cagaacccct gaagaacacg aaacctgtag ccaacttgtt 3000
gacagaatgg tcaagagagc actggacgca gaaggcactt gcacgggtga acacggtgtt 3060
ggtattggta aaagagagta cttgctcgaa gaattaggtg aagcacccgt cgatttgatg 3120
agaaagatta agctagctat tgacccaaag agaatcatga acccggacaa aatctttaaa 3180
actgatccaa acgagcccgc taatgattac aggtgagtcg actaagaagt tttgttaaaa 3240
ataaatcatt ttttaattga gcattcttat tcctatttta tttaaatagt tttatgtatt 3300
gttagctaca tacaacagtt taaatcaaat tttctttttc ccaagtccaa aatggaggtt 3360
tattttgatg acccgcatgc gattatgttt tgaaagtata agactacata catgtacata 3420
tatttaaaca tgtaaacccg tccattatat tgccgggcag accccgggtc gagatctccc 3480
gagatctccc gagtttatca ttatcaatac tgccatttca aagaatacgt aaataattaa 3540
tagtagtgat tttcctaact ttatttagtc aaaaaattgg ccttttaatt ctgctgtaac 3600
ccgtacatgc ccaaaatagg gggcgggtta cacagaatat ataacatcat aggtgtctgg 3660
gtgaacagtt tattcctggc atccactaaa tataatggag cccgcttttt ttaagctggc 3720
atccagaaaa aaaaagaatc ccagcaccaa aatattgttt tcttcaccaa ccatcagttc 3780
ataggtccat tctcttagcg caactacaca gaacaggggc acaaacaggc aaaaaacggg 3840
cacaacctca atggagtgat gcaacctgct tggagtaaat gatgacacaa ggcaattgac 3900
ctacgcatgt atctatctca ttttcttaca ccttctatta ccttctgctc tctctgattt 3960
ggaaaaagct gaaaaaaaag gttgaaacca gttccctgaa attattcccc tatttgacta 4020
ataagtatat aaagacggta ggtattgatt gtaattctgt aaatctattt cttaaacttc 4080
ttaaattcta cttttatagt tagtcttttt tttagtttaa aacaccaaga acttagtttc 4140
gaataaacac acataaacaa acaaatctag aatgctaaaa tacaaacctt tactaaaaat 4200
ctcgaagaac tgtgaggctg ctatcctcag agcgtctaag actagattga acacaatccg 4260
cgcgtacggt tctaccgttc caaaatccaa gtcgttcgaa caagactcaa gaaaacgcac 4320
acagtcatgg actgccttga gagtcggtgc aattctagcc gctactagtt ccgtggcgta 4380
tctaaactgg cataatggcc aaatagacaa cgagccgaaa ctggatatga ataaacaaaa 4440
gatttcgccc gctgaagttg ccaagcataa caagcccgat gattgttggg ttgtgatcaa 4500
tggttacgta tacgacttaa cgcgattcct accaaatcat ccaggtgggc aggatgttat 4560
caagtttaac gccgggaaag atgtcactgc tatttttgaa ccactacatg ctcctaatgt 4620
catcgataag tatatagctc ccgagaaaaa attgggtccc cttcaaggat ccatgcctcc 4680
tgaacttgtc tgtcctcctt atgctcctgg tgaaactaag gaagatatcg ctagaaaaga 4740
acaactaaaa tcgctgctac ctcctctaga taatattatt aacctttacg actttgaata 4800
cttggcctct caaactttga ctaaacaagc gtgggcctac tattcctccg gtgctaacga 4860
cgaagttact cacagagaaa accataatgc ttatcatagg attttttca aaccaaagat 4920 ccttgtagat gtacgcaaag tagacatttc aactgacatg ttgggttctc atgtggatgt 4980
tcccttctac gtgtctgcta cagctttgtg taaactggga aaccccttag aaggtgaaaa 5040
agatgtcgcc agaggttgtg gccaaggtgt gacaaaagtc ccacaaatga tatctacttt 5100
ggcttcatgt tcccctgagg aaattattga agcagcaccc tctgataaac aaattcaatg 5160
gtaccaacta tatgttaact ctgatagaaa gatcactgat gatttggtta aaaatgtaga 5220
aaagctgggt gtaaaggcat tatttgtcac tgtggatgct ccaagtttag gtcaaagaga 5280
aaaagatatg aagctgaaat tttccaatac aaaggctggt ccaaaagcga tgaagaaaac 5340
taatgtagaa gaatctcaag gtgcttcgag agcgttatca aagtttattg acccctcttt 5400
gacttggaaa gatatagaag agttgaagaa aaagacaaaa ctacctattg ttatcaaagg 5460
tgttcaacgt accgaagatg ttatcaaagc agcagaaatc ggtgtaagtg gggtggttct 5520
atccaatcat ggtggtagac aattagattt ttcaagggct cccattgaag tcctggctga 5580
aaccatgcca atcctggaac aacgtaactt gaaggataag ttggaagttt tcgtggacgg 5640
tggtgttcgt cgtggtacag atgtcttgaa agcgttatgt ctaggtgcta aaggtgttgg 5700
tttgggtaga ccattcttgt atgcgaactc atgctatggt cgtaatggtg ttgaaaaagc 5760
cattgaaatt ttaagagatg aaattgaaat gtctatgaga ctattaggtg ttactagcat 5820
tgcggaattg aagcctgatc ttttagatct atcaacacta aaggcaagaa cagttggagt 5880
accaaacgac gtgctgtata atgaagttta tgagggacct actttaacag aatttgagga 5940
tgcatgatta attaaacagg ccccttttcc tttgtcgata tcatgtaatt agttatgtca 6000
cgcttacatt cacgccctcc tcccacatcc gctctaaccg aaaaggaagg agttagacaa 6060
cctgaagtct aggtccctat ttattttttt atagttatgt tagtattaag aacgttattt 6120
atatttcaaa tttttctttt ttttctgtac aaacgcgtgt acgcatgtaa cgggcagacg 6180
gccggccata acttcgtata atgtatgcta tacgaagtta tggcaacggt tcatcatctc 6240
atggatctgc acatgaacaa acaccagagt caaacgacgt tgaaattgag gctactgcgc 6300
caattgatga caatacagac gatgataaca aaccgaagtt atctgatgta gaaaaggatt 6360
agagatgcta agagatagtg atgatatttc ataaataatg taattctata tatgttaatt 6420
accttttttg cgaggcatat ttatggtgaa ggataagttt tgaccatcaa agaaggttaa 6480
tgtggctgtg gtttcagggt ccataaagct tttcaattca tcttttttttt ttttgttctt 6540 tttttgatt ccggtttctt tgaaattttt ttgattcggt aatctccgag cagaaggaag 6600
aacgaaggaa ggagcacaga cttagattgg tatatatacg catatgtggt gttgaagaaa 6660
catgaaattg cccagtattc ttaacccaac tgcacagaac aaaaacctgc aggaaacgaa 6720
gataaatcat gtcgaaagct acatataagg aacgtgctgc tactcatcct agtcctgttg 6780

```
ctgccaagct atttaatatc atgcacgaaa agcaaacaaa cttgtgtgct tcattggatg   6840
ttcgtaccac caaggaatta ctggagttag ttgaagcatt aggtcccaaa atttgtttac   6900
taaaaacaca tgtggatatc ttgactgatt tttccatgga gggcacagtt aagccgctaa   6960
aggcattatc cgccaagtac aattttttac tcttcgaaga cagaaaattt gctgacattg   7020
gtaatacagt caaattgcag tactctgcgg gtgtatacag aatagcagaa tgggcagaca   7080
ttacgaatgc acacggtgtg gtgggcccag gtattgttag cggtttgaag caggcggcgg   7140
aagaagtaac aaaggaacct agaggccttt tgatgttagc agaattgtca tgcaagggct   7200
ccctagctac tggagaatat actaagggta ctgttgacat tgcgaagagc gacaaagatt   7260
ttgttatcgg ctttattgct caaagagaca tgggtggaag agatgaaggt tacgattggt   7320
tgattatgac ac                                                       7332
```

<210> SEQ ID NO 81
<211> LENGTH: 7717
<212> TYPE: DNA
<213> ORGANISM: Artificial Sequence
<220> FEATURE:
<223> OTHER INFORMATION: Sequence put together from multiple organisms: Saccharomyces cerevisiae and Aspergillus nidulans

<400> SEQUENCE: 81

```
tcctattcgg agatacaggc aacaagtgat agagggccca ttatgaatac gcacctctat     60
gtatttccga gatacgatta ctccagttcc tcttacaaga aatgcataaa aatagttaca    120
attaattaga acaagaactt atttagaaca cgttcacact gagtaagaac tcttgtccct    180
tattagcctt gatagtgctg aaaaaaagaa aaaaaacaaa aaaaagaaat aaaataacgg    240
caaacagcaa aggccacaga accgtattca tgttacttct gcaatatcaa tcacttactg    300
gcaagtgcgt ataaattaaa cctatttctt tatcatcata tttacttata tctttaacag    360
attccaaacc ctaaagtgtc cgaattttca atagggcgaa cttgaagaat aaccaaggtc    420
aataatatat cttttagtat aaccctgaaa tttgccctat agaaatctag ggtttctgtg    480
tggtttccgg gtgagtcata cggctttttt gaatttcttt ttttgcagtt gtctctatca    540
atgaaaattt cgaggaagac gataaggtta agataagtag ataagagaat gatacgagat    600
aaagcacaaa ttagcagaaa gaagagtggt tgcgaacaga gtaaaccgaa tcagggaatc    660
ccttttttgca aaaacatcaa ttatcctttt ctttttttta cgtatatatc tggaacagaa    720
atatataagt tactattata cttatagttg gatccagttt ttaatctgtc gtcaatcgaa    780
agtttatttc agagttcttc agacttctta actcctgtaa aaacaaaaaa aaaaaaaggc    840
atagcactcg agtttaaacg gccagaaaaa ggaagtgttt ccctccttct tgaattgatg    900
ttaccctcat aaagcacgtg gcctcttatc gagaaagaaa ttaccgtcgc tcgtgatttg    960
tttgcaaaaa gaacaaaact gaaaaaaccc agacacgctc gacttcctgt cttcctgttg   1020
attgcagctt ccaatttcgt cacacaacaa ggtcctagcg acggctcaca ggttttgtaa   1080
caagcaatcg aaggttctgg aatggcggga aagggtttag taccacatgc tatgatgccc   1140
actgtgatct ccagagcaaa gttcgttcga tcgtactgtt actctctctc tttcaaacag   1200
aattgtccga atcgtgtgac aacaacagcc tgttctcaca cactcttttc ttctaaccaa   1260
gggggtggtt tagtttagta gaacctcgtg aaacttacat ttacatatat ataaacttgc   1320
ataaattggt caatgcaaga aatacatatt tggtcttttc taattcgtag tttttcaagt   1380
tcttagatgc tttctttttc tctttttac agatcatcaa ggaagtaatt atttttacaa    1440
```

-continued

```
gtctaggcta gcatgttgtg gaagcgtact tgcacaaggc taataaagcc tattgcacaa   1500
cctagaggaa ggctggtgag aagatcatgc tacagatacg cctcaacagg cacaggcagc   1560
accgacagca gcagtcagtg gttaaaatac tctgtcatcg cctcttcagc tactctattc   1620
ggttatttgt tcgctaagaa cctctattct agggagacta aggaggacct gatagagaaa   1680
ctggaaatgg tcaaaaagat cgacccagta aattctacgt taaagctgtc ctcattggac   1740
tcaccagact atttgcacga cccggccaag atcgataagg ttgttgagga cctgaagcag   1800
gtgctgggaa acaagcctga aaactactct gatgcgaaat ccgatttgga cgcccattca   1860
gatacctact tcaacacgca tcacccctct ctcgagcaaa gacctaggat tatattattc   1920
cctcatacta ccgaagaagt ttccaaaatt ttgaaaatat gtcacgataa caacatgcca   1980
gttgtaccct tctcgggcgg aacgtccttg gaggggcact tcctgcctac aagaattgga   2040
gataccataa ccgtagacct gtccaagttt atgaataacg tcgtaaaatt tgacaagctg   2100
gacctggaca tcaccgtgca ggccggtcta ccctgggagg atttgaatga ctatttgagc   2160
gaccacggtt tgatgtttgg ctgtgaccct ggtccaggtg cacagattgg tggttgcatt   2220
gctaattctt gttcaggaac caacgcctac cgttacggta ccatgaagga gaatattata   2280
aacatgacta tagtgttgcc ggacgggacc atcgtcaaga cgaagaaaag acccagaaag   2340
tcgagcgctg gctataactt aaatgggtta tttgtgggaa gtgaaggtac cttaggtatt   2400
gttactgaag ctactgtcaa gtgtcatgtc aagcccaaag ctgaaactgt tgcggtggta   2460
tcctttgata ctatcaagga tgcggccgca tgtgcttcta atctgactca gagtggtatt   2520
catttgaacg ccatggagtt actggatgaa aatatgatga agttgatcaa cgcatctgaa   2580
tccacggaca gatgtgattg ggtagagaaa ccaactatgt ttttcaagat tggtgggaga   2640
tctcccaaca ttgtcaatgc tcttgtggat gaagttaagg ctgtcgccca gttaaatcac   2700
tgcaacagtt ttcagtttgc taaagatgat gacgaaaaat tggaattatg ggaagctaga   2760
aaggtcgcgc tatggtctgt gctagacgct gataagagca aagacaaatc tgctaaaatt   2820
tggacaactg atgtagctgt tcctgtgtcg cagttcgaca aggttattca cgaaactaaa   2880
aaggacatgc aagctagtaa gctgatcaac gccattgttg gtcatgcagg tgatggtaac   2940
ttccatgcat tcatcgtcta cagaacccct gaagaacacg aaacctgtag ccaacttgtt   3000
gacagaatgg tcaagagagc actggacgca gaaggcactt gcacgggtga acacggtgtt   3060
ggtattggta aaagagagta cttgctcgaa gaattaggtg aagcacccgt cgatttgatg   3120
agaaagatta agctagctat tgacccaaag agaatcatga acccggacaa aatctttaaa   3180
actgatccaa acgagcccgc taatgattac aggtgagtcg actaagaagt tttgttaaaa   3240
ataaatcatt ttttaattga gcattcttat tcctatttta tttaaatagt tttatgtatt   3300
gttagctaca tacaacagtt taaatcaaat ttttcttttc ccaagtccaa aatggaggtt   3360
tattttgatg acccgcatgc gattatgttt tgaaagtata agactacata catgtacata   3420
tatttaaaca tgtaaacccg tccattatat tgccgggcag accccgggtc gagatctccc   3480
gagatctccc gagtttatca ttatcaatac tgccatttca aagaatacgt aaataattaa   3540
tagtagtgat ttcctaact  ttatttagtc aaaaaattgg ccttttaatt ctgctgtaac   3600
ccgtacatgc ccaaaatagg gggcgggtta cacagaatat ataacatcat aggtgtctgg   3660
gtgaacagtt tattcctggc atccactaaa tataatggag cccgcttttt ttaagctggc   3720
atccagaaaa aaaaagaatc ccagcaccaa aatattgttt tcttcaccaa ccatcagttc   3780
ataggtccat tctcttagcg caactacaca gaacaggggc acaaacaggc aaaaaacggg   3840
```

```
cacaacctca atggagtgat gcaacctgct tggagtaaat gatgacacaa ggcaattgac   3900
ctacgcatgt atctatctca ttttcttaca ccttctatta ccttctgctc tctctgattt   3960
ggaaaaagct gaaaaaaaag gttgaaacca gttccctgaa attattcccc tatttgacta   4020
ataagtatat aaagacggta ggtattgatt gtaattctgt aaatctattt cttaaacttc   4080
ttaaattcta cttttatagt tagtcttttt tttagtttaa aacaccaaga acttagtttc   4140
gaataaacac acataaacaa acaaatctag aatgctaaaa tacaaacctt tactaaaaat   4200
ctcgaagaac tgtgaggctg ctatcctcag agcgtctaag actagattga acacaatccg   4260
cgcgtacggt tctaccgttc caaaatccaa gtcgttcgaa caagactcaa gaaaacgcac   4320
acagtcatgg actgccttga gagtcggtgc aattctagcc gctactagtt ccgtggcgta   4380
tctaaactgg cataatggcc aaatagacaa cgagccgaaa ctggatatga ataaacaaaa   4440
gatttcgccc gctgaagttg ccaagcataa caagcccgat gattgttggg ttgtgatcaa   4500
tggttacgta tacgacttaa cgcgattcct accaaatcat ccaggtgggc aggatgttat   4560
caagtttaac gccgggaaag atgtcactgc tatttttgaa ccactacatg ctcctaatgt   4620
catcgataag tatatagctc ccgagaaaaa attgggtccc cttcaaggat ccatgcctcc   4680
tgaacttgtc tgtcctcctt atgctcctgg tgaaactaag gaagatatcg ctagaaaaga   4740
acaactaaaa tcgctgctac ctcctctaga taatattatt aacctttacg actttgaata   4800
cttggcctct caaactttga ctaaacaagc gtgggcctac tattcctccg gtgctaacga   4860
cgaagttact cacagagaaa accataatgc ttatcatagg atttttttca aaccaaagat   4920
ccttgtagat gtacgcaaag tagacatttc aactgacatg ttgggttctc atgtggatgt   4980
tcccttctac gtgtctgcta cagctttgtg taaactggga aaccccttag aaggtgaaaa   5040
agatgtcgcc agaggttgtg gccaaggtgt gacaaaagtc ccacaaatga tatctacttt   5100
ggcttcatgt tcccctgagg aaattattga agcagcaccc tctgataaac aaattcaatg   5160
gtaccaacta tatgttaact ctgatagaaa gatcactgat gatttggtta aaaatgtaga   5220
aaagctgggt gtaaaggcat tatttgtcac tgtggatgct ccaagtttag gtcaaagaga   5280
aaaagatatg aagctgaaat tttccaatac aaaggctggt ccaaaagcga tgaagaaaac   5340
taatgtagaa gaatctcaag gtgcttcgag agcgttatca aagtttattg acccctcttt   5400
gacttggaaa gatatagaag agttgaagaa aaagacaaaa ctacctattg ttatcaaagg   5460
tgttcaacgt accgaagatg ttatcaaagc agcagaaatc ggtgtaagtg ggggtggttct   5520
atccaatcat ggtggtagac aattagattt ttcaagggct cccattgaag tcctggctga   5580
aaccatgcca atcctggaac aacgtaactt gaaggataag ttggaagttt tcgtggacgg   5640
tggtgttcgt cgtggtacag atgtcttgaa agcgttatgt ctaggtgcta aaggtgttgg   5700
tttgggtaga ccattcttgt atgcgaactc atgctatggt cgtaatggtg ttgaaaaagc   5760
cattgaaatt ttaagagatg aaattgaaat gtctatgaga ctattaggtg ttactagcat   5820
tgcggaattg aagcctgatc ttttagatct atcaacacta aaggcaagaa cagttggagt   5880
accaaacgac gtgctgtata atgaagttta tgagggacct actttaacag aatttgagga   5940
tgcatgatta attaaacagg cccctttcc tttgtcgata tcatgtaatt agttatgtca   6000
cgcttacatt cacgccctcc tcccacatcc gctctaaccg aaaaggaagg agttagacaa   6060
cctgaagtct aggtccctat ttattttttt atagttatgt tagtattaag aacgttattt   6120
atatttcaaa tttttctttt ttttctgtac aaacgcgtgt acgcatgtaa cgggcagacg   6180
```

gccggccata acttcgtata atgtatgcta tacgaagtta tccttacatc acacccaatc 6240
ccccacaagt gatcccccac acaccatagc ttcaaaatgt ttctactcct tttttactct 6300
tccagatttt ctcggactcc gcgcatcgcc gtaccacttc aaaacaccca agcacagcat 6360
actaaatttc ccctctttct tcctctaggg tggcgttaat tacccgtact aaaggtttgg 6420
aaaagaaaaa agagaccgcc tcgtttcttt ttcttcgtcg aaaaaggcaa taaaaatttt 6480
tatcacgttt ctttttcttg aaaaattttt tttttgattt ttttctcttt cgatgacctc 6540
ccattgatat ttaagttaat aaatggtctt caatttctca agtttcagtt tcgtttttct 6600
tgttctatta caactttttt tacttcttgc tcattagaaa gaaagcatag caatctaatc 6660
taagttttaa ttacaaaatg ccacaatcct gggaagaatt ggccgccgac aaacgtgccc 6720
gtttggctaa aaccattcct gacgaatgga aggttcaaac tttgcctgcc gaagattccg 6780
ttattgattt cccaaagaag tccggtattt tgtctgaggc tgaattgaag attaccgaag 6840
cctctgctgc tgatttggtc tccaagttgg ccgctggtga gttgacttct gttgaagtca 6900
ctttggcttt ttgtaagaga gctgctattg ctcaacaatt aaccaactgt gctcacgaat 6960
tcttcccaga tgctgcttta gctcaagcta gagaattaga tgaatactac gctaagcata 7020
agagaccagt tggtccatta cacggtttac caatctcttt aaaggaccaa ttgcgtgtta 7080
agggttacga aacctccatg ggttacattt cctggttaaa caaatacgat gaaggtgatt 7140
ccgtcttaac caccatgttg agaaaagctg gtgctgtttt ctacgttaag acctctgtcc 7200
cacaaacctt gatggtctgt gaaaccgtca acaacatcat tggtagaact gtcaatccaa 7260
gaaacaaaaa ttggtcctgt ggtggttctt ctggtggtga aggtgctatt gttggtatta 7320
gaggtggtgt tattggtgtc ggtactgaca ttggtggttc cattagagtc ccagctgctt 7380
tcaacttttt atacggtttg agaccatctc acggtagatt gccatatgct aaaatggcta 7440
actctatgga aggtcaagaa accgttcact ccgtcgttgg tcctatcact cactccgtcg 7500
aagacttgag attgttcacc aaatctgtct tgggtcaaga accttggaag tacgactcta 7560
aggtcatccc catgccatgg agacaatctg aatctgacat cattgcctct aagattaaga 7620
atggtggttt gaacattggt tattacaatt tcgacggtaa cgtcttgcca cacccaccaa 7680
ttttacgtgg tgtcgaaact accgttgccg ctttggc 7717

<210> SEQ ID NO 82
<211> LENGTH: 4983
<212> TYPE: DNA
<213> ORGANISM: Artificial Sequence
<220> FEATURE:
<223> OTHER INFORMATION: Sequence put together from multiple organisms: Saccharomyces cerevisiae and Saccharomyces bayanus

<400> SEQUENCE: 82
tccatggagg gcacagttaa gccgctaaag gcattatccg ccaagtacaa tttttttactc 60 ttcgaagaca gaaaatttgc tgacattggt aatacagtca aattgcagta ctctgcgggt 120
gtatacagaa tagcagaatg ggcagacatt acgaatgcac acggtgtggt gggcccaggt 180
attgttagcg gtttgaagca ggcggcggaa gaagtaacaa aggaacctag aggccttttg 240
atgttagcag aattgtcatg caagggctcc ctagctactg gagaatatac taagggtact 300
gttgacattg cgaagagcga caaagatttt gttatcggct ttattgctca aagagacatg 360
ggtggaagag atgaaggtta cgattggttg attatgacac ccggtgtggg tttagatgac 420
aagggagacg cattgggtca acagtataga accgtggatg atgtggtctc tacaggatct 480

-continued

```
gacattatta ttgttggaag aggactattt gcaaagggaa gggatgctaa ggtagagggt    540
gaacgttaca gaaaagcagg ctgggaagca tatttgagaa gatgcggcca gcaaaactaa    600
aaaactgtat tataagtaaa tgcatgtata ctaaactcac aaattagagc ttcaatttaa    660
ttatatcagt tattacccgg gaatctcggt cgtaatgatt tttataatga cgaaaaaaaa    720
aaaattggaa agaaaaagct tcatggcctt tataaaaagg aaccatccaa tacctcgcca    780
gaaccaagta acagtatttt acggggcaca aatcaagaac aataagacag gactgtaaag    840
atggacgcat tgaactccaa agaacaacaa gagttccaaa aagtagtgga acaaaagcaa    900
atgaaggatt tcatgcgttt gataacttcg tataatgtat gctatacgaa gttatctcga    960
gatctcccct aaaccgtgga atatttcgga tatcctttg ttgtttccgg gtgtacaata   1020
tggacttcct cttttctggc aaccaaaccc atacatcggg attcctataa taccttcgtt   1080
ggtctcccta acatgtaggt ggcggagggg agatatacaa tagaacagat accagacaag   1140
acataatggg ctaaacaaga ctacaccatt tacactgcct cattgatggt ggtacataac   1200
gaactaatac tgtagcccta gacttgatag ccatcatcat atcgaagttt cactaccctt   1260
tttccatttg ccatctattg aagtaataat aggcgcatgc aacttctttt tttttttttt   1320
ttttctctct cccccgttgt tgtctcacca tatccgcaat gacaaaaaaa tgatggaaga   1380
cactaaagga aaaaattaac gacaaagaca gcaccaacag atgtcgttgt tccagagctg   1440
atgaggggta tctcgaagca cacgaaactt tttccttcct tcattcacgc acactactct   1500
ctaatgagca acggtatacg gccttccttc cagttacttg aatttgaaat aaaaaaaagt   1560
ttgctgtctt gctatcaagt ataaatagac ctgcaattat taatcttttg tttcctcgtc   1620
attgttctcg ttccctttct tccttgtttc tttttctgca caatatttca agctatacca   1680
agcatacaat caactatctc atatacatct agaatgtcgt caacaacaga ggacaaaaat   1740
tccaatgaac aacagcaacc cgctgccaga aagctatact acaacacaag cacgtttgcc   1800
gagccacccc tggtcgatga agccggtaac cccataaact acgaaccgga agtctacaac   1860
ccggaccacg aaaagctgta ccacaatcca tcgctgcccg tgacctcaat tcaggacact   1920
agagatgacg agttactgga aagagtttac agtgtcgacc aagaagtaga atacgaagag   1980
gacgaagcag acaaaccgaa tctgagtctc gcatccataa aaaattatgc tttgacaaga   2040
ttcacgtctt tgttgcgcgt tcacgaggtc tccttgacaa acatcaaccc gatcccggaa   2100
ttgaggaaga tgacgttgca aaattggaac tattttttca tggggtattt agcctggttg   2160
acagccgcct ggtgtttctt ttgtgtttca gtgtcagtag ctccgctatc tgaactgtat   2220
gatagaccca ccaaggatat aacctggggg ttggggctgg tgttgttcgt tcgctcagcc   2280
ggtgcgatta tattcggttt atggacagat aaggcttcca gaaaatggcc ctacatcacc   2340
tgtttgtttt tatttgtcat tgcgcagctt tgtactccat ggtgtgacac ttaccaaaaa   2400
tttctgggcg ttagatggat tacaggtata gccatgggtg ggatttatgg gtgtgcttct   2460
gcaacagcca tagaagatgc tccagtgaaa gcacgttcat tcctatcagg tctctttttt   2520
tctgcatatg ccatggggtt tatcttcgca atcatttttt acagagcctt tggctacttc   2580
agggaagacg gctggaaaat attgttctgg tttagcattt tcttaccaat cttactaatt   2640
ttctggagat tactatggcc tgaaacaaaa tatttcacca aagtcttgaa ggctcgtaga   2700
ctaatactaa gtgacgctgt gaaagccaac ggtggcgaac ctctgcccaa ggccaatttc   2760
aaacaaaaga tggtgtctgt gaaaaaaact gtacaaaaat actggctgtt gtttgcctat   2820
ctagtcatta tgttggttgg tccaaattac ttgacccacg cctctcagga tttgttgcca   2880
```

```
accatgctgc gtgcccaact agggttgtcc aaggatgccg tcactgttat tgtggttgtc   2940
accaacatcg gtgctatctg tggtggtatg atatttggtc aactaatgga agttactggt   3000
agaagattag gcctgttgat tgcgtgcgta atgggaggtt gttttaccta tcctgcattt   3060
atgttgagaa gcgagaaagc tattctggga gctggattca tgttatactt ttgtgtgttt   3120
ggtgtctggg gtattttgcc aatccacctg gctgaactgg ctcctgccga cgcaagggct   3180
ttggtcgctg gtttatccta ccaattgggt aatttggcct cagcagcagc ctctacaatt   3240
gagacggaat tagcaggaaa gtatccatta gaggtggatt cctctggtac cgttataaag   3300
gaagattacg cgaaagttat ggccatccta actggggccg ttttcatctt tactttttgt   3360
tgtgtctttg tagggcatga aaaattccat cgcgatctat cttctccagt tatgaagaaa   3420
tacataactc aagtggaagt ttacgaagct gatggtgttt caatcagtga aattgtggaa   3480
caaaagacag aatacggttc tgtgcaaatg gttgattcca atatctcaaa gacatttgaa   3540
gaacatgttg aaactgtttg attattaatt aatttaccag cttactatcc ttcttgaaaa   3600
tatgcactct atatctttta gttcttaatt gcaacacata gatttgctgt ataacgaatt   3660
ttatgctatt tttttaattt ggagttcggt gatgaaagtg tcacagcgaa tttcctcaca   3720
tgtagggacc gaattgttta caagttctct gtaccaccat ggagacatca aagattgaaa   3780
atctatggaa agatatggac ggtagcaaca agaatatagc acgagccgcg gagttcattt   3840
cgttactttt gatatcgctc acaactattg cgaagcgctt cagtgaaaaa atcataagga   3900
aaagttgtaa atattattgg tagtattcgt ttggtaaagt agagggggta atttttcccc   3960
tttattttgt tcatacattc ttaaattgct ttgcctctcc ttttggaaag ctatacttcg   4020
gagcactgtt gagcgaaggc tcaggccggc atatgacgtt ttattacctt tgatcacatt   4080
tccacgccat ttcgcattct caccctcata agtcatacac cgaaaagaaa gtttaaggga   4140
tcaatgagct tactataatc tcagtatatt tatttttatc gatgattcac cacaacaatc   4200
ttgctcccga aaagaaagca gacggagtag aagcatttga aactccttca gaccttcaag   4260
tatatatata tatatatata tatgtatatg tgtacatttt cacgctaata ctaatgtata   4320
attagaagat aatttttact catttttcgt tatcttcacg tcacccgaac ctagaaccaa   4380
atgtcatttt cacgatatgt aaatagtgaa ataggcaaaa acgccaaaaa gtagtaagcg   4440
caacatacac taaaccatta aagaatatct cgaccagaat ctaacagata tacatgttcc   4500
gataatgtct gagttaggtg agtattctaa attagaaaac aaagagctta gaacggagtt   4560
tgaattgaca aattttcctt ttccaggcac aactgataac gactccgatg acggaagcca   4620
agggcagaac tctttgaata tcattactcc tgacatggat gatactctgg ttaatgatgt   4680
acttcgagaa aacgataaaa agtctagtat gagaatggct tttatgaatc tagcaaactc   4740
tattcttggt gccggaataa ttactcagcc gttcgcgatc aaaaatgctg gtatattagg   4800
cgggctatta tcatacgtag ccctcggatt tatagttgat tggacgttaa gacttattgt   4860
cattaacttg actcttgctg gcaagagaac ataccagggt acggtcgaac atgtaatggg   4920
taaaaaaggg aaattgctga ttctatttac aaacgggtta tttgcatttg gtggatgtat   4980
tgg                                                                  4983
```

<210> SEQ ID NO 83
<211> LENGTH: 615
<212> TYPE: PRT
<213> ORGANISM: Saccharomyces bayanus

<400> SEQUENCE: 83

```
Met Ser Ser Thr Thr Glu Asp Lys Asn Ser Asn Glu Gln Gln Gln Pro
1               5                   10                  15

Ala Ala Arg Lys Leu Tyr Tyr Asn Thr Ser Thr Phe Ala Glu Pro Pro
            20                  25                  30

Leu Val Asp Glu Ala Gly Asn Pro Ile Asn Tyr Glu Pro Glu Val Tyr
        35                  40                  45

Asn Pro Asp His Glu Lys Leu Tyr His Asn Pro Ser Leu Pro Val Thr
    50                  55                  60

Ser Ile Gln Asp Thr Arg Asp Asp Glu Leu Leu Glu Arg Val Tyr Ser
65                  70                  75                  80

Val Asp Gln Glu Val Glu Tyr Glu Glu Asp Glu Ala Asp Lys Pro Asn
                85                  90                  95

Leu Ser Leu Ala Ser Ile Lys Asn Tyr Ala Leu Thr Arg Phe Thr Ser
            100                 105                 110

Leu Leu Arg Val His Glu Val Ser Leu Thr Asn Ile Asn Pro Ile Pro
        115                 120                 125

Glu Leu Arg Lys Met Thr Leu Gln Asn Trp Asn Tyr Phe Phe Met Gly
    130                 135                 140

Tyr Leu Ala Trp Leu Thr Ala Ala Trp Cys Phe Phe Cys Val Ser Val
145                 150                 155                 160

Ser Val Ala Pro Leu Ser Glu Leu Tyr Asp Arg Pro Thr Lys Asp Ile
                165                 170                 175

Thr Trp Gly Leu Gly Leu Val Leu Phe Val Arg Ser Ala Gly Ala Ile
            180                 185                 190

Ile Phe Gly Leu Trp Thr Asp Lys Ala Ser Arg Lys Trp Pro Tyr Ile
        195                 200                 205

Thr Cys Leu Phe Leu Phe Val Ile Ala Gln Leu Cys Thr Pro Trp Cys
    210                 215                 220

Asp Thr Tyr Gln Lys Phe Leu Gly Val Arg Trp Ile Thr Gly Ile Ala
225                 230                 235                 240

Met Gly Gly Ile Tyr Gly Cys Ala Ser Ala Thr Ala Ile Glu Asp Ala
                245                 250                 255

Pro Val Lys Ala Arg Ser Phe Leu Ser Gly Leu Phe Phe Ser Ala Tyr
            260                 265                 270

Ala Met Gly Phe Ile Phe Ala Ile Ile Phe Tyr Arg Ala Phe Gly Tyr
        275                 280                 285

Phe Arg Glu Asp Gly Trp Lys Ile Leu Phe Trp Phe Ser Ile Phe Leu
    290                 295                 300

Pro Ile Leu Leu Ile Phe Trp Arg Leu Leu Trp Pro Glu Thr Lys Tyr
305                 310                 315                 320

Phe Thr Lys Val Leu Lys Ala Arg Arg Leu Ile Leu Ser Asp Ala Val
                325                 330                 335

Lys Ala Asn Gly Gly Glu Pro Leu Pro Lys Ala Asn Phe Lys Gln Lys
            340                 345                 350

Met Val Ser Val Lys Lys Thr Val Gln Lys Tyr Trp Leu Leu Phe Ala
        355                 360                 365

Tyr Leu Val Ile Met Leu Val Gly Pro Asn Tyr Leu Thr His Ala Ser
    370                 375                 380

Gln Asp Leu Leu Pro Thr Met Leu Arg Ala Gln Leu Gly Leu Ser Lys
385                 390                 395                 400

Asp Ala Val Thr Val Ile Val Val Val Thr Asn Ile Gly Ala Ile Cys
                405                 410                 415
```

```
Gly Gly Met Ile Phe Gly Gln Leu Met Glu Val Thr Gly Arg Arg Leu
            420                 425                 430

Gly Leu Leu Ile Ala Cys Val Met Gly Gly Cys Phe Thr Tyr Pro Ala
        435                 440                 445

Phe Met Leu Arg Ser Glu Lys Ala Ile Leu Gly Ala Gly Phe Met Leu
    450                 455                 460

Tyr Phe Cys Val Phe Gly Val Trp Gly Ile Leu Pro Ile His Leu Ala
465                 470                 475                 480

Glu Leu Ala Pro Ala Asp Ala Arg Ala Leu Val Ala Gly Leu Ser Tyr
                485                 490                 495

Gln Leu Gly Asn Leu Ala Ser Ala Ala Ala Ser Thr Ile Glu Thr Glu
            500                 505                 510

Leu Ala Gly Lys Tyr Pro Leu Glu Val Asp Ser Ser Gly Thr Val Ile
        515                 520                 525

Lys Glu Asp Tyr Ala Lys Val Met Ala Ile Leu Thr Gly Ala Val Phe
    530                 535                 540

Ile Phe Thr Phe Cys Cys Val Phe Val Gly His Glu Lys Phe His Arg
545                 550                 555                 560

Asp Leu Ser Ser Pro Val Met Lys Lys Tyr Ile Thr Gln Val Glu Val
                565                 570                 575

Tyr Glu Ala Asp Gly Val Ser Ile Ser Glu Ile Val Glu Gln Lys Thr
            580                 585                 590

Glu Tyr Gly Ser Val Gln Met Val Asp Ser Asn Ile Ser Lys Thr Phe
        595                 600                 605

Glu Glu His Val Glu Thr Val
    610                 615


<210> SEQ ID NO 84
<211> LENGTH: 5192
<212> TYPE: DNA
<213> ORGANISM: Artificial Sequence
<220> FEATURE:
<223> OTHER INFORMATION: Sequence put together from multiple organisms:
      Saccharomyces cerevisiae and Kluyveromyces lactis

<400> SEQUENCE: 84

tccatggagg gcacagttaa gccgctaaag gcattatccg ccaagtacaa ttttttactc      60

ttcgaagaca gaaaatttgc tgacattggt aatacagtca aattgcagta ctctgcgggt     120

gtatacagaa tagcagaatg ggcagacatt acgaatgcac acggtgtggt gggcccaggt     180

attgttagcg gtttgaagca ggcggcggaa gaagtaacaa aggaacctag aggccttttg     240

atgttagcag aattgtcatg caagggctcc ctagctactg gagaatatac taagggtact     300

gttgacattg cgaagagcga caaagatttt gttatcggct ttattgctca aagagacatg     360

ggtggaagag atgaaggtta cgattggttg attatgacac ccggtgtggg tttagatgac     420

aagggagacg cattgggtca acagtataga accgtggatg atgtggtctc tacaggatct     480

gacattatta ttgttggaag aggactattt gcaaagggaa gggatgctaa ggtagagggt     540

gaacgttaca gaaaagcagg ctgggaagca tatttgagaa gatgcggcca gcaaaactaa     600

aaaactgtat tataagtaaa tgcatgtata ctaaactcac aaattagagc ttcaatttaa     660

ttatatcagt tattacccgg gaatctcggt cgtaatgatt tttataatga cgaaaaaaaa     720

aaaattggaa agaaaaagct tcatggcctt tataaaaagg aaccatccaa tacctcgcca     780

gaaccaagta acagtatttt acggggcaca aatcaagaac aataagacag gactgtaaag     840
```

atggacgcat tgaactccaa agaacaacaa gagttccaaa aagtagtgga acaaaagcaa 900
atgaaggatt tcatgcgttt gataacttcg tataatgtat gctatacgaa gttatctcga 960
ggaagcccga aagagttatc gttactccga ttattttgta cagctgatgg gaccttgccg 1020
tcttcatttt tttttttttc acctatagag ccgggcagag ctgcccggct caactaaggg 1080
ccggaaaaaa aacggaaaaa agaaagccaa gcgtgtagac gtagtataac agtatatctg 1140
acacgcacgt gatgaccacg taatcgcatc gcccctcaca tctcacctct caccgctgac 1200
tcagcttcac taaaaaggaa aatatatact ctttcccagg caaggtgaca gcggtccccg 1260
tctcctccac aaaggcctct cctggggttt gagcaagtct aagtttacgt agcataaaaa 1320
ttctcggatt gcgtcaaata ataaaaaaag taactccact tctacttcta catcggaaaa 1380
acattccatt cacatatcgt ctttggccta tcttgttttg tccttggtag atcaggtcag 1440
tacaaacgca acacgaaaga acaaaaaaag aagaaaaaca gaaggccaag acagggtcaa 1500
tgagactgtt gtcctcctac tgtccctatg tctctggccg atcacgcgcc attgtccctc 1560
agaaacaaat caaacaccca caccccgggc acccaaagtc cccacccaca ccaccaatac 1620
gtaaacgggg cgccccctgc aggccctcct gcgcgcggcc tcccgccttg cttctctccc 1680
ctccctttc tttttccagt tttccctatt ttgtcccttt ttccgcacaa caagtatcag 1740
aatgggttca tcaaatctat ccaacctaat tcgcacgtag actggcttgg tattggcagt 1800
ttcgcagtta tatatatact accatgagtg aaactgttac gttaccttaa attctttctc 1860
cctttaattt tcttttatct tactctccta cataagacat caagaaacaa ttgtatattg 1920
tacacccccc cccctccaca aacacaaata ttgataatat aaagtctaga atgaataaca 1980
acaacattac accagagtca gactcaatga agagtaacga taacgatcaa accaatgatt 2040
acatgccaga tgtggctgat ttcgatcata cacaaacaaa cacaaacgaa attgctagag 2100
caatttctca cccaggttct gttctgtcaa gagttgcaag ctacgtcagc agaaaggaca 2160
gatacgtaga cgagaatggc aatgaagttt ggcaagacga tgaagtgagt atcctaatgg 2220
aggaagatga gactcctgat ttcacatgga aaaacattag acattacgct atcactagat 2280
tcactacatt gacagaactt cacagagtgt ctatggaaaa catcaaccca attccagaat 2340
tgagaaaaat gacattacat aattggaact acttctttat ggggtatgcc gcgtggttgt 2400
gtgctgcttg ggcatttttc gccgtttccg ttagtacagc ccctcttgca accctttatg 2460
gcaaggaaac aaaagacatt tcatggggtc tatccttagt cttattcgtc agatctgctg 2520
gagcgattat ctttggcatc tggaccgaca attactccag aaagtggcca tacattacat 2580
gcttaggtct tttcttgatc tgtcagcttt gcacaccttg ggcaaagacc tacactcaat 2640
tcttgggagt tcgttggatt tccggtatcg caatgggtgg aatttacgcc tgtgcttctg 2700
caacagcgat tgaggatgca ccagtaaagg ctcgttcttt cttatccggc ttattcttca 2760
ctgcctacgc catgggtttt atcttcgcaa taatctttta cagagcattc ttaaacgtca 2820
acggtgaaaa ctactggaag gttcaattct ggttttcaat atggttacca gctgtactga 2880
tattgtggag actcgtatgg ccagaaacta agtacttcac caaagtacta aaagctagac 2940
aactaatgcg tgatgatgca atagccaaaa acggtggtca accactccca aagttgtctt 3000
tcaagcaaaa gttcgccaat gtgaaaaaga ccgttagtaa atactggctt ttgtttggtt 3060
acttaattct cttgttggtt ggtcctaact acctaacaca cgcctctcaa gacttgtttc 3120
ctacaatgtt aagagcacaa ttgagatttt ctgaagatgc tgtcaccgtg gccattgtag 3180
ttgtttgtct gggtagcatt gctgggggga tgtttttcgg acagttgatg gagatcactg 3240
gtagaagagt tggcctacta ttggccctaa tcatggctgg ctgctttact taccctgcct 3300
tcatgcttaa aacttcatct gcagtgctgg gggcaggctt tatgctctgg ttctcaatct 3360
taggtgtgtg gggtgtttta ccaatccatt tatcagaatt gtcccctcca gaagctagag 3420
cattagtctc tggattagca tatcagctgg gtaatctagc ttcagcagct tctgttgtta 3480
tagagaatga tttggcggat ttgtatccaa tagaatggaa ttctgctgga gaagttacaa 3540
acaaggacta ctctaaggta atggctattc ttacaggttc ttcagtcatt ttcactttcg 3600
tgttggtttt cgttggtcac gaaaagtttc atagagattt gtcatcccca catcttaagt 3660
catacatcga gagagtcgat caaacagaag aggtcgcagc tatgactgga tctactgcga 3720
actctatctc tagtaagcct tcagatgatc agctcgaaaa agtttcagtc tagttaatta 3780
atttaccagc ttactatcct tcttgaaaat atgcactcta tatcttttag ttcttaattg 3840
caacacatag atttgctgta taacgaattt tatgctattt ttttaatttg gagttcggtg 3900
atgaaagtgt cacagcgaat ttcctcacat gtagggaccg aattgtttac aagttctctg 3960
taccaccatg gagacatcaa agattgaaaa tctatggaaa gatatggacg gtagcaacaa 4020
gaatatagca cgagccgcgg agttcatttc gttacttttg atatcgctca caactattgc 4080
gaagcgcttc agtgaaaaaa tcataaggaa aagttgtaaa tattattggt agtattcgtt 4140
tggtaaagta gagggggtaa tttttcccct ttattttgtt catacattct taaattgctt 4200
tgcctctcct tttggaaagc tatacttcgg agcactgttg agcgaaggct caggccggca 4260
tatgacgttt tattaccttt gatcacattt ccacgccatt tcgcattctc accctcataa 4320
gtcatacacc gaaaagaaag tttaagggat caatgagctt actataatct cagtatattt 4380
atttttatcg atgattcacc acaacaatct tgctcccgaa aagaaagcag acggagtaga 4440
agcatttgaa actccttcag accttcaagt atatatatat atatatatat atgtatatgt 4500
gtacattttc acgctaatac taatgtataa ttagaagata atttttactc atttttcgtt 4560
atcttcacgt cacccgaacc tagaaccaaa tgtcattttc acgatatgta aatagtgaaa 4620
taggcaaaaa cgccaaaaag tagtaagcgc aacatacact aaaccattaa agaatatctc 4680
gaccagaatc taacagatat acatgttccg ataatgtctg agttaggtga gtattctaaa 4740
ttagaaaaca aagagcttag aacggagttt gaattgacaa attttccttt tccaggcaca 4800
actgataacg actccgatga cggaagccaa gggcagaact ctttgaatat cattactcct 4860
gacatggatg atactctggt taatgatgta cttcgagaaa acgataaaaa gtctagtatg 4920
agaatggctt ttatgaatct agcaaactct attcttggtg ccggaataat tactcagccg 4980
ttcgcgatca aaaatgctgg tatattaggc gggctattat catacgtagc cctcggattt 5040
atagttgatt ggacgttaag acttattgtc attaacttga ctcttgctgg caagagaaca 5100
taccagggta cggtcgaaca tgtaatgggt aaaaaaggga aattgctgat tctatttaca 5160
aacgggttat ttgcatttgg tggatgtatt gg 5192

<210> SEQ ID NO 85
<211> LENGTH: 4825
<212> TYPE: DNA
<213> ORGANISM: Artificial Sequence
<220> FEATURE:
<223> OTHER INFORMATION: Sequence put together from multiple organisms:
Saccharomyces cerevisiae and Kluyveromyces lactis

<400> SEQUENCE: 85
tccatggagg gcacagttaa gccgctaaag gcattatccg ccaagtacaa ttttttactc 60

```
ttcgaagaca gaaaatttgc tgacattggt aatacagtca aattgcagta ctctgcgggt    120
gtatacagaa tagcagaatg ggcagacatt acgaatgcac acggtgtggt gggcccaggt    180
attgttagcg gtttgaagca ggcggcggaa gaagtaacaa aggaacctag aggccttttg    240
atgttagcag aattgtcatg caagggctcc ctagctactg gagaatatac taagggtact    300
gttgacattg cgaagagcga caaagatttt gttatcggct ttattgctca aagagacatg    360
ggtggaagag atgaaggtta cgattggttg attatgacac ccggtgtggg tttagatgac    420
aagggagacg cattgggtca acagtataga accgtggatg atgtggtctc tacaggatct    480
gacattatta ttgttggaag aggactattt gcaaagggaa gggatgctaa ggtagagggt    540
gaacgttaca gaaaagcagg ctgggaagca tatttgagaa gatgcggcca gcaaaactaa    600
aaaactgtat tataagtaaa tgcatgtata ctaaactcac aaattagagc ttcaatttaa    660
ttatatcagt tattacccgg gaatctcggt cgtaatgatt tttataatga cgaaaaaaaa    720
aaaattggaa agaaaaagct tcatggcctt tataaaaagg aaccatccaa tacctcgcca    780
gaaccaagta acagtatttt acggggcaca aatcaagaac aataagacag gactgtaaag    840
atggacgcat tgaactccaa agaacaacaa gagttccaaa aagtagtgga acaaaagcaa    900
atgaaggatt tcatgcgttt gataacttcg tataatgtat gctatacgaa gttatctcga    960
ggaagagact aatcaaagaa tcgttttctc aaaaaattta atatcttaac tgatagtttg   1020
atcaaagggg caaaacgtag gggcaaacaa acggaaaaat cgtttctcaa attttctgat   1080
gccaagaact ctaaccagtc ttatctaaaa attgccttat gatccgtctc tccggttaca   1140
gcctgtgtaa ctgattaatc ctgcctttct aatcaccatt ctaatgtttt aattaaggga   1200
ttttgtcttc attaacggct ttcgctcata aaaatgttat gacgttttgc ccgcaggcgg   1260
gaaaccatcc acttcacgag actgatctcc tctgccggaa caccgggcat ctccaactta   1320
taagttggag aaataagaga atttcagatt gagagaatga aaaaaaaaaa aaaaaaggca   1380
gaggagagca taaaaatggg gttcactttt tggtaaagct atagcatgcc tatcacatat   1440
aaatagagtg ccagtagcga cttttttcac actcgaaata ctcttactac tgctctcttg   1500
ttgtttttat cacttcttgt ttcttcttgg taaatagaat atcaagctac aaaaagcata   1560
caatcaacta tcaactatta actatatcgt aatacactct agaatgaata acaacaacat   1620
tacaccagag tcagactcaa tgaagagtaa cgataacgat caaaccaatg attacatgcc   1680
agatgtggct gatttcgatc atacacaaac aaacacaaac gaaattgcta gagcaatttc   1740
tcacccaggt tctgttctgt caagagttgc aagctacgtc agcagaaagg acagatacgt   1800
agacgagaat ggcaatgaag tttggcaaga cgatgaagtg agtatcctaa tggaggaaga   1860
tgagactcct gatttcacat ggaaaaacat tagacattac gctatcacta gattcactac   1920
attgacagaa cttcacagag tgtctatgga aaacatcaac ccaattccag aattgagaaa   1980
aatgacatta cataattgga actacttctt tatggggtat gccgcgtggt tgtgtgctgc   2040
ttgggcattt ttcgccgttt ccgttagtac agcccctctt gcaacccttt atggcaagga   2100
aacaaaagac atttcatggg gtctatcctt agtcttattc gtcagatctg ctggagcgat   2160
tatctttggc atctggaccg acaattactc cagaaagtgg ccatacatta catgcttagg   2220
tcttttcttg atctgtcagc tttgcacacc ttgggcaaag acctacactc aattcttggg   2280
agttcgttgg atttccggta tcgcaatggg tggaatttac gcctgtgctt ctgcaacagc   2340
gattgaggat gcaccagtaa aggctcgttc tttcttatcc ggcttattct tcactgccta   2400
```

-continued

```
cgccatgggt tttatcttcg caataatctt ttacagagca ttcttaaacg tcaacggtga   2460
aaactactgg aaggttcaat tctggttttc aatatggtta ccagctgtac tgatattgtg   2520
gagactcgta tggccagaaa ctaagtactt caccaaagta ctaaaagcta gacaactaat   2580
gcgtgatgat gcaatagcca aaaacggtgg tcaaccactc ccaaagttgt ctttcaagca   2640
aaagttcgcc aatgtgaaaa agaccgttag taaatactgg cttttgtttg gttacttaat   2700
tctcttgttg gttggtccta actacctaac acacgcctct caagacttgt ttcctacaat   2760
gttaagagca caattgagat tttctgaaga tgctgtcacc gtggccattg tagttgtttg   2820
tctgggtagc attgctgggg ggatgttttt cggacagttg atggagatca ctggtagaag   2880
agttggccta ctattggccc taatcatggc tggctgcttt acttaccctg ccttcatgct   2940
taaaacttca tctgcagtgc tgggggcagg ctttatgctc tggttctcaa tcttaggtgt   3000
gtggggtgtt ttaccaatcc atttatcaga attgtcccct ccagaagcta gagcattagt   3060
ctctggatta gcatatcagc tgggtaatct agcttcagca gcttctgttg ttatagagaa   3120
tgatttggcg gatttgtatc caatagaatg gaattctgct ggagaagtta caaacaagga   3180
ctactctaag gtaatggcta ttcttacagg ttcttcagtc attttcactt tcgtgttggt   3240
tttcgttggt cacgaaaagt ttcatagaga tttgtcatcc ccacatctta agtcatacat   3300
cgagagagtc gatcaaacag aagaggtcgc agctatgact ggatctactg cgaactctat   3360
ctctagtaag ccttcagatg atcagctcga aaaagtttca gtctagttaa ttaatttacc   3420
agcttactat ccttcttgaa aatatgcact ctatatcttt tagttcttaa ttgcaacaca   3480
tagatttgct gtataacgaa ttttatgcta tttttttaat ttggagttcg gtgatgaaag   3540
tgtcacagcg aatttcctca catgtaggga ccgaattgtt tacaagttct ctgtaccacc   3600
atggagacat caaagattga aaatctatgg aaagatatgg acggtagcaa caagaatata   3660
gcacgagccg cggagttcat ttcgttactt ttgatatcgc tcacaactat tgcgaagcgc   3720
ttcagtgaaa aaatcataag gaaaagttgt aaatattatt ggtagtattc gtttggtaaa   3780
gtagaggggg taatttttcc cctttatttt gttcatacat tcttaaattg ctttgcctct   3840
ccttttggaa agctatactt cggagcactg ttgagcgaag gctcaggccg gcatatgacg   3900
ttttattacc tttgatcaca tttccacgcc atttcgcatt ctcaccctca taagtcatac   3960
accgaaaaga aagtttaagg gatcaatgag cttactataa tctcagtata tttatttta   4020
tcgatgattc accacaacaa tcttgctccc gaaaagaaag cagacggagt agaagcattt   4080
gaaactcctt cagaccttca agtatatata tatatatata tatatgtata tgtgtacatt   4140
ttcacgctaa tactaatgta taattagaag ataattttta ctcatttttc gttatcttca   4200
cgtcacccga acctagaacc aaatgtcatt ttcacgatat gtaaatagtg aaataggcaa   4260
aaacgccaaa aagtagtaag cgcaacatac actaaaccat taaagaatat ctcgaccaga   4320
atctaacaga tatacatgtt ccgataatgt ctgagttagg tgagtattct aaattagaaa   4380
acaaagagct tagaacggag tttgaattga caaatttcc ttttccaggc acaactgata   4440
acgactccga tgacggaagc caagggcaga actctttgaa tatcattact cctgacatgg   4500
atgatactct ggttaatgat gtacttcgag aaaacgataa aaagtctagt atgagaatgg   4560
cttttatgaa tctagcaaac tctattcttg gtgccggaat aattactcag ccgttcgcga   4620
tcaaaaatgc tggtatatta ggcgggctat tatcatacgt agccctcgga tttatagttg   4680
attggacgtt aagacttatt gtcattaact tgactcttgc tggcaagaga acataccagg   4740
gtacggtcga acatgtaatg ggtaaaaaag ggaaattgct gattctattt acaaacgggt   4800
```

tatttgcatt tggtggatgt attgg 4825

<210> SEQ ID NO 86
<211> LENGTH: 5157
<212> TYPE: DNA
<213> ORGANISM: Artificial Sequence
<220> FEATURE:
<223> OTHER INFORMATION: Sequence put together from multiple organisms:
Saccharomyces cerevisiae and Kluyveromyces lactis

<400> SEQUENCE: 86
tccatggagg gcacagttaa gccgctaaag gcattatccg ccaagtacaa tttttttactc 60 ttcgaagaca gaaaatttgc tgacattggt aatacagtca aattgcagta ctctgcgggt 120
gtatacagaa tagcagaatg ggcagacatt acgaatgcac acggtgtggt gggcccaggt 180
attgttagcg gtttgaagca ggcggcggaa gaagtaacaa aggaacctag aggccttttg 240
atgttagcag aattgtcatg caagggctcc ctagctactg gagaatatac taagggtact 300
gttgacattg cgaagagcga caaagatttt gttatcggct ttattgctca aagagacatg 360
ggtggaagag atgaaggtta cgattggttg attatgacac ccggtgtggg tttagatgac 420
aagggagacg cattgggtca acagtataga accgtggatg atgtggtctc tacaggatct 480
gacattatta ttgttggaag aggactattt gcaaagggaa gggatgctaa ggtagagggt 540
gaacgttaca gaaaagcagg ctgggaagca tatttgagaa gatgcggcca gcaaaactaa 600
aaaactgtat tataagtaaa tgcatgtata ctaaactcac aaattagagc ttcaatttaa 660
ttatatcagt tattacccgg gaatctcggt cgtaatgatt tttataatga cgaaaaaaaa 720
aaaattggaa agaaaaagct tcatggcctt tataaaaagg aaccatccaa tacctcgcca 780
gaaccaagta acagtatttt acggggcaca aatcaagaac aataagacag gactgtaaag 840
atggacgcat tgaactccaa agaacaacaa gagttccaaa aagtagtgga acaaaagcaa 900
atgaaggatt tcatgcgttt gataacttcg tataatgtat gctatacgaa gttatctcga 960
ggacaaccag gacgtaaagg gtagcctccc cataacataa actcaataaa atatatagtc 1020
ttcaacttga aaaaggaaca agctcatgca aagaggtggt acccgcacgc cgaaatgcat 1080
gcaagtaacc tattcaaagt aatatctcat acatgtttca tgagggtaac aacatgcgac 1140
tgggtgagca tatgttccgc tgatgtgatg tgcaagataa acaagcaaga cagaaactaa 1200
cttcttcttc atgtaataaa cacaccccgc gtttatttac ctatctttaa acttcaacac 1260
cttatatcat aactaatatt tcttgagata agcacactgc acccatacct tccttaaaaa 1320
cgtagcttcc agtttttggt ggttctggct tccttcccga ttccgcccgc taaacgcata 1380
attttgttgc ctggtggcat ttgcaaaatg cataacctat gcatttaaaa gattatgtat 1440
gctcttctga cttttcgtgt gatgaggctc gtggaaaaaa tgaataattt atgaatttga 1500
gaacaatttt gtgttgttac ggtattttac tatggaataa tcaatcaatt gaggatttta 1560
tgcaaatatc gtttgaatat ttttccgacc ctttgagtac ttttcttcat aattgcataa 1620
tattgtccgc tgcccgtttt tctgttagac ggtgtcttga tctacttgct atcgttcaac 1680
accaccttat tttctaacta ttttttttt agctcatttg aatcagctta tggtgatggc 1740
acatttttgc ataaacctag ctgtcctcgt tgaacatagg aaaaaaaaat atataaacaa 1800
ggctctttca ctctccttgg aatcagattt gggtttgttc cctttatttt catatttctt 1860
gtcatattct tttctcaatt attatcttct actcataacc tcacgcaaaa taacacagtc 1920
aaatcaatct ctagaatgaa taacaacaac attacaccag agtcagactc aatgaagagt 1980

```
aacgataacg atcaaaccaa tgattacatg ccagatgtgg ctgatttcga tcatacacaa   2040
acaaacacaa acgaaattgc tagagcaatt tctcacccag gttctgttct gtcaagagtt   2100
gcaagctacg tcagcagaaa ggacagatac gtagacgaga atggcaatga agtttggcaa   2160
gacgatgaag tgagtatcct aatggaggaa gatgagactc ctgatttcac atggaaaaac   2220
attagacatt acgctatcac tagattcact acattgacag aacttcacag agtgtctatg   2280
gaaaacatca acccaattcc agaattgaga aaaatgacat tacataattg gaactacttc   2340
tttatggggt atgccgcgtg gttgtgtgct gcttgggcat ttttcgccgt ttccgttagt   2400
acagcccctc ttgcaaccct ttatggcaag gaaacaaaag acatttcatg ggtctatcc    2460
ttagtcttat tcgtcagatc tgctggagcg attatctttg gcatctggac cgacaattac   2520
tccagaaagt ggccatacat tacatgctta ggtcttttct tgatctgtca gctttgcaca   2580
ccttgggcaa agacctacac tcaattcttg ggagttcgtt ggatttccgg tatcgcaatg   2640
ggtggaattt acgcctgtgc ttctgcaaca gcgattgagg atgcaccagt aaaggctcgt   2700
tctttcttat ccggcttatt cttcactgcc tacgccatgg gttttatctt cgcaataatc   2760
ttttacagag cattcttaaa cgtcaacggt gaaaactact ggaaggttca attctggttt   2820
tcaatatggt taccagctgt actgatattg tggagactcg tatggccaga aactaagtac   2880
ttcaccaaag tactaaaagc tagacaacta atgcgtgatg atgcaatagc caaaaacggt   2940
ggtcaaccac tcccaaagtt gtctttcaag caaaagttcg ccaatgtgaa aaagaccgtt   3000
agtaaatact ggcttttgtt tggttactta attctcttgt tggttggtcc taactaccta   3060
acacacgcct ctcaagactt gtttcctaca atgttaagag cacaattgag attttctgaa   3120
gatgctgtca ccgtggccat tgtagttgtt tgtctgggta gcattgctgg ggggatgttt   3180
ttcggacagt tgatggagat cactggtaga agagttggcc tactattggc cctaatcatg   3240
gctggctgct ttacttaccc tgccttcatg cttaaaactt catctgcagt gctgggggca   3300
ggctttatgc tctggttctc aatcttaggt gtgtggggtg ttttaccaat ccatttatca   3360
gaattgtccc ctccagaagc tagagcatta gtctctggat tagcatatca gctgggtaat   3420
ctagcttcag cagcttctgt tgttatagag aatgatttgg cggatttgta tccaatagaa   3480
tggaattctg ctggagaagt tacaaacaag gactactcta aggtaatggc tattcttaca   3540
ggttcttcag tcattttcac tttcgtgttg gttttcgttg gtcacgaaaa gtttcataga   3600
gatttgtcat ccccacatct taagtcatac atcgagagag tcgatcaaac agaagaggtc   3660
gcagctatga ctggatctac tgcgaactct atctctagta agccttcaga tgatcagctc   3720
gaaaaagttt cagtctagtt aattaattta ccagcttact atccttcttg aaaatatgca   3780
ctctatatct tttagttctt aattgcaaca catagatttg ctgtataacg aattttatgc   3840
tattttttta atttggagtt cggtgatgaa agtgtcacag cgaatttcct cacatgtagg   3900
gaccgaattg tttacaagtt ctctgtacca ccatggagac atcaaagatt gaaaatctat   3960
ggaaagatat ggacggtagc aacaagaata tagcacgagc cgcggagttc atttcgttac   4020
ttttgatatc gctcacaact attgcgaagc gcttcagtga aaaaatcata aggaaaagtt   4080
gtaaatatta ttggtagtat tcgtttggta aagtagaggg ggtaattttt cccctttatt   4140
ttgttcatac attcttaaat tgctttgcct ctccttttgg aaagctatac ttcggagcac   4200
tgttgagcga aggctcaggc cggcatatga cgttttatta cctttgatca catttccacg   4260
ccatttcgca ttctcaccct cataagtcat acaccgaaaa gaaagtttaa gggatcaatg   4320
```

agcttactat aatctcagta tatttatttt tatcgatgat tcaccacaac aatcttgctc 4380
ccgaaaagaa agcagacgga gtagaagcat ttgaaactcc ttcagacctt caagtatata 4440
tatatatata tatatatgta tatgtgtaca ttttcacgct aatactaatg tataattaga 4500
agataatttt tactcatttt tcgttatctt cacgtcaccc gaacctagaa ccaaatgtca 4560
ttttcacgat atgtaaatag tgaaataggc aaaaacgcca aaaagtagta agcgcaacat 4620
acactaaacc attaaagaat atctcgacca gaatctaaca gatatacatg ttccgataat 4680
gtctgagtta ggtgagtatt ctaaattaga aaacaaagag cttagaacgg agtttgaatt 4740
gacaaatttt ccttttccag gcacaactga taacgactcc gatgacggaa gccaagggca 4800
gaactctttg aatatcatta ctcctgacat ggatgatact ctggttaatg atgtacttcg 4860
agaaaacgat aaaaagtcta gtatgagaat ggcttttatg aatctagcaa actctattct 4920
tggtgccgga ataattactc agccgttcgc gatcaaaaat gctggtatat taggcgggct 4980
attatcatac gtagccctcg gatttatagt tgattggacg ttaagactta ttgtcattaa 5040
cttgactctt gctggcaaga gaacatacca gggtacggtc gaacatgtaa tgggtaaaaa 5100
agggaaattg ctgattctat ttacaaacgg gttatttgca tttggtggat gtattgg 5157

<210> SEQ ID NO 87
<211> LENGTH: 5600
<212> TYPE: DNA
<213> ORGANISM: Artificial Sequence
<220> FEATURE:
<223> OTHER INFORMATION: Sequence put together from multiple organisms: Saccharomyces cerevisiae, Kluyveromyces lactis, and Aspergillus nidulans

<400> SEQUENCE: 87
gaaggtgcta ttgttggtat tagaggtggt gttattggtg tcggtactga cattggtggt 60
tccattagag tcccagctgc tttcaacttt ttatacggtt tgagaccatc tcacggtaga 120
ttgccatatg ctaaaatggc taactctatg gaaggtcaag aaaccgttca ctccgtcgtt 180
ggtcctatca ctcactccgt cgaagacttg agattgttca ccaaatctgt cttgggtcaa 240
gaaccttgga agtacgactc taaggtcatc ccaatgccat ggagacaatc tgaatctgac 300
atcattgcct ctaagattaa gaatggtggt ttgaacattg gttattacaa tttcgacggt 360
aacgtcttgc cacacccacc aattttacgt ggtgtcgaaa ctaccgttgc cgctttggcc 420
aaggctggtc acaccgttac tccatggact ccatacaagc atgatttcgg tcatgacttg 480
atttcccaca tctatgctgc tgatggttct gccgacgtca tgagagacat ttctgcctct 540
ggtgagccag ccatccctaa cattaaggac ttgttgaacc caaatattaa ggctgttaac 600
atgaacgaat tgtgggacac tcatttacaa aagtggaact atcaaatgga atacttggaa 660
aagtggcgtg aagctgaaga aaaagctggt aaggaattgg acgctattat cgctccaatt 720
actcctaccg ccgctgtcag acacgatcaa ttcagatact acggttacgc ctccgttatt 780
aacttattgg atttcacctc tgttgtcgtc ccagtcactt tcgctgataa gaatattgat 840
aagaagaacg aatcttttaa agctgtttcc gaattggatg ctttggttca agaagaatac 900
gacccagagg cttatcacgg tgctcctgtt gctgttcaag ttattggtag aagattgtcc 960
gaagagagaa ctttggctat cgccgaagaa gtcggtaaat tgttgggtaa cgtcgtcact 1020
ccataagcga atttcttatg atttatgatt tttattatta aataagttat aaaaaaaata 1080
agtgtataca aattttaaag tgactcttag gttttaaaac gaaaattctt attcttgagt 1140
aactctttcc tgtaggtcag gttgctttct caggtatagc atgaggtcgc tcttattgac 1200
cacacctcta ccggcatgcc gagcaaatgc ctgcaaatcg ctccccattt cacccaattg 1260
tagatatgct aactccagca atgagttgat gaatctcggt gtgtatttta tgtcctcaga 1320
ggacaacaca taacttcgta taatgtatgc tatacgaagt tatctcgagg aagcccgaaa 1380
gagttatcgt tactccgatt attttgtaca gctgatggga ccttgccgtc ttcatttttt 1440
tttttttcac ctatagagcc gggcagagct gcccggctca actaagggcc ggaaaaaaaa 1500
cggaaaaaag aaagccaagc gtgtagacgt agtataacag tatatctgac acgcacgtga 1560
tgaccacgta atcgcatcgc ccctcacatc tcacctctca ccgctgactc agcttcacta 1620
aaaaggaaaa tatatactct ttcccaggca aggtgacagc ggtccccgtc tcctccacaa 1680
aggcctctcc tggggtttga gcaagtctaa gtttacgtag cataaaaatt ctcggattgc 1740
gtcaaataat aaaaaaagta actccacttc tacttctaca tcggaaaaac attccattca 1800
catatcgtct ttggcctatc ttgttttgtc cttggtagat caggtcagta caaacgcaac 1860
acgaaagaac aaaaaaagaa gaaaaacaga aggccaagac agggtcaatg agactgttgt 1920
cctcctactg tccctatgtc tctggccgat cacgcgccat tgtccctcag aaacaaatca 1980
aacacccaca ccccgggcac ccaaagtccc cacccacacc accaatacgt aaacggggcg 2040
ccccctgcag gccctcctgc gcgcggcctc ccgccttgct tctctcccct ccctttttctt 2100
tttccagttt tccctatttt gtcccttttt ccgcacaaca agtatcagaa tgggttcatc 2160
aaatctatcc aacctaattc gcacgtagac tggcttggta ttggcagttt cgcagttata 2220
tatatactac catgagtgaa actgttacgt taccttaaat tctttctccc tttaattttc 2280
ttttatctta ctctcctaca taagacatca agaaacaatt gtatattgta caccccccccc 2340
cctccacaaa cacaaatatt gataatataa agtctagaat gaataacaac aacattacac 2400
cagagtcaga ctcaatgaag agtaacgata acgatcaaac caatgattac atgccagatg 2460
tggctgattt cgatcataca caaacaaaca caaacgaaat tgctagagca atttctcacc 2520
caggttctgt tctgtcaaga gttgcaagct acgtcagcag aaaggacaga tacgtagacg 2580
agaatggcaa tgaagtttgg caagacgatg aagtgagtat cctaatggag gaagatgaga 2640
ctcctgattt cacatggaaa aacattagac attacgctat cactagattc actacattga 2700
cagaacttca cagagtgtct atggaaaaca tcaacccaat tccagaattg agaaaaatga 2760
cattacataa ttggaactac ttctttatgg ggtatgccgc gtggttgtgt gctgcttggg 2820
catttttcgc cgtttccgtt agtacagccc ctcttgcaac cctttatggc aaggaaacaa 2880
aagacatttc atggggtcta tccttagtct tattcgtcag atctgctgga gcgattatct 2940
ttggcatctg gaccgacaat tactccagaa agtggccata cattacatgc ttaggtcttt 3000
tcttgatctg tcagctttgc acaccttggg caaagaccta cactcaattc ttgggagttc 3060
gttggatttc cggtatcgca atgggtggaa tttacgcctg tgcttctgca acagcgattg 3120
aggatgcacc agtaaaggct cgttctttct tatccggctt attcttcact gcctacgcca 3180
tgggttttat cttcgcaata atcttttaca gagcattctt aaacgtcaac ggtgaaaact 3240
actggaaggt tcaattctgg ttttcaatat ggttaccagc tgtactgata ttgtggagac 3300
tcgtatggcc agaaactaag tacttcacca aagtactaaa agctagacaa ctaatgcgtg 3360
atgatgcaat agccaaaaac ggtggtcaac cactcccaaa gttgtctttc aagcaaaagt 3420
tcgccaatgt gaaaaagacc gttagtaaat actggctttt gtttggttac ttaattctct 3480
tgttggttgg tcctaactac ctaacacacg cctctcaaga cttgtttcct acaatgttaa 3540

```
gagcacaatt gagattttct gaagatgctg tcaccgtggc cattgtagtt gtttgtctgg   3600

gtagcattgc tggggggatg tttttcggac agttgatgga gatcactggt agaagagttg   3660

gcctactatt ggccctaatc atggctggct gctttactta ccctgccttc atgcttaaaa   3720

cttcatctgc agtgctgggg gcaggcttta tgctctggtt ctcaatctta ggtgtgtggg   3780

gtgttttacc aatccattta tcagaattgt cccctccaga agctagagca ttagtctctg   3840

gattagcata tcagctgggt aatctagctt cagcagcttc tgttgttata gagaatgatt   3900

tggcggattt gtatccaata gaatggaatt ctgctggaga agttacaaac aaggactact   3960

ctaaggtaat ggctattctt acaggttctt cagtcatttt cactttcgtg ttggttttcg   4020

ttggtcacga aaagtttcat agagatttgt catccccaca tcttaagtca tacatcgaga   4080

gagtcgatca aacagaagag gtcgcagcta tgactggatc tactgcgaac tctatctcta   4140

gtaagccttc agatgatcag ctcgaaaaag tttcagtcta gttaattaat ttaccagctt   4200

actatccttc ttgaaaatat gcactctata tcttttagtt cttaattgca acacatagat   4260

ttgctgtata acgaatttta tgctattttt ttaatttgga gttcggtgat gaaagtgtca   4320

cagcgaattt cctcacatgt agggaccgaa ttgtttacaa gttctctgta ccaccatgga   4380

gacatcaaag attgaaaatc tatggaaaga tatggacggt agcaacaaga atatagcacg   4440

agccgcggag ttcatttcgt tacttttgat atcgctcaca actattgcga agcgcttcag   4500

tgaaaaaatc ataaggaaaa gttgtaaata ttattggtag tattcgtttg gtaaagtaga   4560

gggggtaatt tttccccttt attttgttca tacattctta aattgctttg cctctccttt   4620

tggaaagcta tacttcggag cactgttgag cgaaggctca ggccggcata tgacgtttta   4680

ttacctttga tcacatttcc acgccatttc gcattctcac cctcataagt catacaccga   4740

aaagaaagtt taagggatca atgagcttac tataatctca gtatatttat ttttatcgat   4800

gattcaccac aacaatcttg ctcccgaaaa gaaagcagac ggagtagaag catttgaaac   4860

tccttcagac cttcaagtat atatatatat atatatatat gtatatgtgt acattttcac   4920

gctaatacta atgtataatt agaagataat ttttactcat ttttcgttat cttcacgtca   4980

cccgaaccta gaaccaaatg tcattttcac gatatgtaaa tagtgaaata ggcaaaaacg   5040

ccaaaaagta gtaagcgcaa catacactaa accattaaag aatatctcga ccagaatcta   5100

acagatatac atgttccgat aatgtctgag ttaggtgagt attctaaatt agaaaacaaa   5160

gagcttagaa cggagtttga attgacaaat tttccttttc caggcacaac tgataacgac   5220

tccgatgacg gaagccaagg gcagaactct ttgaatatca ttactcctga catggatgat   5280

actctggtta atgatgtact tcgagaaaac gataaaaagt ctagtatgag aatggctttt   5340

atgaatctag caaactctat tcttggtgcc ggaataatta ctcagccgtt cgcgatcaaa   5400

aatgctggta tattaggcgg gctattatca tacgtagccc tcggatttat agttgattgg   5460

acgttaagac ttattgtcat taacttgact cttgctggca agagaacata ccagggtacg   5520

gtcgaacatg taatgggtaa aaaagggaaa ttgctgattc tatttacaaa cgggttattt   5580

gcatttggtg gatgtattgg                                               5600
```

<210> SEQ ID NO 88
<211> LENGTH: 5233
<212> TYPE: DNA
<213> ORGANISM: Artificial Sequence
<220> FEATURE:
<223> OTHER INFORMATION: Sequence put together from multiple organisms: Saccharomyces cerevisiae, Kluyveromyces lactis, and Aspergillus nidulans

<400> SEQUENCE: 88
gaaggtgcta ttgttggtat tagaggtggt gttattggtg tcggtactga cattggtggt 60
tccattagag tcccagctgc tttcaacttt ttatacggtt tgagaccatc tcacggtaga 120
ttgccatatg ctaaaatggc taactctatg gaaggtcaag aaaccgttca ctccgtcgtt 180
ggtcctatca ctcactccgt cgaagacttg agattgttca ccaaatctgt cttgggtcaa 240
gaaccttgga agtacgactc taaggtcatc ccaatgccat ggagacaatc tgaatctgac 300
atcattgcct ctaagattaa gaatggtggt ttgaacattg gttattacaa tttcgacggt 360
aacgtcttgc cacacccacc aattttacgt ggtgtcgaaa ctaccgttgc cgctttggcc 420
aaggctggtc acaccgttac tccatggact ccatacaagc atgatttcgg tcatgacttg 480
atttcccaca tctatgctgc tgatggttct gccgacgtca tgagagacat ttctgcctct 540
ggtgagccag ccatccctaa cattaaggac ttgttgaacc caaatattaa ggctgttaac 600
atgaacgaat tgtgggacac tcatttacaa aagtggaact atcaaatgga atacttggaa 660
aagtggcgtg aagctgaaga aaaagctggt aaggaattgg acgctattat cgctccaatt 720
actcctaccg ccgctgtcag acacgatcaa ttcagatact acggttacgc ctccgttatt 780
aacttattgg atttcacctc tgttgtcgtc ccagtcactt tcgctgataa gaatattgat 840
aagaagaacg aatcttttaa agctgtttcc gaattggatg ctttggttca agaagaatac 900
gacccagagg cttatcacgg tgctcctgtt gctgttcaag ttattggtag aagattgtcc 960
gaagagagaa ctttggctat cgccgaagaa gtcggtaaat tgttgggtaa cgtcgtcact 1020
ccataagcga atttcttatg atttatgatt tttattatta aataagttat aaaaaaaata 1080
agtgtataca aattttaaag tgactcttag gttttaaaac gaaaattctt attcttgagt 1140
aactctttcc tgtaggtcag gttgctttct caggtatagc atgaggtcgc tcttattgac 1200
cacacctcta ccggcatgcc gagcaaatgc ctgcaaatcg ctccccattt cacccaattg 1260
tagatatgct aactccagca atgagttgat gaatctcggt gtgtatttta tgtcctcaga 1320
ggacaacaca taacttcgta taatgtatgc tatacgaagt tatctcgagg aagagactaa 1380
tcaaagaatc gttttctcaa aaaatttaat atcttaactg atagtttgat caaaggggca 1440
aaacgtaggg gcaaacaaac ggaaaaatcg tttctcaaat tttctgatgc caagaactct 1500
aaccagtctt atctaaaaat tgccttatga tccgtctctc cggttacagc ctgtgtaact 1560
gattaatcct gcctttctaa tcaccattct aatgttttaa ttaagggatt ttgtcttcat 1620
taacggcttt cgctcataaa aatgttatga cgttttgccc gcaggcggga aaccatccac 1680
ttcacgagac tgatctcctc tgccggaaca ccgggcatct ccaacttata agttggagaa 1740
ataagagaat ttcagattga gagaatgaaa aaaaaaaaaa aaaaggcaga ggagagcata 1800
aaaatggggt tcacttttg gtaaagctat agcatgccta tcacatataa atagagtgcc 1860
agtagcgact tttttcacac tcgaaatact cttactactg ctctcttgtt gtttttatca 1920
cttcttgttt cttcttggta aatagaatat caagctacaa aaagcataca atcaactatc 1980
aactattaac tatatcgtaa tacactctag aatgaataac aacaacatta caccagagtc 2040
agactcaatg aagagtaacg ataacgatca aaccaatgat tacatgccag atgtggctga 2100
tttcgatcat acacaaacaa acacaaacga aattgctaga gcaatttctc acccaggttc 2160
tgttctgtca agagttgcaa gctacgtcag cagaaaggac agatacgtag acgagaatgg 2220
caatgaagtt tggcaagacg atgaagtgag tatcctaatg gaggaagatg agactcctga 2280

-continued

```
tttcacatgg aaaaacatta gacattacgc tatcactaga ttcactacat tgacagaact   2340
tcacagagtg tctatggaaa acatcaaccc aattccagaa ttgagaaaaa tgacattaca   2400
taattggaac tacttcttta tggggtatgc cgcgtggttg tgtgctgctt gggcattttt   2460
cgccgtttcc gttagtacag cccctcttgc aacccttat ggcaaggaaa caaaagacat   2520
ttcatggggt ctatccttag tcttattcgt cagatctgct ggagcgatta tctttggcat   2580
ctggaccgac aattactcca gaaagtggcc atacattaca tgcttaggtc ttttcttgat   2640
ctgtcagctt tgcacacctt gggcaaagac ctacactcaa ttcttgggag ttcgttggat   2700
ttccggtatc gcaatgggtg gaatttacgc ctgtgcttct gcaacagcga ttgaggatgc   2760
accagtaaag gctcgttctt tcttatccgg cttattcttc actgcctacg ccatgggttt   2820
tatcttcgca ataatctttt acagagcatt cttaaacgtc aacggtgaaa actactggaa   2880
ggttcaattc tggttttcaa tatggttacc agctgtactg atattgtgga gactcgtatg   2940
gccagaaact aagtacttca ccaaagtact aaaagctaga caactaatgc gtgatgatgc   3000
aatagccaaa aacggtggtc aaccactccc aaagttgtct ttcaagcaaa agttcgccaa   3060
tgtgaaaaag accgttagta aatactggct tttgtttggt tacttaattc tcttgttggt   3120
tggtcctaac tacctaacac acgcctctca agacttgttt cctacaatgt taagagcaca   3180
attgagattt tctgaagatg ctgtcaccgt ggccattgta gttgtttgtc tgggtagcat   3240
tgctgggggg atgtttttcg gacagttgat ggagatcact ggtagaagag ttggcctact   3300
attggcccta atcatggctg gctgctttac ttaccctgcc ttcatgctta aaacttcatc   3360
tgcagtgctg gggggcaggct ttatgctctg gttctcaatc ttaggtgtgt ggggtgtttt   3420
accaatccat ttatcagaat tgtcccctcc agaagctaga gcattagtct ctggattagc   3480
atatcagctg ggtaatctag cttcagcagc ttctgttgtt atagagaatg atttggcgga   3540
tttgtatcca atagaatgga attctgctgg agaagttaca aacaaggact actctaaggt   3600
aatggctatt cttacaggtt cttcagtcat tttcactttc gtgttggttt tcgttggtca   3660
cgaaaagttt catagagatt tgtcatcccc acatcttaag tcatacatcg agagagtcga   3720
tcaaacagaa gaggtcgcag ctatgactgg atctactgcg aactctatct ctagtaagcc   3780
ttcagatgat cagctcgaaa aagtttcagt ctagttaatt aatttaccag cttactatcc   3840
ttcttgaaaa tatgcactct atatctttta gttcttaatt gcaacacata gatttgctgt   3900
ataacgaatt ttatgctatt tttttaattt ggagttcggt gatgaaagtg tcacagcgaa   3960
tttcctcaca tgtagggacc gaattgttta caagttctct gtaccaccat ggagacatca   4020
aagattgaaa atctatggaa agatatggac ggtagcaaca agaatatagc acgagccgcg   4080
gagttcattt cgttactttt gatatcgctc acaactattg cgaagcgctt cagtgaaaaa   4140
atcataagga aaagttgtaa atattattgg tagtattcgt ttggtaaagt agaggggggta   4200
atttttcccc tttattttgt tcatacattc ttaaattgct ttgcctctcc ttttggaaag   4260
ctatacttcg gagcactgtt gagcgaaggc tcaggccggc atatgacgtt ttattacctt   4320
tgatcacatt tccacgccat ttcgcattct caccctcata agtcatacac cgaaaagaaa   4380
gtttaaggga tcaatgagct tactataatc tcagtatatt tatttttatc gatgattcac   4440
cacaacaatc ttgctcccga aaagaaagca gacggagtag aagcatttga aactccttca   4500
gaccttcaag tatatatata tatatatata tatgtatatg tgtacatttt cacgctaata   4560
ctaatgtata attagaagat aatttttact catttttcgt tatcttcacg tcacccgaac   4620
ctagaaccaa atgtcatttt cacgatatgt aaatagtgaa ataggcaaaa acgccaaaaa   4680
```

gtagtaagcg caacatacac taaaccatta aagaatatct cgaccagaat ctaacagata 4740
tacatgttcc gataatgtct gagttaggtg agtattctaa attagaaaac aaagagctta 4800
gaacggagtt tgaattgaca aattttcctt ttccaggcac aactgataac gactccgatg 4860
acggaagcca agggcagaac tctttgaata tcattactcc tgacatggat gatactctgg 4920
ttaatgatgt acttcgagaa aacgataaaa agtctagtat gagaatggct tttatgaatc 4980
tagcaaactc tattcttggt gccggaataa ttactcagcc gttcgcgatc aaaaatgctg 5040
gtatattagg cgggctatta tcatacgtag ccctcggatt tatagttgat tggacgttaa 5100
gacttattgt cattaacttg actcttgctg gcaagagaac ataccagggt acggtcgaac 5160
atgtaatggg taaaaaaggg aaattgctga ttctatttac aaacgggtta tttgcatttg 5220
gtggatgtat tgg 5233

<210> SEQ ID NO 89
<211> LENGTH: 5565
<212> TYPE: DNA
<213> ORGANISM: Artificial Sequence
<220> FEATURE:
<223> OTHER INFORMATION: Sequence put together from multiple organisms: Saccharomyces cerevisiae, Kluyveromyces lactis, and Aspergillus nidulans

<400> SEQUENCE: 89
gaaggtgcta ttgttggtat tagaggtggt gttattggtg tcggtactga cattggtggt 60
tccattagag tcccagctgc tttcaacttt ttatacggtt tgagaccatc tcacggtaga 120
ttgccatatg ctaaaatggc taactctatg gaaggtcaag aaaccgttca ctccgtcgtt 180
ggtcctatca ctcactccgt cgaagacttg agattgttca ccaaatctgt cttgggtcaa 240
gaaccttgga agtacgactc taaggtcatc ccaatgccat ggagacaatc tgaatctgac 300
atcattgcct ctaagattaa gaatggtggt ttgaacattg gttattacaa tttcgacggt 360
aacgtcttgc cacacccacc aattttacgt ggtgtcgaaa ctaccgttgc cgctttggcc 420
aaggctggtc acaccgttac tccatggact ccatacaagc atgatttcgg tcatgacttg 480
atttcccaca tctatgctgc tgatggttct gccgacgtca tgagagacat ttctgcctct 540
ggtgagccag ccatccctaa cattaaggac ttgttgaacc caaatattaa ggctgttaac 600
atgaacgaat tgtgggacac tcatttacaa aagtggaact atcaaatgga atacttggaa 660
aagtggcgtg aagctgaaga aaaagctggt aaggaattgg acgctattat cgctccaatt 720
actcctaccg ccgctgtcag acacgatcaa ttcagatact acggttacgc ctccgttatt 780
aacttattgg atttcacctc tgttgtcgtc ccagtcactt tcgctgataa gaatattgat 840
aagaagaacg aatcttttaa agctgtttcc gaattggatg ctttggttca agaagaatac 900
gacccagagg cttatcacgg tgctcctgtt gctgttcaag ttattggtag aagattgtcc 960
gaagagagaa ctttggctat cgccgaagaa gtcggtaaat tgttgggtaa cgtcgtcact 1020
ccataagcga atttcttatg atttatgatt tttattatta aataagttat aaaaaaaata 1080
agtgtataca aattttaaag tgactcttag gttttaaaac gaaaattctt attcttgagt 1140
aactctttcc tgtaggtcag gttgctttct caggtatagc atgaggtcgc tcttattgac 1200
cacacctcta ccggcatgcc gagcaaatgc ctgcaaatcg ctccccattt cacccaattg 1260
tagatatgct aactccagca atgagttgat gaatctcggt gtgtatttta tgtcctcaga 1320
ggacaacaca taacttcgta taatgtatgc tatacgaagt tatctcgagg acaaccagga 1380

```
cgtaaagggt agcctcccca taacataaac tcaataaaat atatagtctt caacttgaaa   1440
aaggaacaag ctcatgcaaa gaggtggtac ccgcacgccg aaatgcatgc aagtaaccta   1500
ttcaaagtaa tatctcatac atgtttcatg agggtaacaa catgcgactg ggtgagcata   1560
tgttccgctg atgtgatgtg caagataaac aagcaagaca gaaactaact tcttcttcat   1620
gtaataaaca caccccgcgt ttatttacct atctttaaac ttcaacacct tatatcataa   1680
ctaatatttc ttgagataag cacactgcac ccataccttc cttaaaaacg tagcttccag   1740
tttttggtgg ttctggcttc cttcccgatt ccgcccgcta aacgcataat tttgttgcct   1800
ggtggcattt gcaaaatgca taacctatgc atttaaaaga ttatgtatgc tcttctgact   1860
tttcgtgtga tgaggctcgt ggaaaaaatg aataatttat gaatttgaga acaattttgt   1920
gttgttacgg tattttacta tggaataatc aatcaattga ggattttatg caaatatcgt   1980
ttgaatattt ttccgaccct ttgagtactt ttcttcataa ttgcataata ttgtccgctg   2040
cccgtttttc tgttagacgg tgtcttgatc tacttgctat cgttcaacac caccttattt   2100
tctaactatt tttttttag ctcatttgaa tcagcttatg gtgatggcac atttttgcat   2160
aaacctagct gtcctcgttg aacataggaa aaaaaaatat ataaacaagg ctctttcact   2220
ctccttggaa tcagatttgg gtttgttccc tttattttca tatttcttgt catattcttt   2280
tctcaattat tatcttctac tcataacctc acgcaaaata acacagtcaa atcaatctct   2340
agaatgaata acaacaacat tacaccagag tcagactcaa tgaagagtaa cgataacgat   2400
caaaccaatg attacatgcc agatgtggct gatttcgatc atacacaaac aaacacaaac   2460
gaaattgcta gagcaatttc tcacccaggt tctgttctgt caagagttgc aagctacgtc   2520
agcagaaagg acagatacgt agacgagaat ggcaatgaag tttggcaaga cgatgaagtg   2580
agtatcctaa tggaggaaga tgagactcct gatttcacat ggaaaaacat tagacattac   2640
gctatcacta gattcactac attgacagaa cttcacagag tgtctatgga aaacatcaac   2700
ccaattccag aattgagaaa aatgacatta cataattgga actacttctt tatggggtat   2760
gccgcgtggt tgtgtgctgc ttgggcattt ttcgccgttt ccgttagtac agcccctctt   2820
gcaacccttt atggcaagga aacaaaagac atttcatggg gtctatcctt agtcttattc   2880
gtcagatctg ctggagcgat tatctttggc atctggaccg acaattactc cagaaagtgg   2940
ccatacatta catgcttagg tcttttcttg atctgtcagc tttgcacacc ttgggcaaag   3000
acctacactc aattcttggg agttcgttgg atttccggta tcgcaatggg tggaatttac   3060
gcctgtgctt ctgcaacagc gattgaggat gcaccagtaa aggctcgttc tttcttatcc   3120
ggcttattct tcactgccta cgccatgggt tttatcttcg caataatctt ttacagagca   3180
ttcttaaacg tcaacggtga aaactactgg aaggttcaat tctggttttc aatatggtta   3240
ccagctgtac tgatattgtg gagactcgta tggccagaaa ctaagtactt caccaaagta   3300
ctaaaagcta gacaactaat gcgtgatgat gcaatagcca aaaacggtgg tcaaccactc   3360
ccaaagttgt ctttcaagca aaagttcgcc aatgtgaaaa agaccgttag taaatactgg   3420
cttttgtttg gttacttaat tctcttgttg gttggtccta actacctaac acacgcctct   3480
caagacttgt ttcctacaat gttaagagca caattgagat tttctgaaga tgctgtcacc   3540
gtggccattg tagttgtttg tctgggtagc attgctgggg ggatgttttt cggacagttg   3600
atggagatca ctggtagaag agttggccta ctattggccc taatcatggc tggctgcttt   3660
acttaccctg ccttcatgct taaaacttca tctgcagtgc tgggggcagg ctttatgctc   3720
tggttctcaa tcttaggtgt gtggggtgtt ttaccaatcc atttatcaga attgtcccct   3780
```

-continued

```
ccagaagcta gagcattagt ctctggatta gcatatcagc tgggtaatct agcttcagca   3840
gcttctgttg ttatagagaa tgatttggcg gatttgtatc caatagaatg gaattctgct   3900
ggagaagtta caaacaagga ctactctaag gtaatggcta ttcttacagg ttcttcagtc   3960
attttcactt tcgtgttggt tttcgttggt cacgaaaagt ttcatagaga tttgtcatcc   4020
ccacatctta agtcatacat cgagagagtc gatcaaacag aagaggtcgc agctatgact   4080
ggatctactg cgaactctat ctctagtaag ccttcagatg atcagctcga aaaagtttca   4140
gtctagttaa ttaatttacc agcttactat ccttcttgaa aatatgcact ctatatcttt   4200
tagttcttaa ttgcaacaca tagatttgct gtataacgaa ttttatgcta ttttttaat    4260
ttggagttcg gtgatgaaag tgtcacagcg aatttcctca catgtaggga ccgaattgtt   4320
tacaagttct ctgtaccacc atggagacat caaagattga aaatctatgg aaagatatgg   4380
acggtagcaa caagaatata gcacgagccg cggagttcat ttcgttactt ttgatatcgc   4440
tcacaactat tgcgaagcgc ttcagtgaaa aaatcataag gaaaagttgt aaatattatt   4500
ggtagtattc gtttggtaaa gtagaggggg taatttttcc cctttatttt gttcatacat   4560
tcttaaattg ctttgcctct ccttttggaa agctatactt cggagcactg ttgagcgaag   4620
gctcaggccg gcatatgacg ttttattacc tttgatcaca tttccacgcc atttcgcatt   4680
ctcaccctca taagtcatac accgaaaaga aagtttaagg gatcaatgag cttactataa   4740
tctcagtata tttattttta tcgatgattc accacaacaa tcttgctccc gaaaagaaag   4800
cagacggagt agaagcattt gaaactcctt cagaccttca agtatatata tatatatata   4860
tatatgtata tgtgtacatt ttcacgctaa tactaatgta taattagaag ataattttta   4920
ctcatttttc gttatcttca cgtcacccga acctagaacc aaatgtcatt ttcacgatat   4980
gtaaatagtg aaataggcaa aaacgccaaa aagtagtaag cgcaacatac actaaaccat   5040
taaagaatat ctcgaccaga atctaacaga tatacatgtt ccgataatgt ctgagttagg   5100
tgagtattct aaattagaaa acaaagagct tagaacggag tttgaattga caaattttcc   5160
ttttccaggc acaactgata acgactccga tgacggaagc caagggcaga actctttgaa   5220
tatcattact cctgacatgg atgatactct ggttaatgat gtacttcgag aaaacgataa   5280
aaagtctagt atgagaatgg cttttatgaa tctagcaaac tctattcttg gtgccggaat   5340
aattactcag ccgttcgcga tcaaaaatgc tggtatatta ggcgggctat tatcatacgt   5400
agccctcgga tttatagttg attggacgtt aagacttatt gtcattaact tgactcttgc   5460
tggcaagaga acataccagg gtacggtcga acatgtaatg ggtaaaaaag ggaaattgct   5520
gattctattt acaaacgggt tatttgcatt tggtggatgt attgg                   5565
```

GENETICALLY MODIFIED LACTATE-CONSUMING YEASTS AND FERMENTATION PROCESSES USING SUCH GENETICALLY MODIFIED YEASTS

CROSS-REFERENCE TO RELATED APPLICATIONS

This application is a national phase application of PCT/US2017/051720, filed Sep. 15, 2017, entitled GENETICALLY MODIFIED LACTATE-CONSUMING YEASTS AND FERMENTATION PROCESSES USING SUCH GENETICALLY MODIFIED YEASTS, which claims the benefit of U.S. Provisional Patent Application No. 62/395,792, filed Sep. 16, 2016, entitled GENETICALLY MODIFIED LACTATE-CONSUMING YEASTS AND FERMENTATION PROCESSES USING SUCH GENETICALLY MODIFIED YEASTS, each of which is hereby incorporated by reference herein in its entirety.

SEQUENCE LISTING

The entire contents of the ASCII text file entitled "N00478_ST25.txt," created on Sep. 15, 2017, and having a size of 506 kilobytes, is incorporated herein by reference in its entirety.

BACKGROUND OF THE INVENTION

Industrial yeast fermentation processes often use corn process streams, for example corn steepwater, as a fermentation substrate. These process streams contain starches that can be converted to sugars via treatment with saccharification enzymes. In current fermentation processes, gluconse or other sugars serve as the carbon source for fermentation. However, such process streams can contain a significant amount of lactate which cannot be efficiently used as a carbon source by yeasts, especially in the presence of gluconse.

SUMMARY OF THE INVENTION

Described herein are genetically modified yeasts that can consume lactate during fermentation. In one aspect, the yeasts can use lactate as a carbon source to form a fermentation product. In one aspect, the yeasts can consume lactate and gluconse simultaneously during a fermentation process to produce a fermentation product. In some embodiments, the fermentation product is ethanol (EtOH). In some embodiments, the yeast is a genetically modified *Saccharomyces cerevisiae* yeast. In some embodiments, the yeast is transformed to express a heterologous monocarboxylate/proton symporter, e.g., a JEN1 symporter. In some embodiments, the yeast is transformed to express one or more heterologous genes encoding a lactate dehydrogenase (cytochrome) (EC 1.1.2.3 or 1.1.2.4).

In one aspect, the genetically modified yeast comprises a heterologous gene encoding a monocarboxylic/monocarboxylate transporter and one or more heterologous genes encoding lactate dehydrogenase (cytochrome) (classified as EC 1.1.2.3 or 1.1.2.4), wherein the yeast is capable of consuming lactate and producing ethanol when the yeast is present in a fermentation medium comprising lactate and hexose. In some embodiments, the yeast is capable of consuming D-lactate, L-lactate, or a mixture thereof. In some embodiments, the yeast is capable of consuming both D-lactate and L-lactate. In some embodiments, the yeast has a L-lactate consumption rate of at least 0.030, 0.035, 0.040, 0.045, or 0.050 g $L^{-1}h^{-1}$ when the concentration of hexose in the fermentation medium is 150 g/L or greater. In some embodiments, the yeast has a L-lactate consumption rate of at least 0.015, 0.020, 0.025, 0.030, 0.035, or 0.040 $gL^{-1}h^{-1}$ when the concentration of hexose in the fermentation medium is 5 g/L or greater. In some embodiments, the yeast has a D-lactate consumption rate of at least 0.005, 0.006, 0.007, 0.008, 0.009, 0.010, 0.015, 0.020, 0.025, or 0.030 $gL^{-1}h^{-1}$ when the concentration of hexose in the fermentation medium is 150 g/L or greater. In some embodiments, the yeast has a D-lactate consumption rate of at least 0.015, 0.020, 0.025, 0.030, 0.035, or 0.040 $gL^{-1}h^{-1}$ when the concentration of hexose in the fermentation medium is 5 g/L or greater. In some embodiments, the lactate consumption rate of D-lactate, L-lactate, or total lactate for the yeast is determined according to the "Evaluation Protocol for Lactate Consumption" described later herein.

In some embodiments, the yeast has a total lactate consumption rate (i.e., consumption of both D- and L-lactate) of at least 0.550, 0.555, 0.600 or 0.650 $gL^{-1}h^{-1}$ between time 0 and 7 hours in a simultaneous saccharification fermentation (SSF) process. In some embodiments, the yeast has a total lactate consumption rate of at least 0.130, 0.140, 0.150, 0.160, or 0.170 $gL^{-1}h^{-1}$ between time 7 hours and 48 hours in a SSF process. In some embodiments, the yeast has a total lactate consumption rate of at least 0.200, 0.210, 0.220, 0.230, 0.240, or 0.250 $gL^{-1}h^{-1}$ between time 0 and 48 hours in a SSF process. In some embodiments, the total lactate consumption rate is determined according to the method for SSF shake flask assay in Example 4 described later herein.

In one aspect, the one or more heterologous lactate dehydrogenase (cytochrome) genes comprise an overexpressed D-lactate dehydrogenase (DLD) gene (EC 1.1.2.4). In one aspect, the one or more heterologous lactate dehydrogenase (cytochrome) genes comprise an overexpressed cytochrome b2 (CYB2) gene (EC 1.1.2.3). In some embodiments, the one or more heterologous lactate dehydrogenase (cytochrome) genes comprise an overexpressed DLD gene and an overexpressed CYB2 gene. In some embodiments, the one or more DLD genes is from the yeast genus of *Saccharomyces, Issatchenkia*, and/or *Kluyveromyces*. In some embodiments, the one or more DLD genes encodes for a DLD polypeptide having an amino acid sequence with a sequence identity of at least 90 or 95% to the DLD polypeptide from one or more of the following yeast species: *Saccharomyces cerevisiae, Issatchenkia orientalis, Saccharyomyces kluyveri, Saccharyomyces bayanus, Kluyveromyces dobzhanskii, Kluyveromyces marxianus*, or *Kluyveromyces lactis*. In some embodiments, the yeast encodes for a polypeptide having an amino acid sequence with a sequence identity of at least 50%, 55%, 65%, 70%, 75%, 80%, 85%, 90%, 95%, 97%, or 99% to any one of the following amino acid sequences: SEQ ID NO: 40, SEQ ID NO: 42, SEQ ID NO: 64, SEQ ID NO: 66, SEQ ID NO: 68, SEQ ID NO: 70, SEQ ID NO: 72, or SEQ ID NO: 74.

In some embodiments, the one or more CYB2 genes is from the yeast genus of *Saccharomyces, Issatchenkia, Zygosaccharomyces*, and/or *Kluyveromyces*. In some embodiments, the one or more CYB2 genes encodes for a CYB2 polypeptide having an amino acid sequence with a sequence identity of at least 90 or 95% to the CYB2 polypeptide from one or more of the following yeast species: *Saccharomyces cerevisiae, Issatchenkia orientalis, Saccharyomyces kluyveri, Saccharyomyces bayanus, Zygosaccharomyces rouxii, Kluyveromyces dobzhanskii*, or *Kluyveromyces lactis*. In some embodiments, the yeast encodes for a polypeptide having an amino acid sequence with a sequence identity of at least 50%, 55%, 65%, 70%, 75%, 80%, 85%, 90%, 95%, 97%, or 99% to any one of the following amino acid sequences: SEQ ID NO: 15, SEQ ID NO: 17, SEQ ID NO: 54, SEQ ID NO: 56, SEQ ID NO: 58, SEQ ID NO: 60, or SEQ ID NO: 62.

In one aspect, the yeast comprises heterologous genes other than a DLD, a CYB2, or a heterologous monocarboxylate/proton symporter. In some embodiments, the yeast comprises a heterologous gene encoding a lactate racemase.

In one aspect, the genetically modified yeast comprises a heterologous gene encoding a monocarboxylate/proton symporter (JEN1) and a heterologous gene encoding glucoamylase, wherein the yeast is capable of consuming lactate and producing ethanol when the yeast is present in a fermentation medium comprising lactate, and further comprising hexose, starch, or a combination thereof. In one aspect, any of the above yeasts be transformed with a heterologous glucoamylase gene. In some embodiments, the yeast can encode for a glucoamylase from *Saccharomycopsis fibuligera* or *Rhizopus oryzae*. In some embodiments, the yeast encodes for a glucoamylase polypeptide having at least 80%, 85%, 90%, or 95% sequence identity to the wild type glucoamylase polypeptide from *Saccharomycopsis fibuligera*. Embodiments of glucoamylase polypeptides that can be encoded by the yeast, and also the DNA sequences encoding such peptides that can be integrated in the yeast, are further described in International Patent Application No. PCT/US17/045493, filed 4 Aug. 2017, which is hereby incorporated by reference in its entirety, including all SEQ IDs associated therewith.

In one aspect, the host yeast that is genetically modified is of the species *Saccharomyces*. In some embodiments, the host yeast is *Saccharomyces cerevisiae*. In some embodiments, the genetically modified yeast comprises a *Saccharomyces cerevisiae* yeast, wherein the yeast comprises a heterologous gene encoding a monocarboxylate/proton symporter (e.g., JEN1). In some embodiments, the host yeast is a *Saccharomyces cerevisiae* yeast that is commercially available for use in ethanol production, such as ETHANOL RED™ yeast, which at the time of this disclosure is available from Lesaffre or a subsidiary thereof.

In one aspect, the yeast is capable of producing ethanol at a fermentation production rate of at least 1.0 g $L^{-1}$ $h^{-1}$, 2.0 g $L^{-1}$ $h^{-1}$, 3.0 g $L^{-1}$ $h^{-1}$, 3.3 g $L^{-1}$ $h^{-1}$, or 3.75 g $L^{-1}$ $h^{-1}$. In one aspect, the yeast is capable of producing ethanol at a titer greater than 80 g/L, 90 g/L, 100 g/L, 110 g/L, 120 g/L, 125 g/L 130 g/L, 135 g/L, 140 g/L, 145 g/L, 150 g/L, 155 g/L, 160 g/L, or 165 g/L. In one aspect, the yeast is (a) capable of producing ethanol at a titer of greater than 90 g/L, 100 g/L, 110 g/L, 120 g/L, 130 g/L, or 140 g/L; (b) thermotolerant at temperatures in the range of 33° C. to 40° C., 33° C. to 39° C., 33° C. to 38° C., 33° C. to 37° C., 34° C. to 37° C., 35° C. to 37° C., or 36° C. to 38° C.; or both (a) and (b).

In one aspect, the heterologous gene encoding a monocarboxylic/monocarboxylate transporter is from a yeast of the genus *Kluyveromyces*. In some embodiments, the heterologous gene encoding a monocarboxylic/monocarboxylate transporter is from *Kluyveromyces lactis*. In some embodiments, the yeast encodes for a polypeptide having an amino acid sequence with a sequence identity of at least 50%, 55%, 65%, 70%, 75%, 80%, 85%, 90%, 95%, 97%, or 99% to any one of the following amino acid sequences: SEQ ID NO: 24, SEQ ID NO: 26, SEQ ID NO: 28, SEQ ID NO: 76, or SEQ ID NO: 78. In some embodiments, the yeast comprises one or more of the following residues at the indicated positions in SEQ ID NO: 15, SEQ ID NO: 17, SEQ ID NO: 54, SEQ ID NO: 56, SEQ ID NO: 58, SEQ ID NO: 60, or SEQ ID NO: 62: Lys349, Tyr143, Tyr254, and His373. In one aspect, yeast is used for the production of ethanol or a bioproduct other than ethanol.

In one aspect, the present disclosure relates to fermentation processes using a genetically modified yeast, for example any of the genetically modified yeasts described above. In some embodiments, the process is any process for fermenting a medium to produce ethanol using such genetically modified yeasts. In some embodiments, the process is a continuous fermentation process for manufacturing ethanol comprising: providing a fermentation medium comprising hexose or hexose oligomers, fermenting the fermentation medium with a genetically modified yeast comprising a heterologous monocarboxylate/proton symporter (JEN1) gene, adding one or more feed streams comprising lactate to the fermentation medium, and removing at least one output stream comprising ethanol from the fermentation medium, wherein the average hexose or hexose oligomer concentration of the fermentation medium is at least 5 g/L, the volumetric oxygen uptake rate of the process is at least 0.5 mmol $O_2$/(L·h), and the process produces ethanol at an overall rate of at least 1.0 g $L^{-1}$ $h^{-1}$, and the yeast consumes lactate, wherein the at least one output stream contains less than 90% of the lactate added in the one or more feed streams. In some embodiments, the lactate concentration of one or more feed streams has an average lactate concentration of at least 1 g/L. In some embodiments, the feed stream is a vegetable process stream. In some embodiments, the vegetable process stream is a corn process stream or a wheat process stream. In some embodiments, the ethanol titer at the end of the pre-fermenter step is in the range of 20 to 80 g/L. In some embodiments, the lactate consumption rate in the propagator step and/or pre-fermenter step is at least 0.550, 0.600, or 0.650 g $L^{-1}$ $h^{-1}$. In some embodiments, the ethanol titer of the at least one output stream is at least 90, 100, 110, 120, 130, 140, 150, or 160 g/L.

In some embodiments, the process is a process for manufacturing ethanol comprising: fermenting a medium using a genetically modified yeast comprising a heterologous monocarboxylate/proton symporter (JEN1) gene, wherein the medium comprises gluconse or gluconse oligomers at a concentration of at least 5 g/L at the start of fermentation, the lactate content of the medium is at least 1 g/L at the start of fermentation, at least 35, 40, 45, 50% or more of the lactate is consumed at the end of fermentation, and the final ethanol titer is at least 90 g/L. In some embodiments, the process has a volumetric oxygen uptake rate (OUR) is at least 0.5, 1, 2, 3, 4, 5, 6, 7, 8, 9, 10, 20, 50, or 100 mmol $O_2$/(L·h).

In one aspect, the lactate can be L-lactate, D-lactate, or a mixture thereof. In some embodiments, the pH of the fermentation medium is in the range of about 2 to 7. In some embodiments, the fermentation temperature is in the range of 25 to 45° C., 25 to 40° C., 25 to 35° C., 25 to 30° C., 30 to 45° C., 30 to 40° C., 25 to 38° C., 28 to 38° C., or 30 to 39v° C. In some embodiments, the final ethanol titer of the process is at least 80, 90, 100, 110, 120, 130, 135, 140, 145, 150, 155, or 160 g/liter.

In some embodiments, the dry solids of the fermentation medium is at least 30, 40, 50, 60, 70, or 80 g/L in the fermentation medium. In some embodiments, the dry solids of the fermentation feed is at least 120, 130, 140, or 150 g/L.

In one aspect, the process is a process for manufacturing ethanol comprising: fermenting a medium using a *Saccharomyces cerevisiae* yeast, for example Ethanol Red™ yeast (commercially available from Lesaffre), wherein the medium comprises gluconse or gluconse oligomers and lactate, the OUR is at least 0.5, 1, 2, 3, 4, 5, 6, 7, 8, 9, or 10 mmol $O_2$/(L·h), the lactate content of the medium is at least 1, 2, 3 or 4 g/L at the start of fermentation, at least 35, 40, 45, or 50% of the lactate is consumed at the end of fermentation, and the final ethanol titer is at least 90 g/L.

In one aspect, the method is a method for producing a genetically modified yeast with improved lactate consumption comprising overexpressing one or more heterologous genes encoding a lactate dehydrogenase (cytochrome) (classified as EC 1.1.2.3 or 1.1.2.4) or a heterologous monocarboxylate/proton symporter, and subjecting the yeast to evolution for a characteristic, wherein the yeast is capable of consuming lactate and producing ethanol when the yeast is present in a fermentation medium comprising lactate and gluconse. In some embodiments, the characteristic is increased growth rate of the yeast on lactate and/or increased ethanol production of the yeast in the presence of lactate.

In one aspect, in any of the above methods or processes or yeasts, the yeast encodes for a polypeptide having an amino acid sequence with a sequence identity of at least 50%, 55%, 65%, 70%, 75%, 80%, 85%, 90%, 95%, 97%, or 99% to any one of the following amino acid sequence: SEQ ID NO: 24, SEQ ID NO: 26, SEQ ID NO: 28, SEQ ID NO: 76, or SEQ ID NO: 78. In some embodiments, the yeast comprises one or more of the following residues at the indicated positions in SEQ ID NO: 15, SEQ ID NO: 17, SEQ ID NO: 54, SEQ ID NO: 56, SEQ ID NO: 58, SEQ ID NO: 60, or SEQ ID NO: 62: Lys349, Tyr143, Tyr254, and His373.

In one aspect, in any of the above methods or processes or yeasts, the yeast includes a heterologous nucleic acid regulatory sequence associated with the heterologous gene encoding a monocarboxylic/monocarboxylate transporter. In some embodiments, the heterologous nucleic acid regulatory sequence comprises the ADH1 promoter. In some embodiments, the heterologous nucleic acid regulatory sequence comprises the ADH2 promoter, the PDC1 promoter, or the GPD1 promoter.

In one aspect, the genetically modified yeasts are suitable for ethanol production at a commercially acceptable performance. Accordingly, in any of the above embodiments, the yeast and processes using the yeast are associated with commercially relevant final ethanol titers, ethanol titers at the end of fermentation, or process streams or materials removed from the process having ethanol concentrations of at least 90, 100, 110, 120, 130, 140, 150, or 160 g/L. Further, in some embodiments, any of the above yeasts has a D-, L-, and/or total lactate consumption rate that is greater than a yeast without a heterologous gene encoding a monocarboxylic/monocarboxylate transporter.

In one aspect, any of the genetically modified yeasts comprising a heterologous gene encoding a monocarboxylic/monocarboxylate transporter described above or elsewhere herein are described as capable of consuming lactate and producing ethanol while glucose is present, i.e., while in a fermentation medium comprising glucose. In some embodiments, the fermentation medium comprises a measurable, non-zero concentration of glucose. However, it is contemplated herein that in some embodiments, the gluconse concentration of the fermentation medium may not be practically measurable because the gluconse may be added to the fermentation medium or otherwise generated within the fermentation medium from gluconse oligomers in such a manner that the yeast present in the fermentation medium will consume the gluconse immediately. Therefore, it is to be understood that a "fermentation medium comprising gluconse" can include a fermentation medium wherein the gluconse is not practically measurable due to the gluconse being consumed by the yeast as soon as it is generated or added to the fermentation medium.

It is also to be understood that the elements or aspects of any embodiment of the processes, methods, or compositions described above can be applied to any other embodiment, as would be understood by a person skilled in the art.

BRIEF DESCRIPTION OF THE DRAWINGS

The following detailed description of the invention will be better understood when read in conjunction with the appended drawings. It should be understood, however, that the invention is not limited to the precise arrangements and instrumentalities of the embodiments shown in the drawings.

FIG. 1, comprising

FIG. 2, comprising

FIG. 3, comprising

FIGS. 4A and 4B, is a set of graphs showing D,L-lactate consumption and ethanol production in simultaneous saccharification fermentation (SSF) shake flask assays for *Saccharomyces cerevisiae* reference strains (1 and 1-10) and a strain containing an overexpressed CYB2b and a JEN1 (1-25).

FIGS. 5A and 5B, is a set of graphs showing D,L-lactate consumption and ethanol production in SSF shake flask assays for *Saccharomyces cerevisiae* reference strains (1 and 1-10) and a strain containing two copies of both an overexpressed ScCYB2 and a K1JEN1 (1-41).

DETAILED DESCRIPTION

Figures 1A, 1B:
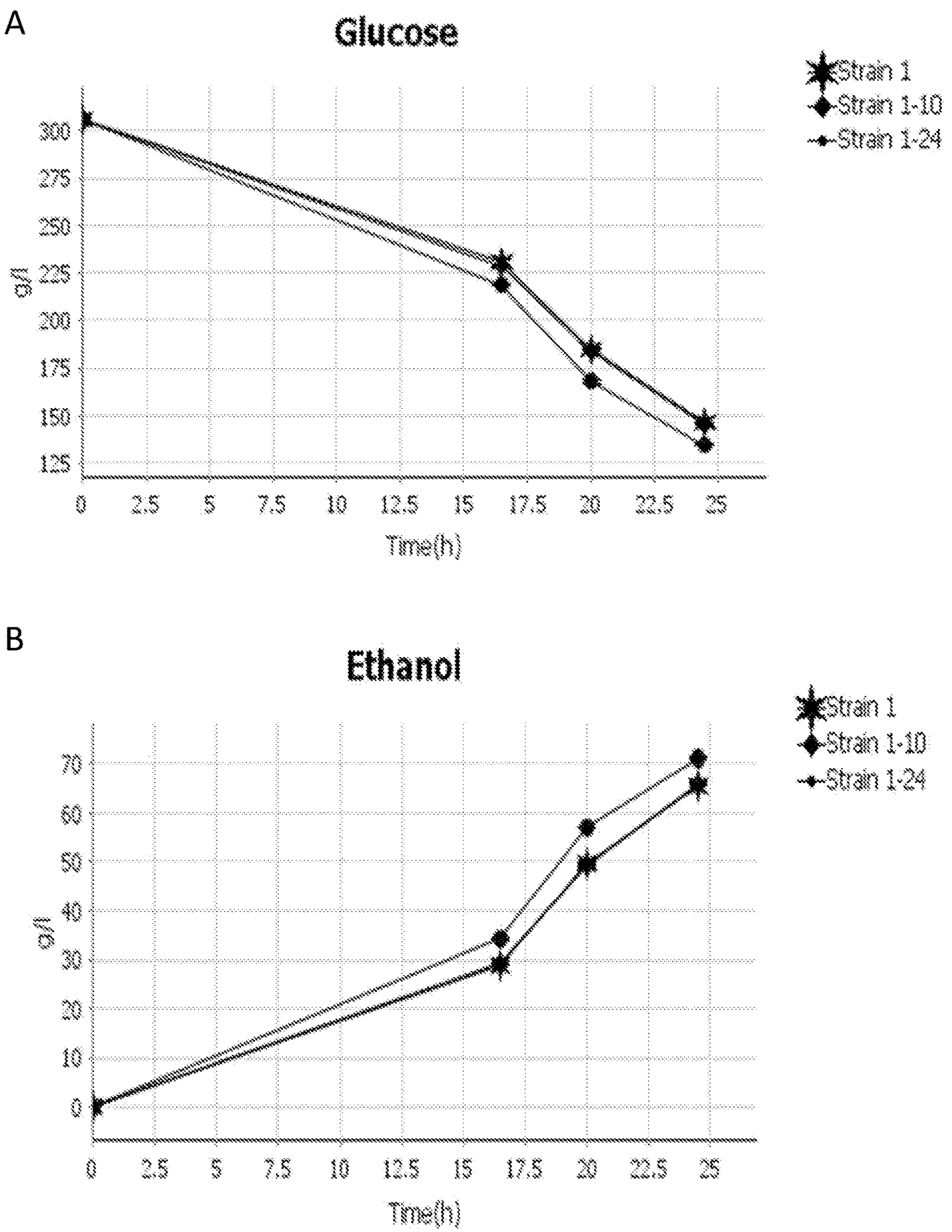
FIGS. 1A through 1C, is a set of graphs showing gluconse consumption, ethanol production, and L-lactate consumption in fermentation shake flask assays for *Saccharomyces cerevisiae* reference strains (1 and 1-10) and a strain containing an overexpressed CYB2 and JEN1 (1-24).

It is to be understood that the figures and descriptions of the present invention provided herein have been simplified to illustrate elements that are relevant for a clear understanding of the present invention, while eliminating other elements found in the related field(s) of art. Those of ordinary skill in the art would recognize that other elements or steps may be desirable or required in implementing the present invention. However, because such elements or steps are well known in the art or do not facilitate a better understanding of the present invention, a discussion of such elements or steps is not provided herein.

Definitions

Unless defined otherwise, all technical and scientific terms used herein have the same meaning as commonly understood by one skilled in the art to which this invention belongs. As used herein, each of the following terms has the meaning associated with it as defined in this section.

As used herein, the terms "genetically modified," "genetically engineered," and the like refer to the altering of the genetic material of an organism in any way using any genetic engineering technique, including techniques using clustered regularly interspaced short palindromic repeats (CRISPR) and CRISPR-associated proteins, i.e., CRISPR/cas systems.

As used herein, "inoculation" is defined as the point in time wherein a microorganism capable of producing a fermentation product is introduced into a fermentation medium.

The terms "bioproduct," "fermentation product," and the like are used interchangeably herein and refer to a compound or mixture of compounds produced by an organism via fermentation of a carbon source.

As used herein, "end of fermentation" is defined as the point in time where a fermentation process meets a predetermined endpoint criteria. The predetermined endpoint criteria can include any of the following: a predetermined time interval, exhaustion of the desired fraction of carbon source supplied, cessation of carbon source consumption, or cessation of fermentation product formation. In one embodiment, "end of fermentation" is defined as the point in time where harvesting of the bioproduct is started. As would be understood by a person skilled in the art, "end of fermentation" can refer to a point in time that is different depending on the scale and purpose of the fermentation process. For a large-scale production fermentation process, the "end of fermentation" is preferably the point at which harvesting of the bioproduct is started, i.e., after product formation has effectively stopped. As would be understood by a person skilled in the art, the endpoint criteria for a batch process applies to the entire batch, whereas the endpoint criteria for a continuous process may apply to only a portion of the process, for example a single vessel or unit operation associated with the process, e.g., the process step associated with the pre-fermenter, or may apply to the entire continuous process, i.e., to an output parameter of the continuous process.

As used herein, "cell dry weight" refers to the concentration of dry cell mass present in a fermentation medium at the time of measurement, as measured in a fermentation sample. Cell dry weight is commonly expressed in units of grams/liter (g/L).

As used herein, "cell dry weight at inoculation" refers to the concentration of dry cell mass present in a fermentation medium immediately following inoculation, as measured in a fermentation sample. For fed-batch fermentations, the initial cell dry weight is calculated based on the final volume of fermentation medium. Measurement of dry cell weight is a method known to those skilled in the art. Cell dry weight at inoculation is commonly expressed in units of g/L.

As used herein, "cell dry weight at end of fermentation" refers to the concentration of dry cell mass present in a fermentation medium at the end of fermentation, as measured in a fermentation sample. Cell dry weight at end of fermentation is commonly expressed in units of g/L.

As used herein, "final titer" refers to the concentration of a substance in the fermentation broth at the end of fermentation. The final titer is commonly expressed in units of g/L.

As used herein, "initial titer" refers to the concentration of a substance present at inoculation. The initial titer is commonly expressed in units of g/L.

As used herein, "batch time" refers to the amount of time that has elapsed between the inoculation and the end of fermentation. The batch time is commonly expressed in units of hours (h).

As used herein, "fermentation production rate" for a batch process refers to the final titer minus initial titer of fermentation product (final titer minus initial titer) divided by the batch time. The production rate is commonly expressed in units of grams per liter-hour ($g\ L^{-1}\ h^{-1}$). When applied to a continuous or semi-continuous process, the "fermentation production rate" is determined using methods known in the art.

As used herein, the "specific production rate" refers to the fermentation production rate divided by the cell dry weight at the end of fermentation. The specific production rate is commonly expressed in units of (g product) $(g\ cells)^{-1}\ h^{-1}$. When applied to a continuous or semi-continuous process, the "specific production rate" is determined using methods known in the art.

As used herein, "product yield" of a fermentation product refers to a ratio of two quantities: a) mass of product (e.g., ethanol) produced in the course of the fermentation (numerator) b) the mass of carbon source added to the fermentation (denominator). The product yield as a percentage is commonly expressed in units of gram per gram (g/g) times 100. Particular note should be taken that product yield is calculated as a ratio of masses. The mass of fermentation product produced should account for the mass of fermentation product present in the fermentation medium at the end of the batch, as well as the mass of any fermentation product harvested during the course of the batch, less the mass of fermentation product present at the start of batch, and further less the mass of any fermentation product added during the course of the batch. The mass of carbon source added to the batch should include the mass of all carbon source(s) present in the fermenter at the start of the batch in addition to the mass of any carbon source(s) added during the course of the batch.

As used herein, "oxygen uptake rate" ("OUR") refers to the volumetric rate at which oxygen is consumed during a fermentation. Inlet and outlet oxygen concentrations can be measured with exhaust gas analysis, for instance by mass spectrometers. OUR can be calculated by one of ordinary skill in the relevant arts using the Direct Method described in Bioreaction Engineering Principles 2nd Edition, 2003, Kluwer Academic/Plenum Publishers, p. 449, equation 1, which is hereby incorporated by reference. Volumetric OUR is commonly measured in units of $(mmol\ O_2)\ L^{-1}\ h^{-1}$.

As used herein, "specific oxygen uptake rate" refers to the specific rate at which oxygen is consumed during a fermentation. It is calculated as the ratio of the OUR to the measured cell dry weight. Specific OUR is commonly measured in units of $mmol\ O_2$ $(g\ cell\ dry\ weight)^{-1}\ h^{-1}$.

The term "exogenous" as used herein with regard to genetic components means that the genetic component is present in a modified version of a microorganism, but is not present in the genome of a native form of the particular microorganism cell. In some embodiments, the exogenous genetic component can be a modified form of a component that was native to the cell, it can be derived from another organism, it can be a modified form of a component derived from another organism, or it can be a synthetically-derived component. For example, the *Kluyveromyces lactis* JEN1 gene is exogenous when introduced into *S. cerevisiae*. The term “exogenous” as used herein with regard to a molecule means the molecule originates from outside an organism being referenced, e.g., an enzyme that is exogenous to an organism present in a fermentation broth refers to an enzyme that is not produced and/or secreted by the organism present in the fermentation broth.

As used herein, the term “heterologous” refers to a molecule or activity that is from a source that is different than the referenced organism. In some embodiments, a gene that is referred to as heterologous to a referenced organism is a gene not found in the organism. In some embodiments, an activity that is referred to as heterologous to a referenced organism is an activity not typically associated with that organism. For example, a heterologous activity in a referenced organism can include an overexpression of a gene that is found in the organism. In some embodiments, heterologous can refer to the inclusion of multiple copies of a gene that is found in a referenced organism, i.e., more copies than are typically found in the referenced organism. In some embodiments, a heterologous gene can refer to the inclusion of a gene in a different locus than where the gene is found in the native version of a referenced organism.

Inspection of nucleic acid or amino acid sequences for two nucleic acids or two polypeptides will reveal sequence identity and similarities between the compared sequences.

Sequence alignment and generation of sequence identity include global alignments and local alignments which are carried out using computational approaches. An alignment can be performed using BLAST (National Center for Biological Information (NCBI) Basic Local Alignment Search Tool) version 2.2.31 software with default parameters Amino acid % sequence identity between amino acid sequences can be determined using standard protein BLAST with the following default parameters: Max target sequences: 100; Short queries: Automatically adjust parameters for short input sequences; Expect threshold: 10; Word size: 6; Max matches in a query range: 0; Matrix: BLOSUM62; Gap Costs: (Existence: 11, Extension: 1); Compositional adjustments: Conditional compositional score matrix adjustment; Filter: none selected; Mask: none selected. Nucleic acid % sequence identity between nucleic acid sequences can be determined using standard nucleotide BLAST with the following default parameters: Max target sequences: 100; Short queries: Automatically adjust parameters for short input sequences; Expect threshold: 10; Word size: 28; Max matches in a query range: 0; Match/Mismatch Scores: 1, −2; Gap consts: Linear; Filter: Low complexity regions; Mask: Mask for lookup table only. A sequence having an identity score of XX % (for example, 80%) with regard to a reference sequence using the NCBI BLAST version 2.2.31 algorithm with default parameters is considered to be at least XX % identical or, equivalently, have XX % sequence identity to the reference sequence.

As used herein, the terms “lactate,” “lactic acid,” and the like, are used interchangeably unless specifically noted otherwise, and can refer to lactic acid, the conjugate base of lactic acid (lactate), or salts thereof. It is contemplated herein that lactic acid is primarily in the form of the conjugate base when utilized by the organisms described herein, but that the lactic acid or salt forms can also be present and/or utilized by the organisms, as would be understood by a person skilled in the art. Further, “lactate” or “lactic acid” can refer to D-Lactate, L-Lactate, or a mixture thereof. Unless either D- or L-lactate is specifically recited herein, the term “lactate” refers to a mixture of D- and L-enantiomers.

As used herein, the term “hexose” refers to a 6-carbon sugar or a mixture of 6-carbon sugars. In some embodiments, the hexose is gluconse or is a mixture of sugars that includes gluconse. Throughout this disclosure, any description that refers specifically to gluconse alone is also applicable to any hexose or mixture of hexoses.

As used herein, the terms “monocarboxylic transporter,” “monocarboxylate transporter,” “monocarboxylate/proton symporter,” “monocarboxylic acid permease,” “monocarboxylate permease,” “carboxylic acid permease,” and the like are used interchangeably, and refer to transporters that carry monocarboxylate molecules, such as lactate and pyruvate, across cell membranes.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 7 should be considered to have specifically disclosed subranges such as from 1 to 3, from 1 to 4, from 1 to 6, from 2 to 5, from 3 to 5, etc., as well as individual numbers within that range, for example, 1, 2, 3, 3.6, 4, 5, 5.8, 6, 7, and any whole and partial increments in between. This applies regardless of the breadth of the range.

Description

Described herein are genetically modified organisms, methods for producing such organisms, and fermentation processes using such organisms. The organisms can consume lactate during a fermentation process while producing a bioproduct. In one aspect, the organisms can consume lactate in the presence of gluconse while producing a bioproduct. Therefore, the present invention relates to organisms and processes that can use lactate as a carbon source for fermentation instead of, or in addition to, carbohydrates. Accordingly, the organisms and processes are useful for fermenting substrates containing lactate, such as corn or other vegetable processing streams.

Many fermentation substrate feed streams, including corn process streams, contain some amount of lactate. For example, the growth of lactate-producing *Lactobacilli* is often promoted in the steeping step of wet corn milling processes to assist in the breakdown of the corn into its various components. However, most or all of the lactate remains unconsumed in the fermentation broth in currently available fermentation processes. Therefore, the processes and organisms of the present invention can provide a benefit over currently available processes or organisms by consuming a higher percentage of the available carbon sources in the feed stream, resulting in improved fermentation yields, production rates, and/or efficiency.

Genetically Modified Yeasts and Methods for Producing Such Yeasts

In one aspect, the present invention relates to genetically modified yeasts and methods for producing such yeasts. In some embodiments, the genetically modified yeast is of the genus *Saccharomyces*. In some embodiments, the yeast is a genetically modified *Saccharomyces cerevisiae* yeast. In one aspect, the yeast is genetically modified to include one or more traits that enable the yeast to consume lactate or improve the lactate consumption capability of the yeast while producing a fermentation product. In some embodiments, the yeast can consume lactate at a faster rate than a yeast without the modification(s) described herein, especially when hexose or hexose oligomers such as gluconse are present in the fermentation broth. In some embodiments, the yeast can consume D-lactate, L-lactate, or both D-lactate and L-lactate at a faster rate than a yeast without the modification(s) described herein. In some embodiments, the yeast can produce a bioproduct at a higher titer and/or produce a bioproduct at a faster rate than a yeast without the modification(s) described herein. In some embodiments, the bioproduct is ethanol.

The genetic modifications can include transforming a yeast to contain one or more heterologous genes that relate to lactate consumption or utilization. Non-limiting examples of genetic modifications include: transforming the yeast to overexpress one or more native-type gene(s); transforming the yeast to include multiple copies of one or more native-type gene(s); transforming the yeast with one or more exogenous gene(s); and/or transforming the yeast to include multiple copies of one or more exogenous gene(s).

In one aspect, the genetic modifications can relate to lactate transport, for example transforming a yeast to express a heterologous monocarboxylate/proton symporter gene. In some embodiments, the monocarboxylate/proton symporter gene is from a yeast of the genus *Kluyveromyces*. In some embodiments, the monocarboxylate/proton symporter gene is a *K Lactis* (SEQ ID NO: 27), a *K. marxianus* (SEQ ID NO: 73), or a *K. dobzhanskii* (SEQ ID NO: 71) JEN1 symporter gene. In some embodiments, the monocarboxylate/proton symporter gene is from a yeast of the genus *Yarrowia*, for example *Yarrowia lypolitica* (SEQ ID NO: 79). In some embodiments, the monocarboxylate/proton symporter gene is from a genus of yeast other than genus *Kluyveromyces* or *Yarrowia*, for example, but not limited to, *Saccharomyces* or *Issatchenkia*. In some embodiments, the monocarboxylate/proton symporter gene is from *S. cerevisiae* or *I. orientalis* (SEQ ID NO: 23, SEQ ID NO: 25). In some embodiments, the genetically modified yeast encodes for a polypeptide having an amino acid sequence with a sequence identity of at least 65%, 70%, 75%, 80%, 85%, 90%, 95%, 97%, or 99% to at least one of the following amino acid sequences: SEQ ID NO: 24, SEQ ID NO: 26, SEQ ID NO: 28, SEQ ID NO: 76, or SEQ ID NO: 78. In some embodiments, the yeast encodes for a polypeptide having an amino acid sequence with a sequence identity of at least 70%, 74% or 75% to either the *K. Lactis* (SEQ ID NO: 28) or *K. dobzhanskii* (SEQ ID NO: 76) JEN1 polypeptides, or both.

In some embodiments, the genetic modifications can relate to lactate consumption or utilization. In some embodiments, the yeast is transformed to express one or more heterologous genes encoding a lactate dehydrogenase (cytochrome) (EC 1.1.2.3 or 1.1.2.4). In some embodiments, the yeast is transformed to express a heterologous cytochrome b2 (CYB2) gene. In some embodiments, the CYB2 gene is a *S. cerevisiae* (SEQ ID NO: 13) or *I. orientalis* CYB2 (SEQ ID NO: 16) gene. In some embodiments, the CYB2 gene is from *S. kluyveri* (SEQ ID NO: 53), *S. bayanus* (SEQ ID NO: 55), *Z. rouxii* (SEQ ID NO: 57), *K. lactis* (SEQ ID NO: 59), or *K. dobzhanskii* (SEQ ID NO: 61). In some embodiments, the genetically modified yeast having a heterologous CYB2 gene encodes for a polypeptide having an amino acid sequence with a sequence identity of at least 50%, 55%, 60%, 65%, 70%, 75%, 80%, 85%, 90%, 95%, 97%, or 99% to at least one of the following amino acid sequences: SEQ ID NO: 15, SEQ ID NO: 17, SEQ ID NO: 54, SEQ ID NO: 56, SEQ ID NO: 58, SEQ ID NO: 60, or SEQ ID NO: 62.

In some embodiments, the yeast is transformed to express a heterologous D-lactate dehydrogenase (DLD) gene. In some embodiments, the DLD gene is a *S. cerevisiae* (SEQ ID NO: 39) or *I. orientalis* DLD (SEQ ID NO: 41) gene. In some embodiments, the DLD gene is from *S. kluyveri* (SEQ ID NO: 63), *S. bayanus* (SEQ ID NO: 65), *A. fumigatus* (SEQ ID NO: 67), *K. lactis* (SEQ ID NO: 69), *K. dobzhanskii* (SEQ ID NO: 71), or *K. marxianus* (SEQ ID NO: 73). In some embodiments, the genetically modified yeast having a heterologous DLD gene encodes for a polypeptide having an amino acid sequence with a sequence identity of at least 50%, 55%, 60%, 65%, 70%, 75%, 80%, 85%, 90%, 95%, 97%, or 99% to at least one of the following amino acid sequences: SEQ ID NO: 40, SEQ ID NO: 42, SEQ ID NO:64, SEQ ID NO: 66, SEQ ID NO:68, SEQ ID NO: 70, SEQ ID NO: 72, or SEQ ID NO: 74. In some embodiments, the yeast is transformed to express both a heterologous CYB2 gene and a DLD gene.

In one aspect, the genetically modified yeast can be transformed to include any combination of heterologous monocarboxylate/proton symporter genes and lactate dehydrogenase genes. In some embodiments, the yeast contains a heterologous monocarboxylate/proton symporter gene, a heterologous CYB2 gene, and a heterologous DLD gene. In some embodiments, the yeast contains a heterologous monocarboxylate/proton symporter gene and a heterologous CYB2 gene. In some embodiments, the yeast contains a heterologous monocarboxylate/proton symporter gene and a heterologous DLD gene. In some embodiments, the yeast contains more than one copy of any of a heterologous monocarboxylate/proton symporter gene, a heterologous CYB2 gene, and/or a heterologous DLD gene, i.e., the yeast can be transformed with two or more copies of a heterologous monocarboxylate/proton symporter gene; two or more copies of a heterologous CYB2 gene; and/or two or more copies of a heterologous DLD gene. Further, the yeast can be modified to contain heterologous genes from any combination of species, for example, a *S. cerevisiae* yeast can be modified to contain one or more copies of a *K. lactis* JEN1, one or more copies of a heterologous *S. cerevisiae* CYB2, and one or more copies of a heterologous *S. cerevisiae* DLD. Accordingly, the yeast can encode for a polypeptide having an amino acid sequence with a sequence identity of at least 50%, 55%, 60%, 65%, 70%, 75%, 80%, 85%, 90%, 95%, 97%, or 99% to one, two, three, or more of a monocarboxylate/proton symporter-related, CYB2-related, and/or DLD-related amino acid sequence, for example at least one of SEQ ID NO: 24, SEQ ID NO: 26, SEQ ID NO: 28, SEQ ID NO: 76, SEQ ID NO: 78, SEQ ID NO: 15, SEQ ID NO: 17, SEQ ID NO: 54, SEQ ID NO: 56, SEQ ID NO: 58, SEQ ID NO: 60, SEQ ID NO: 62, SEQ ID NO: 40, SEQ ID NO: 42, SEQ ID NO:64, SEQ ID NO: 66, SEQ ID NO:68, SEQ ID NO: 70, SEQ ID NO: 72, or SEQ ID NO: 74.

While not wishing to be bound by theory, it is contemplated herein that the lactate consumed by the organism is converted primarily to pyruvate, and at least a portion of the pyruvate is converted to the desired fermentation product. Even lactate that is consumed by the organism for respiration can provide a benefit because the organism is using lactate instead of other potentially preferred carbon sources such as gluconse.

Strains of *Saccharomyces cerevisiae* that can consume D-lactate and produce ethanol have been described (Wakamatsu et al., 2013, Biosci. Biotechnol. Biochem. 77(5) 1114-1116). However, the strains described in Wakamatsu produced ethanol from a fermentation medium containing only lactate, and not from a medium that also contains gluconse. Further, Andrade described that JEN1 expression is inhibited by the presence of gluconse (Andrade et al., 2001, Fungal Genetics and Biology 32, 105-111). Therefore, currently available yeast strains cannot consume significant amounts of lactate and gluconse simultaneously while producing a fermentation product at a commercially useful rate. Further, it is known that many yeasts produce some lactic acid rather than consuming lactic acid during fermentation. However, the present invention relates to genetically modified yeasts that can surprisingly use both lactate and gluconse as a carbon source simultaneously to produce a fermentation product at rates suitable for commercial applications. In one aspect, the genetically modified yeast can consume L-lactate at significantly higher rates than currently available yeast, whether or not gluconse or another hexose is present.

In one aspect, the yeast can be genetically modified to consume D-lactate, L-lactate, or a mixture of D- and L-lactate. Vegetable processing streams that contain lactate typically contain a mixture of D-lactate and L-lactate enantiomers, for example a racemic mixture or a mixture containing some ratio of D- and L-lactate other than 50:50. In one aspect, the yeast can be genetically modified to contain a heterologous lactate racemase-expressing gene. A yeast that contains a racemase expressing gene can be used to improve the lactate-consuming characteristics of the yeast. For example, a genetically modified yeast according to the present invention that can consume D-lactate more quickly than L-lactate can be modified to express a lactate racemase. As the D-lactate is consumed more quickly by the yeast, the racemase can be used to convert L-lactate to D-lactate to improve the overall rate of lactate consumption.

As described above, the yeast can include heterologous JEN1, DLD, and/or CYB2 gene(s), resulting in encoding polypeptides having a minimum sequence identity to certain amino acid sequences listed herein. In some embodiments, signature patterns at positions corresponding to specific residue ranges have been identified. In some embodiments, the yeast of the present invention is transformed with a construct having these patterns conserved. Accordingly, in some embodiments, the yeast can encode for polypeptides having a signature pattern at certain amino acid residue positions.

In one aspect, the genetically modified yeast encodes for a CYB2 protein having the following amino acid residues conserved at the specified positions: Lys349, Tyr143, Tyr254 and His373. Xia describes the involvement of these residues in the catalytic oxidation of lactate to pyruvate (Xia and Mathews, 1990, J. of Molecular Biology. 212 pp. 837-863, which is hereby incorporated by reference in its entirety). In some embodiments, the yeast of the present invention encodes a polypeptide having a sequence identity of at least 40%, 45%, 50%, 55%, 60%, 65%, 70%, 75%, 80%, 85%, 90%, or 95% to SEQ ID NO: 15, SEQ ID NO: 17, SEQ ID NO: 54, SEQ ID NO: 56, SEQ ID NO: 58, SEQ ID NO: 60, or SEQ ID NO: 62, that includes one or more of the following amino acid residues at the indicated positions: Lys349, Tyr143, Tyr254 and His373. The amino acids Lys349, Tyr143, Tyr254 and His373 have a role in the mechanism of lactate oxidation via interaction with pyruvate. In some embodiments, such a yeast includes a heterologous CYB2 gene from any of the following species: *S. bayanus, S. kluyveri, Zygosaccharomyces rouxii, K. lactis, K. dobzhanskii, K. marxianus, I. orientalis, Aspergillus fumigatus*, or *A. niger*. In some embodiments, such a yeast also includes at least one heterologous monocarboxylate/proton symporter gene and encodes for a polypeptide having a sequence identity of at least 50%, 55%, 60%, 65%, 70%, 75%, 80%, 85%, 90%, 95%, or 99% to SEQ ID NO: 24, SEQ ID NO: 26, SEQ ID NO: 28, SEQ ID NO: 76, or SEQ ID NO: 78. In some embodiments, such a yeast also includes at least one heterologous DLD gene and encodes for a polypeptide having a sequence identity of at least 50%, 55%, 60%, 65%, 70%, 75%, 80%, 85%, 90%, 95%, or 99% to SEQ ID NO: 40, SEQ ID NO: 42, SEQ ID NO: 64, SEQ ID NO: 66, SEQ ID NO: 68, SEQ ID NO: 70, SEQ ID NO: 72, or SEQ ID NO: 74.

In one aspect, the genetically modified yeast can consume D-lactate, L-lactate, or a mixture thereof at a faster rate than currently available yeasts. In some embodiments, the genetically modified yeast can consume D-lactate and/or L-lactate, in conditions where currently available yeasts cannot consume D-lactate and/or L-lactate. In one aspect, it is useful to measure the lactate consumption rate according to the Evaluation Protocol for Lactate Consumption described later herein. In some embodiments, the yeast has a L-lactate consumption rate of at least 0.030 $gL^{-1}h^{-1}$ when the concentration of hexose is 150 g/L or greater. In some embodiments, the yeast has a L-lactate consumption rate of at least 0.035, 0.040, 0.045, or 0.050 $gL^{-1}h^{-1}$ when the concentration of hexose is 150 g/L or greater. In some embodiments, the yeast has a L-lactate consumption rate of at least 0.015, 0.020, 0.025, 0.030, 0.035, or 0.040 $gL^{-1}h^{-1}$ when the concentration of hexose is 5 g/L or greater. In some embodiments, the yeast has a D-lactate consumption rate of at least 0.005, 0.006, 0.007, 0.008, 0.009, 0.010, 0.015, 0.020, 0.025, or 0.030 $gL^{-1}h^{-1}$ when the concentration of hexose is 150 g/L or greater. In some embodiments, the yeast has a D-lactate consumption rate of at least 0.015, 0.020, 0.025, 0.030, 0.035, or 0.040 $gL^{-1}h^{-1}$ when the concentration of hexose is 5 g/L or greater.

In some embodiments, the yeast can include other genetic modifications. In one aspect, the yeast can be transformed to express enzymes useful for improving the production of a bioproduct. In one aspect, the yeast can be transformed to contain genes related to expressing enzymes that are typically added to a fermentation process, for example, enzymes used to generate gluconse or another hexose from hexose oligomers. In one aspect, the yeast can be transformed to reduce or eliminate the conversion of the carbon source(s) to undesired compounds. In some embodiments, the yeast can include one or more genetic modifications useful for improving any other aspects of an ethanol production process. Non-limiting examples of genetic modifications that can useful for an ethanol-producing yeast include transforming the yeast to express a heterologous gene for producing glucoamylase (EC 3.2.1.3), for example the yeast expresses a glucoamylase from *Saccharomycopsis fibuligera* or *Rhizopus oryzae*; transforming the yeast to express a heterologous gene for consuming isomaltose; and/or transforming the yeast to reduce the formation of glycerol in the yeast during fermentation. In some embodiments, the yeast can be transformed to secrete a heterologous lactate oxidase. Further, the yeast can be transformed to secrete heterologous catalase in addition to the lactate oxidase to consume hydrogen peroxide.

In some embodiments, the genetic modifications to the yeast associated with increasing the consumption of lactate (e.g., a yeast modified to include a heterologous CYB2 gene, DLD gene, and/or JEN1 gene) can also relate to the reduction of glycerol produced by the yeast during fermentation. The reduction of glycerol produced during fermentation can increase the amount of carbon transformed from the carbon source(s) (e.g., gluconse and/or lactate) into the fermentation product. Accordingly, the yeast can produce a higher yield of a fermentation product, such as ethanol, and generate a lower amount of glycerol than a yeast that does not include the genetic modifications associated with increased lactate consumption.

In some embodiments, the yeast can be further engineered by a method other than genetic modification. In some embodiments, after the yeast is genetically modified as described above, the yeast is evolved. In some such embodiments, the evolution can include propagating the yeast for multiple generations to allow for the yeast to naturally select for certain characteristics.

In some embodiments, the yeast can be modified by mutagenesis. In some such embodiments, the yeast can be selected for certain characteristics after mutagenesis. In some embodiments, the mutagenesis can include subjecting the yeast to ultraviolet radiation and/or chemical treatment. In some embodiments, the selected characteristics of the yeast can include heat tolerance, ethanol tolerance, inhibitor tolerance, improved growth rate, and/or by-product reduction.

Accordingly, in one aspect, the present invention also relates to a method for evolving a yeast that can consume lactate while producing a fermentation product. In some embodiments, the method includes the steps of: transforming a yeast to express one or more heterologous genes associated with increased lactate consumption, then evolving the yeast and selecting the yeast based on a desired characteristic. In some embodiments, the method includes the steps of: transforming a yeast to express one or more heterologous genes associated with increased lactate consumption, exposing the yeast to an environment capable of causing mutagenesis, and selecting the yeast for one or more desired characteristics. In one aspect, the method for evolving the yeast can use any yeast described herein, i.e., a genetically modified yeast transformed to increase lactate consumption during fermentation.

In one aspect, the non-natural yeast of the present invention has the ability to grow, and/or can produce a fermentation product at temperatures that are greater than those in which yeast, for example *Saccharomyces cerevisiae*, typically are used in fermentation processes. For example, *S. cerevisiae* typically have optimal growth at a temperature of about 30° C. In some embodiments, the yeast has a greater tolerance to elevated temperatures, such as 32° C. or greater, such as in the range of greater than 32° C. to about 40° C. Exemplary ranges for elevated temperature are $T_1$ to $T_2$, wherein $T_1$ is selected from 32.2° C., 32.4° C., 32.6° C., 32.8° C., 33° C., 33.2° C., 33.3° C., 33.4° C., 33.6° C., 33.8° C., 34° C., 34.2° C., 34.4° C., 34.6° C., 34.8° C., 35° C., and 36° C.; and $T_2$ is selected from 36° C., 37° C., 38° C., 39° C., and 40° C. For the purposes of this disclosure, a yeast is considered "thermotolerant" if the yeast can continue to grow, reproduce, and/or produce a fermentation product during or after being exposed to a fermentation medium having an elevated temperature.

During a fermentation process the fermentation medium can reach an elevated temperature of 32° C. or greater during one or more time(s) during the fermentation process. The temperature can be elevated during part of the fermentation period, or during the entire fermentation period. The temperature can be elevated for 5 minutes of greater, 10 minutes of greater, 30 minutes or greater, 1 hour or greater, 2 hours or greater, 5 hours or greater, or 10 hours or greater. The time of elevated temperature can also be expressed as a total of the overall fermentation period, such as about 0.1% to 100%, about 0.1% to about 75%, about 0.1% to about 50%, about 0.1% to about 25%, about 0.1% to about 10%, about 0.1% to about 5%, about 0.1% to about 2.5%, about 0.1% to about 1%, or about 0.1% to about 0.5% of the fermentation period.

The engineered yeast can also provide a commercially relevant titer of ethanol during or after the period of elevated temperature. For example, during or after the period of elevated temperature, for example, any of the ranges corresponding to $T_1$ to $T_2$, the ethanol titer can be in the range of about 110 g/L to about 170 g/L, in the range of about 125 g/L to about 170 g/L, or in the range of about 140 g/L to about 170 g/L. Accordingly, the engineered yeast described herein can produce ethanol at a commercially useful titer during or after a period of high temperature that would typically cause issues in other currently available yeast strains used in ethanol-producing fermentation processes. Such issues include but are not limited to: death to a significant percentage of yeast cells; deleterious effects on the ability of the yeast to reproduce; and/or reduction or elimination of the ability of the yeast to produce a fermentation product.

An engineered *S. cerevisiae* described herein can be put under temperature selection pressure to select for strains that demonstrate increased tolerance to growth at higher temperatures. The engineered yeast can be subjected to random mutagenesis (e.g., UV, chemical) prior to application of the higher temperature selection to generate mutation(s) that can confer improved tolerance to growth at these higher temperatures. For example, an engineered yeast of the disclosure can have a specific growth rate at a temperature in the range of 32° C. or greater that that is 10%, 20%, 30%, 40%, or 50% greater than the growth rate of a reference yeast. In some embodiments, the reference yeast is a yeast expressing a *Saccharomycopsis fibuligera* glucoamylase that is capable of producing ethanol at a titer of at least 90 g/L. In one aspect, this disclosure also relates to a method for producing a yeast product suitable for use in a fermentation process. In some embodiments, such a method includes the steps of growing a yeast, for example any of the engineered yeasts described herein, and isolating the yeast from the medium used to grow the yeast. The method can further include the step of drying the yeast to form a yeast product. Drying the yeast can improve the shelf-life of the yeast. In some embodiments, the dried yeast has a moisture content of less than 5%, less than 4%, less than 3%, less than 2%, or less than 1%.

Fermentation Processes

In one aspect, the present invention relates to fermentation processes. In one aspect, the fermentation processes can be any process using an embodiment of the genetically modified yeasts described herein to produce a fermentation product. In some embodiments, the fermentation product is ethanol. In some embodiments, the fermentation product can be an alcohol other than ethanol, for example, but not limited to, n-propanol, iso-propanol, n-butanol, iso-butanol, butadiene, or isoprene.

An exemplary fermentation process can include the steps of providing a fermentation medium that contains a carbon source, adding a yeast to the fermentation medium, fermenting the medium with the yeast to produce a bioproduct, and harvesting the bioproduct. In one aspect, the carbon source in the medium can include starches, sugars, organic acids, or a mixture thereof. In some embodiments, the carbon source in the medium is a mixture of gluconse oligomers, gluconse, and/or lactate.

In one aspect, a lactate-containing vegetable process stream is used as the fermentation medium or is added to the fermentation medium at some point in the fermentation process. In one aspect, the processes of the present invention can be used to ferment a fermentation medium containing a significant amount of lactate in addition to gluconse and/or glucose oligomers. Non-limiting examples of fermentation media containing a significant amount of lactate include media having at least 0.1, at least 0.5, at least 1, at least 2, at least 3, at least 4, or at least 5 g/L lactate. In some embodiments, the fermentation media can have a lactate content in the range of about 1-20, 2-20, 3-20, 4-20, 5-20, 1-15, 3-15, or 5-15 g/L at the start of fermentation. In some embodiments, the fermentation media can have a lactate content in the range of about 1-50, 15-30, or 20-30 g/L at the start of fermentation. For example, in some embodiments, light steep water (LSW) can contain about 25 g/L lactate.

In some embodiments, the processes described herein can be used to consume most or all of the lactate in the fermentation medium. In some embodiments, the processes can be used to consume only a portion of the lactate in the fermentation medium. The consumption of lactate during the process can depend on a number of factors, including, but not limited to: the characteristics of the yeast used; the rate of oxygen added to the process; the amount of oxygen present at the start of fermentation; the glucose concentration in the fermentation medium, pH, and temperature.

In one aspect, as would be understood by a person skilled in the art, the composition of the medium can vary during fermentation. For example, glucose or another hexose can be generated from oligomers during fermentation via enzymatic activity, then consumed. Accordingly, in some embodiments, the glucose content can be very low or even undetectable at some points of the fermentation if glucose is consumed by the yeast faster than it is generated from the gluconse oligomers. In some embodiments, for example fed-batch fermentation, the medium can be continuously or semi-continuously supplemented with a feed stream, such as a vegetable process feed stream. In some embodiments, the lactate content can be very low or even undetectable at some points of the fermentation due to consumption by the yeast, and then more lactate can be added to the medium via a vegetable process feed stream.

Accordingly, in one aspect, the concentrations of various components of the fermentation medium for the processes described herein can be an average concentration. Average concentrations of components can be calculated via known methods in the art, for example by taking the average of the concentration of a component in the fermentation medium at the start of fermentation and the concentration of the same component in the fermentation medium of the end of fermentation. Such a calculation of average can also account for the concentration of the component in any input and/or output streams during the fermentation process. Further, for a continuous fermentation process, the average concentration of a component can refer to the average concentration in any single vessel, or it can refer to the average concentration over the entire process, i.e., accounting for all feed streams and all output streams of the process.

In some embodiments, at least 5%, 10%, 15%, 20%, 25%, 30%, 35%, 35%, 40%, 45%, 50%, 55%, 60%, 65%, 70%, 75%, 80%, 85%, 90%, 95%, or 99% of the lactate present in the fermentation medium and/or added to the fermentation medium is consumed by the end of fermentation. In some embodiments, the rate of lactate consumption during fermentation is in the range of 0.01 to 1.5 g $L^{-1}$ $h^{-1}$, 0.05 to 1 g $L^{-1}$ $h^{-1}$, or 0.1 to 1 g $L^{-1}$ $h^{-1}$. In some embodiments, the rate of lactate consumption during fermentation is at least 0.01 g $L^{-1}$ $h^{-1}$, 0.05 g $L^{-1}$ $h^{-1}$, 0.1 g $L^{-1}$ $h^{-1}$, 0.5 g $L^{-1}$ $h^{-1}$, or 1 g $L^{-1}$ $h^{-1}$. In some embodiments, the rates of lactate consumption listed above can refer to the average lactate consumption during fermentation. In some embodiments, the rates of lactate consumption listed above can refer to the lactate consumption during the first portion of the fermentation process, for example, over the first 10 hours, 8 hours, 6 hours, 4 hours, 2 hours, 1 hours, or 30 min of the fermentation process. In some embodiments, the rates of lactate consumption listed above refer to the rate of lactate consumption when glucose is present. In some embodiments, the glucose concentration is at least 0.1 g/L, 1 g/L, 10 g/L, 20 g/L, or 30 g/L when the rate of lactate consumption during fermentation is at least 0.01 g $L^{-1}$ $h^{-1}$, 0.05 g $L^{-1}$ $h^{-1}$, 0.1 g $L^{-1}$ $h^{-1}$, 0.5 g $L^{-1}$ $h^{-1}$, or 1 g $L^{-1}$ $h^{-1}$.

In some embodiments, the amount of total lactate in the fermentation medium at the end of fermentation is in the range of 0 to 3 g/L, 0 to 1 g/L, 0 to 0.5 g/L, 0 to 0.1 g/L, 0.001 to 3 g/L, 0.001 to 1 g/L or 0.001 to 0.1 g/L. In some embodiments, the amount of total lactate in the fermentation medium at the end of fermentation is less than 3 g/L, 2 g/L, 1 g/L, 0.5 g/L, or 0.1 g/L. In some embodiments, the amount of L-lactate in the fermentation medium at the end of fermentation is in the range of 0 to 3 g/L, 0 to 1 g/L, 0 to 0.5 g/L, 0 to 0.1 g/L, 0.001 to 1 g/L or 0.001 to 0.1 g/L. In some embodiments, the amount of L-lactate in the fermentation medium at the end of fermentation is less than 3 g/L, 2 g/L, 1 g/L, 0.5 g/L, or 0.1 g/L. In some embodiments, the amount of D-lactate in the fermentation medium at the end of fermentation is in the range of 0 to 3 g/L, 0 to 1 g/L, 0 to 0.5 g/L, 0 to 0.1 g/L, 0.001 to 1 g/L or 0.001 to 0.1 g/L. In some embodiments, the amount of D-lactate in the fermentation medium at the end of fermentation is less than 3 g/L, 2 g/L, 1 g/L, 0.5 g/L, or 0.1 g/L.

In one aspect, the process of the present invention can be used to produce ethanol at commercially significant rates and/or titers. In some embodiments, the rate of ethanol produced can be 1 to 6 g $L^{-1}$ $h^{-1}$, 1 to 5.5 g $L^{-1}$ $h^{-1}$, or 1 to 5 g $L^{-1}$ $h^{-1}$. In some embodiments, the ethanol titer at the end of fermentation is at least 90 g/L, 100 g/L, 110 g/L, 120 g/L, 125 g/L, 130 g/L, 131 g/L, 132 g/L, 133 g/L, 134 g/L, or at least 135 g/L. In some embodiments, the ethanol titer at the end of fermentation is in the range of 120 g/L to 155 g/L, 130 to 155 g/L, 135 to 155 g/L, 130 to 150 g/L, or 130 to 140 g/L.

In one aspect, the process can use a yeast other than the genetically-modified yeasts described herein, for example the commercially available ETHANOL RED™ yeast (available from Lesaffre/Fermentis), and the process can be run using a high oxygen uptake rate and/or a lower glucose concentration to promote lactate consumption.

In one aspect, the process can be used to consume L-lactate, D-lactate, or a mixture of L- and D-lactate. In one aspect, the process can include using a lactate racemase to improve the lactate-consuming characteristics of the yeast. In some embodiments, the yeast used in the process can be a genetically-modified yeast that secretes a lactate racemase. In some embodiments, the exogenous lactate racemase can be added to process instead of, or in addition to, lactate racemase secreted by the yeast. Other exogenous enzymes can be added to the process. For example, in some embodiments an exogenous lactate oxidase can be added to the process. In one such embodiment, exogenous catalase can be added to the process to decompose hydrogen peroxide formed by the activity of the exogenous lactate oxidase.

Batch Fermentation Processes

In one aspect, the process of the present invention can be a batch fermentation process. In some embodiments, the batch process of the present invention is a dry-grind or dry-milling ethanol production process. Batch fermentation processes, including dry-grind ethanol processes are well-known in the art. As would be understood by a person skilled in the art, lactate can be formed during the dry milling of corn or other vegetable matter, for example, as a result of bacterial contamination. In one aspect, the genetically modified yeast of the present invention can be used in a batch fermentation process to produce a fermentation product using lactate as a carbon source.

An exemplary batch fermentation process includes the steps of providing a fermentation medium that contains lactate and/or other carbon sources such as carbohydrates and fermenting the medium using a genetically modified yeast of a type described herein. In some embodiments, the yeast contains a heterologous monocarboxylate/proton symporter (e.g., JEN1) gene. In some embodiments, the medium contains glucose or glucose oligomers at concentration of at least 0.5, 1, 2, or 3 g/L at the start of fermentation. In some embodiments, the lactate concentration is at least 0.5, 1, 2, 3, 4, 5, or 6 g/L at the start of fermentation. In some embodiments, the lactate concentration is in the range of 1 to 20 g/L, 1 to 15 g/L, 1 to 10 g/L, 1 to 8 g/L, or 1 to 5 g/L at the start of fermentation. In some embodiments, at least 20, 30, 40, 50, 60, 70, 80, 90, 95, or 99% of the total lactate is consumed at the end of fermentation. In some embodiments, at least 50, 60, 70, 80, 90, 95, or 99% of the D-lactate is consumed at the end of fermentation. In some embodiments, at least 50, 60, 70, 80, 90, 95, or 99% of the L-lactate is consumed at the end of fermentation.

In one aspect, the batch fermentation process is run with a minimum volumetric oxygen uptake rate (OUR) for at least a part of the process. In some embodiments, the OUR is at least 0.5, 1.0, or 1.5 mmol $O_2/(L \cdot h)$ during at least part of the process. In some embodiments, the OUR is in the range of 0.5 to 5.0 mmol $O_2/(L \cdot h)$ during at least part of the process. In some embodiments, the OUR is in the range of 3.5 to 4.5 mmol $O_2/(L \cdot h)$ during at least part of the process. In some embodiments, the OUR is at least 0.5, 1.0, or 1.5 mmol $O_2/(L \cdot h)$ for the initial part of the process. In some embodiments, the OUR is at least about 0.5 or 1.0, or 1.5 mmol $O_2/(L \cdot h)$ for the first 6, 8, or 10 hours of the process. In some embodiments, the OUR is reduced or about zero during part of the process. In some embodiments, the OUR is less than 0.5 or 1.0 mmol $O_2/(L \cdot h)$ after about the first 6, 8, 10, 12, 15, or 20 hours of the process.

Continuous Fermentation Processes

In one aspect, the process of the present invention can be a continuous or a semi-continuous fermentation process. In some embodiments, the continuous process of the present invention is a wet corn milling ethanol production process. Continuous fermentation processes, including wet milling ethanol processes are well-known in the art. In some embodiments, a fermentation process having a continuous mode of operation includes multiple fermenters that operate in series in which a starch hydrolysate is supplied in the first fermenter, which is fed to second fermenter and so on until the starch hydrolysate is converted to ethanol. In some embodiments, continuous operation can be operated using between 1 to 10 or 2 to 7 fermenters. In some embodiments, a continuous fermentation process can be performed in a single vessel, in which feedstock can be added and product-containing broth can be removed on a continuous or semi-continuous schedule.

An exemplary continuous fermentation process for manufacturing ethanol comprises the following steps: providing an initial fermentation medium that contains glucose or glucose oligomers, fermenting the fermentation medium with a genetically modified yeast, adding one or more feed streams comprising lactate to the fermentation medium, and removing at least one output stream comprising ethanol from the fermentation medium. In some embodiments, the initial fermentation medium can contain lactate and/or other carbon sources in addition to glucose or glucose oligomers. In one aspect, the genetically modified yeast is a yeast according to any of the embodiments of a genetically modified yeast described herein. In some embodiments, the yeast contains a heterologous monocarboxylate/proton symporter (e.g., JEN1) gene.

In some embodiments, the initial fermentation medium is added to a pre-fermenter or growth fermenter vessel, where the genetically modified yeast is added and grown until a desired biomass is achieved. In some embodiments, the conditions of the process in the pre-fermenter are set to favor cell growth over fermentation product formation. In some embodiments, the contents of the pre-fermenter vessel can then be transferred to a second fermenter vessel. In the second fermenter vessel, the conditions of the process are set to favor the formation of fermentation product over cell growth. In some embodiments, additional fermentation medium is added to the second fermenter vessel, either in a single portion or in a continuous or semi-continuous manner. In some embodiments, the additional fermentation medium added to the second fermenter vessel contains lactate and/or other carbon sources. The second fermenter referred to above can also be referred to as a "propagator." In some embodiments, the contents of the second fermenter vessel can be transferred to a third fermenter vessel. The process conditions of the third fermenter vessel can be the same or different as the second fermenter vessel. In some embodiments, the contents of third fermenter vessel can be transferred to one or more additional fermenter vessels, as would be understood by a person skilled in the art of continuous fermentation processes. In some embodiments, the bioproduct, e.g., ethanol, is isolated from the contents of the final fermenter vessel.

In some embodiments, the average glucose concentration of the fermentation medium in the pre-fermenter vessel is in the range of 10 to 20 g/L. In some embodiments, the average glucose concentration of the fermentation medium in the second fermenter vessel is in the range of 30 to 40 g/L. In some embodiments, the average glucose concentration of the fermentation medium in the third fermenter vessel, or any additional fermenter vessel, is in the range of 30 to 40 g/L. In some embodiments, the average glucose concentration of the fermentation medium in the final fermenter vessel is in the range of 0 to 5 g/L. In some embodiments, the average glucose concentration of the fermentation medium in the pre-fermenter vessel, propagator vessel, or in any of the fermentation vessels is in the range of 0-5, 2-5, 1-10, 5-10, 5-15, 5-20, 10-20, 15-25, 20-30, 25-35, 30-40, or 35-45 g/L. In some embodiments, the average glucose concentration of the fermentation in the pre-fermenter vessel, propagator vessel, or in any of the fermentation vessels is maintained in a range that is greater than or equal to the glucose concentration associated with glucose repression in a yeast. In some embodiments, the glucose concentration associated with glucose repression in a yeast is in the range of 2 to 5 g/L. Accordingly, in such embodiments, the average glucose concentration of the fermentation medium in the pre-fermenter vessel or in any of the fermentation vessels can be maintained at a level greater than or equal to 2, 3, 4, or 5 g/L.

Other fermentation conditions can be adjusted and/or maintained in the continuous fermentation process, including, but not limited to: temperature, pH, volumetric or specific oxygen uptake rate (OUR), or the concentration of any carbon source or any fermentation medium nutrient. In some embodiments, the temperature in the pre-fermenter vessel, propagator vessel, or in any other fermentation vessel can be in the range of 20-45, 20-40, 20-30, 25-35, or 30-40° C. In some embodiments, the pH in the pre-fermenter vessel, propagator vessel, or in any other fermentation vessel can be in the range of 2 to 7, 3 to 6, 4.5 to 5.5, or 3.5 to 4.5. As would be understood by a person skilled in the art, the pH at the start of fermentation can be lower than the pH at the end of fermentation as a result of lactate being consumed by the yeast. Accordingly, the pH at the end of fermentation can be in a different range of those listed above than the pH at the start of fermentation. In some embodiments, the volumetric OUR in the pre-fermenter vessel, propagator vessel, or in any other fermentation vessel is at least 0.5 mmol $O_2/(L \cdot h)$ or at least 1 mmol $O_2/(L \cdot h)$. In some embodiments, the volumetric OUR in the pre-fermenter vessel, propagator vessel, or in any other fermentation vessel is in the range of 0.1 to 5 mmol $O_2/(L \cdot h)$, 3 to 5 mmol $O_2/(L \cdot h)$, 0.2 to 1 mmol $O_2/(L \cdot h)$, 0.4 to 0.6 mmol $O_2/(L \cdot h)$, 4 to 200 mmol $O_2/(L \cdot h)$, 8 to 10 mmol $O_2/(L \cdot h)$, or 4 to 30 mmol $O_2/(L \cdot h)$. In some embodiments, the volumetric OUR in the pre-fermenter vessel, propagator vessel, or in any other fermentation vessel is at least 4 mmol $O_2/(L \cdot h)$, at least 5 mmol $O_2/(L \cdot h)$, at least 6 mmol $O_2/(L \cdot h)$, at least 7 mmol $O_2/(L \cdot h)$, or at least 8 mmol $O_2/(L \cdot h)$.

In some embodiments, the cell density in the pre-fermenter vessel is in the range of 3 to 10 g/L or 5 to 10 g/L. In some embodiments, the cell density in the propagator vessel is in the range of 10 to 50 g/L.

In one aspect, as described herein, the yeast consumes lactate during the fermentation process. In some embodiments, the total lactate content in the sum of all output streams is less than 90% of the lactate added to the fermentation process, i.e., the lactate content in sum of all input or feed streams. In some embodiments, the total lactate content in the output of the fermentation process is less than 99%, 95%, 85%, 80%, 75%, 70%, 65%, 60%, 55%, 50%, 45%, 40%, 35%, 30%, 25%, 20%, 15%, or 10% of the input to the fermentation process. In some embodiments, the total D-lactate content in the output of the fermentation process is less than 99%, 95%, 90%, 85%, 80%, 75%, 70%, 65%, 60%, 55%, 50%, 45%, 40%, 35%, 30%, 25%, 20%, 15%, or 10% of the input to the fermentation process. In some embodiments, the total L-lactate content in the output of the fermentation process is less than 99%, 95%, 90%, 85%, 80%, 75%, 70%, 65%, 60%, 55%, 50%, 45%, 40%, 35%, 30%, 25%, 20%, 15%, or 10% of the input to the fermentation process.

The continuous fermentation processes described herein can produce ethanol or another bioproduct at commercially significant rates. In some embodiments, the processes can produce the bioproduct at a rate of at least 0.5, 1.0, 1.5, 2.0, 2.5, 3.0, or 3.2 g $L^{-1}$ $h^{-1}$.

Advantages in Producing Certain Bioproducts

In one aspect, the lactate-consuming characteristics of the yeast can provide advantages in producing certain bioproducts, or in certain fermentation processes. The genetically modified yeasts and fermentation processes described herein can be used to make ethanol or other bioproducts of interest. Other bioproducts, include alcohols other than ethanol, lactic acid, 3-hydroxypropionic acid (3-HP), and succinic acid.

In some embodiments, the yeasts described herein can be useful for making enantiomerically-pure lactic acid. For example, by consuming one enantiomer with relatively high specificity, the yeast can produce D-lactic acid or L-lactic acid having enantiomeric purities of greater than 95%, 97%, 98%, 99%, 99.5% or more.

In some embodiments, the yeasts can improve the production of organic acids such as succinic acid or 3-HP. For example, it can be problematic to separate lactic acid from an organic acid product when recovering the organic acid product from the fermentation broth in downstream processing. By consuming lactate, the yeasts described herein can improve the efficiency of downstream processing and/or improve the purity of the final organic acid product.

In one aspect, the yeasts described herein can enable the use of vegetable process streams in fermentation processes that cannot typically use such streams. Vegetable process streams, such as corn steep liquor, are not typically used to produce bioproducts other than ethanol due to impurities such as lactate present in these streams. By consuming the lactate, the yeasts of the present invention can enable vegetable process streams to be used in a wide variety of fermentation processes.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Evaluation Protocol for Lactate Consumption

The protocol described below is used to determine the consumption of L-lactate, D-lactate, or a mixture of D- and L-lactate (i.e., "total lactate") by a yeast strain.

A yeast strain is selected and streaked out on a ScD-Ura plate and incubated at 30° C. until single colonies are visible (1-2 days) or grown overnight in 4 ml of YP+100 g/L D-gluconse in a 14 ml culture tube as a liquid culture at 30° C./250 rpm to generate seed biomass. A shake flask is inoculated with seed cell slurry to reach an initial OD600 of 0.1-0.3. Immediately prior to inoculating, 60 mL of shake flask medium is added to a 250 mL non-baffled shake flask (Corning 4995-250) fitted with a screw cap containing a gas-permeable seal (corning 1395-45LTMC). The shake flask medium is prepared according to Verduyn (Verduyn, et al., 1992, Yeast. Vol. 8, 501-517, which is hereby incorporated by reference in its entirety), with the exception of substituting manganese tetrahydrate with manganese dihydrate. The medium is supplemented with D-gluconse to target an initial D-gluconse concentration. For example, the medium is supplemented with 250 grams of D-gluconse per liter of media. To evaluate L-lactate consumption only, sodium L-lactate (e.g., Sigma; catalog number L7022) is used. To evaluate D-lactate consumption only, sodium D-lactate (e.g., Sigma; catalog number 71716) is used. To evaluate a mixture of D- and L-lactate, a mixture of about 50% D-lactate and 50% L-lactate is used. The pH of the media is adjusted to pH 4.5, and sterile filtered prior to use. The inoculated flask is incubated at 30° C. with shaking in an orbital shake at 75 rpm for at least 40 hours. Samples are taken and analyzed for gluconse, ethanol, and lactate concentration in the broth during fermentation using high performance liquid chromatography with a refractive index detector.

A lactate consumption rate is calculated between two time points: the time of inoculation ($t_0$) and another time point later in the fermentation ($t_1$). The time $t_1$ is a measure of hours (h) after inoculation. Samples are taken at these two time points and the lactate concentration in both samples is measured. The measured lactate concentration in the sample taken at to is designated $[HLA]_0$ and has units of ($gL^{-1}$). Likewise, the measured lactate concentration in the sample taken at $t_1$ is designated $[HLA]_1$ and has units of ($gL^{-1}$). The lactate consumption rate is then calculated as follows resulting in units of ($gL^{-1}h^{-1}$):

$$\text{Lactate consumption rate}=([HLA]_0)/t_1$$

When D-lactate is measured, the calculation will yield a D-lactate consumption rate. Likewise, when L-lactate is measured, the calculation will yield a L-lactate consumption rate and when total lactate is measured, the calculation will yield a total lactate consumption rate.

For example, a shake flask experiment is sampled at inoculation ($t_0$=0 h) and 48 hours later ($t_1$=48 h). The total lactate in both samples is measured with the following results: $[HLA]_0$=25.0 $gL^{-1}$; and $[HLA]_1$=15.9 $gL^{1}$. Then total lactate consumption rate is calculated as follows:

$$(25.0-15.9)/48=0.190\ gL^{-1}h^{-1}.$$

The total lactate consumption rate is 0.190 $gL^{-1}h^{-1}$.

Example 1

Generation of Amylolytic *Saccharomyces cerevisiae* Strains

Described below are genetically modified *Saccharomyces cerevisiae* yeast strains. The strains described include strains having genetic modifications that improve the lactate-consuming ability of ethanol producing yeasts.

Strain 1-3: ura3Δ *Saccharomyces cerevisiae* Base Strain

Strain 1 (Ethanol Red™) is transformed with SEQ ID NO: 1. SEQ ID NO: 1 contains the following elements: i) an expression cassette for a mutant version of a 3-deoxy-D-arabino-heptulosonate-7-phosphate (DAHP) synthase gene from *Saccharomyces cerevisiae* (ARO4-OFP); and ii) flanking DNA for targeted chromosomal integration into the URA3 locus. Transformants were selected on synthetic complete media containing 3.5 g/L of p-fluorophenylalanine, and 1 g/L L-tyrosine (ScD-PFP). Resulting transformants were streaked for single colony isolation on ScD-PFP. A single colony was selected. Correct integration of SEQ ID NO: 1 into one allele of locus A was verified by PCR in the single colony. A PCR verified isolate was designated Strain 1-1.

Stain 1-1 was transformed with SEQ ID NO: 2. SEQ ID NO: 2 contains the following elements: i) an expression cassette for an acetamidase (amdS) gene from *Aspergillus nidulans*; and ii) flanking DNA for targeted chromosomal integration into the URA3 locus. Transformants were selected on Yeast Nitrogen Base (without ammonium sulfate or amino acids) containing 80 mg/L uracil and 1 g/L acetamide as the sole nitrogen source. Resulting transformants were streaked for single colony isolation on Yeast Nitrogen Base (without ammonium sulfate or amino acids) containing 80 mg/L uracil and 1 g/L acetamide as the sole nitrogen source. A single colony was selected. Correct integration of SEQ ID NO: 2 into the second allele of locus A was verified by PCR in the single colony. A PCR verified isolate is designated Strain 1-2.

Strain 1-2 was co-transformed with SEQ ID NO: 3 and SEQ ID NO: 4. SEQ ID NO:3 contains the following elements: i) an open reading frame for a cre recombinase from P1 bacteriophage, and ii) flanking DNA homologous to SEQ ID NO:4. SEQ ID NO: 4 contains the following elements: i) a 2μ origin of replication; ii) a URA3 selectable marker from *Saccharomyces cerevisiae*; and iii) flanking DNA containing a PGK promoter and CYC1 terminator from *Saccharomyces cerevisiae*. Transformants were selected on synthetic dropout media lacking uracil (ScD-Ura). Resulting transformants were streaked for single colony isolation on ScD-Ura. A single colony was selected. The isolated colony was screened for growth on ScD-PFP and Yeast Nitrogen Base (without ammonium sulfate or amino acids) containing 80 mg/L uracil and 1 g/L acetamide as the sole nitrogen source. Loss of the ARO4-OFP and amdS genes was verified by PCR. The PCR verified isolate was streaked to YNB containing 5-FOA to select for loss of the 2μ plasmid. The PCR verified isolate was designated Strain 1-3.

Strain 1-4: *Saccharomyces cerevisiae* Expressing two Codon Optimized Variants of the *Saccharomycopsis fibuligera* Glucoamylase at one Allele of CYB2

Strain 1-3 was co-transformed with SEQ ID NO: 5 and SEQ ID NO: 6. SEQ ID NO:5 contains the following elements: i) DNA homologous to the 5' region of the native CYB2 gene; and ii) an expression cassette for a unique codon optimized variant of the *Saccharomycopsis fibuligera* glucoamylase, under control of the TDH3 promoter and CYC1 terminator; and iii) the URA3 promoter as well as a portion of the URA3 gene. SEQ ID NO: 6 contains the following elements: i) a portion of the URA3 gene and terminator; and ii) an expression cassette for a unique codon optimized variant of the *Saccharomycopsis fibuligera* glucoamylase, under control of the PGK promoter and RPL3 terminator; and iii) DNA homologous to the 3' region of the native CYB2 gene. Transformants were selected on ScD-Ura. Resulting transformants were streaked for single colony isolation on ScD-Ura. A single colony was selected. Correct integration of SEQ ID NO: 5 and SEQ ID NO: 6 at one allele of CYB2 was verified by PCR. The PCR verified isolate was designated Strain 1-4.

Strain 1-5: *Saccharomyces cerevisiae* Expressing Four Codon Optimized Variants of the *Saccharomycopsis fibuligera* Glucoamylase at Both Alleles of CYB2

Strain 1-4 was co-transformed with SEQ ID NO: 7 and SEQ ID NO: 8. SEQ ID NO: 7 contains the following elements: i) DNA homologous to the 5' region of the native CYB2 gene; and ii) an expression cassette for a unique codon optimized variant of the *Saccharomycopsis fibuligera* glucoamylase, under control of the TDH3 promoter and CYC1 terminator; and iii) the TEF1 promoter and a portion of the *Aspergillus nidulans* acetamidase gene (amdS). SEQ ID NO: 8 contains the following elements: i) a portion of the *Aspergillus nidulans* acetamidase gene (amdS) and ADH1 terminator; and ii) an expression cassette for a unique codon optimized variant of the *Saccharomycopsis fibuligera* glucoamylase, under control of the PGK promoter and RPL3 terminator; and iii) DNA homologous to the 3' region of the native CYB2 gene. Transformants were selected on Yeast Nitrogen Base (without ammonium sulfate or amino acids) containing 80 mg/L uracil and 1 g/L acetamide as the sole nitrogen source. Resulting transformants were streaked for single colony isolation on Yeast Nitrogen Base (without ammonium sulfate or amino acids) containing 80 mg/L uracil and 1 g/L acetamide as the sole nitrogen source. A single colony was selected. Correct integration of SEQ ID NO: 7 and SEQ ID NO: 8 at the remaining allele of CYB2 was verified by PCR. The PCR verified isolate was designated Strain 1-5.

Strain 1-6: Recycling the URA3 and amdS markers via cre recombinase in Strain 1-5

Strain 1-5 was transformed with SEQ ID NO: 9. SEQ ID NO: 9 contains the following elements: i) an expression cassette for a mutant version of a 3-deoxy-D-arabino-heptulosonate-7-phosphate (DAHP) synthase gene from *Saccharomyces cerevisiae* (ARO4-OFP); 2) an expression cassette for a cre recombinase from P1 bacteriophage; 3) an expression cassette containing the native URA3, and 4) the *Saccharomyces cerevisiae* CEN6 centromere. Transformants were selected on synthetic complete media containing 3.5 g/L of p-fluorophenylalanine, and 1 g/L L-tyrosine (ScD-PFP). Resulting transformants were streaked for single colony isolation on ScD-PFP. A single colony was selected. The PCR verified isolate was designated Strain 1-6.

Strain 1-8: Transformation of Strain 1-6 with Two Copies of the *Saccharomyces cerevisiae* IMA1 and Two Copies of the *Saccharomyces mikatae* MAL11-1.

Strain 1-6 was transformed with SEQ ID NO: 10. SEQ ID NO: 10 contains 5' homology to integration locus C, an expression cassette for the ScIMA1, an expression cassette for the URA3 marker, an expression cassette for the SmMAL11-1, and 3' homology to integration locus C locus. Transformants are selected on ScD-Ura. Resulting transformants are streaked for single colony isolation on ScD-Ura. A single colony is selected. Presence of the integration at locus C is verified by PCR. The PCR verified isolate is saved as Strain 1-7.

Strain 1-7 was transformed with SEQ ID NO: 11. SEQ ID NO: 11 contains 5' homology to integration locus C, an expression cassette for the ScIMA1, an expression cassette for the *Aspergillus nidulans* acetamidase gene (amdS), an expression cassette for the SmMAL11-1, and 3' homology to the integration locus C. Transformants were selected on Yeast Nitrogen Base (without ammonium sulfate or amino acids) containing 1 g/L acetamide as the sole nitrogen source. Resulting transformants were streaked for single colony isolation on Yeast Nitrogen Base (without ammonium sulfate or amino acids) containing 1 g/L acetamide as the sole nitrogen source. A single colony was selected. Correct integration of SEQ ID NO: 11 at the remaining allele of locus C was verified by PCR. The PCR verified isolate was designated Strain 1-8.

Strain 1-9: Recycling the URA3 and amdS Markers via cre Recombinase in Strain 1-8

Strain 1-8 was transformed with SEQ ID NO: 9. SEQ ID NO: 9 contains the following elements: i) an expression cassette for a mutant version of a 3-deoxy-D-arabino-heptulosonate-7-phosphate (DAHP) synthase gene from *Saccharomyces cerevisiae* (ARO4-OFP); 2) an expression cassette for a cre recombinase from P1 bacteriophage; 3) an expression cassette containing the native URA3, and 4) the *Saccharomyces cerevisiae* CEN6 centromere. Transformants were selected on synthetic complete media containing 3.5 g/L of p-fluorophenylalanine, and 1 g/L L-tyrosine (ScD-PFP). Resulting transformants were streaked for single colony isolation on ScD-PFP. A single colony was selected. The PCR verified isolate was designated Strain 1-9.

Strain 1-10: Restoring the Native URA3 at the Original Locus in Strain 1-9

Strain 1-9 was transformed with SEQ ID NO: 12. SEQ ID NO: 12 contains the follow elements: 1) an expression cassette for the native URA3, with 5' and 3' homology to the disrupted URA3 locus in Strain 1-6. Transformants were selected on ScD-ura. Resulting transformants were streaked for single colony isolate on ScD-ura. A single colony was selected. The PCR verified isolate was designated Strain 1-10.

Strain 1-11 *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* cytochrome b2.

Strain 1-9 is co-transformed with SEQ ID NO: 13 (pGPL5) and SEQ ID NO: 14 (pGPL7). SEQ ID NO: 13 contains the following elements in order: 1) flanking sequence corresponding to the upstream region of the *S. cerevisiae* CAN1 gene 2) an expression cassette containing a TDH3 promoter, *Saccharomyces cerevisiae* cytochrome b2 (CYB2) in SEQ ID NO: 15 and CYC1 terminator, and 3) 1 oxP recombination sequence and the 5' portion of an expression cassette for an orotidine-5'-phosphate decarboxylase (URA3). SEQ ID NO: 14 contains the following elements in order: 1) the 3' portion of an expression cassette for an orotidine-5'-phosphate decarboxylase (URA3) and a 1 oxP recombination sequence, 2) a cassette containing an ADH1 promoter and GAL10 terminator, and 4) flanking sequence corresponding to the downstream region of the *S. cerevisiae* CAN1 gene. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-11.

Strain 1-12: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Issatchenkia orientalis* Cytochrome b2.

Strain 1-9 is co-transformed with SEQ ID NO: 14 and SEQ ID NO: 16. SEQ ID NO: 16 is similar to SEQ ID NO: 13 with the following difference: the *Saccharomyces cerevisiae* cytochrome b2 gene in SEQ ID NO: 13 is replaced with the *Issatchenkia orientalis* cytochrome b2 (SEQ ID NO: 17). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-12.

Strain 1-13: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Aspergillus niger* Lactic Oxidase.

Strain 1-9 is co-transformed with SEQ ID NO: 14 and SEQ ID NO: 18. SEQ ID NO: 18 is similar to SEQ ID NO: 13 with the following difference: the *Saccharomyces cerevisiae* cytochrome b2 gene in SEQ ID NO: 13 is replaced with the *Aspergillus niger* lactic oxidase with the C-terminal perixosomal targeting sequence removed (SEQ ID NO: 19). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-13.

Strain 1-14: *Saccharomyces cerevisiae* Expressing a Modified *Saccharomycopsis fibuligera* Glucoamylase, a *Saccha-*

*romyces cerevisiae* Isomaltase and a *Saccharomyces mikatae* Maltose Transporter, and a *Yarrowia lipolytica* Lactic Oxidase.

Strain 1-9 is co-transformed with SEQ ID NO: 14 and SEQ ID NO: 20. SEQ ID NO: 20 is similar to SEQ ID NO: 13 with the following difference: the *Saccharomyces cerevisiae* cytochrome b2 gene in SEQ ID NO: 13 is replaced with the *Yarrowia lipolytica* lactic oxidase with the C-terminal perixosomal targeting sequence removed SEQ ID NO: 21. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-14.

Strain 1-15: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Issatchenkia orientalis* Monocarboxylate/Proton Symporter (JEN1).

Strain 1-9 is co-transformed with SEQ ID NO: 22 (pGPL6) and SEQ ID NO: 23 (pESL4). SEQ ID NO: 22 contains the following elements in order: 1) flanking sequence corresponding to the upstream region of the *S. cerevisiae* CAN1 gene 2) a cassette containing a TDH3 promoter, and CYC1 terminator, and 3) loxP recombination sequence and the 5' portion of an expression cassette for an orotidine-5'-phosphate decarboxylase (URA3). SEQ ID NO: 23 contains the following elements in order: 1) the 3' portion of an expression cassette for an orotidine-5'-phosphate decarboxylase (URA3) and a loxP recombination sequence, 2) an expression cassette containing an ADH1 promoter, *Issatchenkia orientalis* monocarboxylate/proton symporter (JEN1) found in SEQ ID NO: 24, and a GAL10 terminator, and 4) flanking sequence corresponding to the downstream region of the *S. cerevisiae* CAN1 gene. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-15.

Strain 1-16: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* Monocarboxylate/Proton Symporter (JEN1).

Strain 1-9 is co-transformed with SEQ ID NO: 22 and SEQ ID NO: 25 (pESL1). SEQ ID NO: 25 is similar to SEQ ID NO: 23 with the following difference: the *Issatchenkia orientalis* monocarboxylate/proton symporter gene (JEN1) in SEQ ID NO: 23 is replaced with the *Saccharomyces cerevisiae* monocarboxylate/proton symporter (JEN1) gene (SEQ ID NO: 26). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-16.

Strain 1-17: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Kluyveromyces lactis* Monocarboxylate/Proton Symporter (JEN1).

Strain 1-9 is co-transformed with SEQ ID NO: 22 and SEQ ID NO: 27 (pESL7). SEQ ID NO: 27 is similar to SEQ ID NO: 23 with the following difference: the *Issatchenkia orientalis* monocarboxylate/proton symporter gene (JEN1) in SEQ ID NO: 23 is replaced with the *Kluyveromyces lactis* monocarboxylate/proton symporter (JEN1) gene (SEQ ID NO: 28). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-17.

Strain 1-18: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* Acetate Transporter ($ADY2^{Leu219Val,\ Ala252Gly}$).

Strain 1-9 is co-transformed with SEQ ID NO: 22 and SEQ ID NO: 29 (pESL8). SEQ ID NO: 29 is similar to SEQ ID NO: 23 with the following difference: the *Issatchenkia orientalis* monocarboxylate/proton symporter gene (JEN1) in SEQ ID NO: 23 is replaced with the *Saccharomyces cerevisiae* acetate transporter ($ADY2^{Leu219Val,\ Ala252Gly}$) gene (SEQ ID NO: 30). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-18.

Strain 1-19: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Aggregatibacter actinomycetemcomitans* LDH and a *Saccharomyces cerevisiae* Monocarboxylate/Proton Symporter (JEN1).

Strain 1-9 is co-transformed with SEQ ID NO: 25 and SEQ ID NO: 31. SEQ ID NO: 31 is similar to SEQ ID NO: 13 with the following difference: the *Saccharomyces cerevisiae* cytochrome b2 gene in SEQ ID NO: 13 is replaced with the *Aggregatibacter actinomycetemcomitans* LDH (SEQ ID NO: 32). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-19.

Strain 1-20: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Ornithorhynchus anatinus* LDH and a *Saccharomyces cerevisiae* Monocarboxylate/Proton Symporter (JEN1).

Strain 1-9 is co-transformed with SEQ ID NO: 25 and SEQ ID NO: 33. SEQ ID NO: 33 is similar to SEQ ID NO: 13 with the following difference: the *Saccharomyces cerevisiae* cytochrome b2 gene in SEQ ID NO: 13 is replaced with the *Ornithorhynchus anatinus* LDH (SEQ ID NO: 34). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-20.

Strain 1-21: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Issatchenkia orientalis* Cytochrome b2 and an *Issatchenkia orientalis* Monocarboxylate/Proton Symporter (JEN1).

Strain 1-9 is co-transformed with SEQ ID NO: 16 and SEQ ID NO: 23. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-21.

Strain 1-22: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Issatchenkia orientalis* Cytochrome b2 and a *Saccharomyces cerevisiae* Monocarboxylate/Proton Symporter (JEN1).

Strain 1-9 is co-transformed with SEQ ID NO: 16 and SEQ ID NO: 25. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-22.

Strain 1-23: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Issatchenkia orientalis* Cytochrome b2 and a *Kluyveromyces lactis* Monocarboxylate/Proton Symporter (JEN1).

Strain 1-9 is co-transformed with SEQ ID NO: 16 and SEQ ID NO: 27. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-23.

Strain 1-24: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* Cytochrome b2 and a *Saccharomyces cerevisiae* Monocarboxylate/Proton Symporter (JEN1).

Strain 1-9 is co-transformed with SEQ ID NO: 13 and SEQ ID NO: 25. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-24.

Strain 1-25: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* Cytochrome b2 and a *Kluyveromyces lactis* Monocarboxylate/Proton Symporter (JEN1).

Strain 1-9 is co-transformed with SEQ ID NO: 13 and SEQ ID NO: 27. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-25.

Strain 1-26: *Saccharomyces cerevisiae* Epressing a mMdified *Saccharomycopsis fibuligera* Glucoamylase, a *Saccharomyces cerevisiae* Isomaltase and a *Saccharomyces mikatae* Maltose Transporter, and an *Aspergillus niger* Lactic Oxidase and a *Saccharomyces cerevisiae* Monocarboxylate/Proton Symporter (JEN1).

Strain 1-9 is co-transformed with SEQ ID NO: 18 and SEQ ID NO: 25. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-26.

Strain 1-27: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Yarrowia lipolytica* Lactic Oxidase and a *Saccharomyces cerevisiae* Monocarboxylate/Proton Symporter (JEN1).

Strain 1-9 is co-transformed with SEQ ID NO: 20 and SEQ ID NO: 25. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-27.

Strain 1-28: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Acetobacter aceti* D-Lactic Oxidase and a *Kluyveromyces lactis* Monocarboxylate/Proton Symporter (JEN1).

Strain 1-9 is co-transformed with SEQ ID NO: 35 and SEQ ID NO: 27. SEQ ID NO: 35 is similar to SEQ ID NO: 13 with the following difference: the *Saccharomyces cerevisiae* cytochrome b2 gene in SEQ ID NO: 13 is replaced with the *Acetobacter aceti* D-lactic oxidase (SEQ ID NO: 36). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-28.

Strain 1-29: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Gluconobacter oxydans* D-Lactic Oxidase and a *Kluyveromyces lactis* Monocarboxylate/Proton Symporter (JEN1).

Strain 1-9 is co-transformed with SEQ ID NO: 37 and SEQ ID NO: 27. SEQ ID NO: 37 is similar to SEQ ID NO: 13 with the following difference: the *Saccharomyces cerevisiae* cytochrome b2 gene in SEQ ID NO: 13 is replaced with the *Gluconobacter oxydans* D-lactic oxidase (SEQ ID NO: 38). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-29.

Strain 1-30: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* D-Lactic Dehydrogenase and a *Kluyveromyces lactis* Monocarboxylate/Proton Symporter (JEN1).

Strain 1-9 is co-transformed with SEQ ID NO: 39 and SEQ ID NO: 27. SEQ ID NO: 39 is similar to SEQ ID NO: 13 with the following difference: the *Saccharomyces cerevisiae* cytochrome b2 gene in SEQ ID NO: 13 is replaced with the *Saccharomyces cerevisiae* D-lactic dehydrogenase (SEQ ID NO: 40). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-30.

Strain 1-31: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Issatchenkia orientalis* D-lactic Dehydrogenase A and a *Kluyveromyces lactis* Monocarboxylate/Proton Symporter (JEN1).

Strain 1-9 is co-transformed with SEQ ID NO: 41 and SEQ ID NO: 27. SEQ ID NO: 41 is similar to SEQ ID NO: 13 with the following difference: the *Saccharomyces cerevisiae* cytochrome b2 gene in SEQ ID NO: 13 is replaced with the *Issatchenkia orientalis* D-lactic dehydrogenase (SEQ ID NO: 42). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-31.

Strain 1-32: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Issatchenkia orientalis* D-Lactic Dehydrogenase B and a *Kluyveromyces lactis* Monocarboxylate/Proton Symporter (JEN1).

Strain 1-9 is co-transformed with SEQ ID NO: 43 and SEQ ID NO: 27. SEQ ID NO: 43 is similar to SEQ ID NO: 13 with the following difference: the *Saccharomyces cerevisiae* cytochrome b2 gene in SEQ ID NO: 13 is replaced with the *Issatchenkia orientalis* D-lactic dehydrogenase (SEQ ID NO: 44). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-32.

Strain 1-33: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Issatchenkia orientalis* D-Lactic Dehydrogenase C and a *Kluyveromyces lactis* Monocarboxylate/Proton Symporter (JEN1).

Strain 1-9 is co-transformed with SEQ ID NO: 45 and SEQ ID NO: 27. SEQ ID NO: 45 is similar to SEQ ID NO: 13 with the following difference: the *Saccharomyces cerevisiae* cytochrome b2 in SEQ ID NO: 13 is replaced with the *Issatchenkia orientalis* D-lactic dehydrogenase (SEQ ID NO: 46). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-33.

Strain 1-34: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, Integration Locus Control.

Strain 1-9 is co-transformed with SEQ ID NO: 14 and SEQ ID NO: 22. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-34.

Strain 1-35: *Saccharomyces cerevisiae* Expressing a *Kluyveromyces lactis* Monocarboxylate/Proton Symporter (JEN1).

Strain 1-3 is co-transformed with SEQ ID NO: 22 and SEQ ID NO: 27 (pESL7). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-35.

Strain 1-36: *Saccharomyces cerevisiae* Expressing a *Saccharomyces cerevisiae* Cytochrome b2 and a *Kluyveromyces lactis* Monocarboxylate/Proton Symporter (JEN1).

Strain 1-3 is co-transformed with SEQ ID NO: 13 and SEQ ID NO: 27. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-36.

Strain 1-37: *Saccharomyces cerevisiae* Expressing a *Saccharomyces cerevisiae* D-Lactic Dehydrogenase and a *Kluyveromyces lactis* Monocarboxylate/Proton Symporter (JEN1).

Strain 1-3 is co-transformed with SEQ ID NO: 40 and SEQ ID NO: 27. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-37.

Strain 1-38: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Lactobacillus fermentum* Lactate Racemase and a *Kluyveromyces lactis* Monocarboxylate/Proton Symporter (JEN1).

Strain 1-9 is co-transformed with SEQ ID NO: 47 and SEQ ID NO: 27. SEQ ID NO: 47 is similar to SEQ ID NO: 13 with the following difference: the *Saccharomyces cerevisiae* cytochrome b2 in SEQ ID NO: 13 is replaced with the *Lactobacillus fermentum* lactate racemase (SEQ ID NO: 48). Transformants are selected on ScD-Ura. Resulting transformants are streaked for single colony isolation on ScD-Ura. Single colonies are selected, and the correct integration of the expression cassette is confirmed by PCR.

Three independent transformants are tested in a shake flask fermentation and a representative isolate is designated Strain 1-38.

Strain 1-39: *Saccharomyces cerevisiae* Expressing a *Lactobacillus fermentum* Lactate Racemase and a *Kluyveromyces lactis* Monocarboxylate/Proton Symporter (JEN1).

Strain 1-3 is co-transformed with SEQ ID NO: 47 and SEQ ID NO: 27. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-39.

Strain 1-40: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* Cytochrome b2 and a *Saccharomyces cerevisiae* Acetate Transporter ($ADY2^{Leu219Val,\ Ala252Gly}$).

Strain 1-9 is co-transformed with SEQ ID NO: 13 and SEQ ID NO: 29. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-25.

Strain 1-41: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and 2 copies of a *Saccharomyces cerevisiae* Cytochrome b2 and a *Kluyveromyces lactis* Monocarboxylate/Proton Symporter (JEN1).

Strain 1-25 was transformed with SEQ ID NO: 49 and SEQ ID NO: 50. SEQ ID NO: 49 contains the following elements in order: 1) flanking sequence corresponding to the upstream region of the *S. cerevisiae* CAN1, 2) a cassette containing a TDH3 promoter, the *Saccharyomyces cerevisiae* CYB2, and CYC1 terminator, and 3) loxP recombination sequence and the 5' portion of the expression cassette for the *Aspergillus nidulans* acetamidase gene (amdS). SEQ ID NO: 50 contains the following elements in order: 1) the 3' portion of an expression cassette for the *Aspergillus nidulans* acetamidase (amdS), and a loxP recombination sequence, 2) an expression cassette containing an ADH1 promoter, *Kluyveromyces lactis* monocarboxylate/proton symporter (JEN1), and a GAL10 terminator, and 4) flanking sequence corresponding to the downstream region of the *S. cerevisiae* CAN1. Transformants were selected on Yeast Nitrogen Base (without ammonium sulfate or amino acids) containing 1 g/L acetamide as the sole nitrogen source. Resulting transformants were streaked for single colony isolation on Yeast Nitrogen Base (without ammonium sulfate or amino acids) containing 1 g/L acetamide as the sole nitrogen source. Single colonies are selected, and the correct integration of the expression cassette is confirmed by PCR. Three independent transformants are tested in a shake flask fermentation and a representative isolate is designated Strain 1-41.

Strain 1-42: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces kluyveri* Cytochrome b2 and a *Kluyveromyces lactis* Monocarboxylate/Proton Symporter (JEN1).

Strain 1-9 is co-transformed with SEQ ID NO: 53 and SEQ ID NO: 27. SEQ ID NO: 53 is similar to SEQ ID NO: 13 with the following difference: the *Saccharomyces cerevisiae* cytochrome b2 in SEQ ID NO: 13 is replaced with the *Saccharomyces kluyveri* cytochrome b2 (SEQ ID NO: 54). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-42.

Strain 1-43: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces bayanus* Cytochrome b2 and a *Kluyveromyces lactis* Monocarboxylate/Proton Symporter (JEN1).

Strain 1-9 is co-transformed with SEQ ID NO: 55 and SEQ ID NO: 27. SEQ ID NO: 55 is similar to SEQ ID NO: 13 with the following difference: the *Saccharomyces cerevisiae* cytochrome b2 in SEQ ID NO: 13 is replaced with the *Saccharomyces bayanus* cytochrome b2 (SEQ ID NO: 56). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-43.

Strain 1-44: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a Cytochrome b2 and a *Kluyveromyces lactis* Monocarboxylate/Proton Symporter (JEN1).

Strain 1-9 is co-transformed with SEQ ID NO: 57 and SEQ ID NO: 27. SEQ ID NO: 57 is similar to SEQ ID NO: 13 with the following difference: the *Saccharomyces cerevisiae* cytochrome b2 in SEQ ID NO: 13 is replaced with the *Zygosaccharomyces rouxii* cytochrome b2 (SEQ ID NO: 58). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-44.

Strain 1-45: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Kluyveromyces lactis* Cytochrome b2 and a *Kluyveromyces lactis* Monocarboxylate/Proton symporter (JEN1).

Strain 1-9 is co-transformed with SEQ ID NO: 59 and SEQ ID NO: 27. SEQ ID NO: 59 is similar to SEQ ID NO: 13 with the following difference: the *Saccharomyces cerevisiae* cytochrome b2 in SEQ ID NO: 13 is replaced with the *Kluyveromyces lactis* cytochrome b2 (SEQ ID NO: 60). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-45.

Strain 1-46: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Kluyveromyces dobzhanskii*

Cytochrome b2 and a *Kluyveromyces lactis* Monocarboxylate/Proton Symporter (JEN1).

Strain 1-9 is co-transformed with SEQ ID NO: 61 and SEQ ID NO: 27. SEQ ID NO: 61 is similar to SEQ ID NO: 13 with the following difference: the *Saccharomyces cerevisiae* cytochrome b2 gene in SEQ ID NO: 13 is replaced with the *Kluyveromyces dobzhanskii* cytochrome b2 (SEQ ID NO: 62). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-46.

Strain 1-47: *Saccharomyces cerevisiae* Expressing a modified *Saccharomycopsis fibuligera* Glucoamylase, a *Saccharomyces cerevisiae* Isomaltase and a *Saccharomyces mikatae* Maltose Transporter, and a *Saccharomyces kluyveri* D-Lactic Dehydrogenase and a *Kluyveromyces lactis* Monocarboxylate/Proton Symporter (JEN1).

Strain 1-9 is co-transformed with SEQ ID NO: 63 and SEQ ID NO: 27. SEQ ID NO: 63 is similar to SEQ ID NO: 13 with the following difference: the *Saccharomyces cerevisiae* cytochrome b2 in SEQ ID NO: 13 is replaced with the *Saccharomyces kluyveri* D-lactic dehydrogenase (SEQ ID NO: 64). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-47.

Strain 1-48: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces bayanus* D-Lactic Dehydrogenase and a *Kluyveromyces lactis* Monocarboxylate/Proton Symporter (JEN1).

Strain 1-9 is co-transformed with SEQ ID NO: 65 and SEQ ID NO: 27. SEQ ID NO: 63 is similar to SEQ ID NO: 13 with the following difference: the *Saccharomyces cerevisiae* cytochrome b2 in SEQ ID NO: 13 is replaced with the *Saccharomyces bayanus* D-lactic dehydrogenase (SEQ ID NO: 66). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-48.

Strain 1-49: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and an *Aspergillus fumigatus* D-Lactic Dehydrogenase and a *Kluyveromyces lactis* Monocarboxylate/Proton Symporter (JEN1).

Strain 1-9 is co-transformed with SEQ ID NO: 67 and SEQ ID NO: 27. SEQ ID NO: 67 is similar to SEQ ID NO: 13 with the following difference: the *Saccharomyces cerevisiae* cytochrome b2 in SEQ ID NO: 13 is replaced with the *Aspergillus fumigatus* D-lactic dehydrogenase (SEQ ID NO: 68). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-49.

Strain 1-50: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Kluyveromyces lactis* D-Lactic Dehydrogenase and a *Kluyveromyces lactis* Monocarboxylate/Proton Symporter (JEN1).

Strain 1-9 is co-transformed with SEQ ID NO: 69 and SEQ ID NO: 27. SEQ ID NO: 69 is similar to SEQ ID NO: 13 with the following difference: the *Saccharomyces cerevisiae* cytochrome b2 in SEQ ID NO: 13 is replaced with the *Kluyveromyces lactis* D-lactic dehydrogenase (SEQ ID NO: 70). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-50.

Strain 1-51: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Kluyveromyces dobzhanskii* D-Lactic Dehydrogenase and a *Kluyveromyces lactis* Monocarboxylate/Proton Symporter (JEN1).

Strain 1-9 is co-transformed with SEQ ID NO: 71 and SEQ ID NO: 27. SEQ ID NO: 71 is similar to SEQ ID NO: 13 with the following difference: the *Saccharomyces cerevisiae* cytochrome b2 in SEQ ID NO: 13 is replaced with the *Kluyveromyces dobzhanskii* D-lactic dehydrogenase (SEQ ID NO: 72). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-51.

Strain 1-52: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Kluyveromyces marxianus* D-Lactic Dehydrogenase and a *Kluyveromyces lactis* Monocarboxylate/Proton Symporter (JEN1).

Strain 1-9 is co-transformed with SEQ ID NO: 73 and SEQ ID NO: 27. SEQ ID NO: 73 is similar to SEQ ID NO: 13 with the following difference: the *Saccharomyces cerevisiae* cytochrome b2 in SEQ ID NO: 13 is replaced with the *Kluyveromyces marxianus* D-lactic dehydrogenase (SEQ ID NO: 74). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-52.

Strain 1-53: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* D-Lactic Dehydrogenase, a *Saccharomyces cerevisiae* Cytochrome b2, and a *Kluyveromyces dobzhanskii* Monocarboxylate/Proton Symporter (JEN1).

Strain 1-9 is co-transformed with SEQ ID NO: 80 and SEQ ID NO: 75. SEQ ID NO: 80 contains the following elements in order: 1) flanking sequence corresponding to the upstream region of the *S. cerevisiae* CAN1 2) an expression cassette containing a PGK promoter, *Saccharomyces cerevisiae* D-lactic dehydrogenase (DLD1) in SEQ ID NO: 40 and RPL3 terminator 3) an expression cassette containing a TDH3 promoter, *Saccharomyces cerevisiae* cytochrome b2 (CYB2) in SEQ ID NO: 15 and CYC1 terminator, and 4) loxP recombination sequence and the 5' portion of an expression cassette for an orotidine-5'-phosphate decarboxylase (URA3). SEQ ID NO: 75 is similar to SEQ ID NO: 23 with the following difference: the *Issatchenkia orientalis* monocarboxylate/proton symporter (JEN1) in SEQ ID NO: 23 is replaced with the *Kluyveromyces dobzhanskii* monocarboxylate/proton symporter (JEN1) protein (SEQ ID NO: 76). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-53.

Strain 1-54: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* D-Lactic Dehydrogenase, a *Saccharomyces cerevisiae* Cytochrome b2, and a *Kluyveromyces marxianus* Monocarboxylate/Proton Symporter (JEN1).

Strain 1-9 is co-transformed with SEQ ID NO: 80 and SEQ ID NO: 77. SEQ ID NO: 77 is similar to SEQ ID NO: 23 with the following difference: the *Issatchenkia orientalis* monocarboxylate/proton symporter (JEN1) in SEQ ID NO: 23 is replaced with the *Kluyveromyces marxianus* monocarboxylate/proton symporter (JEN1) (SEQ ID NO: 78). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-54.

Strain 1-55: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* D-Lactic Dehydrogenase, a *Saccharomyces cerevisiae* Cytochrome b2, and a *Yarrowia lypolitica* Monocarboxylate/Proton Symporter (JEN6).

Strain 1-9 is co-transformed with SEQ ID NO: 80 and SEQ ID NO: 79. SEQ ID NO: 79 is similar to SEQ ID NO: 23 with the following difference: the *Issatchenkia orientalis* monocarboxylate/proton symporter (JEN1) in SEQ ID NO: 23 is replaced with the *Yarrowia lypolitica* monocarboxylate/proton symporter (JEN6) (SEQ ID NO: 52). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-55.

Strain 1-56: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and a *Saccharomyces cerevisiae* D-Lactic Dehydrogenase, a *Saccharomyces cerevisiae* Cytochrome b2, and a *Kluyveromyces lactis* Monocarboxylate/Proton Symporter (JEN1).

Strain 1-9 is co-transformed with SEQ ID NO: 80 and SEQ ID NO: 27. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-56.

Strain 1-57: *Saccharomyces cerevisiae* Expressing a Modified *Saccharomycopsis fibuligera* Glucoamylase, a *Saccharomyces cerevisiae* Isomaltase and a *Saccharomyces mikatae* Maltose Transporter, and Two Copies of a *Saccharomyces cerevisiae* D-Lactic Dehydrogenase, a *Saccharomyces cerevisiae* Cytochrome b2, and a *Kluyveromyces lactis* Monocarboxylate/Proton Symporter (JEN1).

Strain 1-56 is co-transformed with SEQ ID NO: 81 and SEQ ID NO: 50. SEQ ID NO: 81 is similar to SEQ ID NO: 80 with the difference being that the 5' portion of the URA3 marker is replaced with the 5' portion of the amdS marker. Transformants are selected on YNB+acetamide plates. Resulting transformants are streaked for single colony isolation on YNB+acetamide plates. Single colonies are selected, and the correct integration of the expression cassette is confirmed by PCR. Three independent transformants are tested in a shake flask fermentation and a representative isolate is designated Strain 1-57.

Strain 1-58: *S. cerevisiae* Expressing a Modified *S. fibuligera* Glucoamylase, a *S. cerevisiae* Isomaltase and a *S. mikatae* Maltose Transporter, and a *S. cerevisiae* D-Lactic Dehydrogenase, a *S. cerevisiae* Cytochrome b2, and a *S. cerevisiae* Monocarboxylate/Proton Symporter (JEN1).

Strain 1-9 is co-transformed with SEQ ID NO: 80 and SEQ ID NO: 25. Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-58.

Strain 1-59: *S. cerevisiae* Expressing a Modified *S. fibuligera glucoamylase*, a *S. cerevisiae* Isomaltase and a *S. mikatae maltose* Transporter, and a *S. cerevisiae* D-Lactic Dehydrogenase, a *S. cerevisiae* Cytochrome b2, and a *S. bayanus* Monocarboxylate/Proton Symporter (JEN1).

Strain 1-9 is co-transformed with SEQ ID NO: 80 and SEQ ID NO: 82. SEQ ID NO: 82 is similar to SEQ ID NO: 50 with the following difference: the *K. lactis* JEN1 in SEQ ID NO: 50 is replaced with the *S. bayanus* JEN1 (SEQ ID NO: 83). Transformants are selected on ScD-Ura. Resulting transformants are streaked for single colony isolation on ScD-Ura. Single colonies are selected, and the correct integration of the expression cassette is confirmed by PCR. Three independent transformants are tested in a shake flask fermentation and a representative isolate is designated Strain 1-59.

Strain 1-60: *S. cerevisiae* Expressing a Modified *S. fibuligera* Glucoamylase, a *S. cerevisiae* Isomaltase and a *S. mikatae maltose* Transporter, and a *S. cerevisiae* D-Lactic Dehydrogenase, a *S. cerevisiae* Cytochrome b2, and a *K. lactis* Monocarboxylate/Proton Symporter (JEN1).

Strain 1-9 is co-transformed with SEQ ID NO: 80 and SEQ ID NO: 84. SEQ ID NO: 84 is similar to SEQ ID NO: 27 with the difference being that the ADH1 promoter SEQ ID NO: 27 is replaced with the GPD1 promoter. Transformants are selected on ScD-Ura, and the resulting transformants are streaked for single colony isolation on ScD-Ura. Single colonies are selected, and the correct integration of the expression cassette is confirmed by PCR.

Three independent transformants that were confirmed by PCR to contain a single copy of the expression cassette, were transformed for the second copy of the expression cassette using SEQ ID NO: 81 and SEQ ID NO: 87. SEQ ID NO: 87 is similar to SEQ ID NO: 50 with the difference being that the ADH1 promoter in SEQ ID NO: 50 is replaced with the GPD1 promoter. Transformants are selected on YNB+acetamide plates. Resulting transformants are streaked for single colony isolation on YNB+acetamide plates. Single colonies are selected, and the correct integration of the expression cassette is confirmed by PCR. Three independent transformants are tested in a shake flask fermentation and a representative isolate is designated Strain 1-60.

Strain 1-61: S. cerevisiae Expressing a Modified S. fibuligera Glucoamylase, a S. cerevisiae Isomaltase and a S. mikatae Maltose Transporter, and a S. cerevisiae D-Lactic Dehydrogenase, a S. cerevisiae Cytochrome b2, and a K. lactis Monocarboxylate/Proton Symporter (JEN1).

Strain 1-9 is co-transformed with SEQ ID NO: 80 and SEQ ID NO: 85. SEQ ID NO: 85 is similar to SEQ ID NO: 27 with the difference being that the ADH1 promoter SEQ ID NO: 27 is replaced with the ADH2 promoter. Transformants are selected on ScD-Ura, and the resulting transformants are streaked for single colony isolation on ScD-Ura. Single colonies are selected, and the correct integration of the expression cassette is confirmed by PCR.

Three independent transformants that were confirmed by PCR to contain a single copy of the expression cassette, were transformed for the second copy of the expression cassette using SEQ ID NO: 81 and SEQ ID NO: 88. SEQ ID NO: 88 is similar to SEQ ID NO: 50 with the difference being that the ADH1 promoter in SEQ ID NO: 50 is replaced with the ADH2 promoter. Transformants are selected on YNB+acetamide plates. Resulting transformants are streaked for single colony isolation on YNB+acetamide plates. Single colonies are selected, and the correct integration of the expression cassette is confirmed by PCR. Three independent transformants are tested in a shake flask fermentation and a representative isolate is designated Strain 1-61.

Strain 1-62: S. cerevisiae Expressing a Modified S. fibuligera Glucoamylase, a S. cerevisiae Isomaltase and a S. mikatae maltose Transporter, and a S. cerevisiae D-Lactic Dehydrogenase, a S. cerevisiae Cytochrome b2, and a K. lactis Monocarboxylate/Proton Symporter (JEN1).

Strain 1-9 is co-transformed with SEQ ID NO: 80 and SEQ ID NO: 86. SEQ ID NO: 86 is similar to SEQ ID NO: 27 with the difference being that the ADH1 promoter SEQ ID NO: 27 is replaced with the PDC1 promoter. Transformants are selected on ScD-Ura, and the resulting transformants are streaked for single colony isolation on ScD-Ura. Single colonies are selected, and the correct integration of the expression cassette is confirmed by PCR.

Three independent transformants that were confirmed by PCR to contain a single copy of the expression cassette, were transformed for the second copy of the expression cassette using SEQ ID NO: 81 and SEQ ID NO: 89. SEQ ID NO: 89 is similar to SEQ ID NO: 50 with the difference being that the ADH1 promoter in SEQ ID NO: 50 is replaced with the PDC1 promoter. Transformants are selected on YNB+acetamide plates. Resulting transformants are streaked for single colony isolation on YNB+acetamide plates. Single colonies are selected, and the correct integration of the expression cassette is confirmed by PCR. Three independent transformants are tested in a shake flask fermentation and a representative isolate is designated Strain 1-62.

TABLE 1

Summary Descriptions of Engineered Yeast

| Strain | Parent | Description |
|---|---|---|
| Strain 1 | N/A | Saccharomyces cerevisiae (Lasaffre, Ethanol Red) |
| Strain 1-1 | Strain 1 | ura3Δ/URA3, ARO4-OFP+ |
| Strain 1-2 | Strain 1-1 | ura3Δ, ARO4-OFP+, amdS+ |
| Strain 1-3 | Strain 1-2 | ura3Δ |
| Strain 1-4 | Strain 1-3 | Saccharomycopsis fibuligera GLA1+; URA3+, |
| Strain 1-5 | Strain 1-4 | Saccharomycopsis fibuligera GLA1+; URA3+; amdS+ |
| Strain 1-6 | Strain 1-5 | Saccharomycopsis fibuligera GLA1+; ura3− |
| Strain 1-7 | Strain 1-6 | Saccharomycopsis fibuligera GLA1+; Saccharomyces cerevisae IMA1+, Saccharomyces mikatae MAL11+; URA3+ |
| Strain 1-8 | Strain 1-7 | Saccharomycopsis fibuligera GLA1+; Saccharomyces cerevisae IMA1+, Saccharomyces mikatae MAL11+; URA3+, amdS+ |
| Strain 1-9 | Strain 1-8 | Saccharomycopsis fibuligera GLA1+; Saccharomyces cerevisae IMA1+, Saccharomyces mikatae MAL11+; ura3− |
| Strain 1-10 | Strain 1-9 | Saccharomycopsis fibuligera GLA1+; Saccharomyces cerevisae IMA1+, Saccharomyces mikatae MAL11+; URA3+ |
| Strain 1-11 | Strain 1-9 | Saccharomycopsis fibuligera GLA1+; Saccharomyces cerevisae IMA1+, Saccharomyces mikatae MAL11+; Saccharomyces cerevisae CYB2+; URA3+ |
| Strain 1-12 | Strain 1-9 | Saccharomycopsis fibuligera GLA1+; Saccharomyces cerevisae IMA1+, Saccharomyces mikatae MAL11+; Issatchenkia orientalis CYB2+; URA3+ |
| Strain 1-13 | Strain 1-9 | Saccharomycopsis fibuligera GLA1+; Saccharomyces cerevisae IMA1+, Saccharomyces mikatae MAL11+; Aspergillus niger L-LOX+; URA3+ |
| Strain 1-14 | Strain 1-9 | Saccharomycopsis fibuligera GLA1+; Saccharomyces cerevisae IMA1+, Saccharomyces mikatae MAL11+; Yarrowia lipolytica L-LOX+; URA3+ |
| Strain 1-15 | Strain 1-9 | Saccharomycopsis fibuligera GLA1+; Saccharomyces cerevisae IMA1+, Saccharomyces mikatae MAL11+; Issatchenkia orientalis JEN1+; URA3+ |
| Strain 1-16 | Strain 1-9 | Saccharomycopsis fibuligera GLA1+; Saccharomyces cerevisae IMA1+, Saccharomyces mikatae MAL11+; Saccharomyces cerevisae JEN1+; URA3+ |
| Strain 1-17 | Strain 1-9 | Saccharomycopsis fibuligera GLA1+; Saccharomyces cerevisae IMA1+, Saccharomyces mikatae MAL11+; Kluyveromyces lactis JEN1+; URA3+ |
| Strain 1-18 | Strain 1-9 | Saccharomycopsis fibuligera GLA1+; Saccharomyces cerevisae IMA1+, Saccharomyces mikatae MAL11+; Saccharomyces cerevisae ADY2 (ADY2Leu219Val, Ala252Gly)+; URA3+ |
| Strain 1-19 | Strain 1-9 | Saccharomycopsis fibuligera GLA1+; Saccharomyces cerevisae IMA1+, Saccharomyces mikatae MAL11+; Aggregatibacter actinomycetemcomitans LDH, Saccharomyces cerevisae JEN1+; URA3+ |
| Strain 1-20 | Strain 1-9 | Saccharomycopsis fibuligera GLA1+; Saccharomyces cerevisae IMA1+, Saccharomyces mikatae MAL11+; Ornithorhynchus anatinus LDH, Saccharomyces cerevisae JEN1+; URA3+ |
| Strain 1-21 | Strain 1-9 | Saccharomycopsis fibuligera GLA1+; Saccharomyces cerevisae IMA1+, Saccharomyces mikatae MAL11+; Issatchenkia orientalis CYB2+, Issatchenkia orientalis JEN1+; URA3+ |
| Strain 1-22 | Strain 1-9 | Saccharomycopsis fibuligera GLA1+; Saccharomyces cerevisae IMA1+, Saccharomyces mikatae MAL11+; Issatchenkia orientalis CYB2+, Saccharomyces cerevisae JEN1+; URA3+ |
| Strain 1-23 | Strain 1-9 | Saccharomycopsis fibuligera GLA1+; Saccharomyces cerevisae IMA1+, Saccharomyces mikatae MAL11+; Issatchenkia orientalis CYB2+, Kluyveromyces lactis JEN1+; URA3+ |

TABLE 1-continued

Summary Descriptions of Engineered Yeast

| Strain | Parent | Description |
| --- | --- | --- |
| Strain 1-24 | Strain 1-9 | *Saccharomycopsis fibuligera* GLA1+; *Saccharomyces cerevisae* IMA1+, *Saccharomyces mikatae* MAL11+; *Saccharomyces cerevisae* CYB2+, *Saccharomyces cerevisae* JEN1+; URA3+ |
| Strain 1-25 | Strain 1-9 | *Saccharomycopsis fibuligera* GLA1+; *Saccharomyces cerevisae* IMA1+, *Saccharomyces mikatae* MAL11+; *Saccharomyces cerevisae* CYB2+, *Kluyveromyces lactis* JEN1+; URA3+ |
| Strain 1-26 | Strain 1-9 | *Saccharomycopsis fibuligera* GLA1+; *Saccharomyces cerevisae* IMA1+, *Saccharomyces mikatae* MAL11+; *Aspergillus niger* L-LOX, *Saccharomyces cerevisae* JEN1+; URA3+ |
| Strain 1-27 | Strain 1-9 | *Saccharomycopsis fibuligera* GLA1+; *Saccharomyces cerevisae* IMA1+, *Saccharomyces mikatae* MAL11+; *Yarrowia lipolytica* L-LOX, *Saccharomyces cerevisae* JEN1+; URA3+ |
| Strain 1-28 | Strain 1-9 | *Saccharomycopsis fibuligera* GLA1+; *Saccharomyces cerevisae* IMA1+, *Saccharomyces mikatae* MAL11+; *A. aceti* D-LOX+, *Kluyveromyces lactis* JEN1+; URA3+ |
| Strain 1-29 | Strain 1-9 | *Saccharomycopsis fibuligera* GLA1+; *Saccharomyces cerevisae* IMA1+, *Saccharomyves mikatae* MAL11+; *Gluconobacter oxydans* D-LOX+, *Kluyveromyces lactis* JEN1+; URA3+ |
| Strain 1-30 | Strain 1-9 | *Saccharomycopsis fibuligera* GLA1+; *Saccharomyces cerevisae* IMA1+, *Saccharomyces mikatae* MAL11+; *Saccharomyces cerevisae* DLD1+, *Kluyveromyces lactis* JEN1+; URA3+ |
| Strain 1-31 | Strain 1-9 | *Saccharomycopsis fibuligera* GLA1+; *Saccharomyces cerevisae* IMA1+, *Saccharomyces mikatae* MAL11+; *Issatchenkia orientalis* DLD1a+, *Kluyveromyces lactis* JEN1+; URA3+ |
| Strain 1-32 | Strain 1-9 | *Saccharomycopsis fibuligera* GLA1+; *Saccharomyces cerevisae* IMA1+, *Saccharomyces mikatae* MAL11+; *Issatchenkia orientalis* DLD1b+, *Kluyveromyces lactis* JEN1+; URA3+ |
| Strain 1-33 | Strain 1-9 | *Saccharomycopsis fibuligera* GLA1+; *Saccharomyces cerevisae* IMA1+, *Saccharomyces mikatae* MAL11+; *Issatchenkia orientalis* DLD1c+, *Kluyveromyces lactis* JEN1+; URA3+ |
| Strain 1-34 | Strain 1-9 | *Saccharomycopsis fibuligera* GLA1+; *Saccharomyces cerevisae* IMA1+, *Saccharomyces mikatae* MAL11+; CAN1 site control; URA3+ |
| Strain 1-35 | Strain 1-3 | ura3Δ; *Kluyveromyces lactis* JEN1+; URA3+ |
| Strain 1-36 | Strain 1-3 | ura3Δ; *Saccharomyces cerevisae* CYB2+, *Kluyveromyces lactis* JEN1+; URA3+ |
| Strain 1-37 | Strain 1-3 | ura3Δ; *Saccharomyces cerevisae* DLD1+, *Kluyveromyces lactis* JEN1+; URA3+ |
| Strain 1-38 | Strain 1-9 | *Saccharomycopsis fibuligera* GLA1+; *Saccharomyces cerevisae* IMA1+; *Saccharomyces mikatae* MAL11+; *Lactobacillus fermentum lactate racemase* +, *Kluyveromyces lactis* JEN1+; URA3+ |
| Strain 1-39 | Strain 1-3 | ura3Δ; *Lactobacillus fermentum lactate racemase* +, *Kluyveromyces lactis* JEN1+; URA3+ |
| Strain 1-40 | Strain 1-9 | *Saccharomycopsis fibuligera* GLA1; *Saccharomyces cerevisae* IMA1+, *Saccharomyces mikatae* MAL11+; *Saccharomyces cerevisae* CYB2+, *Saccharomyces cerevisae* ADY2 (ADY2Leu219Val, Ala252Gly)+; URA3+ |
| Strain 1-41 | Strain 1-25 | *Saccharomycopsis fibuligera* GLA1+; *Saccharomyces cerevisae* IMA1+, *Saccharomyces mikatae* MAL11+; 2x *Saccharomyces cerevisae* CYB2+, 2x *Kluyveromyces lactis* JEN1+; URA3+ |
| Strain 1-42 | Strain 1-9 | *Saccharomycopsis fibuligera* GLA1+; *Saccharomyces cerevisae* IMA1+, *Saccharomyces mikatae* MAL11+; *Saccharomyces kluyveri* CYB2+, *Kluyveromyces lactis* JEN1+; URA3+ |
| Strain 1-43 | Strain 1-9 | *Saccharomycopsis fibuligera* GLA1+; *Saccharomyces cerevisae* IMA1+, *Saccharomyces mikatae* MAL11+; *Saccharomyces bayanus* CYB2+, *Kluyveromyces lactis* JEN1+; URA3+ |
| Strain 1-44 | Strain 1-9 | *Saccharomycopsis fibuligera* GLA1+; *Saccharomyces cerevisae* IMA1+, *Saccharomyces mikatae* MAL11+; *Zygosaccharomyces rouxii* CYB2+, *Kluyveromyces lactis* JEN1+; URA3+ |
| Strain 1-45 | Strain 1-9 | *Saccharomycopsis fibuligera* GLA1+; *Saccharomyces cerevisae* IMA1+, *Saccharomyces mikatae* MAL11+; *Kluyveromyces lactis* CYB2+, *Kluyveromyces lactis* JEN1+; URA3+ |
| Strain 1-46 | Strain 1-9 | *Saccharomycopsis fibuligera* GLA1+; *Saccharomyces cerevisae* IMA1+, *Saccharomyces mikatae* MAL11+; *Kluyveromyces dobzhanskii* CYB2+, *Kluyveromyces lactis* JEN1+; URA3+ |
| Strain 1-47 | Strain 1-9 | *Saccharomycopsis fibuligera* GLA1+; *Saccharomyces cerevisae* IMA1+; *Saccharomyces mikatae* MAL11+; *Saccharomyces kluyveri* DLD1+, *Kluyveromyces lactis* JEN1+; URA3+ |
| Strain 1-48 | Strain 1-9 | *Saccharomycopsis fibuligera* GLA1+; *Saccharomyces cerevisae* IMA1+, *Saccharomyces mikatae* MAL11+; *Saccharomyces bayanus* DLD1+, *Kluyveromyces lactis* JEN1+; URA3+ |
| Strain 1-49 | Strain 1-9 | *Saccharomycopsis fibuligera* GLA1+; *Saccharomyces cerevisae* IMA1+ , *Saccharomyces mikatae* MAL11+; *Aspergillus fumigatus* DLD1+, *Kluyveromyces lactis* JEN1+; URA3+ |
| Strain 1-50 | Strain 1-9 | *Saccharomycopsis fibuligera* GLA1+; *Saccharomyces cerevisae* IMA1+, *Saccharomyces mikatae* MAL11+; *Kluyveromyces lactis* DLD1+, *Kluyveromyces lactis* JEN1+; URA3+ |
| Strain 1-51 | Strain 1-9 | *Saccharomycopsis fibuligera* GLA1+; *Saccharomyces cerevisae* IMA1+, *Saccharomyces mikatae* MAL11+; *Kluyveromyces dobzhanskii* DLD1+, *Kluyveromyces lactis* JEN1+; URA3+ |
| Strain 1-52 | Strain 1-9 | *Saccharomycopsis fibuligera* GLA1+; *Saccharomyces cerevisae* IMA1+, *Saccharomyces mikatae* MAL11+; *Kluyveromyces marxianus* DLD1+, *Kluyveromyces lactis* JEN1+; URA3+ |
| Strain 1-53 | Strain 1-9 | *Saccharomycopsis fibuligera* GLA1+; *Saccharomyces cerevisae* IMA1+, *Saccharomyces mikatae* MAL11+; *Saccharyomyces cerevisiae* DLD1+, *Saccharyomyces* cerevisiae CYB2+, *Kluyveromyves dobzhanskii* JEN1+; URA3+ |
| Strain 1-54 | Strain 1-9 | *Saccharomycopsis fibuligera* GLA1+; *Saccharomyces cerevisae* IMA1+, *Saccharomyces mikatae* MAL11+; *Saccharyomyces cerevisiae* DLD1+, *Saccharyomyces cerevisiae* CYB2+, *Kluyveromyves marxianus* JEN1+; URA3+ |
| Strain 1-55 | Strain 1-9 | *Saccharomycopsis fibuligera* GLA1+; *Saccharomyces cerevisae* IMA1+, *Saccharomyces mikatae* MAL11+; *Saccharyomyces cerevisiae* DLD1+, *Saccharyomyces cerevisiae* CYB2+, *Yarrowia lypolitica* JEN6+; URA3+ |
| Strain 1-56 | Strain 1-9 | *Saccharomycopsis fibuligera* GLA1+; *Saccharomyces cerevisae* IMA1+, *Saccharomyces mikatae* MAL11+; *Saccharyomyces cerevisiae* DLD1+, *Saccharyomyces cerevisiae* CYB2+, *Kluyveromyces lactis* JEN1+; URA3+ |
| Strain 1-57 | Strain 1-56 | *Saccharomycopsis fibuligera* GLA1+; *Saccharomyces cerevisae* IMA1+, *Saccharomyces mikatae* MAL11+; *Saccharyomyces cerevisiae* DLD1+, *Saccharyomyces cerevisiae* CYB2+, *Kluyveromyces lactis* JEN1+; URA3+ |
| Strain 1-58 | Strain 1-9 | *Saccharomycopsis fibuligera* GLA1+; *Saccharomyces cerevisae* IMA1+, *Saccharomyces mikatae* MAL11+; *Saccharyomyces cerevisiae* DLD1+, *Saccharyomyces cerevisiae* CYB2+, *Saccharyomyces cerevisiae* JEN1+; URA3+ |
| Strain 1-59 | Strain 1-9 | *Saccharomycopsis fibuligera* GLA1+; *Saccharomyces cerevisae* IMA1+, *Saccharomyces mikatae* MAL11+; *Saccharyomyces cerevisiae* DLD1+, *Saccharyomyces cerevisiae* CYB2+, *Saccharyomyces bayanus* JEN1+; URA3+ |
| Strain 1-60 | Strain 1-9 | *Saccharomycopsis fibuligera* GLA1+; *Saccharomyces cerevisae* IMA+, *Saccharomyces mikatae* MAL11+; *Saccharyomyces cerevisiae* DLD1+, *Saccharyomyces cerevisiae* CYB2+, *Kluyveromyces lactis* JEN1+; URA3+ |
| Strain 1-61 | Strain 1-9 | *Saccharomycopsis fibuligera* GLA1+; *Saccharomyces cerevisae* IMA1+, *Saccharomyces mikatae* MAL11+; *Saccharyomyces cerevisiae* DLD1+, *Saccharyomyces cerevisiae* CYB2+, *Kluyveromyces lactis* JEN1+; URA3+ |

TABLE 1-continued

Summary Descriptions of Engineered Yeast

| Strain | Parent | Description |
|---|---|---|
| Strain 1-62 | Strain 1-9 | *Saccharomycopsis fibuligera* GLA1+; *Saccharomyces cerevisae* IMA1+, *Saccharomyces mikatae* MAL11+; *Saccharyomyces cerevisiae* DLD1+, *Saccharyomyces cerevisiae* CYB2+, *Kluyveromyces lactis* JEN1+; URA3+ |

Example 2

Evaluation of L-Lactate Consumption in Engineered *Saccharomyces cerevisaie* Strains Using an Ethanol Fermentation Shake Flask Assay Described below are evaluations and associated data for ethanol fermentations run using selected yeast strains from Example 1. Strains 1 and 1-10 are reference strains used as comparators for various engineered strains. Strain 1 is a *Saccharomyces cerevisiae* yeast having commercially suitable ethanol tolerance. Strain 1-10 is a strain derived from strain 1 that is also suitable for commercial ethanol production.

Shake Flask Evaluation using Defined Media.

Selected strains from those listed in Table 1 are streaked out on a ScD-Ura plate and incubated at 30° C. until single colonies are visible (1-2 days) or grown overnight in 4 ml of YP+100 g/L D-gluconse in a 14 ml culture tube as a liquid culture at 30° C./250 rpm to generate seed biomass. A shake flask is inoculated with seed cell slurry to reach an initial $OD_{600}$ of 0.1-0 3 Immediately prior to inoculating, 60 mL of shake flask medium is added to a 250 mL non-baffled shake flask (Corning 4995-250) fitted with a screw cap containing a gas-permeable seal (corning 1395-45LTMC). The shake flask medium is prepared according to Verduyn (Verduyn, et al., 1992, Yeast. Vol. 8, 501-517), with the exception of substituting manganese tetrahydrate with manganese dihydrate. The medium is supplemented with D-gluconse to target an initial D-gluconse concentration of between 250 grams to 300 grams of D-gluconse per liter of media. Additionally, the media is supplemented with sodium L-lactate (Sigma; catalog number L7022). The pH of the media is adjusted to pH 4.5, and sterile filtered prior to use.

The inoculated flask is incubated at 30° C. with shaking in an orbital shake at 75 rpm for at least 40 hours. Samples are taken and analyzed for gluconse, ethanol and lactate concentration in the broth during fermentation using high performance liquid chromatography with a refractive index detector.

Example 2A

Evaluation of Overexpression of CYB2 in Strain 1-9

As shown in Table 2 below, a strain having a native CYB2 knocked-out (strain 1-10) does not appear to consume any L-lactate. The increase in L-lactate may be due to evaporation of water during the fermentation, resulting in a slight concentration increase. However, strains containing an overexpressed CYB2 (strains 1-11 and 1-12) perform similarly to a strain with a native CYB2 (Strain 1). Specifically, strains with a CYB2 consume very small amounts of L-Lactate while producing commercially significant ethanol amounts primarily by consuming gluconse.

TABLE 2

L-Lactic acid consumption in a fermentation shake flask assay for *Saccharomyces cerevisiae* strains, including strains containing an overexpressed CYB2.

| | Starting Concentration (g/L) (0 hours) | | | Mid-Point Concentration (g/L) (23 hours) | | | Final Concentration (g/L) (48 hours) | | |
|---|---|---|---|---|---|---|---|---|---|
| Strain | Glucose | Ethanol | L-Lactate | Glucose | Ethanol | L-Lactate | Glucose | Ethanol | L-Lactate |
| Strain 1 | 256.1 | 0 | 2.9 | 57.4 | 84.6 | 2.8 | 0.9 | 110.7 | 2.5 |
| Strain 1-10 | 256.1 | 0 | 2.9 | 57.7 | 84.4 | 3 | 1 | 111.8 | 3.1 |
| Strain 1-11 | 256.1 | 0 | 2.9 | 56.5 | 85.7 | 2.7 | 0.6 | 111.5 | 2.5 |
| Strain 1-12 | 256.1 | 0 | 2.9 | 61.4 | 83.2 | 2.7 | 1.3 | 111.7 | 2.5 |

Example 2B

Evaluation of Overexpression of CYB2 and *S. cerevisiae* JEN1 in Strain 1-9

Figure 1C:
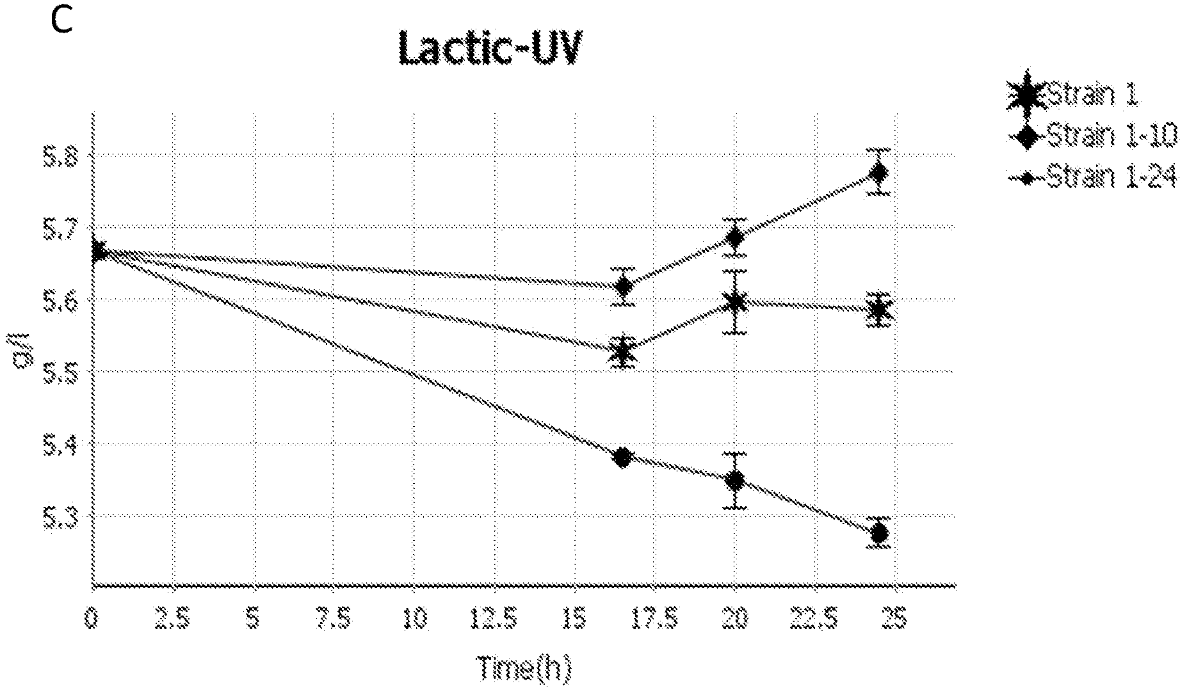

As shown in Table 3 below, strains having both an overexpressed CYB2 and an overexpressed *S. cerevisiae* JEN1 (strains 1-22 and 1-24) show significant L-lactate consumption with a high amount of gluconse still present in the fermentation broth. However, a strain having native CYB2 and JEN1 (strain 1) consumes L-lactate mostly only after the gluconse concentration is very low, while strains having no CYB2 (strains 1-10, 1-16, and 1-34) do not consume L-lactate. FIGS. 1A-1C show data for strain 1-24 corresponding to a second fermentation shake flask run.

TABLE 3

L-lactate consumption in fermentation shake flask assays for *Saccharomyces cerevisiae* strains, including strains containing an overexpressed CYB2 and *S. cerevisiae* JEN1.

| Strain | Starting Concentration (g/L) (0 hours) | | | Mid-Point Concentration (g/L) (20 hours) | | | Final Concentration (g/L) (41 hours) | | |
| --- | --- | --- | --- | --- | --- | --- | --- | --- | --- |
| | Glucose | Ethanol | L-Lactate | Glucose | Ethanol | L-Lactate | Glucose | Ethanol | L-Lactate |
| Strain 1 | 254.9 | 0 | 5.2 | 111 | 60.6 | 5.1 | 0.2 | 110 | 4.4 |
| Strain 1-10 | 254.9 | 0 | 5.2 | 110.3 | 61.2 | 5.3 | 0.3 | 111 | 5.4 |
| Strain 1-16 | 254.9 | 0 | 5.2 | 123.2 | 53.1 | 5.2 | 0.4 | 105.7 | 5.4 |
| Strain 1-22 | 254.9 | 0 | 5.2 | 100.9 | 63.5 | 4.8 | 0 | 110 | 4.5 |
| Strain 1-24 | 254.9 | 0 | 5.2 | 98.4 | 63.5 | 4.7 | 0 | 110.2 | 4.3 |
| Strain 1-34 | 254.9 | 0 | 5.2 | 111.5 | 59.6 | 5.2 | 0 | 109.7 | 5.3 |

Example 2C

Evaluation of Overexpression of CYB2 and Inclusion of Kl JEN1 and ScADY2 in Strain 1-9

As shown in Table 4 below, a strain having a native CYB2, JEN1, and ADY2 shows minimal L-lactate consumption in the presence of gluconse. Strain having an overexpressed CYB2 and either an overexpressed JEN1 (strain 1-24) or an ADY2 with mutations (strain 1-40) show significantly higher L-lactate consumption in the presence of gluconse. A strain having an overexpressed CYB2 and a *K. lactis* JEN1 (strain 1-25) has the highest L-lactate consumption. Further, strains 1-24, 1-25, and 1-40 show significantly higher ethanol titer than strain 1.

TABLE 4

L-lactate consumption in fermentation shake flask assays for *Saccharomyces cerevisiae* strains, including strains containing an overexpressed CYB2 and either a Klactis JEN1 or a ScADY2 with mutations.

| Strain | Starting Concentration (g/L) (0 hours) | | | Mid-Point Concentration (g/L) (20 hours) | | | L-Lactate consumption rate (gL$^{-1}$h$^{-1}$) 20 h | Final Concentration (g/L) (41 hours) | | | L-Lactate consumption rate (gL$^{-1}$h$^{-1}$) 41 h |
| --- | --- | --- | --- | --- | --- | --- | --- | --- | --- | --- | --- |
| | Glucose | EtOH | L-Lactate | Glucose | EtOH | L-Lactate | | Glucose | EtOH | L-Lactate | |
| Strain 1 | 308.5 | 0 | 5.7 | 209.3 | 60.6 | 5.1 | 0.029 | 52.1 | 109.4 | 5.3 | 0.010 |
| Strain 1-10 | 308.5 | 0 | 5.7 | 202.6 | 61.2 | 5.3 | 0.020 | 40.6 | 114.1 | 6.1 | −0.010 |
| Strain 1-24 | 308.5 | 0 | 5.7 | 202.1 | 63.5 | 4.8 | 0.044 | 37.9 | 116 | 4.7 | 0.024 |
| Strain 1-25 | 308.5 | 0 | 5.7 | 199.2 | 63.5 | 4.7 | 0.049 | 36.7 | 118 | 4 | 0.041 |
| Strain 1-40 | 308.5 | 0 | 5.7 | 199.2 | 43.6 | 5.7 | 0.000 | 30.3 | 120.5 | 4.7 | 0.024 |

Example 2D

Evaluation of Overexpression of Lactic Oxidase in Strain 1-9

Strains with an overexpressed lactic oxidase (L-LOX) might be expected to show improved L-lactate consumption. However, as shown in Table 5 below, strains having an overexpressed L-LOX (strains 1-13 and 1-14) do not show improved L-lactate consumption versus the comparator strains.

TABLE 5

L-lactate consumption in *Saccharomyces cerevisiae* strains, including strains containing an overexpressed lactic oxidase in fermentation shake flask assays.

| | Starting Concentration (g/L) (0 hours) | | | Mid-Point Concentration (g/L) (20 hours) | | | Final Concentration (g/L) (41 hours) | | |
|---|---|---|---|---|---|---|---|---|---|
| Strain | Glucose | Ethanol | L-Lactate | Glucose | Ethanol | L-Lactate | Glucose | Ethanol | L-Lactate |
| Strain 1 | 254.9 | 0 | 5.2 | 111 | 60.6 | 5.1 | 0.2 | 110 | 4.4 |
| Strain 1-10 | 254.9 | 0 | 5.2 | 110.3 | 61.2 | 5.3 | 0.3 | 111 | 5.4 |
| Strain 1-13 | 254.9 | 0 | 5.2 | 112.1 | 59.5 | 5.2 | 0.2 | 109.8 | 5.3 |
| Strain 1-14 | 254.9 | 0 | 5.2 | 104.7 | 62.1 | 5.2 | 0 | 110.9 | 5.3 |
| Strain 1-34 | 254.9 | 0 | 5.2 | 111.5 | 59.6 | 5.2 | 0 | 109.7 | 5.3 |

Example 2E

Evaluation of Overexpression of Lactic Oxidase and an Overexpressed JEN1 in Strain 1-9

As discussed above, strains with an overexpressed lactic oxidase (L-LOX) might be expected to show improved L-lactate consumption, but do not show improved L-lactate consumption. Further, as shown in Table 6 below, strains having an overexpressed JEN1 (strains 1-26 and 1-27) and a L-LOX also do not show improved L-lactate consumption.

In addition, a strain having an *I. orientalis* CYB2 and an *I. orientalis* JEN1 (strain 1-21) exhibits the same L-lactate consumption as strain 1, but with lower ethanol production and gluconse consumption, even though the parent wild-type organism (*I. orientalis*) can grow on L-lactate as a carbon source.

TABLE 6

L-lactate consumption in fermentation shake flask assays for *Saccharomyces cerevisiae* strains, including strains containing an overexpressed lactic oxidase and an overexpressed JEN1, and a strain having *I. orientalis* CYB2 and *I. orientalis* JEN1.

| | Starting Concentration (g/L) (0 hours) | | | Final Concentration (g/L) (41.3 hours) | | |
|---|---|---|---|---|---|---|
| Strain | Glucose | Ethanol | L-Lactate | Glucose | Ethanol | L-Lactate |
| Strain 1 | 307.1 | 0 | 5.5 | 17.9 | 120.5 | 4.5 |
| Strain 1-10 | 307.1 | 0 | 5.5 | 25 | 116.8 | 5.5 |
| Strain 1-16 | 307.1 | 0 | 5.5 | 53.7 | 99.7 | 5.4 |
| Strain 1-21 | 307.1 | 0 | 5.5 | 28.8 | 112.9 | 4.5 |

TABLE 6-continued

L-lactate consumption in fermentation shake flask assays for *Saccharomyces cerevisiae* strains, including strains containing an overexpressed lactic oxidase and an overexpressed JEN1, and a strain having *I. orientalis* CYB2 and *I. orientalis* JEN1.

| | Starting Concentration (g/L) (0 hours) | | | Final Concentration (g/L) (41.3 hours) | | |
|---|---|---|---|---|---|---|
| Strain | Glucose | Ethanol | L-Lactate | Glucose | Ethanol | L-Lactate |
| Strain 1-26 | 307.1 | 0 | 5.5 | 20.4 | 116.5 | 5.5 |
| Strain 1-27 | 307.1 | 0 | 5.5 | 20.2 | 114.8 | 5.6 |

Example 2F

Evaluation of Overexpression of a Lactate Dehydrogenase in Combination with a Sc JEN1 in Strain 1-9

Strains including an overexpressed lactate dehydrogenase might be expected to show improved L-lactate consumption, especially if anaerobic fermentation is expected. However, Table 7 shows that strains including a lactate dehydrogenase (LDH) (strains 1-19 and 1-20) actually produce L-lactate instead of consuming L-lactate.

TABLE 7

| L-lactate consumption in fermentation shake flask assays for *Saccharomyces cerevisiae* strains, including strains containing an overexpressed lactate dehydrogenase and JEN1 transporter. | | | | | | |
|---|---|---|---|---|---|---|
| | Starting Concentration (g/L) (0 hours) | | | Final Concentration (g/L) (41.3 hours) | | |
| Strain | Glucose | Ethanol | L-Lactate | Glucose | Ethanol | L-Lactate |
| Strain 1 | 307.1 | 0 | 5.5 | 17.9 | 120.5 | 4.5 |
| Strain 1-10 | 307.1 | 0 | 5.5 | 25.0 | 116.8 | 5.5 |
| Strain 1-19 | 307.1 | 0 | 5.5 | 29.0 | 106.4 | 15.4 |
| Strain 1-20 | 307.1 | 0 | 5.5 | 100.7 | 67.7 | 33.3 |
| Strain 1-16 | 307.1 | 0 | 5.5 | 53.7 | 99.7 | 5.4 |

Example 2G

Evaluation of Various Heterologous CYB2 Genes with *K. lactis* JEN1 in Strain 1-9

As shown in Table 8, a strain containing a *Z. rouxii* CYB2 (strain 1-44) or a *K. lactis* CYB2 (strain 1-45) showed higher L-lactate consumption and higher ethanol titer than the strain with a Sc CYB2. Strains with other CYB2 (1-42, 1-43, and 1-46) showed significant L-lactate consumption and commercially relevant ethanol titers.

TABLE 8

| L-lactate consumption in fermentation shake flask assays for *Saccharomyces cerevisiae* strains, including strains containing an overexpressed CYB2 and *K. lactis* JEN1 | | | | | | | | | |
|---|---|---|---|---|---|---|---|---|---|
| | Starting Concentration (g/L) (0 hours) | | | Mid-Point Concentration (g/L) (19.5 hours) | | | Final Concentration (g/L) (40 hours) | | |
| Strain | Glucose | Ethanol | L-Lactate | Glucose | Ethanol | L-Lactate | Glucose | Ethanol | L-Lactate |
| Strain 1 | 282.0 | 0 | 5.5 | 157.3 | 53.8 | 5.5 | 2.3 | 126.6 | 4.7 |
| Strain 1-10 | 282.0 | 0 | 5.5 | 165.0 | 53.9 | 5.8 | 9.9 | 122.5 | 5.7 |
| Strain 1-17 | 282.0 | 0 | 5.5 | 149.7 | 59.4 | 5.2 | 8.0 | 125.1 | 5.6 |
| Strain 1-25 | 282.0 | 0 | 5.5 | 144.3 | 59.8 | 5.0 | 0.6 | 128.2 | 3.9 |
| Strain 1-42 | 282.0 | 0 | 5.5 | 151.3 | 58.8 | 4.5 | 4.6 | 126.8 | 3.1 |
| Strain 1-43 | 282.0 | 0 | 5.5 | 147.4 | 57.8 | 5.1 | 6.5 | 126.8 | 4.1 |
| Strain 1-44 | 282.0 | 0 | 5.5 | 143.1 | 59.5 | 4.6 | 2.0 | 129.0 | 3.0 |
| Strain 1-45 | 282.0 | 0 | 5.5 | 149.3 | 57.1 | 4.4 | 2.4 | 129.1 | 3.0 |
| Strain 1-46 | 282.0 | 0 | 5.5 | 151.3 | 58.3 | 4.6 | 6.6 | 126.7 | 3.5 |

Example 2I

Evaluation of Various Heterologous Monocarboxylate/Proton Symporters in Strain 1-9

As shown in Table 9, two strains with *Kluyveromyces* JEN1 (*K. dobzhanskii*, strain 1-53; *K. lactis*, strain 1-56) showed the highest lactate consumption and ethanol titers. The strains including a *Kluyveromyces marxianus* JEN1 (strain 1-54) and *Yarrowia lypolitica* JEN6 (strain 1-55) also showed improved lactate consumption compared to reference strains.

TABLE 9

Total lactate consumption (mixture of L- and D-lactate) in fermentation shake flask assays for *S. cerevisiae* strains, including strains containing an overexpressed *S. cerevisiae* DLD1, *S. cerevisiae* CYB2, and JEN1 or JEN6.

| | Starting Concentration (g/L) (0 hours) | | | Mid-Point Concentration (g/L) (19.5 hours) | | | Final Concentration (g/L) (40 hours) | | |
|---|---|---|---|---|---|---|---|---|---|
| Strain | Glucose | Ethanol | Total Lactate | Glucose | Ethanol | Total Lactate | Glucose | Ethanol | Total Lactate |
| Strain 1 | 275.9 | 0.0 | 8.1 | 159.2 | 47.3 | 7.8 | 4.8 | 120.9 | 7.0 |
| Strain 1-10 | 275.9 | 0.0 | 8.1 | 158.6 | 47.8 | 7.9 | 8.0 | 120.4 | 7.7 |
| Strain 1-53 | 275.9 | 0.0 | 8.1 | 155.6 | 50.6 | 7.1 | 7.5 | 121.5 | 5.4 |
| Strain 1-54 | 275.9 | 0.0 | 8.1 | 155.7 | 49.3 | 7.2 | 6.7 | 118.6 | 6.0 |
| Strain 1-55 | 275.9 | 0.0 | 8.1 | 180.2 | 40.7 | 7.4 | 19.0 | 115.5 | 6.3 |
| Strain 1-56 | 275.9 | 0.0 | 8.1 | 155.0 | 50.2 | 7.2 | 3.9 | 122.8 | 4.7 |

Example 3

Evaluation of D-Lactate Consumption in Engineered *Saccharomyces cerevisiae* Strains Using an Ethanol Fermentation Shake Flask Assay Described below are evaluations and associated data for ethanol fermentations run using selected yeast strains from Example 1. Shake flask evaluation is performed as described in Example 2, except sodium D-lactate (Sigma; catalog number 71716) is used instead of sodium L-Lactate.

Example 3A

Evaluation of Overexpression of a JEN1 Transporter in Strain 1-9

Figures 2A, 2B:
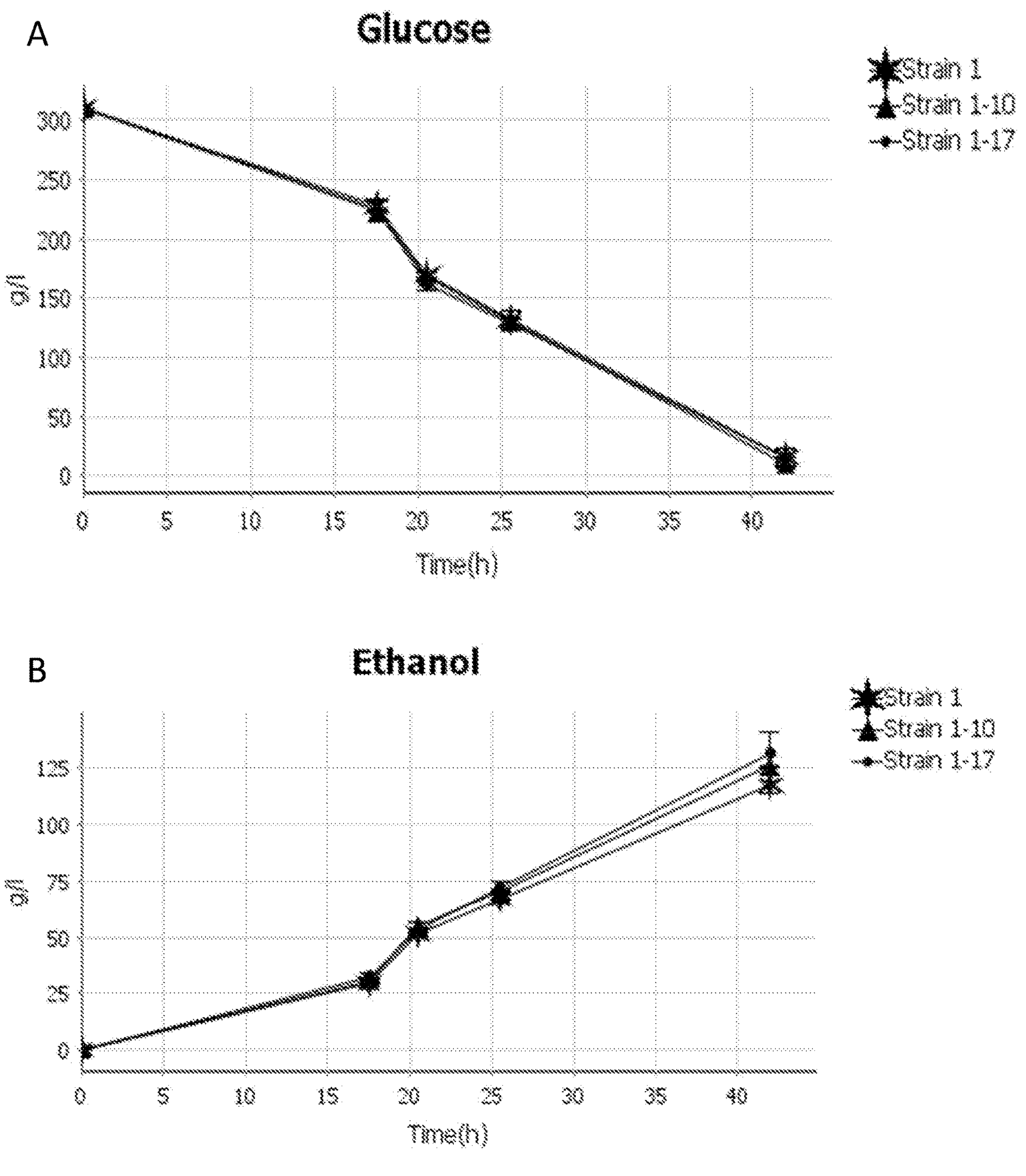
FIGS. 2A through 2C, is a set of graphs showing gluconse consumption, ethanol production, and D-lactate consumption in fermentation shake flask assays for *Saccharomyces cerevisiae* reference strains (1 and 1-10) and a strain containing an overexpressed *Kluyveromyces lactis* JEN1 (1-17).
Figure 2C:
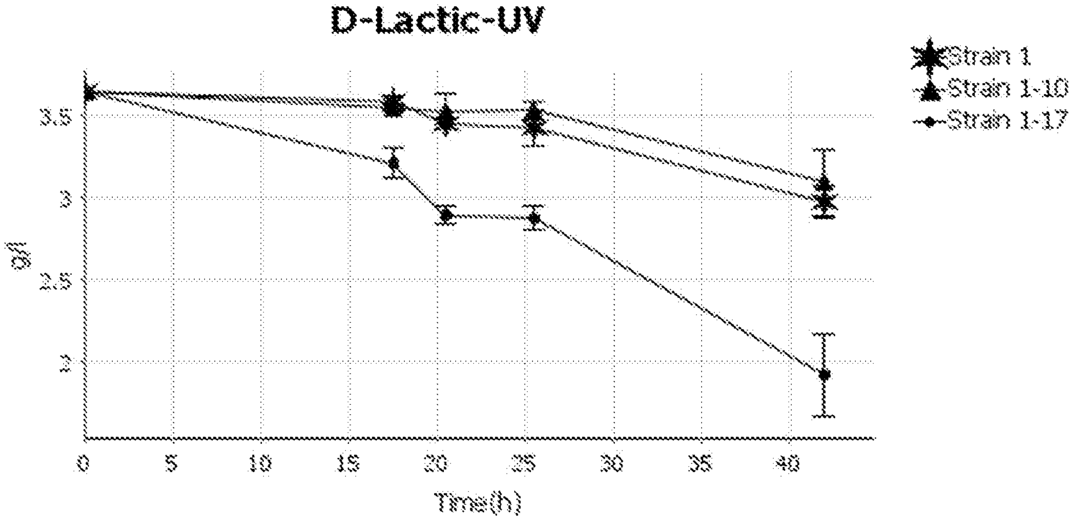

As shown in Table 10 and FIGS. 2A-2C, a strain containing an overexpressed *K. lactis* JEN1 had significantly higher D-lactate consumption and also significantly higher ethanol titer than the reference strains (strains 1 and 1-10) or strains containing other overexpressed JEN1 genes (strains 1-15 and 1-16).

TABLE 10

D-lactate consumption in *Saccharomyces cerevisiae* strains, including strains containing an overexpressed JEN1 in fermentation shake flask assays.

| | Starting Concentration (g/L) (0 hours) | | | Mid-point Concentration (g/L) (20.5 hours) | | | | Final Concentration (g/L) (42 hours) | | | |
|---|---|---|---|---|---|---|---|---|---|---|---|
| Strain | Glucose | EtOH | D-lactate | Glucose | EtOH | D-Lactate | D-Lactate Consumption rate $gL^{-1}h^{-1}$ 20.5 h | Glucose | EtOH | D-Lactate | D-Lactate Consumption rate $gL^{-1}h^{-1}$ 42 h |
| Strain 1 | 309.1 | 0 | 3.6 | 169.8 | 51.1 | 3.5 | 0.005 | 15.5 | 117.9 | 3.0 | 0.014 |
| Strain 1-10 | 309.1 | 0 | 3.6 | 167.9 | 54.6 | 3.5 | 0.005 | 9.2 | 125.8 | 3.1 | 0.012 |
| Strain 1-15 | 309.1 | 0 | 3.6 | 165.2 | 52.9 | 3.4 | 0.010 | 29.8 | 116.8 | 2.9 | 0.017 |

TABLE 10-continued

D-lactate consumption in *Saccharomyces cerevisiae* strains, including strains containing an overexpressed JEN1 in fermentation shake flask assays.

| Strain | Starting Concentration (g/L) (0 hours) Glucose | EtOH | D-lactate | Mid-point Concentration (g/L) (20.5 hours) Glucose | EtOH | D-Lactate | D-Lactate Consumption rate $gL^{-1}h^{-1}$ 20.5 h | Final Concentration (g/L) (42 hours) Glucose | EtOH | D-Lactate | D-Lactate Consumption rate $gL^{-1}h^{-1}$ 42 h |
|---|---|---|---|---|---|---|---|---|---|---|---|
| Strain 1-16 | 309.1 | 0 | 3.6 | 187.5 | 44.6 | 3.4 | 0.010 | 52.1 | 102.0 | 3.0 | 0.014 |
| Strain 1-17 | 309.1 | 0 | 3.6 | 161.6 | 53.0 | 2.9 | 0.034 | 15.1 | 131.7 | 1.9 | 0.041 |

Example 3B

Evaluation of Overexpression of a *Saccharomyces cerevisae* ADY2$^{(ADY2Leu219Val,\ Ala252Gly)}$ Permease in Strain 1-9

As shown in Table 11, D-lactate consumption and ethanol production are significantly higher in a strain containing a *K. lactis* JEN1 than in the reference strains, while a strain containing ADY2 (strain 1-18) shows performance similar to the reference strains.

TABLE 11

D-lactate consumption in *Saccharomyces cerevisiae* strains containing an overexpressed JEN1 in fermentation shake flask assays.

| Strain | Starting Concentration (g/L) (0 hours) Glucose | Ethanol | D-lactate | Final Concentration (g/L) (42 hours) Glucose | Ethanol | D-Lactate |
|---|---|---|---|---|---|---|
| Strain 1 | 307.0 | 0 | 3.5 | 41.5 | 114.1 | 3.1 |
| Strain 1-10 | 307.0 | 0 | 3.6 | 32.6 | 119.2 | 3.0 |
| Strain 1-17 | 307.0 | 0 | 3.6 | 29.1 | 120.7 | 1.7 |

TABLE 11-continued

D-lactate consumption in *Saccharomyces cerevisiae* strains containing an overexpressed JEN1 in fermentation shake flask assays.

| Strain | Starting Concentration (g/L) (0 hours) Glucose | Ethanol | D-lactate | Final Concentration (g/L) (42 hours) Glucose | Ethanol | D-Lactate |
|---|---|---|---|---|---|---|
| Strain 1-18 | 307.0 | 0 | 3.6 | 44.5 | 115.0 | 3.1 |

Example 3C

Evaluation of Overexpression of a D-Lactate Dehydrogenase and a *K. lactis* JEN1 in Strain 1-9

Figure 3A:
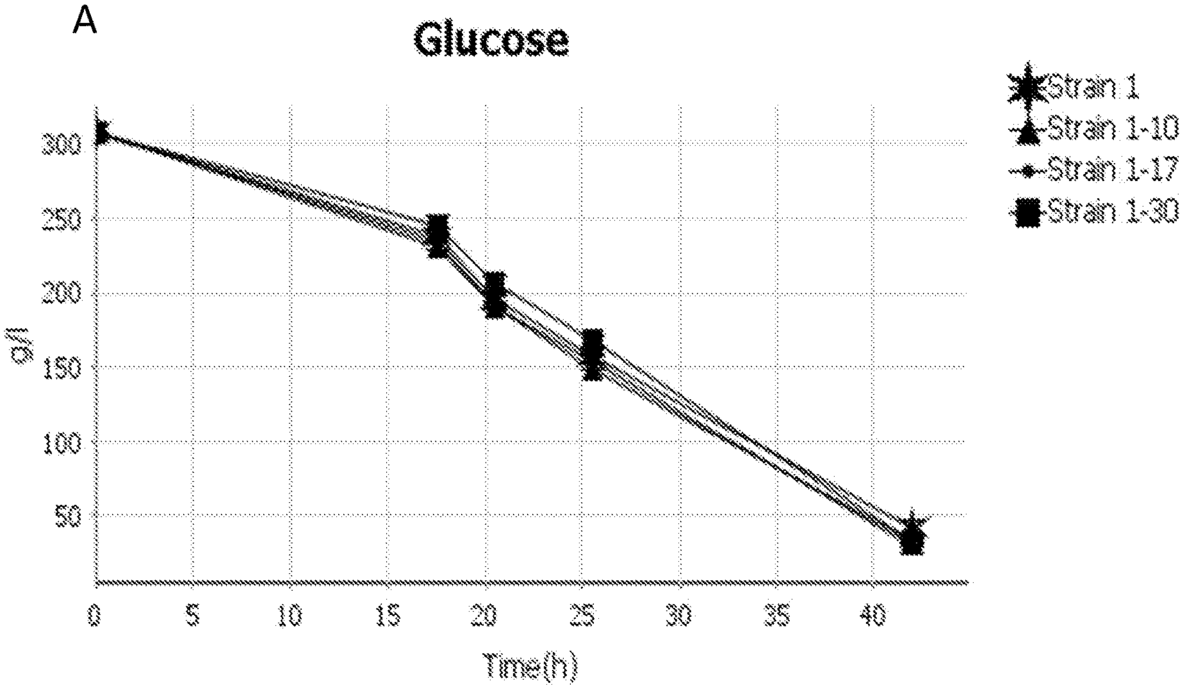
FIGS. 3A through 3C, is a set of graphs showing gluconse consumption, ethanol production, and D-lactate consumption in fermentation shake flask assays for *Saccharomyces cerevisiae* reference strains (1 and 1-10), a strain containing an overexpressed *K. lactis* JEN1 (1-17) and a strain containing an overexpressed *K. lactis* JEN1 and an overexpressed ScDLD1 (1-30).
Figure 3B:
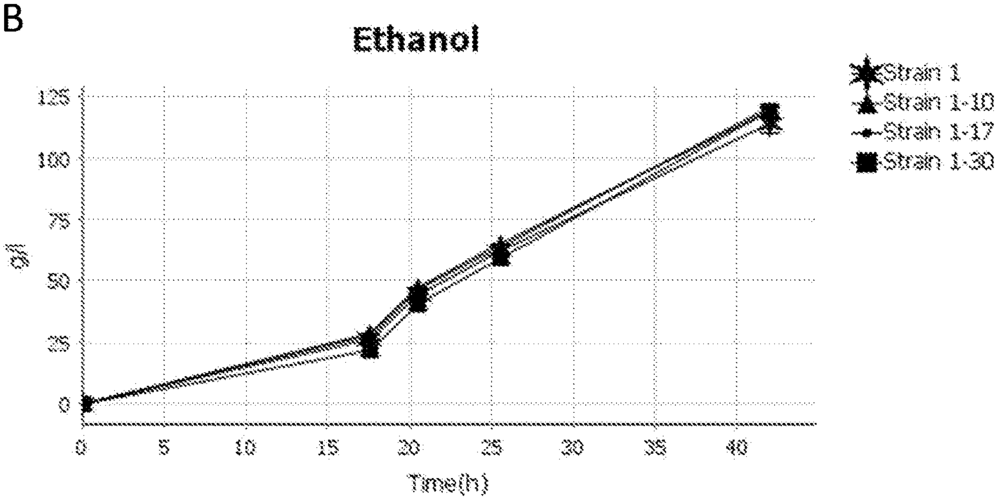
Figure 3C:
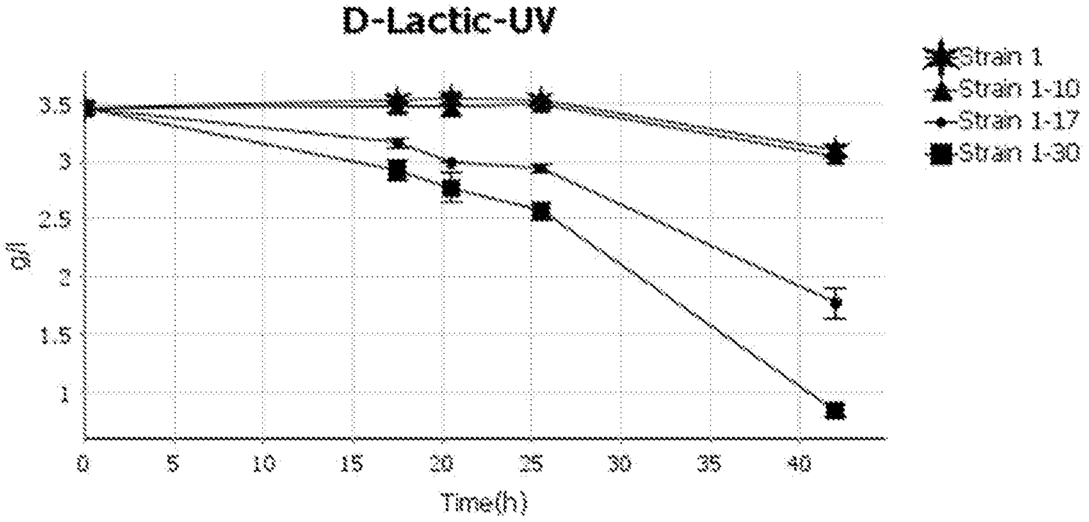

As shown in FIGS. 3A-3C, a strain containing a *K. Lactis* JEN1 and an overexpressed DLD (strain 1-30) shows significantly improved D-lactate consumption and a higher ethanol titer than the reference strains. Further, the D-lactate consumption of strain 1-30 is significantly improved over a strain having only the *K. Lactis* JEN1 (strain 1-17).

Example 3D

Evaluation of *Issatchenkia orientalis* D-Lactate Dehydrogenase and *K. lactis* JEN1 in Strain 1-9

Table 12 below shows data for three homolog strains containing a *K. Lactis* JEN1 and an overexpressed *I. orientalis* DLD (strains 1-31, 1-32, and 1-33). Each of these three homologs shows improved D-lactate consumption compared to a reference strain (1-10).

TABLE 12

D-lactate consumption in fermentation shake flask assays of *Saccharomyces cerevisiae* strains containing an overexpressed D-lactate oxidase and a *K. lactis* JEN1.

| Strain | Starting Concentration (g/L) (0 hours) Glucose | Ethanol | D-lactate | Mid-point Concentration (g/L) (20.5 hours) Glucose | Ethanol | D-Lactate | Final Concentration (g/L) (42 hours) Glucose | Ethanol | D-Lactate |
|---|---|---|---|---|---|---|---|---|---|
| Strain 1-10 | 301.3 | 0 | 3.9 | 191.8 | 42.3 | 3.7 | 29.9 | 117.8 | 3.3 |
| Strain 1-31 | 301.3 | 0 | 3.9 | 194.7 | 41.6 | 2.9 | 37.4 | 114.9 | 1.3 |

TABLE 12-continued

D-lactate consumption in fermentation shake flask assays of *Saccharomyces cerevisiae* strains containing an overexpressed D-lactate oxidase and a *K. lactis* JEN1.

| Strain | Starting Concentration (g/L) (0 hours) | | | Mid-point Concentration (g/L) (20.5 hours) | | | Final Concentration (g/L) (42 hours) | | |
|---|---|---|---|---|---|---|---|---|---|
| | Glucose | Ethanol | D-lactate | Glucose | Ethanol | D-Lactate | Glucose | Ethanol | D-Lactate |
| Strain 1-32 | 301.3 | 0 | 3.9 | 190.8 | 42.9 | 3.3 | 29.3 | 119.3 | 2.1 |
| Strain 1-33 | 301.3 | 0 | 3.9 | 194.2 | 41.6 | 2.9 | 34.7 | 113.4 | 1.0 |

Example 3E

Evaluation of Overexpressed D-Lactate Oxidase and *K. lactis* JEN1 in Strain 1-9

As shown in Table 13 below, strains containing an overexpressed D-lactate oxidase (D-LOX) and a *K. lactis* JEN1 (strains 1-28 and 1-29) show improved D-lactate consumption compared to reference strains (strains 1 and 1-10), but show less D-lactate consumption than a strain containing only a *K. lactis* JEN1 (strain 1-17). A strain containing a D-LOX might be expected to show improved D-lactate consumption, however, as seen with the L-LOX strains described above, the inclusion of D-LOX does not improve the D-lactate consumption.

TABLE 13

D-lactate consumption in fermentation shake flask assays of *Saccharomyces cerevisiae* strains containing an overexpressed D-lactate oxidase and a *K. lactis* JEN1.

| Strain | Starting Concentration (g/L) (0 hours) | | | Final Concentration (g/L) (42 hours) | | |
|---|---|---|---|---|---|---|
| | Glucose | Ethanol | D-lactate | Glucose | Ethanol | D-Lactate |
| Strain 1 | 307.0 | 0 | 3.5 | 41.5 | 114.1 | 3.1 |
| Strain 1-10 | 307.0 | 0 | 3.6 | 32.6 | 119.2 | 3.0 |

TABLE 13-continued

D-lactate consumption in fermentation shake flask assays of *Saccharomyces cerevisiae* strains containing an overexpressed D-lactate oxidase and a *K. lactis* JEN1.

| Strain | Starting Concentration (g/L) (0 hours) | | | Final Concentration (g/L) (42 hours) | | |
|---|---|---|---|---|---|---|
| | Glucose | Ethanol | D-lactate | Glucose | Ethanol | D-Lactate |
| Strain 1-17 | 307.0 | 0 | 3.6 | 29.1 | 120.7 | 1.7 |
| Strain 1-28 | 307.0 | 0 | 3.6 | 94.3 | 97.9 | 2.6 |
| Strain 1-29 | 307.0 | 0 | 3.6 | 43.0 | 116.3 | 2.0 |

Example 3F

Evaluation of Various Heterologous DLD Genes with *K. lactis* JEN1 in Strain 1-9

As shown in Table 14, a strain containing a *K. lactis* DLD (1-50) had the highest ethanol titer and L-lactate consumption than other strains with selected DLDs. However, the other strains (1-47, 1-48, 1-49, 1-51, and 1-52) all showed significant D-lactate consumption and commercially relevant ethanol titers.

TABLE 14

D-lactate consumption in fermentation shake flask assays for *Saccharomyces cerevisiae* strains, including strains containing an overexpressed DLD1 and *K. lactis* JEN1.

| Strain | Starting Concentration (g/L) (0 hours) | | | Mid-Point Concentration (g/L) (19.5 hours) | | | Final Concentration (g/L) (40 hours) | | |
|---|---|---|---|---|---|---|---|---|---|
| | Glucose | Ethanol | D-Lactate | Glucose | Ethanol | D-Lactate | Glucose | Ethanol | D-Lactate |
| Strain 1 | 282.7 | 0.0 | 4.1 | 146.2 | 59.0 | 4.0 | 1.1 | 127.5 | 3.5 |
| Strain 1-10 | 282.7 | 0.0 | 4.1 | 140.4 | 59.9 | 3.9 | 1.8 | 127.4 | 3.5 |
| Strain 1-17 | 282.7 | 0.0 | 4.1 | 140.6 | 61.5 | 3.6 | 1.9 | 128.6 | 2.5 |
| Strain 1-30 | 282.7 | 0.0 | 4.1 | 135.5 | 64.1 | 3.0 | 4.2 | 127.1 | 1.7 |

TABLE 14-continued

D-lactate consumption in fermentation shake flask assays for *Saccharomyces cerevisiae* strains, including strains containing an overexpressed DLD1 and *K. lactis* JEN1.

| | Starting Concentration (g/L) (0 hours) | | | Mid-Point Concentration (g/L) (19.5 hours) | | | Final Concentration (g/L) (40 hours) | | |
|---|---|---|---|---|---|---|---|---|---|
| Strain | Glucose | Ethanol | D-Lactate | Glucose | Ethanol | D-Lactate | Glucose | Ethanol | D-Lactate |
| Strain 1-47 | 282.7 | 0.0 | 4.1 | 140.9 | 60.9 | 3.1 | 3.1 | 127.1 | 1.8 |
| Strain 1-48 | 282.7 | 0.0 | 4.1 | 138.3 | 62.3 | 3.5 | 2.7 | 128.0 | 2.8 |
| Strain 1-49 | 282.7 | 0.0 | 4.1 | 146.4 | 60.5 | 3.5 | 5.8 | 125.2 | 2.6 |
| Strain 1-50 | 282.7 | 0.0 | 4.1 | 139.4 | 62.1 | 3.0 | 1.3 | 129.3 | 1.7 |
| Strain 1-51 | 282.7 | 0.0 | 4.1 | 164.7 | 50.9 | 3.2 | 11.3 | 122.2 | 2.0 |
| Strain 1-52 | 282.7 | 0.0 | 4.1 | 154.4 | 55.6 | 3.2 | 2.8 | 125.3 | 2.4 |

Example 4

Evaluation of a Genetically Modified *Saccharomyces cerevisiae* Strain in a Simultaneous Saccharification Fermentation (SSF) Shake Flask Assay A *Saccharomyces cerevisiae* strain containing an overexpressed *S. cerevisiae* CYB2 and a *Kluyvermyces lactis* JEN1 is evaluated for consumption of lactic acid and D-gluconse, and also production of ethanol. Strains obtained as described in Example 1.

Strains are struck to a ScD-ura plate and incubated at 25° C. until single colonies are visible (2-3 days). Cells from the ScD-ura plate are scraped into sterile shake flask medium and the optical density ($OD_{600}$) is measured. Optical density is measured at wavelength of 600 nm with a 1 cm path length using a model Genesys20 spectrophotometer (Thermo Scientific). A shake flask is inoculated with the cell slurry to reach an initial $OD_{600}$ of 0.1. Immediately prior to inoculating, 50 mL of shake flask medium is added to a 250 mL non-baffled shake flask (Corning 4995-250) fitted with a screw cap containing a gas-permeable seal (corning 1395-45LTMC). The shake flask medium consists of 850 g partially hydrolyzed corn starch, 150 g filtered light steep water, 10 g water, 25 g glucose, and 1 g urea. Duplicate flasks for each strain are incubated at 30° C. with shaking in an orbital shake at 100 rpm for 48 hours. Samples are taken and analyzed for metabolite concentrations in the broth during fermentation by HPLC with refractive index and UPLC with ELSD detection. Lactic acid (both D- and L-) is a component of the light steep water and is produced through contamination of the light steep water by lactic acid producing bacteria. The fraction of the D- and L-lactic acid in the light steep water varies between lots, and the absolute amount is not predictable. In general, the fraction of D- and L-lactic is a 50:50 racemic mix of the two enantiomers is at a total concentration of approximately 25 grams of lactic acid per liter of light steep water. Light steep water also contains low levels of gluconse.

Figure 4:
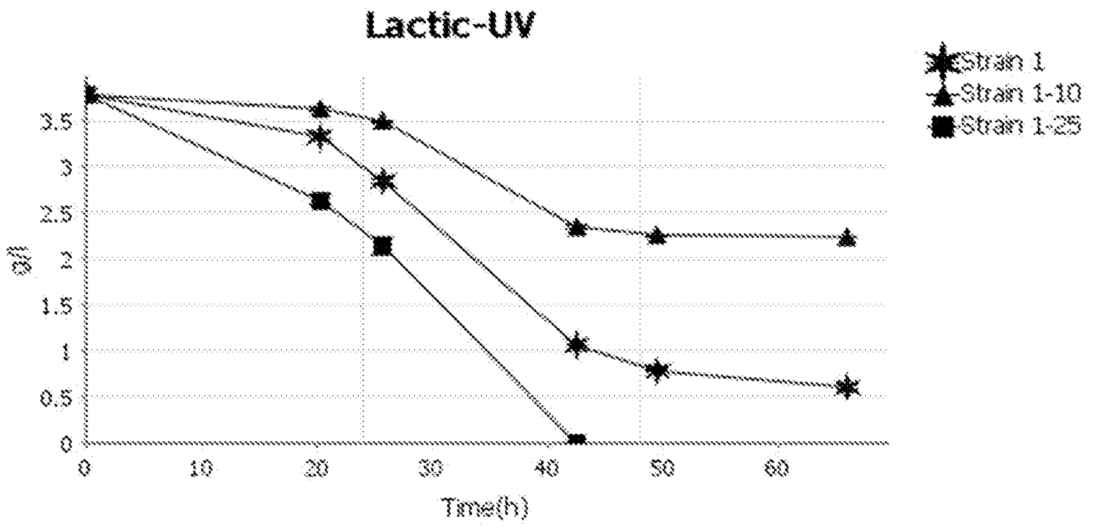
FIG. 4, comprising
Figure 4:
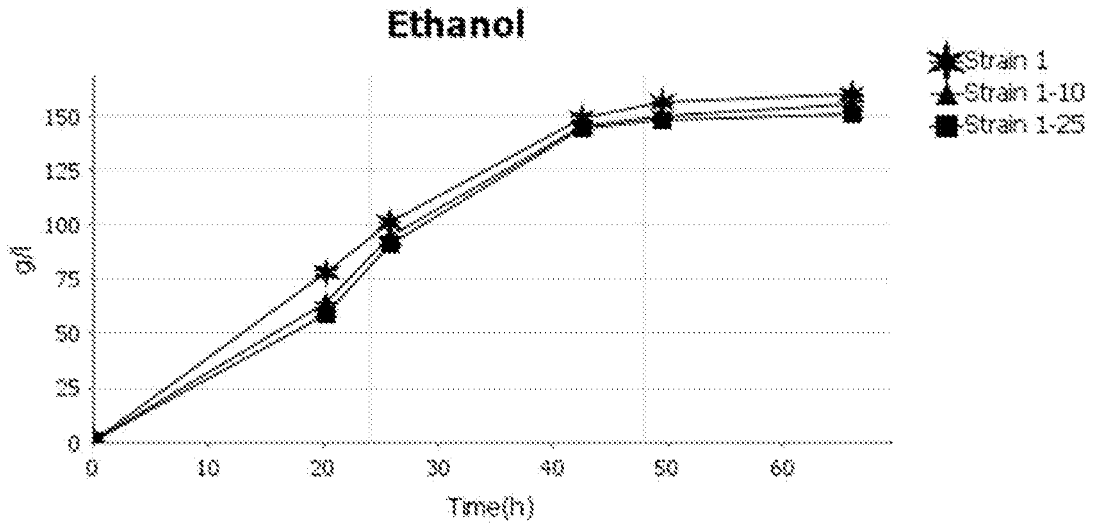

As shown in FIGS. 4A and 4B, a strain containing an overexpressed CYB2 and a *K. Lactis* JEN1 (strain 1-25) consumes most or all of D,L-lactate while producing a similar amount of ethanol compared to the reference strains.

Example 5

Performance of Genetically Modified Yeast Strain in SSF with Relatively Low Levels of Gluconse and Relatively High Levels of D,L-Lactate Strain 1-41 is obtained as described in Example 1. Strain 1-41 is strain 1-9 containing 2 copies of the ScCYB2 and 2 copies of the K1JEN1. Strains are run in a shake flask fermentation according to Example 4, with the following differences: 1) the shake flask medium of this Example (Example 5) is light steep water; 2) the shake flasks are inoculated with a cell slurry to reach an initial $OD_{600}$ of 4.0; 3) the non-baffled shake flasks are fitted with a Morton cap; and 4) the flasks are incubated in an orbital shaker at 150 rpm.

Figure 5:
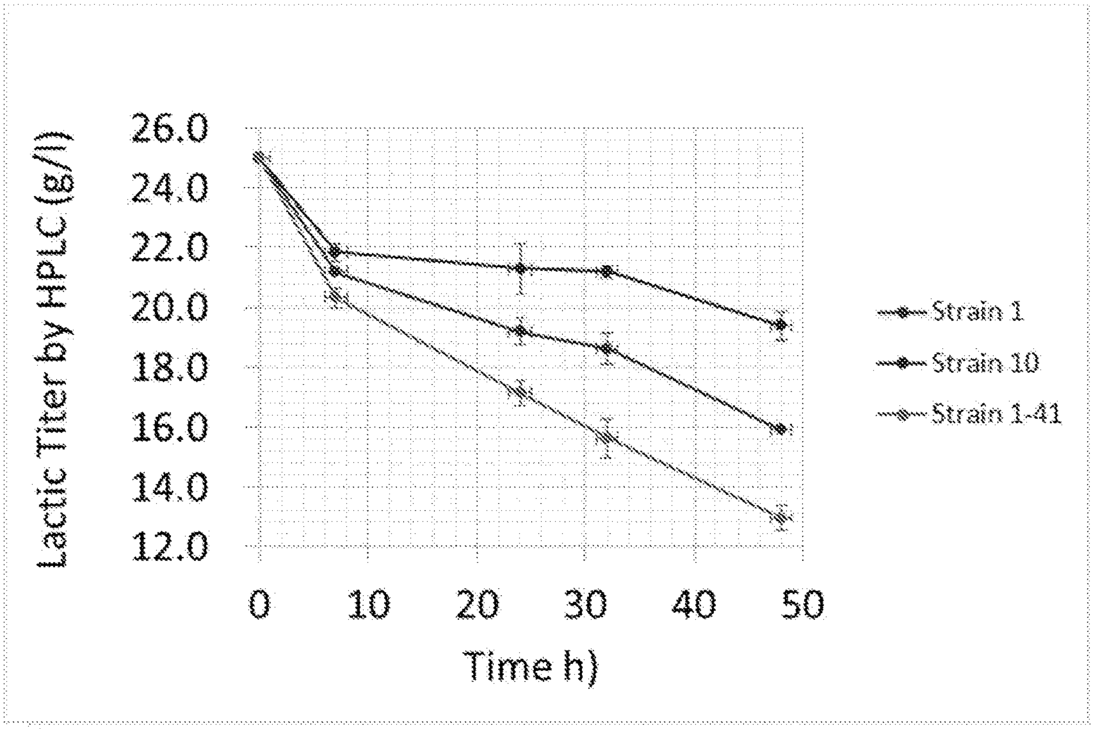
FIG. 5, comprising
Figure 5:
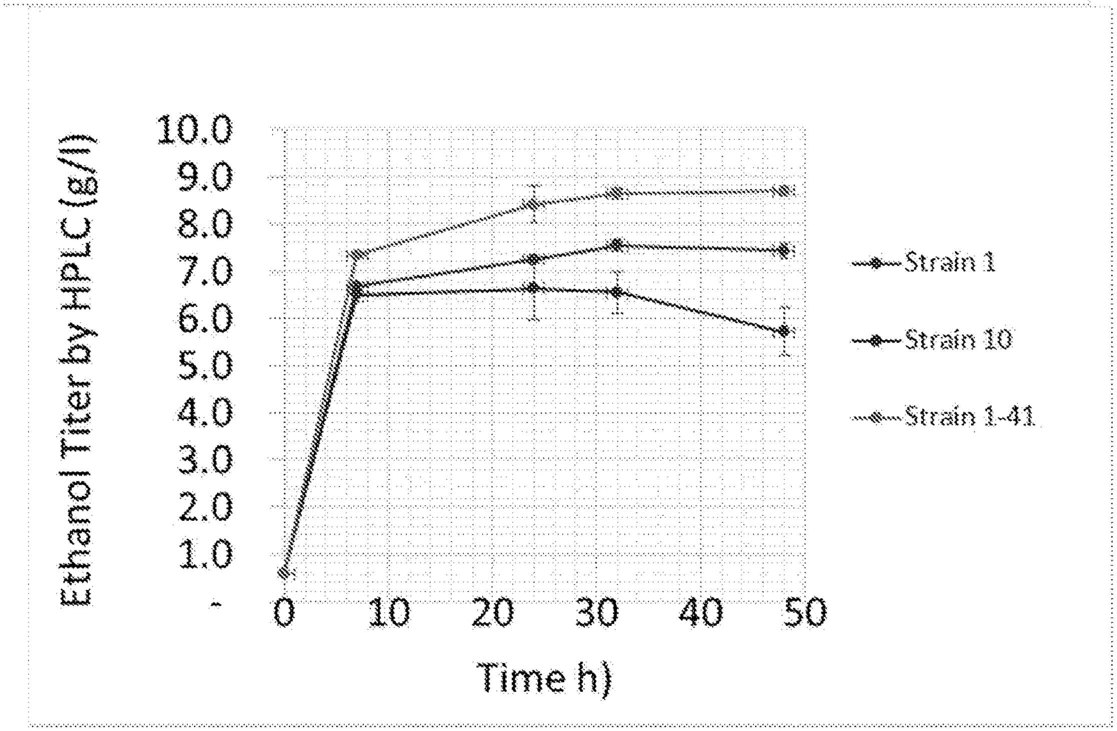

As shown in Tables 15 and 16 and FIGS. 5A and 5B, the strain containing overexpression of ScCYB2 and also containing K1JEN1 (1-41) consumed significantly more D,L-lactate than the reference strains, while producing a significantly higher ethanol titer than the reference strains.

TABLE 15

Overexpression of a ScCYB2 and Kl JEN1 in Strain 1-9 in a simultaneous saccharification shake flask assay

| Strain | Starting Concentration (g/L) (0 hours) | | | Mid-point Concentration (g/L) (7 hours) | | | Final Concentration (g/L) (48 hours) | | |
|---|---|---|---|---|---|---|---|---|---|
| | Glucose | EtOH | Lactate | Glucose | EtOH | Lactate | Glucose | EtOH | Lactate |
| Strain 1 | 11.65 | 0.59 | 25 | 0 | 6.7 | 21.2 | 0 | 7.4 | 15.9 |
| Strain 1-10 | 11.65 | 0.59 | 25 | 0 | 6.5 | 21.8 | 0 | 5.7 | 19.4 |
| Strain 1-41 | 11.65 | 0.59 | 25 | 0.16 | 7.3 | 20.3 | 0 | 8.7 | 13.0 |

TABLE 16

Rate of total lactate consumption (D- and L- Lactate)

| Strain | Total Lactate consumption rate (g $L^{-1}h^{-1}$) 0 to 7 hours | 7 hours to 48 hours | 0 to 48 hours |
|---|---|---|---|
| Strain 1 | 0.543 | 0.129 | 0.190 |
| Strain 1-10 | 0.457 | 0.059 | 0.117 |
| Strain 1-41 | 0.671 | 0.178 | 0.250 |

Example 6

L-Lactate Consumption in Genetically Modified Yeast Strains with Selected Heterologous Monocarboxylic/Monocarboxylate Transporters

*S. cerevisiae* strains containing selected heterologous monocarboxylic/monocarboxylate transporters are evaluated for L-lactate transport/consumption. As shown previously, *K. lactis* JEN1 has a higher affinity for D-lactate transport compared to L-lactate transport. Shake flask assays are performed using defined media with only L-lactate present. Dextrose concentrations are not measured, but are expected to be about 150 g/L at 20 h.

Figure 6:
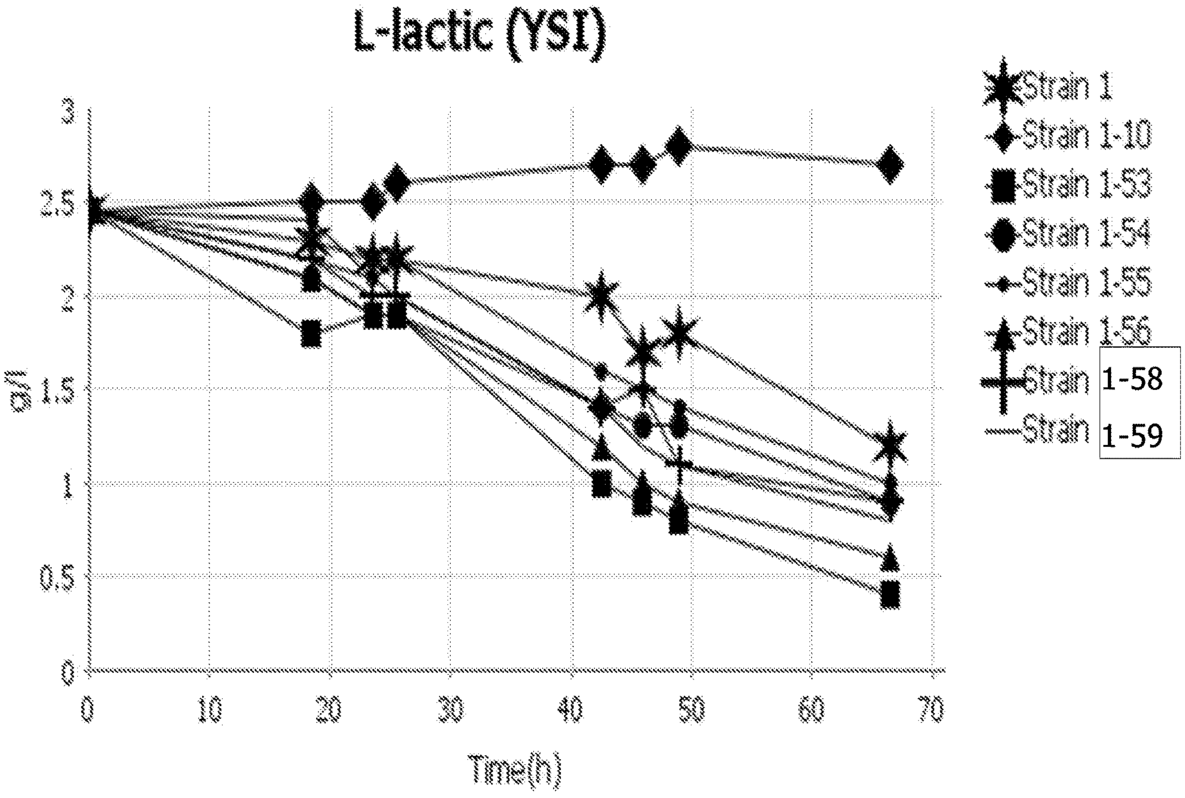
FIG. 6 is a graph showing L-lactate consumption in shake flask assays for *Saccharomyces cerevisiae* reference strains (1 and 1-10) and strains containing an overexpressed *S. cerevisiae* DLD1 and *S. cerevisiae* CYB2, and selected monocarboxylate/proton symporters.

As shown in Table 17 and FIG. 6, all heterologous monocarboxylic/monocarboxylate transporters tested exhibit improved L-lactate consumption compared to reference strains (strains 1 and 1-10).

TABLE 17

L-lactate consumption in fermentation shake flask assays for *S. cerevisiae* strains, including strains containing an overexpressed *S. cerevisiae* DLD1, *S. cerevisiae* CYB2, selected heterologous monocarboxylic/monocarboxylate transporters.

| Strain | Final Concentration (g/L) (41 hours) Glucose | Ethanol | L-Lactate |
|---|---|---|---|
| 1 | 0.2 | 130.8 | 1.3 |
| 1-10 | 0.2 | 130.7 | 2.9 |

TABLE 17-continued

L-lactate consumption in fermentation shake flask assays for *S. cerevisiae* strains, including strains containing an overexpressed *S. cerevisiae* DLD1, *S. cerevisiae* CYB2, selected heterologous monocarboxylic/monocarboxylate transporters.

| Strain | Final Concentration (g/L) (41 hours) Glucose | Ethanol | L-Lactate |
|---|---|---|---|
| 1-53 | 0.2 | 132.3 | 0.4 |
| 1-54 | 0.2 | 131.4 | 1.0 |
| 1-55 | 0.3 | 133.3 | 1.0 |
| 1-56 | 0.2 | 132.1 | 0.6 |
| 1-58 | 0.1 | 131.8 | 0.8 |
| 1-59 | 0.2 | 132.1 | 0.8 |

Example 7

Performance of Genetically Modified Yeast Strain in Production-Scale Ethanol Fermentaion Process A continuous fermentation process for producing ethanol is run on commercial scale using a reference strain with no lactic acid consumption pathway (strain 1-10) and (separately) a strain with an exogenous lactic consumption pathway enabled (strain 1-57) using an initial fermentation media including light steep water (LSW). Stage 1 is the propagator and Stage 2 is the pre-fermenter.

The changing concentration of D/L-lactic at the different stages reflects a number of changes to the composition of the fermentation broth due to inlet streams and dilution of the broth. Dilution levels are substantially the same for each strain at each stage. Therefore, relevant comparisons are the changing ratio of D/L-lactic for strain 1-10 vs. strain 1-57 within any given stage.

As shown in Table 18, a strain having a native CYB2 knocked-out and no exogenous lactic acid consumption pathway (strain 1-10) shows higher concentrations of both L- and D-lactic in each of Stage 1 and Stage 2, relative to a strain with the exogenous lactic consumption pathway enabled (strain 1-57).

TABLE 18

| Lactate consumption by genetically modified yeast strains on production scale | | | | | | | | | |
|---|---|---|---|---|---|---|---|---|---|
| | raw LSW | | | Stage 1 | | | Stage 2 | | |
| | L-lactic (g/L) | D-lactic (g/L) | Total Lactic (g/L) | L-lactic (g/L) | D-lactic (g/L) | Total Lactic (g/L) | L-lactic (g/L) | D-lactic (g/L) | Total Lactic (g/L) |
| Strain 1-10 | 14.5 ±2.7 | 9.8 ±1.6 | 24.3 ±4.1 | 7.8 ±0.8 | 4.2 ±1.8 | 12.0 ±1.6 | 4.9 ±0.3 | 2.1 ±0.9 | 6.9 ±0.3 |
| Strain 1-57 | 13 ±3.1 | 11.1 ±3.4 | 24.1 ±6.5 | 5.6 ±0.7 | 1.7 ±0.3 | 7.3 ±0.3 | 3.9 ±0.5 | 0.5 ±0.8 | 4.4 ±0.9 |

Example 8

Evaluation of Promoters for Driving Expression of a JEN1 Transporter

Alternative promoters to the promoter used in strain 1-57 (ADH1) are evaluated for driving expression of a JEN1 transporter. Strains were evaluated in a simultaneous saccharification fermentation (SSF) shake flask assay. These shake flasks serve as a proxy for assessing early fermentation burden of the selected strains.

In one aspect, as shown in Table 19, strains with alternative promoters to the promoter used in strain 1-57 (i.e., strains 1-60, 1-61, and 1-62) show significantly higher ethanol titers at the mid-point (22 h), therefore exhibiting reduced fermentation burden.

In another aspect, strain 1-57 is shown to generate significantly less glycerol with a corresponding significant increase in ethanol titer compared to all other strains. All strains with an enabled exogenous lactate-consumption pathway demonstrate lactate consumption and also the same or higher final ethanol titer compared to the reference strains. This demonstrates that strains with an enabled exogenous lactate-consumption pathway combined with selected promoters can achieve higher ethanol titers and/or the same ethanol titer at an earlier time point, either of which can provide a significant commercial advantage (i.e., increased throughput or reduced cycle time, or both).

TABLE 19

| SSF shake flask assays for selected strains | | | | | | | | | | | | |
|---|---|---|---|---|---|---|---|---|---|---|---|---|
| | Starting Concentration (g/L) (0 hours) | | | | Mid-Point Concentration (g/L) (22 hours) | | | | End Point Concentration (g/L) (68 hours) | | | |
| Strain | Glucose | EtOH | Glycerol | Total Lactate | Glucose | EtOH | Glycerol | Total Lactate | Glucose | EtOH | Glycerol | Total Lactate |
| Strain 1 | 34.4 | 0.2 | 0.1 | 2.4 | 37.6 | 73.8 | 6.6 | 2.5 | 0.6 | 150.4 | 9.3 | 1.5 |
| Strain 1-10 | 34.4 | 0.2 | 0.1 | 2.4 | 22.1 | 71.7 | 5.6 | 2.8 | 0.0 | 150.3 | 8.6 | 2.2 |
| Strain 1-57 | 34.4 | 0.2 | 0.1 | 2.4 | 15.8 | 67.7 | 4.3 | 2.0 | 0.0 | 154 | 7.3 | 0.0 |
| Strain 1-60 | 34.4 | 0.2 | 0.1 | 2.4 | 18.6 | 73.2 | 5.4 | 2.1 | 0.0 | 152.6 | 8.2 | 0.2 |
| Strain 1-61 | 34.4 | 0.2 | 0.1 | 2.4 | 23 | 74.2 | 5.7 | 2.5 | 0.0 | 150.3 | 8.6 | 0.8 |
| Strain 1-62 | 34.4 | 0.2 | 0.1 | 2.4 | 18.4 | 74.3 | 5.1 | 2.0 | 0.0 | 151.6 | 7.8 | 0.0 |

Example 9

Batch SSF with Selected Strains

Strain 1-62 is benchmarked against Strain 1-10 in a lab scale batch fermentation process. The feedstock consists of a partially saccharified starch stream with a starting percent dextrose concentration between 20-35%. The starting pH is between 3.5 and 4.5 and the operating temperature is 31° C. An average OUR of 0.66 mmol $O_2$/(L·h) is recorded from 20 hours elapsed fermentation time (EFT) to the end of fermentation (40 hours EFT), and the vessels are run until free dextrose concentrations are 0.2-0.5 (40 hours EFT). The data represents the average of three independent fermentation vessels per strain.

The starting dextrose concentration is cross validated using a carbohydrate column (87C) to determine the free dextrose, DP2, DP3 and DP4+ concentrations in the T0+ samples and are multiplied by their respective chemical gain factors to determine the dextrose sum. This method is cross validated using an enzymatic hydrolysis method. Dextrose sum results are averaged for each vessel.

As shown in Table 20, strain 1-62 (having an exogenous lactate-consumption pathway) demonstrates a significantly higher ethanol titer and lactate consumption, and also shows significantly lower glycerol generation, than the reference strain.

TABLE 20

4 L SSF batch fermenter data for strain 1-10 vs. strain 1-62

| | Starting Concentration (n = 3) | | | | Average Final Titer @ 40 hours (n = 3) | | | |
|---|---|---|---|---|---|---|---|---|
| | Total Dextrose (g/Kg) | Glycerol (g/Kg) | Lactate (g/Kg) | Ethanol (g/kg) | Total Dextrose (g/Kg) | Glycerol (g/Kg) | Lactate (g/Kg) | Ethanol (g/kg) |
| Strain 1-10 | 256.6 ±2.8 | 2.0 ±0.3 | 6.6 ±0.8 | 0.2 ±0.0 | 0.6 ±0.3 | 10.4 ±0.5 | 5.6 ±0.7 | 111 ±1.2 |
| Strain 1-62 | 254.8 ±1.5 | 2.0 ±0.3 | 6.6 ±0.8 | 0.2 ±0.1 | 0.9 ±0.5 | 8.8 ±0.4 | 4.4 ±0.7 | 114.4 ±0.2 |

Exemplary Embodiments

The embodiments in this section are designated sequentially with letters A through Z, then AA through AZ, then BA, and so on.

A. A genetically modified yeast comprising a heterologous gene encoding a monocarboxylic/monocarboxylate transporter and one or more heterologous genes encoding lactate dehydrogenase (cytochrome) (classified as EC 1.1.2.3 or 1.1.2.4), wherein the yeast is capable of consuming lactate and producing ethanol when the yeast is present in a fermentation medium comprising lactate and hexose.

B. The yeast of embodiment A, wherein the yeast has a L-lactate consumption rate of at least 0.030 0.035, 0.040, 0.045, or 0.050 $gL^{-1}h^{-1}$ when the concentration of hexose in the fermentation medium is 150 g/L or greater at a sampling time of 21 h, as measured according to the Evaluation Protocol for Lactate Consumption.

C. The yeast of embodiment A, wherein the yeast has a L-lactate consumption rate of at least 0.015, 0.020, 0.025, 0.030, 0.035, or 0.040 $gL^{-1}h^{-1}$ when the concentration of hexose in the fermentation medium is 5 g/L or greater at a sampling time of 48 h, as measured according to the Evaluation Protocol for Lactate Consumption.

D. The yeast of embodiment A, wherein the yeast has a D-lactate consumption rate of at least 0.005, 0.006, 0.007, 0.008, 0.009, 0.010, 0.015, 0.020, 0.025, or 0.030 $gL^{-1}h^{-1}$ when the concentration of hexose in the fermentation medium is 150 g/L or greater at a sampling time of 21 h, as measured according to the Evaluation Protocol for Lactate Consumption.

E. The yeast of embodiment A, wherein the yeast has a D-lactate consumption rate of at least 0.015, 0.020, 0.025, 0.030, 0.035, or 0.040 $gL^{-1}h^{-1}$ when the concentration of hexose in the fermentation medium is 5 g/L or greater at a sampling time of 48 h, as measured according to the Evaluation Protocol for Lactate Consumption.

F. The yeast of any of embodiments A-E, wherein the D-, L-, and/or total lactate consumption rate of the yeast is greater than a yeast without a heterologous gene encoding a monocarboxylic/monocarboxylate transporter.

G. The yeast of embodiment A, wherein the yeast has a total lactate consumption rate of at least 0.550, 0.555, 0.600 or 0.650 $gL^{-1}h^{-1}$ between time 0 and 7 hours in a simultaneous saccharification fermentation (SSF) process.

H. The yeast of embodiment A, wherein the yeast has a total lactate consumption rate of at least 0.130, 0.140, 0.150, 0.160, or 0.170 $gL^{-1}h^{-1}$ between time 7 hours and 48 hours in a SSF process.

I. The yeast of embodiment A, wherein the yeast has a total lactate consumption rate of at least 0.200, 0.210, 0.220, 0.230, 0.240, or 0.250 $gL^{-1}h^{-1}$ between time 0 and 48 hours in a SSF process.

J. The yeast of any of embodiments G-I, wherein the total lactate consumption rate is determined according to the method for SSF shake flask assay in Example 5.

K. The yeast of any of embodiments A-J, wherein the yeast is capable of consuming D-lactate, L-lactate, or a mixture thereof.

L. The yeast of any of embodiments A-K, wherein the one or more heterologous lactate dehydrogenase (cytochrome) genes comprise an overexpressed D-lactate dehydrogenase (DLD) gene.

M. The yeast of any of embodiments A-K, wherein the one or more heterologous lactate dehydrogenase (cytochrome) genes comprise an overexpressed cytochrome b2 (CYB2) gene.

N. The yeast of any of embodiments A-K, wherein the one or more heterologous lactate dehydrogenase (cytochrome) genes comprise an overexpressed DLD gene and an overexpressed CYB2 gene.

O. The yeast of any of embodiments L-N, wherein the one or more DLD genes is from one or more of the following yeast species: *Saccharomyces cerevisiae, Issatchenkia orientalis, Saccharyomyces kluyveri, Saccharyomyces bayanus, Kluyveromyces dobzhanskii, Kluyveromyces marxianus,* or *Kluyveromyces lactis.*

P. The yeast of any of embodiments A-O, wherein the yeast encodes for a polypeptide having an amino acid sequence with a sequence identity of at least 50%, 55%, 65%, 70%, 75%, 80%, 85%, 90%, 95%, 97%, or 99% to any one of the following amino acid sequences: SEQ ID NO: 40, SEQ ID NO: 42, SEQ ID NO: 64, SEQ ID NO: 66, SEQ ID NO: 68, SEQ ID NO: 70, SEQ ID NO: 72, or SEQ ID NO: 74.

Q. The yeast of any of embodiments M-N, wherein the one or more CYB2 genes is from one or more of the following yeast species: *Saccharomyces cerevisiae, Issatchenkia orientalis, Saccharyomyces kluyveri, Saccharyomyces bayanus, Zygosaccharomyces rouxii, Kluyveromyces dobzhanskii*, or *Kluyveromyces lactis.*

R. The yeast of any of embodiments A-Q, wherein the yeast encodes for a polypeptide having an amino acid sequence with a sequence identity of at least 50%, 55%, 65%, 70%, 75%, 80%, 85%, 90%, 95%, 97%, or 99% to any one of the following amino acid sequences: SEQ ID NO: 15, SEQ ID NO: 17, SEQ ID NO: 54, SEQ ID NO: 56, SEQ ID NO: 58, SEQ ID NO: 60, or SEQ ID NO: 62.

S. The yeast of any of embodiments A-R which comprises a heterologous gene encoding a lactate racemase.

T. A genetically modified yeast comprising a heterologous gene encoding a monocarboxylate/proton symporter and a heterologous gene encoding a glucoamylase, wherein the yeast is capable of consuming lactate and producing ethanol when the yeast is present in a fermentation medium comprising lactate and hexose, starch, or a combination of hexose and starch.

U. The yeast of any of embodiments A-T, wherein the yeast encodes for a glucoamylase from *Saccharomycopsis fibuligera* or *Rhizopus oryzae.*

V. The yeast of any of embodiments A-U, wherein the yeast is of the genus *Saccharomyces.*

W. The yeast of embodiment V, wherein the yeast is of the species *Saccharomyces cerevisiae.*

X. A genetically modified yeast comprising a yeast of the species *Saccharomyces cerevisiae*, wherein the yeast comprises a heterologous gene encoding a monocarboxylate/proton symporter.

Y. The yeast of embodiment X, wherein the yeast is obtained by genetically modifying a *Saccharomyces cerevisiae* host yeast and wherein the host yeast is ETHANOL RED™ (commercially available from Lesaffre).

Z. The yeast of any of embodiments A-Y which is capable of producing ethanol at a fermentation production rate of at least 1.0 g $L^{-1}$ $h^{-1}$, 2.0 g $L^{-1}$ $h^{-1}$, 3.0 g $L^{-1}$ $h^{-1}$, 3.3 g $L^{-1}$ $h^{-1}$, or 3.75 g $L^{-1}$ $h^{-1}$.

AA. The yeast of any of embodiments A-Z which is capable of producing ethanol at a titer greater than 80 g/L, 90 g/L, 100 g/L, 110 g/L, 120 g/L, 125 g/L 130 g/L, 135 g/L, 140 g/L, 145 g/L, 150 g/L, 155 g/L, 160 g/L, or 165 g/L.

AB. The yeast of any of embodiments A-AA (i.e., A-Z and AA) which is (a) capable of producing ethanol at a titer of greater than 90 g/L, 100 g/L, 110 g/L, 120 g/L, 130 g/L, or 140 g/L; (b) thermotolerant at temperatures in the range of 33° C. to 40° C., 33° C. to 39° C., 33° C. to 38° C., 33° C. to 37° C., 34° C. to 37° C., 35° C. to 37° C., or 36° C. to 38° C.; or both (a) and (b).

AC. The yeast of any of embodiments A-AB, wherein the heterologous gene encoding a monocarboxylic/monocarboxylate transporter is from a yeast of the genus *Kluyveromyces.*

AD. The yeast of any of embodiments A-AC, wherein the heterologous gene encoding a monocarboxylic/monocarboxylate transporter is from *Kluyveromyces lactis.*

AE. The yeast of any of embodiments A-AD, wherein the yeast encodes for a polypeptide having an amino acid sequence with a sequence identity of at least 50%, 55%, 65%, 70%, 75%, 80%, 85%, 90%, 95%, 97%, or 99% to any one of the following amino acid sequences: SEQ ID NO: 24, SEQ ID NO: 26, SEQ ID NO: 28, SEQ ID NO: 76, or SEQ ID NO: 78.

AF. The yeast of embodiment AE, comprising one or more of the following residues at the indicated positions in SEQ ID NO: 15, SEQ ID NO: 17, SEQ ID NO: 54, SEQ ID NO: 56, SEQ ID NO: 58, SEQ ID NO: 60, or SEQ ID NO: 62: Lys349, Tyr143, Tyr254, and His373.

AG. Use of the yeast of any of embodiments A-AF for the production of ethanol or a bioproduct other than ethanol.

AH. A process for producing ethanol comprising fermenting a substrate with the yeast of any of embodiments A-AG.

AI. A continuous fermentation process for manufacturing ethanol comprising: providing a fermentation medium comprising hexose or hexose oligomers, fermenting the fermentation medium with a genetically modified yeast comprising a heterologous monocarboxylate/proton symporter (JEN1) gene, adding one or more feed streams comprising lactate to the fermentation medium, and removing at least one output stream comprising ethanol from the fermentation medium, wherein the average hexose or hexose oligomer concentration of the fermentation medium is at least 5 g/L, the volumetric oxygen uptake rate of the process is at least 0.5 mmol $O_2/(L \cdot h)$, and the process produces ethanol at an overall rate of at least 1.0 g $L^{-1}$ $h^{-1}$, and the yeast consumes lactate, wherein the at least one output stream contains less than 90% of the lactate added in the one or more feed streams.

AJ. The process of embodiment AI, wherein lactate concentration of one or more feed streams has an average lactate concentration of at least 1 g/L.

AK. The process of any of embodiments AI-AJ, wherein the feed stream is a vegetable process stream.

AL. The process of embodiment AK, wherein the vegetable process stream is a corn process stream or a wheat process stream.

AM. The process of any of embodiments AH-AL, wherein the ethanol titer at the end of the pre-fermenter step is in the range of 20 to 80 g/L.

AN. The process of any of embodiments AH-AM, wherein the L-lactate consumption rate in the propagator step or pre-fermenter step is at least 0.030 0.035, 0.040, 0.045, or 0.050 $gL^{-1}h^{-1}$.

AO. The process of any of embodiments AH-AN, wherein the D-lactate consumption rate in the propagator step or pre-fermenter step 0.005, 0.006, 0.007, 0.008, 0.009, 0.010, 0.015, 0.020, 0.025, or 0.030 $gL^{-1}h^{-1}$.

AP. The process of any of embodiments AH-AO, wherein the ethanol titer of the at least one output stream is at least 90, 100, 110, 120, 130, 140, 150, or 160 g/L.

AQ. A process for manufacturing ethanol comprising: fermenting a medium using a genetically modified yeast comprising a heterologous monocarboxylate/proton symporter gene, wherein the medium comprises gluconse or gluconse oligomers at a concentration of at least 5 g/L at the start of fermentation, the lactate content of the medium is at least 1 g/L at the start of fermentation, at least 40% of the lactate is consumed at the end of fermentation, and the final ethanol titer is at least 90 g/L.

AR. The process of any of embodiments AH-AQ, having a volumetric oxygen uptake rate (OUR) of at least 0.5, 1, 2, 3, or 4 mmol $O_2/(L \cdot h)$.

AS. A process for manufacturing ethanol comprising: fermenting a medium using a *S. cerevisiae* yeast, wherein the medium comprises gluconse or gluconse oligomers and lactate, the OUR is at least 0.5 mmol $O_2$/(L·h), the lactate content of the medium is at least 1 g/L at the start of fermentation, at least 35% of the lactate present in the medium at the start of fermentation and/or added to the medium during fermentation is consumed by the end of fermentation, and the final ethanol titer is at least 90 g/L.

AT. The process of embodiment AS, wherein the OUR is at least 1, 2, 3, 4, 5, 6, 7, 8, 9, or 10 mmol $O_2$/(L·h).

AU. The process of any of embodiments AS-AT, wherein the lactate content of the medium is at least 2, 3, 4, or 5 g/L at the start of fermentation.

AV. The process of any of embodiments AS-AU, wherein at least 40, 45, or 50% of the lactate present in the medium at the start of fermentation and/or added to the medium during fermentation is consumed by the end of fermentation AW. The process of any of embodiments AH-AV, wherein the yeast is the yeast of any of embodiments A-Y.

AX. The process of any of embodiments AH-AW, wherein the lactate is L-lactate, D-lactate, or a mixture thereof.

AY. The process of any of embodiments AH-AX, wherein the pH of the fermentation medium is in the range of about 2 to 7.

AZ. The process of any of embodiments AH-AY, wherein the fermentation temperature is in the range of 25 to 45° C., 25 to 40° C., 25 to 35° C., 30 to 40° C., or 28 to 38° C.

BA. The process of any of embodiments AH-AZ, wherein the dry solids of the fermentation medium is at least 30, 40, 50, 60, 70, or 80 g/L BB. The process of any of embodiments AH-BA, wherein the dry solids of the fermentation feed is in the range of 120 to 150 g/L.

BC. The process of any of embodiments AH-BB, wherein the ethanol titer at the end of fermentation is at least 80, 90, 100, 110, 120, 130, 135, 140, 145, 150, 155, or 160 g/liter.

BD. A method for producing a genetically modified yeast with improved lactate consumption comprising overexpressing one or more heterologous genes encoding a lactate dehydrogenase (cytochrome) (classified as EC 1.1.2.3 or 1.1.2.4) or a heterologous monocarboxylate/proton symporter, and subjecting the yeast to evolution for a characteristic, wherein the yeast is capable of consuming lactate and producing ethanol when the yeast is present in a fermentation medium comprising lactate and gluconse.

BE. The method of embodiment BD, wherein the characteristic is increased growth rate on lactate.

BF. The process or method of any of embodiments AH-BE, wherein the yeast encodes for a polypeptide having an amino acid sequence with a sequence identity of at least 50%, 55%, 65%, 70%, 75%, 80%, 85%, 90%, 95%, 97%, or 99% to any one of the following amino acid sequence: SEQ ID NO: 24, SEQ ID NO: 26, SEQ ID NO: 28, SEQ ID NO: 76, or SEQ ID NO: 78.

BG. The process or method of embodiment BF, wherein the yeast comprises one or more of the following residues at the indicated positions in SEQ ID NO: 15, SEQ ID NO: 17, SEQ ID NO: 54, SEQ ID NO: 56, SEQ ID NO: 58, SEQ ID NO: 60, or SEQ ID NO: 62: Lys349, Tyr143, Tyr254, and His373.

BH. The process, method, or yeast of any of embodiments A-BG, wherein the yeast comprises a heterologous nucleic acid regulatory sequence.

BI. The process, method, or yeast of embodiment BH, wherein the heterologous nucleic acid regulatory sequence is associated with the heterologous gene encoding a monocarboxylic/monocarboxylate transporter.

BJ. The process, method, or yeast of embodiments BH or BI, wherein the heterologous nucleic acid regulatory sequence comprises the ADH1 promoter.

BK. The process, method, or yeast of embodiments BH or BI, wherein the heterologous nucleic acid regulatory sequence comprises the ADH2 promoter, the PDC1 promoter, or the GPD1 promoter.

It is also to be understood that the elements or aspects of any of the above embodiments of the processes, methods, or compositions described above can be applied to any other embodiment, even if not explicitly stated herein.

The disclosures of each and every patent, patent application, or publication cited herein are hereby incorporated by reference in their entirety. While this invention has been disclosed with reference to specific embodiments, other embodiments and variations of this invention may be devised by others skilled in the art without departing from the true spirit and scope of the invention. The appended claims are intended to be construed to include all such embodiments and variations.

The invention claimed is:

1. A genetically modified yeast comprising:

a heterologous gene encoding monocarboxylic/monocarboxylate transporter polypeptide having monocarboxylic/monocarboxylate transporter activity, wherein the said monocarboxylic/monocarboxylate transporter polypeptide comprises an amino acid sequence having at least 90% sequence identity to any one of the following amino acid sequences: SEQ ID NO: 24, SEQ ID NO: 26, SEQ ID NO: 28, SEQ ID NO: 76, or SEQ ID NO: 78, and one or more heterologous genes encoding a lactate dehydrogenase polypeptide having lactate dehydrogenase activity, wherein the said lactate dehydrogenase polypeptide comprises an amino acid sequence having at least 90% sequence identity to any one of the following amino acid sequences: SEQ ID NO: 40, SEQ ID NO: 42, SEQ ID NO: 64, SEQ ID NO: 66, SEQ ID NO: 68, SEQ ID NO: 70, SEQ ID NO: 72, or SEQ ID NO: 74, and wherein the yeast is capable of consuming lactate and producing ethanol at a titer greater than 80 g/L when the yeast is present in a fermentation medium comprising lactate and hexose.

2. The yeast of claim 1, wherein the yeast has a L-lactate consumption rate of at least 0.015 $gL^{-1}h^{-1}$ when the concentration of hexose in the fermentation medium is 5 g/L or greater at a sampling time of 48 h, as measured according to the Evaluation Protocol for Lactate Consumption.

3. The yeast of claim 1, wherein the yeast has a D-lactate consumption rate of at least 0.015 $gL^{-1}h^{-1}$ when the concentration of hexose in the fermentation medium is 5 g/L or greater at a sampling time of 48 h, as measured according to the Evaluation Protocol for Lactate Consumption.

4. The yeast of claim 1, wherein the D-, L-, and/or total lactate consumption rate of the yeast is greater than a yeast without a heterologous gene encoding a monocarboxylic/monocarboxylate transporter.

5. The yeast of claim 1, wherein the yeast is capable of consuming both D-lactate and L-lactate when the yeast is present in a fermentation medium comprising lactate and hexose.

6. The yeast of claim 1, wherein the yeast is genetically modified from a host yeast of the species *Saccharomyces cerevisiae.*

7. A process for producing ethanol comprising fermenting a substrate with the yeast of claim 1.

8. The process of claim 7, having a volumetric oxygen uptake rate (OUR) of at least 0.5 mmol $O_2/(L \cdot h)$.

9. The process of claim 7, wherein the ethanol titer at the end of fermentation is at least 100 g/liter.

* * * * *